US012410137B2

(12) United States Patent
Rabea et al.

(10) Patent No.: US 12,410,137 B2
(45) Date of Patent: Sep. 9, 2025

(54) FATTY ACID AMIDE HYDROLASE MODULATORS, COMPOSITIONS COMPRISING THE SAME AND USES THEREOF

(71) Applicant: APOGEE PHARMACEUTICALS, INC., Burnaby (CA)

(72) Inventors: Safwat Mohamed Rabea, Richmond (CA); KK Durgarao Viswanadham, Vancouver (CA); Gopi Kishore Valluru, Saint-Laurent (CA); Kaiji Hu, Burnaby (CA)

(73) Assignee: APOGEE PHARMACEUTICALS, INC., Burnaby (CA)

( * ) Notice: Subject to any disclaimer, the term of this patent is extended or adjusted under 35 U.S.C. 154(b) by 0 days.

(21) Appl. No.: 18/775,819

(22) Filed: Jul. 17, 2024

(65) Prior Publication Data

US 2025/0129027 A1    Apr. 24, 2025

Related U.S. Application Data

(60) Provisional application No. 63/513,940, filed on Jul. 17, 2023.

(51) Int. Cl.

| C07D 213/80 | (2006.01) |
| A61K 31/443 | (2006.01) |
| A61K 31/4436 | (2006.01) |
| A61K 31/4439 | (2006.01) |
| A61K 31/5377 | (2006.01) |
| C07D 213/30 | (2006.01) |
| C07D 213/82 | (2006.01) |
| C07D 401/04 | (2006.01) |
| C07D 405/04 | (2006.01) |
| C07D 409/04 | (2006.01) |
| C07D 413/04 | (2006.01) |
| C07D 413/14 | (2006.01) |
| C07D 417/04 | (2006.01) |
| C07D 471/08 | (2006.01) |
| C07D 491/107 | (2006.01) |

(52) U.S. Cl.
CPC .......... *C07D 213/80* (2013.01); *A61K 31/443* (2013.01); *A61K 31/4436* (2013.01); *A61K 31/4439* (2013.01); *A61K 31/5377* (2013.01); *C07D 213/30* (2013.01); *C07D 213/82* (2013.01); *C07D 401/04* (2013.01); *C07D 405/04* (2013.01); *C07D 409/04* (2013.01); *C07D 413/04* (2013.01); *C07D 413/14* (2013.01); *C07D 417/04* (2013.01); *C07D 471/08* (2013.01); *C07D 491/107* (2013.01)

(58) Field of Classification Search
CPC .................................................. C07D 213/80
USPC .................................................. 514/210.16
See application file for complete search history.

(56) References Cited

U.S. PATENT DOCUMENTS

| 2006/0173184 A1 | 8/2006 | Apodaca |
| 2007/0004741 A1 | 1/2007 | Apodaca |
| 2009/0062294 A1 | 3/2009 | Apodaca |
| 2011/0172230 A1 | 7/2011 | Ishii et al. |

FOREIGN PATENT DOCUMENTS

| WO | 98/37077 A1 | 8/1998 |
| WO | 99/42107 A1 | 8/1999 |
| WO | 2006/074025 A1 | 7/2006 |
| WO | 2008/024139 A2 | 2/2008 |
| WO | 2008/047229 A2 | 4/2008 |
| WO | 2008/023720 A1 | 1/2010 |
| WO | 2010/068452 A1 | 6/2010 |
| WO | 2010/068453 A1 | 6/2010 |

OTHER PUBLICATIONS

Ahn et al., "Discovery and Characterization of a Highly Selective FAAH Inhibitor that Reduces Inflammatory Pain," Chemistry & Biology 2009, 16, 4, 411-420.
Ahn et al., "Fatty acid amide hydrolase as a potential therapeutic target for the treatment of pain and CNS disorders," Expert Opin. Drug Discov. 2009, 4, 7, 763-784.
Bisogno et al., "Fatty Acid Amide Hydrolase, an Enzyme with Many Bioactive Substrates. Possible Therapeutic Implications," Current Pharmaceutical Design 2002, 8, 7, 533-547.
Boger et al., "Fatty Acid Amide Hydrolase Substrate Specificity," Bioorganic & Medicinal Chemistry Letters 2000, 10, 2613-2616.
Fazio et al., "Advances in the discovery of fatty acid amide hydrolase inhibitors: what does the future hold?," Expert Opin. Drug Discov. 2020, 15, 7, 765-778.
Fernández-Ruiz et al., "Cannabinoids in Neurodegenerative Disorders and Stroke/Brain Trauma: From Preclinical Models to Clinical Applications," Neurotherapeutics 2015, 12, 4, 793-806.
Fowler et al., "Fatty acid amide hydrolase: biochemistry, pharmacology, and therapeutic possibilities for an enzyme hydrolyzing anandamide, 2-arachidonoylglycerol, palmitoylethanolamide, and oleamide," Biochemical Pharmacology 2001, 62, 5, 517-526.
Godlewski et al., "Inhibitor of fatty acid amide hydrolase normalizes cardiovascular function in hypertension without adverse metabolic effects," Chemistry & Biology 2010, 17, 11, 1256-1266.
"Handbook of Pharmaceutical Salts: Properties Selection and Use," Organic Process Research & Development 2003, 7, 2, 222-223.
Jayamanne et al., "Actions of the FAAH inhibitor URB597 in neuropathic and inflammatory chronic pain models," British Journal of Pharmacology 2006, 147, 3, 281-288.

(Continued)

Primary Examiner — Kahsay Habte
(74) Attorney, Agent, or Firm — RAPHAEL BELLUM PLLC

(57) ABSTRACT

The present disclosure relates to fatty acid amide hydrolase (FAAH) modulators, inhibitors, or FAAH modulators and inhibitors and methods and uses thereof. The FAAH modulators, inhibitors, or FAAH modulators and inhibitors may be compounds having Formula I, II, III or IV. Pharmaceutical compositions comprising the FAAH modulators, inhibitors, or FAAH modulators and inhibitors are also provided.

20 Claims, 2 Drawing Sheets

(56) References Cited

OTHER PUBLICATIONS

Labar et al., "Fatty Acid Amide Hydrolase: From Characterization to Therapeutics," Chemistry & Biodiversity 2007, 4, 8, 1882-1902.
Lodola et al., "Fatty acid amide hydrolase inhibitors: a patent review (2009-2014)," Expert Opinion on Therapuetic Patents 2015, 25, 11,1247-1266.
McDougall et al., "Early blockade of joint inflammation with a fatty acid amide hydrolase inhibitor decreases end-stage osteoarthritis pain and peripheral neuropathy in mice," Arthritis Res Ther. 2017, 19, 106.
McKinney et al., "Structure and function of fatty acid amide hydrolase," Annu. Rev. Biochem. 2005, 74, 411-432.
O'Brien et al., "Investigation of the Alamar Blue (resazurin) fluorescent dye for the assessment of mammalian cell cytotoxicity," Eur. J. Biochem. 2000, 267, 17, 5421-5426.
Paulus et al., "The effects of FAAH inhibition on the neural basis of anxiety-related processing in healthy male subjects: A randomized clinical trial," Neuropsychopharmacology 2021, 46, 1011-1019.
Piomelli et al., "Pharmacological profile of FAAH Inhibitor KDS-4103 (URB597)," CND Drug Reviews 2006, 12, 1, 21-38.
Remington et al., "Remington's pharmaceutical sciences," 1990, Easton, Pa .: Mack Pub. Co.
Schmidt et al., "Cannabinoid receptor subtypes 1 and 2 mediate long-lasting neuroprotection and improve motor behavior deficits after transient focal cerebral ischemia," Neuroscience 2012, 227, 313-326.
Schmidt et al., "The effects of inhibition of fatty acid amide hydrolase (FAAH) by JNJ-42165279 in social anxiety disorder: a double-blind, randomized, placebo-controlled proof-of-concept study," Neuropsychopharmacology 2021, 46,1004-1010.
Saghatelian et al., "A FAAH-Regulated Class of N-Acyl Taurines That Activates TRP Ion Channels," Biochemistry 2006, 45, 30, 9007-9015.
U.S. Appl. No. 61/263,477, filed Nov. 23, 2009.
U.S. Appl. No. 61/184,606, filed Jun. 5, 2009.

FATTY ACID AMIDE HYDROLASE MODULATORS, COMPOSITIONS COMPRISING THE SAME AND USES THEREOF

FIELD OF INVENTION

The present disclosure relates to novel compounds that are fatty acid amide hydrolase (FAAH) inhibitors or modulators, compositions comprising the compounds and uses of the compounds and compositions. In particular, the novel compounds are useful for treating diseases, disorders or conditions that benefit from inhibition or modulation of FAAH. The novel compounds include prodrugs, pharmaceutically acceptable salts and pharmacologically active metabolites thereof.

BACKGROUND

Fatty acid amide hydrolase (FAAH) is a member of the serine hydrolase family of enzymes capable of modulating the endocannabinoid system (eCB). It is an integral membrane protein that is expressed in high levels in several brain regions, especially in the neurons of the hippocampus, cerebellum, neocortex and olfactory bulb. FAAH is primarily responsible for catalyzing the inactivation of endocannabinoid anandamide (AEA) via hydrolysis to arachidonic acid and ethanolamine. It is also able to hydrolyze a variety of other important bioactive fatty acid amides, including 2-arachidonoylglycerol, N-palmitoylethanolamide, N-oleoylethanolamide and oleamide (Fowler et al., 2001 [1]; Labar & Michaux, 2007 [2]; and Bisogno et al., 2002 [3]).

The cannabinoid system and its functions can be modulated by cannabinoid receptor antagonists/agonists and by inhibition of the endocannabinoid synthesizing/degrading enzymes, including FAAH. Genetic or pharmacological inhibition of FAAH leads to elevated levels of AEA providing increased stimulation of the cannabinoid CB1 and CB2 receptors and producing beneficial physiological effects related to the activation of the cannabinoid receptors (Ahn et al., 2009 [4]). In addition, increasing the concentration of endocannabinoids, rather than administering exogenous agonistic agents of the receptors, may reduce psychotropic cannabinoid-like adverse effects. Therefore, modulators of the FAAH enzyme constitute a therapeutic strategy for the treatment of pain, anxiety, post-traumatic stress disorder, inflammation, and other disorders involving the endocannabinoid system (Femndez-Ruiz et al., 2015 [5]; Schmidt. et al., 2012 [6]; and Fazio et al., 2021 [7]).

Inhibition of FAAH by small-molecule inhibitors has been reported to provide beneficial pharmacological effects in animal models and humans (Jayamanne et al., 2006 [8]; Ahn et al, 2009 [9]; Paulus et al., 2021 [10]; and Lodola et al., 2015 [11]). In addition to AEA, inhibition of FAAH also affects the endogenous levels of several other bioactive amides, ester lipids and their associated pathways, including, but not limited to, transient receptor potential family of calcium channels, non-cannabinoid receptors (such as GPR118) and nuclear receptors (such as Peroxisome Proliferator-Activated Receptors alpha or gamma), and could lead to beneficial outcomes in pain, inflammation and anxiety disorder (McDougall et al., 2017, [12]; Schmidt et al., 2021 [13]; and Saghatelian et al., 2006 [14]).

Chemical series of heteroaryl-substituted ureas have been reported in various publications as FAAH modulators. Certain piperazinyl and piperidinyl compounds as FAAH modulators are described in Intl. Patent Appl. No. WO 2006/074025, Intl. Patent Appl. Ser. No. PCT/US2009/065757, Intl. Patent Appl. Ser. No. PCT/US2009/065752, U.S. Appl. Publ. No. US 2009/0062294, and U.S. provisional Appl. Ser. No. 61/263,477. Various ureas are reported as small-molecule FAAH modulators in US Patent Publication Nos. US 2006/173184 and US 2007/0004741, in Intl. Patent Appl. Nos. WO 2008/023720, WO 2008/047229, and WO 2008/024139. Certain aryl-substituted heterocyclic urea derivatives are described in U.S. provisional Appl. No. 61/184,606. Certain piperazine-1-carboxamide and piperidine-1-carboxamide derivatives are described in Intl. Patent Appl. No. WO 2008/023720. Certain piperazine derivatives are described in Intl. Patent Appl. No. WO 99/42107. Certain N-aralkylpiperazines are described in Intl. Patent Appl. No. WO 98/37077.

However, there remains a need for potent FAAH inhibitor or modulators with improved properties.

SUMMARY OF THE INVENTION

This disclosure relates to novel molecules of formula (I-IV), their prodrug forms, pharmaceutically acceptable salts thereof, or combination thereof, process for their preparation, methods, composition and formulation in a delivery system for the prevention and/or treatment of diseases or medical conditions benefited by the inhibition of FAAH enzyme. The composition and/or formulation include disclosed compounds as at least one active ingredient. Furthermore, molecules, pharmaceutical composition and formulation may be combined with one or more therapeutic agents or compounds to prevent and/or treat diseases or medical conditions.

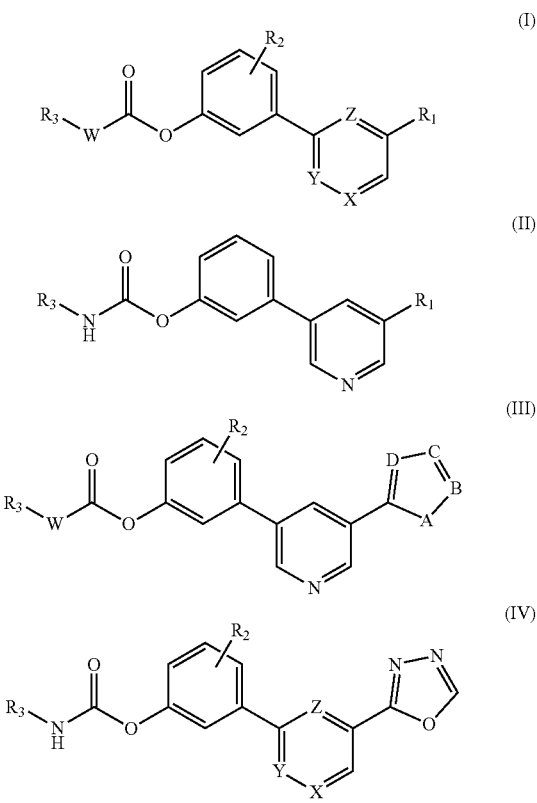

This disclosure is also directed to a method of testing the inhibition of FAAH and MAGL enzymes in both in vitro and in vivo systems.

Compounds of Formula (I-IV) may act as FAAH modulators, inhibitors, or as modulators and inhibitors. Inhibition of FAAH will slow the normal degradation of endogenous endocannabinoid ligand anandamide (AEA) and thereby allow the accumulation of AEA. The higher level of AEA induces increased stimulation of cannabinoid receptors CB1 and CB2 and produce diverse physiological effects related to the activation the cannabinoid receptors.

The compounds of Formula (I-IV), compositions and formulations may be used in methods for the treatment or prevention of disease states, disorders, and conditions mediated by FAAH activity, such as, but not limited to pain, inflammatory disorder, anxiety and mood disorder, cardiovascular diseases, metabolic disorder, neurodegenerative disorders, cancer, or epilepsy.

In one aspect the disclosure, provides a compound of Formula I.

(I)

a prodrug thereof, a pharmaceutically acceptable salt thereof, or a pharmaceutically active metabolite thereof; wherein W may be NH, N(CH$_3$), or none, wherein when W may be none R$_3$ may be directly attached to C(O) by a single bond;

X may be CH or N;
Y may be CH or N;
Z may be CH or N;
wherein X, Y and Z cannot all be CH or N;
R$_1$ may be independently —C(O)OR$_4$, —C(O)NHOH, —C(O)NHNH$_2$, CF$_3$, CHO, CN or heteroaryl; wherein R$_4$ may be independently C$_1$-C$_8$ alkyl;
R$_2$ may be independently hydrogen, halogen, alkyl, alkoxy, thioalkyl, haloalkoxy, wherein R$_2$ may be linked via any position on the phenyl ring;
R$_3$ may be independently C$_5$-C$_{20}$ alkyl, C$_3$-C$_8$ cycloalkyl, C$_4$-C$_8$ heterocycloalkyl, C$_{6-12}$ fused heterocycloakyl, C$_{6-12}$ spirocycloalkyl, or aryl, wherein R$_3$ may be unsubstituted or substituted at a carbon ring member with halogen or alkyl group.

In one embodiment R$_1$ may be monocycles: 2-pyrrolyl, 2-furanyl, 2-thienyl, 2-oxazolyl, 5-isoxazolyl, 2-thiazolyl, 1,3,4-oxadiazolyl, 1,2,4-oxadiazolyl, 1,3,4-thiadiazolyl, 1,2,4-triazolyl, or 1,2,3,4-tetrazolyl.

In another embodiment R$_2$ may be H, OH, OCH$_3$, SCH$_3$, F, OCF$_3$, CN, or N(CH$_3$)$_2$.

Furthermore, R$_2$ may be independently OH, OCH$_3$, SCH$_3$, or N(CH$_3$)$_2$.

It is further provided a compound of Formula I: wherein
W may be NH;
X may be N;
Y may be CH;
Z may be CH;
R$_1$ may be oxadiazole, oxazole, thiazole, pyrazole or imidazole;
R$_2$ may be halogen, hydroxy, C$_1$-C$_4$ alkoxy, cyano, or fluoroalkyl; and
R$_3$ may be C$_1$-C$_8$ alkyl or C$_3$-C$_8$ cycloalkyl.

It is also provided a compound of Formula I: wherein
W may be NH;
X may be N;
Y may be CH;
Z may be CH;
R$_1$ may be oxadiazole;
R$_2$ may be halogen, hydroxy, C$_1$-C$_4$ alkoxy, cyano, or fluoroalkyl; and
R$_3$ may be C$_1$-C$_8$ alkyl or C$_3$-C$_8$ cycloalkyl.

In some embodiments, the compound of Formula I may have the formula of any one of the compounds of Example 1-Example 268.

In some embodiments, the compound of Formula I may have the formula of any one of the compounds of Examples 4, 9, 10, 24, 47, 51, 64, 72, 73, 87, 105, 109, 115, 128, 129, 130, 131, 132, 134, 137, 156, 157, 160, 165, 167, 174, 194, 195, 207, 213, 219, 226, 256 and 263.

In another aspect it is provided a compound having Formula II:

(II)

a prodrug thereof, a pharmaceutically acceptable salt thereof, or a pharmaceutically active metabolite thereof; wherein R$_1$ may be independently —C(O)OR$_4$, —C(O)NHOH, —C(O)NHNH$_2$, CF$_3$, CHO, CN; wherein R$_4$ may be independently C$_1$-C$_8$ alkyl;
R$_3$ may be independently C$_5$-C$_{18}$ alkyl, C$_3$-C$_8$ cycloalkyl, C$_{6-12}$ fused heterocycloakyl, or aryl.

In some embodiments R$_1$ may be oxadiazole, oxazole, thiazole, pyrazole or imidazole; and R$_3$ may be C$_1$-C$_8$ alkyl or C$_3$-C$_8$ cycloalkyl.

In another embodiment R$_1$ may be oxadiazole; and R$_3$ may be C$_1$-C$_8$ alkyl or C$_3$-C$_8$ cycloalkyl.

In some embodiments, the compound of Formula II may have the formula of any one of the compounds of Examples 1-34.

In some embodiments, the compound of Formula II may have the formula of any one of the compounds of Examples 1-5, 8-12, 14-18, 26, 27, 30-32, and 34.

In another embodiments, the compound of Formula II may have the formula of any one of the compounds of Examples 4, 9, 10 and 24.

In another aspect the disclosure, provides a compound of Formula III:

(III)

a prodrug thereof, a pharmaceutically acceptable salt thereof, or a pharmaceutically active metabolite thereof; wherein W may be NH, N(CH$_3$), or none, wherein when W may be none R$_3$ may be directly attached to C(O) by a single bond;

A may be O, S, or NH;
B may be CH or N;
C may be CH or N;
D may be CH or N;
R$_2$ may be independently hydrogen, halogen, alkyl, alkoxy, thioalkyl, or haloalkoxy; wherein
R$_2$ may be linked via any position on the phenyl ring;
R$_3$ may be independently C$_5$-C$_{20}$ alkyl, C$_3$-C$_8$ cycloalkyl, C$_4$-C$_8$ heterocycloalkyl, C$_{6-12}$ fused heterocycloakyl, C$_{6-12}$ spirocycloalkyl, aryl, wherein R$_3$ may be unsubstituted or substituted at a carbon ring member with halogen or alkyl group.

In one embodiment, R$_2$ may be H, OH, OCH$_3$, SCH$_3$, F, OCF$_3$, CN or N(CH$_3$)$_2$.

In another embodiment it is provided a compound of Formula III: wherein
A may be O;
B may be CH;
C may be N;
D may be N;
R$_2$ may be halogen, hydroxy, C$_1$-C$_4$ alkoxy, cyano, or fluoroalkyl; and
R$_3$ may be C$_1$-C$_8$ alkyl or C$_3$-C$_8$ cycloalkyl.

In yet another embodiment it is provided a compound of Formula III, wherein A may be S;
B may be CH;
C may be N;
D may be N;
R$_2$ may be halogen, hydroxy, C$_1$-C$_4$ alkoxy, cyano, or fluoroalkyl; and
R$_3$ may be C$_1$-C$_8$ alkyl or C$_3$-C$_8$ cycloalkyl.

In a further embodiment it is provided a compound of Formula III, wherein
A may be O;
B may be CH;
C may be CH;
D may be N;
R$_2$ may be halogen, hydroxy, C$_1$-C$_4$ alkoxy, cyano, or fluoroalkyl; and
R$_3$ may be C$_1$-C$_8$ alkyl or C$_3$-C$_8$ cycloalkyl.

In a further embodiment it is provided a compound of Formula III, wherein
A may be O;
B may be CH;
C may be N;
D may be CH;
R$_2$ may be halogen, hydroxy, C$_1$-C$_4$ alkoxy, cyano, or fluoroalkyl; and
R$_3$ may be C$_1$-C$_8$ alkyl or and C$_3$-C$_8$ cycloalkyl.

In some embodiments, the compound of Formula III may have the formula of any one of the compounds of Examples 35-255.

In other embodiments, the compound of Formula III may have the formula of any one of the compounds of Examples 35, 40, 41, 47, 48, 50-53, 59, 60, 62-65, 72-74, 78, 80, 81, 83, 85-88, 105-110, 115-117, 119-121, 127, 128, 130-139, 147, 149, 156, 157, 159-161, 163-167, 169, 174, 179, 180, 186, 192-195, 204-208, 212-214, 218, 219, 220, 222, 229, 226, 232, and 238.

Furthermore, in some embodiments, the compound of Formula III may have the formula of any one of the compounds of Examples 47, 51, 64, 72, 73, 87, 105, 109, 115, 128, 129, 130-134, 137,156, 157, 160, 165, 167, 174, 194, 195, 207, 213, 219, and 226.

In another aspect the disclosure, provides a compound of Formula IV:

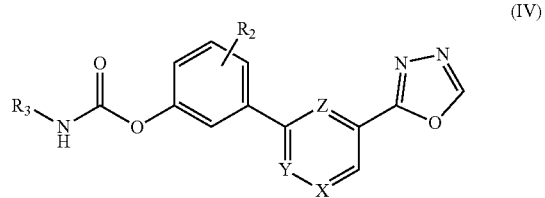

(IV)

a prodrug thereof, a pharmaceutically acceptable salt thereof, or a pharmaceutically active metabolite thereof; wherein
X may be CH or N;
Y may be CH or N;
Z may be CH or N;
wherein X, Y and Z cannot all be CH or N;
R$_2$ may be H, OH, or OCH$_3$;
R$_3$ may be independently C$_5$-C$_{20}$ alkyl, or C$_3$-C$_8$ cycloalkyl; wherein R$_3$ may be unsubstituted or substituted at a carbon ring member with halogen or alkyl group.

In a further embodiment it is provided a compound of Formula IV, wherein
X may be N;
Y may be CH;
Z may be CH;
R$_2$ may be halogen, hydroxy, C$_1$-C$_4$ alkoxy, cyano, or fluoroalkyl; and
R$_3$ may be C$_1$-C$_8$ alkyl or C$_3$-C$_8$ cycloalkyl.

In another embodiment it is provided a compound of Formula IV, wherein
X may be N;
Y may be CH;
Z may be CH;
R$_2$ may be hydroxy or C$_1$-C$_4$ alkoxy; and
R$_3$ may be C$_1$-C$_8$ alkyl or C$_3$-C$_8$ cycloalkyl.

In a further embodiment it is provided a compound of Formula IV, wherein
X may be N;
Y may be CH;
Z may be CH;
R$_2$ may be C$_1$-C$_4$ alkoxy; and
R$_3$ may be C$_1$-C$_8$ alkyl or C$_3$-C$_8$ cycloalkyl.

In other embodiments, the compound of Formula IV may have the formula of any one of the compounds of Examples 256-268.

In yet other embodiments, the compound of Formula IV may have the formula of any one of the compounds of Examples 256, 257, 262-264, and 266-268.

In a further embodiments, the compound of Formula III may have the formula of any one of the compounds of Examples 256 or 263.

In the compound of Formula I, II, III or IV, X, Y and Z cannot all be CH or N. For example, X and Y may be N and Z may be CH; X and Y may be CH and Z may be N; X and Z may be N and Y may be CH; X and Z may be CH and Y may be N; Y and Z may be N and X may be CH; Y and Z may be CH and X may be N.

The disclosure further provided pharmaceutical composition comprising at least one compound as described herewith. Accordingly, the pharmaceutical composition may comprise one or more than one compound of Formula I, II, III, IV, or a combination thereof a compound. The pharmaceutical composition may further comprise one or more pharmaceutically acceptable excipients or adjuvants.

The pharmaceutical composition may comprise an effective amount of at least one compound as described herewith, wherein the effective amount may be between about 0.0001 to about 1,000 mg. The pharmaceutical composition may further comprise one or more additional therapeutic agent. The one or more additional therapeutic agent may be selected from the group consisting of non-steroidal anti-inflammatory drugs (NSAIDs), anti-anxiety agents, antidepressants, antiepileptic drugs, anti-Alzheimer's agents, antipsychotic drugs, antihemorrhagic agents, benzodiazepines, acetylcholinesterase inhibitors, alpha-adrenoreceptor antagonists, alpha-adrenergic receptor agonists, β-blockers, angiotensin-converting enzymes inhibitors (ACEI), serotonin (5-HT) reuptake inhibitors, serotonin and noradrenaline reuptake inhibitors (SNRIs), antirheumatic drug, and anticancer medications. Compounds having formula I, II, III, or IV as described herewith or the pharmaceutical composition comprising a compound having formula I, II, III, or IV as described herewith may be used in inhibiting or modulating the activity of fatty acid amide hydrolase (FAAH). Furthermore, compounds having formula I, II, III, or IV as described herewith or the pharmaceutical composition comprising a compound having formula I, II, III, or IV as described herewith may be used to in treating a disease, disorder or condition which benefits from the inhibition or modulation of fatty acid amide hydrolase (FAAH) activity.

The disease, disorder or condition may be selected from the group consisting of pain, inflammation, anxiety, mood disorders, metabolic diseases, cardiovascular diseases, autoimmune diseases, central nervous system (CNS) diseases, liver diseases, respiratory diseases, and kidney diseases.

In a further aspect a method of treating a disease, disorder or condition which benefits from the inhibition or modulation of fatty acid amide hydrolase (FAAH) activity by administering to a subject in need thereof a compounds having formula I, II, III, or IV as described herewith or the pharmaceutical composition comprising a compound having formula I, II, III, or IV as described are provided.

The disease, disorder or condition may be selected from the group consisting of pain (including but not limited to acute pain, chronic pain, nociceptive pain, and non-nociceptive pain), inflammatory diseases (including but not limited to inflammatory bowel disease, neuroinflammation, neuropathy), anxiety and mood disorder, sleep disorder, eating disorders, obesity, cardiovascular diseases (including but not limited to hypertension, coronary heart disease, ischemia, congestive heart failure, atherosclerosis, myocardial infarction, and peripheral vascular disease), dyslipidemia (including but not limited to hyperlipidemia, hypoalphalipoproteinemia, hypertriglyceridemia, hypercholesterolemia, and low high-density lipoprotein (HDL)), diabetes (type 1 and type 2), allergic airway disease (including but not limited to cough, asthma, and chronic obstructive diseases), cerebrovascular disorders (including stroke, cerebral vasospasm, and learning and memory disorders), drug or alcohol withdrawal, addiction, liver diseases (including but not limited to non-alcoholic fatty liver disease (NAFLD), non-alcoholic steatohepatitis (NASH), and hepatitis), cancer, chemotherapy-induced nausea and vomiting (CINV), neurodegenerative disease (including but not limited to Alzheimer and Parkinson diseases), central nervous system (CNS) disorders (including but not limited to depression, post-traumatic stress disorder, schizophrenia, seizures, and cognitive disorders), autoimmune diseases (including but not limited to psoriasis, rheumatoid arthritis, Crohn's disease, systemic lupus erythematosis, Sjogren's syndrome, Huntington's chorea, and multiple sclerosis), skin disorders (including but not limited to itching, eczema, pruritis, dermatitis, impaired wound healing), gastrointestinal disorders (including but not limited to nausea, gastrointestinal motility disorder, and paralytic ileus), eye diseases (including but not limited to cataract, and glaucoma).

This summary of the disclosure does not necessarily describe all features of the invention.

DETAILED DESCRIPTION

Figure 1:
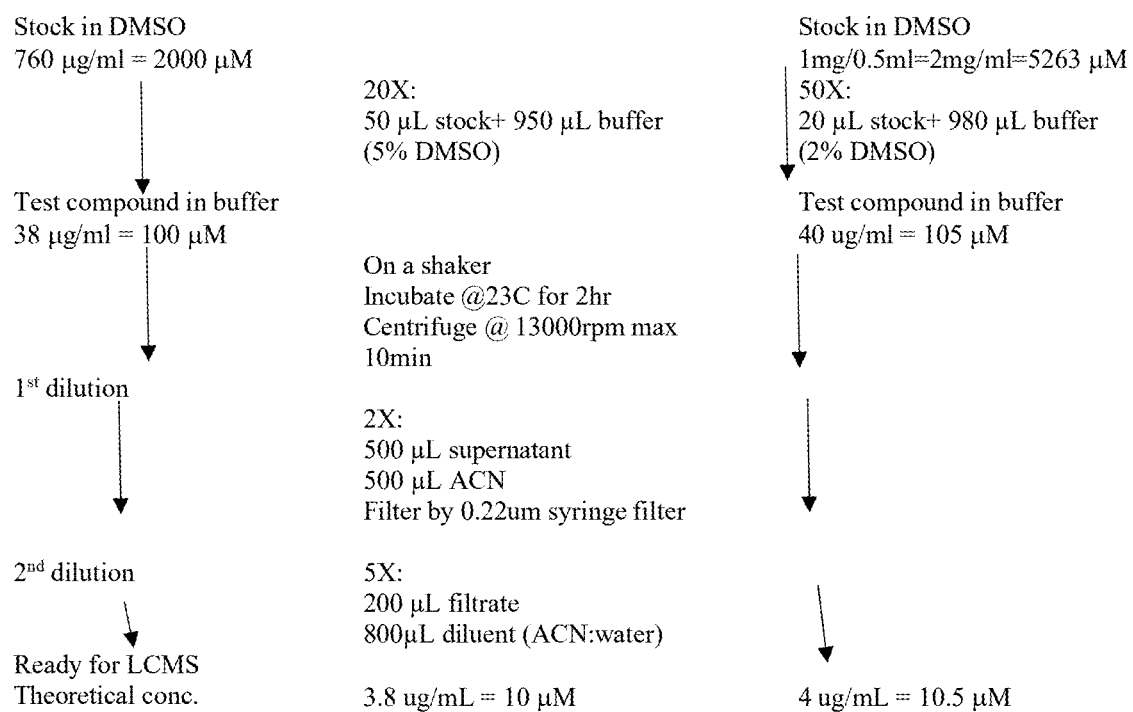
FIG. 1 depicts the protocol for sample preparation in solubility experiments.
Figure 2:
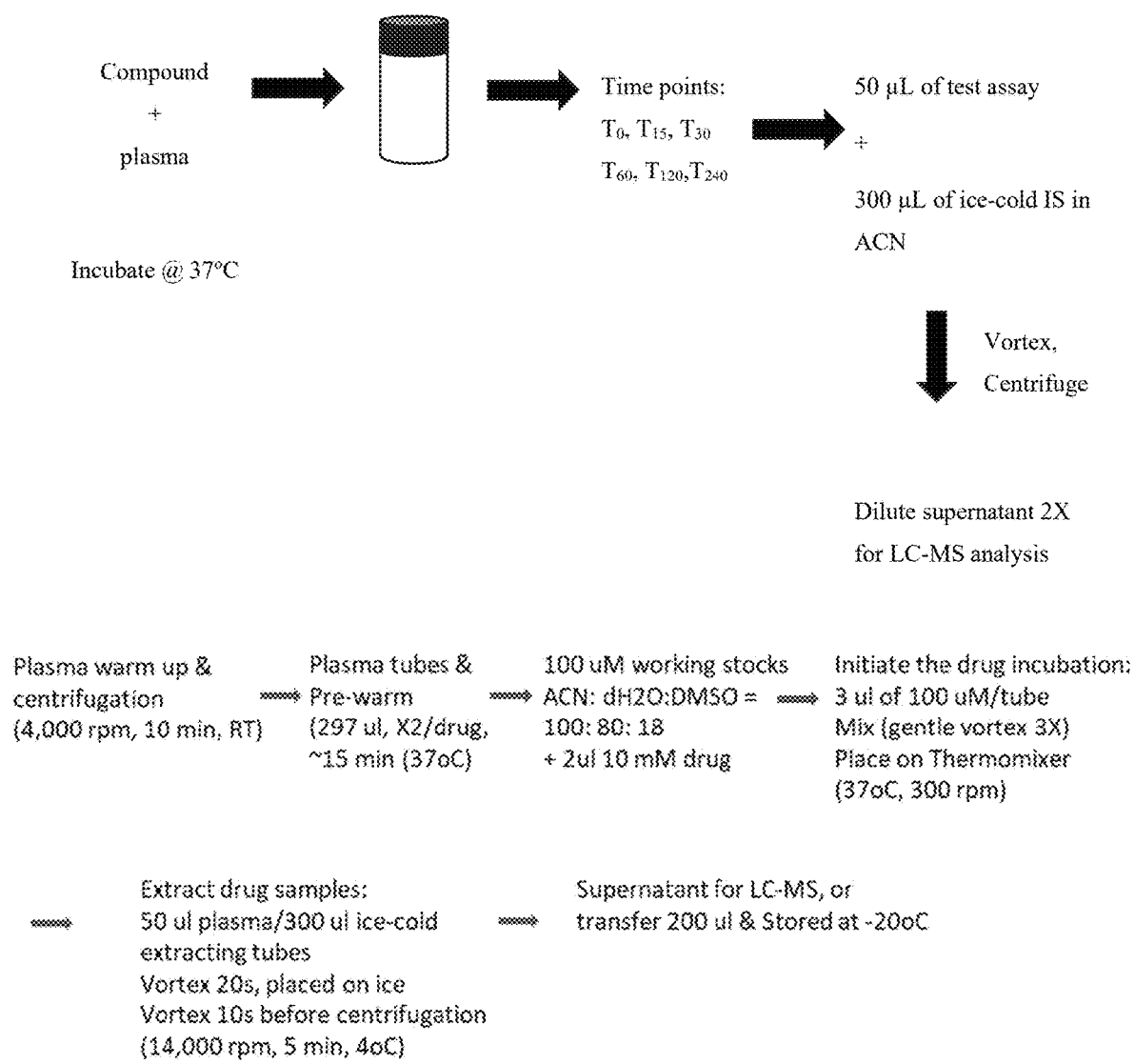
FIG. 2 depicts the protocol for plasma stability experiments.

Features of the invention will become more apparent from the following description which includes a description of example embodiments of the invention.

The present disclosure provided fatty acid amide hydrolase (FAAH) modulators, inhibitors, or FAAH modulators and inhibitors. The FAAH modulators, inhibitors, or FAAH modulators and inhibitors may contain a basic amine charge center. Without wishing to be bound by theory, it is believed that the basic amine charge center bestows beneficial pharmacological and chemical properties to the FAAH modulators, inhibitors, or FAAH modulators and inhibitors described herewith.

The FAAH modulators, inhibitors, or FAAH modulators and inhibitors disclosed herewith have improved characteristic, such as improved FAAH inhibitor activity, increased solubility, increased plasma stability, increased oral bioavailability or a combination thereof when compared to known reference compounds such as for example URB597 or JNJ-42165279. Furthermore the FAAH modulators, inhibitors, or FAAH modulators and inhibitors disclosed herewith may exhibit less cross reactivity to other enzymes of the endocannabinoid system such for example monoacylglycerol lipase (MAGL).

The FAAH modulators, inhibitors, or FAAH modulators and inhibitors may be compounds having Formula I, II, III or IV (also referred to as Formula I-IV). Furthermore, the FAAH modulators, inhibitors, or modulators and inhibitors may also be pharmaceutical derivatives of the compounds of Formula I, II, III or IV.

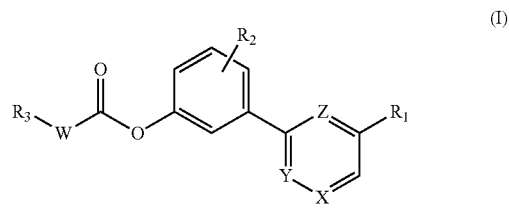

(I)

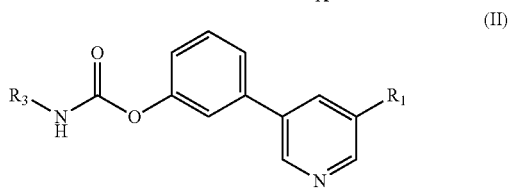

(II)

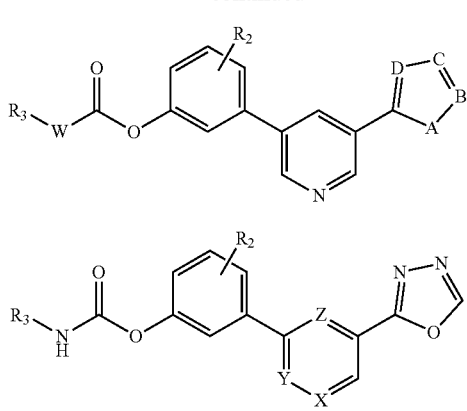

In an embodiment the FAAH modulators, inhibitors, or FAAH modulators and inhibitors may be compounds having Formula (I) with a basic charge site. In another embodiment the FAAH modulators, inhibitors, or FAAH modulators and inhibitors may be compounds having Formula (II) with a basic nitrogen center comprising for example a pyridine ring. Without wishing to be bound by theory, it was found that the compounds comprising a basic charge site or a basic nitrogen center, as described herewith, have greater solubility compared to compounds that lack a basic nitrogen center or a basic charge site. It was further found that the compounds comprising a basic charge site or a basic nitrogen center, as described herewith may have greater metabolic stability, greater oral bioavailability, or greater metabolic stability and greater oral bioavailability, compared to compounds that lack a basic nitrogen center or a basic charge site. In addition it was found that the compounds exhibit greater ability to penetrate into the central nervous system and/or brain.

Accordingly, the current disclosure also provides compounds having Formula (I) with a basic charge site and/or compounds having Formula (II) with a basic nitrogen center, wherein the compounds have greater solubility, greater metabolic stability, greater oral bioavailability, greater penetration into the central nervous system, greater penetration into the brain or a combination thereof compared to compound that lack a basic nitrogen center or a basic charge site.

Accordingly, the present disclosure is directed to novel compounds of Formula (I-IV) described herein, pharmaceutical derivatives thereof, or a combination thereof. The compounds of Formula (I-IV) according to the present disclosure have intrinsic FAAH inhibitory properties and improved characteristics as described herewith and are therefore useful in the treatment of diseases or medical conditions which benefit from the inhibition of FAAH activity.

The present disclosure relates to compounds of Formula (I) wherein compound has the following formula:

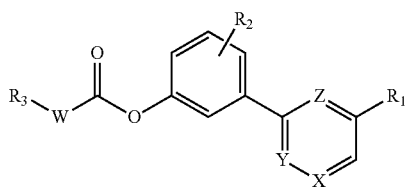

a prodrug thereof, a pharmaceutically acceptable salt thereof, or a pharmaceutically active metabolite thereof; wherein W represents NH, N(CH$_3$), or none. When W is none R$_3$ is directly attached to C(O) by a single bond;

X represents CH or N;

Y represents CH or N;

Z represents CH or N;

X, Y and Z cannot all be CH or N;

R$_1$ can independently be —C(O)OR$_4$, —C(O)NHOH, —C(O)NHNH$_2$, CF$_3$, CHO, CN or heteroaryl;

heteroaryl rings include, but are not limited to the following monocycles: 2-pyrrolyl, 2-furanyl, 2-thienyl, 2-oxazolyl, 5-isoxazolyl, 2-thiazolyl, 1,3,4-oxadiazolyl, 1,2,4-oxadiazolyl, 1,3,4-thiadiazolyl, 1,2,4-triazolyl, 1,2,3,4-tetrazolyl; R$_4$ can independently be C$_1$-C$_8$ alkyl;

R$_2$ can independently be hydrogen, halogen, alkyl, alkoxy, thioalkyl, haloalkoxy. The R$_2$ groups can be linked via any position on the phenyl ring. Examples of R$_2$ include H, OH, OCH$_3$, SCH$_3$, F, OCF$_3$, CN, N(CH$_3$)$_2$; R$_3$ can independently be C$_5$-C$_{20}$ alkyl, C$_3$-C$_8$ cycloalkyl, C$_4$-C$_8$ heterocycloalkyl, C$_{6-12}$ fused heterocycloalkyl, C$_{6-12}$ spirocycloalkyl, or aryl. R$_3$ may be unsubstituted or substituted at a carbon ring member with halogen or alkyl group.

In one embodiment R$_2$ may independently be OH, OCH$_3$, SCH$_3$, or N(CH$_3$)$_2$.

In another embodiment the compound may have Formula (I), wherein

W represents NH;

X represents N;

Y represents CH;

Z represents CH;

R$_1$ may be oxadiazole, oxazole, thiazole, pyrazole or imidazole;

R$_2$ may be halogen, hydroxy, C$_1$-C$_4$ alkoxy, cyano, or fluoroalkyl; and

R$_3$ may be C$_1$-C$_8$ alkyl or C$_3$-C$_8$ cycloalkyl.

In another embodiment the compound may have Formula (I), wherein

W represents NH;

X represents N;

Y represents CH;

Z represents CH;

R$_1$ may be oxadiazole;

R$_2$ may be halogen, hydroxy, C$_1$-C$_4$ alkoxy, cyano, or fluoroalkyl; and

R$_3$ may be C$_1$-C$_8$ alkyl or C$_3$-C$_8$ cycloalkyl.

In one embodiment the compound may have the formula of any one of the compounds of Example 1-Example 268. In an embodiment the FAAH modulators, inhibitors, or FAAH modulators and inhibitors may comprise any one of the compounds of Example 1-Example 268 or combinations thereof. In a preferred embodiment the compound may have the formula of any one of the compounds of Examples 4, 9, 10, 24, 47, 51, 64, 72, 73, 87, 105, 109, 115, 128, 130, 131, 132, 134, 137, 156, 157, 160, 165, 167, 174, 194, 195, 207, 213, 219, 226, 256 and 263.

The FAAH modulators, inhibitors, or FAAH modulators and inhibitors disclosed herewith may exhibit improved stability in human plasma (also refered to as improved plasma stability), improved aqueous solubility, or a combination thereof. For example, the compounds of Examples 83, 146, 158, 172, 194, 225, and 231 showed improved plasma stability, improved aqueous solubility, or improved plasma stability and aqueous solubility compared to reference compound URB597 (see Table 5). Accordingly, it is also provided compounds of Formula (I), (II), (III) or (IV) which exhibit improved plasma stability, improved aqueous solubility, or improved plasma stability and aqueous solubility. For example, in one embodiment the compounds may be compounds of Examples 83, 146, 158, 172, 194, 191, 225, and 231 which exhibit improved plasma stability, improved aqueous solubility, or improved plasma stability and aqueous solubility.

The FAAH modulators, inhibitors, or FAAH modulators and inhibitors disclosed herewith may exhibit improved bioavailability. For example compounds of Example 158 and Example 172 exhibit>50% oral bioavailability in rat (see Examples 272 and 273). Accordingly, it is also provided compounds of Formula (I), (II), (III) or (IV) which exhibit improved bioavailability.

For example, in one embodiment the compounds may be compounds of Examples 158 or Example 172.

The FAAH modulators, inhibitors, or FAAH modulators and inhibitors disclosed herewith may exhibit improved brain penetration compared to the reference compounds. For example the compound of Example 172 exhibits an improved brain penetration (Brain/Plasma ratio>0.15) (see Example 273). Accordingly, it is also provided compounds of Formula (I), (II), (III) or (IV) which exhibit improved brain penetration. For example, in one embodiment the compounds may be a compound of Example 172.

Another embodiment provides a compound of Formula (II)

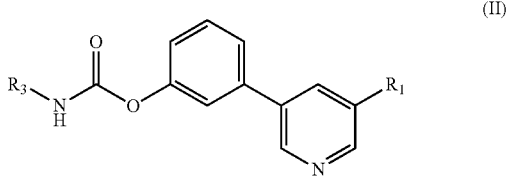

(II)

a prodrug thereof, a pharmaceutically acceptable salt thereof, or a pharmaceutically active metabolite thereof; wherein $R_1$ can independently be —C(O)OR$_4$, —C(O)NHOH, —C(O)NHNH$_2$, CF$_3$, CHO, CN; R$_4$ can independently be $C_1$-$C_8$ alkyl;

$R_3$ can independently be $C_5$-$C_{18}$ alkyl, $C_3$-$C_8$ cycloalkyl, $C_{6-12}$ fused heterocycloakyl, or aryl.

In another embodiment the compound may have Formula (II), wherein $R_1$ may be oxadiazole, oxazole, thiazole, pyrazole or imidazole; and $R_3$ may be $C_1$-$C_8$ alkyl or $C_3$-$C_8$ cycloalkyl.

In another embodiment the compound may have Formula (II), wherein $R_1$ may be oxadiazole; and $R_3$ may be $C_1$-$C_8$ alkyl or $C_3$-$C_8$ cycloalkyl.

Examples of certain useful compounds of Formula II include:

Example 1: ethyl 5-(3-((pentylcarbamoyl)oxy)phenyl) nicotinate

Example 2: ethyl 5-(3-((heptylcarbamoyl)oxy)phenyl) nicotinate

Example 3: ethyl 5-(3-((octylcarbamoyl)oxy)phenyl) nicotinate

Example 4: ethyl 5-(3-((tetradecylcarbamoyl)oxy)phenyl) nicotinate

Example 5: ethyl 5-(3-((cyclopentylcarbamoyl)oxy)phenyl)nicotinate

Example 6: ethyl 5-(3-((cyclohexylcarbamoyl)oxy)phenyl)nicotinate

Example 7: ethyl 5-(3-(((4-fluorophenyl)carbamoyl)oxy) phenyl)nicotinate

Example 8: methyl 5-(3-((pentylcarbamoyl)oxy)phenyl) nicotinate

Example 9: methyl 5-(3-((heptylcarbamoyl)oxy)phenyl) nicotinate

Example 10: methyl 5-(3-((octylcarbamoyl)oxy)phenyl) nicotinate

Example 11: methyl 5-(3-((cyclopentylcarbamoyl)oxy) phenyl)nicotinate

Example 12: methyl 5-(3-((cyclohexylcarbamoyl)oxy) phenyl)nicotinate

Example 13: methyl 5-(3-((((1s,3s)-adamantan-1-yl)carbamoyl)oxy)phenyl)nicotinate Example 14: 3-(5-formylpyridin-3-yl)phenyl pentylcarbamate Example 15: 3-(5-formylpyridin-3-yl)phenyl heptylcarbamate Example 16: 3-(5-formylpyridin-3-yl)phenyl octylcarbamate Example 17: 3-(5-formylpyridin-3-yl)phenyl (cyclohexylmethyl)carbamate Example 18: 3-(5-formylpyridin-3-yl)phenyl cyclopentylcarbamate Example 19: 3-(5-formylpyridin-3-yl)phenyl cyclohexylcarbamate Example 20: 3-(5-formylpyridin-3-yl)phenyl cyclohepylcarbamate Example 21: 3-(5-formylpyridin-3-yl)phenyl ((1s,3s)-adamantan-1-yl)carbamate Example 22: 3-(5-(hydroxycarbamoyl)pyridin-3-yl)phenyl heptylcarbamate Example 23: 3-(5-(hydroxycarbamoyl)pyridin-3-yl)phenyl octylcarbamate Example 24: 3-(5-(hydroxycarbamoyl)pyridin-3-yl)phenyl tetradecylcarbamate Example 25: 3-(5-(hydrazinecarbonyl)pyridin-3-yl)phenyl octylcarbamate Example 26: 3-(5-cyanopyridin-3-yl)phenyl heptylcarbamate Example 27: 3-(5-cyanopyridin-3-yl)phenyl octylcarbamate Example 28: 3-(5-cyanopyridin-3-yl)phenyl cyclohexylcarbamate Example 29: 3-(5-cyanopyridin-3-yl)phenyl cyclohptylcarbamate Example 30: 3-(5-(trifluoromethyl)pyridin-3-yl)phenyl octylcarbamate Example 31: 3-(5-(trifluoromethyl)pyridin-3-yl)phenyl (cyclohexylmethyl)carbamate Example 32: 3-(5-(trifluoromethyl)pyridin-3-yl)phenyl cyclopentylcarbamate Example 33: 3-(5-(trifluoromethyl)pyridin-3-yl)phenyl cyclohexylcarbamate Example 34: 3-(5-(trifluoromethyl)pyridin-3-yl)phenyl cycloheptylcarbamate Accordingly, in one embodiment the FAAH modulator, inhibitor, or FAAH inhibitor and modulators may be any one of the compounds of Examples 1-34. In a preferred embodiment the FAAH modulator, inhibitor, or FAAH modulator and inhibitor may be any one of the compound of Examples 1, 2, 3, 4, 5, 8-12, 14, 15, 16, 17, 18, 26, 27, 30-32, or 34. In another embodiment, the FAAH modulator, inhibitor, or FAAH modulator and inhibitor may be any one of the compound of Examples 14, or 15. Furthermore, in another embodiment, the FAAH modulator, inhibitor, or FAAH modulator and inhibitor may be any one of the compounds of Examples 4, 9, 10, or 24.

Another embodiment provides a compound of Formula (III)

(III)

a prodrug thereof, a pharmaceutically acceptable salt thereof, or a pharmaceutically active metabolite thereof; wherein W is NH, N(CH$_3$), or none, wherein when W is none R$_3$ is directly attached to C(O) by a single bond;

A represents 0, S, or NH;

B represents CH or N;

C represents CH or N;

D represents CH or N;

R$_2$ can independently be hydrogen, halogen, alkyl, alkoxy, thioalkyl, or haloalkoxy. The R$_2$ groups can be linked via any position on the phenyl ring. Examples of R$_2$ include H, OH, OCH$_3$, SCH$_3$, F, OCF$_3$, CN, N(CH$_3$)$_2$;

R$_3$ can independently be C$_5$-C$_{20}$ alkyl, C$_3$-C$_8$ cycloalkyl, C$_4$-C$_8$ heterocycloalkyl, C$_{6-12}$ fused heterocycloakyl, C$_{6-12}$ spirocycloalkyl, aryl. R$_3$ may be unsubstituted or substituted at a carbon ring member with halogen or alkyl group.

In another embodiment the compound may have Formula (III), wherein

A may be O;
B may be CH;
C may be N;
D may be N;
R$_2$ may be halogen, hydroxy, C$_1$-C$_4$ alkoxy, cyano, or fluoroalkyl; and
R$_3$ may be C$_1$-C$_8$ alkyl or C$_3$-C$_8$ cycloalkyl.

In another embodiment the compound may have Formula (III), wherein

A may be S;
B may be CH;
C may be N;
D may be N;
R$_2$ may be halogen, hydroxy, C$_1$-C$_4$ alkoxy, cyano, or fluoroalkyl; and
R$_3$ may be C$_1$-C$_8$ alkyl or C$_3$-C$_8$ cycloalkyl.

In another embodiment the compound may have Formula (III), wherein

A may be O;
B may be CH;
C may be CH;
D may be N;
R$_2$ may be halogen, hydroxy, C$_1$-C$_4$ alkoxy, cyano, or fluoroalkyl; and
R$_3$ may be C$_1$-C$_8$ alkyl or C$_3$-C$_8$ cycloalkyl.

In another embodiment the compound may have Formula (III), wherein

A may be O;
B may be CH;
C may be N;
D may be CH;
R$_2$ may be halogen, hydroxy, C$_1$-C$_4$ alkoxy, cyano, or fluoroalkyl; and
R$_3$ may be C$_1$-C$_8$ alkyl or and C$_3$-C$_8$ cycloalkyl.

Examples of certain useful compounds of Formula III include:

Example 35: 3-(5-(1H-pyrrol-2-yl)pyridin-3-yl)phenyl octylcarbamate

Example 36: 3-(5-(1H-pyrrol-2-yl)pyridin-3-yl)phenyl (cyclohexylmethyl)carbamate Example 37: 3-(5-(1H-pyrrol-2-yl)pyridin-3-yl)phenyl benzylcarbamate Example 38: 3-(5-(1H-pyrrol-2-yl)pyridin-3-yl)phenyl cyclopentylcarbamate Example 39: 3-(5-(1H-pyrrol-2-yl)pyridin-3-yl)phenyl cyclohexylcarbamate Example 40: 3-(5-(1H-pyrrol-2-yl)pyridin-3-yl)phenyl cycloheptylcarbamate Example 41: 3-(5-(1H-pyrrol-2-yl)pyridin-3-yl)-4-methoxyphenyl octylcarbamate Example 42: 3-(5-(1H-pyrrol-2-yl)pyridin-3-yl)-4-methoxyphenyl (cyclohexylmethyl)carbamate Example 43: 3-(5-(1H-pyrrol-2-yl)pyridin-3-yl)-4-methoxyphenyl benzylcarbamate Example 44: 3-(5-(1H-pyrrol-2-yl)pyridin-3-yl)-4-methoxyphenyl cyclopentylcarbamate Example 45: 3-(5-(1H-pyrrol-2-yl)pyridin-3-yl)-4-methoxyphenyl cyclohexylcarbamate Example 46: 3-(5-(1H-pyrrol-2-yl)pyridin-3-yl)-4-methoxyphenyl cycloheptylcarbamate Example 47: 3-(5-(furan-2-yl)pyridin-3-yl)phenyl octylcarbamate Example 48: 3-(5-(furan-2-yl)pyridin-3-yl)phenyl (cyclohexylmethyl)carbamate Example 49: 3-(5-(furan-2-yl)pyridin-3-yl)phenyl benzylcarbamate Example 50: 3-(5-(furan-2-yl)pyridin-3-yl)phenyl cyclopentylcarbamate Example 51: 3-(5-(furan-2-yl)pyridin-3-yl)phenyl cyclohexylcarbamate Example 52: 3-(5-(furan-2-yl)pyridin-3-yl)phenyl cycloheptylcarbamate Example 53: 3-(5-(furan-2-yl)pyridin-3-yl)-4-methoxyphenyl octylcarbamatess Example 54: 3-(5-(furan-2-yl)pyridin-3-yl)-4-methoxyphenyl (cyclohexylmethyl)carbamate Example 55: 3-(5-(furan-2-yl)pyridin-3-yl)-4-methoxyphenyl benzylcarbamate Example 56: 3-(5-(furan-2-yl)pyridin-3-yl)-4-methoxyphenyl cyclopentylcarbamate Example 57: 3-(5-(furan-2-yl)pyridin-3-yl)-4-methoxyphenyl cyclohexylcarbamate Example 58: 3-(5-(furan-2-yl)pyridin-3-yl)-4-methoxyphenyl cycloheptylcarbamate Example 59: 3-(5-(thiophen-2-yl)pyridin-3-yl)phenyl octylcarbamate Example 60: 3-(5-(thiophen-2-yl)pyridin-3-yl)phenyl (cyclohexylmethyl)carbamate Example 61: 3-(5-(thiophen-2-yl)pyridin-3-yl)phenyl benzylcarbamate Example 62: 3-(5-(thiophen-2-yl)pyridin-3-yl)phenyl cyclopentylcarbamate Example 63: 3-(5-(thiophen-2-yl)pyridin-3-yl)phenyl cyclohexylcarbamate Example 64: 3-(5-(thiophen-2-yl)pyridin-3-yl)phenyl cycloheptylcarbamate
Example 65: 4-methoxy-3-(5-(thiophen-2-yl)pyridin-3-yl)phenyl octylcarbamate
Example 66: 4-methoxy-3-(5-(thiophen-2-yl)pyridin-3-yl)phenyl (cyclohexylmethyl)carbamate
Example 67: 4-methoxy-3-(5-(thiophen-2-yl)pyridin-3-yl)phenyl benzylcarbamate
Example 68: 4-methoxy-3-(5-(thiophen-2-yl)pyridin-3-yl)phenyl cyclopentylcarbamate
Example 69: 4-methoxy-3-(5-(thiophen-2-yl)pyridin-3-yl)phenyl cyclohexylcarbamate
Example 70: 4-methoxy-3-(5-(thiophen-2-yl)pyridin-3-yl)phenyl cycloheptylcarbamate
Example 71: 3-(5-(oxazol-2-yl)pyridin-3-yl)phenyl pentylcarbamate
Example 72: 3-(5-(oxazol-2-yl)pyridin-3-yl)phenyl heptylcarbamate
Example 73: 3-(5-(oxazol-2-yl)pyridin-3-yl)phenyl octylcarbamate
Example 74: 3-(5-(oxazol-2-yl)pyridin-3-yl)phenyl (cyclohexylmethyl)carbamate
Example 75: 3-(5-(oxazol-2-yl)pyridin-3-yl)phenyl cyclopentylcarbamate
Example 76: 3-(5-(oxazol-2-yl)pyridin-3-yl)phenyl cyclohexylcarbamate
Example 77: 3-(5-(oxazol-2-yl)pyridin-3-yl)phenyl ((1s,3s)-adamantan-1-yl)carbamate
Example 78: 4-methoxy-3-(5-(oxazol-2-yl)pyridin-3-yl)phenyl octylcarbamate
Example 79: 4-methoxy-3-(5-(oxazol-2-yl)pyridin-3-yl)phenyl (cyclohexylmethyl)carbamate
Example 80: 4-methoxy-3-(5-(oxazol-2-yl)pyridin-3-yl)phenyl cyclopentylcarbamate
Example 81: 4-methoxy-3-(5-(oxazol-2-yl)pyridin-3-yl)phenyl cyclohexylcarbamate
Example 82: 4-methoxy-3-(5-(oxazol-2-yl)pyridin-3-yl)phenyl (4-methylcyclohexyl)carbamate
Example 83: 4-methoxy-3-(5-(oxazol-2-yl)pyridin-3-yl)phenyl cycloheptylcarbamate
Example 84: 2-methoxy-5-(5-(oxazol-2-yl)pyridin-3-yl)phenyl octylcarbamate
Example 85: 4-fluoro-3-(5-(oxazol-2-yl)pyridin-3-yl)phenyl cyclopentylcarbamate
Example 86: 4-fluoro-3-(5-(oxazol-2-yl)pyridin-3-yl)phenyl (4-methylcyclohexyl)carbamate
Example 87: 4-fluoro-3-(5-(oxazol-2-yl)pyridin-3-yl)phenyl cycloheptylcarbamate
Example 88: 3-(5-(oxazol-2-yl)pyridin-3-yl)-4-(trifluoromethoxy)phenyl octylcarbamate
Example 89: 3-(5-(oxazol-2-yl)pyridin-3-yl)-4-(trifluoromethoxy)phenyl cyclohexylcarbamate
Example 90: 3-(5-(oxazol-2-yl)pyridin-3-yl)-4-(trifluoromethoxy)phenyl(4-methylcyclohexyl)carbamate
Example 91: 3-(5-(oxazol-2-yl)pyridin-3-yl)-4-(trifluoromethoxy)phenyl cycloheptylcarbamate
Example 92: 2-methyl-5-(5-(oxazol-2-yl)pyridin-3-yl)phenyl octylcarbamate
Example 93: 2-methyl-5-(5-(oxazol-2-yl)pyridin-3-yl)phenyl (cyclohexylmethyl)carbamate
Example 94: 2-methyl-5-(5-(oxazol-2-yl)pyridin-3-yl)phenyl benzylcarbamate
Example 95: 2-methyl-5-(5-(oxazol-2-yl)pyridin-3-yl)phenyl cyclohexylcarbamate
Example 96: 3-methyl-5-(5-(oxazol-2-yl)pyridin-3-yl)phenyl (4-methylcyclohexyl)carbamate
Example 97: 2-methyl-5-(5-(oxazol-2-yl)pyridin-3-yl)phenyl cycloheptylcarbamate
Example 98: 2-methyl-5-(5-(oxazol-2-yl)pyridin-3-yl)phenyl cyclooctylcarbamate
Example 99: 3-methyl-5-(5-(oxazol-2-yl)pyridin-3-yl)phenyl (cyclohexylmethyl)carbamate
Example 100 3-methyl-5-(5-(oxazol-2-yl)pyridin-3-yl)phenyl benzylcarbamate
Example 101: 3-methyl-5-(5-(oxazol-2-yl)pyridin-3-yl)phenyl cyclohexylcarbamate
Example 102: 3-methyl-5-(5-(oxazol-2-yl)pyridin-3-yl)phenyl (4-methylcyclohexyl)carbamate
Example 103: 3-methyl-5-(5-(oxazol-2-yl)pyridin-3-yl)phenyl cycloheptylcarbamate
Example 104: 3-methyl-5-(5-(oxazol-2-yl)pyridin-3-yl)phenyl cyclooctylcarbamate
Example 105: 3-(5-(isoxazol-5-yl)pyridin-3-yl)phenyl octylcarbamate
Example 106: 3-(5-(isoxazol-5-yl)pyridin-3-yl)phenyl cyclopentylcarbamate
Example 107: 3-(5-(isoxazol-5-yl)pyridin-3-yl)phenyl cyclohexylcarbamate
Example 108: 3-(5-(isoxazol-5-yl)pyridin-3-yl)phenyl cycloheptylcarbamate
Example 109: 3-(5-(isoxazol-5-yl)pyridin-3-yl)-4-methoxyphenyl octylcarbamate
Example 110: 3-(5-(isoxazol-5-yl)pyridin-3-yl)-4-methoxyphenyl (cyclohexylmethyl)carbamate
Example 111: 3-(5-(isoxazol-5-yl)pyridin-3-yl)-4-methoxyphenyl benzylcarbamate
Example 112: 3-(5-(isoxazol-5-yl)pyridin-3-yl)-4-methoxyphenyl cyclopentylcarbamate
Example 113: 3-(5-(isoxazol-5-yl)pyridin-3-yl)-4-methoxyphenyl cyclohexylcarbamate
Example 114: 3-(5-(isoxazol-5-yl)pyridin-3-yl)-4-methoxyphenyl cycloheptylcarbamate
Example 115: 3-(5-(thiazol-2-yl)pyridin-3-yl)phenyl octylcarbamate
Example 116: 3-(5-(thiazol-2-yl)pyridin-3-yl)phenyl (cyclohexylmethyl)carbamate
Example 117: 3-(5-(thiazol-2-yl)pyridin-3-yl)phenyl benzylcarbamate
Example 118: 3-(5-(thiazol-2-yl)pyridin-3-yl)phenyl cyclopentylcarbamate
Example 119: 3-(5-(thiazol-2-yl)pyridin-3-yl)phenyl cyclohexylcarbamate
Example 120: 3-(5-(thiazol-2-yl)pyridin-3-yl)phenyl cycloheptylcarbamate
Example 121: 4-methoxy-3-(5-(thiazol-2-yl)pyridin-3-yl)phenyl octylcarbamate
Example 122: 4-methoxy-3-(5-(thiazol-2-yl)pyridin-3-yl)phenyl (cyclohexylmethyl)carbamate
Example 123: 4-methoxy-3-(5-(thiazol-2-yl)pyridin-3-yl)phenyl benzylcarbamate
Example 124: 4-methoxy-3-(5-(thiazol-2-yl)pyridin-3-yl)phenyl cyclopentylcarbamate
Example 125: 4-methoxy-3-(5-(thiazol-2-yl)pyridin-3-yl)phenyl cyclohexylcarbamate
Example 126: 4-methoxy-3-(5-(thiazol-2-yl)pyridin-3-yl)phenyl cycloheptylcarbamate
Example 127: 3-(5-(1,3,4-oxadiazol-2-yl)pyridin-3-yl)phenyl pentylcarbamate
Example 128: 3-(5-(1,3,4-oxadiazol-2-yl)pyridin-3-yl)phenyl hexylcarbamate
Example 129: 3-(5-(1,3,4-oxadiazol-2-yl)pyridin-3-yl)phenyl heptylcarbamate Example 130: 3-(5-(1,3,4-oxadiazol-2-yl)pyridin-3-yl)phenyl octylcarbamate
Example 131: 3-(5-(1,3,4-oxadiazol-2-yl)pyridin-3-yl)phenyl dodecylcarbamate
Example 132: 3-(5-(1,3,4-oxadiazol-2-yl)pyridin-3-yl)phenyl tetradecylcarbamate
Example 133: 3-(5-(1,3,4-oxadiazol-2-yl)pyridin-3-yl)phenyl octadecylcarbamate
Example 134: 3-(5-(1,3,4-oxadiazol-2-yl)pyridin-3-yl)phenyl (cyclohexylmethyl)carbamate
Example 135: 3-(5-(1,3,4-oxadiazol-2-yl)pyridin-3-yl)phenyl benzylcarbamate
Example 136: 3-(5-(1,3,4-oxadiazol-2-yl)pyridin-3-yl)phenyl (3-phenylpropyl)carbamate
Example 137: 3-(5-(1,3,4-oxadiazol-2-yl)pyridin-3-yl)phenyl (cyclohexylmethyl)carbamate
Example 138: 3-(5-(1,3,4-oxadiazol-2-yl)pyridin-3-yl)phenyl cyclopentylcarbamate
Example 139: 3-(5-(1,3,4-oxadiazol-2-yl)pyridin-3-yl)phenyl cyclohexylcarbamate
Example 140: 3-(5-(1,3,4-oxadiazol-2-yl)pyridin-3-yl)phenyl naphthalen-1-ylcarbamate
Example 141: 3-(5-(1,3,4-oxadiazol-2-yl)pyridin-3-yl)phenyl piperidine-1-carboxylate
Example 142: 3-(5-(1,3,4-oxadiazol-2-yl)pyridin-3-yl)phenyl cyclohexyl(methyl)carbamate
Example 143: 3-(5-(1,3,4-oxadiazol-2-yl)pyridin-3-yl)phenyl 2-methylpiperidine-1-carboxylate
Example 144: 3-(5-(1,3,4-oxadiazol-2-yl)pyridin-3-yl)phenyl cycloheptyl(methyl)carbamate
Example 145: 3-(5-(1,3,4-oxadiazol-2-yl)pyridin-3-yl)phenyl azocane-1-carboxylate
Example 146: 3-(5-(1,3,4-oxadiazol-2-yl)pyridin-3-yl)phenyl 2-azaspiro[3.3]heptane-2-carboxylate
Example 147: 3-(5-(1,3,4-oxadiazol-2-yl)pyridin-3-yl)phenyl spiro[3.3]heptan-2-ylcarbamate
Example 148: 3-(5-(1,3,4-oxadiazol-2-yl)pyridin-3-yl)phenyl 3-azabicyclo[3.1.0]hexane-3-carboxylate
Example 149: 3-(5-(1,3,4-oxadiazol-2-yl)pyridin-3-yl)phenyl hexahydrocyclopenta[c]pyrrole-2(1H)-carboxylate
Example 150: 3-(5-(1,3,4-oxadiazol-2-yl)pyridin-3-yl)phenyl 8-azabicyclo[3.2.1]octane-8-carboxylate
Example 151: 3-(5-(1,3,4-oxadiazol-2-yl)pyridin-3-yl)phenyl morpholine-4-carboxylate
Example 152: 3-(5-(1,3,4-oxadiazol-2-yl)pyridin-3-yl)phenyl 2-oxa-6-azaspiro[3.3]heptane-6-carboxylate
Example 153: 3-(5-(1,3,4-oxadiazol-2-yl)pyridin-3-yl)phenyl 2-oxa-7-azaspiro[3.5]nonane-7-carboxylate
Example 154: 3-(5-(1,3,4-oxadiazol-2-yl)pyridin-3-yl)phenyl heptyl(methyl)carbamate
Example 155: 3-(5-(1,3,4-oxadiazol-2-yl)pyridin-3-yl)phenyl dibutylcarbamate
Example 156: 3-(5-(1,3,4-oxadiazol-2-yl)pyridin-3-yl)-4-hydroxyphenyl heptylcarbamate
Example 157: 3-(5-(1,3,4-oxadiazol-2-yl)pyridin-3-yl)-4-hydroxyphenyl octylcarbamate
Example 158: 3-(5-(1,3,4-oxadiazol-2-yl)pyridin-3-yl)-4-hydroxyphenyl cyclohexylcarbamate
Example 159 3-(5-(1,3,4-oxadiazol-2-yl)pyridin-3-yl)-4-hydroxyphenyl (4-methylcyclohexyl)carbamate
Example 160: 3-(5-(1,3,4-oxadiazol-2-yl)pyridin-3-yl)-5-hydroxyphenyl heptylcarbamate
Example 161: 3-(5-(1,3,4-oxadiazol-2-yl)pyridin-3-yl)-5-hydroxyphenyl (cyclohexylmethyl)carbamate
Example 162: 3-(5-(1,3,4-oxadiazol-2-yl)pyridin-3-yl)-5-hydroxyphenyl benzylcarbamate
Example 163: 3-(5-(1,3,4-oxadiazol-2-yl)pyridin-3-yl)-5-hydroxyphenyl cyclopentylcarbamate
Example 164: 3-(5-(1,3,4-oxadiazol-2-yl)pyridin-3-yl)-5-hydroxyphenyl cyclohexylcarbamate
Example 165: 3-(5-(1,3,4-oxadiazol-2-yl)pyridin-3-yl)-5-hydroxyphenyl cycloheptylcarbamate
Example 166: 3-(5-(1,3,4-oxadiazol-2-yl)pyridin-3-yl)-4-methoxyphenyl heptylcarbamate
Example 167: 3-(5-(1,3,4-oxadiazol-2-yl)pyridin-3-yl)-4-methoxyphenyl octylcarbamate
Example 168: 3-(5-(1,3,4-oxadiazol-2-yl)pyridin-3-yl)-4-methoxyphenyl (cyclohexylmethyl)carbamate
Example 169: 3-(5-(1,3,4-oxadiazol-2-yl)pyridin-3-yl)-4-methoxyphenyl cyclopentylcarbamate
Example 170: 3-(5-(1,3,4-oxadiazol-2-yl)pyridin-3-yl)-4-methoxyphenyl cyclohexylcarbamate
Example 171: 3-(5-(1,3,4-oxadiazol-2-yl)pyridin-3-yl)-4-methoxyphenyl (4-methylcyclohexyl)carbamate
Example 172: 3-(5-(1,3,4-oxadiazol-2-yl)pyridin-3-yl)-4-methoxyphenyl cycloheptylcarbamate
Example 173: 3-(5-(1,3,4-oxadiazol-2-yl)pyridin-3-yl)-4-methoxyphenyl cyclooctylcarbamate
Example 174: 3-(5-(1,3,4-oxadiazol-2-yl)pyridin-3-yl)-5-methoxyphenyl octylcarbamate
Example 175: 3-(5-(1,3,4-oxadiazol-2-yl)pyridin-3-yl)-5-methoxyphenyl (cyclohexylmethyl)carbamate
Example 176: 3-(5-(1,3,4-oxadiazol-2-yl)pyridin-3-yl)-5-methoxyphenyl benzylcarbamate
Example 177: 3-(5-(1,3,4-oxadiazol-2-yl)pyridin-3-yl)-5-methoxyphenyl cyclopentylcarbamate
Example 178: 3-(5-(1,3,4-oxadiazol-2-yl)pyridin-3-yl)-5-methoxyphenyl cyclohexylcarbamate
Example 179: 3-(5-(1,3,4-oxadiazol-2-yl)pyridin-3-yl)-5-methoxyphenyl cycloheptylcarbamate
Example 180: 3-(5-(1,3,4-oxadiazol-2-yl)pyridin-3-yl)-4-(dimethylamino)phenyl octylcarbamate
Example 181: 3-(5-(1,3,4-oxadiazol-2-yl)pyridin-3-yl)-4-(dimethylamino)phenyl (cyclohexylmethyl)carbamate
Example 182: 3-(5-(1,3,4-oxadiazol-2-yl)pyridin-3-yl)-4-(dimethylamino)phenyl benzylcarbamate
Example 183: 3-(5-(1,3,4-oxadiazol-2-yl)pyridin-3-yl)-4-(dimethylamino)phenyl cyclopentylcarbamate
Example 184: 3-(5-(1,3,4-oxadiazol-2-yl)pyridin-3-yl)-4-(dimethylamino)phenyl cyclohexylcarbamate
Example 185: 3-(5-(1,3,4-oxadiazol-2-yl)pyridin-3-yl)-4-(dimethylamino)phenyl cycloheptylcarbamate
Example 186: 3-(5-(1,3,4-oxadiazol-2-yl)pyridin-3-yl)-4-(methylthio)phenyl octylcarbamate
Example 187: 3-(5-(1,3,4-oxadiazol-2-yl)pyridin-3-yl)-4-(methylthio)phenyl (cyclohexylmethyl)carbamate
Example 188: 3-(5-(1,3,4-oxadiazol-2-yl)pyridin-3-yl)-4-(methylthio)phenyl benzylcarbamate
Example 189: 3-(5-(1,3,4-oxadiazol-2-yl)pyridin-3-yl)-4-(methylthio)phenyl cyclopentylcarbamate
Example 190: 3-(5-(1,3,4-oxadiazol-2-yl)pyridin-3-yl)-4-(methylthio)phenyl cyclohexylcarbamate
Example 191: 3-(5-(1,3,4-oxadiazol-2-yl)pyridin-3-yl)-4-(methylthio)phenyl cycloheptylcarbamate
Example 192: 3-(5-(1,3,4-oxadiazol-2-yl)pyridin-3-yl)-4-fluorophenyl cyclohexylcarbamate
Example 193: 3-(5-(1,3,4-oxadiazol-2-yl)pyridin-3-yl)-4-fluorophenyl (4-methylcyclohexyl)carbamate
Example 194: 3-(5-(1,3,4-oxadiazol-2-yl)pyridin-3-yl)-4-fluorophenyl cycloheptylcarbamate
Example 195: 3-(5-(1,3,4-oxadiazol-2-yl)pyridin-3-yl)-5-fluorophenyl heptyl carbamate Example 196: 3-(5-(1,3,4-oxadiazol-2-yl)pyridin-3-yl)-5-fluorophenyl benzylcarbamate
Example 197: 3-(5-(1,3,4-oxadiazol-2-yl)pyridin-3-yl)-5-fluorophenyl cyclohexylcarbamate
Example 198: 3-(5-(1,3,4-oxadiazol-2-yl)pyridin-3-yl)-5-fluorophenyl cycloheptylcarbamate
Example 199: 3-(5-(1,3,4-oxadiazol-2-yl)pyridin-3-yl)-4-(trifluoromethoxy)phenyl octylcarbamate
Example 200: 3-(5-(1,3,4-oxadiazol-2-yl)pyridin-3-yl)-4-(trifluoromethoxy)phenyl cyclohexylcarbamate
Example 201: 3-(5-(1,3,4-oxadiazol-2-yl)pyridin-3-yl)-4-(trifluoromethoxy)phenyl (4-methylcyclohexyl)carbamate
Example 202: 3-(5-(1,3,4-oxadiazol-2-yl)pyridin-3-yl)-4-(trifluoromethoxy)phenyl cycloheptylcarbamate
Example 203: 3-(5-(1,3,4-oxadiazol-2-yl)pyridin-3-yl)-4-(trifluoromethoxy)phenyl phenylcarbamate
Example 204: 3-(5-(1,2,4-oxadiazol-5-yl)pyridin-3-yl)phenyl (cyclohexylmethyl)carbamate
Example 205: 3-(5-(1,2,4-oxadiazol-5-yl)pyridin-3-yl)phenyl cyclohexylcarbamate
Example 206: 3-(5-(1,2,4-oxadiazol-5-yl)pyridin-3-yl)phenyl cycloheptylcarbamate
Example 207: 3-(5-(1,3,4-thiadiazol-2-yl)pyridin-3-yl)phenyl octylcarbamate
Example 208: 3-(5-(1,3,4-thiadiazol-2-yl)pyridin-3-yl)phenyl (cyclohexylmethyl)carbamate
Example 209: 3-(5-(1,3,4-thiadiazol-2-yl)pyridin-3-yl)phenyl benzylcarbamate
Example 210: 3-(5-(1,3,4-thiadiazol-2-yl)pyridin-3-yl)phenyl cyclopentylcarbamate
Example 211: 3-(5-(1,3,4-thiadiazol-2-yl)pyridin-3-yl)phenyl cyclohexylcarbamate
Example 212: 3-(5-(1,3,4-thiadiazol-2-yl)pyridin-3-yl)phenyl cycloheptylcarbamate
Example 213: 3-(5-(1,3,4-thiadiazol-2-yl)pyridin-3-yl)-4-methoxyphenyl octylcarbamate
Example 214: 3-(5-(1,3,4-thiadiazol-2-yl)pyridin-3-yl)-4-methoxyphenyl (cyclohexylmethyl)carbamate
Example 215: 3-(5-(1,3,4-thiadiazol-2-yl)pyridin-3-yl)-4-methoxyphenyl benzylcarbamate
Example 216: 3-(5-(1,3,4-thiadiazol-2-yl)pyridin-3-yl)-4-methoxyphenyl cyclopentylcarbamate
Example 217: 3-(5-(1,3,4-thiadiazol-2-yl)pyridin-3-yl)-4-methoxyphenyl cyclohexylcarbamate
Example 218: 3-(5-(1,3,4-thiadiazol-2-yl)pyridin-3-yl)-4-methoxyphenyl cycloheptylcarbamate
Example 219: 3-(5-(1H-1,2,4-triazol-5-yl)pyridin-3-yl)phenyl octyl carbamate
Example 220: –(5-(1H-1,2,4-triazol-5-yl)pyridin-3-yl)phenyl (cyclohexylmethyl)carbamate
Example 221: 3-(5-(1H-1,2,4-triazol-5-yl)pyridin-3-yl)phenyl benzylcarbamate
Example 222: 3-(5-(1H-1,2,4-triazol-5-yl)pyridin-3-yl)phenyl (naphthalen-2-ylmethyl)carbamate
Example 223: 3-(5-(1H-1,2,4-triazol-5-yl)pyridin-3-yl)phenyl cyclopentylcarbamate
Example 224: 3-(5-(1H-1,2,4-triazol-5-yl)pyridin-3-yl)phenyl cyclohexylcarbamate
Example 225: 3-(5-(1H-1,2,4-triazol-5-yl)pyridin-3-yl)phenyl cycloheptyl carbamate
Example 226: 3-(5-(1H-1,2,4-triazol-5-yl)pyridin-3-yl)-4-hydroxyphenyl octylcarbamate
Example 227: 3-(5-(1H-1,2,4-triazol-5-yl)pyridin-3-yl)-4-hydroxyphenyl (cyclohexylmethyl)carbamate
Example 228: 3-(5-(1H-1,2,4-triazol-5-yl)pyridin-3-yl)-4-hydroxyphenyl benzylcarbamate
Example 229: 3-(5-(1H-1,2,4-triazol-5-yl)pyridin-3-yl)-4-hydroxyphenyl cyclopentylcarbamate
Example 230: 3-(5-(1H-1,2,4-triazol-5-yl)pyridin-3-yl)-4-hydroxyphenyl cyclohexylcarbamate
Example 231: 3-(5-(1H-1,2,4-triazol-5-yl)pyridin-3-yl)-4-hydroxyphenyl cycloheptylcarbamate
Example 232: 3-(5-(1H-1,2,4-triazol-5-yl)pyridin-3-yl)-4-methoxyphenyl octylcarbamate
Example 233: 3-(5-(1H-1,2,4-triazol-5-yl)pyridin-3-yl)-4-methoxyphenyl (cyclohexylmethyl)carbamate
Example 234: 3-(5-(1H-1,2,4-triazol-5-yl)pyridin-3-yl)-4-methoxyphenyl benzylcarbamate
Example 235: 3-(5-(1H-1,2,4-triazol-5-yl)pyridin-3-yl)-4-methoxyphenyl cyclopentylcarbamate
Example 236: 3-(5-(1H-1,2,4-triazol-5-yl)pyridin-3-yl)-4-methoxyphenyl cyclohexylcarbamate
Example 237: 3-(5-(1H-1,2,4-triazol-5-yl)pyridin-3-yl)-4-methoxyphenyl cycloheptylcarbamate
Example 238: 3-(5-(1H-tetrazol-5-yl)pyridin-3-yl)phenyl octylcarbamate
Example 239: 3-(5-(1H-tetrazol-5-yl)pyridin-3-yl)phenyl (cyclohexylmethyl)carbamate
Example 240: 3-(5-(1H-tetrazol-5-yl)pyridin-3-yl)phenyl benzylcarbamate
Example 241: 3-(5-(1H-tetrazol-5-yl)pyridin-3-yl)phenyl cyclopentylcarbamate
Example 242: 3-(5-(1H-tetrazol-5-yl)pyridin-3-yl)phenyl cyclohexylcarbamate
Example 243: 3-(5-(1H-tetrazol-5-yl)pyridin-3-yl)phenyl cycloheptylcarbamate
Example 244: 3-(5-(1H-tetrazol-5-yl)pyridin-3-yl)-4-hydroxyphenyl octylcarbamate
Example 245: 3-(5-(1H-tetrazol-5-yl)pyridin-3-yl)-4-hydroxyphenyl (cyclohexylmethyl)carbamate
Example 246: 3-(5-(1H-tetrazol-5-yl)pyridin-3-yl)-4-hydroxyphenyl benzylcarbamate
Example 247: 3-(5-(1H-tetrazol-5-yl)pyridin-3-yl)-4-hydroxyphenyl cyclopentylcarbamate
Example 248: 3-(5-(1H-tetrazol-5-yl)pyridin-3-yl)-4-hydroxyphenyl cyclohexylcarbamate
Example 249: 3-(5-(1H-tetrazol-5-yl)pyridin-3-yl)-4-hydroxyphenyl cycloheptylcarbamate
Example 250: 3-(5-(1H-tetrazol-5-yl)pyridin-3-yl)-4-methoxyphenyl octylcarbamate
Example 251: 3-(5-(1H-tetrazol-5-yl)pyridin-3-yl)-4-methoxyphenyl (cyclohexylmethyl)carbamate
Example 252: 3-(5-(1H-tetrazol-5-yl)pyridin-3-yl)-4-methoxyphenyl benzylcarbamate
Example 253: 3-(5-(1H-tetrazol-5-yl)pyridin-3-yl)-4-methoxyphenyl cyclopentylcarbamate
Example 254: 3-(5-(1H-tetrazol-5-yl)pyridin-3-yl)-4-methoxyphenyl cyclohexylcarbamate
Example 255: 3-(5-(1H-tetrazol-5-yl)pyridin-3-yl)-4-methoxyphenyl cycloheptylcarbamate Accordingly, in one embodiment the FAAH modulator, inhibitor, or FAAH inhibitor and modulators may be any one of the compounds of Examples 35-255. In a preferred embodiment the FAAH modulator, inhibitor, or FAAH modulator and inhibitor may be any one the compound of Examples 35, 40, 41, 47, 48, 50-53, 59, 60, 62-65, 72-74, 78, 80, 81, 83, 85-88, 105-110, 115-117, 119-121, 127, 128, 129, 130-139, 147, 149, 156, 157, 159-161, 163-167, 169, 174, 179, 180, 186, 192-195, 204-208, 212-214, 219, 220, 222, 226, 232, or 238. In another preferred embodiment, the FAAH modulator, inhibitor, or FAAH modulator and inhibitor may be any one of the compound of Examples 127, 128, 129, 136, 138, 139, 163, 164, or 179. Furthermore, in another preferred embodiment, the FAAH modulator, inhibitor, or FAAH modulator and inhibitor may be any one of the compounds of Examples 47, 51, 64, 72, 73, 87, 105, 109, 115, 128, 129, 130-134, 137,156, 157, 160, 165, 167, 174, 194, 195, 207, 213, 219, or 226. In another preferred embodiment, the FAAH modulator, inhibitor, or FAAH modulator and inhibitor may be any one of the compounds of Examples 83, 146, 158, 172, 194, 191, 225, and 231. In a further another preferred embodiment, the FAAH modulator, inhibitor, or FAAH modulator and inhibitor the compound of Example 158 or 172. In another preferred embodiment the compound may have the formula of Example 172.

Another embodiment provides a compound of Formula (IV)

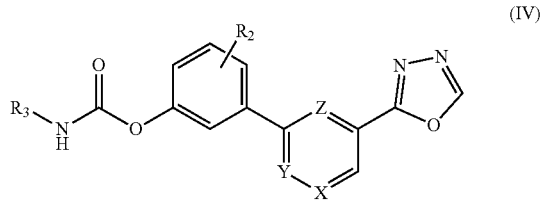

a prodrug thereof, a pharmaceutically acceptable salt thereof, or a pharmaceutically active metabolite thereof; wherein X represents CH or N;
Y represents CH or N;
Z represents CH or N;
X, Y and Z cannot all be CH or N;
$R_2$ represents H, OH, or $OCH_3$;
$R_3$ can independently be $C_5$-$C_{20}$ alkyl, $C_3$-$C_8$ cycloalkyl. $R_3$ may be unsubstituted or substituted at a carbon ring member with halogen or alkyl group.

In another embodiment the compound may have Formula (IV), wherein
X may be N;
Y may be CH;
Z may be CH;
$R_2$ may be halogen, hydroxy, $C_1$-$C_4$ alkoxy, cyano, or fluoroalkyl; and
$R_3$ may be $C_1$-$C_8$ alkyl or $C_3$-$C_8$ cycloalkyl.

In another embodiment the compound may have Formula (IV), wherein
X may be N;
Y may be CH;
Z may be CH;
$R_2$ may be hydroxy or $C_1$-$C_4$ alkoxy; and
$R_3$ may be $C_1$-$C_8$ alkyl or $C_3$-$C_8$ cycloalkyl.

In another embodiment the compound may have Formula (IV), wherein
X may be N;
Y may be CH;
Z may be CH;
$R_2$ may be $C_1$-$C_4$ alkoxy; and
$R_3$ may be $C_1$-$C_8$ alkyl or $C_3$-$C_8$ cycloalkyl.

Examples of certain useful compounds of Formula IV include:

Example 256: 3-(4-(1,3,4-oxadiazol-2-yl)pyridin-2-yl)phenyl (2-methylhexyl)carbamate
Example 257: 3-(4-(1,3,4-oxadiazol-2-yl)pyridin-2-yl)phenyl (cyclohexylmethyl)carbamate
Example 258: 3-(4-(1,3,4-oxadiazol-2-yl)pyridin-2-yl)phenyl benzylcarbamate
Example 259: 3-(4-(1,3,4-oxadiazol-2-yl)pyridin-2-yl)phenyl cyclopentylcarbamate
Example 260: 3-(4-(1,3,4-oxadiazol-2-yl)pyridin-2-yl)phenyl cyclohexylcarbamate
Example 261: 3-(4-(1,3,4-oxadiazol-2-yl)pyridin-2-yl)phenyl (4-methylcyclohexyl)carbamate
Example 262: 3-(4-(1,3,4-oxadiazol-2-yl)pyridin-2-yl)phenyl cycloheptylcarbamate
Example 263: 3-(6-(1,3,4-oxadiazol-2-yl)pyrazin-2-yl)phenyl octylcarbamate
Example 264: 3-(6-(1,3,4-oxadiazol-2-yl)pyrazin-2-yl)phenyl (cyclohexylmethyl)carbamate
Example 265: 3-(6-(1,3,4-oxadiazol-2-yl)pyrazin-2-yl)phenyl benzylcarbamate
Example 266: 3-(6-(1,3,4-oxadiazol-2-yl)pyrazin-2-yl)phenyl cyclopentylcarbamate
Example 267: 3-(6-(1,3,4-oxadiazol-2-yl)pyrazin-2-yl)phenyl cyclohexylcarbamate
Example 268: 3-(6-(1,3,4-oxadiazol-2-yl)pyrazin-2-yl)phenyl cycloheptylcarbamate Accordingly, in one embodiment the FAAH modulator, inhibitor, or FAAH inhibitor and modulators may be any one of the compounds of Examples 256-268. In a preferred embodiment the FAAH modulator, inhibitor, or FAAH modulator and inhibitor may be any one the compound of Examples 256, 257, 262, 263, 264, 266, 267 and 268. In a further preferred embodiment, the FAAH modulator, inhibitor, or FAAH modulator and inhibitor may be the compound of Example 256 or 263.

The compounds of this disclosure include any and all of possible isomers, regioisomers, stereoisomers, enantiomers, diastereomers, racemates, tautomers, free form (e.g., amorphous, polymorphs), pharmaceutically acceptable salts, polymorphs, hydrates, and solvates thereof. The disclosed compounds can be also used to prepare prodrugs.

Formula (I-IV) is also intended to represent unlabeled forms as well as isotopically labeled forms of the compounds. Isotopically-labelled compounds are identical to those depicted herein except that one or more atoms are replaced by an atom having atomic mass or mass number different from the atomic mass or mass number usually found in nature. Examples of isotopes that can be incorporated into compounds of the invention include, but are not limited to, isotopes of hydrogen, carbon, nitrogen, oxygen, fluorine, and chlorine, such as $^2H$, $^3H$, $^{13}C$, $^{14}C$, $^{15}N$, $^{17}O$, $^{18}O$, $^{18}F$, and $^{36}Cl$ respectively. Isotopically-labeled compounds of the present disclosure can generally be prepared by following methods analogues to those disclosed in the Examples herein by substituting isotopically-labeled reagents for a non-isotopically labeled reagents. Isotopica labeling of the compounds disclosed may be useful in metabolic studies, reaction kinetic studies, compound and/or substrate tissue distribution assays, and detection or imaging techniques. Such applications of isotopically-labeled compounds are well known to person skill in the art and are therefore within the scope of the present invention.

Compounds of the invention may be synthesized using the conventional methods and utilizing the commercially available reagents and starting materials and/or from compounds described in the chemical literature. "Commercially available chemicals" are obtained from standard commercial sources. It will be readily understood that numerous alterations may be made to the examples and instructions given herein for the synthesis methods and purification of compounds of Formula I-IV.

This disclosure is also directed to a method of inhibition of FAAH enzyme in both in vitro and in vivo systems. The compounds of Formula I-IV may be reversible or irreversible FAAH inhibitor or modulator. Thus, can be used in the treatment of a disease, disorder or condition which benefits from the inhibition or modulation of FAAH activity in a subject.

Definitions

Fatty Acid Amide Hydrolase (FAAH) Inhibitor

Fatty acid amide hydrolase (FAAH, or FAAH-1), also known as oleamide hydrolase or anandamide amidohydrolase is a member of the serine hydrolase family of enzymes. Broadly, it belongs to the class of endocannabinoid hydrolases. It is the principal enzyme responsible for the hydrolysis of Anandamide to Arachidonic acid and ethanolamine. FAAH is an integral membrane protein widely distributed in mammalian tissues that belongs to a large family of enzymes that share a highly conserved 130 amino acid motif designated the "amidase signature" (AS) sequence. AS enzymes possess an unusual serine-serine-lysine catalytic triad, which functions to promote amide bond hydrolysis in a manner analogous to the serine-histidine-aspartic acid triad more commonly observed in serine hydrolases (Dale et al., 2000 [15]; Michele et al., 2005 [16]).

The compounds of Formula I, II, III or IV, may modulate, inhibit or modulate and inhibit Fatty acid amide hydrolase (FAAH). Accordingly, the compounds of Formula I-IV, may be a FAAH inhibitor, a FAAH modulator or a FAAH inhibitor and modulator.

As used herein, the term "modulate", "modulatory", "modulation" or "modulating" refers to a change in the activity e.g., of the FAAH enzyme. As used herein, the term "inhibit", "inhibitory", "inhibition" or "inhibiting" refers to the reduction or suppression of the activity e.g., of the FAAH enzyme or a significant decrease in the baseline activity of a biological activity or process e.g., of the FAAH catalyzed reaction of the FAAH enzyme.

FAAH inhibitors or modulators are classified as reversible or irreversible. The main difference is that reversible enzyme inhibition inactivates enzymes through non-covalent interaction. In contrast, an irreversible inhibitor inactivates the enzyme through covalent binding to form a stable complex with the enzyme. As a result, the enzyme is permanently inactivated or, at best, is slowly reactivated. The compounds of Formula I-IV described herein may be an irreversible inhibitor or modulator of the FAAH enzyme through the carbamoylation of the active site of the enzyme and this would not show any subsequent competition for binding by accumulated endogenous substrates. Irreversible binding enables and maintains the essentially complete inhibition of the enzyme.

Compounds

The term "alkyl", as used herein, refers to a saturated linear or branched-chain monovalent hydrocarbon radical. Unless otherwise specified, an alkyl group contains 5-20 carbon atoms. Examples of alkyl groups include, but are not limited to, pentyl, hexyl, heptyl, octyl and the like.

The term "cycloalkyl" refers to a saturated or partially saturated, monocyclic or fused or spiro polycyclic, carbocycle having from 3 to 12 ring atoms per ring. Examples of cycloalkyl groups include, but are not limited to, cyclobutyl, cyclopentyl, cyclohexyl, cycloheptyl, cyclooctyl, etc.

The term "heterocycloalkyl" refers to a fully saturated cyclic hydrocarbon group containing one or more heteroatom. The term heterocycloalkyl includes fused, spiro or bridged ring systems. Examples of heterocycloalkyl groups include, but are not limited to, 2-azaspiro[3.3]heptane, 3-azabicyclo[3.1.0]hexane, 3-azabicyclo[3.3.0]octane, 8-azabicyclo[3.2.1]octane, 2oxa-6-azaspiro[3.3]heptane, 2oxa-7-azaspiro[3.5]nonane, etc.

The term "aryl" refers to a carbocyclic ring system wherein at least one ring in the system is aromatic and has a single point of attachment to the rest of the molecule. Unless otherwise specified, an aryl group may be monocyclic, bicyclic or tricyclic.

The term "heteroaryl", as used herein, refers to a ring system in which one or more ring members are an independently selected heteroatom. The term heteroaryl also includes fused, spiro or bridged heterocyclic ring systems. Unless otherwise specified, a heterocycle may be monocyclic, bicyclic or tricyclic.

"Fused" bicyclic ring systems comprise two rings which share two adjoining ring atoms.

"Spiro" bicyclic ring systems share only one ring atom (usually a quaternary carbon atom).

The term "halogen" represents chlorine, fluorine, bromine or iodine. The term "halo" represents chloro, fluoro, bromo or iodo.

Pharmaceutically Acceptable Derivative

The term "pharmaceutically acceptable derivative" includes, but is not limited to, a pharmaceutically acceptable salt or prodrug, which after being administered to a patient in need thereof, can directly or indirectly provide the compound of the disclosure or a metabolite or residue thereof. Therefore, "the compound of the disclosure" mentioned herein is also intended to cover various derivative forms of the compound.

Pharmaceutically Acceptable Salt

The term "pharmaceutically acceptable salt" as used herein encompasses any and all pharmaceutically acceptable salt forms. Those compounds of the disclosure that are basic in nature are capable of forming acid salts with various pharmacologically accepted anions. The chemical acids which are used as reagents to prepare acid salts of this disclosure include both inorganic and organic acids. In some embodiments, these salts are prepared in situ during the final isolation and purification of the compounds of the disclosure, or by separately reacting a purified compound in its free form with a suitable acid or base, and isolating the salt thus formed. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002 (Stahl & Wermuth 2002 [17]). In some embodiments, the pharmaceutically acceptable salts of the compounds described herein are pharmaceutically acceptable acid addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and the like.

Prodrugs

In some embodiments, the compounds described herein may exist in prodrug form. The disclosure provides for methods of treating diseases by administering such prodrugs. The disclosure further provides for methods of treating diseases by administering such prodrugs as pharmaceutical compositions.

Metabolites

In some embodiments, the compounds of Formula (I) described herein are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

Combinations

Also contemplated herein are combination therapies, for example, co-administering disclosed compounds of Formula I-IV and an additional therapeutic agent, as part of a specific treatment regimen intended to provide the beneficial effect from the co-action of these therapeutic agents.

The disclosed inhibitory compounds can be combined with one or more agents targeting the endogenous cannabinoid system. Such agents include, but not limited to, MAGL inhibitors, CBT cannabinoid receptor agonists, CB2 cannabinoid receptor agonists, and phytocannabinoids.

The disclosed inhibitory compounds can be combined with one or more additional therapeutic agent may be selected from the group consisting of, but are not limited to, non-steroidal anti-inflammatory drugs (NSAIDs), anti-anxiety agents, antidepressants, antiepileptic drugs, anti-Alzheimer's agents, antipsychotic drugs, antihemorrhagic agents, benzodiazepines, acetylcholinesterase inhibitors, alpha-adrenoreceptor antagonists, alpha-adrenergic receptor agonists, β-blockers, angiotensin-converting enzymes inhibitors (ACEI), serotonin (5-HT) reuptake inhibitors, serotonin and noradrenaline reuptake inhibitors (SNRIs), antirheumatic drug, and anticancer medications.

The effective amount of the compound of Formula I-IV or the synergistic additional molecule may be between about 0.0001 to about 1,000 mg.

The beneficial effect of the combination includes, but is not limited to, pharmacokinetic or pharmacodynamic co-action resulting from the combination of therapeutic agents. Administration of these therapeutic agents in combination typically is carried out over a defined time period (usually days, weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Therapeutic Uses

As discussed above, the compounds according to the present disclosure have intrinsic FAAH inhibition properties.

Without wishing to be bound by theory, it is believed that the compounds of Formula (I-IV) described herein may offer an improved therapeutic outcome to subjects with FAAH-related diseases, disorders and conditions.

The terms "FAAH-related diseases, disorder or conditions" and "disease, disorder or condition benefitting from FAAH inhibition" refers to any disease state, disorder or condition in a subject that has a symptom that is caused directly or indirectly by the FAAH enzyme and where a positive therapeutic outcome by inhibition of the FAAH enzyme is expected.

FAAH inhibitors can find potential applications in the treatment of various diseases including but not limited to pain, inflammation, anxiety and mood disorders, metabolic diseases, cardiovascular diseases, autoimmune diseases, central nervous system (CNS) diseases, liver diseases, respiratory diseases, and kidney diseases.

The compounds of Formula (I-IV) described herein may be used to treat a variety of medical conditions including but not limited to pain (including but not limited to acute pain, chronic pain, nociceptive pain, and non-nociceptive pain), inflammatory diseases (including but not limited to inflammatory bowel disease, neuroinflammation, neuropathy), anxiety and mood disorder, sleep disorder, eating disorders, obesity, cardiovascular diseases (including but not limited to hypertension, coronary heart disease, ischemia, congestive heart failure, atherosclerosis, myocardial infarction, and peripheral vascular disease), dyslipidemia (including but not limited to hyperlipidemia, hypoalphalipoproteinemia, hypertriglyceridemia, hypercholesterolemia, and low high-density lipoprotein (HDL)), diabetes (type 1 and type 2), allergic airway disease (including but not limited to cough, asthma, and chronic obstructive diseases), cerebrovascular disorders (including stroke, cerebral vasospasm, and learning and memory disorders), drug or alcohol withdrawal, addiction, liver diseases (including but not limited to non-alcoholic fatty liver disease (NAFLD), non-alcoholic steatohepatitis (NASH), and hepatitis), cancer, chemotherapy-induced nausea and vomiting (CINV), neurodegenerative disease (including but not limited to Alzheimer and Parkinson diseases), CNS disorders (including but not limited to depression, post-traumatic stress disorder, schizophrenia, seizures, and cognitive disorders), autoimmune diseases (including but not limited to psoriasis, rheumatoid arthritis, Crohn's disease, systemic lupus erythematosis, Sjogren's syndrome, Huntington's chorea, and multiple sclerosis), skin disorders (including but not limited to itching, eczema, pruritis, dermatitis, impaired wound healing), gastrointestinal disorders (including but not limited to nausea, gastrointestinal motility disorder, and paralytic ileus), eye diseases (including but not limited to cataract, and glaucoma).

Compositions

The disclosure is directed to a pharmaceutical formulation comprising at least one compound of Formula IIV. Dosage formulation can be any of a number of dosage forms known in the art. These dosage forms include, but not limited to, tablets, capsules, pills, syrups, solutions, suspensions, emulsions, injection, inhalation, powders, granules, creams, ointments, gels, patches, and solid lipid nanoparticles.

The compositions may be formulated such that they are suitable for oral, parenteral (including but not limited to, intramuscular, subcutaneous, intravenous, intrathecal, intraperitoneal), ophthalmic, topical, transdermal, buccal, sublingual, intranasal, intraocular, rectal, and vaginal.

The compounds of Formula I-IV described herein can be administered to a human patient by itself, or in compositions where they are mixed with suitable excipients and/or adjuvants.

The compositions described herein may be pharmaceutical compositions and may include one or more pharmaceutically acceptable excipient or adjuvant.

The term "excipient" refers to any substance, not itself a therapeutic agent, used as a carrier or vehicle for delivery of a therapeutic agent to a subject or combined with a therapeutic agent (e.g., to create a pharmaceutical composition) to improve its handling or storage properties or to permit or facilitate the formation of a dose unit of the composition. Pharmaceutically acceptable excipients include, by way of illustration and not limitation, diluents, solvents, disintegrants, binders, glidant, lubricants, (physiologically acceptable) surfactant agents, suspending agents, film forming agents, preservatives, sweetening agent, coloring agent, flavoring agents, emulsifying/wetting agent, buffering agents, binders, disintegrants, taste enhancers, thickening agents, penetration enhancers, wetting agents, lubricants, protectives, adsorbents, demulcents, emollients, antioxidants, moisturizers, carriers, buffering agents, solubilizing agents, penetration agents, soothing agents, suspension agents, coating assistants, substances added to mask or counteract a disagreeable odor, fragrances, or taste, substances added to improve appearance or texture of the composition, and combinations thereof.

Dosages

The compounds of Formula I-IV or the composition comprising the compounds of Formula I-IV may be administered in a dose once a day or multiple times a day. The daily dose may be between 0.0001 to about 2,000 mg or any amount therebetween. The dose may vary according to factors such as the disease state, age, sex and weight of the subject, and the ability of the compound to elicit a desired response in the subject. Dosage regimens may be adjusted to provide the optimal therapeutic response.

EXAMPLES

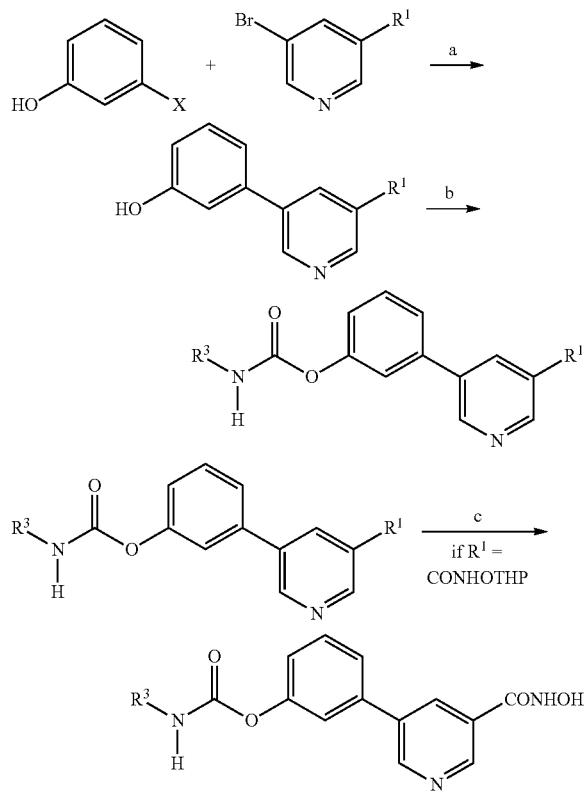

$X = B(OCH_3H_6)_2$, or $B(OH)_2$
$R^1 =$

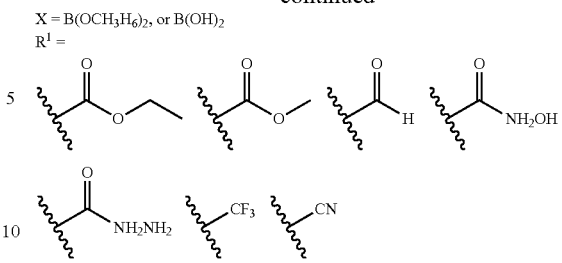

Reagents and conditions: a) Pd(PPh$_3$)$_4$, aq K$_2$CO$_3$, 1,4-dioxane, 90°C., 4-12 h or Pd(dppf)Cl$_2$, KOAc, 1,4-Dioxane, 90° C., 4-12; b) R$^3$—NCO, triethylamine (TEA), acetonitrile (ACN), 75° C., 2-15 h; c) HCl in methanol, room temperature (RT), 2 h.

Synthesis of ethyl 5-(3-hydroxyphenyl)nicotinate

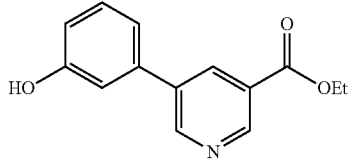 [SMILES: CCOC(=O)c1cncc(-c2cccc(O)c2)c1]

To a stirred solution of ethyl 5-bromonicotinate (0.78 g, 3.62 mmol) in 1,4-dioxane (15 mL) was added (3-hydroxyphenyl)boronic acid (0.50 g, 3.62 mmol) and 0.4M Na$_2$CO$_3$ (15 mL) at RT. The reaction mixture was degassed for 15 minutes then Pd(PPh$_3$)$_4$ (0.02 g, 0.018 mmol) was added. The reaction mixture was heated at 80° C. for 4 h under nitrogen atmosphere. The reaction was monitored by thin-layer chromatography (TLC). after completion, the reaction mixture was cooled to RT then evaporated under reduced pressure. The residue was dissolved in water (15 mL) and pH was adjusted to 2-3 by using 2N HCl. The precipitated solid was filtered, washed with water, and then dried under high vacuum to afford the crude acid (450 mg). To a suspension of acid compound in ethanol (15 mL) was added concentrated H$_2$SO$_4$ (4-drops) at RT then the reaction mixture was heated at 90° C. for 5 h under Nitrogen atmosphere.

The reaction progress was monitored by TLC. After reaction completion, the reaction mixture was cooled to RT and then the solvent was evaporated under reduced pressure. The residue was dissolved in ethyl acetate, washed with NaHCO$_3$ followed by brine. The organic solvent was dried over sodium sulfate then evaporated under reduced pressure. The residue was purified by column chromatography on silica gel eluting with hexane/EtOAc (gradient 10-70% EtOAc) to yield the target compound (400 mg) as an off white solid. $^1$H NMR (400 MHz, DMSO-d6) δ 9.71 (s, 1H), 9.07 (s, 2H), 8.39 (s, 1H), 7.34 (t, J=8.1 Hz, 1H), 7.20 (d, J=8.1 Hz, 1H), 7.12 (s, 1H), 6.87 (dd, J=8.0 Hz, 1H), 4.39 (q, J=16 Hz, 2H), 1.37 (t, J=8.0 Hz, 3H).

Synthesis of ethyl 5-(3-((pentylcarbamoyl)oxy)phenyl)nicotinate (Example-1)

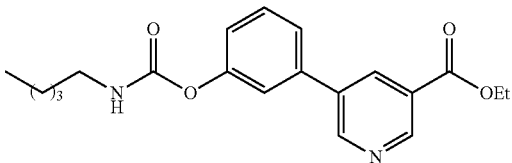

To a solution of ethyl 5-(3-hydroxyphenyl) nicotinate (0.08 g, 0.32 mmol) in anhydrous acetonitrile (2 mL) was added TEA (0.13 mL, 0.98 mmol) and n-pentyl isocyanate (0.03 g, 0.32 mmol) at RT under nitrogen atmosphere. The reaction mixture was stirred at RT for 10 minutes and then heated to 75° C. for 3 h under a nitrogen atmosphere. An additional amount of n-pentyl isocyanate (0.01 g, 0.11 mmol) was added to the reaction mixture, and the reaction was heated for an additional 12 h. The reaction progress was monitored by TLC. After completion, the reaction mixture was cooled to RT, and the solvent was evaporated under reduced pressure. The crude product was purified by flash column chromatography on silica gel, eluting with a hexane/EtOAc gradient (20-25% EtOAc) to yield the target compound (56 mg) as an off white solid. $^1$H NMR (400 MHz, CDCl3) δ 9.14 (s, 1H), 8.93 (s, 1H), 8.54 (s, 1H), 7.27-7.54 (m, 2H), 7.18 (d, J=8.7 Hz, 3H), 5.03 (s, 1H), 4.20-4.52 (m, 2H), 3.22 (q, J=6.8 Hz, 2H), 1.53 (d, J=6.9 Hz, 2H), 1.20-1.49 (m, 7H), 0.76-0.92 (m, 3H)

Synthesis of ethyl 5-(3-((heptylcarbamoyl)oxy)phenyl)nicotinate (Example-2)

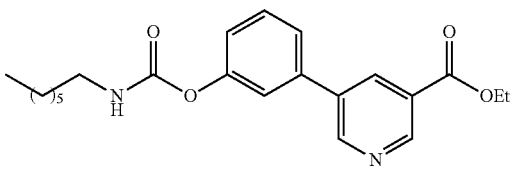

To a solution of ethyl 5-(3-hydroxyphenyl) nicotinate (0.08 g, 0.32 mmol) in anhydrous acetonitrile (2 mL) was added TEA (0.13 mL, 0.98 mmol) and n-heptyl isocyanate (0.0 g, 0.32 mmol) at RT under a nitrogen atmosphere. The reaction mixture was stirred at RT for 10 minutes and then heated to 75° C. for 3 h under nitrogen atmosphere. An additional amount of n-heptyl isocyanate (0.01 g, 0.11 mmol) was added to the reaction mixture, and the reaction was heated for an additional 12 h. The reaction progress was monitored by TLC. After completion, the reaction mixture was cooled to RT and then the solvent was evaporated under reduced pressure. The crude product was purified by flash column chromatography on silica gel, eluting with a hexane/EtOAc gradient (20-25% EtOAc) to yield the target compound (57 mg) as an off white solid. $^1$H NMR (400 MHz, dimethyl sufoxide (DMSO)) δ 9.12 (dt, J=22.0, 1.9 Hz, 2H), 8.47 (q, J=2.0 Hz, 1H), 7.84 (t, J=5.7 Hz, 1H), 7.44-7.69 (m, 3H), 7.21 (dd, J=8.1, 2.2 Hz, 1H), 4.22-4.46 (m, 2H), 3.07 (q, J=6.7 Hz, 2H), 1.18-1.56 (m, 14H), 0.78-1.00 (m, 3H).

Synthesis of ethyl 5-(3-((octylcarbamoyl)oxy)phenyl)nicotinate (Example-3)

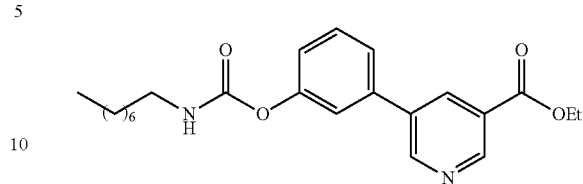

To a solution of ethyl 5-(3-hydroxyphenyl) nicotinate (0.08 g, 0.32 mmol) in anhydrous acetonitrile (2 mL) was added TEA (0.13 mL, 0.98 mmol) and n-octyl isocyanate (0.04 g, 0.32 mmol) at RT under a nitrogen atmosphere. The reaction mixture was stirred at RT for 10 minutes and then heated to 75° C. for 3 h under nitrogen atmosphere. An additional amount of n-octyl isocyanate (0.01 g, 0.11 mmol) was added to the reaction mixture, and the reaction was heated for an additional 12 h. The reaction progress was monitored by TLC. After completion, the reaction mixture was cooled to RT, and the solvent was evaporated under reduced pressure. The crude product was purified by flash column chromatography on silica gel, eluting with a hexane/EtOAc gradient (20-25% EtOAc) to yield the target compound (58 mg) as an off white solid. $^1$H NMR (400 MHz, CDCl3) δ 9.22 (s, 1H), 8.92-9.05 (m, 1H), 8.53 (d, J=2.1 Hz, 1H), 7.39-7.58 (m, 3H), 7.18-7.36 (m, 1H), 5.15 (t, J=5.8 Hz, 1H), 4.48 (q, J=7.1 Hz, 2H), 3.31 (q, J=6.7 Hz, 2H), 1.61 (p, J=7.0 Hz, 3H), 1.22-1.52 (m, 12H), 0.90 (t, J=6.5 Hz, 3H).

Synthesis of ethyl 5-(3-((tetradecylcarbamoyl)oxy)phenyl)nicotinate (Example-4)

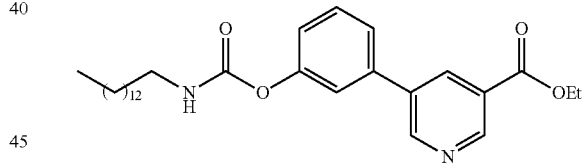

To a solution of ethyl 5-(3-hydroxyphenyl) nicotinate (0.08 g, 0.32 mmol) in anhydrous acetonitrile (2 mL) was added TEA (0.13 mL, 0.98 mmol) and n-tetradecyl isocyanate (0.07 g, 0.32 mmol) at RT under nitrogen atmosphere. The reaction mixture was stirred at RT for 10 minutes and then heated to 75° C. for 3 h under a nitrogen atmosphere. An additional amount of n-tetradecyl isocyanate (0.02 g, 0.11 mmol) was added to the reaction mixture, and the reaction was heated for an additional 12 h. The reaction progress was monitored by TLC. After completion, the reaction mixture was cooled to RT, and the solvent was evaporated under reduced pressure. The crude product was purified by flash column chromatography on silica gel, eluting with a hexane/EtOAc gradient (20-25% EtOAc) to yield the target (56 mg) compound as an off white solid. $^1$H NMR (400 MHz, CDCl3) δ 9.22 (s, 1H), 9.01 (d, J=2.3 Hz, 1H), 8.53 (t, J=2.0 Hz, 1H), 7.38-7.59 (m, 3H), 7.24 (d, J=7.3 Hz, 1H), 5.14 (t, J=5.8 Hz, 1H), 4.48 (q, J=7.2 Hz, 2H), 3.31 (q, J=6.8 Hz, 2H), 1.61 (p, J=7.0 Hz, 3H), 1.18-1.41 (m, 20H), 0.90 (t, J=6.7 Hz, 3H).

Synthesis of ethyl 5-(3-((cyclopentylcarbamoyl)oxy)phenyl)nicotinate (Example-5)

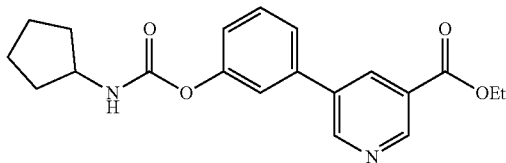 [SMILES: CCOC(=O)c1cncc(-c2cccc(OC(=O)NC3CCCC3)c2)c1]

To a solution of ethyl 5-(3-hydroxyphenyl) nicotinate (0.08 g, 0.32 mmol) in anhydrous acetonitrile (2 mL) under a nitrogen atmosphere was added TEA (0.13 mL, 0.98 mmol) and cyclopentyl isocyanate (0.03 g, 0.32 mmol) at RT. The reaction mixture was stirred at RT for 10 minutes and then heated to 75° C. for 3 h under nitrogen atmosphere. An additional amount of cyclopentyl isocyanate (0.01 g, 0.094 mmol) was added to the reaction mixture, and the reaction was heated for an additional 12 h. The progress of the reaction was monitored by TLC. Upon completion, the reaction mixture was cooled to RT and the solvent was evaporated under reduced pressure. The crude product was purified by flash column chromatography on silica gel, eluting with a hexane/EtOAc gradient (20-25% EtOAc) to yield the target compound (62 mg) as an off white solid. $^1$H NMR (400 MHz, CDCl3) δ 9.23 (d, J=2.1 Hz, 1H), 9.01 (d, J=2.3 Hz, 1H), 8.56 (t, J=2.1 Hz, 1H), 7.38-7.60 (m, 3H), 7.25 (d, J=7.9 Hz, 1H), 5.09 (d, J=7.5 Hz, 1H), 4.48 (qd, J=7.2, 1.5 Hz, 2H), 4.10 (h, J=7.0 Hz, 1H), 2.07 (dq, J=12.6, 6.3 Hz, 2H), 1.71 (dt, J=35.0, 6.2 Hz, 4H), 1.40-1.60 (m, 5H).

Synthesis of ethyl 5-(3-((cyclohexylcarbamoyl)oxy)phenyl)nicotinate (Example-6)

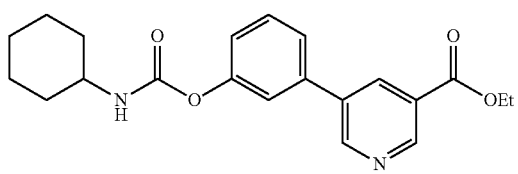 [SMILES: CCOC(=O)c1cncc(-c2cccc(OC(=O)NC3CCCCC3)c2)c1]

To a solution of ethyl 5-(3-hydroxyphenyl) nicotinate (0.22 g, 0.90 mmol) in anhydrous acetonitrile (8 mL) was added TEA (0.15 mL, 1.08 mmol) and cyclohexyl isocyanate (0.115 mL, 0.90 mmol) at RT under nitrogen atmosphere. The reaction mixture was stirred at RT for 10 minutes then heated at 75° C. 3 h under Nitrogen atmosphere. An additional amount of cyclohexyl isocyanate (0.07 g, 0.3 mmol) was added to the reaction mixture and the reaction was heated for an additional 3 h. The reaction progress was monitored by TLC. After reaction completion, the reaction was cooled to RT then evaporated under reduced pressure. The residue was purified by flash column chromatography on silica gel eluting with hexane/EtOAc (gradient 10-70% EtOAc) to yield the target compound (88 mg) as an off white solid. $^1$H NMR (400 MHz, DMSO-d6) δ 9.15 (d, J=4 Hz, 1H), 9.10 (d, J=4 Hz, 1H), 8.48 (s, 1H), 8.48 (s, 1H), 7.81 (d, J=8 Hz, 1H), 7.65 (d, J=8 Hz, 1H), 7.51-7.56 (m, 2H), 7.21 (d, J=8 Hz, 1H), 4.39 (q, J=16 Hz, 2H), 3.3 (s, 1H), 1.37 (t, J=8.0 Hz, 3H), 1.11-1.86 (m, 10H).

Synthesis of ethyl 5-(3-(((4-fluorophenyl)carbamoyl)oxy)phenyl)nicotinate (Example-7)

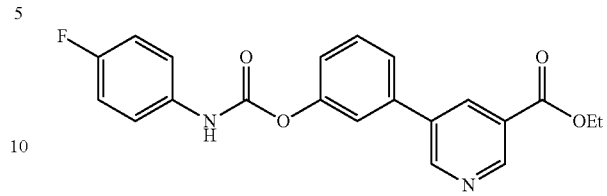

To a solution of ethyl 5-(3-hydroxyphenyl) nicotinate (0.08 g, 0.32 mmol) in anhydrous acetonitrile (2 mL) was added TEA (0.13 mL, 0.98 mmol) and 4-fluorophneyl isocyanate (0.04 g, 0.32 mmol) at RT under a nitrogen atmosphere. The reaction mixture was stirred at RT for 10 minutes and then heated to 75° C. for 3 h under nitrogen atmosphere. An additional amount of 4-fluorophneyl isocyanate (0.01 g, 0.11 mmol) was added to the reaction mixture, and the reaction was heated for an additional 12 h. The reaction progress was monitored by TLC. Upon completion, the reaction mixture was cooled to RT and the solvent was evaporated under reduced pressure. The crude product was purified by flash column chromatography on silica gel, eluting with a hexane/EtOAc gradient (20-25% EtOAc) to yield the target compound (25 mg) as an off white solid. $^1$H NMR (400 MHz, DMSO) δ 1.24-1.55 (m, 3H), 4.24-4.54 (m, 2H), 6.38-6.68 (m, 1H), 6.75-6.98 (m, 1H), 7.05-7.24 (m, 1H), 7.24-7.39 (m, 2H), 7.37-7.65 (m, 2H), 7.64-7.79 (m, 1H), 8.39 (q, J=1.8 Hz, 1H), 8.51 (t, J=2.0 Hz, 1H), 8.70 (s, 1H), 8.98-9.19 (m, 1H), 9.72 (d, J=1.3 Hz, 1H).

Synthesis of methyl 5-(3-hydroxyphenyl)nicotinate

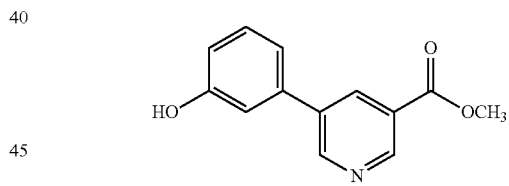

To a stirred solution of methyl 5-bromonicotinate (0.20 g, 0.45 mmol) in 1,4-dioxane (10 mL) were added 3-(4,4,5,5-tetramethyl-1,3,2-dioxaborolan-2-yl)phenol (0.2 g, 0.45 mmol), KOAc (0.27 g, 2.72 mmol) at RT. The reaction mixture was degassed for 15 minutes then Pd(dppf)Cl$_2$ (0.022 g, 0.027 mmol) was added. The reaction mixture was stirred at RT for 30 minutes and then heated at 80° C. overnight under nitrogen atmosphere. The reaction was monitored by TLC, after completion the reaction mixture was cooled to RT and then the solvent was evaporated under reduced pressure. The compound was purified by column chromatography on silica gel eluting with hexane/EtOAc (gradient 10-70% EtOAc) to yield the methyl 5-(3-hydroxyphenyl)nicotinate (120 mg) as an off white solid. $^1$H NMR (400 MHz, DMSO-d6) δ 9.71 (s, 1H), 9.07 (dd, J=8 Hz, 1H), 8.40 (s, 1H), 7.34 (t, J=8 Hz, 1H), 7.20 (d, J=8.1 Hz, 1H), 7.12 (s, 1H), 6.87 (dd, J=8 Hz, 1H), 3.93 (s, 3H).

Synthesis of methyl 5-(3-((pentylcarbamoyl)oxy)phenyl)nicotinate (Example-8)

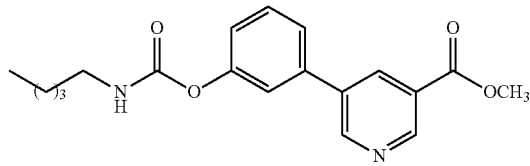

To a solution of methyl 5-(3-hydroxyphenyl) nicotinate (0.08 g, 0.34 mmol) in anhydrous acetonitrile (2 mL) was added TEA (0.14 mL, 1.0 mmol) and n-pentyl isocyanate (0.03 g, 0.34 mmol) at RT under nitrogen atmosphere. The reaction mixture was stirred at RT for 10 minutes and then heated at 75° C. for 3 h under a nitrogen atmosphere. An additional amount of n-pentyl isocyanate (0.01 g, 0.11 mmol) was added to the reaction mixture, and the reaction was heated for an additional 12 h. The reaction progress was monitored by TLC. After completion, the reaction mixture was cooled to RT and the solvent was evaporated under reduced pressure. The crude product was purified by flash column chromatography on silica gel, eluting with a hexane/EtOAc gradient (20-25% EtOAc) to yield the target compound (60 mg) as an off white solid. $^1$H NMR (400 MHz, CDCl3) δ 9.22 (d, J=1.9 Hz, 1H), 9.01 (d, J=2.1 Hz, 1H), 8.50 (t, J=2.1 Hz, 1H), 7.40-7.58 (m, 3H), 7.24 (dt, J=7.7, 1.9 Hz, 1H), 5.13 (s, 1H), 4.01 (d, J=1.5 Hz, 3H), 3.31 (q, J=6.6 Hz, 2H), 1.62 (d, J=14.2 Hz, 2H), 1.39 (q, J=5.2 Hz, 4H), 0.94 (q, J=6.8 Hz, 3H).

Synthesis of methyl 5-(3-((heptylcarbamoyl)oxy)phenyl)nicotinate (Example-9)

To a solution of methyl 5-(3-hydroxyphenyl) nicotinate (0.08 g, 0.34 mmol) in anhydrous acetonitrile (2 mL) was added TEA (0.14 mL, 1.0 mmol) and n-heptyl isocyanate (0.04 g, 0.34 mmol) at RT under a nitrogen atmosphere. The reaction mixture was stirred at RT for 10 minutes and then heated to 75° C. for 3 h under nitrogen atmosphere. An additional amount of n-heptyl isocyanate (0.01 g, 0.11 mmol) was added to the reaction mixture, and the reaction was heated for an additional 12 h. The reaction progress was monitored by TLC. After completion, the reaction mixture was cooled to RT and the solvent was evaporated under reduced pressure. The crude product was purified by flash column chromatography on silica gel, eluting with a hexane/EtOAc gradient (20-25% EtOAc/hexane) to yield the target compound (65 mg) as an off white solid. $^1$H NMR (400 MHz, CDCl3) δ 9.22 (d, J=2.0 Hz, 1H), 9.01 (d, J=2.2 Hz, 1H), 8.50 (t, J=2.1 Hz, 1H), 7.38-7.61 (m, 2H), 7.19-7.33 (m, 1H), 5.13 (t, J=6.1 Hz, 1H), 4.01 (d, J=1.4 Hz, 3H), 3.22-3.37 (m, 2H), 1.62 (p, J=7.2 Hz, 2H), 1.24-1.45 (m, 10H), 0.88-0.95 (m, 3H).

Synthesis of methyl 5-(3-((octylcarbamoyl)oxy)phenyl)nicotinate (Example-10)

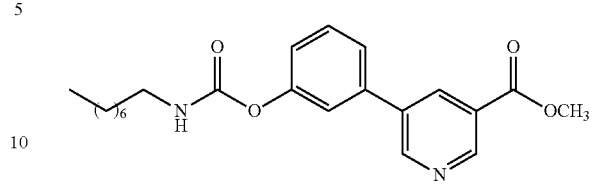

To a suspension of methyl 5-(3-hydroxyphenyl)nicotinate (0.08 g, 0.34 mmol) in anhydrous acetonitrile (2 mL) was added TEA (0.14 mL, 1.0 mmol) and n-octyl isocyanate (0.05 g, 0.34 mmol) at RT under a nitrogen atmosphere. The reaction mixture was stirred at RT for 10 minutes and then heated to 75° C. for 3 h under a nitrogen atmosphere. An additional amount of n-octyl isocyanate (0.01 g, 0.11 mmol) was added to the reaction mixture, which was then heated for an additional 12 h. The reaction progress was monitored by TLC. Upon completion of the reaction, the mixture was cooled to RT and then the sol vent was evaporated under reduced pressure. The crude product was purified by flash column chromatography on silica gel, eluting with a hexane/EtOAc gradient (20-25% EtOAc) to yield the target compound (59 mg) as an off white solid. $^1$H NMR (400 MHz, CDCl3) δ 9.22 (t, J=1.7 Hz, 1H), 9.01 (t, J=1.9 Hz, 1H), 8.50 (t, J=2.1 Hz, 1H), 7.39-7.58 (m, 2H), 7.24 (dt, J=7.8, 1.9 Hz, 1H), 5.13 (d, J=6.6 Hz, 1H), 3.31 (q, J=6.8 Hz, 2H), 3.16 (q, J=6.6 Hz, 1H), 1.61 (q, J=7.2 Hz, 2H), 1.21-1.45 (m, 13H), 0.91 (td, J=6.2, 3.3 Hz, 3H).

Synthesis of methyl 5-(3-((cyclopentylcarbamoyl)oxy)phenyl)nicotinate (Example-11)

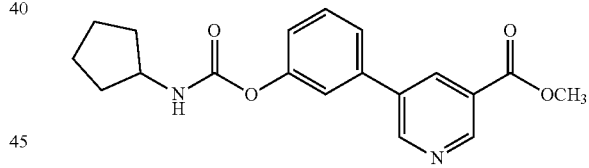

To a solution of methyl 5-(3-hydroxyphenyl)nicotinate (0.08 g, 0.34 mmol) in anhydrous acetonitrile (2 mL) was added TEA (0.14 mL, 1.0 mmol) and cyclopentyl isocyanate (0.03 g, 0.34 mmol) at RT under nitrogen atmosphere. The reaction mixture was stirred at RT for 10 minutes and then heated at 75° C. for 3 h under a nitrogen atmosphere. An additional amount of cyclopentyl isocyanate (0.01 g, 0.11 mmol) was added to the reaction mixture, and the reaction was heated for an additional 12 h. The reaction progress was monitored by TLC. After completion, the reaction mixture was cooled to RT, and the solvent was evaporated under reduced pressure. The crude product was purified by flash column chromatography on silica gel, eluting with a hexane/EtOAc gradient (20-25% EtOAc) to yield the target (52 mg) compound as an off white solid. $^1$H NMR (400 MHz, CDCl3) δ 9.22 (t, J=1.7 Hz, 1H), 9.01 (t, J=2.3 Hz, 1H), 8.50 (t, J=2.2 Hz, 1H), 7.37-7.54 (m, 3H), 7.24 (d, J=7.8 Hz, 1H), 5.09 (d, J=7.5 Hz, 1H), 4.10 (h, J=6.9 Hz, 1H), 4.01 (d, J=1.4 Hz, 3H), 2.07 (dt, J=13.1, 6.4 Hz, 2H), 1.63-1.83 (m, 4H), 1.54 (dq, J=13.2, 6.4 Hz, 2H).

Synthesis of methyl 5-(3-((cyclohexylcarbamoyl)oxy)phenyl)nicotinate (Example-12)

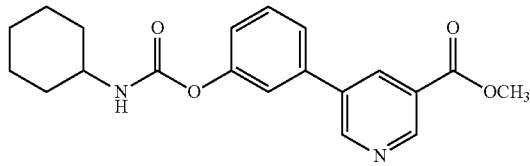 [SMILES: COC(=O)c1cncc(-c2cccc(OC(=O)NC3CCCCC3)c2)c1]

To a solution of methyl 5-(3-hydroxyphenyl)nicotinate (0.09 g, 0.39 mmol) in anhydrous acetonitrile (5 mL) was added TEA (0.06 mL, 0.47 mmol) at RT under nitrogen atmosphere.

The reaction mixture was stirred for 10 minutes and then added cyclohexyl isocyanate (0.05 ml, 0.39 mmol). The reaction mixture was heated at 75° C. for 3 h under nitrogen atmosphere. An additional amount of cyclohexyl isocyanate (0.03 g, 0.13 mmol) was added to the reaction mixture was heated for an additional 2 h. The reaction was monitored by TLC, after completion the reaction mixture was concentrated under reduced pressure. The crude product was purified by flash column chromatography on silica gel eluting with hexane/EtOAc (gradient 10-70% EtOAc) to yield the target compound (60 mg) as an off white solid. $^1$H NMR (400 MHz, DMSO-d6) δ 9.10 (d, J=4 Hz, 1H), 8.48 (s, 1H), 8.48 (s, 1H), 7.81 (d, J=8 Hz, 1H), 7.65 (d, J=8 Hz, 1H), 7.51-7.56 (m, 2H), 7.21 (d, J=8 Hz, 1H), 3.94 (s, 3H), 3.3 (s, 1H), 1.11-1.86 (m, 10H).

Synthesis of methyl 5-(3-(((((1s,3s)-adamantan-1-yl)carbamoyl)oxy)phenyl)nicotinate Example-13

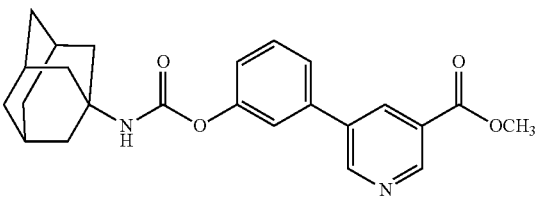 [SMILES: COC(=O)c1cncc(-c2cccc(OC(=O)NC34CC5CC(CC(C5)C3)C4)c2)c1]

To a solution of methyl 5-(3-hydroxyphenyl)nicotinate (0.08 g, 0.34 mmol) in anhydrous acetonitrile (2 mL) was added triethylamine (TEA) (0.14 mL, 1.0 mmol) and adamantyl isocyanate (0.06 g, 0.34 mmol) at RT under a nitrogen atmosphere. The reaction mixture was stirred at RT for 10 minutes and then heated to 75° C. for 3 h under a nitrogen atmosphere. An additional amount of adamantyl isocyanate (0.01 g, 0.11 mmol) was added to the reaction mixture, and the reaction was then heated for an additional 12 h. The reaction progress was monitored by TLC. Upon completion, the reaction mixture was cooled to RT, and the solvent was evaporated under reduced pressure. The crude product was purified by flash column chromatography on silica gel, eluting with a hexane/ethyl acetate gradient (20-25% EtOAc) to yield the target compound (80 mg) as an off white solid. $^1$H NMR (400 MHz, CDCl3) δ 9.22 (d, J=1.9 Hz, 1H), 9.01 (d, J=2.1 Hz, 1H), 8.50 (q, J=1.9 Hz, 1H), 7.40-7.54 (m, 3H), 7.23 (d, J=7.5 Hz, 1H), 4.98 (s, 1H), 4.01 (d, J=1.4 Hz, 3H), 2.15 (s, 3H), 2.01-2.12 (m, 6H), 1.72 (d, J=6.3 Hz, 6H), 1.63 (s, 2H).

Synthesis of 5-(3-hydroxyphenyl)nicotinaldehyde

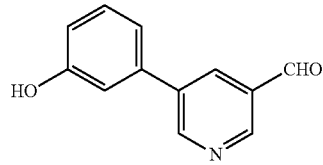 [SMILES: O=Cc1cncc(-c2cccc(O)c2)c1]

To a solution of 5-bromonicotinaldehyde (0.25 g, 1.34 mmol) in 1,4-dioxane (8 mL) was added (3-hydroxyphenyl)boronic acid (0.18 g, 1.34 mmol) and 0.4M Na$_2$CO$_3$ solution (5 mL) at RT. The reaction mixture was degassed for 15 minutes then Pd(PPh$_3$)$_4$ (0.01 g, 0.067 mmol) was added. The reaction mixture was heated to 80° C. for 4 h under nitrogen atmosphere. The reaction progress was monitored by TLC, after completion the reaction mixture was cooled to RT and then the solvent was evaporated under reduced pressure. The crude compound was purified by flash column chromatography on silica gel eluting with hexane/EtOAc (gradient 10-60% EtOAc) to yield the 5-(3-hydroxyphenyl)nicotinaldehyde (120 mg) as an off white solid. $^1$H NMR (400 MHz, DMSO-d6) δ 9.72 (s, 1H), 9.14 (s, 1H), 8.96 (s, 1H), 8.37 (s, 1H), 7.34 (t, J=8.1 Hz, 1H), 7.24 (d, J=4 Hz, 1H), 7.17 (s, 1H), 6.89 (dd, J=8.0 Hz, 1H).

Synthesis of 3-(5-formylpyridin-3-yl)phenyl pentylcarbamate (Example-14)

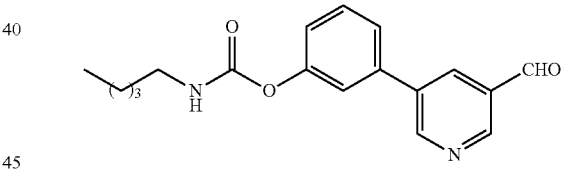

To a suspension of 5-(3-hydroxyphenyl)nicotinaldehyde (0.08 g, 0.40 mmol) in anhydrous acetonitrile (2 mL), TEA (0.16 mL, 1.2 mmol) and n-pentyl isocyanate (0.05 g, 0.40 mmol) were added at RT under a nitrogen atmosphere. The reaction mixture was stirred at RT for 10 minutes and then heated at 75° C. for 3 h under a nitrogen atmosphere. An additional amount of n-pentyl isocyanate (0.01 g, 0.14 mmol) was added to the reaction mixture, and the reaction was heated for an additional 12 h. The reaction progress was monitored by TLC. After completion, the reaction mixture was cooled to RT and then the solvent was evaporated under reduced pressure. The crude product was purified by flash column chromatography on silica gel, eluting with a gradient of hexane/EtOAc (10-15% EtOAc) to yield the target compound (53 mg) as an off white solid. $^1$H NMR (400 MHz, CDCl3) δ 10.12 (s, 1H), 8.99 (dd, J=4.6, 2.1 Hz, 2H), 8.26 (t, J=2.2 Hz, 1H), 7.32-7.50 (m, 3H), 7.16 (ddd, J=7.9, 2.3, 1.4 Hz, 1H), 5.05 (d, J=6.0 Hz, 1H), 3.22 (td, J=7.3, 6.0 Hz, 2H), 1.53 (p, J=7.3 Hz, 2H), 1.18-1.36 (m, 4H), 0.78-0.90 (m, 3H).

Synthesis of 3-(5-formylpyridin-3-yl)phenyl heptylcarbamate (Example-15)

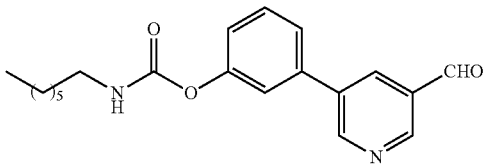

To a suspension of 5-(3-hydroxyphenyl)nicotinaldehyde (0.08 g, 0.40 mmol) in anhydrous acetonitrile (3 mL) was added TEA (0.16 mL, 1.2 mmol) and n-heptyl isocyanate (0.05 g, 0.40 mmol) at RT under nitrogen atmosphere. The reaction mixture was stirred at RT for 10 minutes and then heated at 75° C. for 3 h under nitrogen atmosphere. An additional amount of n-heptyl isocyanate (0.01 g, 0.14 mmol) was added to the reaction mixture, and the reaction was heated for an additional 12 h. The reaction progress was monitored by TLC. After completion, the reaction mixture was cooled to RT and then the solvent was evaporated under reduced pressure.

The crude product was purified by flash column chromatography on silica gel, eluting with hexane/EtOAc (gradient 10-15% EtOAc) to yield the target compound (59 mg) as an off white solid. $^1$H NMR (400 MHz, CDCl3) δ 10.22 (s, 1H), 9.09 (dd, J=4.7, 2.1 Hz, 2H), 8.36 (t, J=2.2 Hz, 1H), 7.37-7.75 (m, 3H), 7.26 (dt, J=7.7, 1.8 Hz, 1H), 5.12 (d, J=6.0 Hz, 1H), 3.32 (q, J=6.8 Hz, 2H), 1.64 (q, J=7.1 Hz, 2H), 1.36 (tdd, J=19.5, 14.0, 10.5 Hz, 8H), 0.80-1.01 (m, 3H).

Synthesis of 3-(5-formylpyridin-3-yl)phenyl octylcarbamate (Example-16)

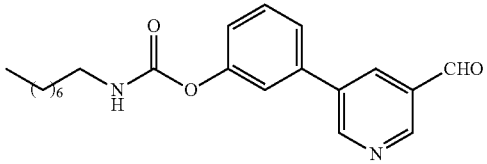

To a suspension of 5-(3-hydroxyphenyl)nicotinaldehyde (0.08 g, 0.40 mmol) in anhydrous acetonitrile (2 mL) was added TEA (0.16 mL, 1.2 mmol) and n-octyl isocyanate (0.06 g, 0.40 mmol) at RT under nitrogen atmosphere. The reaction mixture was stirred at RT for 10 minutes and then heated at 75° C. for 3 h under nitrogen atmosphere. An additional amount of n-octyl isocyanate (0.02 g, 0.14 mmol) was added to the reaction mixture, and the reaction was heated for an additional 12 h. The reaction progress was monitored by TLC. After completion, the reaction mixture was cooled to RT and then the solvent was evaporated under reduced pressure. The crude product was purified by flash column chromatography on silica gel, eluting with hexane/EtOAc (gradient 10-15% EtOAc) to yield the target compound (58 mg) as an off white solid. $^1$H NMR (400 MHz, CDCl3) δ 10.22 (s, 1H), 9.09 (dd, J=5.0, 2.2 Hz, 2H), 8.37 (d, J=2.4 Hz, 1H), 7.41-7.64 (m, 3H), 7.26 (d, J=7.8 Hz, 1H), 5.12 (t, J=5.7 Hz, 1H), 3.32 (q, J=6.8 Hz, 2H), 1.64 (q, J=7.1 Hz, 2H), 1.23-1.49 (m, 10H), 0.91 (h, J=3.3 Hz, 3H).

Synthesis of 3-(5-formylpyridin-3-yl)phenyl (cyclohexylmethyl)carbamate (Example-17)

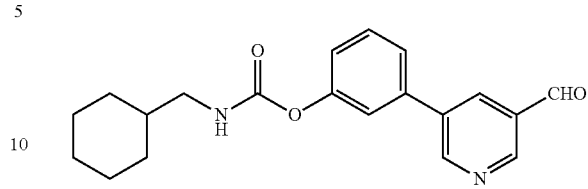

To a suspension of 5-(3-hydroxyphenyl)nicotinaldehyde (0.08 g, 0.40 mmol) in anhydrous acetonitrile (2 mL), TEA (0.16 mL, 1.2 mmol) and cyclohexanemethyl isocyanate (0.05 g, 0.40 mmol) were added at RT under a nitrogen atmosphere. The reaction mixture was stirred at RT for 10 minutes and then heated to 75° C. for 3 h under a nitrogen atmosphere. An additional amount of cyclohexanemethyl isocyanate (0.015 g, 0.14 mmol) was added to the reaction mixture, and the reaction was heated for an additional 12 h. The reaction progress was monitored by TLC. After completion, the reaction mixture was cooled to RT, and then the solvent was evaporated under reduced pressure. The crude product was purified by flash column chromatography on silica gel, eluting with a gradient of hexane/EtOAc (10-15% EtOAc) to yield the target compound (57 mg) as an off white solid. $^1$H NMR (400 MHz, CDCl3) δ 10.19 (s, 1H), 9.05 (d, J=2.0 Hz, 1H), 8.33 (s, 1H), 5.11 (s, 1H), 3.29 (td, J=7.3, 6.0 Hz, 2H), 3.14 (td, J=7.2, 5.5 Hz, 1H), 1.60 (dd, J=8.4, 5.8 Hz, 1H), 1.26-1.44 (m, 11H), 1.44-1.55 (m, 1H), 0.90-1.12 (m, 3H).

Synthesis of 3-(5-formylpyridin-3-yl)phenyl cyclopentylcarbamate (Example-18)

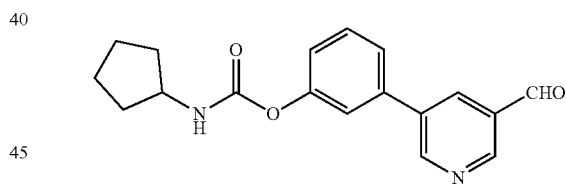

To a suspension of 5-(3-hydroxyphenyl)nicotinaldehyde (0.08 g, 0.40 mmol) in anhydrous acetonitrile (2 mL) was added TEA (0.16 mL, 1.2 mmol) and cyclopentyl isocyanate (0.04 g, 0.40 mmol) at RT under a nitrogen atmosphere. The reaction mixture was stirred at RT for 10 minutes and then heated at 75° C. for 3 h under a nitrogen atmosphere. An additional amount of cyclopentyl isocyanate (0.01 g, 0.14 mmol) was added to the reaction mixture, and the reaction was heated for an additional 3 h. The reaction progress was monitored by TLC. Upon completion, the reaction mixture was cooled to RT and then the solvent was evaporated under reduced pressure. The crude product was purified by flash column chromatography on silica gel, eluting with hexane/EtOAc (gradient 10-15% EtOAc) to yield the target compound (50 mg) as an off white solid. $^1$H NMR (400 MHz, CDCl3) δ 10.22 (s, 1H), 9.09 (dd, J=5.1, 2.2 Hz, 2H), 8.37 (d, J=2.5 Hz, 1H), 7.42-7.69 (m, 3H), 7.26 (d, J=8.0 Hz, 1H), 5.08 (d, J=7.4 Hz, 1H), 3.83-4.35 (m, 2H), 1.85-2.17 (m, 2H), 1.53-1.85 (m, 3H), 1.32-1.53 (m, 2H).

Synthesis of (5-formylpyridin-3-yl)phenyl cyclohexylcarbamate (Example-19)

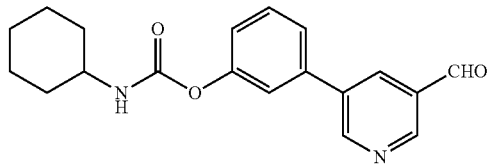 [SMILES: O=Cc1cncc(-c2cccc(OC(=O)NC3CCCCC3)c2)c1]

To a suspension of 5-(3-hydroxyphenyl)nicotinaldehyde (0.08 g, 0.40 mmol) in anhydrous acetonitrile (2 mL) was added TEA (0.16 mL, 1.2 mmol) and cyclohexyl isocyanate (0.05 g, 0.40 mmol) at RT under a nitrogen atmosphere. The reaction mixture was stirred at RT for 10 minutes and then heated at 75° C. for 3 h under a nitrogen atmosphere. An additional amount of cyclohexyl isocyanate (0.01 g, 0.14 mmol) was added to the reaction mixture, and the reaction was heated for an additional 12 h. The reaction progress was monitored by TLC. Upon completion, the reaction mixture was cooled to RT and then the solvent was evaporated under reduced pressure. The crude product was purified by flash column chromatography on silica gel, eluting with hexane/EtOAc (gradient 10-15% EtOAc) to yield the target compound (50 mg) as an off white solid. $^1$H NMR (400 MHz, CDCl3) δ 10.12 (s, 1H), 8.99 (dd, J=5.4, 2.1 Hz, 2H), 8.26 (t, J=2.2 Hz, 1H), 7.34-7.50 (m, 3H), 7.16 (ddd, J=7.8, 2.3, 1.3 Hz, 1H), 4.92 (d, J=8.2 Hz, 1H), 3.51 (ddp, J=10.5, 7.9, 4.0 Hz, 1H), 1.97 (dd, J=12.2, 3.7 Hz, 2H), 1.60-1.75 (m, 2H), 1.08-1.44 (m, 6H).

Synthesis of 3-(5-formylpyridin-3-yl)phenyl cyclohepylcarbamate (Example-20)

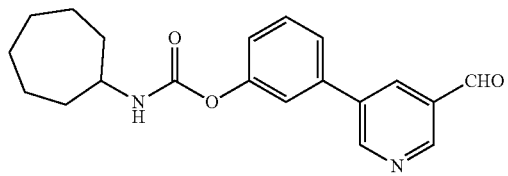 [SMILES: O=Cc1cncc(-c2cccc(OC(=O)NC3CCCCCC3)c2)c1]

To a suspension of 5-(3-hydroxyphenyl)nicotinaldehyde (0.08 g, 0.40 mmol) in anhydrous acetonitrile (2 mL) was added TEA (0.16 mL, 1.2 mmol) and cycloheptyl isocyanate (0.05 g, 0.40 mmol) at RT under a nitrogen atmosphere. The reaction mixture was stirred at RT for 10 minutes and then heated at 75° C. for 3 h under a nitrogen atmosphere. An additional amount of cycloheptyl isocyanate (0.01 g, 0.14 mmol) was added to the reaction mixture, and the reaction was heated for an additional 12 h. The reaction progress was monitored by TLC. Upon completion, the reaction mixture was cooled to RT, and then the solvent was evaporated under reduced pressure. The crude product was purified by flash column chromatography on silica gel, eluting with hexane/EtOAc (gradient 10-15% EtOAc) to yield the target compound (53 mg) as an off white solid. $^1$H NMR (400 MHz, CDCl3) δ 10.19 (s, 1H), 9.06 (dd, J=5.3, 2.1 Hz, 2H), 8.33 (t, J=2.2 Hz, 1H), 7.37-7.67 (m, 3H), 7.14-7.30 (m, 1H), 5.04 (d, J=8.2 Hz, 1H), 3.78 (d, J=10.3 Hz, 1H), 1.97-2.21 (m, 2H), 1.47-1.81 (m, 12H).

Synthesis of 3-(5-formylpyridin-3-yl)phenyl ((1s,3s)-adamantan-1-yl)carbamate (Example-21)

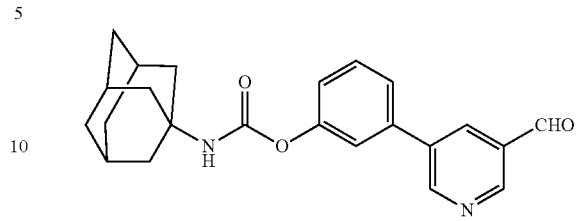

To a suspension of 5-(3-hydroxyphenyl)nicotinaldehyde (0.08 g, 0.40 mmol) in anhydrous acetonitrile (2 mL) was added TEA (0.16 mL, 1.2 mmol) and adamantyl isocyanate (0.07 g, 0.40 mmol) at RT under nitrogen atmosphere. The reaction mixture was stirred at RT for 10 minutes and then heated at 75° C. for 3 h under nitrogen atmosphere. An additional amount of adamantyl isocyanate (0.02 g, 0.14 mmol) was added to the reaction mixture, and the reaction was heated for an additional 12 h. The reaction progress was monitored by TLC. After completion, the reaction mixture was cooled to RT, and then the solvent was evaporated under reduced pressure. The crude product was purified by flash column chromatography on silica gel, eluting with hexane/EtOAc (gradient 10-15% EtOAc) to yield the target compound (59 mg) as an off white solid. $^1$H NMR (400 MHz, CDCl3) δ 10.22 (s, 1H), 9.09 (dd, J=5.4, 2.1 Hz, 2H), 8.36 (t, J=2.2 Hz, 1H), 7.35-7.61 (m, 3H), 7.25 (dt, J=7.9, 1.7 Hz, 1H), 4.98 (s, 1H), 2.06 (s, 4H), 2.11 (d, J=37.6 Hz, 6H), 1.74 (d, J=3.1 Hz, 5H).

Synthesis of 5-(3-hydroxyphenyl)-N-((tetrahydro-2H-pyran-2-yl)oxy)nicotinamide

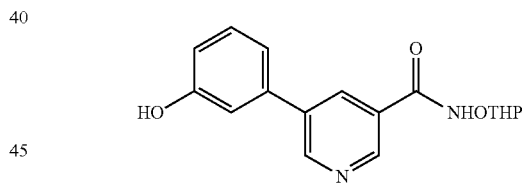

To a stirring solution of the 5-(3-hydroxyphenyl)nicotinic acid (1.0 g, 4.65 mmol) in dry N—N-dimethylformamide (DMF) at RT, EDC HCl (1.06 g, 5.58 mmol) and HOBt (0.91 g, 9.2 mmol) were subsequentially added. After 10 minutes, the o-(tetrahydro-2h-pyran-2-yl)hydroxylamine (0.53 g, 4.6 mmol) was added to the reaction mixture followed by the addition of TEA (1.8 mL, 13.9 mmol). The mixture was stirred under nitrogen atmosphere overnight at RT. The end of the reaction was monitored by TLC. Afterward, the reaction was quenched with saturated NaHCO₃ solution, and the mixture was extracted with ethyl acetate (EtOAc). The organic layer was washed with distilled water, 2N HCl solution and saturated NaCl. The organic layer was then dried over anhydrous Na₂SO₄ and the EtOAc evaporated to give the crude peptide which was purified by flash column chromatography on silica gel eluting with hexane/EtOAc (gradient 60-80% EtOAc) to yield the 5-(3-hydroxyphenyl)-N-((tetrahydro-2H-pyran-2-yl)oxy)nicotinamide (600 mg) as an off white solid.

Synthesis of 3-(5-(((tetrahydro-2H-pyran-2-yl)oxy)carbamoyl)pyridin-3-yl)phenylheptylcarbamate

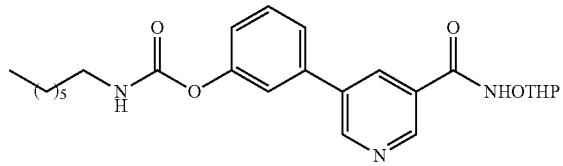

To a suspension of 5-(3-hydroxyphenyl)-N-((tetrahydro-2H-pyran-2-yl)oxy)nicotinamide (0.08 g, 0.25 mmol) in anhydrous acetonitrile (3 mL) was added TEA (0.10 mL, 0.75 mmol) and n-heptyl isocyanate (0.035 g, 0.25 mmol) at RT under nitrogen atmosphere. The reaction mixture was stirred at RT for 10 minutes and then heated at 75° C. for 3 h under nitrogen atmosphere. An additional amount of n-heptyl isocyanate (0.015 g, 0.11 mmol) was added to the reaction mixture and the reaction was heated for an additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 50-60% EtOAc) to yield 3-(5-(((tetrahydro-2H-pyran-2-yl)oxy)carbamoyl)pyridin-3-yl)phenyl heptyllcarbamate (34 mg) as an off white solid. $^1$H NMR (400 MHz, DMSO-d6) δ 11.94 (s, 1H), 9.05 (d, J=2.2 Hz, 1H), 8.92 (d, J=2.0 Hz, 1H), 8.37 (t, J=2.1 Hz, 1H), 7.81 (t, J=5.7 Hz, 1H), 7.64 (dt, J=7.8, 1.2 Hz, 1H), 7.44-7.62 (m, 2H), 7.19 (ddd, J=8.1, 2.3, 1.0 Hz, 1H), 5.05 (t, J=2.8 Hz, 1H), 4.07 (q, J=7.4 Hz, 1H), 3.44-3.81 (m, 1H), 3.07 (td, J=7.1, 5.8 Hz, 2H), 1.40-1.64 (m, 6H), 1.10-1.38 (m, 9H), 0.51-1.10 (m, 3H).

Synthesis of 3-(5-(hydroxycarbamoyl)pyridin-3-yl)phenyl heptylcarbamate (Example-22)

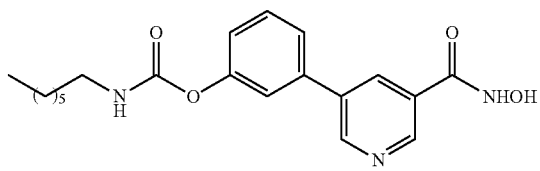

To a solution of 3-(5-(((tetrahydro-2H-pyran-2-yl)oxy)carbamoyl)pyridin-3-yl)phenyl octylcarbamate (0.03, 0.05 mmol), in hydrogen chloride in methanol (2 mL, 4N HCl in methanol) at RT and the reaction stirred over 2 h. The reaction progress monitored by TLC, after completion the reaction mixture solvent was evaporated under reduced pressure. The desired product was purified via recrystallization using ethanol to yield the target compound (25 mg) as an off white solid. $^1$H NMR (400 MHz, DMSO-d6) δ 9.15 (d, J=2.2 Hz, 1H), 9.00 (d, J=1.9 Hz, 1H), 8.61 (t, J=2.1 Hz, 1H), 7.84 (t, J=5.7 Hz, 1H), 7.71 (dt, J=7.8, 1.2 Hz, 1H), 7.49-7.66 (m, 2H), 7.22 (dd, J=8.0, 2.3 Hz, 1H), 3.08 (q, J=6.6 Hz, 1H), 1.49 (p, J=7.2 Hz, 2H), 1.28 (q, J=6.5 Hz, 5H), 0.81-0.95 (m, 3H)

Synthesis of 3-(5-(((tetrahydro-2H-pyran-2-yl)oxy)carbamoyl)pyridin-3-yl)phenyl octylcarbamate

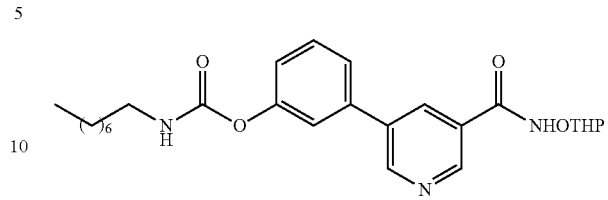

To a suspension of 5-(3-hydroxyphenyl)-N-((tetrahydro-2H-pyran-2-yl)oxy)nicotinamide (0.08 g, 0.25 mmol) in anhydrous acetonitrile (3 mL) was added TEA (0.10 mL, 0.75 mmol) and n-octyl isocyanate (0.038 g, 0.25 mmol) at RT under nitrogen atmosphere. The reaction mixture was stirred at RT for 10 minutes and then heated at 75° C. for 3 h under nitrogen atmosphere. An additional amount of n-octyl isocyanate (0.017 g, 0.11 mmol) was added to the reaction mixture and the reaction was heated for an additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 50-60% EtOAc) to yield the 3-(5-(((tetrahydro-2H-pyran-2-yl)oxy)carbamoyl)pyridin-3-yl)phenyl octylcarbamate (30 mg) as an off white solid. $^1$H NMR (400 MHz, DMSO-d6) δ 11.93 (s, 1H), 9.05 (d, J=2.2 Hz, 1H), 8.92 (d, J=2.0 Hz, 1H), 8.36 (t, J=2.2 Hz, 1H), 7.81 (t, J=5.7 Hz, 1H), 7.39-7.75 (m, 3H), 7.19 (ddd, J=8.1, 2.3, 1.0 Hz, 1H), 5.05 (s, 1H), 3.74-4.37 (m, 1H), 3.49-3.64 (m, 1H), 3.31 (s, 6H), 3.07 (q, J=6.9 Hz, 2H), 1.75 (s, 4H), 1.42-1.67 (m, 6H), 1.16-1.40 (m, 14H), 0.86 (td, J=6.8, 1.9 Hz, 4H).

Synthesis of 3-(5-(hydroxycarbamoyl)pyridin-3-yl)phenyl octylcarbamate (Example-23)

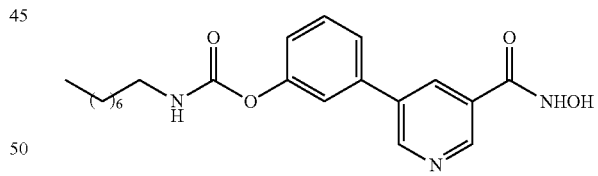

To a solution of 3-(5-(((tetrahydro-2H-pyran-2-yl)oxy)carbamoyl)pyridin-3-yl)phenyl octylcarbamate (0.03, 0.05 mmol), in hydrogen chloride in methanol (2 mL, 4M HCl in methanol) at RT and the reaction was stirred over 2 h. the reaction progress was monitored by TLC, after completion the reaction mixture solvent was evaporated under reduced pressure. The desired product was purified via recrystallization using ethanol to yield the target compound (15 mg) as an off white solid. $^1$H NMR (400 MHz, DMSO-d6) δ 9.15 (d, J=2.2 Hz, 1H), 9.00 (d, J=1.9 Hz, 1H), 8.61 (t, J=2.1 Hz, 1H), 7.84 (t, J=5.7 Hz, 1H), 7.71 (dt, J=8.0, 1.2 Hz, 1H), 7.61 (t, J=2.0 Hz, 1H), 7.56 (t, J=7.9 Hz, 1H), 7.17-7.35 (m, 1H), 3.08 (q, J=6.7 Hz, 2H), 1.14-1.39 (m, 8H), 1.49 (t, J=7.0 Hz, 2H), 0.79-0.91 (m, 3H).

Synthesis of 3-(5-(((tetrahydro-2H-pyran-2-yl)oxy)carbamoyl)pyridin-3-yl)phenyl tetradecylcarbamate

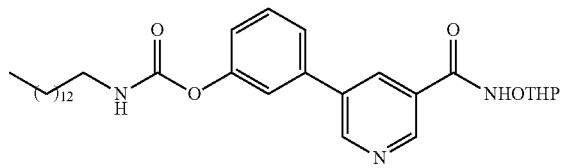

To a suspension of 5-(3-hydroxyphenyl)-N-((tetrahydro-2H-pyran-2-yl)oxy)nicotinamide (0.08 g, 0.25 mmol) in anhydrous acetonitrile (3 mL) was added TEA (0.10 mL, 0.75 mmol) and n-tetradecyl isocyanate (0.053 g, 0.25 mmol) at RT under nitrogen atmosphere. The reaction mixture was stirred at RT for 10 minutes and then heated at 75° C. for 3 h under nitrogen atmosphere. An additional amount of n-tetradecyl isocyanate (0.023 g, 0.11 mmol) was added to the reaction mixture and the reaction was heated for an additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 50-60% EtOAc) to yield the 3-(5-(((tetrahydro-2H-pyran-2-yl)oxy)carbamoyl)pyridin-3-yl)phenyl tetradecylcarbamate (23 mg) as an off white solid. $^1$H NMR (400 MHz, DMSO-d6) δ 11.94 (s, 1H), 9.05 (d, J=2.2 Hz, 1H), 8.92 (d, J=2.0 Hz, 1H), 8.36 (t, J=2.2 Hz, 1H), 7.80 (t, J=5.7 Hz, 1H), 7.64 (dt, J=7.9, 1.2 Hz, 1H), 7.45-7.57 (m, 2H), 7.19 (ddd, J=8.1, 2.3, 1.0 Hz, 1H), 5.05 (d, J=3.1 Hz, 1H), 4.05 (d, J=10.8 Hz, 1H), 3.51-3.67 (m, 1H), 3.07 (q, J=6.6 Hz, 2H), 1.24 (d, J=6.6 Hz, 26H), 1.40-1.66 (m, 5H), 0.70-0.94 (m, 3H).

Synthesis of 3-(5-(hydroxycarbamoyl)pyridin-3-yl)phenyl tetradecylcarbamate (Example-24)

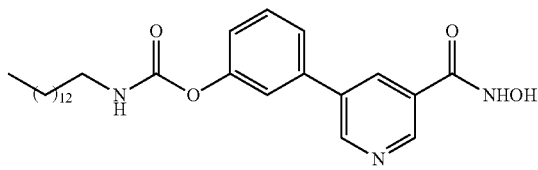

To a solution of 3-(5-(((tetrahydro-2H-pyran-2-yl)oxy)carbamoyl)pyridin-3-yl)phenyl octylcarbamate (0.03, 0.05 mmol), in hydrogen chloride in methanol (2 mL, 4N in Methanol) at RT and the reaction was stirred over 2 h. the reaction progress was monitored by TLC, after completion the reaction mixture solvent was evaporated under reduced pressure. The desired product was purified via recrystallization using methanol to yield the target compound (20 mg) as an off white solid. $^1$H NMR (400 MHz, DMSO-d6) δ 9.11 (d, J=2.2 Hz, 1H), 8.97 (d, J=2.0 Hz, 1H), 8.52 (t, J=2.1 Hz, 1H), 7.83 (t, J=5.7 Hz, 1H), 7.68 (ddd, J=7.8, 1.8, 1.0 Hz, 1H), 7.51-7.60 (m, 2H), 7.21 (ddd, J=8.1, 2.3, 0.9 Hz, 1H), 3.07 (q, J=6.8 Hz, 2H), 1.25 (d, J=6.1 Hz, 15H), 1.30-2.07 (m, 3H), 0.44-1.06 (m, 3H).

Synthesis of 5-(3-hydroxyphenyl)nicotinohydrazide

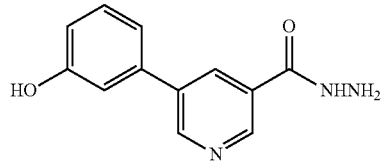 [SMILES: NNC(=O)c1cncc(-c2cccc(O)c2)c1]

To a solution of ethyl 5-(3-hydroxyphenyl)nicotinate (0.25 g, 1.028 mmol) in ethanol (6 mL) was added hydrazine hydrate (0.61 g, 6.16 mmol) at RT. The reaction mixture was heated at 90° C. for 15 h. The reaction progress was monitored by TLC, after completion the reaction was cooled to RT. The precipitated product was collected by filtrations and washed by ethanol. The filtrate was evaporated under reduced pressure and the residue was purified by flash chromatography on silica gel eluting with dichloromethane (DCM)/MeOH (gradient 2-5% MeOH) to yield the 5-(3-hydroxyphenyl)nicotinohydrazide (140 mg) as a pale-yellow solid. $^1$H NMR (400 MHz, DMSO-d6) δ 10.06 (s, 1H), 9.67 (s, 1H), 8.94 (m, 2H), 8.35 (m, 1H), 7.32 (m, 1H), 7.20 (d, J=7.7 Hz, 1H), 6.86 (dd, J=7.8, 1.7 Hz, 1H), 4.60 (s, 2H), 7.14 (s, 1H)

Synthesis of 3-(5-(hydrazinecarbonyl)pyridin-3-yl)phenyl octylcarbamate (Example-25)

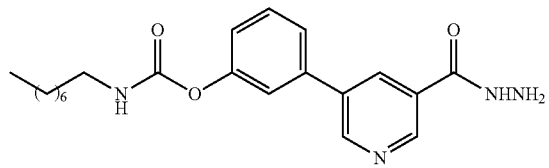

To a suspension of 3-(5-(oxazol-2-yl)pyridin-3-yl)phenol (0.08 g, 0.33 mmol) in anhydrous acetonitrile (6 mL) was added TEA (0.13 mL, 0.99 mmol) and octyl isocyanate (0.041 g, 0.33 mmol) at RT under nitrogen atmosphere. The reaction mixture was stirred at RT for 10 minutes and then heated at 75° C. for 3 h under nitrogen atmosphere. An additional amount of octyl isocyanate (0.013 g, 0.11 mmol) was added to the reaction mixture and the reaction was heated for an additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 80-100% EtOAc) to yield the target compound (80 mg) as an off white solid. $^1$H NMR (400 MHz, DMSO-d6) δ 9.12 (d, J=2.2 Hz, 1H), 8.98 (d, J=2.0 Hz, 1H), 8.55 (t, J=2.1 Hz, 1H), 7.84 (t, J=5.7 Hz, 1H), 7.69 (dt, J=8.0, 1.2 Hz, 1H), 7.50-7.63 (m, 2H), 7.22 (ddd, J=8.1, 2.3, 1.0 Hz, 1H), 3.45-2.83 (m, 2H), 1.48 (d, J=7.2 Hz, 2H), 1.29 (dt, J=10.1, 5.7 Hz, 12H), 0.53-1.02 (m, 3H).

Synthesis of 5-(3-hydroxyphenyl)nicotinonitrile

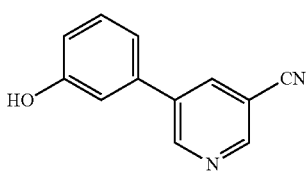 [SMILES: N#Cc1cncc(-c2cccc(O)c2)c1]

To a solution of 5-bromonicotinonitrile (0.23 g, 1.34 mmol) in 1,4-dioxane (8 mL) was added (3-hydroxyphenyl) boronic acid (0.18 g, 1.34 mmol) and 0.4M $Na_2CO_3$ solution (5 mL) at RT. The reaction mixture was degassed for 15 minutes then $Pd(PPh_3)_4$ (0.01 g, 0.067 mmol) was added. The reaction mixture was heated to 80° C. for 4 h under nitrogen atmosphere. The reaction progress was monitored by TLC, after completion the reaction mixture was cooled to RT and then the solvent was evaporated under reduced pressure. The crude compound was purified by flash column chromatography on silica gel eluting with hexane/EtOAc (gradient 10-60% EtOAc) to yield the 5-(3-hydroxyphenyl) nicotinonitrile (120 mg) as an off white solid. $^1$H-NMR (400 MHz, DMSO-d6) δ 9.72 (s, 1H), 9.14 (s, 1H), 8.96 (s, 1H), 8.37 (s, 1H), 7.34 (t, J=8.1 Hz, 1H), 7.24 (d, J=4 Hz, 1H), 6.89 (dd, J=8.0 Hz, 1H), 7.17 (s, 1H).

Synthesis of 3-(5-cyanopyridin-3-yl)phenyl heptylcarbamate (Example-26)

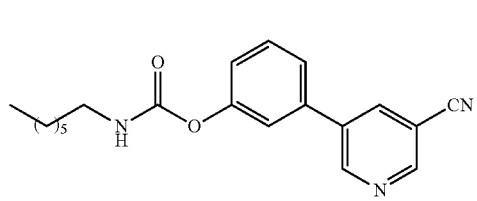

To a suspension of 5-(3-hydroxyphenyl)nicotinonitrile (0.1 g, 0.51 mmol) in anhydrous acetonitrile (2 mL) was added TEA (0.07 mL, 0.51 mmol) and n-heptyl isocyanate (0.08 g, 0.61 mmol) at RT under nitrogen atmosphere. The reaction mixture was stirred at RT for 10 minutes and then heated at 75° C. for 12 h under nitrogen atmosphere. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 15-25% EtOAc) to yield the target compound (88 mg) as an off white solid. $^1$H NMR (400 MHz, CDCl3) δ 8.95 (d, J=2.3 Hz, 1H), 8.79 (d, J=2.0 Hz, 1H), 8.05 (t, J=2.1 Hz, 1H), 7.44 (t, J=7.9 Hz, 1H), 7.26-7.38 (m, 2H), 7.08-7.19 (m, 1H), 5.01 (s, 1H), 3.11-3.37 (m, 2H), 1.16-1.39 (m, 8H), 1.54 (d, J=7.1 Hz, 2H), 0.78-0.86 (m, 3H).

Synthesis of 3-(5-cyanopyridin-3-yl)phenyl octylcarbamate (Example-27)

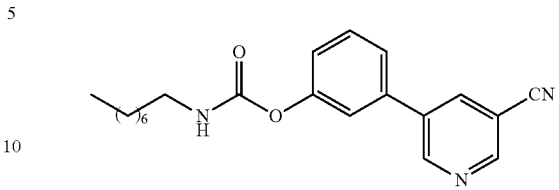

To a suspension of 5-(3-hydroxyphenyl)nicotinonitrile (0.1 g, 0.51 mmol) in anhydrous acetonitrile (2 mL) was added TEA (0.07 mL, 0.51 mmol) and n-octyl isocyanate (0.09 g, 0.61 mmol) at RT under nitrogen atmosphere. The reaction mixture was stirred at RT for 10 minutes and then heated at 75° C. for 3 h under nitrogen atmosphere. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 15-25% EtOAc) to yield the 5-(3-hydroxyphenyl)nicotinonitrile (69 mg) as an off white solid. $^1$H NMR (400 MHz, CDCl3) δ 9.02 (d, J=2.3 Hz, 1H), 8.86 (d, J=2.0 Hz, 1H), 8.12 (t, J=2.1 Hz, 1H), 7.51 (t, J=7.9 Hz, 1H), 7.29-7.46 (m, 2H), 7.03-7.34 (m, 2H), 5.07 (d, J=6.7 Hz, 1H), 3.29 (td, J=7.3, 6.0 Hz, 2H), 1.14-1.39 (m, 10H), 0.63-0.99 (m, 3H), 1.58 (s, 2H).

Synthesis of 3-(5-cyanopyridin-3-yl)phenyl cyclohexylcarbamate (Example-28)

To a suspension of 5-(3-hydroxyphenyl)nicotinonitrile (0.1 g, 0.51 mmol) in anhydrous acetonitrile (2 mL) was added TEA (0.07 mL, 0.51 mmol) and cyclohexyl isocyanate (0.07 g, 0.61 mmol) at RT under nitrogen atmosphere. The reaction mixture was stirred at RT for 10 minutes and then heated at 75° C. for 3 h under nitrogen atmosphere. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 15-25% EtOAc) to yield the target compound (77 mg) as an off white solid. $^1$H NMR (400 MHz, CDCl3) δ 8.95 (d, J=2.3 Hz, 1H), 8.79 (d, J=2.0 Hz, 1H), 8.05 (t, J=2.1 Hz, 1H), 7.43 (t, J=7.9 Hz, 1H), 7.26-7.36 (m, 2H), 7.11-7.19 (m, 1H), 4.93 (d, J=8.1 Hz, 1H), 3.51 (pd, J=6.8, 4.1 Hz, 1H), 1.96 (dq, J=12.1, 3.7 Hz, 3H), 1.68 (dh, J=13.6, 4.3 Hz, 2H), 1.09-1.39 (m, 5H).

Synthesis of 3-(5-cyanopyridin-3-yl)phenyl cycloheptylcarbamate (Example-29)

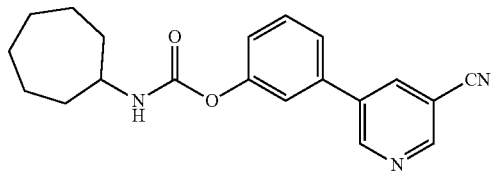 [SMILES: N#Cc1cncc(-c2cccc(OC(=O)NC3CCCCCC3)c2)c1]

To a suspension of 5-(3-hydroxyphenyl)nicotinonitrile (0.1 g, 0.51 mmol) in anhydrous acetonitrile (2 mL) was added TEA (0.07 mL, 0.51 mmol) and cycloheptyl isocyanate (0.08 g, 0.61 mmol) at RT under nitrogen atmosphere. The reaction mixture was stirred at RT for 10 minutes and then heated at 75° C. for 3 h under nitrogen atmosphere. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 15-25% EtOAc) to yield the target compound (73 mg) as an off white solid. $^1$H NMR (400 MHz, CDCl3) δ 8.95 (d, J=2.3 Hz, 1H), 8.79 (d, J=2.0 Hz, 1H), 8.05 (t, J=2.1 Hz, 1H), 7.43 (t, J=7.9 Hz, 1H), 7.29-7.38 (m, 2H), 7.09-7.18 (m, 1H), 5.00 (d, J=8.1 Hz, 1H), 4.06 (d, J=7.8 Hz, 1H), 3.66 (dqd, J=33.9, 8.0, 3.8 Hz, 1H), 1.76-2.05 (m, 3H), 1.43-1.55 (m, 8H).

Synthesis of 3-(5-(trifluoromethyl)pyridin-3-yl)phenol

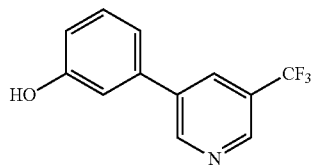 [SMILES: Oc1cccc(-c2cncc(C(F)(F)F)c2)c1]

To a stirred solution of 3-bromo-5-(trifluoromethyl)pyridine (0.10 g, 0.44 mmol) in 1,4-dioxane (6 ml), was added 3-(4,4,5,5-tetramethyl-1,3,2-dioxaborolan-2-yl)phenol (0.12 g, 0.53 mmol), KOAc (0.13 g, 1.32 mmol) at RT under nitrogen atmosphere. The reaction mixture was degassed for 10 minutes then Pd(dppf)Cl$_2$ (0.01 g, 0.013 mmol) was added. The reaction was heated at 80° C. for 12 h under nitrogen atmosphere. The reaction progress was monitored by TLC, after completion the reaction mixture was cooled to RT then evaporated under reduced pressure. The crude product was purified by flash column chromatography on silica gel eluting with hexane/EtOAc (gradient 10-70% EtOAc) to yield the 3-(5-(trifluoromethyl)pyridin-3-yl)phenol (60 mg) as an off white solid. $^1$H-NMR (400 MHz, DMSO-d6): δ 6.89 (dd, J=8.0 Hz, 1H), 7.17 (s, 1H), 7.24 (d, J=4 Hz, 1H), 7.34 (t, J=8.1 Hz, 1H), 8.37 (s, 1H), 8.96 (s, 1H), 9.14 (s, 1H), 9.72 (s, 1H).

Synthesis of 3-(5-(trifluoromethyl)pyridin-3-yl)phenyl octylcarbamate (Example-30)

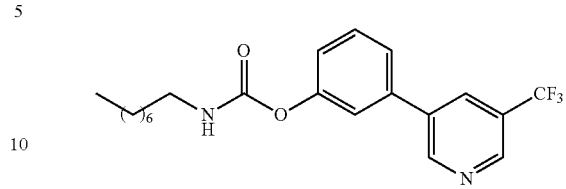

To a solution of 3-(5-(trifluoromethyl)pyridin-3-yl)phenol (0.08 g, 0.33 mmol) in anhydrous acetonitrile (2 mL), add triethylamine (TEA) (0.13 mL, 0.99 mmol) and n-octyl isocyanate (0.05 g, 0.33 mmol) at RT under a nitrogen atmosphere. Stir the reaction mixture at RT for 10 minutes and then heat to 75° C. for 3 h under a nitrogen atmosphere. After 3 h, add an additional amount of n-octyl isocyanate (0.01 g, 0.11 mmol) to the reaction mixture and continue heating for an additional 12 h. Monitor the reaction progress by TLC. Upon completion of the reaction, cool the reaction mixture to RT and evaporate the solvent under reduced pressure. Purify the crude product by flash column chromatography on silica gel, eluting with a hexane/EtOAc gradient (10-15% EtOAc) to yield the target compound (57 mg) as an off white solid. $^1$H NMR (400 MHz, CDCl3) δ 9.05 (d, J=2.2 Hz, 1H), 8.81-8.98 (m, 1H), 8.12 (t, J=2.3 Hz, 1H), 7.37-7.67 (m, 3H), 7.27 (ddd, J=8.0, 2.4, 1.1 Hz, 1H), 5.11 (t, J=5.9 Hz, 1H), 1.34 (qd, J=9.6, 4.8 Hz, 11H), 0.86-1.03 (m, 3H), 1.52-1.76 (m, 3H).

Synthesis of 3-(5-(trifluoromethyl)pyridin-3-yl)phenyl (cyclohexylmethyl)carbamate Example-31

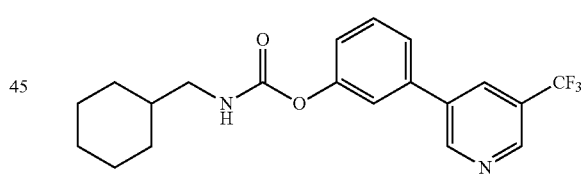

To a solution of 3-(5-(trifluoromethyl)pyridin-3-yl)phenol (0.08 g, 0.33 mmol) in anhydrous acetonitrile (2 mL), add TEA (0.13 mL, 0.99 mmol) and cyclohexanemethyl isocyanate (0.04 g, 0.33 mmol) at RT under a nitrogen atmosphere. Stir the reaction mixture at RT for 10 minutes and then heat to 75° C. for 3 h under a nitrogen atmosphere. After 3 h, add an additional amount of cyclohexanemethyl isocyanate (0.01 g, 0.11 mmol) to the reaction mixture and continue heating for an additional 12 h. Monitor the reaction progress by TLC. Upon completion of the reaction, cool the reaction mixture to RT and evaporate the solvent under reduced pressure. Purify the crude product by flash column chromatography on silica gel, eluting with a hexane/EtOAc gradient (10-15% EtOAc) to yield the target compound (50 mg) as an off white solid. $^1$H NMR (400 MHz, CDCl3) δ 9.05 (d, J=2.2 Hz, 1H), 8.91 (t, J=1.5 Hz, 1H), 8.12 (t, J=2.2 Hz, 1H), 7.36-7.62 (m, 3H), 7.21-7.28 (m, 1H), 5.15 (d, J=7.3 Hz, 1H), 3.17 (t, J=6.5 Hz, 2H), 1.69-1.90 (m, 5H), 1.15-1.42 (m, 4H), 1.02 (qd, J=12.5, 3.8 Hz, 2H).

Synthesis of 3-(5-(trifluoromethyl)pyridin-3-yl)phenyl cyclopentylcarbamate (Example-32)

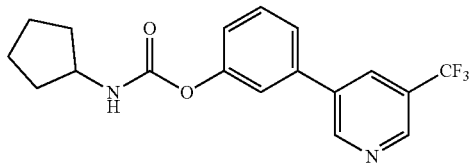 [SMILES: O=C(NC1CCCC1)Oc1cccc(-c2cncc(C(F)(F)F)c2)c1]

To a solution of 3-(5-(trifluoromethyl)pyridin-3-yl)phenol (0.08 g, 0.33 mmol) in anhydrous acetonitrile (2 mL) was added TEA (0.13 mL, 0.99 mmol) and cyclopentyl isocyanate (0.037 g, 0.33 mmol) at RT under nitrogen atmosphere. The reaction mixture was stirred at RT for 10 minutes and then heated to 75° C. for 3 h under a nitrogen atmosphere. An additional amount of cyclopentyl isocyanate (0.01 g, 0.11 mmol) was added to the reaction mixture, and the reaction was then heated for an additional 12 h. The reaction progress was monitored by TLC. Upon completion, the reaction mixture was cooled to RT, and the solvent was evaporated under reduced pressure. The crude product was purified by flash column chromatography on silica gel, eluting with a hexane/ethyl acetate gradient (10-15% EtOAc) to yield the target compound (50 mg) as an off white solid. ¹H NMR (400 MHz, CDCl3) δ 9.01 (d, J=2.2 Hz, 1H), 8.87 (dd, J=2.1, 1.0 Hz, 1H), 8.08 (s, 1H), 7.50 (t, J=7.9 Hz, 1H), 7.40-7.45 (m, 1H), 7.39 (t, J=2.0 Hz, 1H), 7.23 (ddd, J=8.1, 2.3, 1.1 Hz, 1H), 5.05 (d, J=7.5 Hz, 1H), 4.08 (q, J=6.8 Hz, 1H), 1.95-2.36 (m, 3H), 1.60-1.87 (m, 3H), 1.45-1.58 (m, 2H).

Synthesis of 3-(5-(trifluoromethyl)pyridin-3-yl)phenyl cyclohexylcarbamate (Example-33)

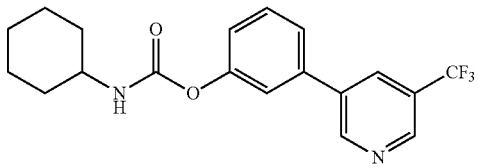 [SMILES: O=C(NC1CCCCC1)Oc1cccc(-c2cncc(C(F)(F)F)c2)c1]

To a solution of 3-(5-(trifluoromethyl)pyridin-3-yl)phenol (0.08 g, 0.33 mmol) in anhydrous acetonitrile (3 mL) was added TEA (0.13 mL, 0.99 mmol) and cyclohexyl isocyanate (0.04 g, 0.33 mmol) at RT under a nitrogen atmosphere. The reaction mixture was stirred at RT for 10 minutes and then heated to 75° C. for 3 h under nitrogen atmosphere. After 3 h, an additional amount of cyclohexyl isocyanate (0.01 g, 0.11 mmol) was added to the reaction mixture, which was then heated for an additional 12 h. The reaction progress was monitored by TLC. Upon completion of the reaction, the mixture was cooled to RT, and the solvent was evaporated under reduced pressure. The crude product was purified by flash column chromatography on silica gel, eluting with a hexane/ethyl acetate gradient (10-15% EtOAc) to yield the target compound (55 mg) as an off white solid. ¹H NMR (400 MHz, CDCl3) δ 9.01 (d, J=2.2 Hz, 1H), 8.87 (dd, J=2.1, 1.0 Hz, 1H), 8.08 (s, 1H), 7.50 (t, J=7.9 Hz, 1H), 7.31-7.47 (m, 2H), 7.21-7.30 (m, 1H), 4.99 (d, J=8.1 Hz, 1H), 3.59 (dq, J=8.1, 3.4 Hz, 1H), 2.03 (dt, J=12.1, 4.0 Hz, 2H), 1.75 (dt, J=13.4, 3.9 Hz, 2H), 1.08-1.58 (m, 6H).

Synthesis of 3-(5-(trifluoromethyl)pyridin-3-yl)phenyl cycloheptylcarbamate (Example-34)

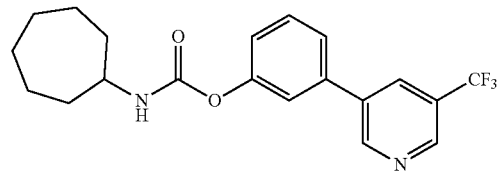 [SMILES: O=C(NC1CCCCCC1)Oc1cccc(-c2cncc(C(F)(F)F)c2)c1]

To a solution of 3-(5-(trifluoromethyl)pyridin-3-yl)phenol (0.08 g, 0.33 mmol) in anhydrous acetonitrile (2 mL) was added triethylamine (TEA) (0.13 mL, 0.99 mmol) and cycloheptyl isocyanate (0.04 g, 0.33 mmol) at RT under a nitrogen atmosphere. The reaction mixture was stirred at RT for 10 minutes and then heated to 75° C. for 3 h under a nitrogen atmosphere. An additional amount of cycloheptyl isocyanate (0.01 g, 0.11 mmol) was added to the reaction mixture, which was then heated for an additional 12 h. The reaction progress was monitored by TLC. Upon completion of the reaction, the mixture was cooled to RT, and the solvent was evaporated under reduced pressure. The crude product was purified by flash column chromatography on silica gel, eluting with a hexane/ethyl acetate gradient (10-15% EtOAc) to yield the target compound (55 mg) as an off white solid. ¹H NMR (400 MHz, CDCl3) δ 8.94 (d, J=2.2 Hz, 1H), 8.80 (d, J=2.1 Hz, 1H), 8.01 (d, J=2.3 Hz, 1H), 7.25-7.51 (m, 3H), 7.16 (ddd, J=8.2, 2.4, 1.2 Hz, 1H), 4.97 (d, J=8.2 Hz, 1H), 3.71 (td, J=8.5, 4.3 Hz, 1H), 1.88-2.15 (m, 2H), 1.39-1.70 (m, 11H).

Scheme II

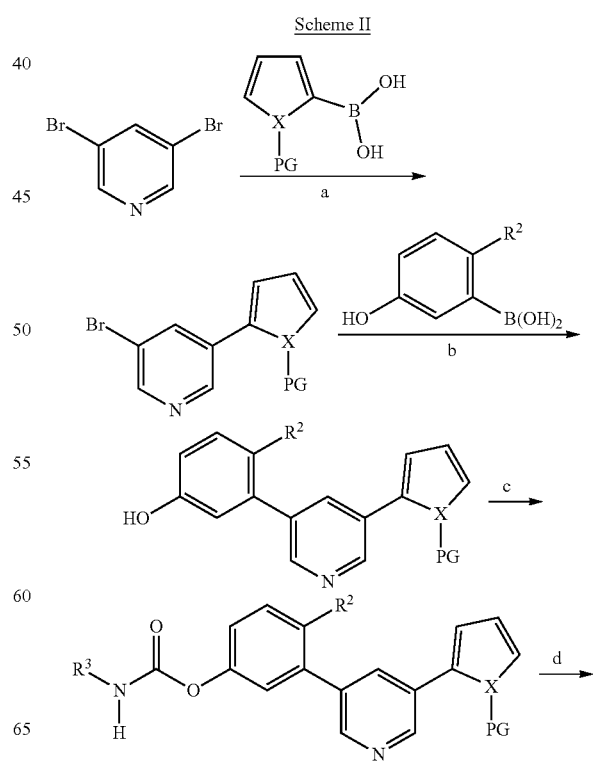

-continued

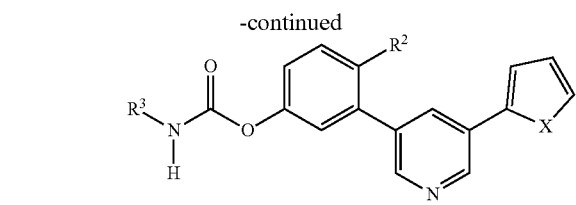

R² = H, OCH₃
X = NH, O, S
PG = Boc (when X = NH)
Reagents and conditions: a) Pd(PPh₃)₄, Cs₂CO₃, 1,4-dioxane, 90-100° C., 2 h; b) Pd(PPh₃)₄, K₂CO₃, 1,4-dioxane, H₂O, 90° C., 5 h; c)R³—NCO, TEA, ACN, 75° C., 2-6 h; e) DCM, TFA, 40° C., 30 min.

Synthesis of tert-butyl 2-(5-bromopyridin-3-yl)-1H-pyrrole-1-carboxylate

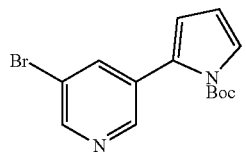 [SMILES: CC(C)(C)OC(=O)n1cccc1-c1cncc(Br)c1]

To a stirred solution of 3,5-dibromopyridine (2 g, 8.44 mmol) in 1,4-dioxane (20 mL) was added (1-(tert-butoxycarbonyl)-1H-pyrrol-2-yl) boronic acid (2.13 g, 10.13 mmol) and Cs₂CO₃ (5.50 g, 16.89 mmol) at RT. The reaction mixture was degassed for 15 minutes then Pd(PPh₃)₄ (0.68 g, 0.591 mmol) was added. The reaction mixture was stirred at 90° C. for 2 h under nitrogen atmosphere. After completion of the reaction (monitored by TLC), the reaction mixture was cooled to RT and then the solvent was evaporated under reduced pressure. The residue was dissolved in ethyl acetate, washed with water followed by brine. The organic layer was dried over sodium sulfate then evaporated under reduced pressure. The residue was purified by automated normal-phase chromatography and eluted with ethyl acetate/petroleum ether to give tert-butyl 2-(5-bromopyridin-3-yl)-1H-pyrrole-1-carboxylate (1.45 g) as an off white solid. MS (ES+APCI) m/z 323.1.

Synthesis of tert-butyl 2-(5-(3-hydroxyphenyl)pyridin-3-yl)-1H-pyrrole-1-carboxylate

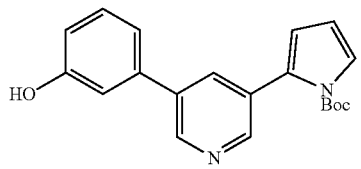 [SMILES: CC(C)(C)OC(=O)n1cccc1-c1cncc(-c2cccc(O)c2)c1]

To a stirred solution of tert-butyl 2-(5-bromopyridin-3-yl)-1H-pyrrole-1-carboxylate (1 g, 3.09 mmol) in 1,4-dioxane (10 mL) and water (1.1 mL) was added (3-hydroxyphenyl)boronic acid (0.512 g, 3.71 mmol) and K₂CO₃ (1.28 g, 9.28 mmol) at RT. The reaction mixture was degassed for 15 minutes then Pd(PPh₃)₄ (0.179 g, 0.155 mmol) was added. The reaction mixture was stirred at 80° C. for 5 h under nitrogen atmosphere. After completion of the reaction (monitored by TLC), the reaction mixture was cooled to RT and then the solvent was evaporated under reduced pressure. The residue was dissolved in ethyl acetate, washed with water followed by brine. The organic layer was dried over sodium sulfate then evaporated under reduced pressure. The residue was purified by automated normal-phase chromatography and eluted with ethyl acetate/petroleum ether to give tert-butyl 2-(5-(3-hydroxyphenyl)pyridin-3-yl)-1H-pyrrole-1-carboxylate (1 g) as an off white solid. MS (ES+APCI) m/z 337.1 (M+1).

Synthesis of tert-butyl 2-(5-(3-((octylcarbamoyl)oxy)phenyl)pyridin-3-yl)-1H-pyrrole-1-carboxylate

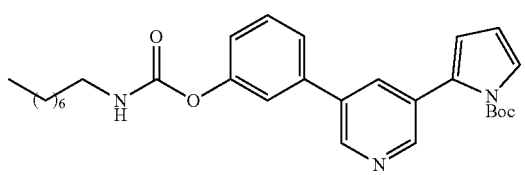

To a stirred solution of tert-butyl 2-(5-(3-hydroxyphenyl)pyridin-3-yl)-1H-pyrrole-1-carboxylate (0.12 g, 0.357 mmol) in anhydrous acetonitrile (2 mL) was added TEA (0.07 mL, 0.428 mmol) and n-octyl isocyanate (0.056 g, 0.35 mmol) at RT under nitrogen atmosphere. The reaction mixture was stirred at RT for 10 minutes and then stirred at 75° C. for 12 h. After completion of the reaction (monitored by liquid chromatography-mass spectrometry (LCMS)), the reaction mixture was concentrated to a residue. The residue was purified by automated normal-phase chromatography and eluted with ethyl acetate/petroleum ether to give tert-butyl 2-(5-(3-((octylcarbamoyl)oxy)phenyl)pyridin-3-yl)-1H-pyrrole-1-carboxylate (0.16 g) as an off white solid. MS (ES+APCI) m/z 492.5 (M+1).

Synthesis of 3-(5-(1H-pyrrol-2-yl)pyridin-3-yl)phenyl octylcarbamate (Example-35)

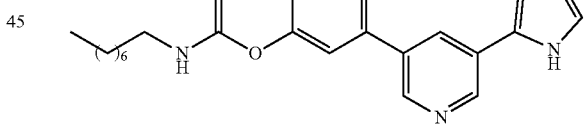

To a stirred solution of tert-butyl 2-(5-(3-((octylcarbamoyl)oxy)phenyl)pyridin-3-yl)-1H-pyrrole-1-carboxylate (0.18 g, 0.366 mmol) in DCM (2 mL) was added TFA (0.56 mL, 7.32 mmol) at 0° C. under nitrogen atmosphere. Then reaction mixture was stirred at 40° C. for 30 minutes. After completion of the reaction (monitored by TLC), the reaction mixture was diluted with 10% sodium bicarbonate solution and extracted with dichloromethane and washed with water. The organic layer was dried over sodium sulfate then evaporated under reduced pressure. The residue was purified by preparative High-Performance Liquid Chromatography (HPLC) (0.1% FA) to yield the target compound (70 mg) as an off white solid. ¹HNMR (400 MHz, DMSO-d6): δ 11.45 (s, 1H), 8.88 (d, J=2.40 Hz, 1H), 8.66 (d, J=2.40 Hz, 1H), 8.29 (t, J=2.00 Hz, 1H), 7.82 (t, J=5.60 Hz, 1H), 7.65 (d, J=8.40 Hz, 1H), 7.55-7.51 (m, 2H), 7.19-7.16 (m, 1H), 6.99-6.98 (m, 1H), 6.79-6.77 (m, 1H), 6.20-6.18 (m, 1H), 3.10-3.05 (m, 2H), 1.49 (t, J=6.80 Hz, 2H), 1.29-1.27 (m, 10H), 0.87 (t, J=7.20 Hz, 3H); MS (ES+APCI) m/z 392.5 (M+1).

Synthesis of tert-butyl 2-(5-(3-(((cyclohexylmethyl) carbamoyl)oxy)phenyl)pyridin-3-yl)-1H-pyrrole-1-carboxylate

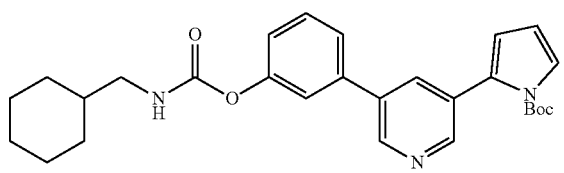 [SMILES: CC(C)(C)OC(=O)n1cccc1-c1cncc(-c2cccc(OC(=O)NCC3CCCCC3)c2)c1]

To a stirred solution of tert-butyl 2-(5-(3-hydroxyphenyl) pyridin-3-yl)-1H-pyrrole-1-carboxylate (0.12 g, 0.357 mmol) in anhydrous acetonitrile (2 mL) was added TEA (0.074 mL, 0.535 mmol) and cyclohexanemethyl isocyanate (0.06 g, 0.42 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by automated normal-phase chromatography and eluted with ethyl acetate/ petroleum ether to give tert-butyl 2-(5-(3-(((cyclohexylmethyl)carbamoyl)oxy)phenyl)pyridin-3-yl)-1H-pyrrole-1-carboxylate (0.15 g, as an off white solid. MS (ES+APCI) m/z 476.3 (M+1).

Synthesis of 3-(5-(1H-pyrrol-2-yl)pyridin-3-yl)phenyl (cyclohexylmethyl)carbamate (Example-36)

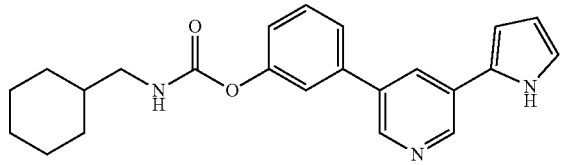 [SMILES: O=C(NCC1CCCCC1)Oc1cccc(-c2cncc(-c3ccc[nH]3)c2)c1]

To a stirred solution of tert-butyl 2-(5-(3-(((cyclohexylmethyl)carbamoyl)oxy)phenyl)pyridin-3-yl)-1H-pyrrole-1-carboxylate (0.15 g, 0.336 mmol) in DCM (2 mL) was added TFA (0.52 mL, 6.73 mmol) at 0° C. under nitrogen atmosphere. Then reaction mixture was stirred at 40° C. for 30 minutes. After completion of the reaction (monitored by TLC), the reaction mixture was diluted with 10% sodium bicarbonate solution and extracted with dichloromethane and washed with water. The organic layer was dried over sodium sulfate then evaporated under reduced pressure. The residue was purified by preparative HPLC (0.10% FA) to yield the target compound (76 mg) as an off white solid. ¹HNMR (400 MHz, DMSO-d6): δ 11.56 (s, 1H), 8.88 (d, J=2.00 Hz, 1H), 8.66 (d, J=2.00 Hz, 1H), 8.29 (t, J=2.00 Hz, 1H), 7.84 (t, J=6.00 Hz, 1H), 7.65 (d, J=8.40 Hz, 1H), 7.54-7.50 (m, 2H), 7.19-7.16 (m, 1H), 7.00-6.98 (m, 1H), 6.80-6.77 (m, 1H), 6.18-6.20 (m, 1H), 2.94 (t, J=6.40 Hz, 2H), 1.75-0.88 (m, 11H); MS (ES+APCI) m/z 376.2 (M+1).

Synthesis of tert-butyl 2-(5-(3-((benzylcarbamoyl) oxy)phenyl)pyridin-3-yl)-1H-pyrrole-1-carboxylate

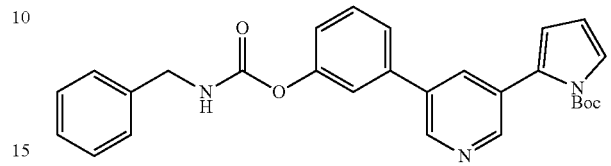

To a stirred solution of tert-butyl 2-(5-(3-hydroxyphenyl) pyridin-3-yl)-1H-pyrrole-1-carboxylate (0.12 g, 0.357 mmol) in anhydrous acetonitrile (2 mL) was added TEA (0.075 mL, 0.535 mmol) and benzyl isocyanate (0.043 g, 0.482 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by automated normal-phase chromatography and eluted with ethyl acetate/petroleum ether to give tert-butyl 2-(5-(3-((benzylcarbamoyl) oxy)phenyl)pyridin-3-yl)-1H-pyrrole-1-carboxylate (160 mg) as an off white solid. MS (ES+APCI) m/z 469.4 (M+1).

Synthesis of 3-(5-(1H-pyrrol-2-yl)pyridin-3-yl)phenyl benzylcarbamate (Example-37)

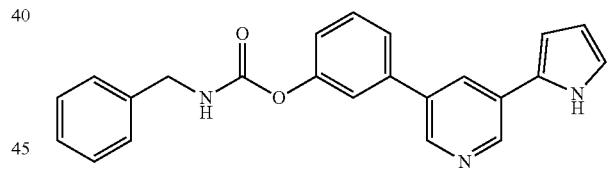

To a stirred solution of tert-butyl 2-(5-(3-((benzylcarbamoyl)oxy)phenyl)pyridin-3-yl)-1H-pyrrole-1-carboxylate (0.15 g, 0.319 mmol) in DCM (2 mL) was added TFA (0.49 mL, 6.39 mmol) at 0° C. under nitrogen atmosphere. Then reaction mixture was stirred at 40° C. for 30 minutes. After completion of the reaction (monitored by TLC), the reaction mixture was diluted with 10% sodium bicarbonate solution and extracted with dichloromethane and washed with water. The organic layer was dried over sodium sulfate then evaporated under reduced pressure. The residue was purified by preparative HPLC (0.1% FA) to yield the target compound (41 mg) as an off white solid. ¹HNMR (400 MHz, DMSO-d6): δ 11.54 (s, 1H), 8.88 (d, J=2.00 Hz, 1H), 8.67 (d, J=2.00 Hz, 1H), 8.41 (t, J=6.00 Hz, 1H), 8.30 (t, J=2.00 Hz, 1H), 7.68-7.52 (m, 3H), 7.39-7.20 (m, 6H), 6.99-6.98 (m, 1H), 6.78 (t, J=4.00 Hz, 1H), 6.20-6.18 (m, 1H), 4.32 (d, J=6.40 Hz, 2H); MS (ES+APCI) m/z 370.3 (M+1).

Synthesis of tert-butyl 2-(5-(3-((cyclopentylcarbamoyl)oxy)phenyl)pyridin-3-yl)-1H-pyrrole-1-carboxylate Synthesis of tert-butyl 2-(5-(3-((cyclohexylcarbamoyl)oxy)phenyl)pyridin-3-yl)-1H-pyrrole-1-carboxylate

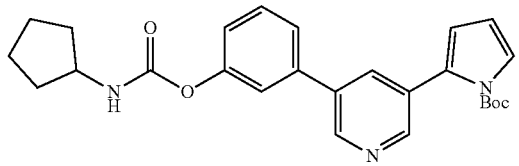 [SMILES: CC(C)(C)OC(=O)n1cccc1-c1cncc(-c2cccc(OC(=O)NC3CCCC3)c2)c1]

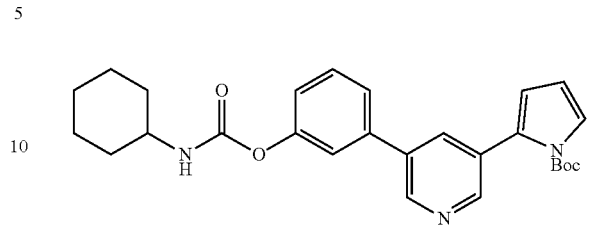

To a stirred solution of tert-butyl 2-(5-(3-hydroxyphenyl)pyridin-3-yl)-1H-pyrrole-1-carboxylate (0.1 g, 0.297 mmol) in anhydrous acetonitrile (2 mL) was added TEA (0.062 mL, 0.45 mmol) and cyclopentyl isocyanate (0.040 g, 0.375 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by automated normal-phase chromatography and eluted with ethyl acetate/petroleum ether to give tert-butyl 2-(5-(3-((cyclopentylcarbamoyl)oxy)phenyl)pyridin-3-yl)-1H-pyrrole-1-carboxylate (120 mg) as an off white solid. MS (ES+APCI) m/z 448.4 (M+1).

To a stirred solution of tert-butyl 2-(5-(3-hydroxyphenyl)pyridin-3-yl)-1H-pyrrole-1-carboxylate (0.1 g, 0.297 mmol) in anhydrous acetonitrile (2 mL) was added TEA (0.064 mL, 0.47 mmol) and cyclohexyl isocyanate (0.045 g, 0.357 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by automated normal-phase chromatography and eluted with ethyl acetate/petroleum ether to give tert-butyl 2-(5-(3-((cyclohexylcarbamoyl)oxy)phenyl)pyridin-3-yl)-1H-pyrrole-1-carboxylate (120 mg) as off white solid. MS (ES+APCI) m/z 462.4 (M+1).

Synthesis of 3-(5-(1H-pyrrol-2-yl)pyridin-3-yl)phenyl cyclopentylcarbamate (Example-38)

Synthesis of 3-(5-(1H-pyrrol-2-yl)pyridin-3-yl)phenyl cyclohexylcarbamate (Example-39)

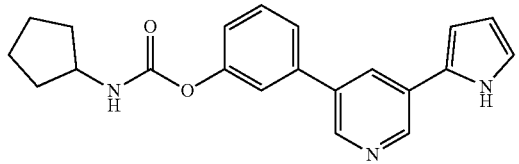 [SMILES: O=C(NC1CCCC1)Oc1cccc(-c2cncc(-c3ccc[nH]3)c2)c1]

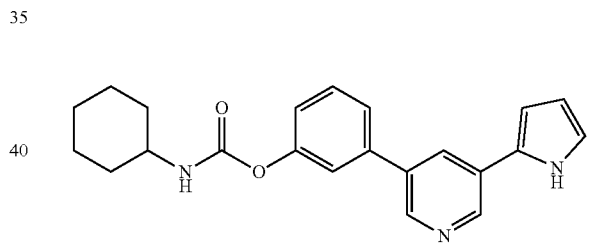

To a stirred solution of tert-butyl 2-(5-(3-((cyclopentylcarbamoyl)oxy)phenyl)pyridin-3-yl)-1H-pyrrole-1-carboxylate (0.12 g, 0.268 mmol) in DCM (2 mL) was added TFA (0.41 mL, 5.36 mmol) at 0° C. under nitrogen atmosphere. Then reaction mixture was stirred at 40° C. for 30 minutes. After completion of the reaction (monitored by TLC), the reaction mixture was diluted with 10% sodium bicarbonate solution and extracted with dichloromethane and washed with water. The organic layer was dried over sodium sulfate then evaporated under reduced pressure. The residue was purified by preparative HPLC (0.1% FA) to yield the target compound (27 mg) as an off white solid. $^1$HNMR (400 MHz, DMSO-d6) δ 11.55 (s, 1H), 8.88 (d, J=2.40 Hz, 1H), 8.66 (d, J=2.40 Hz, 1H), 8.29 (t, J=2.00 Hz, 1H), 7.87 (d, J=7.20 Hz, 1H), 7.65 (d, J=8.00 Hz, 1H), 7.54-7.51 (m, 2H), 7.19-7.17 (m, 1H), 7.00-6.98 (m, 1H), 6.79-6.77 (m, 1H), 6.20-6.18 (m, 1H), 3.90-3.85 (m, 1H), 1.89-1.19 (m, 8H); MS (ES+APCI) m/z 348.4 (M+1).

To a stirred solution of tert-butyl 2-(5-(3-((cyclohexylcarbamoyl)oxy)phenyl)pyridin-3-yl)-1H-pyrrole-1-carboxylate (0.08 g, 0.173 mmol) in DCM (2 mL) was added TFA (0.27 mL, 3.47 mmol) at 0° C. under nitrogen atmosphere. Then reaction mixture was stirred at 40° C. for 30 minutes. After completion of the reaction (monitored by TLC), the reaction mixture was diluted with 10% sodium bicarbonate solution and extracted with dichloromethane and washed with water. The organic layer was dried over sodium sulfate then evaporated under reduced pressure. The residue was purified by preparative HPLC (0.1% FA) to yield the target compound (27 mg) as an off white solid. $^1$H-NMR (400 MHz, DMSO-d6): δ 11.4 (s, 1H), δ 8.88 (d, J=2.00 Hz, 1H), 8.66 (d, J=2.40 Hz, 1H), 8.29 (t, J=2.40 Hz, 1H), 7.80 (d, J=8.00 Hz, 1H), 7.65 (d, J=8.40 Hz, 1H), 7.54-7.50 (m, 2H), 7.19-7.17 (m, 1H), 7.00-6.98 (m, 1H), 6.79-6.77 (m, 1H), 6.20-6.18 (m, 1H), 3.35 (d, J=17.60 Hz, 1H), 1.94-1.56 (m, 5H), 1.36-1.08 (m, 5H); MS (ES+APCI) m/z 362.3 (M+1).

Synthesis of tert-butyl 2-(5-(3-((cycloheptylcarbamoyl)oxy)phenyl)pyridin-3-yl)-1H-pyrrole-1-carboxylate

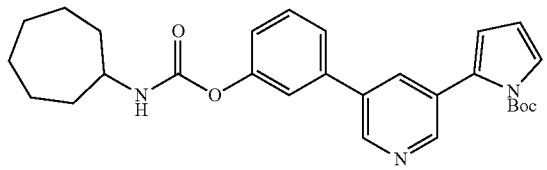 [SMILES: CC(C)(C)OC(=O)n1cccc1-c1cncc(-c2cccc(OC(=O)NC3CCCCCC3)c2)c1]

To a stirred solution of tert-butyl 2-(5-(3-hydroxyphenyl) pyridin-3-yl)-1H-pyrrole-1-carboxylate (0.12 g, 0.357 mmol) in anhydrous acetonitrile (2 mL) was added TEA (0.075 mL, 0.54 mmol) and cycloheptyl isocyanate (0.06 g, 0.428 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by automated normal-phase chromatography and eluted with ethyl acetate/petroleum ether to give tert-butyl 2-(5-(3-((cycloheptylcarbamoyl)oxy)phenyl)pyridin-3-yl)-1H-pyrrole-1-carboxylate (0.15 g) as an off white solid. MS (ES+APCI) m/z 476.3 (M+1).

Synthesis of 3-(5-(1H-pyrrol-2-yl)pyridin-3-yl)phenyl cycloheptylcarbamate (Example-40)

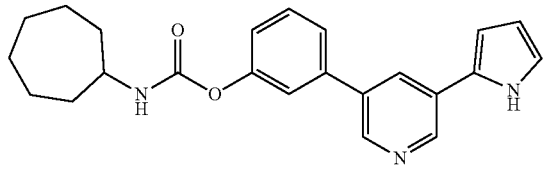 [SMILES: O=C(NC1CCCCCC1)Oc1cccc(-c2cncc(-c3ccc[nH]3)c2)c1]

To a stirred solution of tert-butyl 2-(5-(3-((cycloheptylcarbamoyl)oxy)phenyl)pyridin-3-yl)-1H-pyrrole-1-carboxylate (0.12 g, 0.252 mmol) in DCM (2 mL) was added TFA (0.38 mL, 5.05 mmol) at 0° C. under nitrogen atmosphere. Then reaction mixture was stirred at 40° C. for 30 minutes. After completion of the reaction (monitored by TLC), the reaction mixture was diluted with 10% sodium bicarbonate solution and extracted with dichloromethane and washed with water. The organic layer was dried over sodium sulfate then evaporated under reduced pressure. The residue was purified by preparative HPLC (0.10% FA) to yield the target compound (14 mg) as an off white solid. $^1$HNMR (400 MHz, DMSO-d6): δ 11.50 (s, 1H), 8.88 (d, J=2.40 Hz, 1H), 8.66 (d, J=2.00 Hz, 1H), 8.29 (t, J=2.00 Hz, 1H), 7.83 (d, J=7.60 Hz, 1H), 7.65 (d, J=8.00 Hz, 1H), 7.54-7.50 (m, 2H), 7.19-7.16 (m, 1H), 6.99-6.98 (m, 1H), 6.79-6.77 (m, 1H), 6.20-6.18 (m, 1H), 3.60-3.33 (m, 1H), 1.91-1.31 (m, 12H); MS (ES+APCI) m/z 376.3 (M+1).

Synthesis of tert-butyl 2-(5-(5-hydroxy-2-methoxyphenyl)pyridin-3-yl)-1H-pyrrole-1-carboxylate

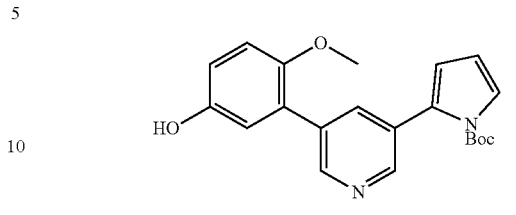

To a stirred solution of tert-butyl 2-(5-bromopyridin-3-yl)-1H-pyrrole-1-carboxylate (0.5 g, 1.55 mmol) in 1,4-dioxane (10 mL) and water (1.1 mL) was added (5-hydroxy-2-methoxyphenyl)boronic acid (0.31 g, 1.86 mmol) and $K_2CO_3$ (0.64 g, 4.64 mmol) at RT. The reaction mixture was degassed for 15 minutes then Pd(PPh$_3$)$_4$ (0.09 g, 0.08 mmol) was added. The reaction mixture was stirred at 80° C. for 5 h under nitrogen atmosphere. After completion of the reaction (monitored by TLC), the reaction mixture was cooled to RT and then the solvent was evaporated under reduced pressure. The residue was dissolved in ethyl acetate, washed with water followed by brine. The organic layer was dried over sodium sulfate then evaporated under reduced pressure. The residue was purified by automated normal-phase chromatography and eluted with ethyl acetate/petroleum ether to give tert-butyl 2-(5-(5-hydroxy-2-methoxyphenyl)pyridin-3-yl)-1H-pyrrole-1-carboxylate (510 mg) as an pale yellow solid. $^1$H-NMR (400 MHz, DMSO-d6): δ 9.13 (s, 1H), 8.57-8.47 (m, 2H), 7.77 (s, 1H), 7.43-7.42 (m, 1H), 6.98 (d, J=12.00 Hz, 1H), 6.81-6.76 (m, 2H), 6.43-6.41 (m, 1H), 6.34 (t, J=4.40 Hz, 1H), 3.68 (s, 3H), 1.32 (s, 9H); MS (ES+APCI) m/z 367.2 (M+1).

Synthesis of tert-butyl 2-(5-(2-methoxy-5-((octylcarbamoyl)oxy)phenyl)pyridin-3-yl)-1H-pyrrole-1-carboxylate

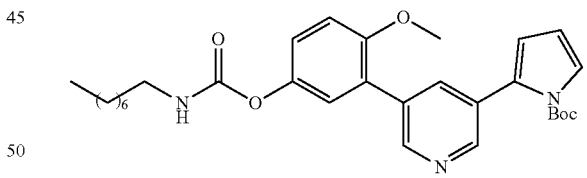

To a stirred solution of tert-butyl 2-(5-(5-hydroxy-2-methoxyphenyl)pyridin-3-yl)-1H-pyrrole-1-carboxylate (0.1 g, 0.27 mmol) in anhydrous acetonitrile (2 mL) was added TEA (0.06 mL, 0.41 mmol) and n-octyl isocyanate (0.05 g, 0.33 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by automated normal-phase chromatography and eluted with ethyl acetate/petroleum ether to give tert-butyl 2-(5-(2-methoxy-5-((octylcarbamoyl)oxy)phenyl)pyridin-3-yl)-1H-pyrrole-1-carboxylate (0.12 g) as off white solid. MS (ES+APCI) m/z 522.2 (M+1).

Synthesis of 3-(5-(1H-pyrrol-2-yl)pyridin-3-yl)-4-methoxyphenyl octylcarbamate

Example-41

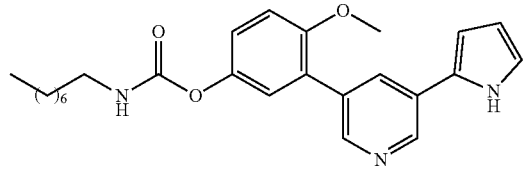

To a stirred solution of tert-butyl 2-(5-(2-methoxy-5-((octylcarbamoyl)oxy)phenyl)pyridin-3-yl)-1H-pyrrole-1-carboxylate (0.18 g, 0.37 mmol) in DCM (2 mL) was added TFA (0.56 mL, 7.32 mmol) at 0° C. under nitrogen atmosphere. Then reaction mixture was stirred at 40° C. for 30 minutes. After completion of the reaction (monitored by TLC), the reaction mixture was diluted with 10% sodium bicarbonate solution and extracted with dichloromethane and washed with water. The organic layer was dried over sodium sulfate then evaporated under reduced pressure. The residue was purified by preparative HPLC (0.10% FA) to yield the target compound (64 mg) as gummy solid. $^1$H-NMR (400 MHz, DMSO-d6): δ 11.60 (s, 1H), 8.89 (d, J=2.00 Hz, 1H), 8.56 (s, 1H), 8.30 (s, 1H), 7.72 (t, J=5.20 Hz, 1H), 7.20 (d, J=16.40 Hz, 3H), 7.01 (s, 1H), 6.80 (s, 1H), 6.21 (s, 1H), 3.82 (s, 3H), 3.08-3.03 (m, 2H), 1.46 (t, J=6.40 Hz, 2H), 1.27 (m, 10H), 0.85 (t, J=6.80 Hz, 3H); MS (ES+APCI) m/z 422.2 (M+1).

Synthesis of tert-butyl 2-(5-(5-(((cyclohexylmethyl)carbamoyl)oxy)-2-methoxyphenyl)pyridin-3-yl)-1H-pyrrole-1-carboxylate

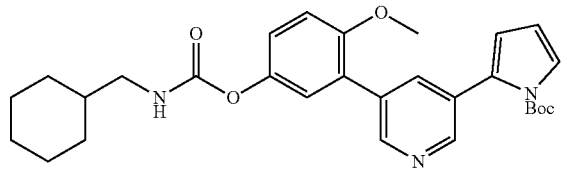 [SMILES: COc1ccc(OC(=O)NCC2CCCCC2)cc1-c1cncc(-c2cccn2C(=O)OC(C)(C)C)c1]

To a stirred solution of tert-butyl 2-(5-(5-hydroxy-2-methoxyphenyl)pyridin-3-yl)-1H-pyrrole-1-carboxylate (0.1 g, 0.27 mmol) in anhydrous acetonitrile (2 mL) was added TEA (0.06 mL, 0.41 mmol) and cyclohexanemethyl isocyanate (0.05 g, 0.33 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by automated normal-phase chromatography and eluted with ethyl acetate/petroleum ether to give tert-butyl 2-(5-(5-(((cyclohexylmethyl)carbamoyl)oxy)-2-methoxyphenyl)pyridin-3-yl)-1H-pyrrole-1-carboxylate (0.12 g) as off white solid. MS (ES+APCI) m/z 506.3 (M+1).

Synthesis of 3-(5-(1H-pyrrol-2-yl)pyridin-3-yl)-4-methoxyphenyl (cyclohexylmethyl)carbamate (Example-42)

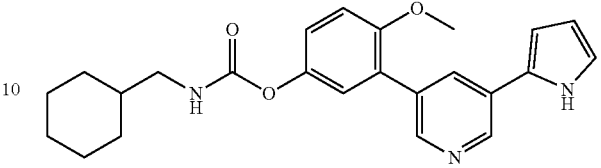

To a stirred solution of tert-butyl 2-(5-(5-(((cyclohexylmethyl)carbamoyl)oxy)-2-methoxyphenyl)pyridin-3-yl)-1H-pyrrole-1-carboxylate (0.11 g, 0.22 mmol) in DCM (2 mL) was added TFA (0.33 mL, 4.35 mmol) at 0° C. under nitrogen atmosphere. Then reaction mixture was stirred at 40° C. for 30 minutes. After completion of the reaction (monitored by TLC), the reaction mixture was diluted with 10% sodium bicarbonate solution and extracted with dichloromethane and washed with water. The organic layer was dried over sodium sulfate then evaporated under reduced pressure. The residue was purified by preparative HPLC (0.1% FA) to yield the target compound (40 mg) as an off white solid. $^1$H-NMR (400 MHz, DMSO-d6): δ 11.49 (s, 1H), 8.83 (d, J=2.40 Hz, 1H), 8.47 (d, J=2.00 Hz, 1H), 8.09 (t, J=2.00 Hz, 1H), 7.73 (t, J=6.00 Hz, 1H), 7.16-7.14 (m, 3H), 6.96-6.95 (m, 1H), 6.72-6.70 (m, 1H), 6.19-6.17 (m, 1H), 3.80 (s, 3H), 2.91 (t, J=6.40 Hz, 2H), 1.73-1.41 (m, 6H), 1.24-0.94 (m, 5H);

MS (ES+APCI) m/z 406.2 (M+1).

Synthesis of tert-butyl 2-(5-(5-((benzylcarbamoyl)oxy)-2-methoxyphenyl)pyridin-3-yl)-1H-pyrrole-1-carboxylate

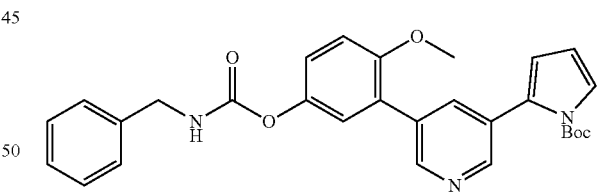

To a stirred solution of tert-butyl 2-(5-(5-hydroxy-2-methoxyphenyl)pyridin-3-yl)-1H-pyrrole-1-carboxylate (0.1 g, 0.27 mmol) in anhydrous acetonitrile (2 mL) was added TEA (0.06 mL, 0.41 mmol) and benzyl isocyanate (0.04 g, 0.33 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by automated normal-phase chromatography and eluted with ethyl acetate/petroleum ether to give tert-butyl 2-(5-(5-((benzylcarbamoyl)oxy)-2-methoxyphenyl)pyridin-3-yl)-1H-pyrrole-1-carboxylate (120 mg) as off white solid. MS (ES+APCI) m/z 500.2 (M+1).

Synthesis of 3-(5-(1H-pyrrol-2-yl)pyridin-3-yl)-4-methoxyphenyl benzylcarbamate

Example-43

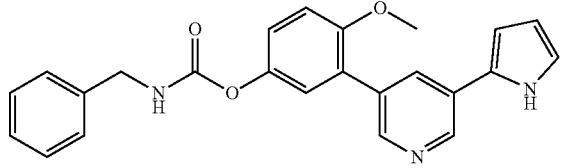

To a stirred solution of tert-butyl 2-(5-(5-((benzylcarbamoyl)oxy)-2-methoxyphenyl)pyridin-3-yl)-1H-pyrrole-1-carboxylate (0.12 g, 0.24 mmol) in DCM (2 mL) was added TFA (0.37 mL, 4.80 mmol) at 0° C. under nitrogen atmosphere. Then reaction mixture was stirred at 40° C. for 30 minutes. After completion of the reaction (monitored by TLC), the reaction mixture was diluted with 10% sodium bicarbonate solution and extracted with dichloromethane and washed with water. The organic layer was dried over sodium sulfate then evaporated under reduced pressure. The residue was purified by preparative HPLC (0.10% FA) to yield the target compound (4 mg) as an off white solid. $^1$H-NMR (400 MHz, DMSO-d6): δ 11.48 (s, 1H), 8.82 (d, J=2.00 Hz, 1H), 8.46 (d, J=2.00 Hz, 1H), 8.29 (t, J=6.40 Hz, 1H), 8.06 (t, J=2.00 Hz, 1H), 7.27-7.38 (m, 5H), 7.19-7.16 (m, 3H), 6.95-6.94 (m, 1H), 6.69 (t, J=3.60 Hz, 1H), 6.18-6.16 (m, 1H), 4.29 (d, J=6.00 Hz, 2H), 3.81 (s, 3H); MS (ES+APCI) m/z 400.2 (M+1).

Synthesis of tert-butyl 2-(5-(5-((cyclopentylcarbamoyl)oxy)-2-methoxyphenyl)pyridin-3-yl)-1H-pyrrole-1-carboxylate

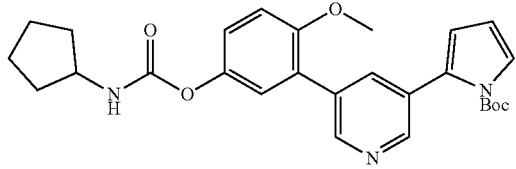 [SMILES: COc1ccc(OC(=O)NC2CCCC2)cc1-c1cncc(-c2cccn2C(=O)OC(C)(C)C)c1]

To a stirred solution of tert-butyl 2-(5-(5-hydroxy-2-methoxyphenyl)pyridin-3-yl)-1H-pyrrole-1-carboxylate (0.1 g, 0.27 mmol) in anhydrous acetonitrile (2 mL) was added TEA (0.06 mL, 0.41 mmol) and cyclopentyl isocyanate (0.04 g, 0.33 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by automated normal-phase chromatography and eluted with ethyl acetate/petroleum ether to give tert-butyl 2-(5-(5-((cyclopentylcarbamoyl)oxy)-2-methoxyphenyl)pyridin-3-yl)-1H-pyrrole-1-carboxylate (110 mg) as off white solid. MS (ES+APCI) m/z 478.3 (M+1).

Synthesis of 3-(5-(1H-pyrrol-2-yl)pyridin-3-yl)-4-methoxyphenyl cyclopentylcarbamate (Example-44)

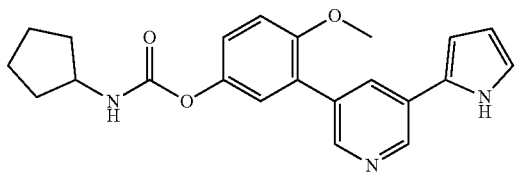

To a stirred solution of tert-butyl 2-(5-(5-((cyclopentylcarbamoyl)oxy)-2-methoxyphenyl)pyridin-3-yl)-1H-pyrrole-1-carboxylate (0.11 g, 0.25 mmol) in DCM (2 mL) was added TFA (0.39 mL, 5.03 mmol) at 0° C. under nitrogen atmosphere. Then reaction mixture was stirred at 40° C. for 30 minutes. After completion of the reaction (monitored by TLC), the reaction mixture was diluted with 10% sodium bicarbonate solution and extracted with dichloromethane and washed with water. The organic layer was dried over sodium sulfate then evaporated under reduced pressure. The residue was purified by preparative HPLC (0.1% FA) to yield the target compound (17 mg) as an off white solid. $^1$H-NMR (400 MHz, DMSO-d6): δ 11.48 (s, 1H), 8.82 (d, J=2.40 Hz, 1H), 8.46 (d, J=2.00 Hz, 1H), 8.06 (t, J=2.00 Hz, 1H), 7.75 (d, J=7.20 Hz, 1H), 7.15 (t, J=3.20 Hz, 3H), 6.95-6.94 (m, 1H), 6.69 (s, 1H), 6.18-6.16 (m, 1H), 3.87-3.80 (m, 4H), 1.85-1.85 (m, 8H); MS (ES+APCI) m/z 378.2 (M+1).

Synthesis of tert-butyl 2-(5-(5-((cyclohexylcarbamoyl)oxy)-2-methoxyphenyl)pyridin-3-yl)-1H-pyrrole-1-carboxylate

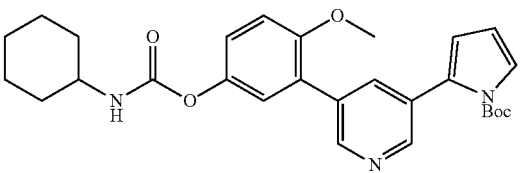 [SMILES: COc1ccc(OC(=O)NC2CCCCC2)cc1-c1cncc(-c2cccn2C(=O)OC(C)(C)C)c1]

To a stirred solution of tert-butyl 2-(5-(5-hydroxy-2-methoxyphenyl)pyridin-3-yl)-1H-pyrrole-1-carboxylate (0.1 g, 0.27 mmol) in anhydrous acetonitrile (2 mL) was added TEA (0.06 mL, 0.41 mmol) and cyclohexyl isocyanate (0.04 g, 0.33 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by automated normal-phase chromatography and eluted with ethyl acetate/petroleum ether to give tert-butyl 2-(5-(5-((cyclohexylcarbamoyl)oxy)-2-methoxyphenyl)pyridin-3-yl)-1H-pyrrole-1-carboxylate (100 mg) as an off white solid. MS (ES+APCI) m/z 492.2 (M+1).

Synthesis of 3-(5-(1H-pyrrol-2-yl)pyridin-3-yl)-4-methoxyphenyl cyclohexylcarbamate (Example-45)

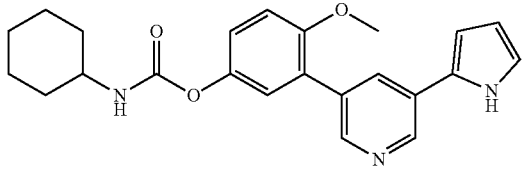 [SMILES: COc1ccc(OC(=O)NC2CCCCC2)cc1-c1cncc(-c2ccc[nH]2)c1]

To a stirred solution of tert-butyl 2-(5-(5-((cyclohexylcarbamoyl)oxy)-2-methoxyphenyl)pyridin-3-yl)-1H-pyrrole-1-carboxylate (0.1 g, 0.24 mmol) in DCM (2 mL) was added TFA (0.37 mL, 4.88 mmol) at 0° C. under nitrogen atmosphere. Then reaction mixture was stirred at 40° C. for 30 minutes. After completion of the reaction (monitored by TLC), the reaction mixture was diluted with 10% sodium bicarbonate solution and extracted with dichloromethane and washed with water. The organic layer was dried over sodium sulfate then evaporated under reduced pressure. The residue was purified by preparative HPLC (0.1% FA) to yield the target compound (47 mg) as an off white solid. $^1$H-NMR (400 MHz, DMSO-d6): δ 11.48 (s, 1H), 8.82 (d, J=2.00 Hz, 1H), 8.46 (d, J=2.00 Hz, 1H), 8.06 (t, J=2.00 Hz, 1H), 7.68 (d, J=8.00 Hz, 1H), 7.15 (d, J=2.80 Hz, 3H), 6.95-6.94 (m, 1H), 6.69 (t, J=3.60 Hz, 1H), 6.18-6.16 (m, 1H), 3.35 (d, J=17.60 Hz, 1H), 3.80 (s, 3H), 1.84-1.55 (m, 5H), 1.29-1.06 (m, 5H); MS (ES+APCI) m/z 392.2 (M+1).

Synthesis of tert-butyl 2-(5-(5-((cycloheptylcarbamoyl)oxy)-2-methoxyphenyl)pyridin-3-yl)-1H-pyrrole-1-carboxylate

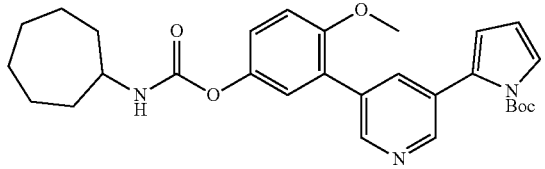 [SMILES: COc1ccc(OC(=O)NC2CCCCCC2)cc1-c1cncc(-c2cccn2C(=O)OC(C)(C)C)c1]

To a stirred solution of tert-butyl 2-(5-(5-hydroxy-2-methoxyphenyl)pyridin-3-yl)-1H-pyrrole-1-carboxylate (0.1 g, 0.27 mmol) in anhydrous acetonitrile (2 mL) was added TEA (0.06 mL, 0.41 mmol) and cycloheptyl isocyanate (0.05 g, 0.33 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by automated normal-phase chromatography and eluted with ethyl acetate/petroleum ether to give tert-butyl 2-(5-(5-((cycloheptylcarbamoyl)oxy)-2-methoxyphenyl)pyridin-3-yl)-1H-pyrrole-1-carboxylate (110 mg) as off white solid. MS (ES+APCI) m/z 506.2 (M+1).

Synthesis of 3-(5-(1H-pyrrol-2-yl)pyridin-3-yl)-4-methoxyphenyl cycloheptylcarbamate (Example-46)

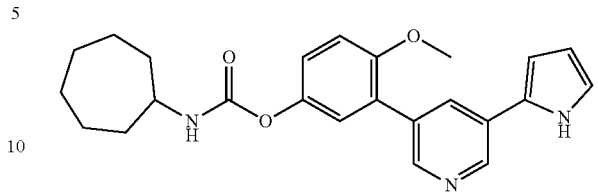

To a stirred solution of tert-butyl 2-(5-(5-((cycloheptylcarbamoyl)oxy)-2-methoxyphenyl)pyridin-3-yl)-1H-pyrrole-1-carboxylate (0.11 g, 0.22 mmol) in DCM (2 mL) was added TFA (0.33 mL, 4.35 mmol) at 0° C. under nitrogen atmosphere. Then reaction mixture was stirred at 40° C. for 30 minutes. After completion of the reaction (monitored by TLC), the reaction mixture was diluted with 10% sodium bicarbonate solution and extracted with dichloromethane and washed with water. The organic layer was dried over sodium sulfate then evaporated under reduced pressure. The residue was purified by preparative HPLC (0.1% FA) to yield the target compound (28 mg) as an off-white solid. $^1$H-NMR (400 MHz, DMSO-d6): δ 11.48 (s, 1H), 8.82 (d, J=2.40 Hz, 1H), 8.82 (d, J=2.40 Hz, 1H), 8.06 (t, J=2.00 Hz, 1H), 7.72 (d, J=8.00 Hz, 1H), 7.14 (t, J=2.00 Hz, 3H), 6.95-6.94 (m, 1H), 6.70-6.68 (m, 1H), 6.18-6.16 (m, 1H), 3.80 (s, 3H), 3.56-3.52 (m, 1H), 1.89-1.36 (m, 12H); MS (ES+APCI) m/z 406.2 (M+1).

Synthesis of 3-bromo-5-(furan-2-yl)pyridine

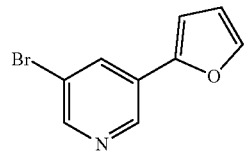 [SMILES: Brc1cncc(-c2ccco2)c1]

To a stirred solution of 3,5-dibromopyridine (2 g, 8.44 mmol) in 1,4-dioxane (20 mL) was added furan-2-ylboronic acid (1.20 g, 10.60 mmol) and Cs$_2$CO$_3$ (5.5 g, 16.88 mmol) at RT. The reaction mixture was degassed for 15 minutes then Pd(PPh$_3$)$_4$ (0.68 g, 0.60 mmol) was added. The reaction mixture was stirred at 100° C. for 2 h under nitrogen atmosphere. After completion of the reaction (monitored by TLC), the reaction mixture was cooled to RT and then the solvent was evaporated under reduced pressure. The residue was purified by automated normal-phase chromatography and eluted with ethyl acetate/petroleum ether to give 3-bromo-5-(furan-2-yl)pyridine (700 mg) as an off white solid. $^1$H-NMR (400 MHz, DMSO-d6): δ 8.93 (d, J=2.00 Hz, 1H), 8.61 (d, J=2.40 Hz, 1H), 8.34 (t, J=2.00 Hz, 1H), 7.88 (d, J=1.20 Hz, 1H), 7.26 (d, J=3.60 Hz, 1H), 6.69-6.677 (m, 1H); MS (ES+APCI) m/z 226.1 (M+2)

Synthesis of 3-(5-(furan-2-yl)pyridin-3-yl)phenol

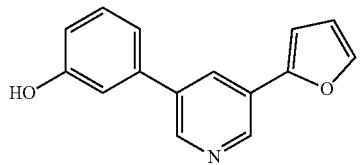 [SMILES: Oc1cccc(-c2cncc(-c3ccco3)c2)c1]

To a stirred solution of 3-bromo-5-(furan-2-yl) pyridine (0.7 g, 3.12 mmol) in 1,4-dioxane (7 mL) and water (0.5 mL) was added (3-hydroxyphenyl)boronic acid (0.47 g, 3.44 mmol) and $K_2CO_3$ (3.05 g, 9.37 mmol) at RT. The reaction mixture was degassed for 15 minutes then $Pd(PPh_3)_4$ (0.18 g, 0.16 mmol) was added. The reaction mixture was stirred at 90° C. for 5 h under nitrogen atmosphere. After completion of the reaction (monitored by TLC), the reaction mixture was cooled to RT and then the solvent was evaporated under reduced pressure. The residue was purified by automated normal-phase chromatography and eluted with ethyl acetate/petroleum ether to give 3-(5-(furan-2-yl)pyridin-3-yl)phenol (0.68 g) as an off white solid. $^1$H-NMR (400 MHz, DMSO-d6): δ 9.64 (s, 1H), 8.92 (d, J=2.80 Hz, 1H), 8.72 (d, J=2.80 Hz, 1H), 8.23 (t, J=2.80 Hz, 1H), 7.86-7.85 (m, 1H), 7.35-7.12 (m, 4H), 6.87-6.84 (m, 1H), 6.68-6.66 (m, 1H); MS (ES+APCI) m/z 238.1 (M+1).

Synthesis of 3-(5-(furan-2-yl)pyridin-3-yl)phenyl octylcarbamate (Example-47)

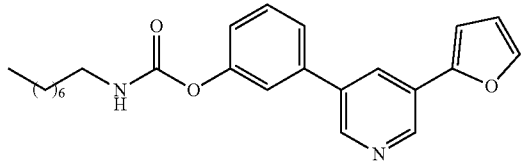

To a stirred solution of 3-(5-(furan-2-yl)pyridin-3-yl)phenol (0.08 g, 0.33 mmol) in anhydrous acetonitrile (2 mL) was added TEA (0.07 mL, 0.50 mmol) and n-octyl isocyanate (0.06 g, 0.40 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (20 mg) as an off white solid. $^1$H-NMR (400 MHz, DMSO-d6): δ 8.95 (d, J=2.00 Hz, 1H), 8.81 (d, J=2.00 Hz, 1H), 8.32 (t, J=2.00 Hz, 1H), 7.88-7.87 (m, 1H), 7.82 (t, J=5.60 Hz, 1H), 7.67-7.51 (m, 3H), 7.29-7.28 (m, 1H), 7.20-7.17 (m, 1H), 6.70-6.68 (m, 1H), 3.08 (t, J=6.0 Hz, 2H), 1.49-1.48 (m, 2H), 1.29-1.26 (m, 10H), 0.86 (t, J=6.80 Hz, 3H); MS (ES+APCI) m/z 493.3 (M+1).

Synthesis of 3-(5-(furan-2-yl)pyridin-3-yl)phenyl (cyclohexylmethyl)carbamate (Example-48)

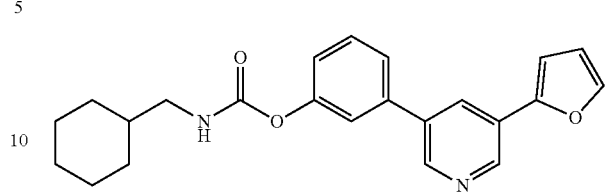

To a stirred solution of 3-(5-(furan-2-yl)pyridin-3-yl)phenol (0.08 g, 0.33 mmol) in anhydrous acetonitrile (2 mL) was added TEA (0.07 mL, 0.50 mmol) and cyclohexanemethyl isocyanate (0.06 g, 0.40 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (57 mg) as an off white solid. $^1$H-NMR (400 MHz, DMSO-d6): δ 8.95 (d, J=2.00 Hz, 1H), 8.81 (d, J=2.40 Hz, 1H), 8.33 (t, J=2.00 Hz, 1H), 7.88-7.83 (m, 2H), 7.67-7.65 (m, 1H), 7.57-7.51 (m, 2H), 7.29-7.28 (m, 1H), 7.20-7.18 (m, 1H), 6.70-6.68 (m, 1H), 2.94 (t, J=6.40 Hz, 2H), 1.75-0.87 (m, 11H);

MS (ES+APCI) m/z 377.3 (M+1).

Synthesis of 3-(5-(furan-2-yl)pyridin-3-yl)phenyl benzylcarbamate (Example-49)

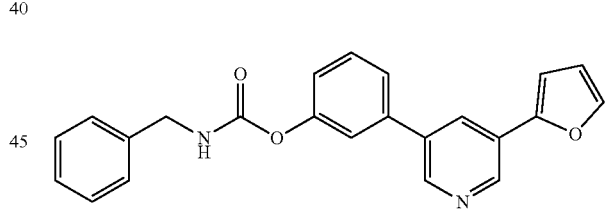

To a stirred solution of 3-(5-(furan-2-yl)pyridin-3-yl)phenol (0.08 g, 0.33 mmol) in anhydrous acetonitrile (2 mL) was added TEA (0.07 mL, 0.47 mmol) and benzyl isocyanate (0.06 g, 0.40 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to give the target compound (50 mg) as an off white solid. $^1$H-NMR (400 MHz, DMSO-d6): δ 8.95 (d, J=2.00 Hz, 1H), 8.82 (d, J=2.00 Hz, 1H), 8.40 (t, J=6.00 Hz, 1H), 8.38-8.33 (m, 1H), 7.87 (d, J=1.20 Hz, 1H), 7.68-7.52 (m, 3H), 7.39-7.34 (m, 4H), 7.30-7.21 (m, 3H), 6.70-6.69 (m, 1H), 4.32 (d, J=6.40 Hz, 2H); MS (ES+APCI) m/z 371.3 (M+1).

Synthesis of 3-(5-(furan-2-yl)pyridin-3-yl)phenyl cyclopentylcarbamate (Example-50)

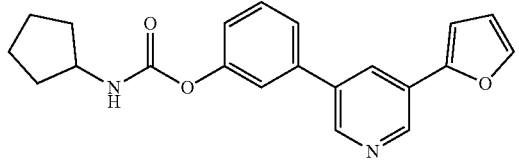 [SMILES: O=C(NC1CCCC1)Oc1cccc(-c2cncc(-c3ccco3)c2)c1]

To a stirred solution of 3-(5-(furan-2-yl)pyridin-3-yl)phenol (0.08 g, 0.33 mmol) in anhydrous acetonitrile (2 mL) was added TEA (0.07 mL, 0.50 mmol) and cyclopentyl isocyanate (0.05 g, 0.40 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (60 mg) as an off white solid. $^1$H-NMR (400 MHz, DMSO-d6): δ 8.95 (d, J=2.00 Hz, 1H), 8.81 (d, J=2.00 Hz, 1H), 8.33 (t, J=2.00 Hz, 1H), 7.88-7.85 (m, 2H), 7.66 (d, J=8.00 Hz, 1H), 7.57-7.51 (m, 2H), 7.29-7.28 (m, 1H), 7.20-7.18 (m, 1H), 6.70-6.68 (m, 1H), 3.90-3.85 (m, 1H), 1.88-1.50 (m, 8H); MS (ES+APCI) m/z 349.3 (M+1).

Synthesis of 3-(5-(furan-2-yl)pyridin-3-yl)phenyl cyclohexylcarbamate (Example-51)

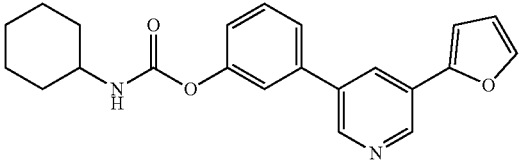 [SMILES: O=C(NC1CCCCC1)Oc1cccc(-c2cncc(-c3ccco3)c2)c1]

To a stirred solution of 3-(5-(furan-2-yl)pyridin-3-yl)phenol (0.08 g, 0.33 mmol) in anhydrous acetonitrile (2 mL) was added TEA (0.07 mL, 0.50 mmol) and cyclohexyl isocyanate (0.05 g, 0.40 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (63 mg) as an off white solid. $^1$H-NMR (400 MHz, DMSO-d6): δ 8.95 (d, J=2.00 Hz, 1H), 8.81 (d, J=2.00 Hz, 1H), 8.33 (t, J=2.40 Hz, 1H), 7.88-7.87 (m, 1H), 7.79 (d, J=8.00 Hz, 1H), 7.66 (d, J=8.40 Hz, 1H), 7.57-7.51 (m, 2H), 7.29-7.28 (m, 1H), 7.20-7.18 (m, 1H), 6.70-6.68 (m, 1H), 3.33 (s, 1H), 1.96-1.56 (m, 5H), 1.33-1.11 (m, 5H); MS (ES+APCI) m/z 363.4 (M+1).

Synthesis of 3-(5-(furan-2-yl)pyridin-3-yl)phenyl cycloheptylcarbamate (Example-52)

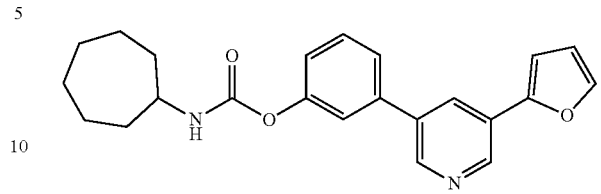

To a stirred solution of 3-(5-(furan-2-yl)pyridin-3-yl)phenol (0.08 g, 0.33 mmol) in anhydrous acetonitrile (2 mL) was added TEA (0.07 mL, 0.50 mmol) and cycloheptyl isocyanate (0.060 g, 0.40 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (58 mg) as an off white solid. $^1$H-NMR (400 MHz, DMSO-d6): δ 8.95 (d, J=2.00 Hz, 1H), 8.81 (d, J=2.40 Hz, 1H), 8.33 (t, J=2.00 Hz, 1H), 7.88-7.82 (m, 2H), 7.65 (d, J=8.00 Hz, 1H), 7.57-7.50 (m, 2H), 7.29-7.28 (m, 1H), 7.29-7.19 (3, 1H), 6.70-6.68 (m, 1H), 3.60-3.53 (m, 1H), 1.91-1.86 (m, 2H), 1.68-1.42 (m, 10H); MS (ES+APCI) m/z 377.3 (M+1).

Synthesis of 3-(5-(furan-2-yl)pyridin-3-yl)-4-methoxyphenol

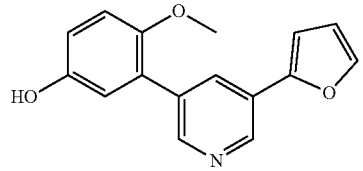 [SMILES: COc1ccc(O)cc1-c1cncc(-c2ccco2)c1]

To a stirred solution of 3-bromo-5-(furan-2-yl)pyridine (0.4 g, 1.78 mmol) in 1,4-dioxane (5 mL) and water (0.5 mL) was added (5-hydroxy-2-methoxyphenyl)boronic acid (0.33 g, 1.96 mmol) and $K_2CO_3$ (1.8 g, 5.40 mmol) at RT. The reaction mixture was degassed for 15 minutes then Pd(PPh$_3$)$_4$ (0.10 g, 0.09 mmol) was added. The reaction mixture was stirred at 90° C. for 5 h under nitrogen atmosphere. After completion of the reaction (monitored by TLC), the reaction mixture was cooled to RT and then the solvent was evaporated under reduced pressure. The residue was dissolved in ethyl acetate, washed with water followed by brine. The organic layer was dried over sodium sulfate then evaporated under reduced pressure. The residue was purified by automated normal-phase chromatography and eluted with ethyl acetate/petroleum ether to yield the target compound (440 mg) as an off white solid. $^1$H-NMR (400 MHz, DMSO-d6): δ 9.16 (s, 1H), 8.88 (t, J=2.80 Hz, 1H), 8.54 (d, J=2.40 Hz, 1H), 8.09 (t, J=2.80 Hz, 1H), 7.84 (t, J=0.80 Hz, 1H), 7.18 (d, J=4.00 Hz, 1H), 7.01-6.98 (m, 1H), 6.83-6.78 (m, 2H), 6.67-6.65 (m, 1H), 3.70 (s, 3H); MS (ES+APCI) m/z 268.3 (M+1).

Synthesis of 3-(5-(furan-2-yl)pyridin-3-yl)-4-methoxyphenyl octylcarbamate (Example-53)

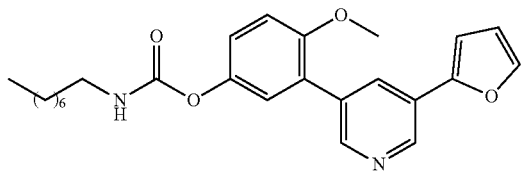

To a stirred solution of 3-(5-(furan-2-yl)pyridin-3-yl)-4-methoxyphenol (0.07 g, 0.28 mmol) in anhydrous acetonitrile (2 mL) was added TEA (0.06 mL, 0.40 mmol) and n-octyl isocyanate (0.05 g, 0.32 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (47 mg) as an off white solid. $^1$H-NMR (400 MHz, DMSO-d6): δ 8.90 (d, J=2.40 Hz, 1H), 8.58 (d, J=2.00 Hz, 1H), 8.13 (t, J=2.00 Hz, 1H), 7.86-7.85 (m, 1H), 7.71 (t, J=5.60 Hz, 1H), 7.20-7.15 (m, 4H), 6.67-6.66 (m, 1H), 3.81 (s, 3H), 3.07-3.02 (m, 2H), 1.46 (t, J=7.20 Hz, 2H), 1.26 (d, J=6.40 Hz, 10H), 0.86 (t, J=6.80 Hz, 3H); MS (ES+APCI) m/z 423.4 (M+1).

Synthesis of 3-(5-(furan-2-yl)pyridin-3-yl)-4-methoxyphenyl (cyclohexylmethyl)carbamate (Example-54)

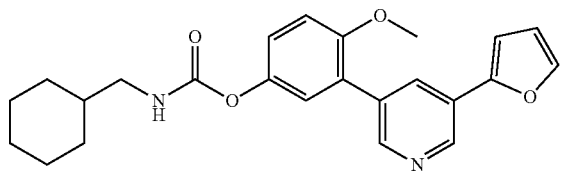

To a stirred solution of 3-(5-(furan-2-yl)pyridin-3-yl)-4-methoxyphenol (0.07 g, 0.28 mmol) in anhydrous acetonitrile (2 mL) was added TEA (0.06 mL, 0.40 mmol) and cyclohexanemethyl isocyanate (0.05 g, 0.32 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to give 3-(5-(furan-2-yl)pyridin-3-yl)-4-methoxyphenyl (cyclohexylmethyl) carbamate (32 mg) as an off white solid. $^1$H-NMR (400 MHz, DMSO-d6): δ 8.90 (d, J=2.00 Hz, 1H), 8.58 (d, J=2.40 Hz, 1H), 8.13 (t, J=2.40 Hz, 1H), 7.85 (d, J=1.20 Hz, 1H), 7.73 (t, J=6.00 Hz, 1H), 7.20-7.15 (m, 4H), 6.68-6.66 (m, 1H), 3.80 (s, 3H), 2.91 (t, J=6.40 Hz, 2H), 1.73-1.61 (m, 5H), 1.46-1.42 (m, 1H), 1.24-1.11 (m, 3H), 0.92 (d, J=12.00 Hz, 2H); MS (ES+APCI) m/z 407.3 (M+1).

Synthesis of 3-(5-(furan-2-yl)pyridin-3-yl)-4-methoxyphenyl benzylcarbamate (Example-55)

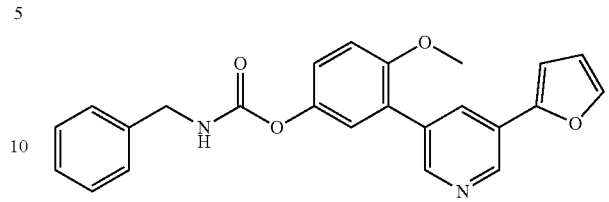

To a stirred solution of 3-(5-(furan-2-yl)pyridin-3-yl)-4-methoxyphenol (0.07 g, 0.28 mmol) in anhydrous acetonitrile (2 mL) was added TEA (0.06 mL, 0.40 mmol) and benzyl isocyanate (0.05 g, 0.32 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (34 mg) as an off white solid. 1H-NMR (400 MHz, DMSO-d6): δ 8.90 (d, J=2.40 Hz, 1H), 8.59 (d, J=2.00 Hz, 1H), 8.30 (t, J=6.40 Hz, 1H), 8.14 (t, J=2.40 Hz, 1H), 7.86 (d, J=1.60 Hz, 1H), 7.38-7.31 (m, 4H), 7.29-7.25 (m, 1H), 7.22-7.15 (m, 4H), 6.67 (d, J=1.60 Hz, 1H), 4.29 (d, J=6.00 Hz, 2H), 3.81 (s, 3H); MS (ES+APCI) m/z 401.3 (M+1).

Synthesis of 3-(5-(furan-2-yl)pyridin-3-yl)-4-methoxyphenyl cyclopentylcarbamate Example-56)

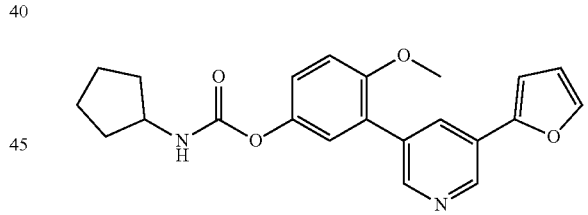

To a stirred solution of 3-(5-(furan-2-yl)pyridin-3-yl)-4-methoxyphenol (0.07 g, 0.28 mmol) in anhydrous acetonitrile (2 mL) was added TEA (0.06 mL, 0.40 mmol) and cyclopentyl isocyanate (0.04 g, 0.32 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (62 mg) as an off white solid. $^1$H-NMR (400 MHz, DMSO-d6): δ 8.90 (d, J=2.00 Hz, 1H), 8.59 (d, J=2.00 Hz, 1H), 8.13 (t, J=2.00 Hz, 1H), 7.86-7.85 (m, 1H), 7.76 (d, J=7.60 Hz, 1H), 7.20-7.15 (m, 4H), 6.68-6.66 (m, 1H), 3.87-3.81 (m, 4H), 1.85-1.80 (m, 2H), 1.69-1.65 (m, 2H), 1.53-1.46 (m, 4H); MS (ES+APCI) m/z 379.3 (M+1).

Synthesis of 3-(5-(furan-2-yl)pyridin-3-yl)-4-methoxyphenyl cyclohexylcarbamate

Example-57

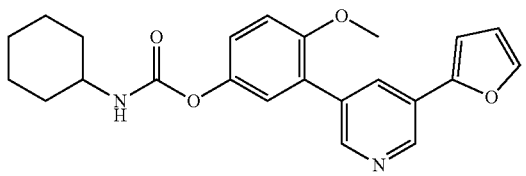 [SMILES: COc1ccc(OC(=O)NC2CCCCC2)cc1-c1cncc(-c2ccco2)c1]

To a stirred solution of 3-(5-(furan-2-yl)pyridin-3-yl)-4-methoxyphenol (0.07 g, 0.26 mmol) in anhydrous acetonitrile (2 mL) was added TEA (0.06 mL, 0.40 mmol) and cyclohexyl isocyanate (0.04 g, 0.32 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (45 mg) as an off white solid. $^1$H-NMR (400 MHz, DMSO-d6): δ 8.90 (d, J=2.40 Hz, 1H), 8.58 (d, J=2.00 Hz, 1H), 8.13 (t, J=2.00 Hz, 1H), 7.86-7.85 (m, 1H), 7.69 (d, J=8.00 Hz, 1H), 7.20-7.15 (m, 4H), 6.68-6.66 (m, 1H), 3.81 (s, 3H), 3.32 (d, J=12.00 Hz, 1H), 1.83 (d, J=8.80 Hz, 2H), 1.72-1.69 (m, 2H), 1.56 (d, J=12.40 Hz, 1H), 1.28-1.10 (m, 5H); MS (ES+APCI) m/z 393.4 (M+1).

Synthesis of 3-(5-(furan-2-yl)pyridin-3-yl)-4-methoxyphenyl cycloheptylcarbamate (Example-58)

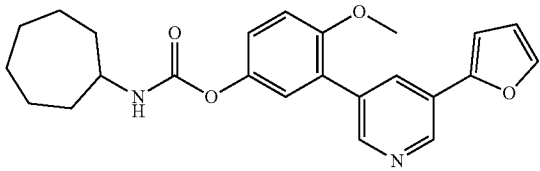 [SMILES: COc1ccc(OC(=O)NC2CCCCCC2)cc1-c1cncc(-c2ccco2)c1]

To a stirred solution of 3-(5-(furan-2-yl)pyridin-3-yl)-4-methoxyphenol (0.07 g, 0.28 mmol) in anhydrous acetonitrile (2 mL) was added TEA (0.06 mL, 0.40 mmol) and cycloheptyl isocyanate (0.05 g, 0.32 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (35 mg) as an off white solid. $^1$H-NMR (400 MHz, DMSO-d6): δ 8.90 (d, J=2.40 Hz, 1H), 8.58 (d, J=2.40 Hz, 1H), 8.13 (t, J=2.00 Hz, 1H), 7.86-7.85 (m, 1H), 7.72 (d, J=7.60 Hz, 1H), 7.20-7.15 (m, 4H), 6.67-6.66 (m, 1H), 3.80 (s, 3H), 3.54 (t, J=4.40 Hz, 1H), 1.89-1.83 (m, 2H), 1.66-1.37 (m, 10H); MS (ES+APCI) m/z 407.3 (M+1).

Synthesis of 3-bromo-5-(thiophen-2-yl)pyridine

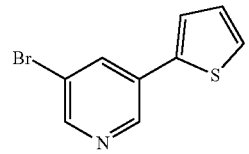 [SMILES: Brc1cncc(-c2cccs2)c1]

To a stirred solution of 3,5-dibromopyridine (1 g, 4.22 mmol) in 1,4-dioxane (10 mL) was added thiophen-2-ylboronic acid (1.13 g, 8.86 mmol) and Cs$_2$CO$_3$ (2.27 g, 6.97 mmol) at RT. The reaction mixture was degassed for 15 minutes then Pd(PPh$_3$)$_4$ (0.34 g, 0.30 mmol) was added.

The reaction mixture was stirred at 100° C. for 2 h under nitrogen atmosphere. After completion of the reaction (monitored by TLC), the reaction mixture was cooled to RT and then the solvent was evaporated under reduced pressure. The residue was purified by automated normal-phase chromatography and eluted with ethyl acetate/petroleum ether to give 3-bromo-5-(thiophen-2-yl) pyridine (400 mg) as an off white solid. MS (ES+APCI) m/z 240.1.

Synthesis of 3-(5-(thiophen-2-yl)pyridin-3-yl)phenol

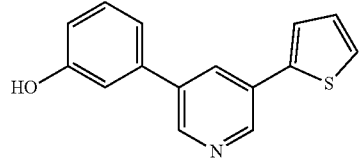 [SMILES: Oc1cccc(-c2cncc(-c3cccs3)c2)c1]

To a stirred solution of 3-bromo-5-(thiophen-2-yl)pyridine (0.4 g, 1.67 mmol) in 1,4-dioxane (4 mL) and water (0.5 mL) was added (3-hydroxyphenyl)boronic acid (0.35 g, 2.50 mmol) and K$_2$CO$_3$ (0.69 g, 5.00 mmol) at RT. The reaction mixture was degassed for 15 minutes then Pd(PPh$_3$)$_4$ (0.1 g, 0.08 mmol) was added. The reaction mixture was stirred at 90° C. for 16 h under nitrogen atmosphere. After completion of the reaction (monitored by TLC), the reaction mixture was cooled to RT and then the solvent was evaporated under reduced pressure. The residue was dissolved in minimum amount of DCM and was added petroleum ether slowly. The precipitated solid was filtered and dried to give 3-(5-(thiophen-2-yl)pyridin-3-yl)phenol (320 mg) as an off white solid. MS (ES+APCI) m/z 254.3 (M+1).

Synthesis of 3-(5-(thiophen-2-yl)pyridin-3-yl)phenyl octylcarbamate (Example-59)

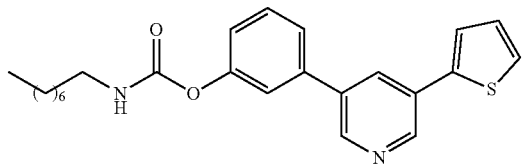

To a stirred solution of 3-(5-(thiophen-2-yl)pyridin-3-yl) phenol (0.08 g, 0.32 mmol) in anhydrous acetonitrile (2 mL)

was added TEA (0.07 mL, 0.47 mmol) and n-octyl isocyanate (0.058 g, 0.38 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (12 mg) as an off white solid. $^1$H NMR (400 MHz, DMSO-d6) δ 8.89 (d, J=2.00 Hz, 1H), 8.82 (d, J=2.00 Hz, 1H), 8.30-8.29 (m, 1H), 7.83-7.80 (m, 2H), 7.71-7.66 (m, 2H), 7.58-7.51 (m, 2H), 7.24-7.18 (m, 2H), 3.10-3.05 (m, 2H), 1.49 (t, J=6.80 Hz, 2H), 1.29-1.25 (m, 10H), 0.86 (t, J=7.20 Hz, 3H); MS (ES+APCI) m/z 409.3 (M+1).

Synthesis of 3-(5-(thiophen-2-yl)pyridin-3-yl)phenyl (cyclohexylmethyl)carbamate Example-60)

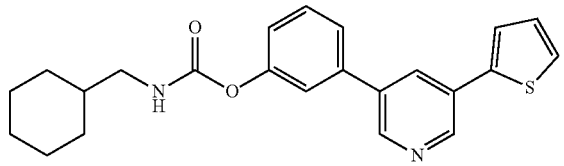 [SMILES: O=C(NCC1CCCCC1)Oc1cccc(-c2cncc(-c3cccs3)c2)c1]

To a stirred solution of 3-(5-(thiophen-2-yl)pyridin-3-yl)phenol (0.08 g, 0.32 mmol) in anhydrous acetonitrile (2 mL) was added TEA (0.07 mL, 0.47 mmol) and cyclohexanemethyl isocyanate (0.053 g, 0.38 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (28 mg) as an off white solid. $^1$HNMR (400 MHz, DMSO-d6) δ 8.89 (d, J=2.40 Hz, 1H), 8.82 (d, J=2.00 Hz, 1H), 8.30 (t, J=2.00 Hz, 1H), 7.86-7.81 (m, 2H), 7.71-7.66 (m, 2H), 7.59-7.51 (m, 2H), 7.24-7.18 (m, 2H), 2.95-2.92 (m, 2H), 1.75-0.87 (m, 11H); MS (ES+APCI) m/z 393.4 (M+1).

Synthesis of 3-(5-(thiophen-2-yl)pyridin-3-yl)phenyl benzylcarbamate (Example-61)

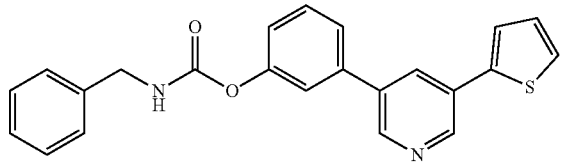 [SMILES: O=C(NCc1ccccc1)Oc1cccc(-c2cncc(-c3cccs3)c2)c1]

To a stirred solution of 3-(5-(thiophen-2-yl)pyridin-3-yl)phenol (0.08 g, 0.32 mmol) in anhydrous acetonitrile (2 mL) was added TEA (0.07 mL, 0.47 mmol) and benzyl isocyanate (0.05 g, 0.38 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (30 mg) as an off white solid. $^1$HNMR (400 MHz, DMSO-d6) δ 8.89 (d, J=2.00 Hz, 1H), 8.83 (d, J=2.00 Hz, 1H), 8.40 (t, J=6.40 Hz, 1H), 8.31 (t, J=2.40 Hz, 1H), 7.82-7.81 (m, 1H), 7.71-7.68 (m, 2H), 7.62 (t, J=1.60 Hz, 1H), 7.54 (t, J=8.00 Hz, 1H), 7.39-7.22 (m, 7H), 4.31 (d, J=6.40 Hz, 2H); MS (ES+APCI) m/z 387.2 (M+1).

Synthesis of 3-(5-(thiophen-2-yl)pyridin-3-yl)phenyl cyclopentylcarbamate (Example-62)

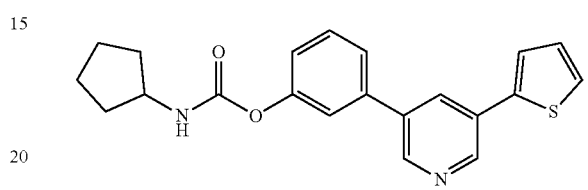

To a stirred solution of 3-(5-(thiophen-2-yl)pyridin-3-yl)phenol (0.08 g, 0.32 mmol) in anhydrous acetonitrile (2 mL) was added TEA (0.07 mL, 0.47 mmol) and cyclopentyl isocyanate (0.042 g, 0.38 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to give yield the target compound (30 mg) as an off white solid. $^1$HNMR (400 MHz, DMSO-d6) δ 8.89 (d, J=2.40 Hz, 1H), 8.82 (d, J=2.00 Hz, 1H), 8.30 (t, J=2.00 Hz, 1H), 7.87-7.81 (m, 2H), 7.71-7.66 (m, 2H), 7.60-7.51 (m, 2H), 7.24-7.19 (m, 2H), 3.90-3.85 (m, 1H), 1.88-1.47 (m, 8H); MS (ES+APCI) m/z 365.3 (M+1).

Synthesis of 3-(5-(thiophen-2-yl)pyridin-3-yl)phenyl cyclohexylcarbamate (Example-63)

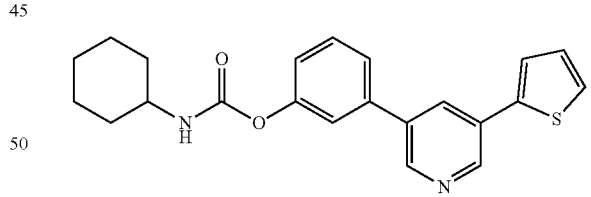

To a stirred solution of 3-(5-(thiophen-2-yl)pyridin-3-yl)phenol (0.08 g, 0.32 mmol) in anhydrous acetonitrile (2 mL) was added TEA (0.07 mL, 0.47 mmol) and cyclohexyl isocyanate (0.05 g, 0.38 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (35 mg) as an off white solid. $^1$HNMR (400 MHz, DMSO-d6) δ 8.89 (d, J=2.40 Hz, 1H), 8.82 (d, J=2.00 Hz, 1H), 8.30 (t, J=2.00 Hz, 1H), 7.82-7.78 (m, 2H), 7.71-7.66 (m, 2H), 7.59-7.51 (m, 2H), 7.24-7.18 (m, 2H), 3.36-3.36 (m, 1H), 1.90-1.08 (m, 10H); MS (ES+APCI) m/z 379.3 (M+1).

Synthesis of 3-(5-(thiophen-2-yl)pyridin-3-yl)phenyl cycloheptylcarbamate (Example-64)

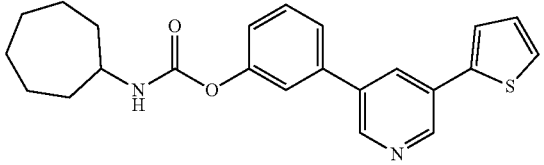

To a stirred solution of 3-(5-(thiophen-2-yl)pyridin-3-yl)phenol (0.08 g, 0.32 mmol) in anhydrous acetonitrile (2 mL) was added TEA (0.07 mL, 0.47 mmol) and cycloheptyl isocyanate (0.053 g, 0.38 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (33 mg) as an off white solid. $^1$HNMR (400 MHz, DMSO-d6) δ 8.89 (d, J=2.00 Hz, 1H), 8.84 (d, J=2.40 Hz, 1H), 8.30 (t, J=2.00 Hz, 1H), 8.29-7.81 (m, 2H), 7.71-7.65 (m, 2H), 7.59-7.50 (m, 2H), 7.24-7.18 (m, 2H), 3.60-3.53 (m, 1H), 1.91-1.86 (m, 2H), 1.67-1.39 (in, 10H); MS (ES+APCI) m/z 393.4 (M+1).

Synthesis of 4-methoxy-3-(5-(thiophen-2-yl)pyridin-3-yl)phenol

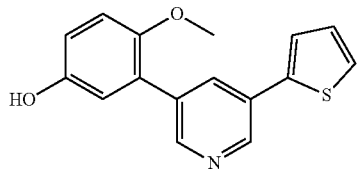 [SMILES: COc1ccc(O)cc1-c1cncc(-c2cccs2)c1]

To a stirred solution of 3-bromo-5-(thiophen-2-yl)pyridine (0.5 g, 2.08 mmol) in 1,4-dioxane (5 mL) and water (0.5 mL) was added (5-hydroxy-2-methoxyphenyl)boronic acid (0.53 g, 3.12 mmol) and $K_2CO_3$ (0.86 g, 6.25 mmol) at RT. The reaction mixture was degassed for 15 minutes then Pd(PPh$_3$)$_4$ (0.12 g, 0.10 mmol) was added. The reaction mixture was stirred at 90° C. for 16 h under nitrogen atmosphere. After completion of the reaction (monitored by TLC), the reaction mixture was cooled to RT and then the solvent was evaporated under reduced pressure. The residue was dissolved in ethyl acetate, washed with water followed by brine. The organic layer was dried over sodium sulfate then evaporated under reduced pressure. The residue was purified by automated normal-phase chromatography and eluted with ethyl acetate/petroleum ether to give 4-methoxy-3-(5-(thiophen-2-yl)pyridin-3-yl)phenol (450 mg) as an off white solid. MS (ES+APCI) m/z 284.1 (M+1).

Synthesis of 4-methoxy-3-(5-(thiophen-2-yl)pyridin-3-yl)phenyl octylcarbamate Example-65

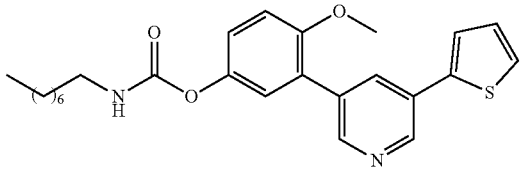

To a stirred solution of 4-methoxy-3-(5-(thiophen-2-yl)pyridin-3-yl)phenol (0.08 g, 0.28 mmol) in anhydrous acetonitrile (2 mL) was added TEA (0.06 mL, 0.34 mmol) and octyl isocyanate (0.05 g, 0.34 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (45 mg) as an off white solid. $^1$HNMR (400 MHz, DMSO-d6) δ 8.85 (d, J=2.40 Hz, 1H), 8.60 (d, J=2.00 Hz, 1H), 8.10 (t, J=2.40 Hz, 1H), 7.72-7.67 (m, 3H), 7.22-7.16 (m, 4H), 3.81 (s, 3H), 3.07-3.02 (m, 2H), 1.46 (t, J=7.20 Hz, 2H), 1.27-1.25 (m, 10H), 0.87-0.84 (m, 3H); MS (ES+APCI) m/z 439.3 (M+1).

Synthesis of 4-methoxy-3-(5-(thiophen-2-yl)pyridin-3-yl)phenyl (cyclohexylmethyl)carbamate (Example-66)

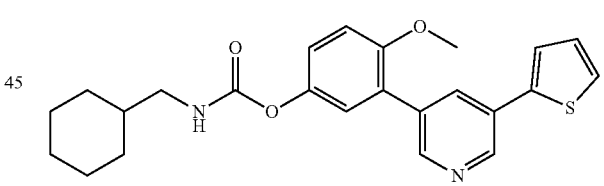

To a stirred solution of 4-methoxy-3-(5-(thiophen-2-yl)pyridin-3-yl)phenol (0.08 g, 0.28 mmol) in anhydrous acetonitrile (2 mL) was added TEA (0.06 mL, 0.34 mmol) and cyclohexanemethyl isocyanate (0.05 g, 0.34 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (36 mg) as an off white solid. $^1$HNMR (400 MHz, DMSO-d6) δ 8.85 (d, J=2.00 Hz, 1H), 8.60 (d, J=2.00 Hz, 1H), 8.10 (t, J=2.00 Hz, 1H), 7.75-7.67 (m, 3H), 7.22-7.15 (m, 4H), 3.81 (s, 3H), 2.91 (t, J=6.40 Hz, 2H), 1.73-0.88 (m, 11H); MS (ES+APCI) m/z 423.3 (M+1).

Synthesis of 4-methoxy-3-(5-(thiophen-2-yl)pyridin-3-yl)phenyl benzylcarbamate

Example-67

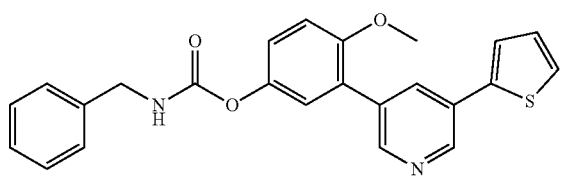 [SMILES: COc1ccc(OC(=O)NCc2ccccc2)cc1-c1cncc(-c2cccs2)c1]

To a stirred solution of 4-methoxy-3-(5-(thiophen-2-yl) pyridin-3-yl)phenol (0.08 g, 0.28 mmol) in anhydrous acetonitrile (2 mL) was added TEA (0.06 mL, 0.34 mmol) and benzyl isocyanate (0.05 g, 0.34 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (42 mg) as an off white solid. $^1$HNMR (400 MHz, DMSO-d6) δ 8.85 (d, J=2.00 Hz, 1H), 8.61 (d, J=2.00 Hz, 1H), 8.29 (t, J=6.40 Hz, 1H), 8.11 (t, J=2.00 Hz, 1H), 7.72-7.67 (m, 2H), 7.38-7.28 (m, 4H), 7.27-7.15 (m, 5H), 4.29 (d, J=6.00 Hz, 2H), 3.81 (s, 3H); MS (ES+APCI) m/z 417.2 (M+1).

Synthesis of 4-methoxy-3-(5-(thiophen-2-yl)pyridin-3-yl)phenyl cyclopentylcarbamate

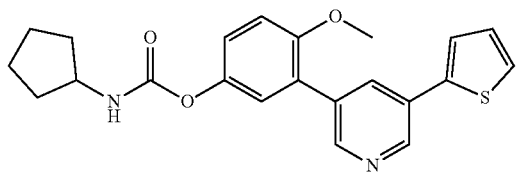 [SMILES: COc1ccc(OC(=O)NC2CCCC2)cc1-c1cncc(-c2cccs2)c1]

To a stirred solution of 4-methoxy-3-(5-(thiophen-2-yl) pyridin-3-yl)phenol (0.08 g, 0.28 mmol) in anhydrous acetonitrile (2 mL) was added TEA (0.06 mL, 0.34 mmol) and cyclopentyl isocyanate (0.04 g, 0.34 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (55 mg) as an off white solid. $^1$HNMR (400 MHz, DMSO-d6) δ 8.85 (d, J=2.40 Hz, 1H), 8.60 (d, J=2.00 Hz, 1H), 8.10 (t, J=2.40 Hz, 1H), 7.77-7.67 (m, 3H), 7.22-7.16 (m, 4H), 3.87-3.84 (m, 1H), 3.81 (s, 3H), 1.84-1.48 (m, 8H); MS (ES+APCI) m/z 395.2 (M+1).

Synthesis of 4-methoxy-3-(5-(thiophen-2-yl)pyridin-3-yl)phenyl cyclohexylcarbamate Example-69

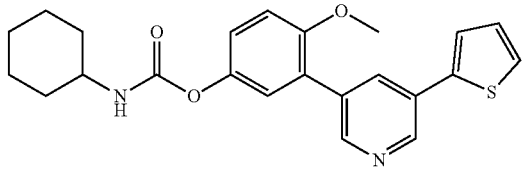 [SMILES: COc1ccc(OC(=O)NC2CCCCC2)cc1-c1cncc(-c2cccs2)c1]

To a stirred solution of 4-methoxy-3-(5-(thiophen-2-yl) pyridin-3-yl)phenol (0.08 g, 0.28 mmol) in anhydrous acetonitrile (2 mL) was added TEA (0.06 mL, 0.34 mmol) and cyclohexyl isocyanate (0.04 g, 0.34 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (10 mg) as an off white solid. $^1$HNMR (400 MHz, DMSO-d6) δ 8.85 (d, J=2.40 Hz, 1H), 8.60 (d, J=2.00 Hz, 1H), 8.10 (t, J=2.40 Hz, 1H), 7.67-7.72 (m, 3H), 7.22-7.20 (m, 2H), 7.16 (d, J=1.20 Hz, 2H), 3.81 (s, 3H), 1.84-1.09 (m, 10H); MS (ES+APCI) m/z 409.3 (M+1).

Synthesis of 4-methoxy-3-(5-(thiophen-2-yl)pyridin-3-yl)phenyl cycloheptylcarbamate

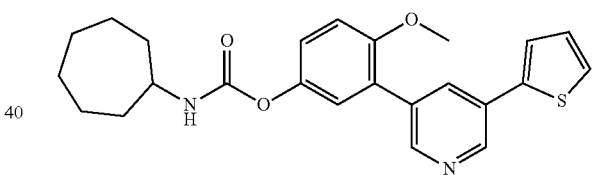

To a stirred solution of 4-methoxy-3-(5-(thiophen-2-yl) pyridin-3-yl)phenol (0.08 g, 0.28 mmol) in anhydrous acetonitrile (2 mL) was added TEA (0.06 mL, 0.34 mmol) and cycloheptyl isocyanate (0.05 g, 0.34 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (35 mg) as an off white solid. $^1$HNMR (400 MHz, DMSO-d6) δ 8.85 (d, J=2.40 Hz, 1H), 8.60 (d, J=2.00 Hz, 1H), 8.10 (t, J=2.00 Hz, 1H), 7.73-7.67 (m, 3H), 7.22-7.15 (m, 4H), 3.81 (s, 3H), 3.57-3.49 (m, 1H), 1.89-1.40 (m, 12H); MS (ES+APCI) m/z 423.2 (M+1)

Scheme III

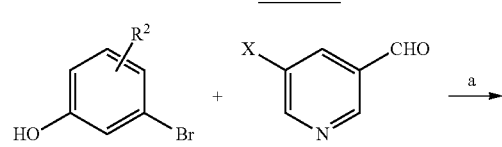

-continued

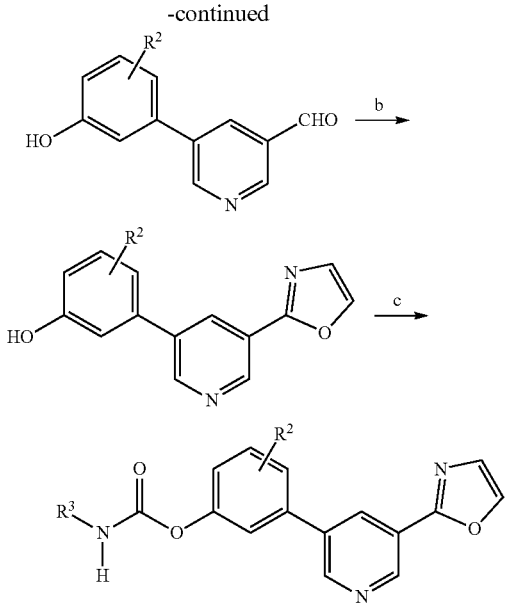

X = —B(OC₃H₆)₂, or —B(OH)₂
R² = H, CH₃, OCH₃, OCF₃, F
Reagents and conditions: a) Pd(PPh₃)₄, aq K₂CO₃, 1,4-dioxane, 90° C., 12 h or Pd(dppf)Cl₂, KOAc, 1,4-dioxane, 80° C., 4 h; b) TOSMIC, K₂CO₃, MeOH, 80° C., 1 h; c) R³—NCO, TEA, ACN, 75° C., 12 h.

Synthesis of 3-(5-(oxazol-2-yl)pyridin-3-yl)phenol

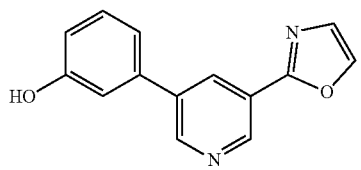 [SMILES: Oc1cccc(-c2cncc(-c3ncco3)c2)c1]

To a solution of TOSMIC (0.068 g, 0.35 mmol) in methanol (6 mL) was added K₂CO₃ (0.14 g, 1.054 mmol) and at RT and stirred for 30 minutes under nitrogen atmosphere. 5-(3-hydroxyphenyl)nicotinaldehyde (0.07 g, 0.35 mmol) was then added to the resulting mixture and stirred at RT for additional 30 minutes. The reaction mixture was heated at 70° C. for 1 h under nitrogen atmosphere. The reaction progress was monitored by TLC, after completion the reaction mixture was cooled to RT and then the solvent was evaporated under reduced pressure. The residue was dissolved in ethyl acetate, washed with water followed by brine. The organic layer was dried over sodium sulfate and then the solvent was evaporated under reduced pressure. The compound was purified by column chromatography on silica gel eluting with hexane/EtOAc (gradient 10-70% EtOAc) to yield the 3-(5-(oxazol-2-yl)pyridin-3-yl)phenol (40 mg) as a white solid. ¹H NMR (400 MHz, DMSO-d6): δ 9.70 (s, 1H), 8.94 (s, 1H), 8.82 (s, 1H), 8.58 (s, 1H), 8.32 (s, 1H), 7.97 (s, 1H), 7.34 (t, J=8.1 Hz, 1H), 7.22 (d, J=8.1 Hz, 1H), 7.15 (s, 1H), 6.87 (dd, J=8.1 Hz, 1H).

Synthesis of 3-(5-(oxazol-2-yl)pyridin-3-yl)phenyl pentylcarbamate (Example-71)

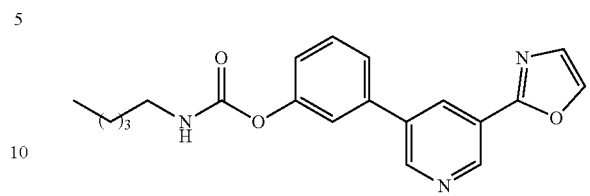

To a stirred solution of 3-(5-(oxazol-2-yl)pyridin-3-yl) phenol (0.08 g, 0.33 mmol) in anhydrous acetonitrile (2 mL) under a nitrogen atmosphere was added TEA (0.05 mL, 0.33 mmol) and n-pentyl isocyanate (0.06 g, 0.40 mmol) at RT. The reaction mixture was stirred at RT for 10 minutes and then heated to 75° C. for 12 h, under nitrogen atmosphere. The progress of the reaction was monitored by TLC. Upon completion, the reaction mixture was cooled to RT, and the solvent was evaporated under reduced pressure. The crude product was purified by flash column chromatography on silica gel, eluting with hexane/EtOAc (gradient 40-60% EtOAc) to yield the target compound (46 mg) as an off white solid. ¹H NMR (400 MHz, CDCl3): δ 8.84 (d, J=2.1 Hz, 1H), 8.73 (d, J=2.2 Hz, 1H), 8.03 (t, J=2.2 Hz, 1H), 7.93 (s, 1H), 7.30-7.47 (m, 4H), 7.15 (ddd, J=7.8, 2.4, 1.4 Hz, 1H), 4.99 (s, 1H), 3.03-3.41 (m, 2H), 1.54 (t, J=7.1 Hz, 2H), 1.11-1.44 (m, 4H), 0.77-0.91 (m, 3H).

Synthesis of 3-(5-(oxazol-2-yl)pyridin-3-yl)phenyl heptylcarbamate (Example-72)

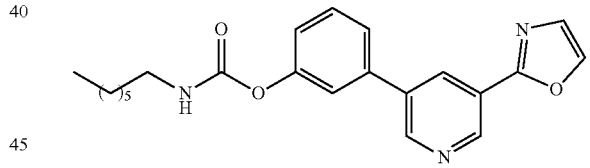

To a stirred solution of 3-(5-(oxazol-2-yl)pyridin-3-yl) phenol (0.08 g, 0.33 mmol) in anhydrous acetonitrile (2 mL) under a nitrogen atmosphere was added TEA (0.05 mL, 0.33 mmol) and n-heptyl isocyanate (0.05 g, 0.33 mmol) at RT. The reaction mixture was stirred at RT for 10 minutes and then heated to 75° C. for 12 h, under nitrogen atmosphere. The progress of the reaction was monitored by TLC. Upon completion, the reaction mixture was cooled to RT, and the solvent was evaporated under reduced pressure. The crude product was purified by flash column chromatography on silica gel, eluting with hexane/EtOAc (gradient 40-60% EtOAc) to yield the target compound (48 mg) as a as an off white solid. ¹H NMR (400 MHz, CDCl3): δ 8.84 (d, J=2.1 Hz, 1H), 8.72 (d, J=2.2 Hz, 1H), 8.02 (t, J=2.1 Hz, 1H), 7.93 (s, 1H), 7.93-7.49 (m, 4H), 7.30-7.15 (m, 1H, J=7.8, 2.3, 1.4 Hz), 3.22 (td, J=7.2, 6.0 Hz, 2H), 1.70-1.41 (m, 4H), 1.41-1.13 (m, 8H), 0.93-0.69 (m, 3H)

Synthesis of 3-(5-(oxazol-2-yl)pyridin-3-yl)phenyl octylcarbamate (Example-73)

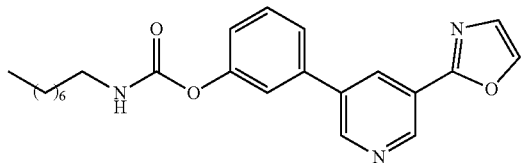

To a stirred solution of 3-(5-(oxazol-2-yl)pyridin-3-yl)phenol (0.08 g, 0.33 mmol) in anhydrous acetonitrile (2 mL) under a nitrogen atmosphere, TEA (0.05 mL, 0.33 mmol) and n-octyl isocyanate (0.05 g, 0.33 mmol) were added at RT. The reaction mixture was stirred at RT for 10 minutes and then heated to 75° C. for 12 h, under nitrogen atmosphere. The progress of the reaction was monitored by TLC. Upon completion, the reaction mixture was cooled to RT, and the solvent was evaporated under reduced pressure. The crude product was purified by flash column chromatography on silica gel, eluting with hexane/EtOAc (gradient 40-60% EtOAc) to yield the target compound (44 mg) as an off white solid. $^1$H NMR (400 MHz, CDCl3): δ 8.91 (d, J=2.1 Hz, 1H), 8.79 (d, J=2.2 Hz, 1H), 8.09 (t, J=2.2 Hz, 1H), 8.00 (s, 1H), 7.51 (s, 1H), 7.42-7.51 (m, 2H), 7.40 (t, J=2.0 Hz, 1H), 7.22 (ddd, J=7.8, 2.3, 1.4 Hz, 1H), 5.10 (t, J=6.0 Hz, 1H), 3.29 (td, J=7.2, 6.0 Hz, 2H), 1.39-2.82 (m, 2H), 1.21-1.38 (m, 10H), 0.97-0.85 (m, 3H).

Synthesis of 3-(5-(oxazol-2-yl)pyridin-3-yl)phenyl (cyclohexylmethyl)carbamate Example-74

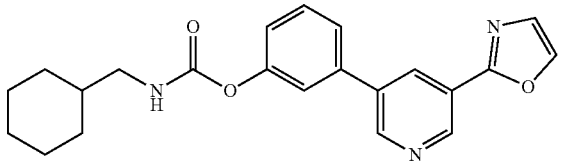

To a stirred solution of 3-(5-(oxazol-2-yl)pyridin-3-yl)phenol (0.08 g, 0.33 mmol) in anhydrous acetonitrile (2 mL) under a nitrogen atmosphere, TEA, (0.05 mL, 0.33 mmol) and cyclohexanemethyl isocyanate (0.05 g, 0.40 mmol) were added at RT. The reaction mixture was stirred at RT for 10 minutes and then heated to 75° C. for 12 h, under nitrogen atmosphere. The progress of the reaction was monitored by TLC. Upon completion, the reaction mixture was cooled to RT, and the solvent was evaporated under reduced pressure. The crude product was purified by flash column chromatography on silica gel, eluting with hexane/EtOAc (gradient 40-60% EtOAc) to yield the target compound (43 mg) as an off white solid. $^1$H NMR (400 MHz, CDCl3): δ 8.91 (d, J=2.1 Hz, 1H), 8.79 (d, J=2.2 Hz, 1H), 8.09 (t, J=2.2 Hz, 1H), 8.00 (s, 1H), 7.51 (s, 1H), 7.43-7.51 (m, 2H), 7.41 (t, J=2.0 Hz, 1H), 7.22 (ddd, J=7.8, 2.3, 1.3 Hz, 1H), 5.14 (t, J=6.2 Hz, 1H), 3.14 (t, J=6.5 Hz, 2H), 1.62-2.22 (m, 5H), 1.15-1.36 (m, 4H), 1.08-0.82 (m, 2H)

Synthesis of 3-(5-(oxazol-2-yl)pyridin-3-yl)phenyl cyclopentylcarbamate (Example-75)

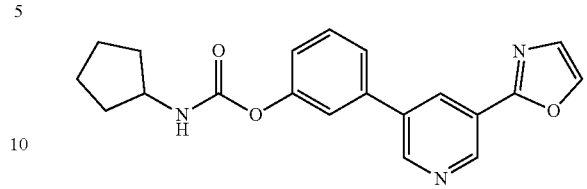

To a stirred solution of 3-(5-(oxazol-2-yl)pyridin-3-yl)phenol (0.08 g, 0.33 mmol) in anhydrous acetonitrile (2 mL) under a nitrogen atmosphere, TEA (0.05 mL, 0.33 mmol) and cyclopentyl isocyanate (0.04 g, 0.40 mmol) were added at RT. The reaction mixture was stirred at RT for 10 minutes and then heated to 75° C. for 12 h, under nitrogen atmosphere. The reaction progress was monitored by TLC. Upon completion, the reaction mixture was cooled to RT and the solvent was evaporated under reduced pressure. The crude product was purified by flash column chromatography on silica gel, eluting with hexane/EtOAc (gradient 40-60% EtOAc) to yield the target compound (42 mg) as an off white solid. $^1$H NMR (400 MHz, DMSO-d6) δ 9.19-9.46 (m, 1H), 8.96-9.24 (m, 1H), 8.34 (s, 1H), 7.67-8.14 (m, 4H), 7.23-7.68 (m, 2H), 5.47 (d, J=7.5 Hz, 1H), 4.41 (q, J=6.8 Hz, 1H), 2.12-2.36 (m, 2H), 1.78-2.19 (m, 4H), 1.62-1.75 (m, 2H), 8.45 (t, J=2.1 Hz, 1H).

Synthesis of 3-(5-(oxazol-2-yl)pyridin-3-yl)phenyl cyclohexylcarbamate (Example-76)

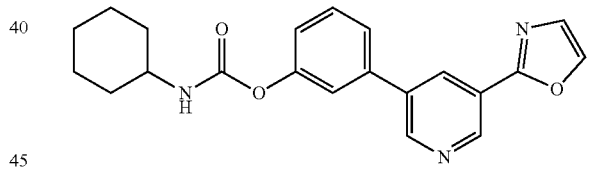

To a stirred suspension of 3-(5-(oxazol-2-yl)pyridin-3-yl)phenol (0.08 g, 0.33 mmol) in anhydrous acetonitrile (2 mL), TEA (0.05 mL, 0.33 mmol) and cyclohexyl isocyanate (0.04 g, 0.39 mmol) were added at RT under a nitrogen atmosphere. The reaction mixture was stirred at RT for 10 minutes and then heated to 75° C. for 12 h, under nitrogen atmosphere. The reaction progress was monitored by TLC. Upon completion, the reaction mixture was cooled to RT, and the solvent was evaporated under reduced pressure. The crude product was purified by flash column chromatography on silica gel, eluting with hexane/EtOAc (gradient 40-60% EtOAc) to yield the target compound (44 mg) as an off white solid. $^1$H NMR (400 MHz, CDCl3) δ 8.91 (d, J=2.1 Hz, 1H), 8.80 (d, J=2.2 Hz, 1H), 8.10 (t, J=2.2 Hz, 1H), 7.43-7.56 (m, 3H), 7.41 (t, J=2.0 Hz, 1H), 7.22 (ddd, J=7.8, 2.3, 1.3 Hz, 1H), 4.97 (d, J=8.2 Hz, 1H), 4.04 (d, J=8.0 Hz, 1H), 3.39-3.70 (m, 1H), 1.52-1.86 (m, 4H), 1.93 (dd, J=12.6, 3.9 Hz, 2H), 1.00-1.43 (m, 2H).

Synthesis of 3-(5-(oxazol-2-yl)pyridin-3-yl)phenyl ((1s,3s)-adamantan-1-yl)carbamate Example-77)

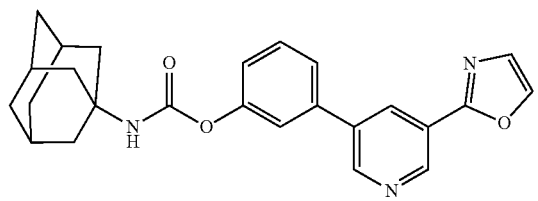 [SMILES: O=C(NC12CC3CC(CC(C3)C1)C2)Oc1cccc(-c2cncc(-c3ncco3)c2)c1]

To a stirred solution of 3-(5-(oxazol-2-yl)pyridin-3-yl)phenol (0.08 g, 0.33 mmol) in anhydrous acetonitrile (2 mL) under a nitrogen atmosphere, TEA (0.05 mL, 0.33 mmol) and adamantyl isocyanate (0.058 g, 0.39 mmol) were added at RT. The reaction mixture was stirred at RT for 10 minutes and then heated to 75° C. for 12 h, under nitrogen atmosphere. The progress of the reaction was monitored by TLC. Upon completion, the reaction mixture was cooled to RT and the solvent was evaporated under reduced pressure. The crude product was purified by flash column chromatography on silica gel, eluting with hexane/EtOAc (gradient 40-60% EtOAc) to yield the target compound (49 mg) as an off white solid. $^1$H NMR (400 MHz, CDCl3) δ 8.84 (d, J=2.1 Hz, 1H), 8.72 (d, J=2.2 Hz, 1H), 8.02 (t, J=2.1 Hz, 1H), 7.93 (s, 1H), 7.31-7.56 (m, 4H), 7.14 (ddd, J=7.9, 2.3, 1.3 Hz, 1H), 4.89 (s, 1H), 2.05 (q, J=3.2 Hz, 3H), 1.89-2.00 (m, 7H), 1.63 (t, J=3.1 Hz, 5H).

Synthesis of Synthesis of 4-methoxy-3-(5-(oxazol-2-yl)pyridin-3-yl)phenol

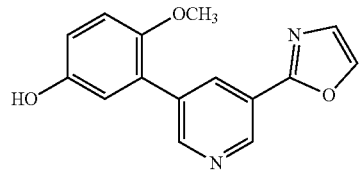 [SMILES: COc1ccc(O)cc1-c1cncc(-c2ncco2)c1]

To a solution of TOSMIC (0.085 g, 0.43 mmol) in methanol (5 mL) was added K$_2$CO$_3$ (0.17 g, 1.29 mmol) and at RT and stirred for 30 minutes under nitrogen atmosphere. 5-(5-hydroxy-2-methoxyphenyl)nicotinaldehyde (0.1 g, 0.43 mmol) was then added to the resulting mixture and stirred at RT for additional 30 minutes. The reaction mixture was heated at 70° C. for 1 h under nitrogen atmosphere. The reaction progress was monitored by TLC, after completion the reaction mixture was cooled to RT and then the solvent was evaporated under reduced pressure. The residue was dissolved in ethyl acetate, washed with water followed by brine. The organic layer was dried over sodium sulfate and then the solvent was evaporated under reduced pressure. The compound was purified by column chromatography on silica gel eluting with hexane/EtOAc (gradient 30-70% EtOAc) to yield the 4-methoxy-3-(5-(oxazol-2-yl)pyridin-3-yl)phenol (65 mg) as a pale-yellow solid.

Synthesis of 4-methoxy-3-(5-(oxazol-2-yl)pyridin-3-yl)phenyl octylcarbamate (Example-78)

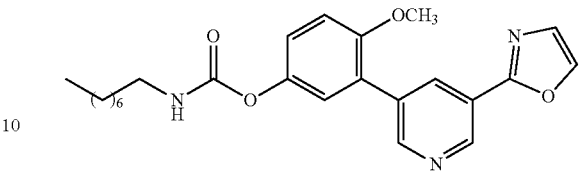

To a stirred solution of 4-methoxy-3-(5-(oxazol-2-yl)pyridin-3-yl)phenol (0.1 g, 0.37 mmol) in anhydrous acetonitrile (2 mL), TEA (0.05 mL, 0.37 mmol), and n-octyl isocyanate (0.06 g, 0.44 mmol) were added at RT under a nitrogen atmosphere. The reaction mixture was stirred at RT for 10 minutes, then heated to 75° C. and stirred for 12 h, under nitrogen atmosphere. The reaction progress was monitored by TLC. Upon completion, the reaction mixture was cooled to RT and the solvent was evaporated under reduced pressure. The residue was purified by flash column chromatography on silica gel, eluting with a hexane/ethyl acetate (EtOAc) gradient (40-60% EtOAc) to yield the target compound (60 mg) as an off white solid. $^1$H NMR (400 MHz, deuterated methanol (MeOD)) δ 8.76 (d, J=2.0 Hz, 1H), 8.56 (d, J=2.0 Hz, 1H), 8.25 (s, 1H), 8.18 (t, J=2.1 Hz, 1H), 7.64 (s, 1H), 7.06 (dd, J=6.1, 3.0 Hz, 3H), 3.08 (t, J=7.0 Hz, 2H), 1.46 (p, J=7.2 Hz, 2H), 1.21 (dd, J=14.5, 8.9 Hz, 11H), 0.78 (d, J=6.9 Hz, 3H).

Synthesis of 4-methoxy-3-(5-(oxazol-2-yl)pyridin-3-yl)phenyl (cyclohexylmethyl) carbamate (Example-79)

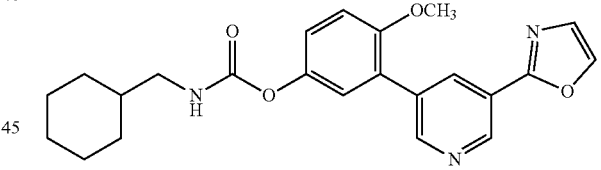

To a stirred solution of 4-methoxy-3-(5-(oxazol-2-yl)pyridin-3-yl)phenol (0.1 g, 0.37 mmol) in anhydrous acetonitrile (2 mL), TEA (0.05 mL, 0.37 mmol), and cyclohexanemethyl isocyanate (0.06 g, 0.44 mmol) were added at RT under a nitrogen atmosphere. The reaction mixture was stirred at RT for 10 minutes, then heated to 75° C. and stirred for 12 h, under nitrogen atmosphere. The reaction progress was monitored by TLC. Upon completion, the reaction mixture was cooled to RT and the solvent was evaporated under reduced pressure. The residue was purified by flash column chromatography on silica gel, eluting with a hexane/ethyl acetate (EtOAc) gradient (40-60% EtOAc) to yield the target compound (55 mg) as an off white solid. $^1$H NMR (400 MHz, DMSO-d6) δ 8.94 (d, J=2.1 Hz, 1H), 8.69 (s, 1H), 8.51 (s, 1H), 8.23 (td, J=2.1, 1.1 Hz, 1H), 7.88 (s, 1H), 7.78 (t, J=5.9 Hz, 1H), 7.44-7.66 (m, 1H), 7.29-7.43 (m, 2H), 7.18 (ddd, J=8.9, 4.1, 2.9 Hz, 1H), 3.26 (s, 3H), 2.85 (t, J=6.4 Hz, 2H), 1.62 (td, J=16.2, 8.8 Hz, 6H), 0.95-1.31 (m, 3H), 0.83 (qd, J=12.7, 3.8 Hz, 2H).

Synthesis of 4-methoxy-3-(5-(oxazol-2-yl)pyridin-3-yl)phenyl cyclopentylcarbamate

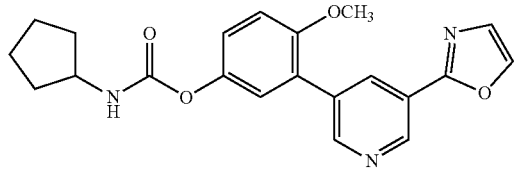 [SMILES: COc1ccc(OC(=O)NC2CCCC2)cc1-c1cncc(-c2ncco2)c1]

To a stirred solution of 4-methoxy-3-(5-(oxazol-2-yl)pyridin-3-yl)phenol (0.1 g, 0.37 mmol) in anhydrous acetonitrile (2 mL), TEA (0.05 mL, 0.37 mmol), and cyclopentyl isocyanate (0.04 g, 0.44 mmol) were added at RT under a nitrogen atmosphere. The reaction mixture was stirred at RT for 10 minutes, then heated to 75° C. and stirred for 12 h, under nitrogen atmosphere. The reaction progress was monitored by TLC. Upon completion, the reaction mixture was cooled to RT and the solvent was evaporated under reduced pressure. The residue was purified by flash column chromatography on silica gel, eluting with a hexane/ethyl acetate (EtOAc) gradient (40-60% EtOAc) to yield the target compound (57 mg) as an off white solid. $^1$H NMR (400 MHz, DMSO-d6) δ 9.01 (d, J=2.1 Hz, 1H), 8.76 (t, J=2.0 Hz, 1H), 8.58 (s, 1H), 8.31 (td, J=2.2, 1.1 Hz, 1H), 7.96 (s, 1H), 7.81 (d, J=7.9 Hz, 1H), 7.35-7.51 (m, 2H), 7.25 (ddd, J=8.9, 4.2, 2.9 Hz, 1H), 3.26 (s, 3H), 1.78-1.91 (m, 2H), 1.71 (t, J=6.3 Hz, 2H), 1.57 (d, J=12.6 Hz, 1H), 1.18-1.40 (m, 4H).

Synthesis of 4-methoxy-3-(5-(oxazol-2-yl)pyridin-3-yl)phenyl cyclohexylcarbamate (Example-81)

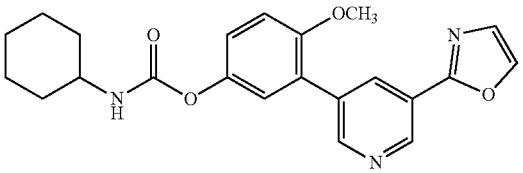 [SMILES: COc1ccc(OC(=O)NC2CCCCC2)cc1-c1cncc(-c2ncco2)c1]

To a stirred solution of 4-methoxy-3-(5-(oxazol-2-yl)pyridin-3-yl)phenol (0.1 g, 0.37 mmol) in anhydrous acetonitrile (2 mL) was added TEA (0.05 mL, 0.37 mmol) and cyclohexyl isocyanate (0.05 g, 0.44 mmol) at RT under nitrogen atmosphere. The reaction mixture was stirred at RT for 10 minutes and then stirred at 75° C. for 12 h, under nitrogen atmosphere. The reaction progress was monitored by TLC. Upon completion, the reaction mixture was cooled to RT and the solvent was evaporated under reduced pressure. The residue was purified by flash column chromatography on silica gel eluting with hexane/EtOAc (gradient 40-60% EtOAc) to yield the target compound to (59 mg) as an off white solid. $^1$H NMR (400 MHz, MeOD) δ 8.77 (d, J=2.0 Hz, 1H), 8.56 (d, J=2.0 Hz, 1H), 8.25 (s, 1H), 8.19 (d, J=2.2 Hz, 1H), 7.65 (s, 1H), 6.95-7.12 (m, 3H), 3.75 (s, 3H), 3.33 (ddt, J=10.4, 7.5, 3.9 Hz, 1H), 1.85 (dd, J=10.0, 5.1 Hz, 2H), 1.68 (dt, J=12.3, 3.6 Hz, 2H), 1.54 (dd, J=10.5, 6.6 Hz, 1H), 1.04-1.37 (m, 5H).

Synthesis of 4-methoxy-3-(5-(oxazol-2-yl)pyridin-3-yl)phenyl (4-methylcyclohexyl)carbamate (Example-82)

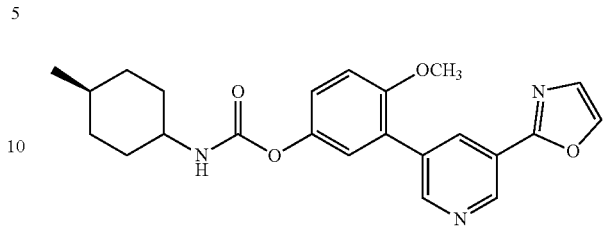

To a stirred solution of 4-methoxy-3-(5-(oxazol-2-yl)pyridin-3-yl)phenol (0.1 g, 0.37 mmol) in anhydrous acetonitrile (2 mL) was added TEA (0.05 mL, 0.37 mmol) and trans-4-Methylcyclohexyl isocyanate (0.06 g, 0.44 mmol) at RT under nitrogen atmosphere. The reaction mixture was stirred at RT for 10 minutes and then stirred at 75° C. for 12 h, under nitrogen atmosphere. The reaction progress was monitored by TLC. Upon completion, the reaction mixture was cooled to RT and the solvent was evaporated under reduced pressure. The residue was purified by flash column chromatography on silica gel eluting with hexane/EtOAc (gradient 40-60% EtOAc) to yield the target compound to (55 mg) as an off white solid. $^1$H NMR (400 MHz, MeOD) δ 8.77 (d, J=2.0 Hz, 1H), 8.56 (d, J=2.0 Hz, 1H), 8.25 (s, 1H), 8.18 (d, J=2.1 Hz, 1H), 7.64 (s, 1H), 6.88-7.31 (m, 3H), 3.75 (s, 3H), 3.22-3.46 (m, 1H), 1.87 (dd, J=13.4, 3.7 Hz, 2H), 1.60-1.80 (m, 2H), 1.10-1.43 (m, 3H), 0.96 (td, J=12.6, 3.3 Hz, 2H), 0.81 (d, J=6.5 Hz, 3H).

Synthesis of 4-methoxy-3-(5-(oxazol-2-yl)pyridin-3-yl)phenyl cycloheptylcarbamate (Example-83)

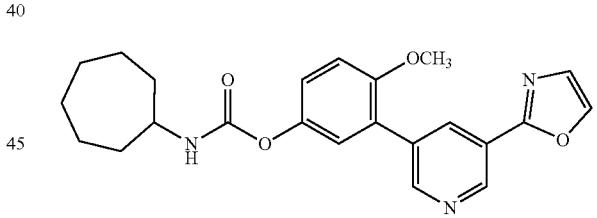

To a stirred solution of 4-methoxy-3-(5-(oxazol-2-yl)pyridin-3-yl)phenol (0.1 g, 0.37 mmol) in anhydrous acetonitrile (2 mL) was added TEA (0.05 mL, 0.37 mmol) and cycloheptyl isocyanate (0.06 g, 0.44 mmol) at RT under nitrogen atmosphere. The reaction mixture was stirred at RT for 10 minutes and then stirred at 75° C. for 12 h, under nitrogen atmosphere. The reaction progress was monitored by TLC. Upon completion, the reaction mixture was cooled to RT and the solvent was evaporated under reduced pressure. The residue was purified by flash column chromatography on silica gel eluting with hexane/EtOAc (gradient 40-60% EtOAc) to yield the target compound (63 mg) as an off white solid. $^1$H NMR (400 MHz, MeOD) δ 8.76 (d, J=2.1 Hz, 1H), 8.56 (d, J=2.1 Hz, 1H), 8.25 (s, 1H), 8.17 (t, J=2.1 Hz, 1H), 7.64 (s, 1H), 6.81-7.23 (m, 3H), 3.74 (s, 3H), 3.55 (dp, J=9.1, 4.4 Hz, 1H), 1.84-1.99 (m, 2H), 1.32-1.73 (m, 10H).

Synthesis of 2-methoxy-5-(5-(oxazol-2-yl)pyridin-3-yl)phenol

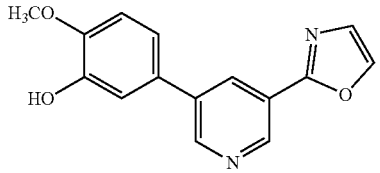 [SMILES: COc1ccc(-c2cncc(-c3ncco3)c2)cc1O]

To a solution of TOSMIC (0.085 g, 0.43 mmol) in methanol (5 mL) was added K$_2$CO$_3$ (0.17 g, 1.29 mmol) and at RT and stirred for 30 minutes under nitrogen atmosphere. 5-(3-hydroxy-4-methoxyphenyl)nicotinaldehyde (0.1 g, 0.43 mmol) was then added to the resulting mixture and stirred at RT for additional 30 minutes. The reaction mixture was heated at 70° C. for 1 h under nitrogen atmosphere. The reaction progress was monitored by TLC, after completion the reaction mixture was cooled to RT and then the solvent was evaporated under reduced pressure. The residue was dissolved in ethyl acetate, washed with water followed by brine. The organic layer was dried over sodium sulfate and then the solvent was evaporated under reduced pressure. The compound was purified by column chromatography on silica gel eluting with hexane/EtOAc (gradient 30-70% EtOAc) to yield the 2-methoxy-5-(5-(oxazol-2-yl)pyridin-3-yl)phenol (65 mg) as a pale-yellow solid.

Synthesis of 2-methoxy-5-(5-(oxazol-2-yl)pyridin-3-yl)phenyl octylcarbamate (Example-84)

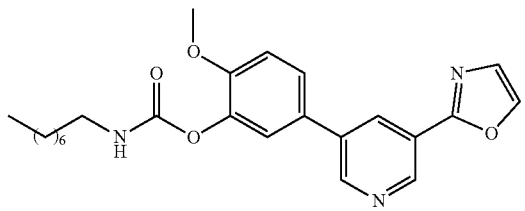

To a stirred solution of 2-methoxy-5-(5-(oxazol-2-yl) pyridin-3-yl)phenol (0.1 g, 0.37 mmol) in anhydrous acetonitrile (2 mL) was added TEA (0.05 mL, 0.37 mmol) and n-octyl isocyante (0.06 g, 0.44 mmol) at RT under nitrogen atmosphere. The reaction mixture was stirred at RT for 10 minutes and then stirred at 75° C. for 12 h, under nitrogen atmosphere. The reaction progress was monitored by TLC. Upon completion, the reaction mixture was cooled to RT and the solvent was evaporated under reduced pressure. The residue was purified by flash column chromatography on silica gel eluting with hexane/EtOAc (gradient 40-60% EtOAc) to yield the target compound (20 mg) as an off white solid. $^1$H NMR (400 MHz, DMSO-d6) δ 9.20 (s, 1H), 8.85-8.68 (m, 2H), 8.50 (d, J=1.4 Hz, 1H), 8.24 (dt, J=39.6, 2.1 Hz, 1H), 7.89 (d, J=4.3 Hz, 1H), 7.75-7.47 (m, 2H), 7.26-7.05 (m, 2H), 3.76 (d, J=2.7 Hz, 3H), 1.45-1.32 (m, 4H), 1.32-1.17 (m, 11H), 0.79 (q, J=5.3 Hz, 3H).

Synthesis of 4-fluoro-3-(5-(oxazol-2-yl)pyridin-3-yl)phenol

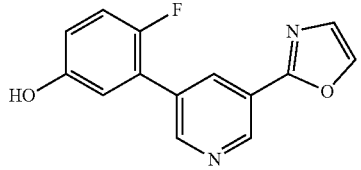 [SMILES: Oc1ccc(F)c(-c2cncc(-c3ncco3)c2)c1]

To a solution of TOSMIC (0.089 g, 0.46 mmol) in methanol (5 mL) was added K$_2$CO$_3$ (0.19 g, 1.38 mmol) and at RT and stirred for 30 minutes under nitrogen atmosphere. 5-(2-fluoro-5-hydroxyphenyl)nicotinaldehyde (0.1 g, 0.46 mmol) was then added to the resulting mixture and stirred at RT for additional 30 minutes. The reaction mixture was heated at 70° C. for 1 h under nitrogen atmosphere. The reaction progress was monitored by TLC, after completion the reaction mixture was cooled to RT and then the solvent was evaporated under reduced pressure. The residue was dissolved in ethyl acetate, washed with water followed by brine. The organic layer was dried over sodium sulfate and then the solvent was evaporated under reduced pressure. The compound was purified by column chromatography on silica gel eluting with hexane/EtOAc (gradient 30-60% EtOAc) to yield the 4-fluoro-3-(5-(oxazol-2-yl)pyridin-3-yl)phenol (70 mg) as a pale-yellow solid.

Synthesis of 4-fluoro-3-(5-(oxazol-2-yl)pyridin-3-yl)phenyl cyclopentylcarbamate Example-85

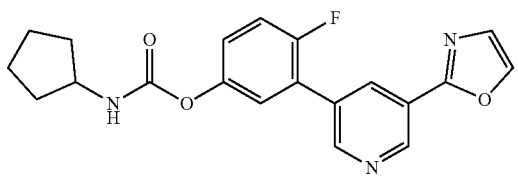 [SMILES: O=C(NC1CCCC1)Oc1ccc(F)c(-c2cncc(-c3ncco3)c2)c1]

To a stirred solution of 4-fluoro-3-(5-(oxazol-2-yl)pyridin-3-yl)phenol (0.1 g, 0.39 mmol) in anhydrous acetonitrile (2 mL), TEA (0.05 mL, 0.39 mmol) and cyclopentyl isocyanate (0.05 g, 0.46 mmol) were added at RT under nitrogen atmosphere. The reaction mixture was stirred at RT for 10 minutes and then heated to 75° C. and stirred for 12 h, under a nitrogen atmosphere. The reaction progress was monitored by TLC. Upon completion, the reaction mixture was cooled to RT and the solvent was evaporated under reduced pressure. The residue was purified by flash column chromatography on silica gel, eluting with a hexane/ethyl acetate (EtOAc) gradient (40-60% EtOAc) to yield the target compound (45 mg) as an off white solid. $^1$H NMR (400 MHz, DMSO-d6) δ 9.48 (s, 1H), 9.23 (dd, J=9.7, 2.0 Hz, 2H), 8.99 (dt, J=21.8, 1.9 Hz, 2H), 8.76-8.31 (m, 2H), 8.24 (td, J=2.1, 1.1 Hz, 1H), 7.69-7.31 (m, 1H), 7.18-6.78 (m, 3H), 3.83 (q, J=6.7 Hz, 1H), 1.91-1.40 (m, 6H), 1.36-1.19 (m, 2H).

Synthesis of 4-fluoro-3-(5-(oxazol-2-yl)pyridin-3-yl)phenyl (4-methylcyclohexyl)carbamate (Example-86)

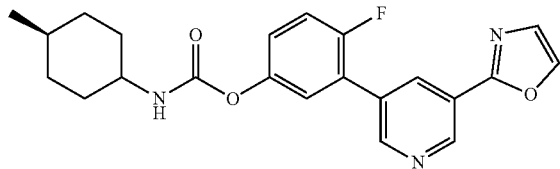

To a stirred solution of 4-fluoro-3-(5-(oxazol-2-yl)pyridin-3-yl)phenol (0.1 g, 0.39 mmol) in anhydrous acetonitrile (2 mL), TEA, (0.05 mL, 0.39 mmol) and trans-4-methylcyclohexyl isocyanate (0.06 g, 0.46 mmol) were added at RT under nitrogen atmosphere. The reaction mixture was stirred at RT for 10 minutes, then heated to 75° C. and stirred for 12 h under a nitrogen atmosphere. The reaction progress was monitored by TLC. Upon completion, the reaction mixture was cooled to RT and the solvent was evaporated under reduced pressure. The residue was purified by flash column chromatography on silica gel, eluting with a hexane/ethyl acetate (EtOAc) gradient (40-60% EtOAc) to yield the target compound (45 mg) as an off white solid. $^1$H NMR (400 MHz, DMSO-d6) δ 9.00 (d, J=2.1 Hz, 1H), 8.75 (t, J=2.0 Hz, 1H), 8.58 (s, 1H), 8.30 (dt, J=3.3, 1.6 Hz, 1H), 7.95 (s, 1H), 7.77 (d, J=7.9 Hz, 1H), 7.68-7.53 (m, 1H), 7.50-7.34 (m, 2H), 7.24 (ddd, J=8.9, 4.1, 2.9 Hz, 1H), 3.30-3.20 (m, 1H), 1.95-1.80 (m, 2H), 1.75-1.60 (m, 3H), 1.31-1.20 (m, 2H), 1.09-0.91 (m, 2H), 0.86 (d, J=6.6 Hz, 3H).

Synthesis of 4-fluoro-3-(5-(oxazol-2-yl)pyridin-3-yl)phenyl cycloheptylcarbamate (Example-87)

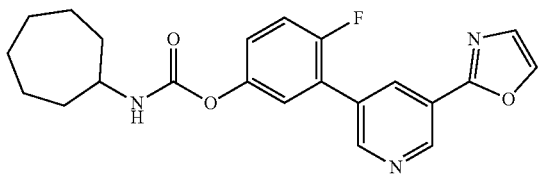 [SMILES: O=C(NC1CCCCCC1)Oc1ccc(F)c(-c2cncc(-c3ncco3)c2)c1]

To a stirred solution of 4-fluoro-3-(5-(oxazol-2-yl)pyridin-3-yl)phenol (0.1 g, 0.39 mmol) in anhydrous acetonitrile (2 mL), TEA, (0.05 mL, 0.39 mmol) and cycloheptyl isocyanate (0.06 g, 0.46 mmol) were added at RT under a nitrogen atmosphere. The reaction mixture was stirred at RT for 10 minutes, then heated to 75° C. and stirred for 12 h under nitrogen atmosphere. The reaction progress was monitored by TLC. Upon completion, the reaction mixture was cooled to RT and the solvent was evaporated under reduced pressure. The residue was purified by flash column chromatography on silica gel, eluting with a hexane/ethyl acetate (EtOAc) gradient (40-60% EtOAc) to yield the target compound (46 mg) as an off white solid. $^1$H NMR (400 MHz, DMSO-d6) δ 9.01 (d, J=2.1 Hz, 1H), 8.76 (t, J=2.0 Hz, 1H), 8.58 (s, 1H), 8.31 (td, J=2.2, 1.1 Hz, 1H), 7.95 (s, 1H), 7.84 (d, J=7.9 Hz, 1H), 7.61-7.35 (m, 2H), 7.25 (ddd, J=8.9, 4.1, 2.9 Hz, 1H), 3.55 (dtd, J=12.4, 9.0, 4.5 Hz, 1H), 1.87 (ddd, J=13.5, 7.2, 3.2 Hz, 2H), 1.68-1.30 (m, 10H).

Synthesis of 3-(5-(oxazol-2-yl)pyridin-3-yl)-4-(trifluoromethoxy)phenol

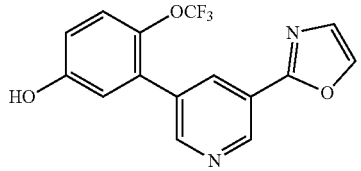 [SMILES: Oc1ccc(OC(F)(F)F)c(-c2cncc(-c3ncco3)c2)c1]

To a solution of TOSMIC (0.068 g, 0.35 mmol) in methanol (5 mL) was added K$_2$CO$_3$ (0.14 g, 1.05 mmol) and at RT and stirred for 30 minutes under nitrogen atmosphere. 5-(5-hydroxy-2-(trifluoromethoxy)phenyl)nicotinaldehyde (0.1 g, 0.35 mmol) was then added to the resulting mixture and stirred at RT for additional 30 minutes. The reaction mixture was heated at 70° C. for 1 h under nitrogen atmosphere. The reaction progress was monitored by TLC, after completion the reaction mixture was cooled to RT and then the solvent was evaporated under reduced pressure. The residue was dissolved in ethyl acetate, washed with water followed by brine. The organic layer was dried over sodium sulfate and then the solvent was evaporated under reduced pressure. The compound was purified by column chromatography on silica gel eluting with hexane/EtOAc (gradient 30-70% EtOAc) to yield the 3-(5-(oxazol-2-yl)pyridin-3-yl)-4-(trifluoromethoxy)phenol (60 mg) as a pale-yellow solid.

Synthesis of 3-(5-(oxazol-2-yl)pyridin-3-yl)-4-(trifluoromethoxy)phenyl octylcarbamate

Example-88

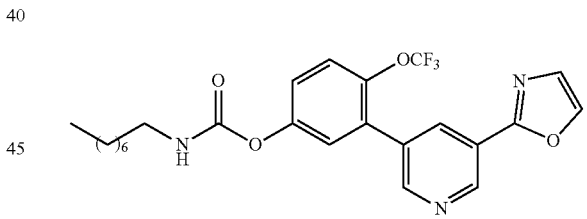

To a stirred solution of 3-(5-(oxazol-2-yl)pyridin-3-yl)-4-(trifluoromethoxy)phenol (0.1 g, 0.31 mmol) in anhydrous acetonitrile (2 mL) was added TEA (0.04 mL, 0.31 mmol) and n-octyl isocyanate (0.05 g, 0.37 mmol) at RT under nitrogen atmosphere. The reaction mixture was stirred at RT for 10 minutes and then stirred at 75° C. for 12 h, under nitrogen atmosphere. The reaction progress was monitored by TLC. Upon completion, the reaction mixture was cooled to RT and the solvent was evaporated under reduced pressure. The residue was purified by flash column chromatography on silica gel eluting with hexane/EtOAc (gradient 40-60% EtOAc) to yield the target compound (55 mg) as an off white solid. $^1$H NMR (400 MHz, DMSO-d6) δ 8.96 (d, J=2.1 Hz, 1H), 8.61 (d, J=2.1 Hz, 1H), 8.51 (s, 1H), 8.18 (t, J=2.1 Hz, 1H), 7.86 (d, J=13.3 Hz, 2H), 7.51 (dq, J=8.9, 1.5 Hz, 1H), 7.40 (d, J=2.9 Hz, 1H), 7.28 (dd, J=9.0, 2.9 Hz, 1H), 3.08-2.90 (m, 2H), 1.54-1.35 (m, 2H), 1.37-1.10 (m, 10H), 0.88-0.69 (m, 3H).

Synthesis of 3-(5-(oxazol-2-yl)pyridin-3-yl)-4-(trifluoromethoxy)phenyl cyclohexylcarbamate (Example-89)

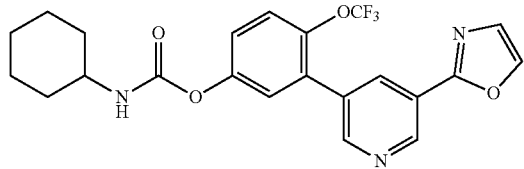 [SMILES: O=C(NC1CCCCC1)Oc1ccc(OC(F)(F)F)c(-c2cncc(-c3ncco3)c2)c1]

To a stirred solution of 3-(5-(oxazol-2-yl)pyridin-3-yl)-4-(trifluoromethoxy)phenol (0.1 g, 0.31 mmol) in anhydrous acetonitrile (2 mL) was added TEA (0.04 mL, 0.31 mmol) and cyclohexyl isocyanate (0.04 g, 0.37 mmol) at RT under nitrogen atmosphere. The reaction mixture was stirred at RT for 10 minutes and then stirred at 75° C. for 12 h, under nitrogen atmosphere. The reaction progress was monitored by TLC. Upon completion, the reaction mixture was cooled to RT and the solvent was evaporated under reduced pressure. The residue was purified by flash column chromatography on silica gel eluting with hexane/EtOAc (gradient 40-60% EtOAc) to yield the target compound (49 mg) as an off white solid. $^1$H NMR (400 MHz, DMSO-d6) δ 9.03 (d, J=2.1 Hz, 1H), 8.68 (d, J=2.1 Hz, 1H), 8.58 (s, 1H), 8.26 (t, J=2.1 Hz, 1H), 7.95 (s, 1H), 7.89 (d, J=7.9 Hz, 1H), 7.58 (dq, J=8.9, 1.4 Hz, 1H), 7.48 (d, J=2.9 Hz, 1H), 7.36 (dd, J=8.9, 2.9 Hz, 1H), 1.92-1.78 (m, 2H), 1.71 (dd, J=9.0, 3.6 Hz, 2H), 1.57 (d, J=12.6 Hz, 2H), 1.40-1.19 (m, 5H).

Synthesis of 3-(5-(oxazol-2-yl)pyridin-3-yl)-4-(trifluoromethoxy)phenyl (4-methylcyclohexyl)carbamate (Example-90)

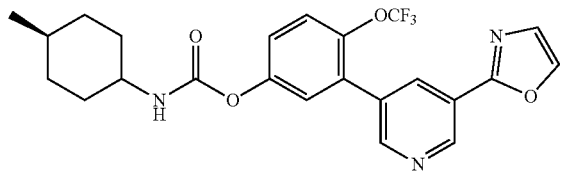

To a stirred solution of 3-(5-(oxazol-2-yl)pyridin-3-yl)-4-(trifluoromethoxy)phenol (0.1 g, 0.31 mmol) in anhydrous acetonitrile (2 mL) was added TEA (0.04 mL, 0.31 mmol) and trans-4-Methylcyclohexyl isocyanate (0.05 g, 0.37 mmol) at RT under nitrogen atmosphere. The reaction mixture was stirred at RT for 10 minutes and then stirred at 75° C. for 12 h, under nitrogen atmosphere. The reaction progress was monitored by TLC. Upon completion, the reaction mixture was cooled to RT and the solvent was evaporated under reduced pressure. The residue was purified by flash column chromatography on silica gel eluting with hexane/EtOAc (gradient 40-60% EtOAc) to yield the target compound (47 mg) as an off white solid. $^1$H NMR (400 MHz, DMSO-d6) δ 9.03 (d, J=2.1 Hz, 1H), 8.68 (d, J=2.1 Hz, 1H), 8.58 (s, 1H), 8.25 (t, J=2.1 Hz, 1H), 7.90 (d, J=37.9 Hz, 2H), 7.57 (dq, J=8.9, 1.4 Hz, 1H), 7.47 (d, J=2.9 Hz, 1H), 7.43-7.05 (m, 1H), 3.55-3.37 (m, 1H), 1.92-1.83 (m, 2H), 1.75-1.64 (m, 2H), 1.37-1.15 (m, 3H), 1.15 (td, J=12.7, 3.5 Hz, 2H), 0.99 (td, J=12.7, 3.5 Hz, 2H), 0.87 (d, J=6.5 Hz, 3H).

Synthesis of 3-(5-(oxazol-2-yl)pyridin-3-yl)-4-(trifluoromethoxy)phenyl cycloheptylcarbamate (Example-91)

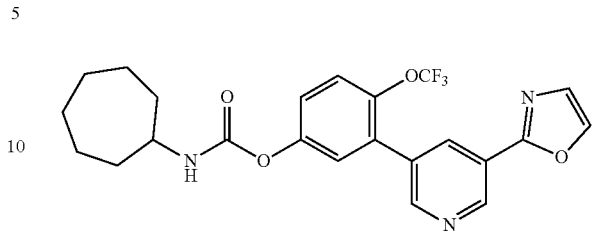

To a stirred solution of 3-(5-(oxazol-2-yl)pyridin-3-yl)-4-(trifluoromethoxy)phenol (0.1 g, 0.31 mmol) in anhydrous acetonitrile (2 mL), TEA (0.04 mL, 0.31 mmol), and cycloheptyl isocyanate (0.05 g, 0.37 mmol) were added at RT under a nitrogen atmosphere. The reaction mixture was stirred at RT for 10 minutes, then heated to 75° C. and stirred for 12 h, under nitrogen atmosphere. The reaction progress was monitored by TLC. Upon completion, the reaction mixture was cooled to RT and the solvent was evaporated under reduced pressure. The residue was purified by flash column chromatography on silica gel, eluting with a hexane/ethyl acetate (EtOAc) gradient (40-60% EtOAc) to yield the target compound (48 mg) as an off white solid. $^1$H NMR (400 MHz, DMSO-d6) δ 8.96 (d, J=2.1 Hz, 1H), 8.61 (d, J=2.1 Hz, 1H), 8.51 (s, 1H), 8.18 (t, J=2.1 Hz, 1H), 7.86 (d, J=11.2 Hz, 2H), 7.50 (dq, J=8.9, 1.5 Hz, 1H), 7.41 (d, J=2.9 Hz, 1H), 7.28 (dd, J=9.0, 2.9 Hz, 1H), 3.48 (qt, J=8.9, 4.5 Hz, 1H), 1.80 (dtd, J=13.9, 7.5, 4.6 Hz, 2H), 1.69-1.26 (m, 11H).

Synthesis of 2-methyl-5-(5-(oxazol-2-yl)pyridin-3-yl)phenol

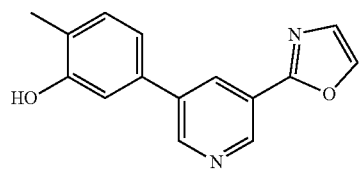 [SMILES: Cc1ccc(-c2cncc(-c3ncco3)c2)cc1O]

To a solution of TOSMIC (0.089 g, 0.46 mmol) in methanol (5 mL) was added K$_2$CO$_3$ (0.19 g, 1.38 mmol) and at RT and stirred for 30 minutes under nitrogen atmosphere. 5-(3-hydroxy-4-methylphenyl)nicotinaldehyde (0.1 g, 0.46 mmol) was then added to the resulting mixture and stirred at RT for additional 30 minutes. The reaction mixture was heated at 70° C. for 1 h under nitrogen atmosphere. The reaction progress was monitored by TLC, after completion the reaction mixture was cooled to RT and then the solvent was evaporated under reduced pressure. The residue was dissolved in ethyl acetate, washed with water followed by brine. The organic layer was dried over sodium sulfate and then the solvent was evaporated under reduced pressure. The compound was purified by column chromatography on silica gel eluting with hexane/EtOAc (gradient 30-50% EtOAc) to yield the 2-methyl-5-(5-(oxazol-2-yl)pyridin-3-yl)phenol (64 mg) as a pale-yellow solid.

Synthesis of 2-methyl-5-(5-(oxazol-2-yl)pyridin-3-yl)phenyl octylcarbamate (Example-92)

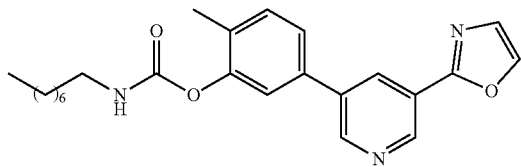

To a stirred solution of 2-methyl-5-(5-(oxazol-2-yl)pyridin-3-yl)phenol (0.1 g, 0.39 mmol) in anhydrous acetonitrile (2 mL), TEA (0.05 mL, 0.39 mmol), and n-octyl isocyanate (0.07 g, 0.47 mmol) were added at RT under a nitrogen atmosphere. The reaction mixture was stirred at RT for 10 minutes, then heated to 75° C. and stirred for 12 h, under nitrogen atmosphere. After completion of the reaction, monitored by TLC, the reaction mixture was concentrated to a residue. The residue was purified by flash column chromatography on silica gel, eluting with a hexane/ethyl acetate (EtOAc) gradient (40-60% EtOAc) to yield the target compound (50 mg) as an off white solid. $^1$H NMR (400 MHz, DMSO-d6) δ 8.92 (dd, J=16.9, 2.1 Hz, 2H), 8.58 (s, 1H), 8.39 (t, J=2.2 Hz, 1H), 7.98 (s, 1H), 7.83 (t, J=5.7 Hz, 1H), 7.62 (dd, J=7.8, 2.0 Hz, 1H), 7.54 (d, J=2.0 Hz, 1H), 7.24-7.51 (m, 1H), 3.16-2.94 (m, 2H), 2.20 (s, 3H), 1.48 (q, J=6.7 Hz, 2H), 1.43-1.15 (m, 10H), 1.06-0.65 (m, 3H).

Synthesis of 2-methyl-5-(5-(oxazol-2-yl)pyridin-3-yl)phenyl (cyclohexylmethyl)carbamate Example-93

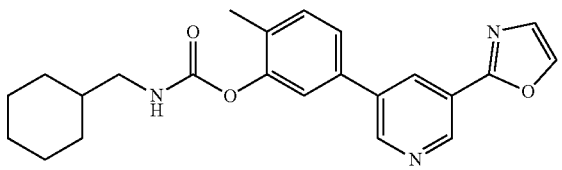 [SMILES: Cc1ccc(-c2cncc(-c3ncco3)c2)cc1OC(=O)NCC1CCCCC1]

To a stirred solution of 2-methyl-5-(5-(oxazol-2-yl)pyridin-3-yl)phenol (0.1 g, 0.39 mmol) in anhydrous acetonitrile (2 mL), TEA (0.05 mL, 0.39 mmol), and cyclohexanemethyl isocyanate (0.06 g, 0.47 mmol) were added at RT under nitrogen atmosphere. The reaction mixture was stirred at RT for 10 minutes, then heated to 75° C. and stirred for 12 h, under nitrogen atmosphere. After completion of the reaction, monitored by TLC, the reaction mixture was concentrated to a residue. The residue was purified by flash column chromatography on silica gel, eluting with a hexane/ethyl acetate (EtOAc) gradient (40-60% EtOAc) to yield the target compound (52 mg) as an off white solid. $^1$H NMR (400 MHz, DMSO-d6) δ 8.92 (dd, J=15.3, 2.1 Hz, 2H), 8.58 (s, 1H), 8.39 (t, J=2.2 Hz, 1H), 7.98 (s, 1H), 7.86 (t, J=6.0 Hz, 1H), 7.62 (dd, J=7.8, 1.9 Hz, 1H), 7.55 (d, J=1.9 Hz, 1H), 7.29-7.48 (m, 1H), 3.00-2.86 (m, 2H), 2.20 (s, 3H), 1.70 (td, J=17.0, 9.0 Hz, 4H), 1.55-1.45 (m, 1H), 1.19 (qt, J=11.9, 9.4 Hz, 4H), 0.92 (qd, J=13.1, 3.9 Hz, 2H).

Synthesis of 2-methyl-5-(5-(oxazol-2-yl)pyridin-3-yl)phenyl benzylcarbamate (Example-94)

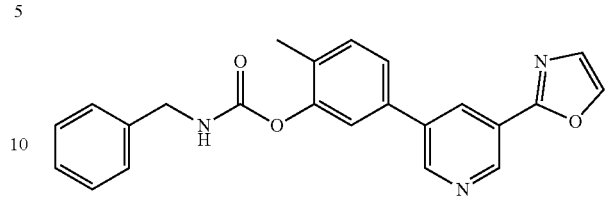

To a stirred solution of 2-methyl-5-(5-(oxazol-2-yl)pyridin-3-yl)phenol (0.1 g, 0.39 mmol) in anhydrous acetonitrile (2 mL), TEA (0.05 mL, 0.39 mmol), and benzyl isocyanate (0.06 g, 0.47 mmol) were added at RT under nitrogen atmosphere. The reaction mixture was stirred at 75° C. for 12 h, under nitrogen atmosphere. After completion of the reaction, monitored by TLC and the reaction mixture was concentrated to a residue. The residue was purified by flash column chromatography on silica gel, eluting with a hexane/ethyl acetate (EtOAc) gradient (40-60% EtOAc) to yield the target compound (49 mg) as an off white solid. $^1$H NMR (400 MHz, DMSO-d6) δ 8.92 (dd, J=13.2, 2.1 Hz, 2H), 8.58 (s, 1H), 8.49-8.22 (m, 2H), 7.98 (s, 1H), 7.74-7.49 (m, 2H), 7.49-7.19 (m, 6H), 4.32 (d, J=6.1 Hz, 2H), 2.21 (s, 3H).

Synthesis of 2-methyl-5-(5-(oxazol-2-yl)pyridin-3-yl)phenyl cyclohexylcarbamate (Example-95)

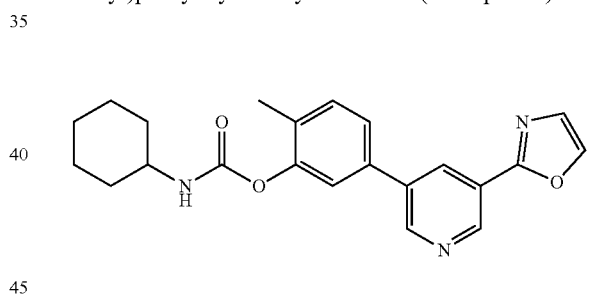

To a stirred solution of 2-methyl-5-(5-(oxazol-2-yl)pyridin-3-yl)phenol (0.1 g, 0.39 mmol) in anhydrous acetonitrile (2 mL), TEA (0.05 mL, 0.39 mmol), and cyclohexyl isocyanate (0.05 g, 0.47 mmol) were added at RT under nitrogen atmosphere. The reaction mixture was stirred at RT for 10 minutes, then heated to 75° C. and stirred for 12 h, under nitrogen atmosphere. After completion of the reaction, monitored by TLC, the reaction mixture was concentrated to a residue. The residue was purified by flash column chromatography on silica gel, eluting with a hexane/ethyl acetate (EtOAc) gradient (40-60% EtOAc) to yield the target compound (49 mg) as an off white solid. $^1$H NMR (400 MHz, DMSO-d6) δ 8.92 (dd, J=14.3, 2.1 Hz, 2H), 8.58 (s, 1H), 8.39 (t, J=2.2 Hz, 1H), 7.98 (s, 1H), 7.80 (d, J=8.0 Hz, 1H), 7.62 (dd, J=7.9, 2.0 Hz, 1H), 7.55 (d, J=1.9 Hz, 1H), 7.48-7.36 (m, 1H), 3.31 (m, 1H), 2.20 (s, 3H), 1.85 (dd, J=8.9, 4.4 Hz, 2H), 1.72 (t, J=5.7 Hz, 2H), 1.57 (d, J=12.5 Hz, 1H), 1.39-1.17 (m, 4H), 1.12 (d, J=10.9 Hz, 1H).

Synthesis of 2-methyl-5-(5-(oxazol-2-yl)pyridin-3-yl)phenyl (4-methylcyclohexyl)carbamate (Example-96)

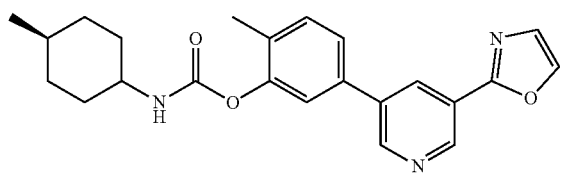

To a stirred solution of 2-methyl-5-(5-(oxazol-2-yl)pyridin-3-yl)phenol (0.1 g, 0.39 mmol) in anhydrous acetonitrile (2 mL), TEA (0.05 mL, 0.39 mmol), and trans-4-methylcyclohexyl isocyanate (0.06 g, 0.47 mmol) were added at RT under nitrogen atmosphere. The reaction mixture was stirred at RT for 10 minutes, then heated to 75° C. and stirred for 12 h, under nitrogen atmosphere. After completion of the reaction, monitored by TLC, the reaction mixture was concentrated to a residue. The residue was purified by flash column chromatography on silica gel, eluting with a hexane/ethyl acetate (EtOAc) gradient (40-60% EtOAc) to yield the target compound (36 mg) as an off white solid. $^1$H NMR (400 MHz, DMSO-d6) δ 8.92 (dd, J=15.1, 2.1 Hz, 2H), 8.58 (s, 1H), 8.39 (t, J=2.2 Hz, 1H), 7.98 (s, 1H), 7.77 (d, J=8.0 Hz, 1H), 7.72-7.51 (m, 2H), 7.51-7.36 (m, 1H), 3.26 (ddt, J=11.7, 8.1, 3.1 Hz, 1H), 2.19 (s, 3H), 2.01-1.85 (m, 2H), 1.85-1.52 (m, 3H), 1.28 (qd, J=12.4, 2.8 Hz, 3H), 0.99 (td, J=12.5, 3.3 Hz, 2H), 0.94-0.79 (m, 3H).

Synthesis of 2-methyl-5-(5-(oxazol-2-yl)pyridin-3-yl)phenyl cycloheptylcarbamate (Example-97)

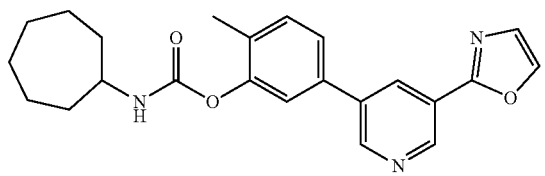 [SMILES: Cc1ccc(-c2cncc(-c3ncco3)c2)cc1OC(=O)NC1CCCCCC1]

To a stirred solution of 2-methyl-5-(5-(oxazol-2-yl)pyridin-3-yl)phenol (0.1 g, 0.39 mmol) in anhydrous acetonitrile (2 mL) was added TEA (0.05 mL, 0.39 mmol) and cycloheptyl isocyanate (0.06 g, 0.47 mmol) at RT under nitrogen atmosphere. The reaction mixture was stirred at RT for 10 minutes, then heated to 75° C. and stirred for 12 h, under nitrogen atmosphere. The reaction progress was monitored by TLC. After completion of the reaction, the mixture was concentrated to a residue. The residue was purified by flash column chromatography on silica gel, eluting with a hexane/EtOAc gradient (40-60% EtOAc) to yield the target compound (37 mg) as an off white solid. $^1$H NMR (400 MHz, DMSO-d6) δ 8.92 (dd, J=14.5, 2.1 Hz, 2H), 8.58 (s, 1H), 8.39 (t, J=2.1 Hz, 1H), 7.98 (s, 1H), 7.85 (d, J=8.0 Hz, 1H), 7.68-7.50 (m, 2H), 7.50-7.28 (m, 1H), 3.54 (ddd, J=9.3, 7.8, 4.6 Hz, 1H), 2.19 (s, 3H), 1.98-1.75 (m, 2H), 1.71-1.42 (m, 10H).

Synthesis of 2-methyl-5-(5-(oxazol-2-yl)pyridin-3-yl)phenyl cyclooctylcarbamate (Example-98)

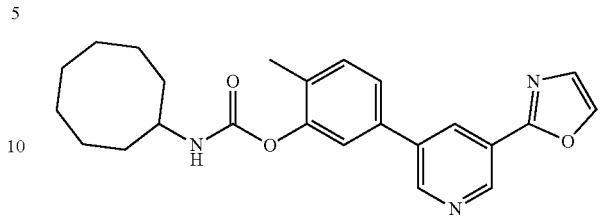

To a stirred solution of 2-methyl-5-(5-(oxazol-2-yl)pyridin-3-yl)phenol (0.1 g, 0.39 mmol) in anhydrous acetonitrile (2 mL) was added TEA (0.05 mL, 0.39 mmol) and cyclooctyl isocyanate (0.07 g, 0.47 mmol) at RT under nitrogen atmosphere. The reaction mixture was stirred at RT for 10 minutes and then heated to 75° C. and stirred for 12 h, under nitrogen atmosphere. The reaction progress was monitored by TLC. After completion of the reaction, the reaction mixture was concentrated to a residue. The residue was purified by flash column chromatography on silica gel, eluting with a hexane/EtOAc gradient (40-60% EtOAc) to yield the target compound (36 mg) as an off white solid. $^1$H NMR (400 MHz, DMSO-d6) δ 8.97 (dd, J=15.5, 2.1 Hz, 2H), 8.63 (s, 1H), 8.45 (t, J=2.2 Hz, 1H), 7.97 (d, J=50.3 Hz, 2H), 7.89 (s, 1H), 7.56-7.79 (m, 2H), 7.40-7.56 (m, 1H), 3.64 (td, J=8.3, 3.9 Hz, 1H), 2.25 (s, 3H), 1.97-1.32 (m, 10H).

Synthesis of 3-methyl-5-(5-(oxazol-2-yl)pyridin-3-yl)phenol

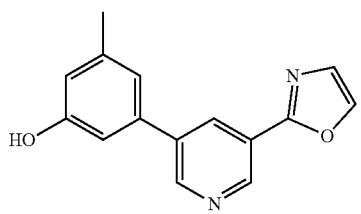 [SMILES: Cc1cc(O)cc(-c2cncc(-c3ncco3)c2)c1]

To a solution of TOSMIC (0.089 g, 0.46 mmol) in methanol (5 mL) was added K$_2$CO$_3$ (0.19 g, 1.38 mmol) and at RT and stirred for 30 minutes under nitrogen atmosphere. 5-(3-hydroxy-5-methylphenyl)nicotinaldehyde (0.1 g, 0.46 mmol) was then added to the resulting mixture and stirred at RT for additional 30 minutes. The reaction mixture was heated at 70° C. for 1 h under nitrogen atmosphere. The reaction progress was monitored by TLC, after completion the reaction mixture was cooled to RT and then the solvent was evaporated under reduced pressure. The residue was dissolved in ethyl acetate, washed with water followed by brine. The organic layer was dried over sodium sulfate and then the solvent was evaporated under reduced pressure. The compound was purified by column chromatography on silica gel eluting with hexane/EtOAc (gradient 30-50% EtOAc) to yield the 3-methyl-5-(5-(oxazol-2-yl)pyridin-3-yl)phenol (64 mg) as a pale-yellow solid.

Synthesis of 3-methyl-5-(5-(oxazol-2-yl)pyridin-3-yl)phenyl (cyclohexylmethyl)carbamate Example-99

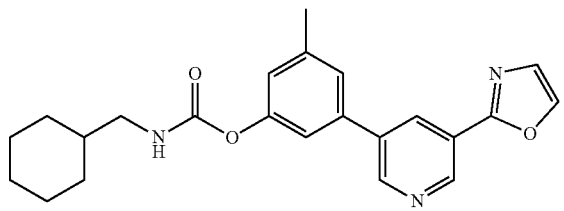 [SMILES: Cc1cc(OC(=O)NCC2CCCCC2)cc(-c2cncc(-c3ncco3)c2)c1]

To a stirred solution of 3-methyl-5-(5-(oxazol-2-yl)pyridin-3-yl)phenol (0.1 g, 0.37 mmol) in anhydrous acetonitrile (2 mL) was added TEA (0.05 mL, 0.37 mmol) and cyclohexanemethyl isocyanate (0.06 g, 0.44 mmol) at RT under nitrogen atmosphere. The reaction mixture was stirred at RT for 10 minutes and then stirred at 75° C. for 12 h, under nitrogen atmosphere. After completion of the reaction (monitored by TLC), the reaction mixture was concentrated to a residue. The residue was purified by flash column chromatography on silica gel, eluting with a hexane/EtOAc gradient (40-60% EtOAc) to yield the target compound (40 mg) as an off white solid. $^1$H NMR (400 MHz, DMSO-d6) δ 8.92 (dd, J=28.2, 2.1 Hz, 1H), 8.38 (t, J=2.1 Hz, 1H), 7.97 (s, OH), 7.82 (t, J=5.9 Hz, OH), 7.45-7.72 (m, 1H), 7.36 (t, J=2.1 Hz, 1H), 7.02 (ddd, J=2.3, 1.5, 0.8 Hz, 1H), 2.92 (t, J=6.4 Hz, 1H), 1.52-1.83 (m, 3H), 1.44 (ddp, J=10.6, 6.9, 3.6 Hz, OH), 1.10-1.34 (m, 2H), 0.82-1.00 (m, 1H).

Synthesis of 3-methyl-5-(5-(oxazol-2-yl)pyridin-3-yl)phenyl benzylcarbamate (Example-100)

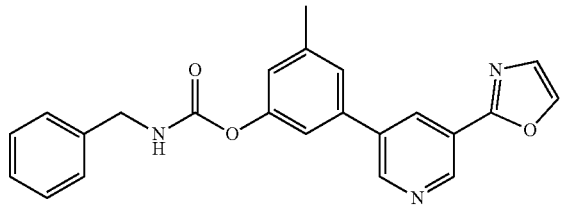 [SMILES: Cc1cc(OC(=O)NCc2ccccc2)cc(-c2cncc(-c3ncco3)c2)c1]

To a stirred solution of 3-methyl-5-(5-(oxazol-2-yl)pyridin-3-yl)phenol (0.1 g, 0.37 mmol) in anhydrous acetonitrile (2 mL) was added TEA (0.05 mL, 0.37 mmol) and benzyl isocyanate (0.05 g, 0.44 mmol) at RT under nitrogen atmosphere. The reaction mixture was stirred at RT for 10 minutes and then heated to 75° C. and stirred for 12 h, under nitrogen atmosphere. The reaction progress was monitored by TLC. After completion of the reaction, the reaction mixture was concentrated to a residue. The residue was purified by flash column chromatography on silica gel, eluting with a hexane/EtOAc gradient (40-60% EtOAc) to yield the target compound (41 mg) as an off white solid. $^1$H NMR (400 MHz, DMSO-d6): δ 9.35-8.73 (m, 2H), 8.60 (s, 1H), J=2.2 Hz, 8.35 (t, 1H), 7.97 (s, 1H), 7.83-7.59 (m, 1H), 7.55-7.13 (m, 8H), 5.09 (s, 2H), 2.40 (s, 3H).

Synthesis of 3-methyl-5-(5-(oxazol-2-yl)pyridin-3-yl)phenyl cyclohexylcarbamate (Example-101)

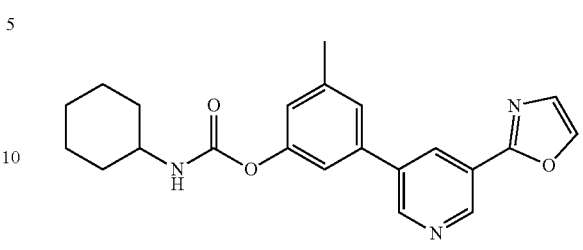

To a stirred solution of 3-methyl-5-(5-(oxazol-2-yl)pyridin-3-yl)phenol (0.1 g, 0.37 mmol) in anhydrous acetonitrile (2 mL) was added TEA (0.05 mL, 0.37 mmol) and cyclohexyl isocyanate (0.05 g, 0.44 mmol) at RT under nitrogen atmosphere. The reaction mixture was stirred at RT for 10 minutes, and then heated to 75° C. and stirred for 12 h, under nitrogen atmosphere. The reaction progress was monitored by TLC. After completion of the reaction, the reaction mixture was concentrated to a residue. The residue was purified by flash column chromatography on silica gel, eluting with a hexane/EtOAc gradient (40-60% EtOAc) to yield the target compound (38 mg) as an off white solid. $^1$H NMR (400 MHz, DMSO-d6): δ 8.92 (dd, J=28.1, 2.1 Hz, 2H), 8.58 (s, 1H), 8.58 (s, 1H), 7.98 (s, 1H), 7.77 (d, J=8.0 Hz, 1H), 7.37-7.56 (m, 1H), 7.36 (d, J=2.2 Hz, 1H), 7.02 (d, J=2.1 Hz, 1H), 3.32 (m, 1H), 1.84 (d, J=9.2 Hz, 2H), 1.71 (t, J=6.8 Hz, 2H), 1.57 (d, J=12.7 Hz, 1H), 1.26 (td, J=11.7, 5.8 Hz, 5H), 2.41 (s, 3H).

Synthesis of 3-methyl-5-(5-(oxazol-2-yl)pyridin-3-yl)phenyl (4-methylcyclohexyl)carbamate (Example-102)

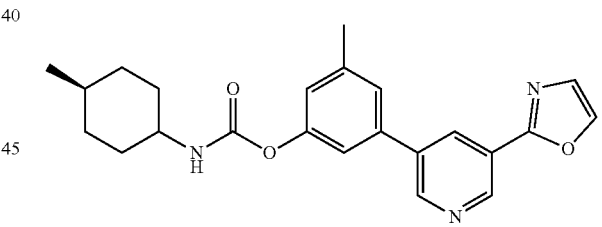

To a stirred solution of 3-methyl-5-(5-(oxazol-2-yl)pyridin-3-yl)phenol (0.1 g, 0.37 mmol) in anhydrous acetonitrile (2 mL) was added TEA (0.05 mL, 0.37 mmol) and trans-4-Methylcyclohexyl isocyanate (0.06 g, 0.44 mmol) at RT under nitrogen atmosphere. The reaction mixture was stirred at RT for 10 minutes, then heated to 75° C. and stirred for 12 h under nitrogen atmosphere. After completion of the reaction (monitored by TLC), the reaction mixture was concentrated to a residue. The residue was purified by flash column chromatography on silica gel, eluting with a hexane/EtOAc gradient (40-60% EtOAc) to yield the target compound (40 mg) as an off white solid. $^1$H NMR (400 MHz, DMSO-d6): δ 8.95 (d, J=2.0 Hz, 1H), 8.88 (d, J=2.2 Hz, 1H), 8.58 (s, 1H), 8.38 (t, J=2.1 Hz, 1H), 7.98 (s, 1H), 7.74 (d, J=8.0 Hz, 1H), 7.54-7.68 (m, 1H), 7.50 (d, J=1.9 Hz, 1H), 7.32-7.43 (m, 1H), 7.02 (d, J=2.0 Hz, 1H), 2.40 (s, 3H), 1.86 (d, J=12.4 Hz, 2H), 1.70 (tt, J=25.4, 11.5 Hz, 3H), 1.20-1.46 (m, 4H), 0.82-0.94 (m, 4H).

Synthesis of 3-methyl-5-(5-(oxazol-2-yl)pyridin-3-yl)phenyl cycloheptylcarbamate (Example-103)

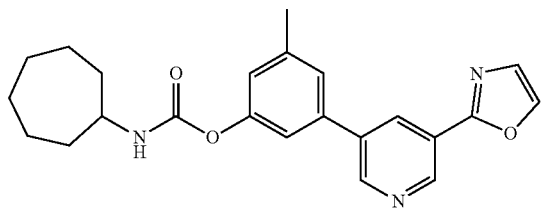 [SMILES: Cc1cc(OC(=O)NC2CCCCCC2)cc(-c2cncc(-c3ncco3)c2)c1]

To a stirred solution of 3-methyl-5-(5-(oxazol-2-yl)pyridin-3-yl)phenol (0.1 g, 0.37 mmol) in anhydrous acetonitrile (2 mL) was added TEA (0.05 mL, 0.37 mmol) and cycloheptyl isocyanate (0.06 g, 0.44 mmol) at RT under nitrogen atmosphere. The reaction mixture was stirred at RT for 10 minutes and then heated to 75° C. and stirred for 12 h, under nitrogen atmosphere. The reaction progress was monitored by TLC. After completion of the reaction, the reaction mixture was concentrated to a residue. The residue was purified by flash column chromatography on silica gel, eluting with a hexane/EtOAc gradient (40-60% EtOAc) to yield the target compound (45 mg) as an off white solid. $^1$H NMR (400 MHz, DMSO-d6): δ 8.98 (dd, J=28.0, 2.1 Hz, 2H), 8.64 (s, 1H), 8.44 (t, J=2.1 Hz, 1H), 8.04 (s, 1H), 7.87 (d, J=8.0 Hz, 1H), 7.56 (d, J=1.9 Hz, 1H), 7.43 (d, J=2.0 Hz, 1H), 7.02-7.18 (m, 1H), 3.62 (dd, J=8.6, 4.3 Hz, 1H), 2.47 (s, 3H), 1.93 (ddd, J=13.7, 7.6, 4.3 Hz, 2H), 1.40-1.76 (m, 10H).

Synthesis of 3-methyl-5-(5-(oxazol-2-yl)pyridin-3-yl)phenyl cyclooctylcarbamate

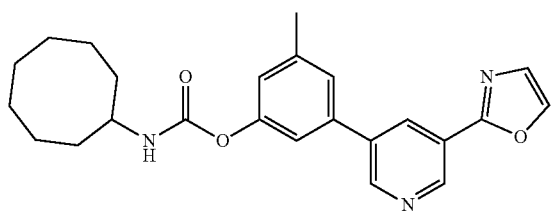 [SMILES: Cc1cc(OC(=O)NC2CCCCCCC2)cc(-c2cncc(-c3ncco3)c2)c1]

To a stirred solution of 3-methyl-5-(5-(oxazol-2-yl)pyridin-3-yl)phenol (0.1 g, 0.37 mmol) in anhydrous acetonitrile (2 mL) was added TEA (0.05 mL, 0.37 mmol) and cyclooctyl isocyanate (0.06 g, 0.44 mmol) at RT under nitrogen atmosphere. The reaction mixture was stirred at RT for 10 minutes and then stirred at 75° C. for 12 h under nitrogen atmosphere. After completion of the reaction (monitored by TLC), the reaction mixture was concentrated to a residue. The residue was purified by flash column chromatography on silica gel, eluting with a hexane/EtOAc gradient (40-60% EtOAc) to yield the target compound (45 mg) as an off white solid. $^1$H NMR (400 MHz, DMSO-d6): δ 8.85 (dd, J=28.1, 2.1 Hz, 2H), 8.51 (s, 1H), 8.31 (t, J=2.2 Hz, 1H), 7.83 (d, J=63.6 Hz, 2H), 7.73 (s, 1H), 7.43 (d, J=1.8 Hz, 1H), 7.29 (t, J=2.0 Hz, 1H), 6.95 (d, J=2.0 Hz, 1H), 3.51 (td, J=8.5, 4.0 Hz, 1H), 2.34 (s, 3H), 1.32-1.68 (m, 12H).

Scheme IV

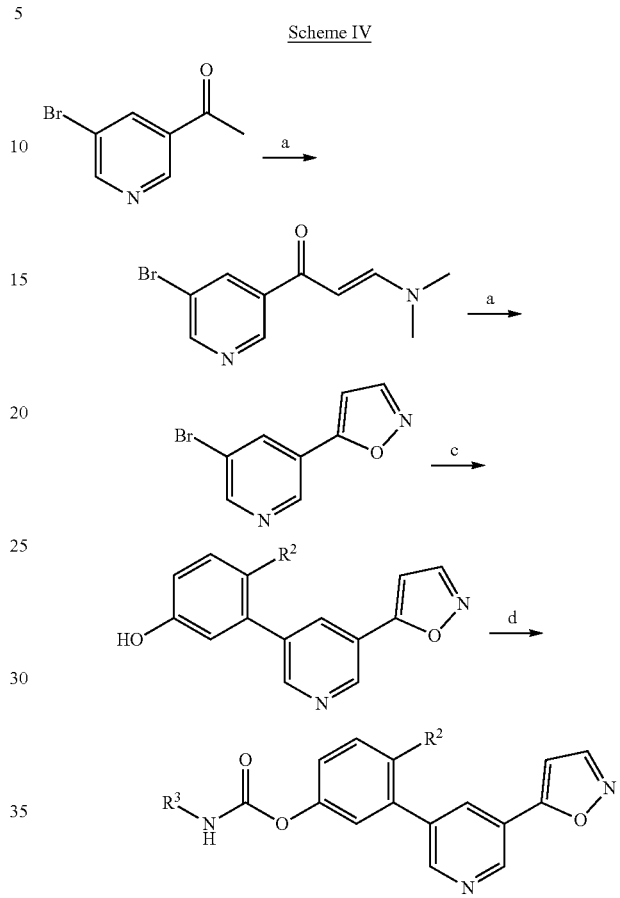

R$^2$ = H, OCH$_3$
Reagents and conditions: a) N, N-dimethylformamide dimethyl acetal (DMF—DMA), 100° C., 5 h; b) NH$_2$—OH, MeOH, 60° C., 6 h; c) Pd(PPh$_3$)$_4$ Na$_2$CO$_3$, toluene/ethanol (EtOH), 90° C., 4-8 h; d) R$^3$—NCO, TEA, ACN:EtOH (1:1), RT, 16 h.

Synthesis of (E)-1-(5-bromopyridin-3-yl)-3-(dimethylamino)prop-2-en-1-one

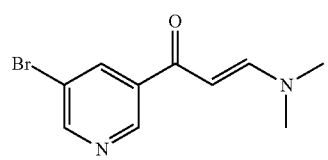

To a stirred solution of 1-(5-bromopyridin-3-yl)ethan-1-one (10 g, 50 mmol) in DMF-DMA (200 mL) and stirred the reaction mixture at 100° C. for 5 h. After completion of the reaction (monitored by TLC), the resulting mixture was concentrated to a residue. The residue was triturated with petroleum ether and filtered the precipitated solid and dried to give (E)-1-(5-bromopyridin-3-yl)-3-(dimethylamino)prop-2-en-1-one (10 g) which was used for next step without further purification. MS (ES+APCI) m/z 257.0 (M+2)

Synthesis of 5-(5-bromopyridin-3-yl)isoxazole

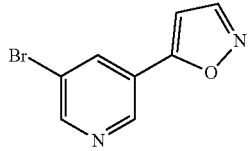 [SMILES: Brc1cncc(-c2ccno2)c1]

To a stirred solution of (E)-1-(5-bromopyridin-3-yl)-3-(dimethylamino)prop-2-en-1-one (4 g, 15.68 mmol) in MeOH (40 mL) was added hydroxylamine hydrochloride (1.63 g, 23.52 mmol) stirred at 60° C. for 6 h under nitrogen atmosphere. After completion of the reaction (monitored by TLC), the reaction mixture was evaporated under reduced pressure. The residue was purified by automated normal-phase chromatography and eluted with ethyl acetate/petroleum ether to give 5-(5-bromopyridin-3-yl)isoxazole (2 g, 57% yield) as an off white solid. $^1$HNMR (400 MHz, DMSO-d6) δ 9.09 (d, J=1.80 Hz, 1H), 8.82 (d, J=2.10 Hz, 1H), 8.76 (d, J=1.80 Hz, 1H), 8.58 (t, J=1.80 Hz, 1H), 7.29 (d, J=2.10 Hz, 1H); MS (ES+APCI) m/z 227.1.0 (M+1).

Synthesis of 3-(5-(isoxazol-5-yl)pyridin-3-yl)phenol

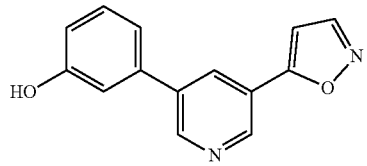 [SMILES: Oc1cccc(-c2cncc(-c3ccno3)c2)c1]

To a stirred solution of 5-(5-bromopyridin-3-yl)isoxazole (0.6 g, 2.67 mmol) in toluene (6 mL) and EtOH (0.6 mL) was added (3-hydroxyphenyl)boronic acid (0.44 g, 3.20 mmol) and Na$_2$CO$_3$ (0.57 g, 5.33 mmol) at RT. The reaction mixture was degassed for 15 minutes then Pd(PPh$_3$)$_4$ (0.22 g, 0.19 mmol) was added. The reaction mixture was stirred at 90° C. for 4 h under nitrogen atmosphere. After completion of the reaction (monitored by TLC), the reaction mixture was cooled to RT and then the solvent was evaporated under reduced pressure. The residue was quenched with water and precipitated solid was filtered and dried to give a residue. The residue was purified by automated normal-phase chromatography and eluted with ethyl acetate/petroleum ether to give 3-(5-(isoxazol-5-yl)pyridin-3-yl)phenol (0.19 g) as pale yellow solid. $^1$HNMR (400 MHz, DMSO-d6) δ 9.69 (s, 1H), 9.08 (d, J=2.00 Hz, 1H), 8.94 (d, J=2.00 Hz, 1H), 8.76 (d, J=2.00 Hz, 1H), 8.46 (t, J=2.00 Hz, 1H), 7.37-7.33 (m, 2H), 7.26-7.24 (m, 1H), 7.18 (t, J=2.00 Hz, 1H), 6.90-6.89 (m, 1H); MS (ES+APCI) m/z 239.2 (M+1).

Synthesis of 3-(5-(isoxazol-5-yl)pyridin-3-yl)phenyl octylcarbamate (Example-105)

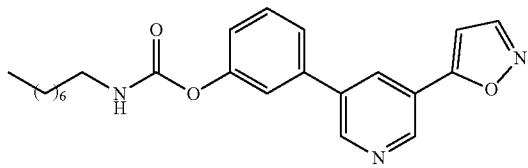

To a stirred solution of 3-(5-(isoxazol-5-yl)pyridin-3-yl)phenol (0.08 g, 0.34 mmol) in anhydrous acetonitrile (1 mL) and EtOH (1 mL) was added TEA (0.05 mL, 0.34 mmol) and n-octyl isocyanate (0.06 g, 0.40 mmol) at RT under nitrogen atmosphere. The reaction mixture was stirred at RT for 16 h. After completion of the reaction (monitored by TLC), the reaction mixture was concentrated to a residue. The residue was purified by preparative HPLC (0.1% FA) to yield the target compound (40 mg) as an off white solid. $^1$HNMR (400 MHz, DMSO-d6) δ 9.11 (d, J=2.00 Hz, 1H), 9.02 (d, J=2.00 Hz, 1H), 8.77 (d, J=2.00 Hz, 1H), 8.55 (t, J=2.00 Hz, 1H), 7.82 (t, J=5.60 Hz, 1H), 7.72-7.70 (m, 1H), 7.61 (t, J=2.00 Hz, 1H), 7.55 (t, J=7.60 Hz, 1H), 7.34 (d, J=2.00 Hz, 1H), 7.22-7.20 (m, 1H), 3.10-3.05 (m, 2H), 1.49 (t, J=7.20 Hz, 2H), 1.29-1.27 (m, 10H), 0.86 (t, J=7.20 Hz, 3H); MS (ES+APCI) m/z 394.3 (M+1).

Synthesis of 3-(5-(isoxazol-5-yl)pyridin-3-yl)phenyl cyclopentylcarbamate (Example-106)

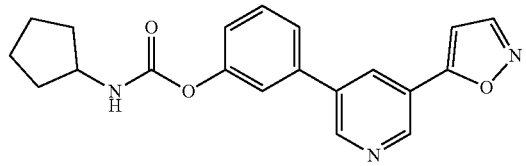 [SMILES: O=C(NC1CCCC1)Oc1cccc(-c2cncc(-c3ccno3)c2)c1]

To a stirred solution of 3-(5-(isoxazol-5-yl)pyridin-3-yl)phenol (0.05 g, 0.21 mmol) in anhydrous acetonitrile (1 mL) and EtOH (1 mL) was added TEA (0.03 mL, 0.21 mmol) and cyclopentyl isocyanate (0.28 g, 0.25 mmol) at RT under nitrogen atmosphere. The reaction mixture was stirred at RT for 16 h. After completion of the reaction (monitored by TLC), the reaction mixture was concentrated to a residue. The residue was purified by preparative HPLC (0.1% FA) to yield the target compound (26 mg) as an off white solid. $^1$HNMR (400 MHz, DMSO-d6) δ 9.11 (d, J=2.00 Hz, 1H), 9.03 (d, J=2.00 Hz, 1H), 8.77 (d, J=2.00 Hz, 1H), 8.56 (t, J=2.00 Hz, 1H), 7.87 (d, J=7.20 Hz, 1H), 7.71 (t, J=7.60 Hz, 1H), 7.63 (t, J=2.00 Hz, 1H), 7.54 (t, J=7.60 Hz, 1H), 7.34 (d, J=2.00 Hz, 1H), 7.23-7.20 (m, 1H), 3.90-3.85 (m, 1H), 1.89-1.47 (m, 8H); MS (ES+APCI) m/z 350.3 (M+1).

Synthesis of 3-(5-(isoxazol-5-yl)pyridin-3-yl)phenyl cyclohexylcarbamate (Example-107)

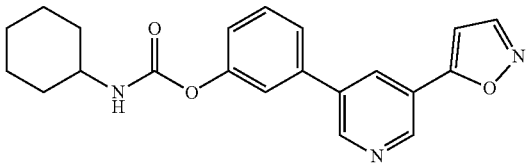 [SMILES: O=C(NC1CCCCC1)Oc1cccc(-c2cncc(-c3ccno3)c2)c1]

To a stirred solution of 3-(5-(isoxazol-5-yl)pyridin-3-yl)phenol (0.05 g, 0.21 mmol) in anhydrous acetonitrile (1 mL) and EtOH (1 mL) was added TEA (0.03 mL, 0.21 mmol) and cyclohexyl isocyanate (0.03 g, 0.25 mmol) at RT under nitrogen atmosphere. The reaction mixture was stirred at RT for 16 h. After completion of the reaction (monitored by TLC), the reaction mixture was concentrated to a residue. The residue was purified by preparative HPLC (0.1% FA) to yield the target compound (25 mg) as an off white solid.

¹HNMR (400 MHz, DMSO-d6) δ 9.11 (d, J=1.60 Hz, 1H), 9.03 (d, J=2.00 Hz, 1H), 8.77 (d, J=1.60 Hz, 1H), 8.56 (t, J=2.00 Hz, 1H), 7.80 (d, J=8.00 Hz, 1H), 7.70 (d, J=8.00 Hz, 1H), 7.62 (d, J=2.00 Hz, 1H), 7.54 (t, J=8.00 Hz, 1H), 7.34 (d, J=2.00 Hz, 1H), 7.21 (dd, J=1.60, 8.20 Hz, 1H), 1.87-1.11 (m, 10H); MS (ES+APCI) m/z 364.3 (M+1).

Synthesis of 3-(5-(isoxazol-5-yl)pyridin-3-yl)phenyl cycloheptylcarbamate (Example-108)

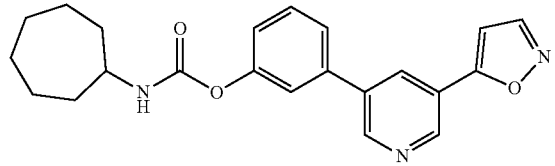 [SMILES: O=C(NC1CCCCCC1)Oc1cccc(-c2cncc(-c3ccno3)c2)c1]

To a stirred solution of 3-(5-(isoxazol-5-yl)pyridin-3-yl)phenol (0.08 g, 0.34 mmol) in anhydrous acetonitrile (1 mL) and EtOH (1 mL) was added TEA (0.05 mL, 0.34 mmol) and cycloheptyl isocyanate (0.05 g, 0.40 mmol) at RT under nitrogen atmosphere. The reaction mixture was stirred at RT for 16 h. After completion of the reaction (monitored by TLC), the reaction mixture was concentrated to a residue. The residue was purified by preparative HPLC (0.1% FA) to yield the target compound (50 mg) as an off white solid. ¹HNMR (400 MHz, DMSO-d6) δ 9.11 (d, J=2.00 Hz, 1H), 9.03 (d, J=2.00 Hz, 1H), 8.77 (d, J=2.00 Hz, 1H), 8.56 (t, J=2.00 Hz, 1H), 7.84 (d, J=8.00 Hz, 1H), 7.70 (d, J=8.00 Hz, 1H), 7.62 (t, J=2.00 Hz, 1H), 7.54 (t, J=7.60 Hz, 1H), 7.34 (d, J=1.60 Hz, 1H), 7.21 (dd, J=1.60, 8.00 Hz, 1H), 3.58-3.54 (m, 1H), 1.91-1.45 (m, 12H); MS (ES+APCI) m/z 378.4 (M+1).

Synthesis of 3-(5-(isoxazol-5-yl)pyridin-3-yl)-4-methoxyphenol

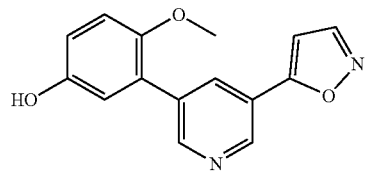 [SMILES: COc1ccc(O)cc1-c1cncc(-c2ccno2)c1]

To a stirred solution of 5-(5-bromopyridin-3-yl)isoxazole (0.5 g, 2.22 mmol) in 1,4-dioxane (5 mL) and water (0.5 mL) was added (5-hydroxy-2-methoxyphenyl)boronic acid (0.45 g, 2.67 mmol) and Cs₂CO₃ (1.45 g, 4.44 mmol) at RT. The reaction mixture was degassed for 15 minutes then Pd(dppf)Cl₂ (0.11 g, 0.16 mmol) was added. The reaction mixture was stirred at 80° C. for 1 h under nitrogen atmosphere. After completion of the reaction (monitored by TLC), the reaction mixture was cooled to RT and then the solvent was evaporated under reduced pressure. The residue was quenched with water and extracted with ethyl acetate, and the combined organic layers were washed with water, brine and concentrated to give a residue. The residue was purified by automated normal-phase chromatography and eluted with ethyl acetate/petroleum ether to give 3-(5-(isoxazol-5-yl)pyridin-3-yl)-4-methoxyphenol (0.4 g) as pale yellow solid. ¹HNMR (400 MHz, DMSO-d6) δ 9.19 (s, 1H), 9.03 (d, J=2.10 Hz, 1H), 8.74 (t, J=1.80 Hz, 2H), 8.31 (t, J=2.10 Hz, 1H), 7.26 (d, J=1.80 Hz, 1H), 7.01 (d, J=9.30 Hz, 1H), 6.84-6.81 (m, 2H), 3.71 (s, 3H); MS (ES+APCI) m/z 269.1 (M+1).

Synthesis of 3-(5-(isoxazol-5-yl) pyridin-3-yl)-4-methoxyphenyl octylcarbamate (Example-109)

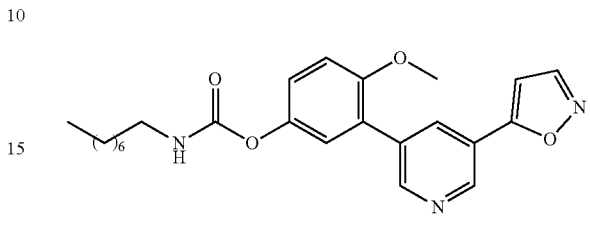

To a stirred solution of 3-(5-(isoxazol-5-yl)pyridin-3-yl)-4-methoxyphenol (0.08 g, 0.30 mmol) in anhydrous acetonitrile (1 mL) and EtOH (1 mL) was added TEA (0.04 mL, 0.30 mmol) and octyl isocyanate (0.05 g, 0.36 mmol) at RT under nitrogen atmosphere. The reaction mixture was stirred at RT for 16 h. After completion of the reaction (monitored by TLC), the reaction mixture was concentrated to a residue. The residue was purified by preparative HPLC (0.1% FA) to yield the target compound (55 mg) as an off white solid. ¹HNMR (400 MHz, DMSO-d6) δ 9.06 (d, J=2.00 Hz, 1H), 8.80 (d, J=2.00 Hz, 1H), 8.75 (d, J=2.00 Hz, 1H), 8.35 (t, J=2.00 Hz, 1H), 7.72 (t, J=5.60 Hz, 1H), 7.27 (d, J=2.00 Hz, 1H), 7.23 (d, J=1.60 Hz, 1H), 7.17 (d, J=1.20 Hz, 2H), 3.82 (s, 3H), 3.08-3.03 (m, 2H), 1.46 (t, J=6.80 Hz, 2H), 1.27-1.26 (m, 10H), 0.85 (t, J=6.80 Hz, 3H); MS (ES+APCI) m/z 424.3 (M+1).

Synthesis of 3-(5-(isoxazol-5-yl)pyridin-3-yl)-4-methoxyphenyl (cyclohexylmethyl)carbamate (Example-110)

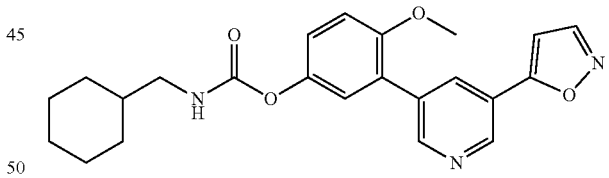

To a stirred solution of 3-(5-(isoxazol-5-yl)pyridin-3-yl)-4-methoxyphenol (0.08 g, 0.30 mmol) in anhydrous acetonitrile (1 mL) and EtOH (1 mL) was added TEA (0.04 mL, 0.30 mmol) and cyclohexylmethyl isocyanate (0.05 g, 0.36 mmol) at RT under nitrogen atmosphere. The reaction mixture was stirred at RT for 16 h. After completion of the reaction (monitored by TLC), the reaction mixture was concentrated to a residue. The residue was purified by preparative HPLC (0.1% FA) to yield the target compound (25 mg) as an off white solid. ¹HNMR (400 MHz, DMSO-d6) δ 9.06 (d, J=2.00 Hz, 1H), 8.80 (d, J=2.00 Hz, 1H), 8.75 (d, J=1.60 Hz, 1H), 8.35 (t, J=2.00 Hz, 1H), 7.74 (t, J=6.00 Hz, 1H), 7.27 (d, J=2.00 Hz, 1H), 7.23 (t, J=1.60 Hz, 1H), 7.17 (d, J=1.60 Hz, 2H), 3.82 (s, 3H), 2.91 (t, J=6.40 Hz, 2H), 1.73-0.88 (m, 11H); MS (ES+APCI) m/z 408.2 (M+1).

Synthesis of 3-(5-(isoxazol-5-yl)pyridin-3-yl)-4-methoxyphenyl benzylcarbamate (Example-111)

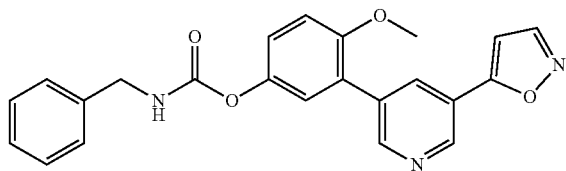 [SMILES: COc1ccc(OC(=O)NCc2ccccc2)cc1-c1cncc(-c2ccno2)c1]

To a stirred solution of 3-(5-(isoxazol-5-yl)pyridin-3-yl)-4-methoxyphenol (0.08 g, 0.30 mmol) in anhydrous acetonitrile (1 mL) and EtOH (1 mL) was added TEA (0.04 mL, 0.30 mmol) and benzyl isocyanate (0.04 g, 0.36 mmol) at RT under nitrogen atmosphere. The reaction mixture was stirred at RT for 16 h. After completion of the reaction (monitored by TLC), the reaction mixture was concentrated to a residue. The residue was purified by preparative HPLC (0.1% FA) to yield the target compound (25 mg) as pale-yellow solid. $^1$HNMR (400 MHz, DMSO-d6) δ 9.06 (d, J=2.00 Hz, 1H), 8.80 (d, J=2.00 Hz, 1H), 8.75 (d, J=2.00 Hz, 1H), 8.35 (t, J=2.00 Hz, 1H), 8.32-8.29 (m, 1H), 7.38-7.32 (m, 4H), 7.28-7.22 (m, 3H), 7.21-7.17 (m, 2H), 4.29 (d, J=6.00 Hz, 2H), 3.82 (s, 3H); MS (ES+APCI) m/z 402.4 (M+1).

Synthesis of 3-(5-(isoxazol-5-yl)pyridin-3-yl)-4-methoxyphenyl cyclopentylcarbamate (Example-112)

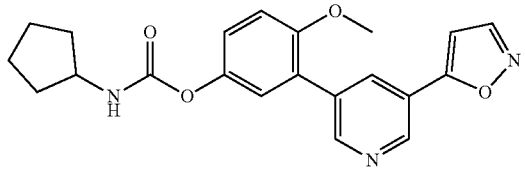 [SMILES: COc1ccc(OC(=O)NC2CCCC2)cc1-c1cncc(-c2ccno2)c1]

To a stirred solution of 3-(5-(isoxazol-5-yl)pyridin-3-yl)-4-methoxyphenol (0.08 g, 0.30 mmol) in anhydrous acetonitrile (1 mL) and EtOH (1 mL) was added TEA (0.04 mL, 0.30 mmol) and cyclopentyl isocyanate (0.04 g, 0.36 mmol) at RT under nitrogen atmosphere. The reaction mixture was stirred at RT for 16 h. After completion of the reaction (monitored by TLC), the reaction mixture was concentrated to a residue. The residue was purified by preparative HPLC (0.1% FA) to yield the target compound (39 mg) as off white solid. $^1$HNMR (400 MHz, DMSO-d6) δ 9.06 (d, J=2.40 Hz, 1H), 8.80 (d, J=2.00 Hz, 1H), 8.75 (d, J=2.00 Hz, 1H), 8.35 (t, J=2.00 Hz, 1H), 7.76 (d, J=7.60 Hz, 1H), 7.27 (d, J=2.00 Hz, 1H), 7.24 (s, 1H), 7.18 (d, J=1.20 Hz, 2H), 3.89-3.84 (m, 1H), 3.82 (s, 3H), 1.85-1.46 (m, 8H); MS (ES+APCI) m/z 380.1 (M+1).

Synthesis of 3-(5-(isoxazol-5-yl)pyridin-3-yl)-4-methoxyphenyl cyclohexylcarbamate (Example-113)

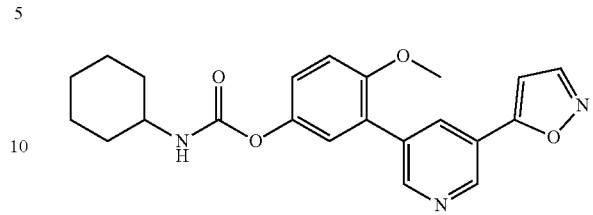

To a stirred solution of 3-(5-(isoxazol-5-yl)pyridin-3-yl)-4-methoxyphenol (0.08 g, 0.30 mmol) in anhydrous acetonitrile (1 mL) and EtOH (1 mL) was added TEA (0.04 mL, 0.30 mmol) and cyclohexyl isocyanate (0.04 g, 0.36 mmol) at RT under nitrogen atmosphere. The reaction mixture was stirred at RT for 16 h. After completion of the reaction (monitored by TLC), the reaction mixture was concentrated to a residue. The residue was purified by preparative HPLC (0.1% FA) to yield the target compound (60 mg) as an off white solid. $^1$HNMR (400 MHz, DMSO-d6) δ 9.06 (d, J=2.00 Hz, 1H), 8.80 (d, J=2.00 Hz, 1H), 8.75 (d, J=2.00 Hz, 1H), 8.35 (t, J=2.00 Hz, 1H), 7.69 (d, J=7.60 Hz, 1H), 7.27 (d, J=2.00 Hz, 1H), 7.24 (s, 1H), 7.17 (d, J=1.60 Hz, 2H), 3.82 (s, 3H), 1.84-1.10 (m, 10H); MS (ES+APCI) m/z 394.1 (M+1).

Synthesis of (3-(5-(isoxazol-5-yl)pyridin-3-yl)-4-methoxyphenyl cycloheptylcarbamate (Example-114)

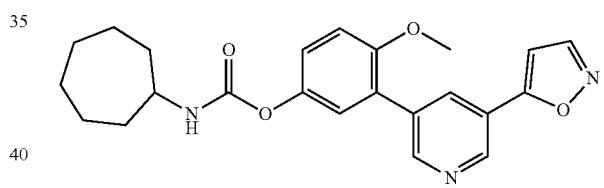

To a stirred solution of 3-(5-(isoxazol-5-yl)pyridin-3-yl)-4-methoxyphenol (0.08 g, 0.30 mmol) in anhydrous acetonitrile (1 mL) and EtOH (1 mL) was added TEA (0.04 mL, 0.30 mmol) and cycloheptyl isocyanate (0.05 g, 0.36 mmol) at RT under nitrogen atmosphere. The reaction mixture was stirred at RT for 16 h. After completion of the reaction (monitored by TLC), the reaction mixture was concentrated to a residue. The residue was purified by preparative HPLC (0.1% FA) to yield the target compound (35 mg) as an off white solid. $^1$HNMR (400 MHz, DMSO-d6) δ 9.06 (d, J=2.00 Hz, 1H), 8.80 (d, J=2.00 Hz, 1H), 8.75 (d, J=1.60 Hz, 1H), 8.35 (t, J=2.00 Hz, 1H), 7.73 (d, J=8.00 Hz, 1H), 7.27 (d, J=2.00 Hz, 1H), 7.23 (d, J=1.20 Hz, 1H), 7.17 (d, J=1.60 Hz, 2H), 3.82 (s, 3H), 3.58-3.51 (m, 1H), 1.89-1.35 (m, 12H); MS (ES+APCI) m/z 408.2 (M+1).

Scheme V

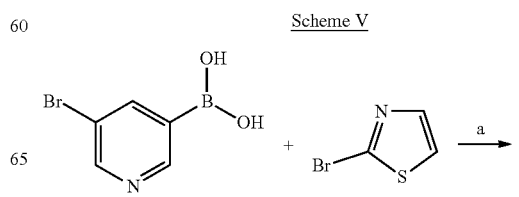

-continued

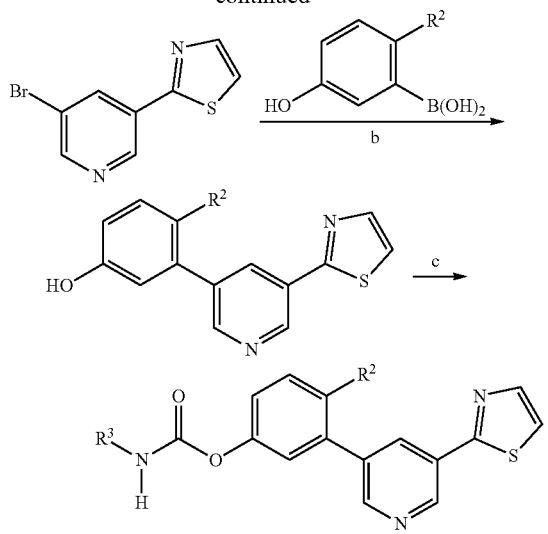

R² = H, OCH₃, Reagents and conditions: a) Pd(PPh₃)₄, Cs₂CO₃, 1,4-dioxane, 100° C., 5 h; b) Pd(PPh₃)₄, K₂CO₃, 1,4-dioxane, H₂O, 90° C., 5 h; c) R³-isocyanate(R³—NCO), TEA, ACN, 75° C., 5 h.

Synthesis of 2-(5-bromopyridin-3-yl)thiazole

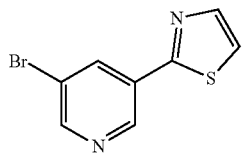 [SMILES: Brc1cncc(-c2nccs2)c1]

To a stirred solution of 2-bromothiazole (12 g, 73.17 mmol) in 1,4-dioxane (120 mL) was added (5-bromopyridin-3-yl)boronic acid (18 g, 87.80 mmol) and Cs₂CO₃ (35.8 g, 109.8 mmol) at RT. The reaction mixture was degassed for 15 minutes then Pd(PPh₃)₄ (5.1 g, 4.40 mmol) was added. The reaction mixture was stirred at 100° C. for 5 h under nitrogen atmosphere. After completion of the reaction (monitored by TLC), the reaction mixture was cooled to RT and then the solvent was evaporated under reduced pressure. The residue was purified by automated normal-phase chromatography and eluted with ethyl acetate/petroleum ether to give 2-(5-bromopyridin-3-yl)thiazole (4.5 g) as an off white solid. ¹H-NMR (400 MHz, DMSO-d6): δ 9.13 (d, J=2.80 Hz, 1H), 8.81 (d, J=3.20 Hz, 1H), 8.53 (t, J=2.80 Hz, 1H), 8.04 (d, J=4.40 Hz, 1H), 7.96 (d, J=4.40 Hz, 1H); MS (ES+APCI) m/z 243.1 (M+2).

Synthesis of 3-(5-(thiazol-2-yl)pyridin-3-yl)phenol

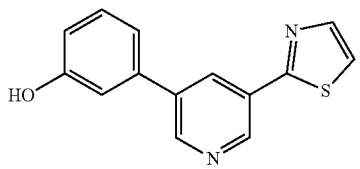 [SMILES: Oc1cccc(-c2cncc(-c3nccs3)c2)c1]

To a stirred solution of 2-(5-bromopyridin-3-yl)thiazole (4.5 g, 18.66 mmol) in 1,4-dioxane (50 mL) and water (5 mL) was added (3-hydroxyphenyl)boronic acid (2.9 g, 20.53 mmol) and K₂CO₃ (18.3 g, 56.0 mmol) at RT. The reaction mixture was degassed for 15 minutes then Pd(PPh₃)₄ (1.1 g, 0.95 mmol) was added. The reaction mixture was stirred at 90° C. for 5 h under nitrogen atmosphere. After completion of the reaction (monitored by TLC), the reaction mixture was cooled to RT and then the solvent was evaporated under reduced pressure. The residue was purified by automated normal-phase chromatography and eluted with ethyl acetate/petroleum ether to give 3-(5-(thiazol-2-yl)pyridin-3-yl)phenol (2.2 g) as an off white solid. ¹H-NMR (400 MHz, DMSO-d6): δ 9.69 (s, 1H), 9.13 (d, J=2.00 Hz, 1H), 8.92 (d, J=2.00 Hz, 1H), 8.43 (t, J=2.40 Hz, 1H), 8.05 (d, J=3.20 Hz, 1H), 7.94 (d, J=3.20 Hz, 1H), 7.35 (t, J=8.00 Hz, 1H), 7.24 (d, J=8.00 Hz, 1H), 7.16 (t, J=2.00 Hz, 1H), 6.89-6.87 (m, 1H); MS (ES+APCI) m/z 255.2 (M+1).

Synthesis of 3-(5-(furan-2-yl)pyridin-3-yl)phenyl octylcarbamate (Example-115)

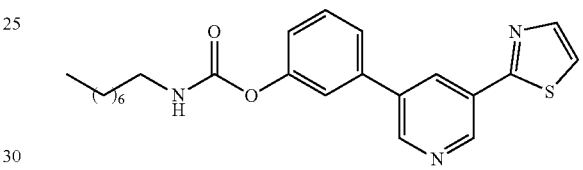

To a stirred solution of 3-(5-(thiazol-2-yl)pyridin-3-yl)phenol (0.07 g, 0.28 mmol) in anhydrous acetonitrile (2 mL) was added TEA (0.06 mL, 0.42 mmol) and n-octyl isocyanate (0.05 g, 0.33 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (70 mg) as an off white solid. ¹H-NMR (400 MHz, DMSO-d6): δ 9.16 (d, J=2.00 Hz, 1H), 8.99 (d, J=2.00 Hz, 1H), 8.50 (t, J=2.00 Hz, 1H), 8.05 (d, J=3.20 Hz, 1H), 7.95 (d, J=3.20 Hz, 1H), 7.82 (t, J=5.60 Hz, 1H), 7.68 (d, J=8.00 Hz, 1H), 7.59 (t, J=2.00 Hz, 1H), 7.54 (t, J=8.00 Hz, 1H), 7.22-7.19 (m, 1H), 3.09 (t, J=6.40 Hz, 2H), 1.50-1.45 (m, 2H), 1.29-1.27 (m, 10H), 0.86 (t, J=6.80 Hz, 3H); MS (ES+APCI) m/z 410.3 (M+1).

Synthesis of 3-(5-(thiazol-2-yl)pyridin-3-yl)phenyl (cyclohexylmethyl)carbamate (Example-116)

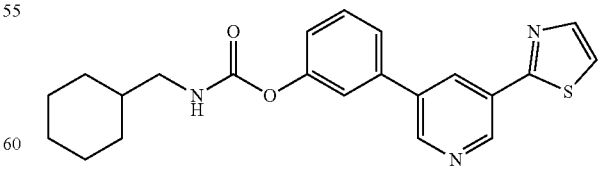

To a stirred solution of 3-(5-(thiazol-2-yl)pyridin-3-yl)phenol (0.07 g, 0.28 mmol) in anhydrous acetonitrile (2 mL) was added TEA (0.06 mL, 0.42 mmol) and cyclohexanemethyl isocyanate (0.050 g, 0.33 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (58 mg) as an off white solid. ¹H-NMR (400 MHz, DMSO-d6): δ 9.16 (d, J=2.00 Hz, 1H), 8.99 (d, J=2.00 Hz, 1H), 8.50 (t, J=2.00 Hz, 1H), 8.05 (d, J=3.20 Hz, 1H), 7.96 (d, J=3.20 Hz, 1H), 7.96 (d, J=3.20 Hz, 1H), 7.85 (t, J=6.00 Hz, 1H), 7.69-7.67 (m, 1H), 7.60 (t, J=2.00 Hz, 1H), 7.54 (t, J=8.00 Hz, 1H), 7.22-7.20 (m, 1H), 2.94 (t, J=6.40 Hz, 2H), 1.75-1.62 (m, 5H), 1.48-1.43 (m, 1H), 1.26-1.13 (m, 3H), 0.96-0.88 (m, 2H); MS (ES+APCI) m/z 394.3 (M+1).

Synthesis of 3-(5-(thiazol-2-yl)pyridin-3-yl)phenyl benzylcarbamate (Example-117)

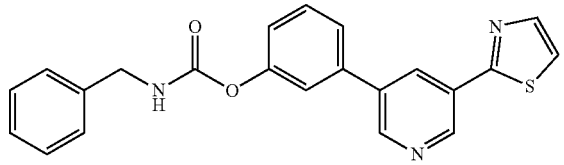 [SMILES: O=C(NCc1ccccc1)Oc1cccc(-c2cncc(-c3nccs3)c2)c1]

To a stirred solution of 3-(5-(thiazol-2-yl)pyridin-3-yl)phenol (0.07 g, 0.275 mmol) in anhydrous acetonitrile (2 mL) was added TEA (0.06 mL, 0.42 mmol) and benzyl isocyanate (0.05 g, 0.33 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (46 mg) as an off white solid. ¹H-NMR (400 MHz, DMSO-d6): δ 9.16 (d, J=2.00 Hz, 1H), 9.00 (d, J=2.40 Hz, 1H), 8.51 (t, J=2.00 Hz, 1H), 8.41 (t, J=6.00 Hz, 1H), 8.05 (d, J=3.20 Hz, 1H), 7.96 (d, J=3.20 Hz, 1H), 7.70 (d, J=8.00 Hz, 1H), 7.64 (t, J=2.00 Hz, 1H), 7.56 (t, J=8.00 Hz, 1H), 7.41-7.34 (m, 4H), 7.30-7.25 (m, 2H), 4.43-4.31 (m, 2H); MS (ES+APCI) m/z 388.3 (M+1).

Synthesis of 3-(5-(thiazol-2-yl)pyridin-3-yl)phenyl cyclopentylcarbamate (Example-118)

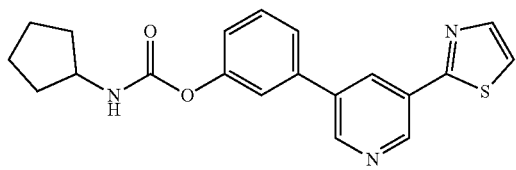 [SMILES: O=C(NC1CCCC1)Oc1cccc(-c2cncc(-c3nccs3)c2)c1]

To a stirred solution of 3-(5-(thiazol-2-yl)pyridin-3-yl)phenol (0.07 g, 0.28 mmol) in anhydrous acetonitrile (2 mL) was added TEA (0.06 mL, 0.42 mmol) and cyclopentyl isocyanate (0.04 g, 0.33 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (24 mg) as an off white solid. ¹H-NMR (400 MHz, DMSO-d6): δ 9.16 (d, J=2.00 Hz, 1H), 8.99 (d, J=2.00 Hz, 1H), 8.50 (t, J=2.40 Hz, 1H), 8.05 (d, J=3.20 Hz, 1H), 7.95 (d, J=3.20 Hz, 1H), 7.87 (d, J=7.60 Hz, 1H), 7.68 (d, J=7.60 Hz, 1H), 7.61 (t, J=1.60 Hz, 1H), 7.54 (t, J=8.00 Hz, 1H), 7.22-7.20 (m, 1H), 3.90-3.85 (m, 1H), 1.89-1.85 (m, 2H), 1.67 (d, J=12.00 Hz, 2H), 1.54-1.51 (m, 4H); MS (ES+APCI) m/z 366.3 (M+1).

Synthesis of 3-(5-(thiazol-2-yl)pyridin-3-yl)phenyl cyclohexylcarbamate (Example-119)

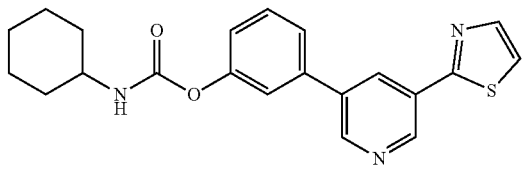 [SMILES: O=C(NC1CCCCC1)Oc1cccc(-c2cncc(-c3nccs3)c2)c1]

To a stirred solution of 3-(5-(thiazol-2-yl)pyridin-3-yl)phenol (0.07 g, 0.28 mmol) in anhydrous acetonitrile (2 mL) was added TEA (0.06 mL, 0.42 mmol) and cyclohexyl isocyanate (0.04 g, 0.33 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (44 mg) as an off white solid. ¹H-NMR (400 MHz, DMSO-d6): δ 9.16 (d, J=2.00 Hz, 1H), 8.99 (d, J=2.40 Hz, 1H), 8.50 (t, J=2.00 Hz, 1H), 8.05 (t, J=1.60 Hz, 1H), 7.95 (d, J=3.20 Hz, 1H), 7.80 (d, J=8.00 Hz, 1H), 7.68 (d, J=8.00 Hz, 1H), 7.60 (t, J=1.60 Hz, 1H), 7.54 (t, J=8.00 Hz, 1H), 7.22-7.20 (m, 1H), 3.33 (s, 1H), 1.86 (d, J=8.40 Hz, 2H), 1.73 (t, J=4.80 Hz, 2H), 1.58 (d, J=12.00 Hz, 1H), 1.34-1.20 (m, 4H), 1.16-1.11 (m, 1H); MS (ES+APCI) m/z 380.3 (M+1).

Synthesis of 3-(5-(thiazol-2-yl)pyridin-3-yl)phenyl cycloheptylcarbamate (Example-120)

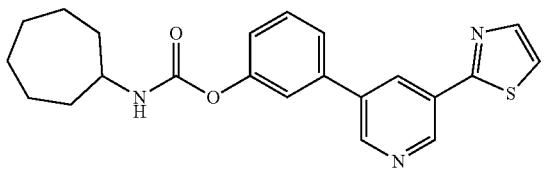 [SMILES: O=C(NC1CCCCCC1)Oc1cccc(-c2cncc(-c3nccs3)c2)c1]

To a stirred solution of 3-(5-(thiazol-2-yl)pyridin-3-yl)phenol (0.07 g, 0.28 mmol) in anhydrous acetonitrile (2 mL) was added TEA (0.06 mL, 0.42 mmol) and cycloheptyl isocyanate (0.05 g, 0.33 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (65 mg) as an off white solid. ¹H-NMR (400 MHz, DMSO-d6): δ 9.16 (d, J=2.40 Hz, 1H), 8.99 (d, J=2.00 Hz, 1H), 8.50 (t, J=2.00 Hz, 1H), 8.05 (t, J=1.60 Hz, 1H), 7.95 (d, J=3.20 Hz, 1H), 7.84 (d, J=8.00 Hz, 1H), 7.68 (d, J=8.00 Hz, 1H), 7.60 (t, J=2.00 Hz, 1H), 7.54 (t, J=8.00 Hz, 1H), 7.22-7.20 (m, 1H), 3.61-3.52 (m, 1H), 1.91-1.86 (m, 2H), 1.68-1.48 (m, 10H); MS (ES+APCI) m/z 394.3 (M+1).

Synthesis of 4-methoxy-3-(5-(thiazol-2-yl)pyridin-3-yl)phenol

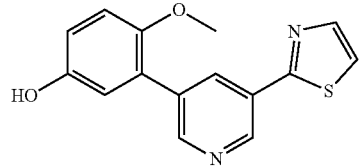 [SMILES: COc1ccc(O)cc1-c1cncc(-c2nccs2)c1]

To a stirred solution of 2-(5-bromopyridin-3-yl)thiazole (0.6 g, 2.48 mmol) in 1,4-dioxane (5 mL) and water (0.5 mL) was added (5-hydroxy-2-methoxyphenyl)boronic acid (0.50 g, 2.74 mmol) and $K_2CO_3$ (2.5 g, 7.47 mmol) at RT. The reaction mixture was degassed for 15 minutes then Pd(PPh$_3$)$_4$ (0.150 g, 0.125 mmol) was added. The reaction mixture was stirred at 90° C. for 5 h under nitrogen atmosphere. After completion of the reaction (monitored by TLC), the reaction mixture was cooled to RT and then the solvent was evaporated under reduced pressure. The residue was dissolved in ethyl acetate, washed with water followed by brine. The organic layer was dried over sodium sulfate then evaporated under reduced pressure. The residue was purified by automated normal-phase chromatography and eluted with ethyl acetate/petroleum ether to give 4-methoxy-3-(5-(thiazol-2-yl)pyridin-3-yl)phenol (600 mg) as an off white solid. $^1$H-NMR (400 MHz, DMSO-d6): δ 9.19 (s, 1H), 9.07 (d, J=2.80 Hz, 1H), 8.73 (d, J=2.80 Hz, 1H), 8.33 (t, J=2.80 Hz, 1H), 8.02 (t, J=2.00 Hz, 1H), 7.91 (d, J=4.40 Hz, 1H), 7.01 (d, J=12.00 Hz, 1H), 6.85-6.81 (m, 2H), 3.71 (s, 3H); MS (ES+APCI) m/z 285.0 (M+1).

Synthesis of 4-methoxy-3-(5-(thiazol-2-yl)pyridin-3-yl)phenyl octylcarbamate (Example-121)

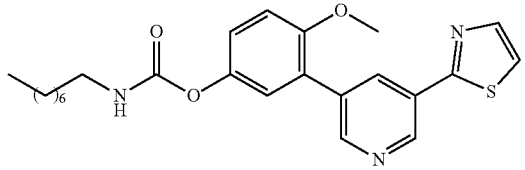

To a stirred solution of 4-methoxy-3-(5-(thiazol-2-yl)pyridin-3-yl)phenol (0.07 g, 0.24 mmol) in anhydrous acetonitrile (2 mL) was added TEA (0.05 mL, 0.37 mmol) and octyl isocyanate (0.05 g, 0.30 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (80 mg) as an off white solid. $^1$H-NMR (400 MHz, DMSO-d6): δ 9.10 (d, J=2.40 Hz, 1H), 8.77 (d, J=2.00 Hz, 1H), 8.37 (t, J=2.00 Hz, 1H), 8.03 (d, J=3.20 Hz, 1H), 7.93 (d, J=3.20 Hz, 1H), 7.72 (t, J=5.60 Hz, 1H), 7.23 (d, J=1.20 Hz, 1H), 7.17 (s, 2H), 3.82 (s, 3H), 3.06 (t, J=6.40 Hz, 2H), 1.48-1.43 (m, 2H), 1.27-1.26 (m, 10H), 0.85 (t, J=7.20 Hz, 3H); MS (ES+APCI) m/z 440.2 (M+1).

Synthesis of 4-methoxy-3-(5-(thiazol-2-yl)pyridin-3-yl)phenyl (cyclohexylmethyl)carbamate (Example-122)

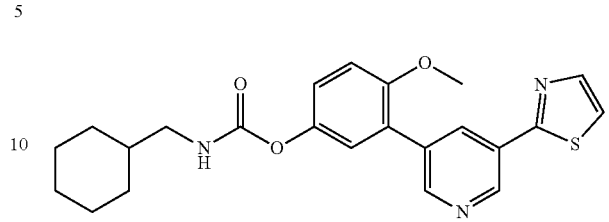

To a stirred solution of 4-methoxy-3-(5-(thiazol-2-yl)pyridin-3-yl)phenol (0.07 g, 0.24 mmol) in anhydrous acetonitrile (2 mL) was added TEA (0.05 mL, 0.37 mmol) and cyclohexanemethyl isocyanate (0.04 g, 0.30 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (63 mg) as an off white solid. $^1$H-NMR (400 MHz, DMSO-d6): δ 9.10 (d, J=2.00 Hz, 1H), 8.77 (d, J=2.40 Hz, 1H), 8.37 (t, J=2.00 Hz, 1H), 8.03 (d, J=3.20 Hz, 1H), 7.93 (d, J=3.20 Hz, 1H), 7.74 (t, J=6.00 Hz, 1H), 7.24 (t, J=1.60 Hz, 1H), 7.17 (d, J=1.60 Hz, 2H), 3.82 (s, 3H), 2.91 (t, J=6.40 Hz, 2H), 1.73-1.61 (m, 5H), 1.46-1.41 (m, 1H), 1.21-1.12 (m, 3H), 0.92 (d, J=11.60 Hz, 2H); MS (ES+APCI) m/z 424.2 (M+1).

Synthesis of 4-methoxy-3-(5-(thiazol-2-yl)pyridin-3-yl)phenyl benzylcarbamate (Example-123)

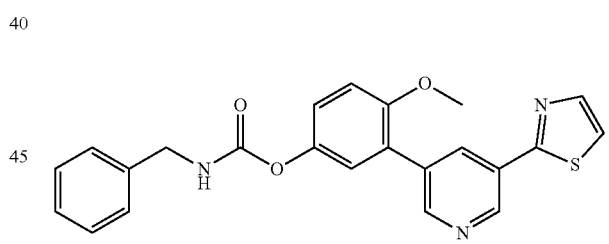

To a stirred solution of 4-methoxy-3-(5-(thiazol-2-yl)pyridin-3-yl)phenol (0.07 g, 0.24 mmol) in anhydrous acetonitrile (2 mL) was added TEA (0.05 mL, 0.37 mmol) and benzyl isocyanate (0.04 g, 0.30 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (40 mg) as an off white solid. $^1$H-NMR (400 MHz, DMSO-d6): δ 9.10 (d, J=2.00 Hz, 1H), 8.78 (d, J=2.00 Hz, 1H), 8.38 (t, J=2.00 Hz, 1H), 8.30 (t, J=6.00 Hz, 1H), 8.03 (d, J=3.20 Hz, 1H), 7.93 (d, J=3.20 Hz, 1H), 7.38-7.32 (m, 4H), 7.28-7.25 (m, 2H), 7.23-7.17 (m, 2H), 4.39-4.28 (m, 2H), 3.82 (s, 3H); MS (ES+APCI) m/z 418.1 (M+1).

Synthesis of 4-methoxy-3-(5-(thiazol-2-yl)pyridin-3-yl)phenyl cyclopentylcarbamate (Example-124)

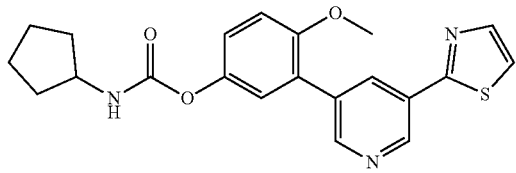 [SMILES: COc1ccc(OC(=O)NC2CCCC2)cc1-c1cncc(-c2nccs2)c1]

To a stirred solution of 4-methoxy-3-(5-(thiazol-2-yl)pyridin-3-yl)phenol (0.07 g, 0.24 mmol) in anhydrous acetonitrile (2 mL) was added TEA (0.05 mL, 0.37 mmol) and cyclopentyl isocyanate (0.04 g, 0.30 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (58 mg) as an off white solid. $^1$H-NMR (400 MHz, DMSO-d6): δ 9.10 (d, J=2.00 Hz, 1H), 8.77 (d, J=2.00 Hz, 1H), 8.37 (t, J=2.00 Hz, 1H), 8.03 (d, J=3.20 Hz, 1H), 7.93 (d, J=3.20 Hz, 1H), 7.76 (d, J=7.20 Hz, 1H), 7.24 (s, 1H), 7.18 (d, J=1.60 Hz, 2H), 3.87-3.82 (m, 4H), 1.85-1.80 (m, 2H), 1.68-1.63 (m, 2H), 1.53-1.46 (m, 4H); MS (ES+APCI) m/z 396.1 (M+1).

Synthesis of 4-methoxy-3-(5-(thiazol-2-yl)pyridin-3-yl)phenyl cyclohexylcarbamate (Example-125)

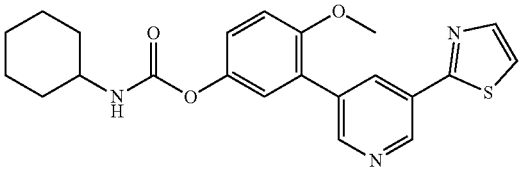 [SMILES: COc1ccc(OC(=O)NC2CCCCC2)cc1-c1cncc(-c2nccs2)c1]

To a stirred solution of 4-methoxy-3-(5-(thiazol-2-yl)pyridin-3-yl)phenol (0.07 g, 0.24 mmol) in anhydrous acetonitrile (2 mL) was added TEA (0.05 mL, 0.37 mmol) and cyclohexyl isocyanate (0.04 g, 0.30 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (30 mg) as an off white solid. $^1$H-NMR (400 MHz, DMSO-d6): δ 9.10 (d, J=2.00 Hz, 1H), 8.77 (d, J=2.00 Hz, 1H), 8.37 (t, J=2.00 Hz, 1H), 8.03 (d, J=3.20 Hz, 1H), 7.93 (d, J=3.20 Hz, 1H), 7.69 (d, J=8.00 Hz, 1H), 7.24 (d, J=1.20 Hz, 1H), 7.17 (d, J=1.60 Hz, 2H), 3.82 (s, 3H), 3.33 (s, 1H), 1.84-1.69 (m, 4H), 1.57 (d, J=12.00 Hz, 1H), 1.29-1.21 (m, 4H), 1.18-1.10 (m, 1H); MS (ES+APCI) m/z 410.1 (M+1).

Synthesis of 4-methoxy-3-(5-(thiazol-2-yl)pyridin-3-yl)phenyl cycloheptylcarbamate (Example-126)

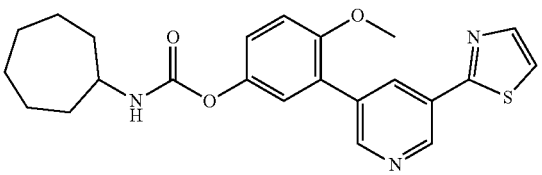 [SMILES: COc1ccc(OC(=O)NC2CCCCCC2)cc1-c1cncc(-c2nccs2)c1]

To a stirred solution of 4-methoxy-3-(5-(thiazol-2-yl)pyridin-3-yl)phenol (0.07 g, 0.24 mmol) in anhydrous acetonitrile (2 mL) was added TEA (0.05 mL, 0.37 mmol) and cycloheptyl isocyanate (0.04 g, 0.30 mmol) at RT under nitrogen atmosphere. The reaction mixture was stirred at RT for 10 minutes and then stirred at 75° C. for 5 h. After completion of the reaction (monitored by LCMS), the reaction mixture was concentrated to a residue. The residue was purified by preparative HPLC (0.1% FA) to yield the target compound (54 mg) as an off white solid. $^1$H-NMR (400 MHz, DMSO-d6): δ 9.10 (d, J=2.00 Hz, 1H), 8.77 (d, J=2.00 Hz, 1H), 8.37 (t, J=2.00 Hz, 1H), 8.03 (d, J=3.20 Hz, 1H), 7.93 (d, J=3.20 Hz, 1H), 7.73 (d, J=8.00 Hz, 1H), 7.24 (d, J=1.60 Hz, 1H), 7.17 (d, J=1.20 Hz, 2H), 3.82 (s, 3H), 3.56-3.52 (m, 1H), 1.89-1.84 (m, 2H), 1.66-1.61 (m, 2H), 1.59-1.52 (m, 6H), 1.50-1.47 (m, 2H); MS (ES+APCI) m/z 424.2 (M+1).

Scheme VI

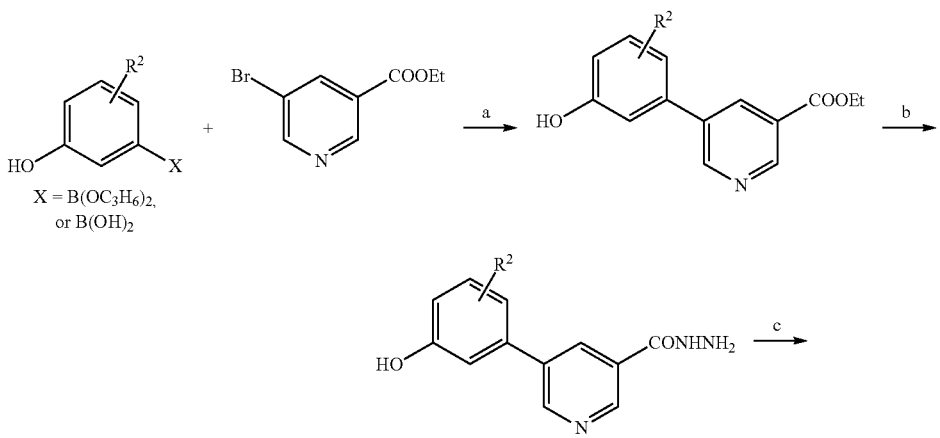

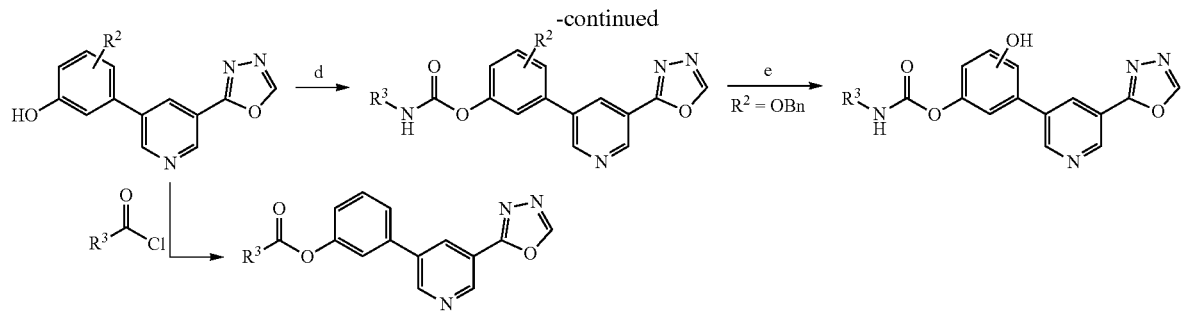

R² = H, OCH₃, OCF₃, SCH₃, N(CH₃)₃, F

Reagents and conditions: a) Pd(PPh₃)₄, K₂CO₃, 1,4-dioxane, H₂O, 90° C., 12 h or Pd(dppf)Cl₂, KOAc, 1,4-Dioxane, 90° C., 12 h; b) NH₂—NH₂•H₂O, EtOH, 60° C., 12 h; c) CH(OC₂H₅)₃, 120-130° C., 5 h d) R³—NCO, TEA, ACN, 75° C., 2-6 h; e) Pd/C, Pd(OH)₂, H₂ gas (balloon), tetrahydrofuran (THF), isopropanol (IPA), RT, 16 h; f) R³COCl, TEA, ACN, 75° C., 6-12 h.

Synthesis of 5-(3-hydroxyphenyl)nicotinohydrazide

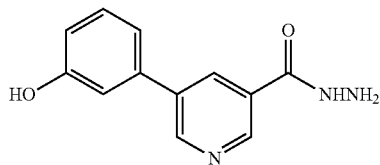 [SMILES: NNC(=O)c1cncc(-c2cccc(O)c2)c1]

To a solution of ethyl 5-(3-hydroxyphenyl)nicotinate (0.25 g, 1.028 mmol) in ethanol (6 mL) was added hydrazine hydrate (0.61 g, 6.16 mmol) at RT. The reaction mixture was heated at 90° C. for 15 h. The reaction progress was monitored by TLC, after completion the reaction was cooled to RT. The precipitated product was collected by filtrations and washed by ethanol. The filtrate was evaporated under reduced pressure and the residue was purified by flash chromatography on silica gel eluting with DCM/MeOH (gradient 2-20% MeOH) to yield the 5-(3-hydroxyphenyl)nicotinohydrazide (180 mg) as a pale yellow solid. ¹H NMR (400 MHz, DMSO-d6) δ 10.06 (s, 1H), 9.67 (s, 1H), 8.94 (m, 2H), 8.35 (m, 1H), 7.32 (m, 1H), 7.20 (d, J=7.7 Hz, 1H), 7.14 (s, 1H), 6.86 (dd, J=7.8, 1.7 Hz, 1H), 4.60 (s, 2H).

Synthesis of 3-(5-(1,3,4-oxadiazol-2-yl)pyridin-3-yl)phenol

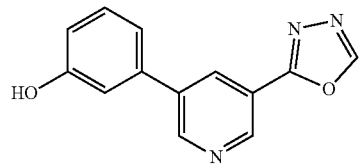 [SMILES: Oc1cccc(-c2cncc(-c3nnco3)c2)c1]

A suspension of 5-(3-hydroxyphenyl)nicotinohydrazide (0.22 g, 0.92 mmol) in triethyl orthoformate (6 mL) was heated to 130° C. for 5 h under nitrogen atmosphere. The reaction progress was monitored by TLC, after completion the reaction mixture was cooled to RT and then the solvent was evaporated under reduced pressure. The compound was purified by column chromatography on silica gel eluting with DCM/MeOH (gradient 2-20% MeOH) to yield the 3-(5-(1,3,4-oxadiazol-2-yl)pyridin-3-yl)phenol (120 mg) as a yellowish solid. ¹H NMR (400 MHz, DMSO-d6): δ 9.73 (s, 1H), 9.49 (s, 1H), 9.17 (d, J=1.8 Hz, 1H), 9.07 (d, J=2.0 Hz, 1H), 8.49 (m, 1H), 7.35 (m, 1H), 7.24 (d, J=7.7 Hz, 1H), 7.16 (s, 1H), 6.89 (dd, J=7.8, 1.5 Hz, 1H).

Synthesis of 3-(5-(1,3,4-oxadiazol-2-yl pyridin-3-yl) phenyl pentylcarbamate (Example-127)

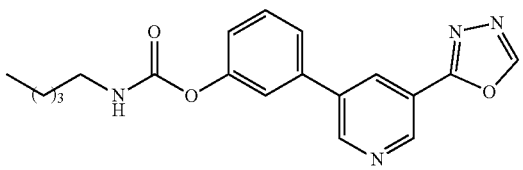

To a suspension of 3-(5-(1,3,4-oxadiazol-2-yl)pyridin-3-yl)phenol (0.08 g, 0.33 mmol) in anhydrous acetonitrile (2 mL) was added TEA (0.04 g, 0.4 mmol) and n-pentyl isocyanate (0.05 g, 0.42 mmol) at RT under nitrogen atmosphere. The reaction mixture was stirred at RT for 10 minutes and then heated at 75° C. for 3 h under nitrogen atmosphere. An additional amount of n-pentyl isocyanate (0.016 g, 0.11 mmol) was added to the reaction mixture and the reaction was heated for an additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-50% EtOAc) to yield the target compound (40 mg) as an off white solid. ¹H NMR (400 MHz, DMSO-d6): δ 9.51 (s, 1H), 9.21 (d, J=2.0 Hz, 1H), 9.16 (d, J=2.3 Hz, 1H), 8.61 (t, J=2.2 Hz, 1H), 7.85 (t, J=5.7 Hz, 1H), 7.70 (d, J=7.8 Hz, 1H), 7.63 (t, J=2.1 Hz, 1H), 7.56 (t, J=7.9 Hz, 1H), 7.22 (dd, J=7.9, 2.3 Hz, 1H), 3.08 (q, J=6.6 Hz, 2H), 0.88-1.37 (m, 9H).

Synthesis of 3-(5-(1,3,4-oxadiazol-2-yl)pyridin-3-yl) phenyl hexylcarbamate (Example-128)

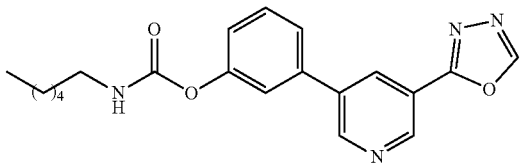

To a suspension of 3-(5-(1,3,4-oxadiazol-2-yl)pyridin-3-yl)phenol (0.1 g, 0.42 mmol) in anhydrous acetonitrile (3 mL) was added TEA (0.07 mL, 0.5 mmol) and n-hexyl isocyanate (0.053 g, 0.42 mmol) at RT under nitrogen atmosphere. The reaction mixture was stirred at RT for 10 minutes and then heated at 75° C. for 3 h under nitrogen atmosphere. An additional amount of n-hexyl isocyanate (0.018 g, 0.14 mmol) was added to the reaction mixture and the reaction was heated for an additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-55% EtOAc) to yield the target compound (42 mg) as an off white solid. $^1$H NMR (400 MHz, DMSO-d6) δ 9.50 (d, J=4.5 Hz, 1H), 9.13-9.24 (m, 2H), 8.60 (t, J=2.1 Hz, 1H), 7.85 (t, J=5.7 Hz, 1H), 7.70 (d, J=7.7 Hz, 1H), 7.62 (t, J=2.0 Hz, 1H), 7.56 (t, J=7.9 Hz, 1H), 7.15-7.28 (m, 1H), 3.08 (q, J=6.6 Hz, 2H), 0.87-1.38 (m, 11H)

Synthesis of 3-(5-(1,3,4-oxadiazol-2-yl)$_{134}$ pyridine-3-yl)phenyl heptylcarbamate (Example-129)

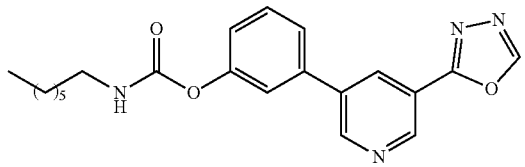

To a suspension of 3-(5-(1,3,4-oxadiazol-2-yl)pyridine-3-yl)phenol (0.08 g, 0.33 mmol) in anhydrous acetonitrile (2 mL) was added TEA (0.04 g, 0.4 mmol) and n-heptyl isocyanate (0.047 g, 0.33 mmol) at RT under nitrogen atmosphere. The reaction mixture was stirred at RT for 10 minutes and then heated at 75° C. for 3 h under nitrogen atmosphere. An additional amount of n-heptyl isocyanate (0.016 g, 0.11 mmol) was added to the reaction mixture and the reaction was heated for additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-55% EtOAc) to yield the target compound (45 mg) as an off white solid. $^1$H NMR (400 MHz, DMSO-d6) δ 9.49 (d, J=1.8 Hz, 1H), 9.21 (d, J=2.1 Hz, 1H), 9.15 (d, J=2.3 Hz, 1H), 8.60 (q, J=2.3 Hz, 1H), 7.81 (t, J=5.7 Hz, 1H), 7.70 (d, J=7.7 Hz, 1H), 7.61 (d, J=2.2 Hz, 1H), 7.55 (td, J=7.9, 1.7 Hz, 1H), 7.22 (d, J=8.1 Hz, 1H), 3.08 (q, J=6.6 Hz, 2H), 0.83-1.34 (m, 13H).

Synthesis of 3-(5-(1,3,4-oxadiazol-2-yl)pyridine-3-yl)phenyl octylcarbamate (Example-130)

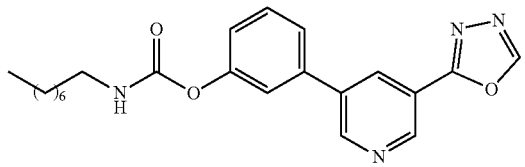

To a suspension of 3-(5-(1,3,4-oxadiazol-2-yl)pyridin-3-yl)phenol (0.08 g, 0.33 mmol) in anhydrous acetonitrile (2 mL) was added TEA (0.04 g, 0.4 mmol) and n-octyl isocyanate (0.05 g, 0.33 mmol) at RT under nitrogen atmosphere. The reaction mixture was stirred at RT for 10 minutes and then heated at 75° C. for 3 h under nitrogen atmosphere. An additional amount of n-octyl isocyanate (0.017 g, 0.11 mmol) was added to the reaction mixture and the reaction was heated for an additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-55% EtOAc) to yield the target compound (43 mg) as an off white solid. $^1$H NMR (400 MHz, DMSO-d6) δ 9.50 (s, 1H), 9.21 (d, J=2.0 Hz, 1H), 9.15 (d, J=2.2 Hz, 1H), 8.60 (t, J=2.3 Hz, 1H), 7.82 (t, J=5.7 Hz, 1H), 7.67-7.73 (m, 1H), 7.61 (t, J=2.1 Hz, 1H), 7.55 (t, J=7.9 Hz, 1H), 7.22 (dd, J=8.0, 2.3 Hz, 1H), 3.08 (q, J=6.6 Hz, 2H), 0.82-1.48 (m, 15H).

Synthesis of 3-(5-(1,3,4-oxadiazol-2-yl)pyridin-3-yl)phenyl dodecylcarbamate (Example-131)

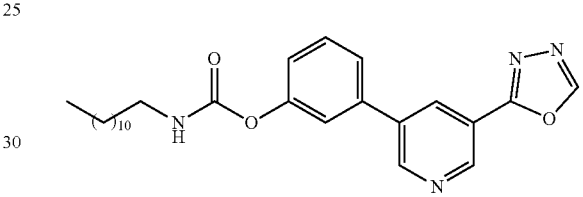

To a suspension of 3-(5-(1,3,4-oxadiazol-2-yl)pyridin-3-yl)phenol (0.08 g, 0.33 mmol) in anhydrous acetonitrile (2 mL) was added TEA (0.04 g, 0.4 mmol) and n-dodecyl isocyanate (0.07 g, 0.33 mmol) at RT under nitrogen atmosphere. The reaction mixture was stirred at RT for 10 minutes and then heated at 75° C. for 3 h under nitrogen atmosphere. An additional amount of n-dodecyl isocyanate (0.023 g, 0.11 mmol) was added to the reaction mixture and the reaction was heated for an additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-55% EtOAc) to yield the target compound (45 mg) as an off white solid. $^1$H NMR (400 MHz, DMSO-d6) δ 9.50 (s, 1H), 9.21 (d, J=2.0 Hz, 1H), 9.15 (d, J=2.2 Hz, 1H), 8.60 (t, J=2.3 Hz, 1H), 7.82 (t, J=5.7 Hz, 1H), 7.67-7.73 (m, 1H), 7.61 (t, J=2.1 Hz, 1H), 7.55 (t, J=7.9 Hz, 1H), 7.22 (dd, J=8.0, 2.3 Hz, 1H), 3.08 (q, J=6.6 Hz, 2H), 0.82-1.38 (m, 23H).

Synthesis of 3-(5-(1,3,4-oxadiazol-2-yl)pyridin-3-yl)phenyl tetradecylcarbamate (Example-132)

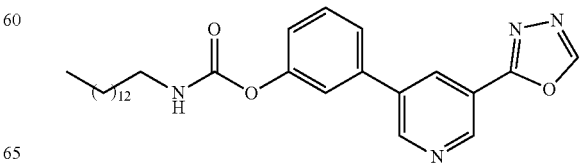

To a suspension of 3-(5-(1,3,4-oxadiazol-2-yl)pyridin-3-yl)phenol (0.08 g, 0.33 mmol) in anhydrous acetonitrile (2 mL) was added TEA (0.04 g, 0.4 mmol) and tetradecyl isocyanate (0.08 g, 0.33 mmol) at RT under nitrogen atmosphere. The reaction mixture was stirred at RT for 10 minutes and then heated at 75° C. for 3 h under nitrogen atmosphere. An additional amount of tetradecyl isocyanate (0.026 g, 0.11 mmol) was added to the reaction mixture and the reaction was heated for an additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-50% EtOAc) to yield the target compound (33 mg) as an off white solid. $^1$H NMR (400 MHz, DMSO-d6) δ 0.85-1.47 (m, 27H), 3.08 (q, J=6.6 Hz, 2H), 7.19-7.26 (m, 1H), 7.55 (t, J=7.9 Hz, 1H), 7.62 (t, J=2.1 Hz, 1H), 7.70 (d, J=7.7 Hz, 1H), 7.84 (t, J=5.8 Hz, 1H), 8.60 (t, J=2.1 Hz, 1H), 9.15 (d, J=2.2 Hz, 1H), 9.21 (d, J=2.0 Hz, 1H), 9.51 (s, 1H). $^1$H NMR (400 MHz, DMSO-d6) δ 9.51 (s, 1H), 9.21 (d, J=2.0 Hz, 1H), 9.15 (d, J=2.2 Hz, 1H), 8.60 (t, J=2.1 Hz, 1H), 7.84 (t, J=5.8 Hz, 1H), 7.70 (d, J=7.7 Hz, 1H), 7.62 (t, J=2.1 Hz, 1H), 7.55 (t, J=7.9 Hz, 1H), 7.19-7.26 (m, 1H), 3.08 (q, J=6.6 Hz, 2H), 0.85-1.47 (m, 27H).

Synthesis of 3-(5-(1,3,4-oxadiazol-2-yl)pyridin-3-yl) phenyl octadecylcarbamate (Example-133)

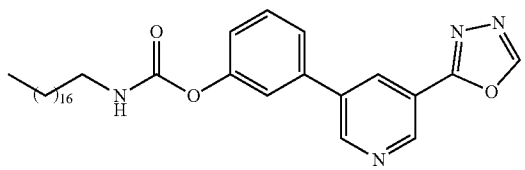

To a suspension of 3-(5-(1,3,4-oxadiazol-2-yl)pyridin-3-yl)phenol (0.08 g, 0.33 mmol) in anhydrous acetonitrile (2 mL) was added TEA (0.04 g, 0.4 mmol) and n-octadecyl isocyanate (0.1 g, 0.33 mmol) at RT under nitrogen atmosphere. The reaction mixture was stirred at RT for 10 minutes and then heated at 75° C. for 3 h under nitrogen atmosphere. An additional amount of n-octadecyl isocyanate (0.032 g, 0.11 mmol) was added to the reaction mixture and the reaction was heated for an additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-50% EtOAc) to yield the target compound (45 mg) as an off white solid. $^1$H NMR (400 MHz, DMSO-d6) δ 9.51 (s, 1H), 9.21 (d, J=2.0 Hz, 1H), 9.15 (s, 1H), 8.60 (s, 1H), 7.83 (d, J=5.7 Hz, 1H), 7.71 (d, J=7.7 Hz, 1H), 7.62 (s, 1H), 7.55 (t, J=7.9 Hz, 1H), 7.22 (d, J=8.1 Hz, 1H), 3.08 (d, J=6.8 Hz, 2H), 0.81-1.48 (m, 35H).

Synthesis of 3-(5-(1,3,4-oxadiazol-2-yl)pyridin-3-yl) phenyl (cyclohexylmethyl)carbamate (Example-134)

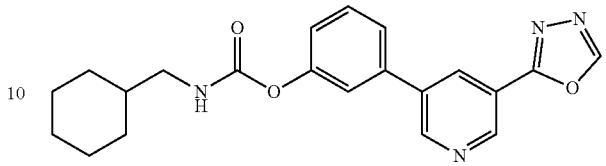

To a suspension of 3-(5-(1,3,4-oxadiazol-2-yl)pyridin-3-yl)phenol (0.1 g, 0.42 mmol) in anhydrous acetonitrile (3 mL) was added TEA (0.07 mL, 0.5 mmol) and cyclohexanemethyl isocyanate (0.06 g, 0.42 mmol) at RT under nitrogen atmosphere. The reaction mixture was stirred at RT for 10 minutes and then heated at 75° C. for 3 h under nitrogen atmosphere. An additional amount of cyclohexanemethyl isocyanate (0.02 mL, 0.14 mmol) was added to the reaction mixture and the reaction was heated for an additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-60% EtOAc) to yield the target compound (60 mg) as an off white solid. $^1$H-NMR (400 MHz, DMSO-d6) δ 9.51 (d, J=1.1 Hz, 1H), 9.21 (d, J=2.0 Hz, 1H), 9.16 (d, J=2.2 Hz, 1H), 8.61 (t, J=2.1 Hz, 1H), 7.86 (t, J=6.0 Hz, 1H), 7.70 (d, J=7.6 Hz, 1H), 7.63 (d, J=2.0 Hz, 1H), 7.55 (t, J=7.9 Hz, 1H), 7.19-7.26 (m, 1H), 2.94 (t, J=6.4 Hz, 2H), 1.99 (s, 1H), 1.11-1.86 (m, 10H)

Synthesis of 3-(5-(1,3,4-oxadiazol-2-yl)pyridin-3-yl) phenyl benzylcarbamate (Example-135)

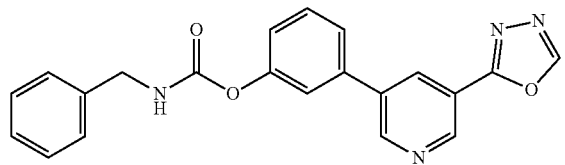 [SMILES: O=C(NCc1ccccc1)Oc1cccc(-c2cncc(-c3nnco3)c2)c1]

To a suspension of 3-(5-(1,3,4-oxadiazol-2-yl)pyridin-3-yl)phenol (0.1 g, 0.42 mmol) in anhydrous acetonitrile (3 mL) was added TEA (0.07 mL, 0.5 mmol) and benzyl isocyanate (0.056 g, 0.42 mmol) at RT under nitrogen atmosphere. The reaction mixture was stirred at RT for 10 minutes and then heated at 75° C. for 3 h under nitrogen atmosphere. An additional amount of benzyl isocyanate (0.02 g, 0.14 mmol) was added to the reaction mixture and the reaction was heated for additional 9 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-60% EtOAc) to yield the target compound (52 mg) as an off white solid. $^1$H-NMR (400 MHz, DMSO-d6) δ 9.53 (s, 1H), 9.22 (d, J=2.1 Hz, 1H), 9.18 (d, J=2.2 Hz, 1H), 8.61 (t, J=2.1 Hz, 1H), 7.93 (t, J=5.7 Hz, 1H), 7.73 (d, J=7.7 Hz, 1H), 7.68 (t, J=2.1 Hz, 1H), 7.58 (t, J=7.7 Hz, 1H), 7.12-7.38 (m, 5H), 3.82 (s, 2H).

Synthesis of 3-(5-(1,3,4-oxadiazol-2-yl)pyridine-3-yl)phenyl (3-phenylpropyl)carbamate (Example-136)

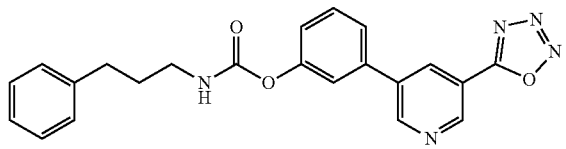 [SMILES: O=C(NCCCc1ccccc1)Oc1cccc(-c2cncc(-c3nnno3)c2)c1]

To a suspension of 3-(5-(1,3,4-oxadiazol-2-yl)pyridine-3-yl)phenol (0.08 g, 0.33 mmol) in anhydrous acetonitrile (2 mL) was added TEA (0.04 g, 0.4 mmol) and 3-phenylpropyl isocyanate (0.053 g, 0.42 mmol) at RT under nitrogen atmosphere. The reaction mixture was stirred at RT for 10 minutes and then heated at 75° C. for 3 h under nitrogen atmosphere. An additional amount of 3-phenylpropyl isocyanate (0.018 g, 0.11 mmol) was added to the reaction mixture and the reaction was heated for an additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 20-50% EtOAc) to yield the target compound (45 mg) as an off white solid. $^1$H NMR (400 MHz, DMSO-d6) δ 9.51 (s, 1H), 9.21 (d, J=2.0 Hz, 1H), 9.16 (d, J=2.2 Hz, 1H), 8.61 (t, J=2.1 Hz, 1H), 7.93 (t, J=5.7 Hz, 1H), 7.71 (d, J=7.7 Hz, 1H), 7.64 (t, J=2.0 Hz, 1H), 7.56 (t, J=7.9 Hz, 1H), 7.34-7.13 (m, 5H), 3.12 (q, J=6.6 Hz, 2H), 2.65 (t, J=7.7 Hz, 2H), 1.80 (p, J=7.4 Hz, 2H)

Synthesis of 3-(5-(1,3,4-oxadiazol-2-yl)pyridin-3-yl)phenyl cycloheptylcarbamate (Example-137)

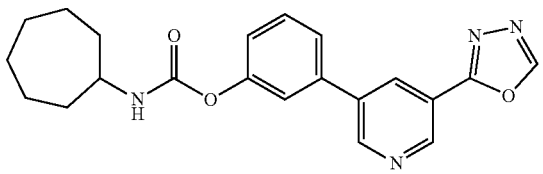 [SMILES: O=C(NC1CCCCCC1)Oc1cccc(-c2cncc(-c3nnco3)c2)c1]

To a suspension of 3-(5-(1,3,4-oxadiazol-2-yl)pyridin-3-yl)phenol (0.1 g, 0.42 mmol) in anhydrous acetonitrile (6 mL) was added TEA (0.07 mL, 0.5 mmol) and cycloheptyl isocyanate (0.05 g, 0.40 mmol) at RT under a nitrogen atmosphere. The reaction mixture was stirred at RT for 10 minutes and then heated at 75° C. for 3 h under a nitrogen atmosphere. An additional amount of cycloheptyl isocyanate (0.01 g, 0.14 mmol) was added to the reaction mixture and the reaction was heated for an additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-60% EtOAc) to yield a target compound (72% yield) as a white solid.

Synthesis of 3-(5-(1,3,4-oxadiazol-2-yl)pyridin-3-yl)phenyl cyclopentylcarbamate (Example-138)

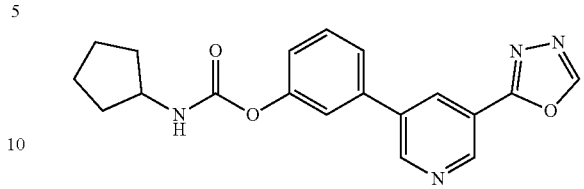

To a suspension of 3-(5-(1,3,4-oxadiazol-2-yl)pyridin-3-yl)phenol (0.1 g, 0.42 mmol) in anhydrous acetonitrile (3 mL) was added TEA (0.07 mL, 0.5 mmol) and cyclopentyl isocyanate (0.046 mL, 0.42 mmol) at RT under nitrogen atmosphere. The reaction mixture was stirred at RT for 10 minutes and then heated at 75° C. for 3 h under nitrogen atmosphere. An additional amount of cyclopentyl isocyanate (0.015 mL, 0.14 mmol) was added to the reaction mixture and the reaction was heated for an additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-50% EtOAc) to yield the target compound (45 mg) as an off white solid. $^1$H-NMR (400 MHz, DMSO-d6): δ 9.51 (s, 1H), 9.21 (s, 1H), 9.15 (s, 1H), 8.61 (t, J=2.1 Hz, 1H), 7.88 (d, J=8.1 Hz, 1H), 7.70 (d, J=8.1 Hz, 1H), 7.64 (s, 1H), 7.55 (t, J=8.1 Hz, 1H), 7.24 (d, J=8.1 Hz, 1H), 3.18 (s, 1H), 1.86-1.11 (m, 8H).

Synthesis of 3-(5-(1,3,4-oxadiazol-2-yl)pyridin-3-yl)phenyl cyclohexylcarbamate (Example-139)

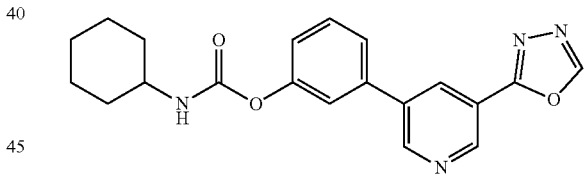

To a suspension of 3-(5-(1,3,4-oxadiazol-2-yl)pyridine-3-yl)phenol (0.11 g, 0.46 mmol) in anhydrous acetonitrile (3 mL) was added TEA (0.076 mL, 0.55 mmol) and cyclohexyl isocyanate (0.06 mL, 0.46 mmol) at RT under nitrogen atmosphere. The reaction mixture was stirred at RT for 10 minutes and then heated at 75° C. for 3 h under nitrogen atmosphere. An additional amount of cyclohexyl isocyanate (0.02 mL, 0.15 mmol) was added to the reaction mixture and the reaction was heated for an additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-60% EtOAc) to yield the target compound (66 mg) as an off white solid. $^1$H-NMR (400 MHz, DMSO-d6) δ 9.51 (s, 1H), 9.21 (s, 1H), 9.15 (s, 1H), 8.60 (t, J=2.1 Hz, 1H), 7.82 (d, J=8.1 Hz, 1H), 7.70 (d, J=8.1 Hz, 1H), 7.63 (s, 1H), 7.55 (t, J=8.1 Hz, 1H), 7.22 (d, J=8.1 Hz, 1H), 3.3 (s, 1H), 1.86-1.11 (m, 10H)

Synthesis of 3-(5-(1,3,4-oxadiazol-2-yl)pyridin-3-yl)phenyl naphthalen-1-ylcarbamate (Example-140)

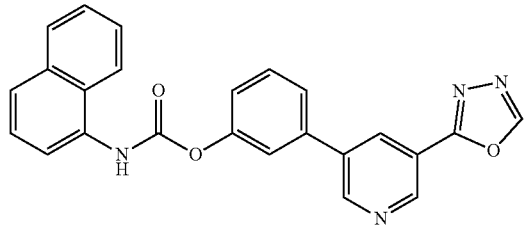 [SMILES: O=C(Nc1cccc2ccccc12)Oc1cccc(-c2cncc(-c3nnco3)c2)c1]

To a suspension of 3-(5-(1,3,4-oxadiazol-2-yl)pyridin-3-yl)phenol (0.1 g, 0.42 mmol) in anhydrous acetonitrile (3 mL) was added TEA (0.07 mL, 0.5 mmol) and 1-naphthyl isocyanate (0.07 g, 0.42 mmol) at RT under nitrogen atmosphere. The reaction mixture was stirred at RT for 10 minutes and then heated at 75° C. for 3 h under nitrogen atmosphere. An additional amount of 1-naphthyl isocyanate (0.023 g, 0.14 mmol) was added to the reaction mixture and the reaction was heated for an additional 12 h. The reaction progress was monitored by TLC, after completion the reaction mixture was cooled to RT and then the solvent was evaporated under reduced pressure. The crude product was purified by flash column chromatography on silica gel eluting with DCM/MeOH (gradient 2-8% MeOH) to yield the target compound (55 mg) as an off white solid. $^1$H NMR (400 MHz, DMSO-d6) δ 9.74 (s, 1H), 9.50 (d, J=1.2 Hz, 1H), 9.19 (d, J=2.0 Hz, 1H), 9.08 (d, J=2.2 Hz, 1H), 8.51 (t, J=2.1 Hz, 1H), 8.05 (d, J=8.2 Hz, 1H), 7.78-7.69 (m, 1H), 7.44-7.32 (m, 3H), 7.23-7.15 (m, 2H), 7.07 (d, J=8.1 Hz, 1H), 6.94-6.86 (m, 1H), 6.70-6.63 (m, 1H).

Synthesis of piperidine-1-carbonyl chloride

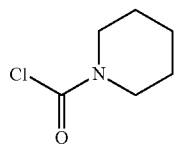

To a stirred solution of Diphosgene (0.47 g, 2.4 mmol) in DCM (2 mL) at 0-5° C. under nitrogen atmosphere was added the solution of cyclohexanamine (0.2 g, 2.0 mmol) in DCM dropwise. N,N-diisopropylethylamine (DIPEA) (0.62 mL, 3.53 mmol) was added, and the resulting mixture was stirred at 0-5° C. for 20 minutes. and then stirred at RT for 20 minutes. After completion of the reaction (monitored by TLC), the reaction mixture was quenched with aq. 1.5N hydrochloric acid solution and extracted with dichloromethane. The combined organic layers were washed with water, brine and concentrated to give piperidine-1-carbonyl chloride which was used for the next step without further purification.

Synthesis of 3-(5-(1,3,4-oxadiazol-2-yl)pyridin-3-yl)phenyl piperidine-1-carboxylate (Example-141)

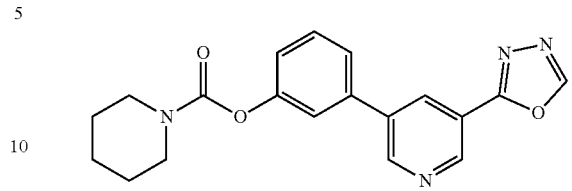

To a stirred solution of 3-(5-(1,3,4-oxadiazol-2-yl)pyridin-3-yl)phenol (0.1 g, 0.42 mmol) in acetonitrile (2 mL) at 0-5° C. under nitrogen atmosphere was added piperidine-1-carbonyl chloride (0.074 g, 0.50 mmol) and TEA (0.07 mL, 0.54 mmol). The resulting mixture was stirred at 75° C. for 16 h. After completion of the reaction (monitored by LCMS), the reaction mixture was concentrated to a residue. The residue was purified by preparative HPLC (0.10% FA) to yield the target compound (68 mg) as an off white solid. $^1$H NMR (400 MHz, DMSO-d6) δ 9.51 (s, 1H), 9.21 (d, J=2.00 Hz, 1H), 9.16 (d, J=2.40 Hz, 1H), 8.62 (t, J=2.00 Hz, 1H), 7.74-7.72 (m, 1H), 7.67 (t, J=2.00 Hz, 1H), 7.56 (t, J=8.00 Hz, 1H), 7.27-7.24 (m, 1H), 3.6 (bs, 2H), 3.43 (bs, 2H) 1.61-1.57 (m, 6H); MS (ES+APCI) m/z 351.4 (M+1).

Synthesis of 2-methylpiperidine-1-carbonyl chloride

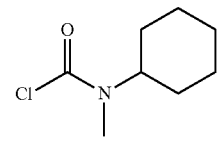

To a stirred solution of diphosgene (0.48 g, 2.42 mmol) in DCM (2 mL) at 0-5° C. under nitrogen atmosphere was added the solution of 2-methylpiperidine (0.2 g, 2.02 mmol) in DCM dropwise. DIPEA (0.7 ml, 4.03 mmol) was added, and the resulting mixture was stirred at 0-5° C. for 20 minutes. and then stirred at RT for 20 minutes. After completion of the reaction (monitored by TLC), the reaction mixture was quenched with aq. 1.5N hydrochloric acid solution and extracted with dichloromethane. The combined organic layers were washed with water, brine and concentrated to give 2-methylpiperidine-1-carbonyl chloride which was used for the next step without further purification.

Synthesis of cyclohexyl(methyl)carbamic chloride

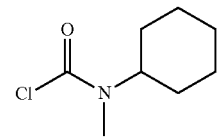

To a stirred solution of Diphosgene (0.42 g, 2.12 mmol) in DCM (2 mL) at 0-5° C. under nitrogen atmosphere was added the solution of N-methylcyclohexanamine (0.2 g, 1.77 mmol) in DCM dropwise. DIPEA (0.62 mL, 3.53 mmol) was added, and the resulting mixture was stirred at 0-5° C.

for 20 minutes. and then stirred at RT for 20 minutes. After completion of the reaction (monitored by TLC), the reaction mixture was quenched with aq. 1.5N hydrochloric acid solution and extracted with dichloromethane. The combined organic layers were washed with water, brine and concentrated to give cyclohexyl(methyl)carbamic chloride which was used for the next step without further purification.

Synthesis of 3-(5-(1,3,4-oxadiazol-2-yl)pyridin-3-yl) phenyl cyclohexyl(methyl)carbamate (Example-142)

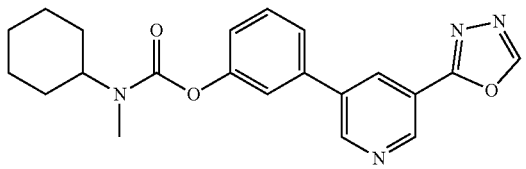 [SMILES: CN(C(=O)Oc1cccc(-c2cncc(-c3nnco3)c2)c1)C1CCCCC1]

To a stirred solution of 3-(5-(1,3,4-oxadiazol-2-yl)pyridin-3-yl)phenol (0.1 g, 0.42 mmol) in acetonitrile (2 mL) at 0-5° C. under nitrogen atmosphere was added cyclohexyl (methyl)carbamic chloride (0.15 g, 0.84 mmol) and TEA (0.2 mL, 1.05 mmol). The resulting mixture was stirred at 75° C. for 16 h. After completion of the reaction (monitored by LCMS), the reaction mixture was concentrated to a residue. The residue was purified by preparative HPLC (0.1% FA) to yield the target compound (49 mg) as an off white solid. $^1$H NMR (400 MHz, DMSO-d6) δ 9.51 (s, 1H), 9.21 (d, J=2.00 Hz, 1H), 9.16 (d, J=2.40 Hz, 1H), 8.62 (t, J=2.40 Hz, 1H), 7.74-7.66 (m, 2H), 7.56 (t, J=8.00 Hz, 1H), 7.25 (d, J=8.00 Hz, 1H), 3.99-3.87 (m, 1H), 2.96-2.84 (m, 3H), 1.81-1.79 (m, 3H), 1.69-1.49 (m, 4H), 1.36-1.30 (m, 2H), 1.17-1.03 (m, 1H);
MS (ES+APCI) m/z 379.3 (M+1).

Synthesis of 3-(5-(1,3,4-oxadiazol-2-yl)pyridin-3-yl) phenyl 2-methylpiperidine-1-carboxylate (Example-143)

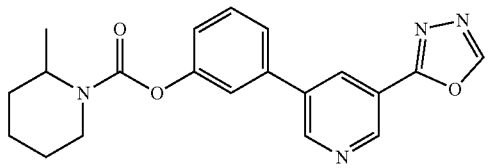 [SMILES: CC1CCCCN1C(=O)Oc1cccc(-c2cncc(-c3nnco3)c2)c1]

To a stirred solution of 3-(5-(1,3,4-oxadiazol-2-yl)pyridin-3-yl)phenol (0.12 g, 0.50 mmol) in acetonitrile (2 mL) at 0-5° C. under nitrogen atmosphere was added azepane-1-carbonyl chloride (0.16 g, 1.00 mmol) and TEA (0.09 mL, 0.65 mmol). The resulting mixture was stirred at 75° C. for 16 h. After completion of the reaction (monitored by LCMS), the reaction mixture was concentrated to a residue. The residue was purified by preparative HPLC (0.10% FA) to yield the target compound (45 mg) as an off white solid. $^1$H NMR (400 MHz, DMSO-d6) δ 9.51 (s, 1H), 9.21 (d, J=2.00 Hz, 1H), 9.16 (d, J=2.40 Hz, 1H), 8.62 (t, J=2.00 Hz, 1H), 7.76-7.74 (m, 1H), 7.71 (t, J=2.00 Hz, 1H), 7.58 (t, J=7.60 Hz, 1H), 7.30-7.27 (m, 1H), 3.68-3.64 (m, 6H); MS (ES+APCI) m/z 365.3 (M+1).

Synthesis of cycloheptyl(methyl)carbamic chloride

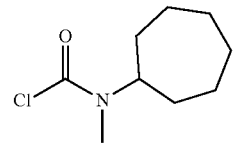

To a stirred solution of diphosgene (0.37 g, 1.89 mmol) in DCM (2 mL) at 0-5° C. under nitrogen atmosphere was added the solution of N-methylcycloheptanamine (0.2 g, 1.57 mmol) in DCM dropwise. DIPEA (0.55 mL, 3.14 mmol) was added, and the resulting mixture was stirred at 0-5° C. for 20 minutes. and then stirred at RT for 20 minutes. After completion of the reaction (monitored by TLC), the reaction mixture was quenched with aq. 1.5N hydrochloric acid solution and extracted with dichloromethane. The combined organic layers were washed with water, brine and concentrated to give cycloheptyl(methyl)carbamic chloride which was used for next step without further purification.

Synthesis of 3-(5-(1,3,4-oxadiazol-2-yl)pyridin-3-yl) phenyl cycloheptyl(methyl)carbamate (Example-144)

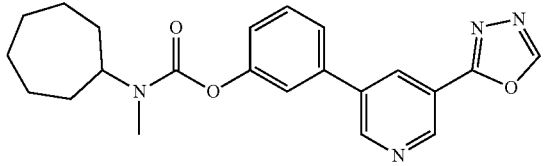 [SMILES: CN(C(=O)Oc1cccc(-c2cncc(-c3nnco3)c2)c1)C1CCCCCC1]

To a stirred solution of 3-(5-(1,3,4-oxadiazol-2-yl)pyridin-3-yl)phenol (0.09 g, 0.38 mmol) in acetonitrile (2 mL) at 0-5° C. under nitrogen atmosphere was added cycloheptyl (methyl)carbamic chloride (0.14 g, 0.75 mmol) and TEA (0.06 mL, 0.49 mmol). The resulting mixture was stirred at 75° C. for 16 h. After completion of the reaction (monitored by LCMS), the reaction mixture was concentrated to a residue. The residue was purified by preparative HPLC (0.1% FA) to yield the target compound (85 mg) as an off white solid. $^1$H NMR (400 MHz, DMSO-d6) δ 9.51 (s, 1H), 9.21 (d, J=2.00 Hz, 1H), 9.16 (d, J=2.40 Hz, 1H), 8.62 (t, J=2.00 Hz, 1H), 7.72 (d, J=8.00 Hz, 1H), 7.66 (s, 1H), 7.56 (t, J=8.00 Hz, 1H), 7.25 (d, J=8.00 Hz, 1H), 4.14-4.01 (m, 1H), 2.96-2.83 (m, 3H), 1.88-1.70 (m, 6H), 1.57-1.43 (m, 6H); MS (ES+APCI) m/z 379.3 (M+1).

Synthesis of cycloheptylcarbamic chloride

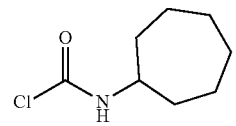 [SMILES: O=C(Cl)NC1CCCCCC1]

To a stirred solution of Diphosgene (0.41 g, 2.12 mmol) in DCM (2 mL) at 0-5° C. under nitrogen atmosphere was added the solution of cycloheptanamine (0.2 g, 1.76 mmol)

in DCM dropwise. DIPEA (0.55 mL, 3.14 mmol) was added, and the resulting mixture was stirred at 0-5° C. for 20 minutes. and then stirred at RT for 20 minutes. After completion of the reaction (monitored by TLC), the reaction mixture was quenched with aq. 1.5N hydrochloric acid solution and extracted with dichloromethane. The combined organic layers were washed with water, brine and concentrated to give cycloheptylcarbamic chloride which was used for next step without further purification.

Synthesis of 3-(5-(1,3,4-oxadiazol-2-yl)pyridin-3-yl) phenyl azepane-1-carboxylate

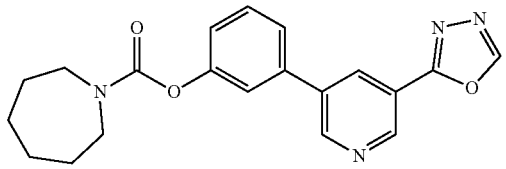 [SMILES: O=C(Oc1cccc(-c2cncc(-c3nnco3)c2)c1)N1CCCCCC1]

To a stirred solution of 3-(5-(1,3,4-oxadiazol-2-yl)pyridin-3-yl)phenol (0.1 g, 0.42 mmol) in acetonitrile (2 mL) at 0-5° C. under nitrogen atmosphere was added azepane-1-carbonyl chloride (0.08 g, 0.50 mmol) and TEA (0.07 mL, 0.54 mmol). The resulting mixture was stirred at 75° C. for 16 h. After completion of the reaction (monitored by LCMS), the reaction mixture was concentrated to a residue. The residue was purified by preparative HPLC (0.10% FA) to yield the target compound (22 mg) as an off white solid. $^1$H NMR (400 MHz, DMSO-d6) δ 9.51 (s, 1H), 9.21 (d, J=2.00 Hz, 1H), 9.16 (d, J=2.40 Hz, 1H), 8.62 (t, J=2.00 Hz, 1H), 7.73 (t, J=7.60 Hz, 1H), 7.66 (t, J=2.00 Hz, 1H), 7.57 (t, J=7.60 Hz, 1H), 7.27-7.24 (m, 1H), 3.59 (t, J=6.00 Hz, 2H), 3.45 (t, J=6.00 Hz, 2H), 1.78 (t, J=5.60 Hz, 2H), 1.70 (t, J=5.60 Hz, 2H), 1.61-1.57 (m, 4H); MS (ES+APCI) m/z 365.3 (M+1).

Synthesis of 2-azaspiro[3.3]heptane-2-carbonyl chloride

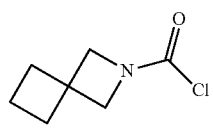

To a stirred solution of diphosgene (0.40 g, 2.01 mmol) in DCM (2 mL) at 0-5° C. under nitrogen atmosphere was added the solution of 2-azaspiro[3.3]heptane (0.16 g, 1.67 mmol) in DCM dropwise. DIPEA (0.58 mL, 3.34 mmol) was added, and the resulting mixture was stirred at 0-5° C. for 20 minutes. and then stirred at RT for 20 minutes. After completion of the reaction (monitored by TLC), the reaction mixture was quenched with aq. 1.5N hydrochloric acid solution and extracted with dichloromethane. The combined organic layers were washed with water, brine and concentrated to give 2-azaspiro[3.3]heptane-2-carbonyl chloride which was used for the next step without further purification.

Synthesis of 3-(5-(1,3,4-oxadiazol-2-yl)pyridin-3-yl) phenyl 2-azaspiro[3.3]heptane-2-carboxylate (Example-146)

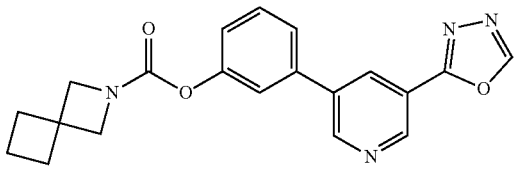 [SMILES: O=C(Oc1cccc(-c2cncc(-c3nnco3)c2)c1)N1CC2(CCC2)C1]

To a stirred solution of 3-(5-(1,3,4-oxadiazol-2-yl)pyridin-3-yl)phenol (0.1 g, 0.42 mmol) in acetonitrile (2 mL) at 0-5° C. under nitrogen atmosphere was added 2-azaspiro [3.3]heptane-2-carbonyl chloride (0.13 g, 0.84 mmol) and TEA (0.07 mL, 0.54 mmol). The resulting mixture was stirred at 75° C. for 16 h. After completion of the reaction (monitored by LCMS), the reaction mixture was concentrated to a residue. The residue was purified by preparative HPLC (0.1% FA) to yield the target compound (60 mg) as an off white solid. $^1$H NMR (400 MHz, DMSO-d6) δ 9.51 (s, 1H), 9.21 (d, J=2.00 Hz, 1H), 9.16 (d, J=2.40 Hz, 1H), 8.61 (t, J=2.00 Hz, 1H), 7.74-7.72 (m, 1H), 7.66 (t, J=2.00 Hz, 1H), 7.56 (t, J=8.00 Hz, 1H), 7.26-7.23 (m, 1H), 4.17 (bs, 2H), 3.98 (bs, 2H), 2.20 (t, J=7.60 Hz, 4H), 1.84-1.77 (m, 2H); MS (ES+APCI) m/z 363.2 (M+1).

Synthesis of 2-isocyanatospiro[3.3]heptane

To a stirred solution of spiro[3.3]heptan-2-amine hydrochloride (0.12 g, 0.81 mmol) in DCM (2 mL) at 0-5° C. under nitrogen atmosphere was added sodium bicarbonate (0.7 g, 8.33 mmol) and triphosgene (0.024 g, 0.08 mmol). The resulting mixture was stirred at 0-5° C. for 20 minutes. and then stirred at RT for 20 minutes. After completion of the reaction (monitored by TLC), the reaction mixture was quenched with aq. 1.5N hydrochloric acid solution and extracted with dichloromethane. The combined organic layers were washed with water, brine and concentrated to give 2-isocyanatospiro[3.3]heptane which was used for the next step without further purification.

Synthesis of 3-(5-(1,3,4-oxadiazol-2-yl)pyridin-3-yl) phenyl spiro[3.3]heptan-2-ylcarbamate (Example-147)

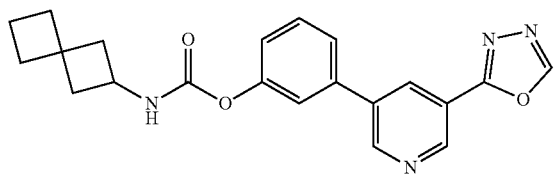 [SMILES: O=C(NC1CC2(CCC2)C1)Oc1cccc(-c2cncc(-c3nnco3)c2)c1]

To a stirred solution of 3-(5-(1,3,4-oxadiazol-2-yl)pyridin-3-yl)phenol (0.1 g, 0.42 mmol) in acetonitrile (2 mL) at 0-5° C. under nitrogen atmosphere was added 2-isocyanatospiro[3.3]heptane (0.11 g, 0.84 mmol) and TEA (0.07 mL, 0.54 mmol). The resulting mixture was stirred at 75° C. for 16 h. After completion of the reaction (monitored by LCMS), the reaction mixture was concentrated to a residue. The residue was purified by preparative HPLC (0.1% FA) to yield the target compound (13 mg) as an off white solid. ¹H NMR (400 MHz, DMSO-d6) δ 9.51 (s, 1H), 9.21 (d, J=2.00 Hz, 1H), 9.15 (d, J=2.40 Hz, 1H), 8.60 (t, J=2.00 Hz, 1H), 8.08 (d, J=8.00 Hz, 1H), 7.70 (d, J=7.60 Hz, 1H), 7.63 (t, J=2.00 Hz, 1H), 1.00 (t, J=8.00 Hz, 1H), 7.23-7.20 (m, 1H), 3.89 (q, J=8.40 Hz, 1H), 2.34-2.29 (m, 2H), 2.03-1.91 (m, 6H), 1.89-1.83 (m, 2H); MS (ES+APCI) m/z 377.3 (M+1).

Synthesis of 3-azabicyclo[3.1.0]hexane-3-carbonyl chloride

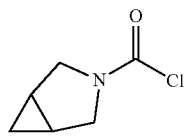

To a stirred solution of diphosgene (0.24 mL, 2.01 mmol) in DCM (2 mL) at 0-5° C. under nitrogen atmosphere was added 3-azabicyclo[3.1.0]hexane (0.2 g, 1.67 mmol) and DIPEA (0.58 mL, 3.34 mmol). The resulting mixture was stirred at 0-5° C. for 20 minutes. and then stirred at RT for 20 minutes. After completion of the reaction (monitored by TLC), the reaction mixture was quenched with aq. 1.5N hydrochloric acid solution and extracted with dichloromethane. The combined organic layers were washed with water, brine and concentrated to give 3-azabicyclo[3.1.0]hexane-3-carbonyl chloride which was used for the next step without further purification.

3-(5-(1,3,4-oxadiazol-2-yl)pyridin-3-yl)phenyl 3-azabicyclo[3.1.0]hexane-3-carboxylate (Example-148)

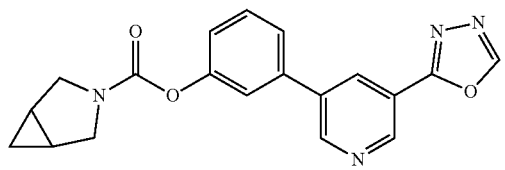 [SMILES: O=C(Oc1cccc(-c2cncc(-c3nnco3)c2)c1)N1CC2CC2C1]

To a stirred solution of 3-(5-(1,3,4-oxadiazol-2-yl)pyridin-3-yl)phenol (0.1 g, 0.42 mmol) in acetonitrile (2 mL) at 0-5° C. under nitrogen atmosphere was added 3-azabicyclo[3.1.0]hexane-3-carbonyl chloride (0.12 g, 0.84 mmol) and TEA (0.07 mL, 0.54 mmol). The resulting mixture was stirred at 75° C. for 16 h. After completion of the reaction (monitored by LCMS), the reaction mixture was concentrated to a residue. The residue was purified by preparative HPLC (0.1% FA) to yield the target compound (12 mg) as gummy solid. ¹H NMR (400 MHz, DMSO-d6) δ 9.51 (s, 1H), 9.21 (d, J=2.00 Hz, 1H), 9.16 (d, J=2.40 Hz, 1H), 8.61 (t, J=2.00 Hz, 1H), 7.74-7.72 (m, 1H), 7.67 (t, J=2.00 Hz, 1H), 7.56 (t, J=8.00 Hz, 1H), 7.27-7.24 (m, 1H), 3.75-3.72 (m, 2H), 3.52 (m, 2H), 1.67-1.59 (m, 2H), 0.80-0.75 (m, 1H), 0.28-0.25 (m, 1H); MS (ES+APCI) m/z 349.3 (M+1).

Synthesis of hexahydrocyclopenta[c]pyrrole-2(1H)-carbonyl chloride

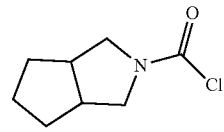 [SMILES: O=C(Cl)N1CC2CCCC2C1]

To a stirred solution of Triphosgene (0.40 g, 1.34 mmol) in DCM (2 mL) at 0-5° C. under nitrogen atmosphere was added DIPEA (0.58 mL, 3.34 mmol) and octahydrocyclopenta[c]pyrrole (0.19 g, 1.67 mmol) was added, and the resulting mixture was stirred at 0-5° C. for 20 minutes. and then stirred at RT for 20 minutes. After completion of the reaction (monitored by TLC), the reaction mixture was quenched with aq. 1.5N hydrochloric acid solution and extracted with dichloromethane. The combined organic layers were washed with water, brine and concentrated to give hexahydrocyclopenta[c]pyrrole-2(1H)-carbonyl chloride which was used for the next step without further purification.

Synthesis of 3-(5-(1,3,4-oxadiazol-2-yl)pyridin-3-yl) phenyl hexahydrocyclopenta[c]pyrrole-2(1H)-carboxylate (Example-149)

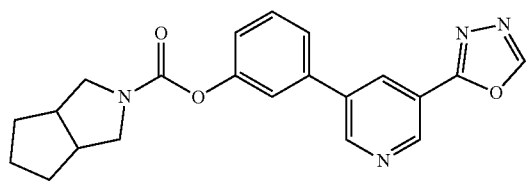 [SMILES: O=C(Oc1cccc(-c2cncc(-c3nnco3)c2)c1)N1CC2CCCC2C1]

To a stirred solution of 3-(5-(1,3,4-oxadiazol-2-yl)pyridin-3-yl)phenol (0.1 g, 0.42 mmol) in acetonitrile (2 mL) at 0-5° C. under nitrogen atmosphere was added hexahydrocyclopenta[c]pyrrole-2(1H)-carbonyl chloride (0.15 g, 0.84 mmol) and TEA (0.07 mL, 0.54 mmol). The resulting mixture was stirred at 75° C. for 16 h. After completion of the reaction (monitored by LCMS), the reaction mixture was concentrated to a residue. The residue was purified by preparative HPLC (0.1% FA) to yield the target compound (55 mg) as an off white solid. ¹H NMR (400 MHz, DMSO-d6) δ 9.51 (s, 1H), 9.21 (d, J=2.00 Hz, 1H), 9.16 (d, J=2.40 Hz, 1H), 8.61 (t, J=2.00 Hz, 1H), 7.73 (t, J=8.00 Hz, 1H), 7.67 (t, J=2.00 Hz, 1H), 7.56 (t, J=8.00 Hz, 1H), 7.27-7.25 (m, 1H), 3.79 (t, J=8.00 Hz, 1H), 3.61 (q, J=8.40 Hz, 1H), 3.53 (m, 1H), 3.16 (q, J=4.40 Hz, 1H), 2.73-2.68 (m, 2H), 1.84-1.73 (m, 3H), 1.62-1.47 (m, 3H); MS (ES+APCI) m/z 377.3 (M+1).

Synthesis of 8-azabicyclo[3.2.1]octane-8-carbonyl chloride

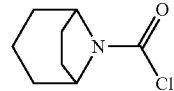

To a stirred solution of triphosgene (0.40 g, 1.35 mmol) in DCM (2 mL) at 0-5° C. under nitrogen atmosphere was added DIPEA (1.18 mL, 6.77 mmol) and 8-azabicyclo[3.2.1]octane hydrochloride (0.25 g, 1.70 mmol) was added and the resulting mixture was stirred at 0-5° C. for 20 minutes. and then stirred at RT for 20 minutes. After completion of the reaction (monitored by TLC), the reaction mixture was quenched with aq. 1.5N hydrochloric acid solution and extracted with dichloromethane. The combined organic layers were washed with water, brine and concentrated to give 8-azabicyclo[3.2.1]octane-8-carbonyl chloride which was used for the next step without further purification.

Synthesis of 3-(5-(1,3,4-oxadiazol-2-yl)pyridin-3-yl) phenyl 8-azabicyclo[3.2.1]octane-8-carboxylate (Example-150)

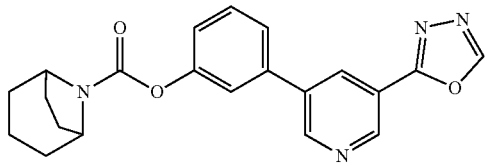 [SMILES: O=C(Oc1cccc(-c2cncc(-c3nnco3)c2)c1)N1C2CCCC1CC2]

To a stirred solution of 3-(5-(1,3,4-oxadiazol-2-yl)pyridin-3-yl)phenol (0.1 g, 0.42 mmol) in acetonitrile (2 mL) at 0-5° C. under nitrogen atmosphere was added 8-azabicyclo[3.2.1]octane-8-carbonyl chloride (0.15 g, 0.84 mmol) and TEA (0.07 mL, 0.54 mmol). The resulting mixture was stirred at 75° C. for 16 h. After completion of the reaction (monitored by LCMS), the reaction mixture was concentrated to a residue. The residue was purified by preparative HPLC (0.1% FA) to yield the target compound (55 mg) as an off white solid. $^1$H NMR (400 MHz, DMSO-d6) δ 9.51 (s, 1H), 9.21 (d, J=2.00 Hz, 1H), 9.16 (d, J=2.40 Hz, 1H), 8.61 (t, J=2.00 Hz, 1H), 7.74-7.72 (m, 1H), 7.67 (t, J=2.00 Hz, 1H), 7.56 (t, J=8.00 Hz, 1H), 7.29-7.26 (m, 1H), 4.39 (d, J=4.80 Hz, 1H), 4.18 (d, J=6.40 Hz, 1H), 2.08-1.93 (m, 2H), 1.85-1.73 (m, 5H), 1.57-1.47 (m, 3H); MS (ES+APCI) m/z 377.3 (M+1).

Synthesis of morpholine-4-carbonyl chloride

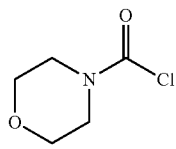

To a stirred solution of Phosgene (1.0 mL, 2.39 mmol, 20% in toluene) in DCM (2 mL) at 0-5° C. under nitrogen atmosphere was added DIPEA (0.60 mL, 3.43 mmol) and morpholine (0.19 g, 1.71 mmol) was added and the resulting mixture was stirred at 0-5° C. for 20 minutes. and then stirred at RT for 20 minutes. After completion of the reaction (monitored by TLC), the reaction mixture was quenched with aq. 1.5N hydrochloric acid solution and extracted with dichloromethane. The combined organic layers were washed with water, brine and concentrated to give morpholine-4-carbonyl chloride which was used for the next step without further purification.

Synthesis of 3-(5-(1,3,4-oxadiazol-2-yl)pyridin-3-yl) phenyl morpholine-4-carboxylate (Example-151)

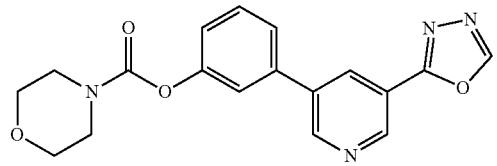 [SMILES: O=C(Oc1cccc(-c2cncc(-c3nnco3)c2)c1)N1CCOCC1]

To a stirred solution of 3-(5-(1,3,4-oxadiazol-2-yl)pyridin-3-yl)phenol (0.1 g, 0.42 mmol) in acetonitrile (2 mL) at 0-5° C. under nitrogen atmosphere was added morpholine-4-carbonyl chloride (0.08 g, 0.50 mmol) and TEA (0.07 mL, 0.54 mmol). The resulting mixture was stirred at 75° C. for 16 h. After completion of the reaction (monitored by LCMS), the reaction mixture was concentrated to a residue. The residue was purified by preparative HPLC (0.1% FA) to yield the target compound (65 mg) as an off white solid. $^1$H NMR (400 MHz, DMSO-d6) δ 9.51 (s, 1H), 9.21 (d, J=2.00 Hz, 1H), 9.16 (d, J=2.40 Hz, 1H), 8.62 (t, J=2.00 Hz, 1H), 7.74-70.72 (m, 1H), 7.67 (t, J=2.00 Hz, 1H), 7.56 (t, J=8.00 Hz, 1H), 7.27-7.24 (m, 1H), 1.61-1.57 (m, 6H); MS (ES+APCI) m/z 353.3 (M+1).

Synthesis of 2-oxa-6-azaspiro[3.3]heptane-6-carbonyl chloride

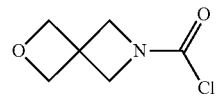

To a stirred solution of phosgene (1.0 mL, 2.57 mmol, 20% in toluene) in DCM (2 mL) at 0-5° C. under nitrogen atmosphere was added DIPEA (0.60 mL, 3.43 mmol) and 2-oxa-6-azaspiro[3.3]heptane (0.17 g, 1.71 mmol) was added and the resulting mixture was stirred at 0-5° C. for 20 minutes. and then stirred at RT for 20 minutes. After completion of the reaction (monitored by TLC), the reaction mixture was quenched with aq. 1.5N hydrochloric acid solution and extracted with dichloromethane. The combined organic layers were washed with water, brine and concentrated to give 2-oxa-6-azaspiro[3.3]heptane-6-carbonyl chloride which was used for the next step without further purification.

Synthesis of 3-(5-(1,3,4-oxadiazol-2-yl)pyridin-3-yl) phenyl 2-oxa-6-azaspiro[3.3]heptane-6-carboxylate (Example-152)

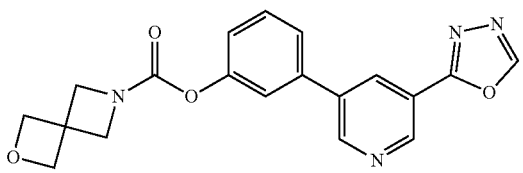 [SMILES: O=C(Oc1cccc(-c2cncc(-c3nnco3)c2)c1)N1CC2(COC2)C1]

To a stirred solution of 3-(5-(1,3,4-oxadiazol-2-yl)pyridin-3-yl)phenol (0.1 g, 0.42 mmol) in acetonitrile (2 mL) at 0-5° C. under nitrogen atmosphere was added 2-oxa-6-azaspiro[3.3]heptane-6-carbonyl chloride (0.14 g, 0.84 mmol) and TEA (0.07 mL, 0.54 mmol). The resulting mixture was stirred at 75° C. for 16 h. After completion of the reaction (monitored by LCMS), the reaction mixture was concentrated to a residue. The residue was purified by preparative HPLC (0.1% FA) to yield the target compound (69 mg) as yellow solid. $^1$H NMR (400 MHz, DMSO-d6) δ 9.51 (s, 1H), 9.21 (d, J=2.00 Hz, 1H), 9.15 (d, J=2.40 Hz, 1H), 8.60 (t, J=2.00 Hz, 1H), 7.73 (d, J=8.00 Hz, 1H), 7.64 (t, J=1.60 Hz, 1H), 7.56 (t, J=8.00 Hz, 1H), 7.24 (dd, J=1.60, 8.00 Hz, 1H), 4.72 (s, 4H), 4.38 (bs, 2H), 4.19 (bs, 2H); MS (ES+APCI) m/z 365.3 (M+1).

Synthesis of 2-oxa-7-azaspiro[3.5]nonane-7-carbonyl chloride

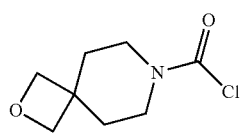 [SMILES: O=C(Cl)N1CCC2(CC1)COC2]

To a stirred solution of diphosgene (0.40 g, 2.01 mmol) in DCM (2 mL) at 0-5° C. under nitrogen atmosphere was added 2-oxa-7-azaspiro[3.5]nonane (0.21 g, 1.67 mmol) and DIPEA (0.58 mL, 3.34 mmol). The resulting mixture was stirred at 0-5° C. for 20 minutes. and then stirred at RT for 20 minutes. After completion of the reaction (monitored by TLC), the reaction mixture was quenched with aq. 1.5N hydrochloric acid solution and extracted with dichloromethane. The combined organic layers were washed with water, brine and concentrated to give 2-oxa-7-azaspiro[3.5]nonane-7-carbonyl chloride which was used for the next step without further purification.

Synthesis of 3-(5-(1,3,4-oxadiazol-2-yl)pyridin-3-yl) phenyl 2-oxa-7-azaspiro[3.5]nonane-7-carboxylate (Example-153)

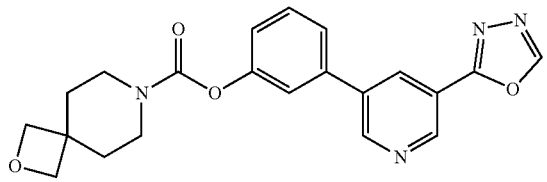 [SMILES: O=C(Oc1cccc(-c2cncc(-c3nnco3)c2)c1)N1CCC2(CC1)COC2]

To a stirred solution of 3-(5-(1,3,4-oxadiazol-2-yl)pyridin-3-yl)phenol (0.1 g, 0.42 mmol) in acetonitrile (2 mL) at 0-5° C. under nitrogen atmosphere was added 2-oxa-7-azaspiro[3.5]nonane-7-carbonyl chloride (0.16 g, 0.84 mmol) and TEA (0.07 mL, 0.54 mmol). The resulting mixture was stirred at 75° C. for 16 h. After completion of the reaction (monitored by LCMS), the reaction mixture was concentrated to a residue. The residue was purified by preparative HPLC (0.1% FA) to yield the target compound (16 mg) as an off white solid. $^1$H NMR (400 MHz, DMSO-d6) δ 9.51 (s, 1H), 9.21 (d, J=2.00 Hz, 1H), 9.16 (d, J=2.40 Hz, 1H), 8.61 (t, J=2.00 Hz, 1H), 7.73 (d, J=8.00 Hz, 1H), 7.67 (t, J=1.60 Hz, 1H), 7.56 (t, J=8.00 Hz, 1H), 7.27-7.24 (m, 1H), 4.37 (s, 4H), 3.56 (bs, 2H), 3.39 (bs, 2H), 1.89-1.86 (m, 4H); MS (ES+APCI) m/z 393.4 (M+1).

Synthesis of methyl(octyl)carbamic chloride

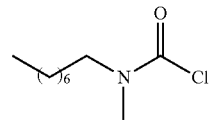

To a stirred solution of triphosgene (0.40 g, 1.35 mmol) in DCM (2 mL) at 0-5° C. under nitrogen atmosphere was added DIPEA (1.18 mL, 6.77 mmol) and N-methyloctan-1-amine (0.24 g, 1.70 mmol) was added, and the resulting mixture was stirred at 0-5° C. for 20 minutes. and then stirred at RT for 20 minutes. After completion of the reaction (monitored by TLC), the reaction mixture was quenched with aq. 1.5N hydrochloric acid solution and extracted with dichloromethane. The combined organic layers were washed with water, brine and concentrated to give dibutylcarbamic chloride which was used for the next step without further purification.

Synthesis of 3-(5-(1,3,4-oxadiazol-2-yl)pyridin-3-yl) phenyl heptyl(methyl)carbamate (Example-154)

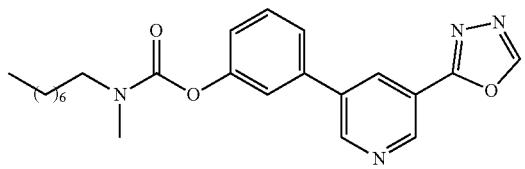

To a stirred solution of 3-(5-(1,3,4-oxadiazol-2-yl)pyridin-3-yl)phenol (0.1 g, 0.42 mmol) in acetonitrile (2 mL) at 0-5° C. under nitrogen atmosphere was added methyl(octyl)carbamic chloride (0.17 g, 0.84 mmol) and TEA (0.07 mL, 0.54 mmol). The resulting mixture was stirred at 75° C. for 16 h. After completion of the reaction (monitored by LCMS), the reaction mixture was concentrated to a residue. The crude product was purified by flash column chromatography on silica gel eluting with hexane/EtOAc (gradient 40-60% EtOAc) to yield the target compound (52 mg) as an off white solid. $^1$H NMR (400 MHz, DMSO-d6) δ 9.50 (s, 1H), 9.21 (d, J=2.0 Hz, 1H), 9.15 (d, J=2.2 Hz, 1H), 8.60 (t, J=2.3 Hz, 1H), 7.82 (t, J=5.7 Hz, 1H), 7.73-7.67 (m, 1H), 7.61 (t, J=2.1 Hz, 1H), 7.55 (t, J=7.9 Hz, 1H), 7.22 (dd, J=8.0, 2.3 Hz, 1H), 3.54 (s, 3H), 3.08 (q, J=6.6 Hz, 2H), 1.48-0.82 (m, 15H)

Synthesis of dibutylcarbamic chloride

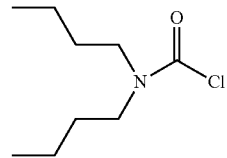

To a stirred solution of triphosgene (0.40 g, 1.35 mmol) in DCM (2 mL) at 0-5° C. under nitrogen atmosphere was added DIPEA (1.18 mL, 6.77 mmol) and dibutylamine (0.23 g, 1.70 mmol) was added and the resulting mixture was stirred at 0-5° C. for 20 minutes. and then stirred at RT for 20 minutes. After completion of the reaction (monitored by TLC), the reaction mixture was quenched with aq. 1.5N hydrochloric acid solution and extracted with dichloromethane. The combined organic layers were washed with water, brine and concentrated to give dibutylcarbamic chloride which was used for the next step without further purification.

Synthesis of 3-(5-(1,3,4-oxadiazol-2-yl)pyridin-3-yl) phenyl dibutylcarbamate (Example-155)

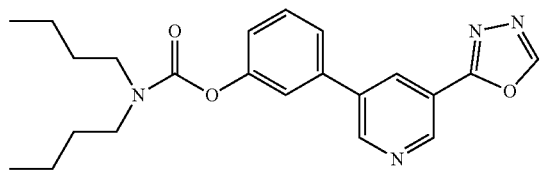 [SMILES: CCCCN(CCCC)C(=O)Oc1cccc(-c2cncc(-c3nnco3)c2)c1]

To a stirred solution of 3-(5-(1,3,4-oxadiazol-2-yl)pyridin-3-yl)phenol (0.1 g, 0.42 mmol) in acetonitrile (2 mL) at 0-5° C. under nitrogen atmosphere was added dibutylcarbamic chloride (0.16 g, 0.84 mmol) and TEA (0.07 mL, 0.54 mmol). The resulting mixture was stirred at 75° C. for 16 h. After completion of the reaction (monitored by LCMS), the reaction mixture was concentrated to a residue. The crude product was purified by flash column chromatography on silica gel eluting with hexane/EtOAc (gradient 40-60% EtOAc) to yield the target compound (55 mg) as an off white solid. $^1$H NMR (400 MHz, DMSO-d6) δ 9.50 (s, 1H), 9.19 (dd, J=21.1, 2.1 Hz, 2H), 8.61 (t, J=2.2 Hz, 1H), 7.72 (ddd, J=7.8, 1.8, 1.0 Hz, 1H), 7.63 (t, J=2.0 Hz, 1H), 7.56 (t, J=7.9 Hz, 1H), 7.23 (ddd, J=8.1, 2.3, 1.0 Hz, 1H), 1.60 (dt, J=37.3, 7.4 Hz, 5H), 1.48-1.23 (m, 4H), 0.93 (dt, J=10.9, 7.3 Hz, 9H).

Synthesis of ethyl ethyl 5-(2-(benzyloxy)-5-hydroxyphenyl)nicotinate

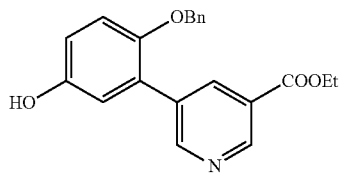 [SMILES: CCOC(=O)c1cncc(-c2cc(O)ccc2OCc2ccccc2)c1]

To a stirred solution of ethyl 5-(4,4,5,5-tetramethyl-1,3,2-dioxaborolan-2-yl)nicotinate (0.99 g, 3.58 mmol) in 1,4-dioxane (36 mL) and water (4 mL) was added 4-(benzyloxy)-3-bromophenol (1 g, 3.58 mmol) and K$_2$CO$_3$ (1.57 g, 14.78 mmol) at RT. The reaction mixture was degassed for 15 minutes then Pd(PPh$_3$)$_4$ (0.57 g, 0.493 mmol) was added. The reaction mixture was stirred at 80° C. for 5 h under nitrogen atmosphere. After completion of the reaction (monitored by TLC), the reaction mixture was cooled to RT and then the solvent was evaporated under reduced pressure. The residue was dissolved in ethyl acetate, washed with water followed by brine. The organic layer was dried over sodium sulfate then evaporated under reduced pressure. The residue was purified by automated normal-phase chromatography and eluted with ethyl acetate/petroleum ether to give ethyl 5-(2-(benzyloxy)-5-hydroxyphenyl)nicotinate (1.1 g) as an off white solid. MS (ES+APCI) m/z 350.3 (M+1).

Synthesis of 5-(2-(benzyloxy)-5-hydroxyphenyl)nicotinohydrazide

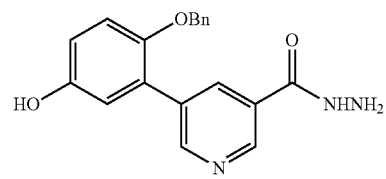 [SMILES: NNC(=O)c1cncc(-c2cc(O)ccc2OCc2ccccc2)c1]

To a stirred solution of ethyl 5-(2-(benzyloxy)-5-hydroxyphenyl)nicotinate (0.6 g, 1.72 mmol) in ethanol (12 mL) was added hydrazine hydrate (1.3 mL, 1.72 mmol) at RT. The reaction mixture was stirred at 60° C. for 15 h. After completion of the reaction (monitored by TLC), the resulting mixture was concentrated to a residue. The residue was co-evaporated with toluene to remove the residual water and repeated the toluene co-evaporation process for 3 to 4 times to give 5-(2-(benzyloxy)-5-hydroxyphenyl)nicotinohydrazide (550 mg), which was used for next step without purification. MS (ES+APCI) m/z 336.4 (M+1).

Synthesis of 3-(5-(1,3,4-oxadiazol-2-yl)pyridin-3-yl)-4-(benzyloxy)phenol

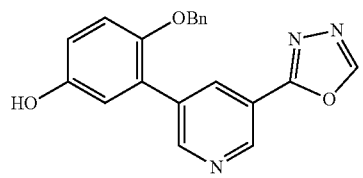

A suspension of 5-(2-(benzyloxy)-5-hydroxyphenyl)nicotinohydrazide (0.95 g, 2.83 mmol) in triethyl orthoformate (14 mL) was added p-toluenesulfonic acid (50 mg, 0.28 mmol) and stirred at 120° C. for 4 h under nitrogen atmosphere. After completion of the reaction (monitored by TLC), the reaction mixture was cooled to RT and concentrated to a residue. The residue was purified by automated normal-phase chromatography and eluted with ethyl acetate/petroleum ether to give 3-(5-(1,3,4-oxadiazol-2-yl)pyridin-3-yl)-5-(benzyloxy)phenol (450 mg). $^1$H NMR (400 MHz, DMSO-d6) δ 9.75 (s, 1H), 9.40 (s, 1H), 9.17 (d, J=2.43 Hz, 1H), 9.08 (d, J=2.80 Hz, 1H), 8.50 (t, J=2.80 Hz, 1H), 7.51-7.32 (m, 5H), 6.93-6.92 (m, 1H), 6.77 (t, J=2.40 Hz, 1H), 6.52 (t, J=2.80 Hz, 1H), 5.17 (s, 2H); MS (ES+APCI) m/z 346.3 (M+1).

Synthesis of 3-(5-(1,3,4-oxadiazol-2-yl)pyridin-3-yl)-4-(benzyloxy)phenyl heptylcarbamate

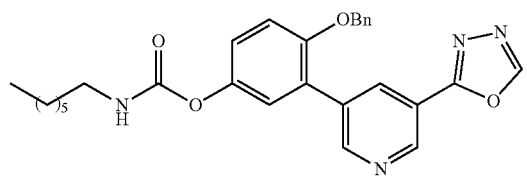

To a suspension of 3-(5-(1,3,4-oxadiazol-2-yl)pyridin-3-yl)-4-(benzyloxy)phenol (0.15 g, 0.44 mmol) in anhydrous acetonitrile (3 mL) was added TEA (0.06 mL, 0.44 mmol) and cyclohexyl isocyanate (0.06 g, 0.52 mmol) at RT under nitrogen atmosphere. The reaction mixture was stirred at RT for 10 minutes and then heated at 75° C. for 12 h under nitrogen atmosphere. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 30-40% EtOAc) to yield the target compound (120 mg) as an off white solid. $^1$H NMR (400 MHz, MeOD) δ 9.08-9.25 (m, 2H), 8.93 (d, J=2.1 Hz, 1H), 8.67 (d, J=2.2 Hz, 1H), 7.03-7.52 (m, 8H), 5.16 (s, 2H), 3.20 (t, J=7.1 Hz, 2H), 1.58 (p, J=7.2 Hz, 2H), 1.19-1.48 (m, 8H), 0.81-1.00 (m, 3H)

Synthesis of 3-(5-(1,3,4-oxadiazol-2-yl)pyridin-3-yl)-4-hydroxyphenyl heptylcarbamate (Example-156)

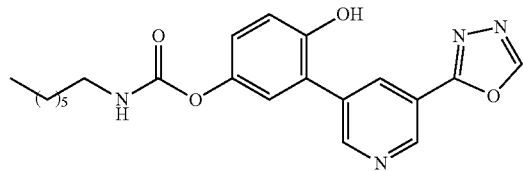

To a solution containing 3-(5-(1,3,4-oxadiazol-2-yl)pyridin-3-yl)-4-hydroxyphenyl heptylcarbamate (0.1, 0.26 mmol) in EtOH (1 mL), 10% Pd/C (0.01 mg) was added, and the reaction mixture was stirred at 50° C. under a hydrogen balloon over 2 h. The completion of the reaction was confirmed TLC, and the reaction mixture was filtered through a celite pad. The filtrate was then dried, and the resulting solid was recrystallized to obtain the pure white crystalline compound (55 mg) as an off white solid. $^1$H NMR (400 MHz, MeOD) δ 9.03 (d, J=20.9 Hz, 2H), 8.88 (d, J=2.1 Hz, 1H), 8.60 (t, J=2.1 Hz, 1H), 7.07 (d, J=2.7 Hz, 1H), 6.62-7.01 (m, 2H), 3.07 (t, J=7.1 Hz, 2H), 1.46 (p, J=7.4 Hz, 2H), 1.12-1.31 (m, 8H), 0.64-0.89 (m, 3H).

Synthesis of 3-(5-(1,3,4-oxadiazol-2-yl)pyridin-3-yl)-4-(benzyloxy)phenyl octylcarbamate

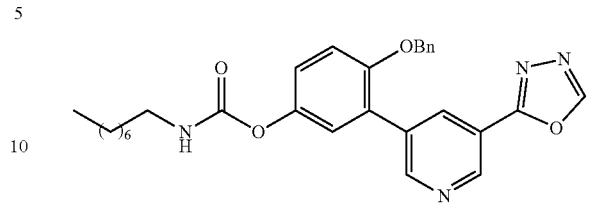

To a suspension of 3-(5-(1,3,4-oxadiazol-2-yl)pyridin-3-yl)-4-(benzyloxy)phenol (0.15 g, 0.44 mmol) in anhydrous acetonitrile (3 mL) was added TEA (0.06 mL, 0.44 mmol) and n-octyl isocyanate (0.08 g, 0.52 mmol) at RT under nitrogen atmosphere. The reaction mixture was stirred at RT for 10 minutes and then heated at 75° C. for 3 h under nitrogen atmosphere. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 30-40% EtOAc) to yield the target compound (125 mg) as an off white solid. $^1$H NMR (400 MHz, MeOD) δ 9.04-9.35 (m, 2H), 8.92 (d, J=2.1 Hz, 1H), 8.66 (t, J=2.1 Hz, 1H), 6.99-7.58 (m, 8H), 5.15 (s, 2H), 3.20 (t, J=7.1 Hz, 2H), 1.59 (h, J=7.8 Hz, 2H), 1.26-1.49 (m, 11H), 0.83-0.95 (m, 3H).

Synthesis of 3-(5-(1,3,4-oxadiazol-2-yl)pyridin-3-yl)-4-hydroxyphenyl octylcarbamate (Example-157)

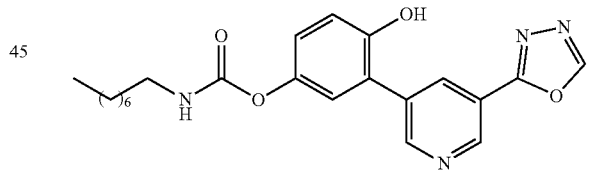

To a solution containing 3-(5-(1,3,4-oxadiazol-2-yl)pyridin-3-yl)-4-(benzyloxy)phenyl octylcarbamate (0.1 mg 0.24 mmol) in EtOH (1 ml), 10% Pd/C (0.01 mg) was added, and the reaction mixture was stirred at 50° C. under a hydrogen a balloon over 2 h. Completion of the reaction was confirmed by TLC, and the reaction mixture was filtered through a celite pad. The filtrate was then dried, and the resulting solid was recrystallized to obtain the pure crystalline compound (65 mg). $^1$H NMR (400 MHz, CD3OD) δ 9.01-9.30 (m, 2H), 8.97 (d, J=2.1 Hz, 1H), 8.69 (t, J=2.1 Hz, 1H), 7.16 (d, J=2.8 Hz, 1H), 6.73-7.07 (m, 2H), 3.16 (t, J=7.1 Hz, 2H), 1.18-1.47 (m, 11H), 1.55 (p, J=7.1 Hz, 2H), 0.76-0.95 (m, 3H).

Synthesis of 3-(5-(1,3,4-oxadiazol-2-yl)pyridin-3-yl)-4-(benzyloxy)phenyl cyclohexylcarbamate

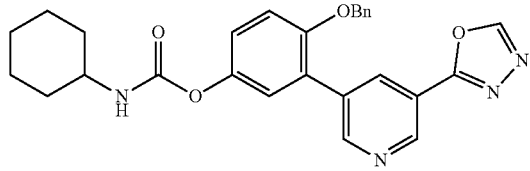 [SMILES: O=C(NC1CCCCC1)Oc1ccc(OCc2ccccc2)c(-c2cncc(-c3nnco3)c2)c1]

To a suspension of 3-(5-(1,3,4-oxadiazol-2-yl)pyridin-3-yl)-4-(benzyloxy)phenol (0.15 g, 0.44 mmol) in anhydrous acetonitrile (3 mL) was added TEA (0.06 mL, 0.44 mmol) and cyclohexyl isocyanate (0.06 g, 0.52 mmol) at RT under nitrogen atmosphere. The reaction mixture was stirred at RT for 10 minutes and then heated at 75° C. for 3 h under nitrogen atmosphere. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 30-40% EtOAc) to yield the target compound (95 mg) as an off white solid. $^1$H NMR (400 MHz, MeOD) δ 9.01-9.28 (m, 2H), 8.93 (d, J=2.1 Hz, 1H), 8.67 (t, J=2.1 Hz, 1H), 6.98-7.50 (m, 8H), 5.16 (s, 2H), 3.46 (td, J=10.5, 5.3 Hz, 1H), 1.91-2.04 (m, 2H), 1.80 (dt, J=12.3, 3.4 Hz, 2H), 1.66 (dd, J=10.6, 6.9 Hz, 1H), 1.06-1.52 (m, 5H).

Synthesis of 3-(5-(1,3,4-oxadiazol-2-yl)pyridin-3-yl)-4-hydroxyphenyl cyclohexylcarbamate (Example-158)

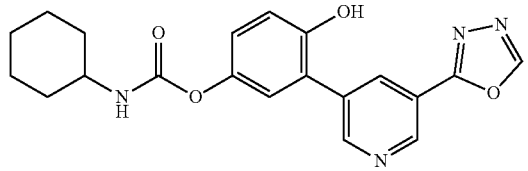

To a solution containing 3-(5-(1,3,4-oxadiazol-2-yl)pyridin-3-yl)-4-(benzyloxy)phenyl cyclohexylcarbamate (0.1 g, 0.21 mmol) in EtOH (1 mL), 10% Pd/C (0.01 mg) was added, and the reaction mixture was stirred at 50° C. under a hydrogen a balloon over 2 h. Completion of the reaction was confirmed by TLC, and the reaction mixture was filtered through a celite pad. The filtrate was then dried, and the resulting solid was recrystallized by using ethanol to obtain the pure white crystalline compound (40 mg). $^1$H NMR (400 MHz, MeOD) δ 9.04 (d, J=2.0 Hz, 1H), 8.99 (s, 1H), 8.87 (d, J=2.0 Hz, 1H), 8.59 (t, J=2.1 Hz, 1H), 7.06 (d, J=2.8 Hz, 1H), 6.72-6.96 (m, 2H), 3.32 (ddt, J=10.3, 7.4, 3.9 Hz, 1H), 1.85 (dd, J=9.9, 4.9 Hz, 2H), 1.68 (dt, J=12.4, 3.5 Hz, 2H), 1.54 (dt, J=12.7, 3.5 Hz, 1H), 1.03-1.42 (m, 5H).

Synthesis of 3-(5-(1,3,4-oxadiazol-2-yl)pyridin-3-yl)-4-hydroxyphenyl(4-methylcyclohexyl)carbamate (Example-159)

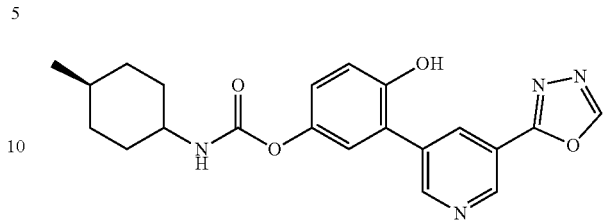

To a solution containing 3-(5-(1,3,4-oxadiazol-2-yl)pyridin-3-yl)-4-(benzyloxy)phenyl (4-methylcyclohexyl)carbamate (0.1 g, 0.21 mmol) in EtOH (1 mL), 10% Pd/C (0.01 mg) was added, and the reaction mixture was stirred at 50° C. under a hydrogen balloon over 2 h. Completion of the reaction was confirmed by TLC, and the reaction mixture was filtered through a celite pad. The filtrate was then dried, and the resulting solid was recrystallized to obtain the pure white crystalline compound (44 mg). $^1$H NMR (400 MHz, MeOD) δ 8.92-9.25 (m, 2H), 8.88 (d, J=2.2 Hz, 1H), 8.60 (t, J=2.1 Hz, 1H), 7.07 (d, J=2.7 Hz, 1H), 6.75-6.98 (m, 2H), 3.24-3.32 (m, 1H), 1.81-1.95 (m, 2H), 1.66 (d, J=12.7 Hz, 2H), 1.20 (qd, J=13.4, 4.0 Hz, 3H), 0.94 (qd, J=13.3, 3.3 Hz, 2H), 0.81 (d, J=6.5 Hz, 3H) Synthesis of ethyl 5-(3-(benzyloxy)-5-hydroxyphenyl)nicotinate

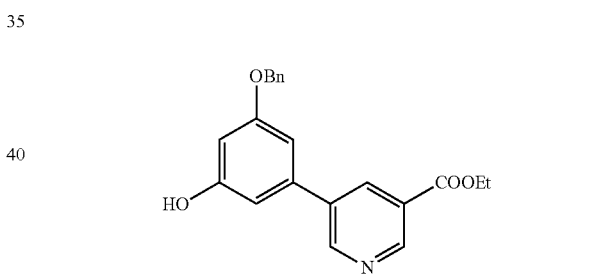

To a stirred solution of ethyl 5-(4,4,5,5-tetramethyl-1,3,2-dioxaborolan-2-yl)nicotinate (0.99 g, 3.58 mmol) in 1,4-dioxane (36 mL) and water (4 mL) was added 3-(benzyloxy)-5-bromophenol (1 g, 3.58 mmol) and K$_2$CO$_3$ (1.57 g, 14.78 mmol) at RT. The reaction mixture was degassed for 15 minutes then Pd(PPh$_3$)$_4$ (0.57 g, 0.493 mmol) was added. The reaction mixture was stirred at 80° C. for 5 h under nitrogen atmosphere. After completion of the reaction (monitored by TLC), the reaction mixture was cooled to RT and then the solvent was evaporated under reduced pressure. The residue was dissolved in ethyl acetate, washed with water followed by brine. The organic layer was dried over sodium sulfate then evaporated under reduced pressure. The residue was purified by automated normal-phase chromatography and eluted with ethyl acetate/petroleum ether to give ethyl 5-(3-(benzyloxy)-5-hydroxyphenyl)nicotinate (1 g) as an off white solid. MS (ES+APCI) m/z 350.3 (M+1).

Synthesis of 5-(3-(benzyloxy)-5-hydroxyphenyl)nicotinohydrazide

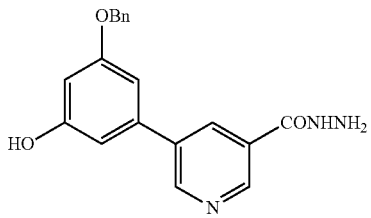

To a stirred solution of ethyl 5-(3-(benzyloxy)-5-hydroxyphenyl)nicotinate (0.6 g, 1.72 mmol) in ethanol (12 mL) was added hydrazine hydrate (1.3 mL, 1.72 mmol) at RT. The reaction mixture was stirred at 60° C. for 15 h. After completion of the reaction (monitored by TLC), the resulting mixture was concentrated to a residue. The residue was co-evaporated with toluene to remove the residual water and repeated the toluene co-evaporation process for 3 to 4 times to give 5-(3-(benzyloxy)-5-hydroxyphenyl)nicotinohydrazide (572 mg), which was used for next step without purification. MS (ES+APCI) m/z 336.4 (M+1).

Synthesis of 3-(5-(1,3,4-oxadiazol-2-yl)pyridin-3-yl)-5-(benzyloxy)phenol

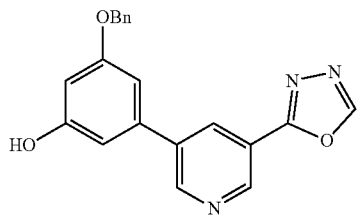

A suspension of 5-(3-(benzyloxy)-5-hydroxyphenyl)nicotinohydrazide (0.95 g, 2.83 mmol) in triethyl orthoformate (14 mL) was added p-toluenesulfonic acid (50 mg, 0.28 mmol) and stirred at 120° C. for 4 h under nitrogen atmosphere. After completion of the reaction (monitored by TLC), the reaction mixture was cooled to RT and concentrated to a residue. The residue was purified by automated normal-phase chromatography and eluted with ethyl acetate/petroleum ether to give 3-(5-(1,3,4-oxadiazol-2-yl)pyridin-3-yl)-5-(benzyloxy)phenol) (450 mg). $^1$H NMR (400 MHz, DMSO-d6) δ 9.77 (s, 1H), 9.49 (s, 1H), 9.17 (d, J=2.40 Hz, 1H), 9.06 (d, J=2.80 Hz, 1H), 8.50 (t, J=2.80 Hz, 1H), 7.50-7.34 (m, 5H), 6.94-6.93 (m, 1H), 6.77 (t, J=2.40 Hz, 1H), 6.52 (t, J=2.80 Hz, 1H), 5.17 (s, 2H); MS (ES+APCI) m/z 346.3 (M+1).

Synthesis of 3-(5-(1,3,4-oxadiazol-2-yl)pyridin-3-yl)-5-(benzyloxy)phenyl octylcarbamate

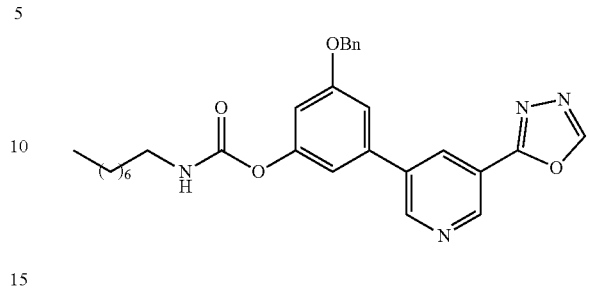

To a stirred solution of 3-(5-(1,3,4-oxadiazol-2-yl)pyridin-3-yl)-5-(benzyloxy)phenol (0.12 g, 0.35 mmol) in anhydrous acetonitrile (3 mL) was added TEA (0.07 mL, 0.52 mmol) and n-octyl isocyanate (0.05 g, 0.35 mmol) at RT under nitrogen atmosphere. The reaction mixture was stirred at RT for 10 minutes and then stirred at 75° C. for 3 h. An additional amount of n-octyl isocyanate (0.01 g, 0.10 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with ethyl acetate/petroleum ether to give 3-(5-(1,3,4-oxadiazol-2-yl)pyridin-3-yl)-5-(benzyloxy)phenyl octylcarbamate (110 mg). MS (ES+APCI) m/z 501.4 (M+1).

Synthesis of 3-(5-(1,3,4-oxadiazol-2-yl)pyridin-3-yl)-5-hydroxyphenyl octylcarbamate (Example-160)

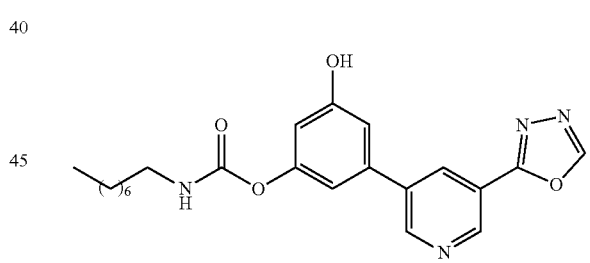

To a stirred solution of 3-(5-(1,3,4-oxadiazol-2-yl)pyridin-3-yl)-5-(benzyloxy)phenyl octylcarbamate (0.11 g, 0.22 mmol, 1 equiv) in THF (3.5 mL) and 2-propanol (1.5 mL) was added 10% Pd/C (55 mg) and Pd(OH)$_2$ (55 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to a residue. The residue was purified by preparative HPLC (0.10% FA) to yield the target compound (36 mg) as an off white solid. $^1$H NMR (400 MHz, DMSO-d6) δ 9.97 (s, 1H), 9.50 (s, 1H), 9.19 (d, J=2.00 Hz, 1H), 9.07 (d, J=2.00 Hz, 1H), 8.50 (t, J=2.40 Hz, 1H), 7.78 (t, J=5.60 Hz, 1H), 7.04-7.01 (m, 2H), 6.62 (t, J=2.00 Hz, 1H), 3.09-3.04 (m, 2H), 1.49-1.44 (m, 2H), 1.28-1.27 (m, 10H), 0.86 (t, J=6.80 Hz, 3H); MS (ES+APCI) m/z 411.4 (M+1).

Synthesis of 3-(5-(1,3,4-oxadiazol-2-yl)pyridin-3-yl)-5-(benzyloxy)phenyl (cyclohexylmethyl)carbamate

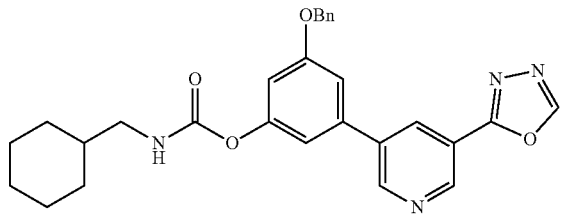 [SMILES: O=C(NCC1CCCCC1)Oc1cc(OCc2ccccc2)cc(-c2cncc(-c3nnco3)c2)c1]

To a stirred solution of 3-(5-(1,3,4-oxadiazol-2-yl)pyridin-3-yl)-5-(benzyloxy)phenol (0.12 g, 0.35 mmol) in anhydrous acetonitrile (3 mL) was added TEA (0.07 mL, 0.52 mmol) and cyclohexanemethyl isocyanate (0.05 g, 0.35 mmol) at RT under nitrogen atmosphere. The reaction mixture was stirred at RT for 10 minutes and then stirred at 75° C. for 3 h. An additional amount of cyclohexanemethyl isocyanate (0.015 g, 0.10 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with ethyl acetate/petroleum ether to give 3-(5-(1,3,4-oxadiazol-2-yl)pyridin-3-yl)-5-(benzyloxy)phenyl (cyclohexylmethyl)carbamate (120 mg). MS (ES+APCI) m/z 485.3 (M+1).

Synthesis of 3-(5-(1,3,4-oxadiazol-2-yl)pyridin-3-yl)-5-hydroxyphenyl (cyclohexylmethyl)carbamate (Example-161)

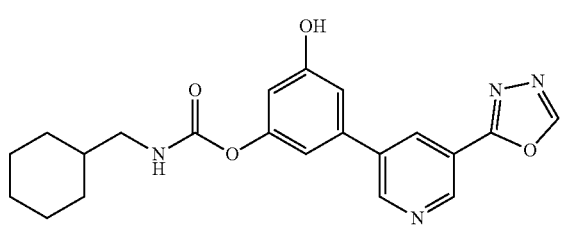 [SMILES: O=C(NCC1CCCCC1)Oc1cc(O)cc(-c2cncc(-c3nnco3)c2)c1]

To a stirred solution of 3-(5-(1,3,4-oxadiazol-2-yl)pyridin-3-yl)-5-(benzyloxy)phenyl cyclopentylcarbamate (0.12 g, 0.25 mmol, 1 equiv) in THF (3.5 mL) and 2-propanol (1.5 mL) was added 10% Pd/C (60 mg) and Pd(OH)$_2$ (60 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to a residue. The residue was purified by preparative HPLC (0.1% FA) to yield the target compound (42 mg) as an off white solid. $^1$H NMR (400 MHz, DMSO-d6) δ 9.96 (s, 1H), 9.50 (t, J=2.00 Hz, 1H), 9.19 (d, J=2.00 Hz, 1H), 9.07 (d, J=2.00 Hz, 1H), 8.51 (t, J=2.00 Hz, 1H), 7.80 (t, J=5.60 Hz, 1H), 7.03-7.02 (m, 2H), 6.62 (t, J=2.00 Hz, 1H), 2.93 (t, J=6.40 Hz, 2H), 1.74-0.87 (m, 11H); MS (ES+APCI) m/z 395.3 (M+1).

Synthesis of 5-(5-(1,3,4-oxadiazol-2-yl)pyridin-3-yl)benzene-1,3-diol

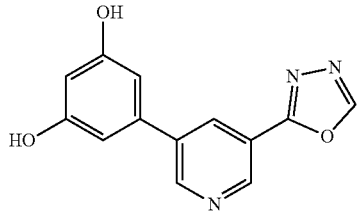 [SMILES: Oc1cc(O)cc(-c2cncc(-c3nnco3)c2)c1]

To a stirred solution of 3-(5-(1,3,4-oxadiazol-2-yl)pyridin-3-yl)-5-(benzyloxy)phenol (0.15 g, 0.43 mmol, 1 equiv) in THF (4 mL) and 2-propanol (2 mL) was added 10% Pd/C (75 mg) and Pd(OH)$_2$ (75 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to give a residue. The residue was purified by automated normal-phase chromatography and eluted with ethyl acetate/petroleum ether to give 5-(5-(1,3,4-oxadiazol-2-yl)pyridin-3-yl)benzene-1,3-diol (60 mg) as an off white solid. MS (ES+APCI) m/z 256.3 (M+1).

Synthesis of 3-(5-(1,3,4-oxadiazol-2-yl)pyridin-3-yl)-5-hydroxyphenyl benzylcarbamate (Example-162)

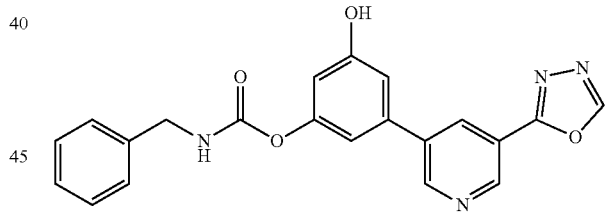

To a stirred solution of 5-(5-(1,3,4-oxadiazol-2-yl)pyridin-3-yl)benzene-1,3-diol (0.06 g, 0.24 mmol) in anhydrous acetonitrile (2.5 mL) was added TEA (0.05 mL, 0.35 mmol) and benzyl isocyanate (0.025 g, 0.19 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (10 mg) as an off white solid. $^1$H NMR (400 MHz, DMSO-d6) δ 10.07 (s, 1H), 9.49 (s, 1H), 9.19 (d, J=2.00 Hz, 1H), 9.08 (d, J=2.00 Hz, 1H), 8.51 (t, J=2.00 Hz, 1H), 8.36 (t, J=6.40 Hz, 1H), 7.39-7.26 (m, 5H), 7.07-7.04 (m, 2H), 6.66 (t, J=2.00 Hz, 1H), 4.30 (d, J=6.00 Hz, 2H); MS (ES+APCI) m/z 389.1 (M+1).

Synthesis of 3-(5-(1,3,4-oxadiazol-2-yl)pyridin-3-yl)-5-(benzyloxy)phenyl cyclopentylcarbamate

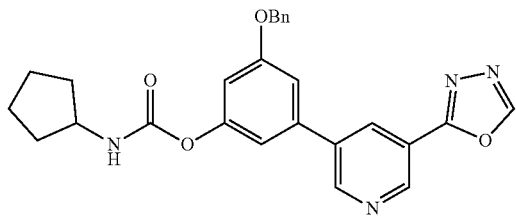 [SMILES: O=C(NC1CCCC1)Oc1cc(OCc2ccccc2)cc(-c2cncc(-c3nnco3)c2)c1]

To a stirred solution of 3-(5-(1,3,4-oxadiazol-2-yl)pyridin-3-yl)-5-(benzyloxy)phenol (0.12 g, 0.35 mmol) in anhydrous acetonitrile (3 mL) was added TEA (0.07 mL, 0.52 mmol) and cyclopentyl isocyanate (0.04 g, 0.35 mmol) at RT under nitrogen atmosphere. The reaction mixture was stirred at RT for 10 minutes and then stirred at 75° C. for 3 h. An additional amount of cyclopentyl isocyanate (0.01 g, 0.10 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with ethyl acetate/petroleum ether to give 3-(5-(1,3,4-oxadiazol-2-yl)pyridin-3-yl)-5-(benzyloxy)phenyl cyclopentylcarbamate (90 mg). MS (ES+APCI) m/z 457.4 (M+1).

Synthesis of 3-(5-(1,3,4-oxadiazol-2-yl)pyridin-3-yl)-5-hydroxyphenyl cyclopentylcarbamate (Example-163)

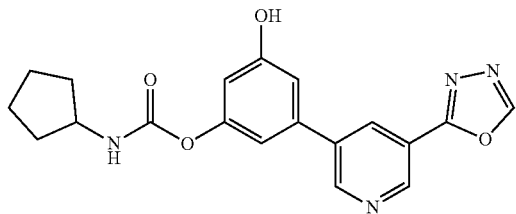 [SMILES: O=C(NC1CCCC1)Oc1cc(O)cc(-c2cncc(-c3nnco3)c2)c1]

To a stirred solution of 3-(5-(1,3,4-oxadiazol-2-yl)pyridin-3-yl)-5-(benzyloxy)phenyl cyclopentylcarbamate (0.09 g, 0.20 mmol) in THF (3 mL) and 2-propanol (1 mL) was added 10% Pd/C (45 mg) and Pd(OH)$_2$ (45 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to a residue. The residue was purified by preparative HPLC (0.1% FA) to yield the target compound (15 mg) as an off white solid. $^1$H NMR (400 MHz, DMSO-d6): δ 9.99 (s, 1H), 9.50 (s, 1H), 9.19 (d, J=2.00 Hz, 1H), 9.07 (d, J=2.40 Hz, 1H), 8.51 (t, J=2.00 Hz, 1H), 7.83 (d, J=7.20 Hz, 1H), 7.03 (d, J=2.00 Hz, 2H), 6.62 (t, J=2.00 Hz, 1H), 3.90-3.82 (m, 1H), 2.52-1.47 (m, 8H); MS (ES+APCI) m/z 367.3 (M+1)

Synthesis of 3-(5-(1,3,4-oxadiazol-2-yl)pyridin-3-yl)-5-(benzyloxy)phenyl cyclohexylcarbamate

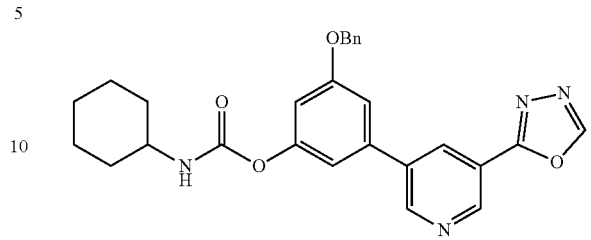

To a stirred solution of 3-(5-(1,3,4-oxadiazol-2-yl)pyridin-3-yl)-5-(benzyloxy)phenol (0.12 g, 0.35 mmol) in anhydrous acetonitrile (3 mL) was added TEA (0.07 mL, 0.52 mmol) and cyclohexyl isocyanate (0.04 g, 0.35 mmol) at RT under nitrogen atmosphere. The reaction mixture was stirred at RT for 10 minutes and then stirred at 75° C. for 3 h. An additional amount of cyclohexyl isocyanate (0.01 g, 0.10 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with ethyl acetate/petroleum ether to give 3-(5-(1,3,4-oxadiazol-2-yl)pyridin-3-yl)-5-(benzyloxy)phenyl cyclohexylcarbamate (100 mg). MS (ES+APCI) m/z 471.4 (M+1).

Synthesis of 3-(5-(1,3,4-oxadiazol-2-yl)pyridin-3-yl)-5-hydroxyphenyl cyclohexylcarbamate (Example-164)

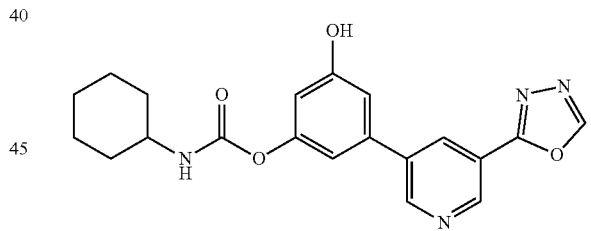

To a stirred solution of 3-(5-(1,3,4-oxadiazol-2-yl)pyridin-3-yl)-5-(benzyloxy)phenyl cyclohexylcarbamate (0.1 g, 0.21 mmol) in THF (3 mL) and 2-propanol (1 mL) was added 10% Pd/C (50 mg) and Pd(OH)$_2$ (50 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to a residue. The residue was purified by preparative HPLC (0.1% FA) to yield the target compound (30 mg) as an off white solid. $^1$H NMR (400 MHz, DMSO-d6) δ 9.96 (s, 1H), 9.50 (s, 1H), 9.19 (d, J=2.00 Hz, 1H), 9.07 (d, J=2.00 Hz, 1H), 8.50 (t, J=2.40 Hz, 1H), 7.76 (d, J=8.00 Hz, 1H), 7.03 (d, J=1.60 Hz, 2H), 6.62 (t, J=2.00 Hz, 1H), 1.85-1.10 (m, 10H); MS (ES+APCI) m/z 381.4 (M+1)

Synthesis of 3-(5-(1,3,4-oxadiazol-2-yl)pyridin-3-yl)-5-(benzyloxy)phenyl cycloheptylcarbamate

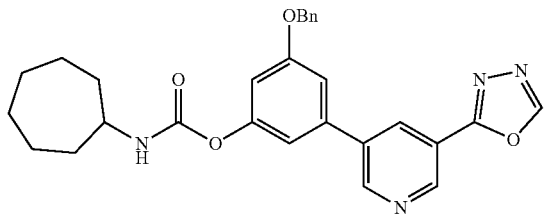 [SMILES: O=C(NC1CCCCCC1)Oc1cc(OCc2ccccc2)cc(-c2cncc(-c3nnco3)c2)c1]

To a stirred solution of 3-(5-(1,3,4-oxadiazol-2-yl)pyridin-3-yl)-5-(benzyloxy)phenol (0.12 g, 0.35 mmol) in anhydrous acetonitrile (3 mL) was added TEA (0.07 mL, 0.52 mmol) and cycloheptyl isocyanate (0.05 g, 0.35 mmol) at RT under nitrogen atmosphere. The reaction mixture was stirred at RT for 10 minutes and then stirred at 75° C. for 3 h. An additional amount of cycloheptyl isocyanate (0.01 g, 0.10 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with ethyl acetate/petroleum ether to give 3-(5-(1,3,4-oxadiazol-2-yl)pyridin-3-yl)-5-(benzyloxy)phenyl cycloheptylcarbamate (120 mg). MS (ES+APCI) m/z 485.3 (M+1).

Synthesis of 3-(5-(1,3,4-oxadiazol-2-yl)pyridin-3-yl)-5-hydroxyphenyl cycloheptylcarbamate (Example-165)

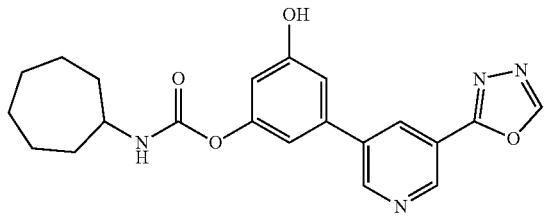 [SMILES: O=C(NC1CCCCCC1)Oc1cc(O)cc(-c2cncc(-c3nnco3)c2)c1]

To a stirred solution of 3-(5-(1,3,4-oxadiazol-2-yl)pyridin-3-yl)-5-hydroxyphenyl cycloheptylcarbamate (0.12 g, 0.25 mmol) in THF (3.5 mL) and 2-propanol (1.5 mL) was added 10% Pd/C (60 mg) and Pd(OH)$_2$ (60 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to a residue. The residue was purified by preparative HPLC (0.1% FA) to yield the target compound (38 mg) as an off white solid. $^1$H NMR (400 MHz, DMSO-d6) δ 9.98 (s, 1H), 9.50 (s, 1H), 9.19 (d, J=2.00 Hz, 1H), 9.07 (d, J=2.00 Hz, 1H), 8.50 (t, J=2.00 Hz, 1H), 7.79 (d, J=8.00 Hz, 1H), 7.02 (d, J=1.60 Hz, 1H), 6.62 (t, J=2.00 Hz, 1H), 3.59-3.52 (m, 1H), 1.90-1.39 (m, 12H); MS (ES+APCI) m/z 395.3 (M+1).

Synthesis of ethyl 2-(5-(5-hydroxy-2-methoxyphenyl)pyridin-3-yl)-2-oxoacetate

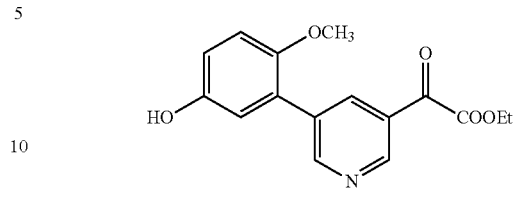

To a stirred solution of ethyl 5-(4,4,5,5-tetramethyl-1,3,2-dioxaborolan-2-yl)nicotinate (1.37 g, 4.93 mmol) in ethanol (36 mL) and toluene (4 mL) was added 3-bromo-4-methoxyphenol (1 g, 4.93 mmol) and Na$_2$CO$_3$ (1.57 g, 14.78 mmol) at RT. The reaction mixture was degassed for 15 minutes then Pd(PPh$_3$)$_4$ (0.57 g, 0.493 mmol) was added. The reaction mixture was stirred at 90° C. for 12 h under nitrogen atmosphere. After completion of the reaction (monitored by TLC), the reaction mixture was cooled to RT and then the solvent was evaporated under reduced pressure. The residue was dissolved in ethyl acetate, washed with water followed by brine. The organic layer was dried over sodium sulfate then evaporated under reduced pressure. The residue was purified by automated normal-phase chromatography and eluted with ethyl acetate/petroleum ether to give ethyl 5-(3-hydroxy-5-methoxyphenyl) nicotinate (840 mg) as an off white solid. MS (ES+APCI) m/z 274.3 (M+1).

Synthesis of 5-(5-hydroxy-2-methoxyphenyl)nicotinohydrazide

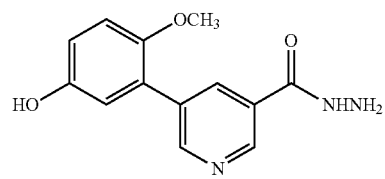 [SMILES: COc1ccc(O)cc1-c1cncc(C(=O)NN)c1]

To a stirred solution of 2-(5-(5-hydroxy-2-methoxyphenyl)pyridin-3-yl)-2-oxoacetate (1.1 g, 4.03 mmol) in ethanol (10 mL) was added hydrazine hydrate (1.9 g, 24.15 mmol) at RT. The reaction mixture was stirred at 50° C. for 15 h. After completion of the reaction (monitored by TLC), the resulting mixture was concentrated to a residue. The residue was co-evaporated with toluene to remove the residual water and repeated the toluene co-evaporation process for 3 to 4 times to give 5-(3-hydroxy-5-methoxyphenyl)nicotinohydrazide (780 mg), which was used for next step without purification. MS (ES+APCI) m/z 260.3 (M+1).

Synthesis of 3-(5-(1,3,4-oxadiazol-2-yl)pyridin-3-yl)-4-methoxyphenol

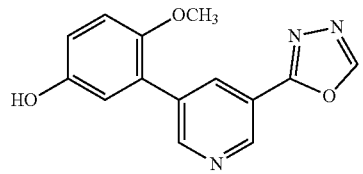 [SMILES: COc1ccc(O)cc1-c1cncc(-c2nnco2)c1]

A suspension of 5-(3-hydroxy-5-methoxyphenyl)nicotinohydrazide (1 g, 3.86 mmol) in triethyl orthoformate (10 mL) was added p-toluenesulfonic acid (66 mg, 0.39 mmol) and stirred at 120° C. for 4 h under nitrogen atmosphere. After completion of the reaction (monitored by TLC), the reaction mixture was cooled to RT and concentrated to a residue. The residue was purified by automated normal-phase chromatography and eluted with ethyl acetate/petroleum ether to give 3-(5-(1,3,4-oxadiazol-2-yl)pyridin-3-yl)-5-methoxyphenol 850 mg). MS (ES+APCI) m/z 270.4 (M+1).

Synthesis of 3-(5-(1,3,4-oxadiazol-2-yl)pyridin-3-yl)-4-methoxyphenyl heptylcarbamate (Example-166)

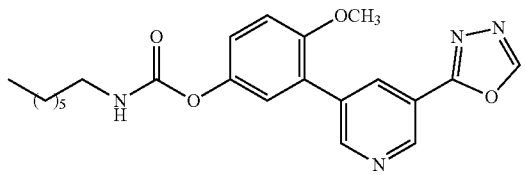

To a suspension of 3-(5-(1,3,4-oxadiazol-2-yl)pyridin-3-yl)-4-methoxyphenol (0.1 g, 0.35 mmol) in anhydrous acetonitrile (2 mL) was added TEA (0.023 mL, 0.23 mmol) and n-heptyl isocyanate (0.051 g, 0.35 mmol) at RT under nitrogen atmosphere. The reaction mixture was stirred at RT for 10 minutes and then heated at 75° C. for 3 h under nitrogen atmosphere. An additional amount of n-heptyl isocyanate (0.015 g, 0.10 mmol) was added to the reaction mixture, and the reaction was heated for an additional 12 h. The reaction progress was monitored by TLC. After completion, the reaction mixture was cooled to RT and the solvent was evaporated under reduced pressure. The crude product was purified by flash column chromatography on silica gel, eluting with a hexane/EtOAc gradient (40-55% EtOAc), to yield the target compound (50 mg) as an off white solid. $^1$H NMR (400 MHz, MeOD) δ 8.83-9.17 (m, 2H), 8.78 (t, J=1.5 Hz, 1H), 8.49 (d, J=2.4 Hz, 1H), 6.95-7.26 (m, 3H), 3.75 (s, 3H), 3.07 (t, J=7.1 Hz, 2H), 1.47 (h, J=8.2 Hz, 2H), 1.12-1.41 (m, 8H), 0.59-0.93 (m, 3H).

Synthesis of 3-(5-(1,3,4-oxadiazol-2-yl)pyridin-3-yl)-4-methoxyphenyl octylcarbamate (Example-167)

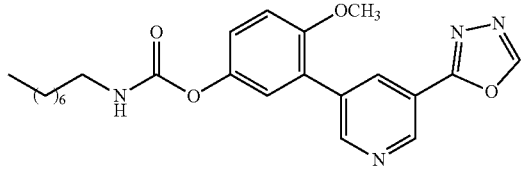

To a suspension of 3-(5-(1,3,4-oxadiazol-2-yl)pyridin-3-yl)-4-methoxyphenol (0.1 g, 0.35 mmol) in anhydrous acetonitrile (2 mL) was added TEA (0.023 mL, 0.16 mmol) and n-octyl isocyanate (0.058 g, 0.35 mmol) at RT under nitrogen atmosphere. The reaction mixture was stirred at RT for 10 minutes and then heated at 75° C. for 12 h under nitrogen atmosphere. The reaction progress was monitored by TLC. Upon completion, the reaction mixture was cooled to RT and the solvent was evaporated under reduced pressure. The crude product was purified by flash column chromatography on silica gel, eluting with a hexane/EtOAc gradient (30-60% EtOAc) to yield the target compound (80 mg) as a white solid. $^1$H NMR (400 MHz, MeOD) δ 8.92-9.22 (m, 2H), 8.78 (d, J=2.1 Hz, 1H), 8.48 (t, J=2.2 Hz, 1H), 6.92-7.15 (m, 3H), 3.75 (s, 3H), 3.07 (t, J=7.1 Hz, 2H), 1.46 (p, J=7.1 Hz, 2H), 1.04-1.38 (m, 10H), 0.65-0.85 (m, 3H).

Synthesis of 3-(5-(1,3,4-oxadiazol-2-yl)pyridin-3-yl)-4-methoxyphenyl (cyclohexylmethyl)carbamate (Example-168)

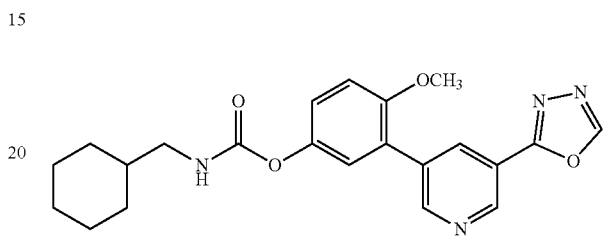

To a stirred solution of 3-(5-(1,3,4-oxadiazol-2-yl)pyridin-3-yl)-4-methoxyphenol (0.1 g, 0.37 mmol) in anhydrous acetonitrile (1 mL) was added TEA (0.05 mL, 0.37 mmol) and cyclohexanemethyl isocyanate (0.06 g, 0.44 mmol) at RT under nitrogen atmosphere. The reaction mixture was stirred at RT for 10 minutes and then heated at 75° C. for 12 h. The reaction progress was monitored by TLC. After completion, the reaction mixture was cooled to RT and concentrated to a residue under reduced pressure. The crude product was purified by flash column chromatography on silica gel, eluting with hexane/EtOAc (gradient 45-60% EtOAc) to yield the target compound (40 mg) as an off white solid. $^1$H NMR (400 MHz, Acetone-d6) δ 9.05 (d, J=2.0 Hz, 1H), 8.95 (s, 1H), 8.80 (d, J=2.1 Hz, 1H), 8.39 (t, J=2.2 Hz, 1H), 6.91-7.24 (m, 3H), 6.59 (d, J=7.3 Hz, 1H), 3.77-3.95 (m, 1H), 3.75 (s, 3H), 2.63 (d, J=1.4 Hz, 2H), 1.81 (dd, J=11.9, 6.9 Hz, 2H), 1.56-1.71 (m, 2H), 1.47 (d, J=9.9 Hz, 4H), 1.47 (d, J=9.9 Hz, 4H), 0.99-1.16 (m, 2H).

Synthesis of 3-(5-(1,3,4-oxadiazol-2-yl)pyridin-3-yl)-4-methoxyphenyl cyclopentylcarbamate (Example-169)

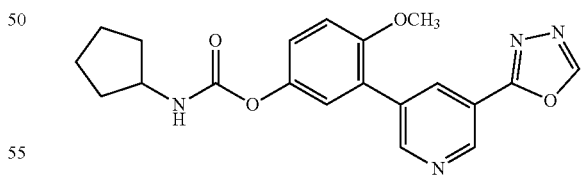

To a stirred solution of 3-(5-(1,3,4-oxadiazol-2-yl)pyridin-3-yl)-4-methoxyphenol (0.1 g, 0.37 mmol) in anhydrous acetonitrile (2 mL) was added TEA (0.05 mL, 0.37 mmol) and cyclopentyl isocyanate (0.04 g, 0.44 mmol) at RT under a nitrogen atmosphere. The reaction mixture was stirred at RT for 10 minutes and then heated to 75° C. for 12 h. The reaction progress was monitored by TLC. Upon completion of the reaction, the reaction mixture was cooled to RT and concentrated to a residue under reduced pressure. The crude product was purified by flash column chromatography on silica gel, eluting with hexane/EtOAc (gradient 45-55% EtOAc) to yield the target compound (43 mg) as an off white solid. ¹H NMR (400 MHz, Acetone-d6) δ 9.20 (d, J=2.0 Hz, 1H), 9.10 (s, 1H), 8.95 (d, J=2.1 Hz, 1H), 8.54 (t, J=2.1 Hz, 1H), 6.94-7.64 (m, 3H), 6.77 (t, J=6.2 Hz, 1H), 3.90 (s, 3H), 1.48-1.90 (m, 4H), 1.13-1.39 (m, 3H), 0.99 (qd, J=11.9, 3.3 Hz, 2H). 3-(5-(1,3,4-oxadiazol-2-yl)pyridin-3-yl)-4-methoxyphenyl cyclohexylcarbamate (Example-170)

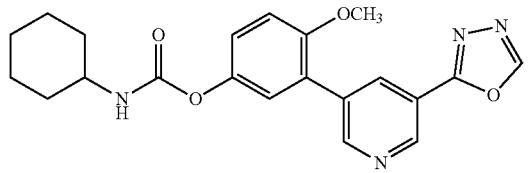

To a stirred solution of 3-(5-(1,3,4-oxadiazol-2-yl)pyridin-3-yl)-4-methoxyphenol (0.1 g, 0.37 mmol) in anhydrous acetonitrile (2 mL) was added TEA (0.05 mL, 0.37 mmol) and cyclohexyl isocyanate (0.05 g, 0.44 mmol) at RT under a nitrogen atmosphere. The reaction mixture was stirred at RT for 10 minutes and then heated to 75° C. for 12 h. After completion of the reaction (monitored by TLC), the reaction mixture was cooled to RT and concentrated to a residue under reduced pressure. The crude product was purified by flash column chromatography on silica gel eluting with a gradient of hexane/EtOAc (40-60% EtOAc) to yield the target compound (40 mg) as an off white solid. ¹H NMR (400 MHz, DMSO-d6) δ 9.47 (s, 1H), 9.16 (d, J=2.1 Hz, 1H), 8.93 (d, J=2.2 Hz, 1H), 8.46 (t, J=2.2 Hz, 1H), 7.69 (d, J=7.9 Hz, 1H), 7.22 (dd, J=28.3, 1.6 Hz, 3H), 3.83 (s, 3H), 1.70 (ddd, J=60.8, 52.5, 10.8 Hz, 5H), 0.79-1.49 (m, 6H).

Synthesis of 3-(5-(1,3,4-oxadiazol-2-yl)pyridin-3-yl)-4-methoxyphenyl (4-methylcyclohexyl)carbamate (Example-171)

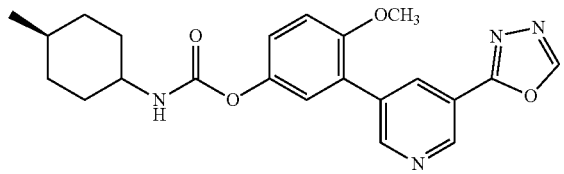

To a stirred solution of 3-(5-(1,3,4-oxadiazol-2-yl)pyridin-3-yl)-4-methoxyphenol (0.1 g, 0.37 mmol) in anhydrous acetonitrile (2 mL) was added TEA (0.05 mL, 0.37 mmol) and trans-4-Methylcyclohexyl isocyanate (0.06 g, 0.44 mmol) at RT under a nitrogen atmosphere. The reaction mixture was stirred at RT for 10 minutes and then heated to 75° C. for 12 h. Upon completion of the reaction (monitored TLC), the reaction mixture was cooled to RT and concentrated to a residue under reduced pressure. The crude product was purified by flash column chromatography on silica gel, eluting with a gradient of hexane/EtOAc (40-60% EtOAc) to yield the target compound (40 mg) as an off white solid. ¹H NMR (400 MHz, DMSO-d6) δ 9.46 (d, J=2.4 Hz, 1H), 9.15 (dd, J=8.2, 2.1 Hz, 1H), 8.91 (dd, J=14.9, 2.1 Hz, 1H), 8.44 (d, J=14.3 Hz, 1H), 7.10-7.51 (m, 2H), 6.67-7.08 (m, 2H), 3.83 (s, 3H), 1.58-1.89 (m, 3H), 1.04-1.48 (m, 3H), 0.96 (td, J=13.6, 6.3 Hz, 4H), 0.86 (m, 3H).

Synthesis of 3-(5-(1,3,4-oxadiazol-2-yl)pyridin-3-yl)-4-methoxyphenyl cycloheptylcarbamate (Example-172)

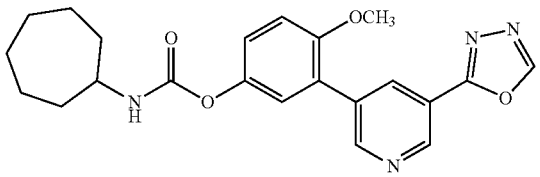 [SMILES: COc1ccc(OC(=O)NC2CCCCCC2)cc1-c1cncc(-c2nnco2)c1]

To a stirred solution of 3-(5-(1,3,4-oxadiazol-2-yl)pyridin-3-yl)-4-methoxyphenol (0.1 g, 0.37 mmol) in anhydrous acetonitrile (2 mL) was added triethylamine (TEA, 0.05 mL, 0.37 mmol) and cycloheptyl isocyanate (0.06 g, 0.44 mmol) at RT under a nitrogen atmosphere. The reaction mixture was stirred at RT for 10 minutes and then heated to 75° C. for 12 h. The progress of the reaction was monitored by TLC. After completion of the reaction, the reaction mixture was cooled to RT and concentrated to a residue under reduced pressure. The crude product was purified by flash column chromatography on silica gel, eluting with a gradient of hexane/EtOAc (40-60% EtOAc) to yield the target compound (45 mg) as an off white solid. ¹H NMR (400 MHz, DMSO-d6) δ 9.47 (s, 1H), 9.00-9.18 (m, 1H), 8.91 (dd, J=15.6, 2.2 Hz, 1H), 8.44 (dt, J=15.0, 2.2 Hz, 1H), 7.74 (d, J=8.0 Hz, 1H), 7.22 (dd, J=30.0, 1.6 Hz, 3H), 3.82 (s, 3H), 3.54 (qt, J=9.1, 4.5 Hz, 1H), 1.74-1.98 (m, 2H), 1.31-1.68 (m, 10H).

Synthesis of 3-(5-(1,3,4-oxadiazol-2-yl)pyridin-3-yl)-4-methoxyphenyl cyclooctylcarbamate (Example-173)

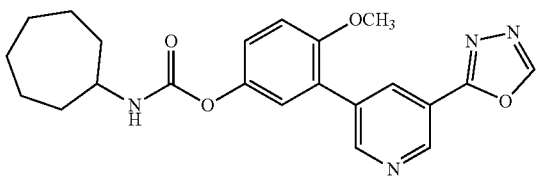 [SMILES: COc1ccc(OC(=O)NC2CCCCCC2)cc1-c1cncc(-c2nnco2)c1]

To a stirred solution of 3-(5-(1,3,4-oxadiazol-2-yl)pyridin-3-yl)-4-methoxyphenol (0.1 g, 0.37 mmol) in anhydrous acetonitrile (2 mL) was added triethylamine (TEA, 0.05 mL, 0.37 mmol) and cyclooctyl isocyanate (0.06 g, 0.44 mmol) at RT under a nitrogen atmosphere. The reaction mixture was stirred at RT for 10 minutes and then heated to 75° C. for 12 h. The progress of the reaction was monitored by TLC. After completion of the reaction, the reaction mixture was cooled to RT and concentrated to a residue under reduced pressure. The crude product was purified by flash column chromatography on silica gel, eluting with a gradient of hexane/EtOAc (40-60% EtOAc) to yield the target compound (40 mg) as an off white solid. ¹H NMR (400 MHz, MeOD) δ 8.95-9.16 (m, 2H), 8.80 (d, J=2.0 Hz, 1H), 8.51 (t, J=2.0 Hz, 1H), 6.92-7.16 (m, 3H), 3.76 (s, 3H), 3.61 (dt, J=9.4, 5.0 Hz, 1H), 1.70-1.84 (m, 2H), 1.40-1.70 (m, 12H).

153

Synthesis of ethyl
5-(3-hydroxy-5-methoxyphenyl)nicotinate

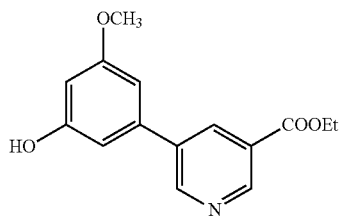

To a stirred solution of ethyl 5-(4,4,5,5-tetramethyl-1,3,2-dioxaborolan-2-yl)nicotinate (1.37 g, 4.93 mmol) in ethanol (36 mL) and toluene (4 mL) was added 3-bromo-5-methoxyphenol (1 g, 4.93 mmol) and $Na_2CO_3$ (1.57 g, 14.78 mmol) at RT. The reaction mixture was degassed for 15 minutes then $Pd(PPh_3)_4$ (0.57 g, 0.493 mmol) was added. The reaction mixture was stirred at 90° C. for 12 h under nitrogen atmosphere. After completion of the reaction (monitored by TLC), the reaction mixture was cooled to RT and then the solvent was evaporated under reduced pressure. The residue was dissolved in ethyl acetate, washed with water followed by brine. The organic layer was dried over sodium sulfate then evaporated under reduced pressure. The residue was purified by automated normal-phase chromatography and eluted with ethyl acetate/petroleum ether to give ethyl 5-(3-hydroxy-5-methoxyphenyl)nicotinate (850 mg) as an off white solid. MS (ES+APCI) m/z 274.3 (M+1).

5-(3-hydroxy-5-methoxyphenyl)nicotinohydrazide

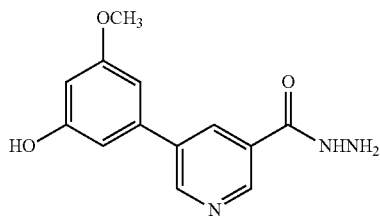 [SMILES: COc1cc(O)cc(-c2cncc(C(=O)NN)c2)c1]

To a stirred solution of ethyl 5-(3-hydroxy-5-methoxyphenyl)nicotinate (1.1 g, 4.03 mmol) in ethanol (10 mL) was added hydrazine hydrate (1.9 g, 24.15 mmol) at RT. The reaction mixture was stirred at 50° C. for 15 h. After completion of the reaction (monitored by TLC), the resulting mixture was concentrated to a residue. The residue was co-evaporated with toluene to remove the residual water and repeated the toluene co-evaporation process for 3 to 4 times to give 5-(3-hydroxy-5-methoxyphenyl)nicotinohydrazide (800 mg), which was used for next step without purification. MS (ES+APCI) m/z 260.3 (M+1).

154

Synthesis of 3-(5-(1,3,4-oxadiazol-2-yl)pyridin-3-yl)-5-methoxyphenol

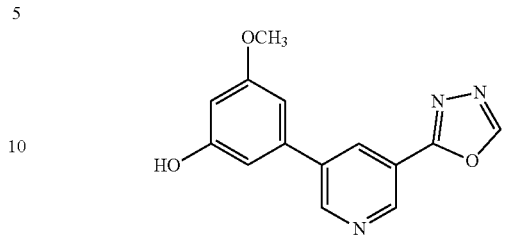

A suspension of 5-(3-hydroxy-5-methoxyphenyl)nicotinohydrazide (1 g, 3.86 mmol) in triethyl orthoformate (10 mL) was added p-toluenesulfonic acid (66 mg, 0.39 mmol) and stirred at 120° C. for 4 h under nitrogen atmosphere. After completion of the reaction (monitored by TLC), the reaction mixture was cooled to RT and concentrated to a residue. The residue was purified by automated normal-phase chromatography and eluted with ethyl acetate/petroleum ether to give 3-(5-(1,3,4-oxadiazol-2-yl)pyridin-3-yl)-5-methoxyphenol (850 mg). MS (ES+APCI) m/z 270.4 (M+1).

Synthesis of 3-(5-(1,3,4-oxadiazol-2-yl)pyridin-3-yl)-5-methoxyphenyl octylcarbamate (Example-174)

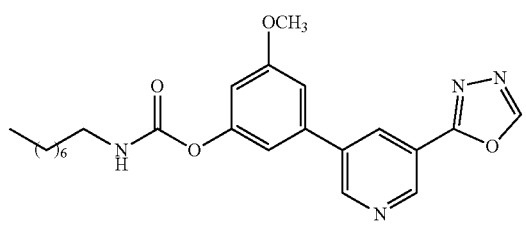

To a stirred solution of 3-(5-(1,3,4-oxadiazol-2-yl)pyridin-3-yl)-5-methoxyphenol (0.08 g, 0.30 mmol) in anhydrous acetonitrile (2 mL) was added TEA (0.06 mL, 0.45 mmol) and octyl isocyanate (0.05 g, 0.30 mmol) at RT under nitrogen atmosphere. The reaction mixture was stirred at RT for 10 minutes and then stirred at 75° C. for 3 h. An additional amount of octyl isocyanate (0.014 g, 0.09 mmol) was added to the reaction mixture and the resulting mixture was stirred for an additional 12 h. After completion of the reaction (monitored by TLC), the reaction mixture was concentrated to a residue. The residue was purified by preparative HPLC (0.1% FA) to yield the target compound (58 mg) as an off white solid. $^1$H NMR (400 MHz, DMSO-d6) δ 9.51 (s, 1H), 9.21 (d, J=2.00 Hz, 1H), 9.15 (d, J=2.00 Hz, 1H), 8.60 (t, J=2.00 Hz, 1H), 7.81 (t, J=5.60 Hz, 1H), 7.26 (t, J=1.60 Hz, 1H), 7.18 (t, J=2.00 Hz, 1H), 6.80 (t, J=2.00 Hz, 1H), 3.87 (s, 3H), 3.10-3.05 (m, 2H), 1.48 (t, J=7.20 Hz, 2H), 1.29-1.27 (m, 10H), 0.86 (t, J=7.20 Hz, 3H); MS (ES+APCI) m/z 425.3 (M+1).

Synthesis of 3-(5-(1,3,4-oxadiazol-2-yl)pyridin-3-yl)-5-methoxyphenyl (cyclohexylmethyl)carbamate (Example-175)

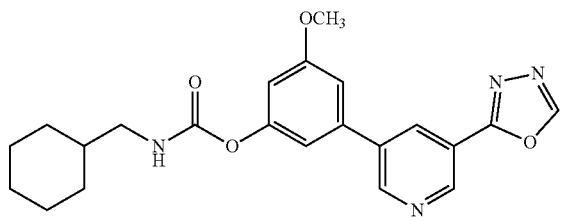 [SMILES: COc1cc(OC(=O)NCC2CCCCC2)cc(-c2cncc(-c3nnco3)c2)c1]

To a stirred solution of 3-(5-(1,3,4-oxadiazol-2-yl)pyridin-3-yl)-5-methoxyphenol (0.08 g, 0.30 mmol) in anhydrous acetonitrile (2 mL) was added TEA (0.06 mL, 0.45 mmol) and cyclohexanemethyl isocyanate (0.04 g, 0.30 mmol) at RT under nitrogen atmosphere. The reaction mixture was stirred at RT for 10 minutes and then stirred at 75° C. for 3 h. An additional amount of cyclohexanemethyl isocyanate (0.01 g, 0.09 mmol) was added to the reaction mixture and the resulting mixture was stirred for an additional 12 h. After completion of the reaction (monitored by LCMS), the reaction mixture was concentrated to a residue. The residue was purified by preparative HPLC (0.1% FA) to yield the target compound (43 mg) as an off white solid. $^1$H NMR (400 MHz, DMSO-d6) δ 9.51 (s, 1H), 9.21 (d, J=2.00 Hz, 1H), 9.15 (d, J=2.40 Hz, 1H), 8.60 (t, J=2.40 Hz, 1H), 8.22 (s, 1H), 7.84 (t, J=6.00 Hz, 1H), 7.27-7.26 (m, 1H), 7.19 (t, J=1.60 Hz, 1H), 6.80 (t, J=2.00 Hz, 1H), 3.87 (s, 3H), 2.93 (t, J=6.40 Hz, 2H), 1.74-1.12 (m, 11H); MS (ES+APCI) m/z 409.4 (M+1).

Synthesis of 3-(5-(1,3,4-oxadiazol-2-yl)pyridin-3-yl)-5-methoxyphenyl benzylcarbamate (Example-176)

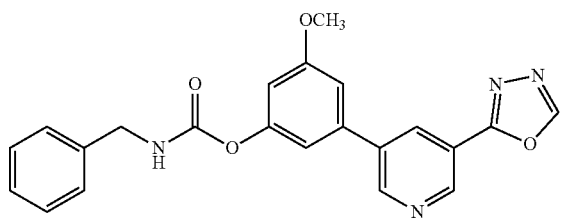 [SMILES: COc1cc(OC(=O)NCc2ccccc2)cc(-c2cncc(-c3nnco3)c2)c1]

To a stirred solution of 3-(5-(1,3,4-oxadiazol-2-yl)pyridin-3-yl)-5-methoxyphenol (0.08 g, 0.30 mmol) in anhydrous acetonitrile (2 mL) was added TEA (0.06 mL, 0.45 mmol) and benzyl isocyanate (0.04 g, 0.30 mmol) at RT under nitrogen atmosphere. The reaction mixture was stirred at RT for 10 minutes and then stirred at 75° C. for 3 h. An additional amount of benzyl isocyanate (0.012 g, 0.09 mmol) was added to the reaction mixture and the resulting mixture was stirred for an additional 12 h. After completion of the reaction (monitored by LCMS), the reaction mixture was concentrated to a residue. The residue was purified by preparative HPLC (0.1% FA) to yield the target compound (10 mg) as an off white solid. $^1$H NMR (400 MHz, DMSO-d6) δ 9.51 (s, 1H), 9.21 (d, J=2.00 Hz, 1H), 9.15 (t, J=8.80 Hz, 1H), 8.61 (t, J=2.40 Hz, 1H), 8.43-8.38 (m, 1H), 7.40-7.23 (m, 7H), 6.84 (t, J=2.00 Hz, 1H), 4.31 (d, J=6.00 Hz, 2H), 3.87 (s, 3H); MS (ES+APCI) m/z 403.3 (M+1).

Synthesis of 3-(5-(1,3,4-oxadiazol-2-yl)pyridin-3-yl)-5-methoxyphenyl cyclopentylcarbamate (Example-177)

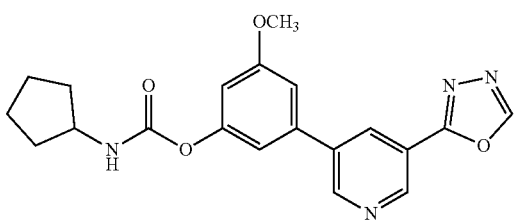 [SMILES: COc1cc(OC(=O)NC2CCCC2)cc(-c2cncc(-c3nnco3)c2)c1]

To a stirred solution of 3-(5-(1,3,4-oxadiazol-2-yl)pyridin-3-yl)-5-methoxyphenol (0.1 g, 0.37 mmol) in anhydrous acetonitrile (2.5 mL) was added TEA (0.08 mL, 0.56 mmol) and cyclopentyl isocyanate (0.04 g, 0.37 mmol) at RT under nitrogen atmosphere. The reaction mixture was stirred at RT for 10 minutes and then stirred at 75° C. for 3 h. An additional amount of cyclopentyl isocyanate (0.01 g, 0.11 mmol) was added to the reaction mixture and the resulting mixture was stirred for an additional 12 h. After completion of the reaction (monitored by LCMS), the reaction mixture was concentrated to a residue. The residue was purified by preparative HPLC (0.1% FA) to yield the target compound (68 mg) as an off white solid. $^1$H NMR (400 MHz, DMSO-d6) δ 9.51 (s, 1H), 9.21 (d, J=2.00 Hz, 1H), 9.15 (d, J=2.00 Hz, 1H), 8.60 (t, J=2.40 Hz, 1H), 7.86 (d, J=7.20 Hz, 1H), 7.26 (t, J=2.00 Hz, 1H), 7.20 (t, J=1.60 Hz, 1H), 6.81 (t, J=2.00 Hz, 1H), 3.87 (s, 4H), 1.86-1.50 (m, 8H); MS (ES+APCI) m/z 381.3 (M+1).

Synthesis of 3-(5-(1,3,4-oxadiazol-2-yl)pyridin-3-yl)-5-methoxyphenyl cyclohexylcarbamate (Example-178)

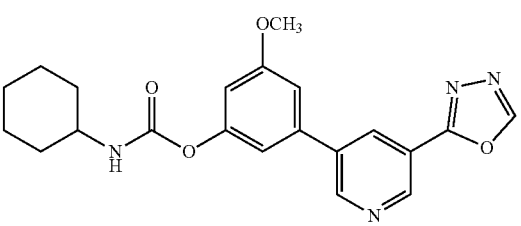 [SMILES: COc1cc(OC(=O)NC2CCCCC2)cc(-c2cncc(-c3nnco3)c2)c1]

To a stirred solution of 3-(5-(1,3,4-oxadiazol-2-yl)pyridin-3-yl)-5-methoxyphenol (0.1 g, 0.37 mmol) in anhydrous acetonitrile (2.5 mL) was added TEA (0.08 mL, 0.56 mmol) and cyclohexyl isocyanate (0.05 g, 0.37 mmol) at RT under nitrogen atmosphere. The reaction mixture was stirred at RT for 10 minutes and then stirred at 75° C. for 3 h. An additional amount of cyclohexyl isocyanate (0.01 g, 0.11 mmol) was added to the reaction mixture and the resulting mixture was stirred for an additional 12 h. After completion of the reaction (monitored by LCMS), the reaction mixture was concentrated to a residue. The residue was purified by preparative HPLC (0.1% FA) to yield the target compound (68 mg) as an off white solid. $^1$H NMR (400 MHz, DMSO-d6) δ 9.50 (s, 1H), 9.21 (d, J=2.00 Hz, 1H), 9.15 (d, J=2.40

Hz, 1H), 8.60 (t, J=2.40 Hz, 1H), 7.79 (d, J=8.00 Hz, 1H), 7.26 (t, J=2.00 Hz, 1H), 7.19 (t, J=1.60 Hz, 1H), 6.80 (t, J=2.40 Hz, 1H), 3.87 (s, 3H), 1.86-1.11 (m, 10H); MS (ES+APCI) m/z 395.3 (M+1).

Synthesis of 3-(5-(1,3,4-oxadiazol-2-yl)pyridin-3-yl)-5-methoxyphenyl cycloheptylcarbamate (Example-179)

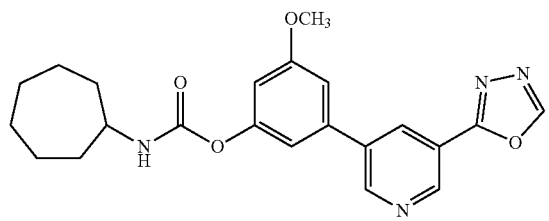 [SMILES: COc1cc(OC(=O)NC2CCCCCC2)cc(-c2cncc(-c3nnco3)c2)c1]

To a stirred solution of 3-(5-(1,3,4-oxadiazol-2-yl)pyridin-3-yl)-5-methoxyphenol (0.08 g, 0.30 mmol) in anhydrous acetonitrile (2 mL) was added TEA (0.06 mL, 0.45 mmol) and cycloheptyl isocyanate (0.04 g, 0.30 mmol) at RT under nitrogen atmosphere. The reaction mixture was stirred at RT for 10 minutes and then stirred at 75° C. for 3 h. An additional amount of cycloheptyl isocyanate (0.01 g, 0.09 mmol) was added to the reaction mixture and the resulting mixture was stirred for an additional 12 h. After completion of the reaction (monitored by LCMS), the reaction mixture was concentrated to a residue. The residue was purified by preparative HPLC (0.1% FA) to yield the target compound (55 mg) as an off white solid. ¹H NMR (400 MHz, DMSO-d6) δ 9.51 (s, 1H), 9.21 (d, J=2.00 Hz, 1H), 9.15 (d, J=2.00 Hz, 1H), 8.60 (t, J=2.40 Hz, 1H), 7.86 (d, J=7.20 Hz, 1H), 7.26 (t, J=2.00 Hz, 1H), 7.20 (t, J=1.60 Hz, 1H), 6.81 (t, J=2.00 Hz, 1H), 3.87 (s, 4H), 1.86-1.50 (m, 8H); MS (ES+APCI) m/z 381.3 (M+1) Synthesis of ethyl 5-(2-(dimethylamino)-5-hydroxyphenyl)nicotinate

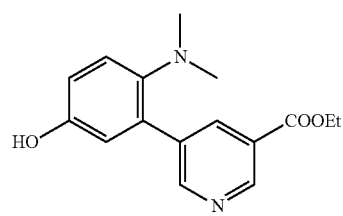 [SMILES: CCOC(=O)c1cncc(-c2cc(O)ccc2N(C)C)c1]

To a stirred solution of ethyl 5-(4,4,5,5-tetramethyl-1,3,2-dioxaborolan-2-yl)nicotinate (0.71 g, 2.55 mmol) in 1,4-dioxane (4 mL) and water (0.45 mL) was added 3-bromo-4-(dimethylamino)phenol (0.5 g, 2.31 mmol) and potassium carbonate (0.96 g, 6.94 mmol) at RT. The reaction mixture was degassed for 15 minutes then PdCl₂(dppf) (0.09 g, 0.12 mmol) was added. The reaction mixture was stirred at 80° C. for 4 h under nitrogen atmosphere. After completion of the reaction (monitored by TLC), the reaction mixture was cooled to RT and then the solvent was evaporated under reduced pressure. The residue was dissolved in ethyl acetate, washed with water followed by brine. The organic layer was dried over sodium sulfate then evaporated under reduced pressure. The residue was purified by automated normal-phase chromatography and eluted with ethyl acetate/petroleum ether to give ethyl 5-(2-(dimethylamino)-5-hydroxyphenyl)nicotinate (520 mg) as a yellow solid. MS (ES+APCI) m/z 287.3 (M+1).

Synthesis of 5-(2-(dimethylamino)-5-hydroxyphenyl)nicotinohydrazide

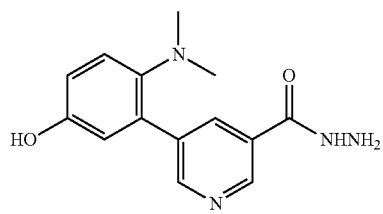 [SMILES: CN(C)c1ccc(O)cc1-c1cncc(C(=O)NN)c1]

To a stirred solution of ethyl 5-(2-(dimethylamino)-5-hydroxyphenyl)nicotinate (0.4 g, 1.40 mmol) in ethanol (8 mL) was added hydrazine hydrate (2 mL, 0.11 mmol) at RT. The reaction mixture was stirred at 60° C. for 15 h. After completion of the reaction (monitored by TLC), the resulting mixture was concentrated to a residue. The residue was co-evaporated with toluene to remove the residual water and repeated the toluene co-evaporation process for 3 to 4 times to give 5-(2-(dimethylamino)-5-hydroxyphenyl)nicotinohydrazide (380 mg) which was used for next step without further purification. MS (ES+APCI) m/z 273.2 (M+1).

Synthesis of 3-(5-(1,3,4-oxadiazol-2-yl)pyridin-3-yl)-4-(dimethylamino)phenol

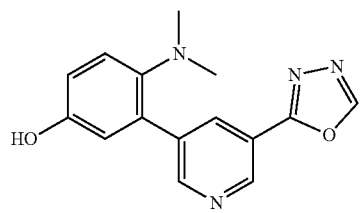 [SMILES: CN(C)c1ccc(O)cc1-c1cncc(-c2nnco2)c1]

A suspension of 5-(2-(dimethylamino)-5-hydroxyphenyl)nicotinohydrazide (0.38 g, 1.40 mmol) in triethyl orthoformate (7.2 mL) was added 4-methylbenzenesulfonic acid (0.024 g, 0.140 mmol) and stirred at 120° C. for 4 h under nitrogen atmosphere. After completion of the reaction (monitored by TLC), the reaction mixture was concentrated to a residue. The residue was purified by automated normal-phase chromatography and eluted with ethyl acetate/petroleum ether to give 3-(5-(1,3,4-oxadiazol-2-yl)pyridin-3-yl)-4-(dimethylamino)phenol (300 mg) as an off white solid. MS (ES+APCI) m/z 283.3 (M+1).

Synthesis of 3-(5-(1,3,4-oxadiazol-2-yl)pyridin-3-yl)-4-(dimethylamino)phenyl octylcarbamate (Example-180)

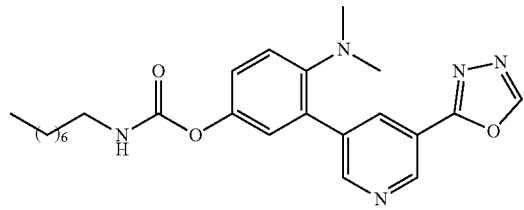

To a stirred solution of 3-(5-(1,3,4-oxadiazol-2-yl)pyridin-3-yl)-4-(dimethylamino)phenol (0.06 g, 0.21 mmol) in anhydrous acetonitrile (2 mL) was added TEA (0.09 mL, 0.64 mmol) and octyl isocyanate (0.04 g, 0.26 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (40 mg) as an off white solid. $^1$H-NMR (400 MHz, MeOD): δ 9.19 (d, J=2.00 Hz, 1H), 9.13 (s, 1H), 8.98 (d, J=2.00 Hz, 1H), 8.71 (t, J=2.00 Hz, 1H), 7.26 (d, J=8.40 Hz, 1H), 7.17-7.12 (m, 2H), 3.19 (t, J=7.20 Hz, 2H), 2.57 (s, 6H), 1.57 (t, J=7.20 Hz, 2H), 1.34 (m, 10H), 0.91 (t, J=7.20 Hz, 3H);

MS (ES+APCI) m/z 438.4 (M+1).

Synthesis of 3-(5-(1,3,4-oxadiazol-2-yl)pyridin-3-yl)-4-(dimethylamino)phenyl (cyclohexylmethyl)carbamate (Example-181)

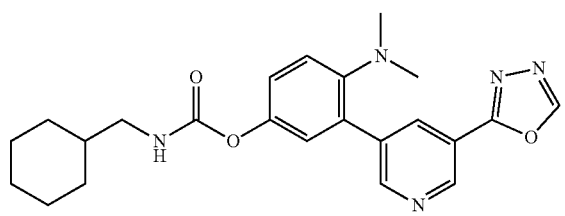 [SMILES: CN(C)c1ccc(OC(=O)NCC2CCCCC2)cc1-c1cncc(-c2nnco2)c1]

To a stirred solution of 3-(5-(1,3,4-oxadiazol-2-yl)pyridin-3-yl)-4-(dimethylamino)phenol (0.06 g, 0.21 mmol) in anhydrous acetonitrile (2 mL) was added TEA (0.09 mL, 0.64 mmol) and cyclohexanemethyl isocyanate (0.04 g, 0.26 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (21 mg) as an off white solid. $^1$H-NMR (400 MHz, MeOD): δ 9.19 (d, J=2.00 Hz, 1H), 9.13 (s, 1H), 8.98 (d, J=2.00 Hz, 1H), 8.71 (t, J=2.00 Hz, 1H), 7.27 (d, J=8.80 Hz, 1H), 7.17-7.12 (m, 2H), 3.04 (d, J=6.80 Hz, 2H), 2.57 (s, 6H), 1.82-1.72 (m, 5H), 1.54 (s, 1H), 1.32-1.24 (m, 3H), 1.00 (t, J=9.60 Hz, 2H), MS (ES+APCI) m/z 422.3 (M+1).

Synthesis of 3-(5-(1,3,4-oxadiazol-2-yl)pyridin-3-yl)-4-(dimethylamino)phenyl benzylcarbamate (Example-182)

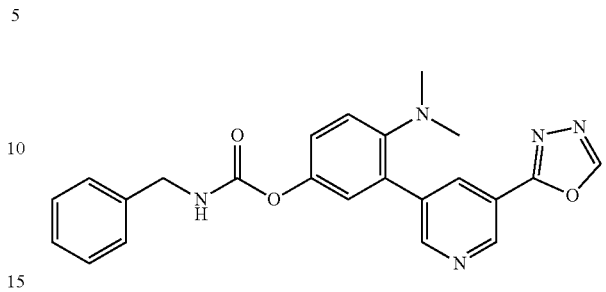

To a stirred solution of 3-(5-(1,3,4-oxadiazol-2-yl)pyridin-3-yl)-4-(dimethylamino)phenol (0.05 g, 0.18 mmol) in anhydrous acetonitrile (2 mL) was added TEA (0.08 mL, 0.53 mmol) and benzyl isocyanate (0.03 g, 0.21 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.10% FA) to yield the target compound (22 mg) as an off white solid. $^1$H-NMR (400 MHz, MeOD): δ 9.19 (d, J=2.00 Hz, 1H), 9.13 (s, 1H), 8.98 (d, J=2.00 Hz, 1H), 8.71 (t, J=2.00 Hz, 1H), 7.36 (m, 4H), 7.27 (m, 2H), 7.19-7.15 (m, 2H), 4.38 (s, 2H), 2.57 (s, 6H); MS (ES+APCI) m/z 416.3 (M+1).

Synthesis of 3-(5-(1,3,4-oxadiazol-2-yl)pyridin-3-yl)-4-(dimethylamino)phenyl cyclopentylcarbamate (Example-183)

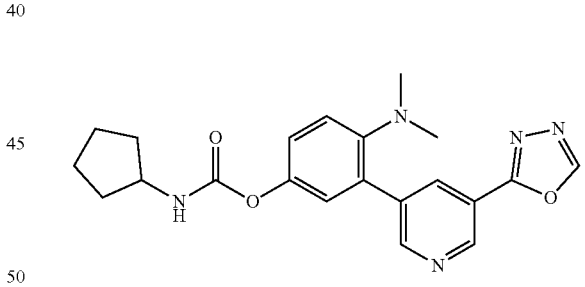

To a stirred solution of 3-(5-(1,3,4-oxadiazol-2-yl)pyridin-3-yl)-4-(dimethylamino)phenol (0.06 g, 0.21 mmol) in anhydrous acetonitrile (2 mL) was added TEA (0.09 mL, 0.64 mmol) and cyclopentyl isocyanate (0.03 g, 0.26 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (40 mg) as an off white solid. $^1$H-NMR (400 MHz, MeOD): δ 9.19 (d, J=2.00 Hz, 1H), 9.13 (s, 1H), 8.98 (d, J=2.00 Hz, 1H), 8.71 (t, J=2.00 Hz, 1H), 7.26 (d, J=8.80 Hz, 1H), 7.17-7.12 (m, 2H), 4.00-3.94 (m, 1H), 2.57 (s, 6H), 1.99-0.95 (m, 2H), 1.79-1.75 (m, 2H), 1.65-1.54 (m, 4H); MS (ES+APCI) m/z 393.1 (M+1).

Synthesis of 3-(5-(1,3,4-oxadiazol-2-yl)pyridin-3-yl)-4-(dimethylamino)phenyl cyclohexylcarbamate (Example-184)

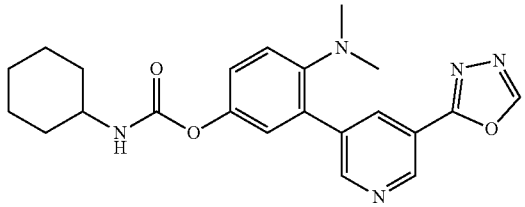 [SMILES: CN(C)c1ccc(OC(=O)NC2CCCCC2)cc1-c1cncc(-c2nnco2)c1]

To a stirred solution of 3-(5-(1,3,4-oxadiazol-2-yl)pyridin-3-yl)-4-(dimethylamino)phenol (0.06 g, 0.21 mmol) in anhydrous acetonitrile (2 mL) was added TEA (0.09 mL, 0.64 mmol) and cyclohexyl isocyanate (0.03 g, 0.25 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (40 mg) as an off white solid. ¹HNMR (400 MHz, MeOD) δ 9.19 (d, J=2.00 Hz, 2H), 8.98 (d, J=2.00 Hz, 1H), 8.71 (t, J=2.00 Hz, 1H), 7.26 (d, J=8.80 Hz, 1H), 7.16-7.12 (m, 2H), 3.48-3.42 (m, 1H), 2.57 (s, 6H), 1.98-1.64 (m, 6H), 1.43-1.29 (m, 4H); MS (ES+APCI) m/z 408.2 (M+1).

Synthesis of 3-(5-(1,3,4-oxadiazol-2-yl)pyridin-3-yl)-4-(dimethylamino)phenyl cycloheptylcarbamate (Example-185)

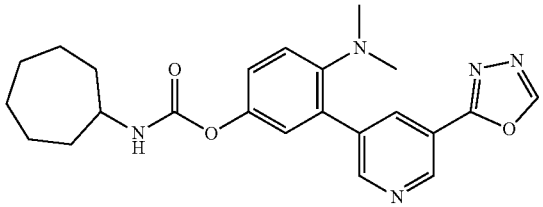 [SMILES: CN(C)c1ccc(OC(=O)NC2CCCCCC2)cc1-c1cncc(-c2nnco2)c1]

To a stirred solution of 3-(5-(1,3,4-oxadiazol-2-yl)pyridin-3-yl)-4-(dimethylamino)phenol (0.06 g, 0.21 mmol) in anhydrous acetonitrile (2 mL) was added TEA (0.09 mL, 0.64 mmol) and cycloheptyl isocyanate (0.04 g, 0.26 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (16 mg) as an off white solid. ¹H-NMR (400 MHz, MeOD): δ 9.19 (d, J=2.00 Hz, 1H), 9.13 (s, 1H), 8.98 (d, J=2.00 Hz, 1H), 8.71 (t, J=2.00 Hz, 1H), 7.26 (d, J=8.80 Hz, 1H), 7.16-7.12 (m, 2H), 4.00-3.94 (m, 1H), 2.57 (s, 6H), 2.01-1.97 (m, 2H), 1.73-1.57 (in, 10H); MS (ES+APCI) m/z 422.3 (M+1).

Synthesis of ethyl 5-(5-hydroxy-2-(methylthio)phenyl)nicotinate

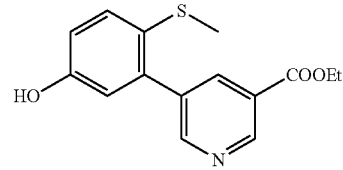 [SMILES: CCOC(=O)c1cncc(-c2cc(O)ccc2SC)c1]

To a stirred solution of ethyl 5-(4,4,5,5-tetramethyl-1,3,2-dioxaborolan-2-yl)nicotinate (0.348 g, 1.255 mmol) in 1,4-dioxane (4 mL) and water (0.45 mL) was added 3-bromo-4-(methylthio)phenol (0.25 g, 1.141 mmol) and potassium carbonate (0.473 g, 3.42 mmol) at RT. The reaction mixture was degassed for 15 minutes then Pd(dppf)Cl₂ (0.066 g, 0.057 mmol) was added. The reaction mixture was stirred at 80° C. for 4 h under nitrogen atmosphere. After completion of the reaction (monitored by TLC), the reaction mixture was cooled to RT and then the solvent was evaporated under reduced pressure. The residue was dissolved in ethyl acetate, washed with water followed by brine. The organic layer was dried over sodium sulfate then evaporated under reduced pressure. The residue was purified by automated normal-phase chromatography and eluted with ethyl acetate/petroleum ether to give ethyl 5-(5-hydroxy-2-(methylthio)phenyl)nicotinate (230 mg) as a yellow solid. MS (ES+APCI) m/z 290.1 (M+1).

Synthesis of 5-(5-hydroxy-2-(methylthio)phenyl)nicotinohydrazide

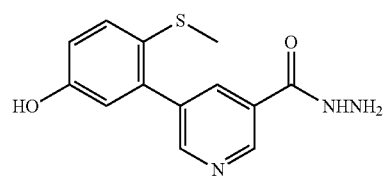 [SMILES: CSc1ccc(O)cc1-c1cncc(C(=O)NN)c1]

To a stirred solution of ethyl 5-(5-hydroxy-2-(methylthio)phenyl)nicotinate (0.23 g, 0.23 g) in ethanol (5 mL) was added hydrazine hydrate (1.5 mL) at RT. The reaction mixture was stirred at 60° C. for 15 h. After completion of the reaction (monitored by TLC), the resulting mixture was concentrated to a residue. The residue was co-evaporated with toluene to remove the residual water and repeated the toluene co-evaporation process for 3 to 4 times to give 5-(5-hydroxy-2-(methylthio)phenyl)nicotinohydrazide (230 mg) which was used for next step without further purification. MS (ES+APCI) m/z 276.2 (M+1).

Synthesis of 3-(5-(1,3,4-oxadiazol-2-yl)pyridin-3-yl)-4-(methylthio)phenol

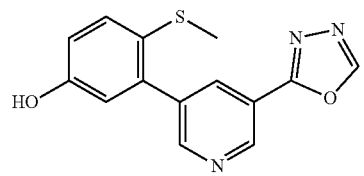 [SMILES: CSc1ccc(O)cc1-c1cncc(-c2nnco2)c1]

To a stirred solution of 5-(5-hydroxy-2-(methylthio)phenyl)nicotinohydrazide (0.23 g, 10.835 mmol) in triethyl orthoformate (4.25 mL) was added 4-methylbenzenesulfonic acid (0.014 g, 0.084 mmol) and stirred at 120° C. for 4 h under nitrogen atmosphere. After completion of the reaction (monitored by TLC), the reaction mixture was concentrated to a residue. The residue was purified by automated normal-phase chromatography and eluted with ethyl acetate/petroleum ether to give 3-(5-(1,3,4-oxadiazol-2-yl)pyridin-3-yl)-4-(methylthio)phenol (150 mg) as an off white solid. MS (ES+APCI) m/z 286.1 (M+1).

Synthesis of 3-(5-(1,3,4-oxadiazol-2-yl)pyridin-3-yl)-4-(dimethylamino)phenyl octylcarbamate (Example-186)

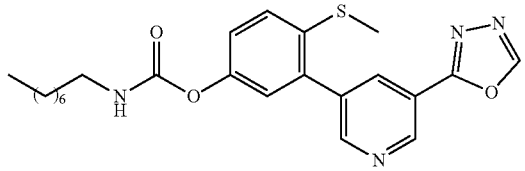

To a stirred solution of 3-(5-(1,3,4-oxadiazol-2-yl)pyridin-3-yl)-4-(methylthio)phenol (0.05 g, 0.175 mmol) in anhydrous acetonitrile (2 mL) was added TEA (0.036 mL, 0.263 mmol) and octyl isocyanate (0.033 g, 0.210 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (20 mg) as an off white solid. $^1$H-NMR (400 MHz, MeOD): δ 9.27 (d, J=2.40 Hz, 1H), 9.14 (s, 1H), 8.83 (d, J=2.00 Hz, 1H), 8.55 (t, J=2.00 Hz, 1H), 7.52 (d, J=8.40 Hz, 1H), 7.25 (dd, J=2.40, 8.60 Hz, 1H), 7.15 (d, J=2.80 Hz, 1H), 3.21-3.18 (m, 2H), 2.43 (s, 3H), 1.61-1.54 (m, 2H), 1.42-1.32 (m, 10H), 0.91 (t, J=6.80 Hz, 3H); MS (ES+APCI) m/z 441.4 (M+1).

Synthesis of 3-(5-(1,3,4-oxadiazol-2-yl)pyridin-3-yl)-4-(methylthio)phenyl (cyclohexylmethyl) carbamate (Example-187)

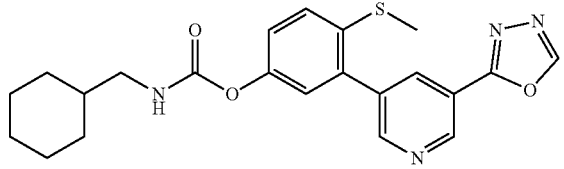 [SMILES: CSc1ccc(OC(=O)NCC2CCCCC2)cc1-c1cncc(-c2nnco2)c1]

To a stirred solution of 3-(5-(1,3,4-oxadiazol-2-yl)pyridin-3-yl)-4-(methylthio)phenol (0.05 g, 0.175 mmol) in anhydrous acetonitrile (2 mL) was added TEA (0.034 mL, 0.263 mmol) and cyclohexanemethyl isocyanate (0.03 g, 0.210 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (2.5 mg) as an off white solid. $^1$H-NMR (400 MHz, MeOD): δ 9.26 (d, J=2.00 Hz, 1H), 9.13 (s, 1H), 8.83 (d, J=2.00 Hz, 1H), 8.55 (t, J=2.40 Hz, 1H), 7.52 (d, J=8.40 Hz, 1H), 7.25 (dd, J=2.40, 8.60 Hz, 1H), 7.16 (d, J=2.40 Hz, 1H), 3.04 (d, J=6.80 Hz, 2H), 2.43 (s, 3H), 1.82-1.00 (m, 11H); MS (ES+APCI) m/z 425.3 (M+1).

Synthesis of 3-(5-(1,3,4-oxadiazol-2-yl)pyridin-3-yl)-4-(methylthio)phenyl benzylcarbamate (Example-188)

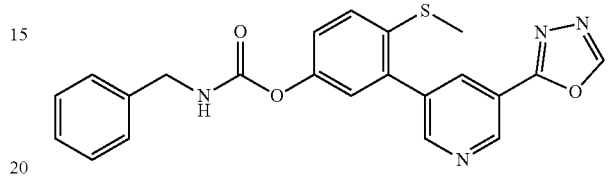

To a stirred solution of 3-(5-(1,3,4-oxadiazol-2-yl)pyridin-3-yl)-4-(methylthio)phenol (0.05 g, 0.175 mmol) in anhydrous acetonitrile (2 mL) was added TEA (0.037 mL, 0.263 mmol) and benzyl isocyanate (0.028 g, 0.210 mmol) at RT under nitrogen atmosphere. The reaction mixture was stirred RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (15.6 mg) as an off white solid. $^1$H-NMR (400 MHz, MeOD): δ 9.26 (d, J=2.00 Hz, 1H), 9.13 (s, 1H), 8.83 (d, J=2.00 Hz, 1H), 8.55 (t, J=2.00 Hz, 1H), 7.52 (d, J=8.80 Hz, 1H), 7.36-7.27 (m, 6H), 7.18 (d, J=2.80 Hz, 1H), 4.39 (s, 2H), 2.43 (s, 3H); MS (ES+APCI) m/z 419.3 (M+1).

Synthesis of 3-(5-(1,3,4-oxadiazol-2-yl)pyridin-3-yl)-4-(methylthio)phenyl cyclopentylcarbamate (Example-189)

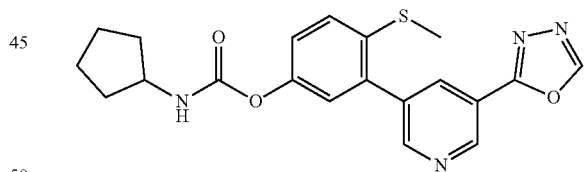

To a stirred solution of 3-(5-(1,3,4-oxadiazol-2-yl)pyridin-3-yl)-4-(methylthio)phenol (0.05 g, 0.175 mmol) in anhydrous acetonitrile (2 mL) was added TEA (0.038 mL, 0.263 mmol) and cyclopentyl isocyanate (0.023 g, 0.210 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (15 mg) as an off white solid. $^1$H-NMR (400 MHz, MeOD): δ 9.26 (d, J=2.00 Hz, 1H), 9.14 (s, 1H), 8.83 (d, J=2.40 Hz, 1H), 8.55 (t, J=2.00 Hz, 1H), 7.52 (d, J=8.40 Hz, 1H), 7.25 (dd, J=2.80, 8.60 Hz, 1H), 7.15 (d, J=2.80 Hz, 1H), 4.01-3.94 (m, 1H), 2.42 (s, 3H), 1.99-1.53 (m, 8H); MS (ES+APCI) m/z 397.3 (M+1).

Synthesis of 3-(5-(1,3,4-oxadiazol-2-yl)pyridin-3-yl)-4-(methylthio)phenyl cyclohexylcarbamate (Example-190)

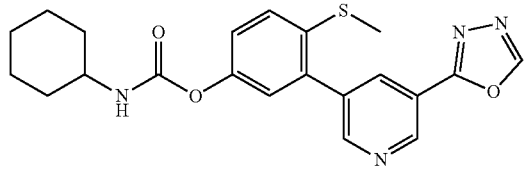 [SMILES: CSc1ccc(OC(=O)NC2CCCCC2)cc1-c1cncc(-c2nnco2)c1]

To a stirred solution of 3-(5-(1,3,4-oxadiazol-2-yl)pyridin-3-yl)-4-(methylthio)phenol (0.05 g, 0.175 mmol) in anhydrous acetonitrile (2 mL) was added TEA (0.034 mL, 0.263 mmol) and cyclohexyl isocyanate (0.026 g, 0.210 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (25 mg) as an off white solid. $^1$HNMR (400 MHz, MeOD): δ 9.26 (d, J=2.00 Hz, 1H), 9.14 (s, 1H), 8.83 (d, J=2.40 Hz, 1H), 8.55 (t, J=2.40 Hz, 1H), 7.52 (d, J=8.80 Hz, 1H), 7.25 (dd, J=2.40, 8.60 Hz, 1H), 7.15 (d, J=2.40 Hz, 1H), 3.51-3.47 (m, 1H), 2.42 (s, 3H), 1.98-0.89 (m, 10H); MS (ES+APCI) m/z 411.1 (M+1).

Synthesis of 3-(5-(1,3,4-oxadiazol-2-yl)pyridin-3-yl)-4-(methylthio)phenyl cycloheptylcarbamate (Example-191)

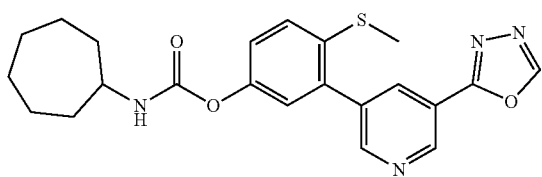 [SMILES: CSc1ccc(OC(=O)NC2CCCCCC2)cc1-c1cncc(-c2nnco2)c1]

To a stirred solution of 3-(5-(1,3,4-oxadiazol-2-yl)pyridin-3-yl)-4-(methylthio)phenol (0.05 g, 0.175 mmol) in anhydrous acetonitrile (2 mL) was added TEA (0.037 mL, 0.263 mmol) and cycloheptyl isocyanate (0.03 g, 0.210 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (14 mg) as an off white solid. $^1$H-NMR (400 MHz, MeOD): δ 9.26 (d, J=2.00 Hz, 1H), 9.14 (s, 1H), 8.83 (d, J=2.00 Hz, 1H), 8.55 (t, J=2.00 Hz, 1H), 7.51 (d, J=8.80 Hz, 1H), 7.25 (dd, J=2.80, 8.60 Hz, 1H), 7.15 (d, J=2.40 Hz, 1H), 3.70-3.65 (m, 1H), 2.42 (s, 3H), 2.01-1.97 (m, 2H), 1.75-1.50 (m, 10H); MS (ES+APCI) m/z 425.3 (M+1).

Synthesis of ethyl 5-(2-fluoro-5-hydroxyphenyl)nicotinate

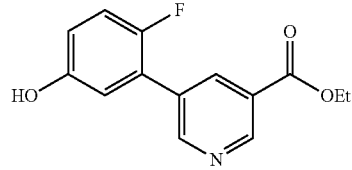 [SMILES: CCOC(=O)c1cncc(-c2cc(O)ccc2F)c1]

To a stirred solution of ethyl 5-(4,4,5,5-tetramethyl-1,3,2-dioxaborolan-2-yl)nicotinate (1.37 g, 4.94 mmol) in ethanol (36 mL) and toluene (4 mL) was added 3-bromo-4-fluorophenol (0.93 g, 4.94 mmol) and Na$_2$CO$_3$ (1.54 g, 14.78 mmol) at RT. The reaction mixture was degassed for 15 minutes then Pd(PPh$_3$)$_4$ (0.57 g, 0.493 mmol) was added. The reaction mixture was stirred at 90° C. for 12 h under nitrogen atmosphere. After completion of the reaction (monitored by TLC), the reaction mixture was cooled to RT and then the solvent was evaporated under reduced pressure. The residue was dissolved in ethyl acetate, washed with water followed by brine. The organic layer was dried over sodium sulfate then evaporated under reduced pressure. The residue was purified by automated normal-phase chromatography and eluted with ethyl acetate/petroleum ether to give ethyl 5-(2-fluoro-5-hydroxyphenyl)nicotinate (820 mg) as an off white solid. MS (ES+APCI) m/z 262.3 (M+1).

5-(2-fluoro-5-hydroxyphenyl)nicotinohydrazide

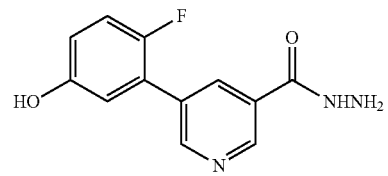 [SMILES: NNC(=O)c1cncc(-c2cc(O)ccc2F)c1]

To a stirred solution of 5-(2-fluoro-5-hydroxyphenyl)nicotinate (1.1 g, 4.21 mmol) in ethanol (10 mL) was added hydrazine hydrate (1.9 g, 24.81 mmol) at RT. The reaction mixture was stirred at 50° C. for 15 h. After completion of the reaction (monitored by TLC), the resulting mixture was concentrated to a residue. The residue was co-evaporated with toluene to remove the residual water and repeated the toluene co-evaporation process for 3 to 4 times to give 5-(2-fluoro-5-hydroxyphenyl)nicotinohydrazide (810 mg), which was used for next step without purification. MS (ES+APCI) m/z 248.2 (M+1).

Synthesis of 3-(5-(1,3,4-oxadiazol-2-yl)pyridin-3-yl)-4-fluorophenol

A suspension of ethyl 5-(2-fluoro-5-hydroxyphenyl)nicotinohydrazide (1 g, 4.0 mmol) in triethyl orthoformate (10 mL) was added p-toluenesulfonic acid (68 mg, 0.4 mmol) and stirred at 120° C. for 4 h under nitrogen atmosphere. After completion of the reaction (monitored by TLC), the reaction mixture was cooled to RT and concentrated to a residue. The residue was purified by automated normal-phase chromatography and eluted with ethyl acetate/petroleum ether to give 3-(5-(1,3,4-oxadiazol-2-yl)pyridin-3-yl)-4-fluorophenol (860 mg). MS (ES+APCI) m/z 258.2 (M+1).

Synthesis of 3-(5-(1,3,4-oxadiazol-2-yl)pyridin-3-yl)-4-fluorophenyl cyclohexylcarbamate (Example-192)

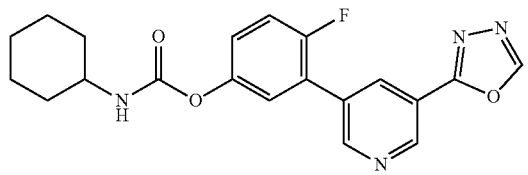 [SMILES: O=C(NC1CCCCC1)Oc1ccc(F)c(-c2cncc(-c3nnco3)c2)c1]

To a stirred solution of 3-(5-(1,3,4-oxadiazol-2-yl)pyridin-3-yl)-4-fluorophenol (0.1 g, 0.39 mmol) in anhydrous acetonitrile (2 mL) was added TEA, (0.05 mL, 0.39 mmol) and cyclohexyl isocyanate (0.05 g, 0.46 mmol) at RT under a nitrogen atmosphere. The reaction mixture was stirred at RT for 10 minutes and then heated to 75° C. for 12 h. The progress of the reaction was monitored by TLC. After completion of the reaction, the reaction mixture was concentrated to a residue under reduced pressure. The crude product was purified by flash column chromatography on silica gel, eluting with a gradient of hexane/ethyl acetate (40-60% EtOAc) to yield the target compound (45 mg) as an off white solid. $^1$H NMR (400 MHz, DMSO-d6) δ 9.49 (s, 1H), 9.24 (d, J=2.0 Hz, 1H), 9.02 (t, J=1.9 Hz, 1H), 8.54 (t, J=1.8 Hz, 1H), 7.81 (d, J=7.9 Hz, 1H), 7.23-7.70 (m, 3H), 1.74-1.97 (m, 2H), 1.57 (d, J=12.6 Hz, 1H), 1.16-1.42 (m, 6H).

Synthesis of 3-(5-(1,3,4-oxadiazol-2-yl)pyridin-3-yl)-4-fluorophenyl (4-methylcyclohexyl)carbamate (Example-193)

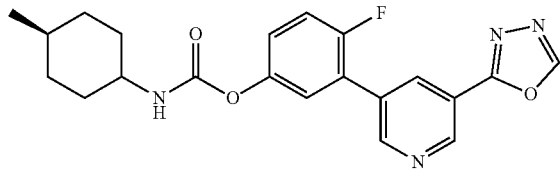

To a stirred solution of 3-(5-(1,3,4-oxadiazol-2-yl)pyridin-3-yl)-4-fluorophenol (0.1 g, 0.39 mmol) in anhydrous acetonitrile (2 mL) was added TEA, (0.05 mL, 0.39 mmol) and trans-4-methylcyclohexyl isocyanate (0.06 g, 0.46 mmol) at RT under a nitrogen atmosphere. The reaction mixture was stirred at RT for 10 minutes, then heated to 75° C. and stirred for 12 h. After completion of the reaction, monitored by TLC, the reaction mixture was concentrated under reduced pressure to a residue. The residue was purified by flash column chromatography on silica gel, eluting with a gradient of hexane/ethyl acetate (40-60% EtOAc) to yield the target compound (45 mg) as an off white solid. $^1$H NMR (400 MHz, DMSO-d6) δ 9.49 (s, 1H), 9.24 (d, J=2.0 Hz, 1H), 9.02 (t, J=1.9 Hz, 1H), 8.54 (dt, J=2.2, 1.0 Hz, 1H), 7.77 (d, J=7.9 Hz, 1H), 7.35-7.66 (m, 2H), 7.27 (ddd, J=8.9, 4.2, 2.9 Hz, 1H), 1.86 (dd, J=13.2, 3.7 Hz, 3H), 1.68 (d, J=13.1 Hz, 2H), 1.26 (qd, J=12.9, 3.3 Hz, 3H), 0.99 (td, J=12.6, 3.4 Hz, 3H), 0.87 (d, J=6.5 Hz, 3H).

Synthesis of 3-(5-(1,3,4-oxadiazol-2-yl)pyridin-3-yl)-4-fluorophenyl cycloheptylcarbamate (Example-194)

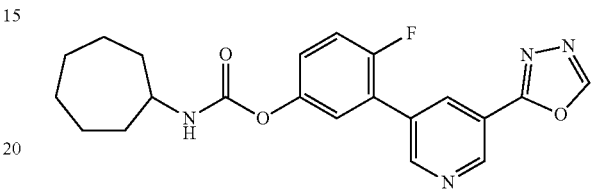

To a stirred solution of 3-(5-(1,3,4-oxadiazol-2-yl)pyridin-3-yl)-4-fluorophenol (0.1 g, 0.39 mmol) in anhydrous acetonitrile (2 mL) was added TEA, (0.05 mL, 0.39 mmol) and cycloheptyl isocyanate (0.06 g, 0.46 mmol) at RT under a nitrogen atmosphere. The reaction mixture was stirred at RT for 10 minutes and then heated to 75° C., where it was stirred for 12 h. After completion of the reaction, monitored by TLC. The reaction mixture was concentrated under reduced pressure to a residue. The residue was purified by flash column chromatography on silica gel, eluting with a gradient of hexane/ethyl acetate (40-60% EtOAc) to yield the target compound (45 mg) as an off white solid. $^1$H NMR (400 MHz, DMSO-d6) δ 9.49 (s, 1H), 9.24 (d, J=2.0 Hz, 1H), 9.02 (t, J=1.9 Hz, 1H), 8.54 (dt, J=3.3, 1.6 Hz, 1H), 7.84 (d, J=7.9 Hz, 1H), 7.53 (dd, J=6.6, 2.9 Hz, 1H), 7.42 (dd, J=10.3, 8.9 Hz, 1H), 7.27 (ddd, J=8.9, 4.2, 2.9 Hz, 1H), 3.45-3.66 (m, 1H), 1.78-1.93 (m, 2H), 1.32-1.75 (m, 10H).

Synthesis of ethyl 5-(3-fluoro-5-hydroxyphenyl)nicotinate

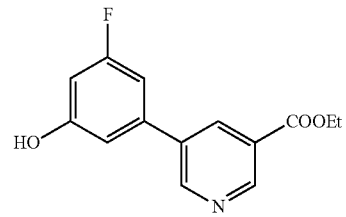 [SMILES: CCOC(=O)c1cncc(-c2cc(O)cc(F)c2)c1]

To a stirred solution of ethyl 5-(4,4,5,5-tetramethyl-1,3,2-dioxaborolan-2-yl)nicotinate (1.37 g, 4.94 mmol) in ethanol (36 mL) and toluene (4 mL) was added 3-bromo-5-fluorophenol (0.93 g, 4.94 mmol) and Na$_2$CO$_3$ (1.54 g, 14.78 mmol) at RT. The reaction mixture was degassed for 15 minutes then Pd(PPh$_3$)$_4$ (0.57 g, 0.493 mmol) was added. The reaction mixture was stirred at 90° C. for 12 h under nitrogen atmosphere. After completion of the reaction (monitored by TLC), the reaction mixture was cooled to RT and then the solvent was evaporated under reduced pressure. The residue was dissolved in ethyl acetate, washed with water followed by brine. The organic layer was dried over sodium sulfate then evaporated under reduced pressure. The residue was purified by automated normal-phase chromatography and eluted with ethyl acetate/petroleum ether to give 5-(3-fluoro-5-hydroxyphenyl)nicotinate (800 mg) as an off white solid. MS (ES+APCI) m/z 262.3 (M+1).

5-(3-fluoro-5-hydroxyphenyl)nicotinohydrazide

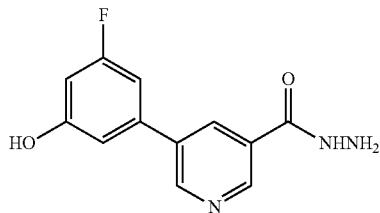 [SMILES: NNC(=O)c1cncc(-c2cc(O)cc(F)c2)c1]

To a stirred solution of 5-(3-fluoro-5-hydroxyphenyl)nicotinate (1.1 g, 4.21 mmol) in ethanol (10 mL) was added hydrazine hydrate (1.9 g, 24.81 mmol) at RT. The reaction mixture was stirred at 50° C. for 15 h. After completion of the reaction (monitored by TLC), the resulting mixture was concentrated to a residue. The residue was co-evaporated with toluene to remove the residual water and repeated the toluene co-evaporation process for 3 to 4 times to give 5-(3-fluoro-5-hydroxyphenyl)nicotinohydrazide (800 mg), which was used for next step without purification. MS (ES+APCI) m/z 248.2 (M+1).

Synthesis of 3-(5-(1,3,4-oxadiazol-2-yl)pyridin-3-yl)-5-fluorophenol

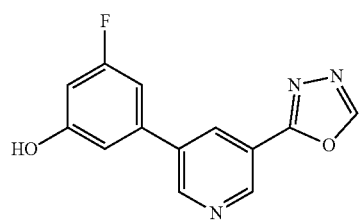

A suspension of ethyl 5-(3-fluoro-5-hydroxyphenyl)nicotinate (1 g, 4.0 mmol) in triethyl orthoformate (10 mL) was added p-toluenesulfonic acid (68 mg, 0.4 mmol) and stirred at 120° C. for 4 h under nitrogen atmosphere. After completion of the reaction (monitored by TLC), the reaction mixture was cooled to RT and concentrated to a residue. The residue was purified by automated normal-phase chromatography and eluted with ethyl acetate/petroleum ether to give 3-(5-(1,3,4-oxadiazol-2-yl)pyridin-3-yl)-5-methoxyphenol (850 mg). $^1$H NMR (400 MHz, DMSO-d6) δ 10.22 (s, 1H), 9.50 (s, 1H), 9.21 (d, J=2.00 Hz, 1H), 9.10 (d, J=2.00 Hz, 1H), 8.54 (t, J=2.00 Hz, 1H), 7.19-7.16 (m, 1H), 7.04 (t, J=1.60 Hz, 1H), 6.71-6.68 (m, 1H); MS (ES+APCI) m/z 258.1 (M+1).

Synthesis of 3-(5-(1,3,4-oxadiazol-2-yl)pyridin-3-yl)-5-fluorophenyl octylcarbamate (Example-195)

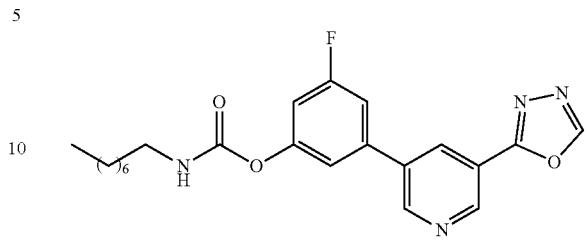

To a stirred solution of 3-(5-(1,3,4-oxadiazol-2-yl)pyridin-3-yl)-5-fluorophenol (0.1 g, 0.39 mmol) in anhydrous acetonitrile (2.5 mL) was added TEA (0.08 mL, 0.58 mmol) and n-octyl isocyanate (0.06 g, 0.39 mmol) at RT under nitrogen atmosphere. The reaction mixture was stirred at RT for 10 minutes and then stirred at 75° C. for 3 h. An additional amount of n-octyl isocyanate (0.02 g, 0.12 mmol) was added to the reaction mixture and the resulting mixture was stirred for an additional 12 h. After completion of the reaction (monitored by LCMS), the reaction mixture was concentrated to a residue. The residue was purified by preparative HPLC (0.1% FA) to yield the target compound (45 mg) as an off white solid. $^1$H NMR (400 MHz, DMSO-d6) δ 9.51 (s, 1H), 9.23 (d, J=2.00 Hz, 1H), 9.18 (d, J=2.40 Hz, 1H), 8.65 (t, J=2.00 Hz, 1H), 7.92 (t, J=5.60 Hz, 1H), 7.68-7.65 (m, 1H), 7.52 (s, 1H), 7.20-7.17 (m, 1H), 3.11-3.06 (m, 1H), 1.49 (t, J=7.20 Hz, 2H), 1.29-1.27 (m, 10H), 0.86 (t, J=6.80 Hz, 3H); MS (ES+APCI) m/z 413.3 (M+1).

Synthesis of 3-(5-(1,3,4-oxadiazol-2-yl)pyridin-3-yl)-5-fluorophenyl benzylcarbamate (Example-196)

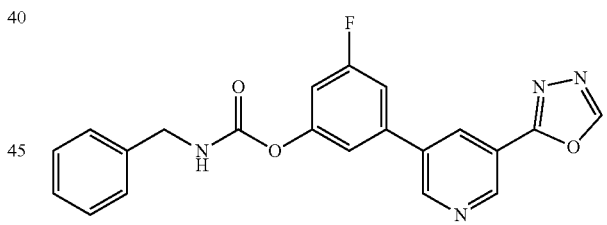

To a stirred solution of 3-(5-(1,3,4-oxadiazol-2-yl)pyridin-3-yl)-5-fluorophenol (0.1 g, 0.39 mmol) in anhydrous acetonitrile (2.5 mL) was added TEA (0.08 mL, 0.58 mmol) and benzyl isocyanate (0.05 g, 0.39 mmol) at RT under nitrogen atmosphere. The reaction mixture was stirred at RT for 10 minutes and then stirred at 75° C. for 3 h. An additional amount of benzyl isocyanate (0.02 g, 0.12 mmol) was added to the reaction mixture and the resulting mixture was stirred for an additional 12 h. After completion of the reaction (monitored by TLC), the reaction mixture was concentrated to a residue. The residue was purified by preparative HPLC (0.1% FA) to yield the target compound (30 mg) as an off white solid. $^1$H NMR (400 MHz, DMSO-d6) δ 9.52 (s, 1H), 9.24 (d, J=2.00 Hz, 1H), 9.19 (d, J=2.40 Hz, 1H), 8.67 (t, J=2.40 Hz, 1H), 8.50 (t, J=6.00 Hz, 1H), 7.71-7.67 (m, 1H), 7.58 (t, J=1.60 Hz, 1H), 7.41-7.34 (m, 4H), 7.30-7.26 (m, 2H), 4.32 (d, J=6.00 Hz, 2H); MS (ES+APCI) m/z 391.3 (M+1).

Synthesis of 3-(5-(1,3,4-oxadiazol-2-yl)pyridin-3-yl)-5-fluorophenyl cyclohexylcarbamate

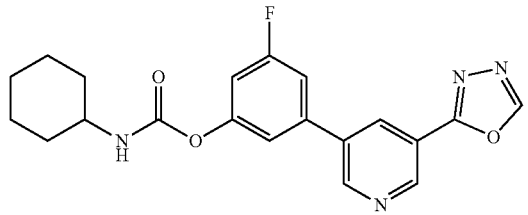 [SMILES: O=C(NC1CCCCC1)Oc1cc(F)cc(-c2cncc(-c3nnco3)c2)c1]

To a stirred solution of 3-(5-(1,3,4-oxadiazol-2-yl)pyridin-3-yl)-5-fluorophenol (0.1 g, 0.39 mmol) in anhydrous acetonitrile (2.5 mL) was added TEA (0.08 mL, 0.58 mmol) and cyclohexyl isocyanate (0.05 g, 0.39 mmol) at RT under nitrogen atmosphere. The reaction mixture was stirred at RT for 10 minutes and then stirred at 75° C. for 3 h. An additional amount of cyclohexyl isocyanate (0.02 g, 0.12 mmol) was added to the reaction mixture and the resulting mixture was stirred for an additional 12 h. After completion of the reaction (monitored by LCMS), the reaction mixture was concentrated to a residue. The residue was purified by preparative HPLC (0.1% FA) to yield the target compound (45 mg) as an off white solid. $^1$H NMR (400 MHz, DMSO-d6) δ 9.27 (d, J=2.00 Hz, 1H), 9.16 (s, 1H), 9.08 (d, J=2.00 Hz, 1H), 8.72 (t, J=2.00 Hz, 1H), 7.48-7.41 (m, 2H), 7.11-7.07 (m, 1H), 3.50-3.46 (m, 1H), 1.23-2.00 (in, 10H); MS (ES+APCI) m/z 383.3 (M+1).

Synthesis of 3-(5-(1,3,4-oxadiazol-2-yl)pyridin-3-yl)-5-fluorophenyl cycloheptylcarbamate (Example-198)

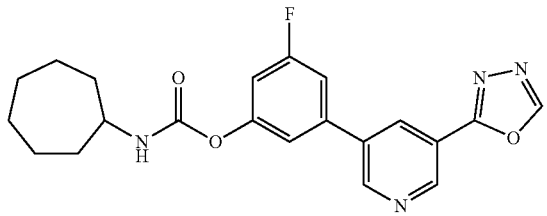 [SMILES: O=C(NC1CCCCCC1)Oc1cc(F)cc(-c2cncc(-c3nnco3)c2)c1]

To a stirred solution of 3-(5-(1,3,4-oxadiazol-2-yl)pyridin-3-yl)-5-fluorophenol (0.1 g, 0.39 mmol) in anhydrous acetonitrile (2.5 mL) was added TEA (0.08 mL, 0.58 mmol) and cycloheptyl isocyanate (0.054 g, 0.39 mmol) at RT under nitrogen atmosphere. The reaction mixture was stirred at RT for 10 minutes and then stirred at 75° C. for 3 h. An additional amount of cycloheptyl isocyanate (0.02 g, 0.12 mmol) was added to the reaction mixture and the resulting mixture was stirred for an additional 12 h. After completion of the reaction (monitored by LCMS), the reaction mixture was concentrated to a residue. The residue was purified by preparative HPLC (0.1% FA) and further recrystallized from ethanol to yield the target compound (30 mg) as an off white solid. $^1$H NMR (400 MHz, DMSO-d6) δ 9.52 (s, 1H), 9.23 (d, J=2.00 Hz, 1H), 9.18 (d, J=2.00 Hz, 1H), 8.66 (t, J=2.00 Hz, 1H), 7.94 (d, J=8.00 Hz, 1H), 7.68-7.65 (m, 1H), 7.53 (s, 1H), 7.21-7.17 (m, 1H), 3.60-3.53 (m, 1H), 1.91-1.40 (m, 12H); MS (ES+APCI) m/z 397.4 (M+1).

Synthesis of ethyl 5-(5-hydroxy-2-(trifluoromethoxy)phenyl)nicotinate

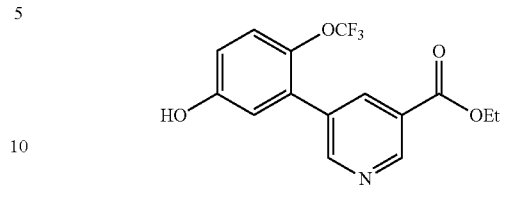

To a stirred solution of ethyl 5-(4,4,5,5-tetramethyl-1,3,2-dioxaborolan-2-yl)nicotinate (1.0 g, 3.61 mmol) in ethanol (36 mL) and toluene (4 mL) was added 3-bromo-4-(trifluoromethoxy)phenol (0.92 g, 3.61 mmol) and Na$_2$CO$_3$ (1.44 g, 10.0 mmol) at RT. The reaction mixture was degassed for 15 minutes then Pd(PPh$_3$)$_4$ (0.41 g, 0.36 mmol) was added. The reaction mixture was stirred at 90° C. for 12 h under nitrogen atmosphere. After completion of the reaction (monitored by TLC), the reaction mixture was cooled to RT and then the solvent was evaporated under reduced pressure. The residue was dissolved in ethyl acetate, washed with water followed by brine. The organic layer was dried over sodium sulfate then evaporated under reduced pressure. The residue was purified by automated normal-phase chromatography and eluted with ethyl acetate/petroleum ether to give ethyl 5-(5-hydroxy-2-(trifluoromethoxy)phenyl)nicotinate (800 mg) as an off white solid. MS (ES+APCI) m/z 328.3 (M+1).

Synthesis of 5-(5-hydroxy-2-(trifluoromethoxy)phenyl)nicotinohydrazide

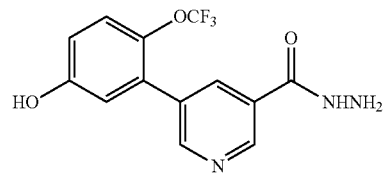 [SMILES: NNC(=O)c1cncc(-c2cc(O)ccc2OC(F)(F)F)c1]

To a stirred solution of ethyl 5-(5-hydroxy-2-(trifluoromethoxy)phenyl)nicotinate (1.1 g, 3.33 mmol) in ethanol (10 mL) was added hydrazine hydrate (1.9 g, 19.99 mmol) at RT. The reaction mixture was stirred at 50° C. for 15 h. After completion of the reaction (monitored by TLC), the resulting mixture was concentrated to a residue. The residue was co-evaporated with toluene to remove the residual water and repeated the toluene co-evaporation process for 3 to 4 times to give 5-(5-hydroxy-2-(trifluoromethoxy)phenyl)nicotinohydrazide (750 mg), which was used for next step without purification. MS (ES+APCI) m/z 341.2 (M+1).

Synthesis of 3-(5-(1,3,4-oxadiazol-2-yl)pyridin-3-yl)-4-(trifluoromethoxy)phenol

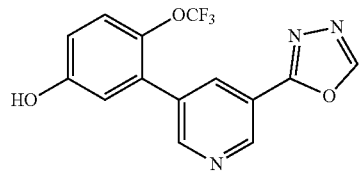 [SMILES: Oc1ccc(OC(F)(F)F)c(-c2cncc(-c3nnco3)c2)c1]

A suspension of 5-(5-hydroxy-2-(trifluoromethoxy)phenyl)nicotinohydrazide (1 g, 4.0 mmol) in triethyl orthoformate (10 mL) was added p-toluenesulfonic acid (68 mg, 0.4 mmol) and stirred at 120° C. for 4 h under nitrogen atmosphere. After completion of the reaction (monitored by TLC), the reaction mixture was cooled to RT and concentrated to a residue. The residue was purified by automated normal-phase chromatography and eluted with ethyl acetate/petroleum ether to give 3-(5-(1,3,4-oxadiazol-2-yl)pyridin-3-yl)-4-(trifluoromethoxy)phenol (800 mg). MS (ES+APCI) m/z 258.2 (M+1).

Synthesis of 3-(5-(1,3,4-oxadiazol-2-yl)pyridin-3-yl)-4-(trifluoromethoxy)phenyl octylcarbamate (Example-199)

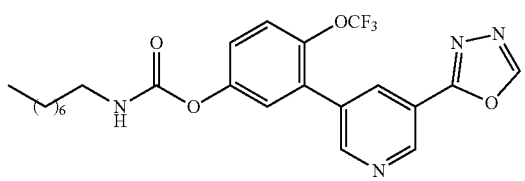

To a stirred solution of 3-(5-(1,3,4-oxadiazol-2-yl)pyridin-3-yl)-4-(trifluoromethoxy)phenol (0.1 g, 0.30 mmol) in anhydrous acetonitrile (2 mL) was added TEA (0.04 mL, 0.30 mmol) and n-octyl isocyanate (0.05 g, 0.37 mmol) at RT under a nitrogen atmosphere. The reaction mixture was stirred at RT for 10 minutes and then heated to 75° C., where it was stirred for 12 h. The completion of the reaction monitored by TLC. The reaction mixture was concentrated to a residue under reduced pressure. The residue was purified by flash column chromatography on silica gel, eluting with a gradient of hexane/ethyl acetate (50-55% EtOAc) to yield the target compound (43 mg) as an off white solid. $^1$H NMR (400 MHz, MeOD) δ 9.19 (d, J=2.0 Hz, 1H), 9.03 (s, 1H), 8.80 (d, J=2.1 Hz, 1H), 8.50 (t, J=2.2 Hz, 1H), 7.44 (d, J=8.8 Hz, 1H), 7.20-7.39 (m, 2H), 3.09 (t, J=7.1 Hz, 2H), 1.10-1.35 (m, 11H), 0.60-0.89 (m, 3H), 1.47 (p, J=7.1 Hz, 2H).

Synthesis of 3-(5-(1,3,4-oxadiazol-2-yl)pyridin-3-yl)-4-(trifluoromethoxy)phenyl cyclohexylcarbamate (Example-200)

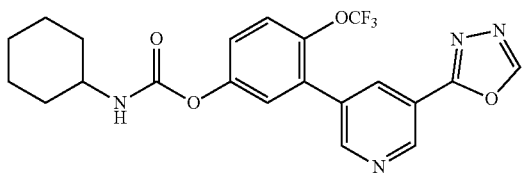 [SMILES: O=C(NC1CCCCC1)Oc1ccc(OC(F)(F)F)c(-c2cncc(-c3nnco3)c2)c1]

To a stirred solution of 3-(5-(1,3,4-oxadiazol-2-yl)pyridin-3-yl)-4-(trifluoromethoxy)phenol (0.1 g, 0.30 mmol) in anhydrous acetonitrile (1 mL) was added TEA (0.04 mL, 0.30 mmol) and cyclohexyl isocyanate (0.04 g, 0.37 mmol) at RT under a nitrogen atmosphere. The reaction mixture was stirred at RT for 10 minutes and then heated at 75° C. for 12 h. After completion of the reaction, monitored by TLC, the reaction mixture was concentrated under reduced pressure to obtain a residue. The residue was purified by flash column chromatography on silica gel, eluting with hexane/EtOAc (gradient 45-55% EtOAc) to yield the target compound (43 mg) as an off white solid. $^1$H NMR (400 MHz, MeOD) δ 9.19 (d, J=2.0 Hz, 1H), 9.03 (s, 1H), 8.80 (d, J=2.1 Hz, 1H), 8.50 (d, J=2.2 Hz, 1H), 7.43 (d, J=8.9 Hz, 1H), 7.13-7.38 (m, 2H), 3.34 (dq, J=7.5, 5.1 Hz, 1H), 1.04-1.35 (m, 5H), 1.46-1.76 (m, 3H), 1.85 (d, J=12.1 Hz, 2H).

Synthesis of 3-(5-(1,3,4-oxadiazol-2-yl)pyridin-3-yl)-4-(trifluoromethoxy)phenyl(4 methylcyclohexyl) carbamate (Example-201)

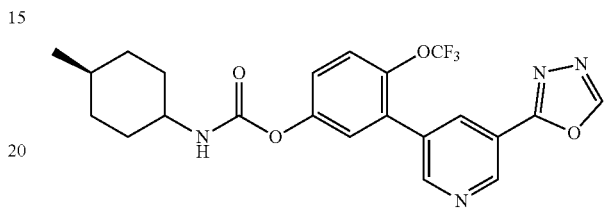

To a stirred solution of 3-(5-(1,3,4-oxadiazol-2-yl)pyridin-3-yl)-4-(trifluoromethoxy)phenol (0.1 g, 0.30 mmol) in anhydrous acetonitrile (1 mL) was added TEA (0.04 mL, 0.30 mmol) and trans-4-methylcyclohexyl isocyanate (0.04 g, 0.37 mmol) at RT under a nitrogen atmosphere. The reaction mixture was stirred at RT for 10 minutes and then heated at 75° C. for 12 h. After completion of the reaction, monitored by TLC, the reaction mixture was concentrated under reduced pressure to obtain a residue. The residue was purified by flash column chromatography on silica gel, eluting with hexane/EtOAc (gradient 45-55% EtOAc) to yield the target compound (43 mg) as an off white solid. $^1$H NMR (400 MHz, MeOD) δ 9.19 (d, J=2.0 Hz, 1H), 9.03 (d, J=0.9 Hz, 1H), 8.79 (d, J=2.1 Hz, 1H), 8.49 (d, J=2.4 Hz, 1H), 7.43 (d, J=8.9 Hz, 1H), 7.12-7.39 (m, 2H), 3.28 (tt, J=11.6, 4.1 Hz, 1H), 1.15-1.37 (m, 3H), 1.60-1.72 (m, 2H), 1.83-1.91 (m, 2H), 0.82 (d, J=6.5 Hz, 3H), 0.89-1.05 (m, 2H).

Synthesis of 3-(5-(1,3,4-oxadiazol-2-yl)pyridin-3-yl)-4-(trifluoromethoxy)phenyl cycloheptylcarbamate (Example-202)

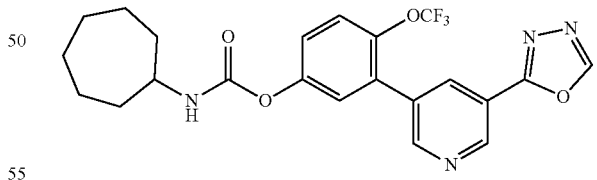

To a stirred solution of 3-(5-(1,3,4-oxadiazol-2-yl)pyridin-3-yl)-4-(trifluoromethoxy)phenol (0.1 g, 0.30 mmol) in anhydrous acetonitrile (1 mL) was added TEA (0.04 mL, 0.30 mmol) and cycloheptyl isocyanate (0.05 g, 0.37 mmol) at RT under a nitrogen atmosphere. The reaction mixture was stirred at RT for 10 minutes and then heated and stirred at 75° C. for 12 h. After completion of the reaction (monitored by TLC), the reaction mixture was concentrated under reduced pressure to a residue. The residue was purified by flash column chromatography on silica gel eluting with a gradient of hexane/EtOAc (50-55% EtOAc) to yield the target compound (43 mg) as an off white solid. ¹H NMR (400 MHz, DMSO-d6) δ 9.01 (d, J=2.1 Hz, 1H), 8.76 (t, J=2.0 Hz, 1H), 8.58 (s, 1H), 8.30 (td, J=2.1, 1.1 Hz, 1H), 7.95 (s, 1H), 7.85 (d, J=7.9 Hz, 1H), 7.54-7.12 (m, 2H), 3.62-3.48 (m, 1H), 1.94-1.78 (m, 2H), 1.70-1.34 (m, 10H).

Synthesis of 3-(5-(1,3,4-oxadiazol-2-yl)pyridin-3-yl)-4-(trifluoromethoxy)phenyl phenylcarbamate (Example-203)

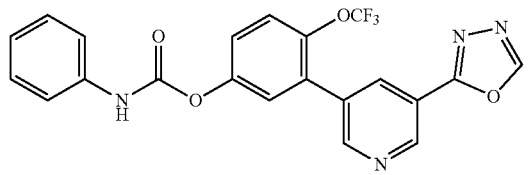 [SMILES: O=C(Nc1ccccc1)Oc1ccc(OC(F)(F)F)c(-c2cncc(-c3nnco3)c2)c1]

To a stirred solution of 3-(5-(1,3,4-oxadiazol-2-yl)pyridin-3-yl)-4-(trifluoromethoxy)phenol (0.1 g, 0.30 mmol) in anhydrous acetonitrile (2 mL) was added TEA (0.04 mL, 0.30 mmol) and phenyl isocyanate (0.04 g, 0.37 mmol) at RT under a nitrogen atmosphere. The reaction mixture was stirred at RT for 10 minutes and then heated to 75° C. and stirred for 12 h. After completion of the reaction (monitored by TLC), the reaction mixture was concentrated under reduced pressure to afford a residue. The residue was purified by flash column chromatography on silica gel, eluting with a gradient of hexane/EtOAc (50-55% EtOAc) to yield the target compound (43 mg) as an off white solid. ¹H NMR (400 MHz, DMSO-d6) δ 10.13 (s, 1H), 9.49 (s, 1H), 9.24 (d, J=2.1 Hz, 1H), 8.90 (d, J=2.2 Hz, 1H), 8.43 (t, J=2.1 Hz, 1H), 7.25-7.56 (m, 2H), 6.91-7.23 (m, 4H), 6.33-6.74 (m, 2H).

Scheme VII

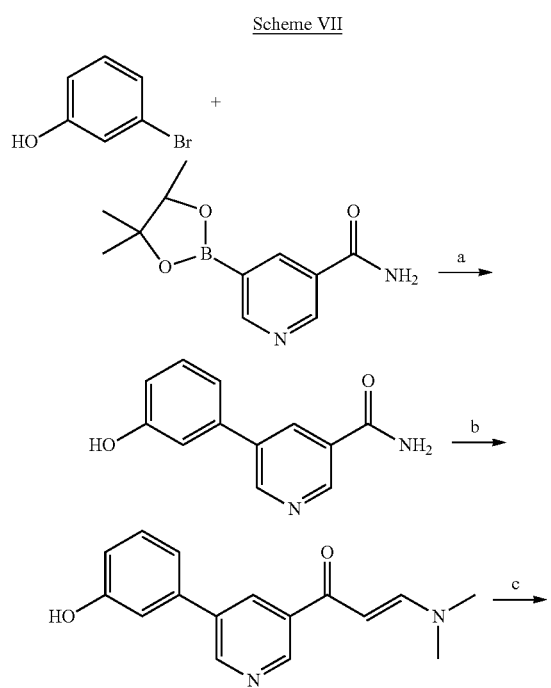

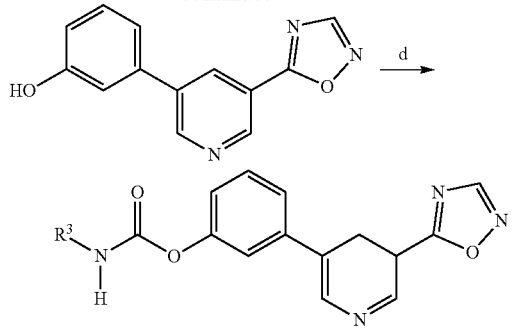

Reagent and Conditions: a) Pd(PPh₃)₄, aq K₂CO₃, 1,4-dioxane, 90° C., 2 h; b) DMF—DMA, Toluene, 100° C., 3 h; c) NH₂—OH, acetate (AcOH), NaOH, 90° C., 3h; d) R²—NCO, TEA, ACN, 75° C., 2-6 h Synthesis of 5-(3-hydroxyphenyl)nicotinamide

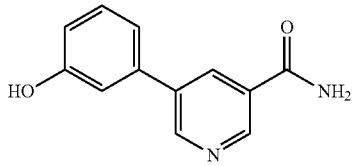 [SMILES: NC(=O)c1cncc(-c2cccc(O)c2)c1]

To a stirred solution of 3-bromophenol (2.0 g, 11.56 mmol) in 1,4-dioxane (20 mL) and water (2 mL) was added 5-(4,4,5,5-tetramethyl-1,3,2-dioxaborolan-2-yl)nicotinamide (3.44 g, 13.87 mmol) and potassium carbonate (3.20 g, 23.12 mmol) at RT. The reaction mixture was degassed for 15 minutes then Pd(PPh₃)₄ (0.67 g, 0.58 mmol) was added. The reaction mixture was stirred at 90° C. for 2 h under nitrogen atmosphere. After completion of the reaction (monitored by TLC), the reaction mixture was cooled to RT and then the solvent was evaporated under reduced pressure. The residue was triturated with methanol and stirred for 20 minutes and the precipitated solid was filtered and dried to give 5-(3-hydroxyphenyl)nicotinamide (1.9 g, as an off white solid. ¹H-NMR (400 MHz, DMSO-d6): δ 9.70 (s, 1H), 9.01-8.95 (m, 2H), 8.42 (t, J=2.40 Hz, 1H), 8.27 (s, 1H), 7.66 (s, 1H), 7.33 (t, J=8.00 Hz, 1H), 7.20 (d, J=7.60 Hz, 1H), 7.14 (t, J=1.60 Hz, 1H), 6.88-6.85 (m, 1H); MS (ES+APCI) m/z 215.2 (M+1).

Synthesis of N-((dimethylamino)methylene)-5-(3-hydroxyphenyl)nicotinamide

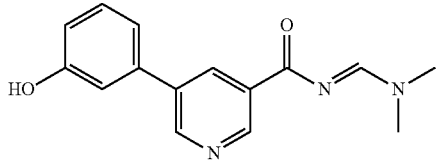 [SMILES: CN(C)/C=N/C(=O)c1cncc(-c2cccc(O)c2)c1]

To a stirred solution of 5-(3-hydroxyphenyl)nicotinamide (1.6 g, 7.70 mmol) in toluene (20 mL) at RT under nitrogen atmosphere was added DMF-DMA (2.75 g, 23.11 mmol). The reaction mixture was stirred at 100° C. for 3 h. After completion of the reaction (monitored by TLC), the reaction mixture was evaporated to a residue. The residue was tritutated with n-hexane and the solid was filtered and dried to give N-((dimethylamino)methylene)-5-(3-hydroxyphenyl)nicotinamide (1.7 g) as off white solid. $^1$H-NMR (400 MHz, DMSO-d6): δ 9.68 (s, 1H), 9.26 (d, J=1.60 Hz, 1H), 8.95 (d, J=2.40 Hz, 1H), 8.70 (s, 1H), 8.54 (t, J=2.00 Hz, 1H), 7.33 (t, J=8.00 Hz, 1H), 7.17 (d, J=7.60 Hz, 1H), 7.10 (t, J=2.00 Hz, 1H), 6.87-6.84 (m, 1H), 3.25 (s, 3H), 3.20 (s, 3H); MS (ES+APCI) m/z 270.3 (M+1).

Synthesis of 3-(5-(1,2,4-oxadiazol-5-yl)pyridin-3-yl)phenol

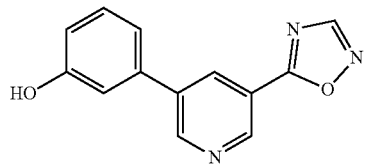 [SMILES: Oc1cccc(-c2cncc(-c3ncno3)c2)c1]

To a stirred solution of hydroxylamine hydrochloride (0.46 g, 6.69 mmol), sodium hydroxide (0.27 g, 6.69 mmol) in 1,4-dioxane (6 mL), acetic acid (10 mL) and water (2.5 mL) was added N-((dimethylamino)methylene)-5-(3-hydroxyphenyl)nicotinamide (1.5 g, 5.57 mmol) at RT. The resulting mixture was stirred at 90° C. for 3 h. After completion of the reaction (monitored by LCMS), the reaction mixture was concentrated and washed with 10% sodium bicarbonate solution and extracted with ethyl acetate. The organic layer was dried over sodium sulfate then evaporated under reduced pressure to give a residue. The residue was purified by automated normal-phase chromatography and eluted with ethyl acetate/petroleum ether to give 3-(5-(1,2,4-oxadiazol-5-yl)pyridin-3-yl)phenol (400 mg) as an off white solid. $^1$H-NMR (400 MHz, DMSO-d6): δ 9.72 (s, 1H), 9.26 (d, J=2.80 Hz, 1H), 9.24 (s, 1H), 9.13 (d, J=3.20 Hz, 1H), 8.59 (t, J=2.80 Hz, 1H), 7.38-7.17 (m, 3H), 6.91-6.88 (m, 1H); MS (ES+APCI) m/z 240.2 (M+2).

Synthesis of 3-(5-(1,2,4-oxadiazol-5-yl)pyridin-3-yl)phenyl (cyclohexylmethyl)carbamate

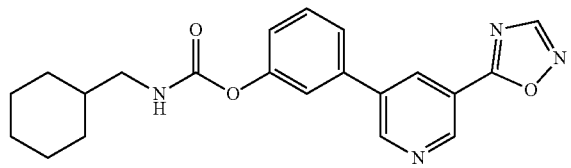 [SMILES: O=C(NCC1CCCCC1)Oc1cccc(-c2cncc(-c3ncno3)c2)c1]

To a stirred solution of 3-(5-(1,2,4-oxadiazol-5-yl)pyridin-3-yl)phenol (0.10 g, 0.42 mmol) in anhydrous acetonitrile (1 mL) and ethanol (1 mL) was added TEA (0.09 mL, 0.63 mmol) and cyclohexanemethyl isocyanate (0.07 g, 0.50 mmol) at RT under nitrogen atmosphere. The reaction mixture was stirred at RT for 30 minutes. After completion of the reaction (monitored by LCMS), the reaction mixture was concentrated to a residue. The residue was purified by preparative HPLC (0.1% FA) to yield the target compound (47 mg) as an off white solid. $^1$H-NMR (400 MHz, DMSO-d6): δ 9.30-9.21 (m, 3H), 8.70 (t, J=2.00 Hz, 1H), 7.85 (t, J=6.00 Hz, 1H), 7.72 (t, J=6.80 Hz, 1H), 7.65 (t, J=2.00 Hz, 1H), 7.56 (t, J=8.00 Hz, 1H), 7.24-7.22 (m, 1H), 2.94 (t, J=6.40 Hz, 2H), 1.75-1.62 (m, 6H), 1.26-1.13 (m, 3H), 0.96-0.88 (m, 2H); MS (ES+APCI) m/z 379.2 (M+1).

Synthesis of 3-(5-(1,2,4-oxadiazol-5-yl)pyridin-3-yl)phenyl cyclohexylcarbamate (Example-205)

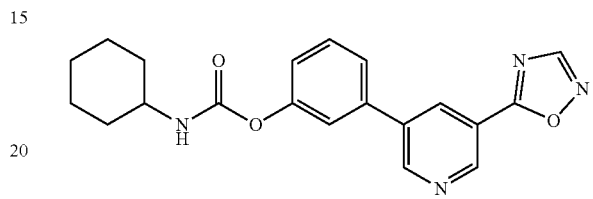

To a stirred solution of 3-(5-(1,2,4-oxadiazol-5-yl)pyridin-3-yl)phenol (0.10 g, 0.42 mmol) in anhydrous acetonitrile (1 mL) and ethanol (1 mL) was added TEA (0.09 mL, 0.63 mmol) and cyclohexyl isocyanate (0.06 g, 0.50 mmol) at RT under nitrogen atmosphere. The reaction mixture was stirred at RT for 30 min. After completion of the reaction (monitored by LCMS), the reaction mixture was concentrated to a residue. The residue was purified by preparative HPLC (0.1% FA) to yield the target compound (68 mg) as an off white solid. $^1$H-NMR (400 MHz, DMSO-d6): δ 9.30-9.21 (m, 3H), 8.70 (t, J=2.40 Hz, 1H), 7.81 (d, J=8.00 Hz, 1H), 7.72 (d, J=8.00 Hz, 1H), 7.65 (t, J=2.00 Hz, 1H), 7.56 (t, J=8.00 Hz, 1H), 7.24-7.22 (m, 1H), 3.36 (s, 1H), 1.86 (d, J=8.00 Hz, 2H), 1.73 (d, J=8.80 Hz, 2H), 1.58 (d, J=12.00 Hz, 1H), 1.30-1.11 (m, 5H); MS (ES+APCI) m/z 365.2 (M+1).

Synthesis of 3-(5-(1,2,4-oxadiazol-5-yl)pyridin-3-yl)phenyl cycloheptylcarbamate

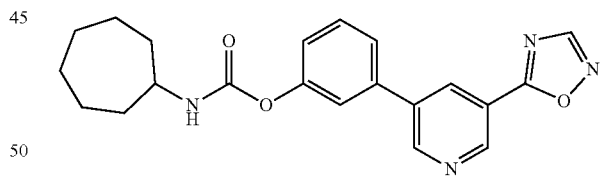

To a stirred solution of 3-(5-(1,2,4-oxadiazol-5-yl)pyridin-3-yl)phenol (0.10 g, 0.42 mmol) in anhydrous acetonitrile (1 mL) and ethanol (1 mL) was added TEA (0.09 mL, 0.63 mmol) and cycloheptyl isocyanate (0.07 g, 0.50 mmol) at RT under nitrogen atmosphere. The reaction mixture was stirred at RT for 30 min. After completion of the reaction (monitored by LCMS), the reaction mixture was concentrated to a residue. The residue was purified by preparative HPLC (0.1% FA) to yield the target compound (45 mg) as an off white solid. $^1$H-NMR (400 MHz, DMSO-d6): δ 9.29-9.21 (m, 3H), 8.70 (t, J=2.00 Hz, 1H), 7.84 (d, J=7.60 Hz, 1H), 7.72-7.65 (m, 2H), 7.55 (t, J=8.00 Hz, 1H), 7.24-7.22 (m, 1H), 3.61-3.53 (m, 1H), 1.91-1.87 (m, 2H), 1.67-1.61 (m, 2H), 1.58-1.51 (m, 6H), 1.51-1.42 (m, 2H); MS (ES+APCI) m/z 379.2 (M+1).

Scheme VIII

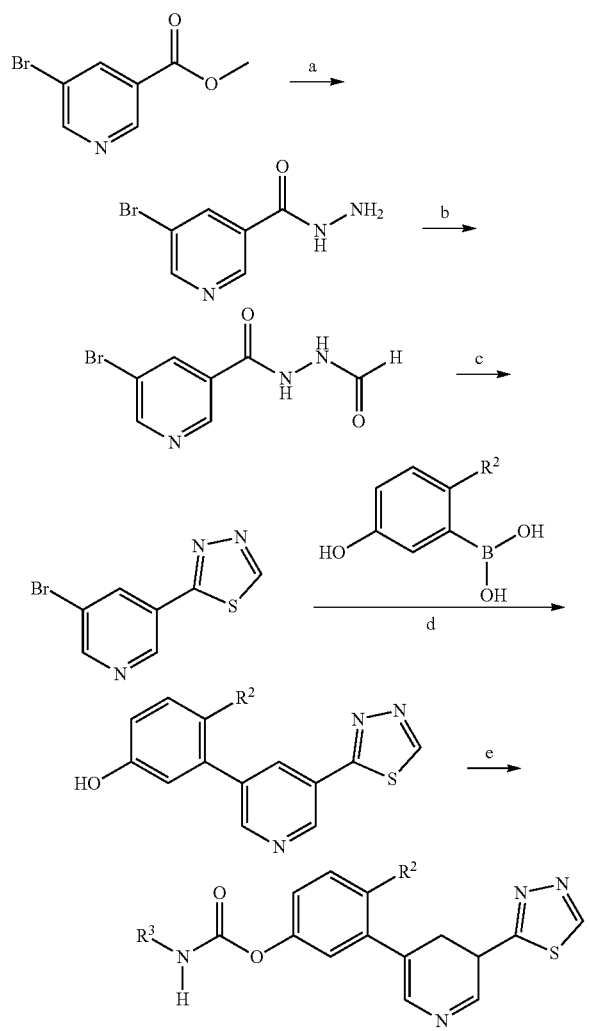

R² = H, OCH₃

Reagent conditions: NH₂—NH₂·H₂O, EtOH, 60° C., 15 h; b) HCOOH, RT, 16 h; c) P₂S₅, pyridine, 115° C., 16 h; d) Pd(PPh₃)₄, aq K₂CO₃, 1,4-dioxane, 80° C., 4 h; e) R²—NCO, TEA, ACN, 75° C., 12 h.

Synthesis of 5-bromonicotinohydrazide

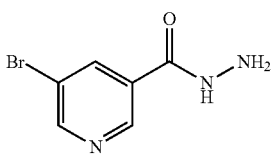 [SMILES: NNC(=O)c1cncc(Br)c1]

To a stirred solution of methyl 5-bromonicotinate (5 g, 23.14 mmol) in ethanol (50 mL) was added hydrazine hydrate (25 mL, 325 mmol) at RT. The reaction mixture was stirred at 60° C. for 15 h. After completion of the reaction (monitored by TLC), the resulting mixture was concentrated to a residue. The residue was co-evaporated with toluene to remove the residual water and repeated the toluene co-evaporation process for 3 to 4 times to give 5-bromonicotinohydrazide (5 g) which was used for next step without further purification. ¹HNMR (400 MHz, DMSO-d6) δ 8.94 (d, J=1.80 Hz, 1H), 8.84 (d, J=2.10 Hz, 1H), 8.37 (t, J=2.10 Hz, 1H); MS (ES+APCI) m/z 216.2

Synthesis of 5-bromo-N'-formylnicotinohydrazide

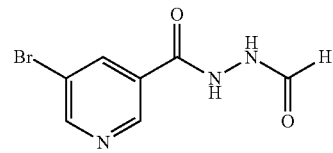 [SMILES: O=CNNC(=O)c1cncc(Br)c1]

To a stirred solution of 5-bromonicotinohydrazide (5 g, 23.14 mmol) in formic acid (10 mL) was stirred at RT for 16 h under nitrogen atmosphere. After completion of the reaction (monitored by TLC), the reaction mixture was evaporated under reduced pressure. The residue was triturated with MTBE and the precipitated solid was filtered and dried to give 5-bromo-N'-formylnicotinohydrazide (5.5 g) as an off white solid. ¹H-NMR (400 MHz, CD₃OD): δ 8.99 (d, J=2.00 Hz, 1H), 8.90-8.87 (m, 1H), 8.47 (t, J=2.00 Hz, 1H), 8.19 (d, J=7.20 Hz, 1H); MS (ES+APCI) m/z 246.0 (M+2).

Synthesis of 2-(5-bromopyridin-3-yl)-1,3,4-thiadiazole

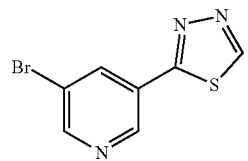 [SMILES: Brc1cncc(-c2nncs2)c1]

To a stirred solution of 5-bromo-N'-formylnicotinohydrazide (5.5 g, 22.54 mmol) in pyridine (55 mL) was added phosphorus pentasulfide (10.02 g, 22.54 mmol) at RT. The reaction mixture was stirred at 115° C. for 16 h. After completion of the reaction (monitored by TLC), the resulting mixture was concentrated to a residue. The residue was quenched with 1.5 N HCl solution and extracted with ethyl acetate. The organic layer was dried over sodium sulfate then evaporated under reduced pressure. The residue was purified by automated normal-phase chromatography and eluted with ethyl acetate/petroleum ether to give 2-(5-bromopyridin-3-yl)-1,3,4-thiadiazole (2.5 g) as yellow solid. ¹HNMR (400 MHz, DMSO-d6) δ 9.76 (s, 1H), 9.20 (d, J=1.50 Hz, 1H), 8.91 (d, J=1.50 Hz, 1H), 8.67 (t, J=1.50 Hz, 1H): MS (ES+APCI) m/z 244.1 (M+2).

Synthesis of 3-(5-(1,3,4-thiadiazol-2-yl)pyridin-3-yl)phenol

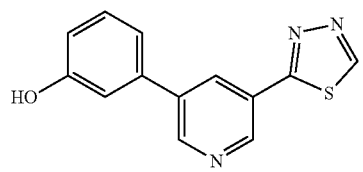 [SMILES: Oc1cccc(-c2cncc(-c3nncs3)c2)c1]

To a stirred solution of 2-(5-bromopyridin-3-yl)-1,3,4-thiadiazole (4.9 g, 20.24 mmol) in 1,4-dioxane (40 mL) and water (10 mL) was added (3-hydroxyphenyl)boronic acid (6.70 g, 48.6 mmol) and K$_2$CO$_3$ (11.19 g, 81 mmol) at RT. The reaction mixture was degassed for 15 minutes then Pd(PPh$_3$)$_4$ (4.68 g, 4.05 mmol) was added. The reaction mixture was stirred at 80° C. for 4 h under nitrogen atmosphere. After completion of the reaction (monitored by TLC), the reaction mixture was cooled to RT and then the solvent was evaporated under reduced pressure. The residue was quenched with water and extracted with ethyl acetate, and the combined organic layers were washed with water, brine and concentrated to give a residue. The residue was purified by automated normal-phase chromatography and eluted with ethyl acetate/petroleum ether to give 3-(5-(1,3,4-thiadiazol-2-yl)pyridin-3-yl)phenol (3.38 g) as pale yellow solid. $^1$H-NMR (400 MHz, DMSO-d$_6$): δ 9.76 (s, 1H), 9.70 (s, 1H), 9.18 (d, J=2.00 Hz, 1H), 9.01 (d, J=2.40 Hz, 1H), 8.52 (t, J=2.40 Hz, 1H), 7.35 (t, J=8.00 Hz, 1H), 7.27-7.25 (m, 1H), 7.19 (t, J=1.60 Hz, 1H), 6.91-6.88 (m, 1H); MS (ES+APCI) m/z 256.3 (M+1).

Synthesis of 3-(5-(1,3,4-thiadiazol-2-yl)pyridin-3-yl)phenyl octylcarbamate (Example-207)

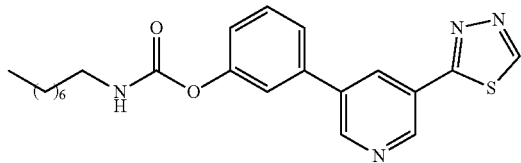

To a stirred solution of 3-(5-(1,3,4-thiadiazol-2-yl)pyridin-3-yl)phenol (0.08 g, 0.32 mmol) in anhydrous acetonitrile (2 mL) was added TEA (0.07 mL, 0.47 mmol) and n-octyl isocyanate (0.058 g, 0.38 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (15 mg) as an off white solid. $^1$HNMR (400 MHz, DMSO-d6) δ 9.77 (s, 1H), 9.22 (d, J=2.40 Hz, 1H), 9.09 (d, J=2.40 Hz, 1H), 8.61 (t, J=2.00 Hz, 1H), 7.83 (t, J=5.60 Hz, 1H), 7.71 (d, J=7.60 Hz, 1H), 7.63 (t, J=1.60 Hz, 1H), 7.55 (t, J=7.60 Hz, 1H), 7.22 (dd, J=1.60, 8.20 Hz, 1H), 3.10-3.05 (m, 2H), 1.49 (t, J=7.20 Hz, 2H), 1.29-1.27 (m, 10H), 0.86 (t, J=6.80 Hz, 3H); MS (ES+APCI) m/z 411.2 (M+1).

Synthesis of 3-(5-(1,3,4-thiadiazol-2-yl)pyridin-3-yl)phenyl (cyclohexylmethyl)carbamate (Example-208)

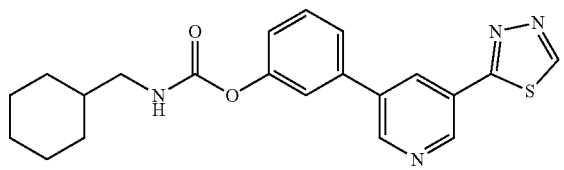 [SMILES: O=C(NCC1CCCCC1)Oc1cccc(-c2cncc(-c3nncs3)c2)c1]

To a stirred solution of 3-(5-(1,3,4-thiadiazol-2-yl)pyridin-3-yl)phenol (0.08 g, 0.32 mmol) in anhydrous acetonitrile (2 mL) was added TEA (0.07 mL, 0.47 mmol) and cyclohexanemethyl isocyanate (0.052 g, 0.38 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (22 mg) as an off white solid. $^1$HNMR (400 MHz, DMSO-d6) δ 9.77 (s, 1H), 9.22 (d, J=2.00 Hz, 1H), 9.09 (d, J=2.40 Hz, 1H), 8.61 (t, J=2.40 Hz, 1H), 7.85 (t, J=6.00 Hz, 1H), 7.71 (d, J=8.00 Hz, 1H), 7.64 (t, J=2.00 Hz, 1H), 7.55 (t, J=8.00 Hz, 1H), 7.23-7.21 (m, 1H), 2.96-2.92 (m, 2H), 1.75-0.96 (m, 11H); MS (ES+APCI) m/z 395.3 (M+1).

Synthesis of 3-(5-(1,3,4-thiadiazol-2-yl)pyridin-3-yl)phenyl benzylcarbamate (Example-209)

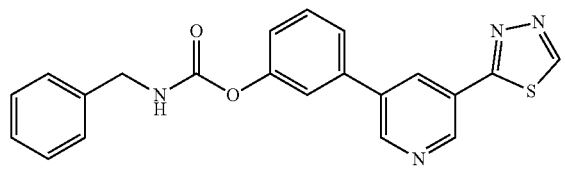 [SMILES: O=C(NCc1ccccc1)Oc1cccc(-c2cncc(-c3nncs3)c2)c1]

To a stirred solution of 3-(5-(1,3,4-thiadiazol-2-yl)pyridin-3-yl)phenol (0.08 g, 0.32 mmol) in anhydrous acetonitrile (2 mL) was added TEA (0.07 mL, 0.47 mmol) and benzyl isocyanate (0.05 g, 0.38 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (24 mg) as an off white solid. $^1$HNMR (400 MHz, DMSO-d6) δ 9.77 (s, 1H), 9.22 (s, 1H), 9.10 (s, 1H), 8.62 (t, J=2.00 Hz, 1H), 8.41 (t, J=6.00 Hz, 1H), 7.73 (d, J=7.60 Hz, 1H), 7.68 (t, J=1.60 Hz, 1H), 7.56 (t, J=8.00 Hz, 1H), 7.36 (t, J=1.60 Hz, 4H), 7.30-7.24 (m, 2H), 4.32 (d, J=6.00 Hz, 2H); MS (ES+APCI) m/z 389.1 (M+1).

Synthesis of 3-(5-(1,3,4-thiadiazol-2-yl)pyridin-3-yl)phenyl cyclopentylcarbamate (Example-210)

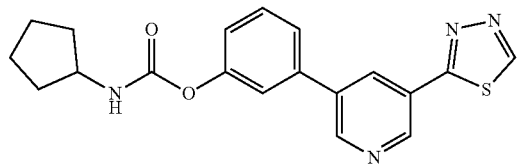 [SMILES: O=C(NC1CCCC1)Oc1cccc(-c2cncc(-c3nncs3)c2)c1]

To a stirred solution of 3-(5-(1,3,4-thiadiazol-2-yl)pyridin-3-yl)phenol (0.08 g, 0.32 mmol) in anhydrous acetonitrile (2 mL) was added TEA (0.07 mL, 0.47 mmol) and cyclopentyl isocyanate (0.042 g, 0.38 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (25 mg) as an off white solid. $^1$HNMR (400 MHz, DMSO-d6) δ 9.77 (s, 1H), 9.22 (d, J=2.00 Hz, 1H), 9.09 (d, J=2.40 Hz, 1H), 8.61 (t, J=2.40 Hz, 1H), 7.87 (d, J=7.60 Hz, 1H), 7.71 (d, J=8.00 Hz, 1H), 7.65 (d, J=1.60 Hz, 1H), 7.55 (t, J=7.60 Hz, 1H), 7.22 (dd, J=1.60, 8.00 Hz, 1H), 3.92-3.83 (m, 1H), 1.89-1.52 (m, 8H); MS (ES+APCI) m/z 367.3 (M+1).

Synthesis of 3-(5-(1,3,4-thiadiazol-2-yl)pyridin-3-yl)phenyl cyclohexylcarbamate (Example-211)

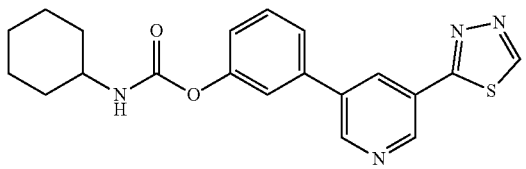 [SMILES: O=C(NC1CCCCC1)Oc1cccc(-c2cncc(-c3nncs3)c2)c1]

To a stirred solution of 3-(5-(1,3,4-thiadiazol-2-yl)pyridin-3-yl)phenol (0.08 g, 0.31 mmol) in anhydrous acetonitrile (2 mL) was added TEA (0.07 mL, 0.47 mmol) and cyclohexyl isocyanate (0.05 g, 0.38 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (23 mg) as an off white solid. ¹HNMR (400 MHz, DMSO-d6) δ 9.77 (s, 1H), 9.22 (d, J=2.40 Hz, 1H), 9.09 (d, J=2.00 Hz, 1H), 8.61 (t, J=2.00 Hz, 1H), 7.80 (d, J=8.00 Hz, 1H), 7.71 (d, J=7.60 Hz, 1H), 7.64 (t, J=2.00 Hz, 1H), 7.55 (t, J=8.00 Hz, 1H), 7.22 (dd, J=1.60, 8.00 Hz, 1H), 3.33-3.32 (m, 1H), 1.87-1.05 (m, 10H); MS (ES+APCI) m/z 381.2 (M+1).

Synthesis of 3-(5-(1,3,4-thiadiazol-2-yl)pyridin-3-yl)phenyl cycloheptylcarbamate (Example-212)

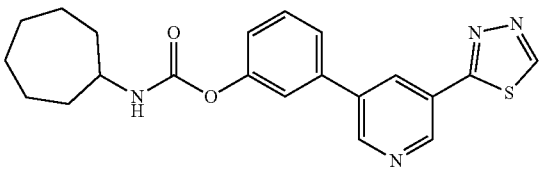 [SMILES: O=C(NC1CCCCCC1)Oc1cccc(-c2cncc(-c3nncs3)c2)c1]

To a stirred solution of 3-(5-(1,3,4-thiadiazol-2-yl)pyridin-3-yl)phenol (0.08 g, 0.32 mmol) in anhydrous acetonitrile (2 mL) was added TEA (0.07 mL, 0.47 mmol) and cycloheptyl isocyanate (0.052 g, 0.38 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (29 mg) as an off white solid. ¹HNMR (400 MHz, DMSO-d6) δ 9.77 (s, 1H), 9.21 (d, J=2.00 Hz, 1H), 9.09 (d, J=2.00 Hz, 1H), 8.61 (t, J=2.00 Hz, 1H), 7.84 (d, J=7.60 Hz, 1H), 7.71 (d, J=8.00 Hz, 1H), 7.64 (t, J=2.00 Hz, 1H), 7.55 (t, J=7.60 Hz, 1H), 7.22 (dd, J=1.60, 8.00 Hz, 1H), 3.59-3.54 (m, 1H), 1.91-1.86 (m, 2H), 1.68-1.44 (m, 10H); MS (ES+APCI) m/z 395.3 (M+1).

Synthesis of 3-(5-(1,3,4-thiadiazol-2-yl)pyridin-3-yl)-4-methoxyphenol

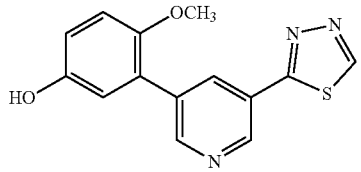

To a stirred solution of 2-(5-bromopyridin-3-yl)-1,3,4-thiadiazole (0.5 g, 2.07 mmol) in 1,4-dioxane (5 mL) and water (0.5 mL) was added (5-hydroxy-2-methoxyphenyl)boronic acid (0.42 g, 2.48 mmol) and K₂CO₃ (0.86 g, 6.20 mmol) at RT. The reaction mixture was degassed for 15 minutes then Pd(PPh₃)₄ (0.12 g, 0.10 mmol) was added. The reaction mixture was stirred at 80° C. for 4 h under nitrogen atmosphere. After completion of the reaction (monitored by TLC), the reaction mixture was cooled to RT and then the solvent was evaporated under reduced pressure. The residue was quenched with 1.5N aqueous HCl and extracted with ethyl acetate, and the combined organic layers were washed with water, brine and concentrated to give a residue. The residue was purified by automated normal-phase chromatography and eluted with ethyl acetate/petroleum ether to give 3-(5-(1,3,4-thiadiazol-2-yl)pyridin-3-yl)-4-methoxyphenol (480 mg) as an pale yellow solid. MS (ES+APCI) m/z 286.3 (M+1).

Synthesis of 3-(5-(1,3,4-thiadiazol-2-yl)pyridin-3-yl)-4-methoxyphenyl octylcarbamate (Example-213)

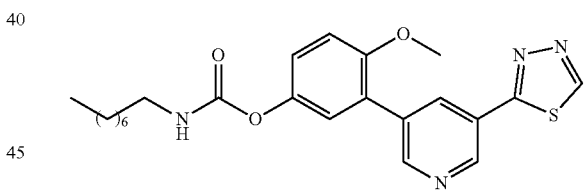

To a stirred solution of 3-(5-(1,3,4-thiadiazol-2-yl)pyridin-3-yl)-4-methoxyphenol (0.08 g, 0.28 mmol) in anhydrous acetonitrile (2 mL) was added TEA (0.06 mL, 0.34 mmol) and octyl isocyanate (0.05 g, 0.34 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (45 mg) as an off white solid. ¹HNMR (400 MHz, DMSO-d6) δ 9.75 (s, 1H), 9.15 (d, J=2.00 Hz, 1H), 8.87 (d, J=2.00 Hz, 1H), 8.46 (t, J=2.00 Hz, 1H), 7.72 (t, J=6.00 Hz, 1H), 7.26 (t, J=1.60 Hz, 1H), 7.18 (d, J=1.60 Hz, 2H), 3.83 (s, 3H), 3.08-3.03 (m, 2H), 1.46 (t, J=6.80 Hz, 2H), 1.27-1.26 (m, 10H), 0.86 (t, J=7.20 Hz, 3H); MS (ES+APCI) m/z 441.2 (M+1).

Synthesis of 3-(5-(1,3,4-thiadiazol-2-yl)pyridin-3-yl)-4-methoxyphenyl (cyclohexylmethyl)carbamate (Example-214)

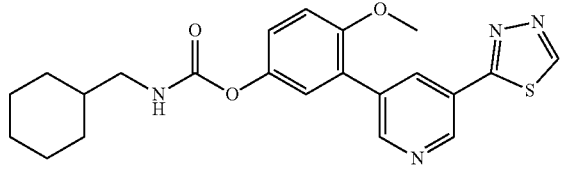

To a stirred solution of 3-(5-(1,3,4-thiadiazol-2-yl)pyridin-3-yl)-4-methoxyphenol (0.08 g, 0.28 mmol) in anhydrous acetonitrile (2 mL) was added TEA (0.06 mL, 0.34 mmol) and cyclohexanemethyl isocyanate (0.05 g, 0.34 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (44 mg) as an off white solid. ¹HNMR (400 MHz, DMSO-d6) δ 9.75 (d, J=1.60 Hz, 1H), 9.16 (s, 1H), 8.87 (s, 1H), 8.46 (t, J=2.00 Hz, 1H), 7.74 (t, J=6.00 Hz, 1H), 7.27 (t, J=1.60 Hz, 1H), 7.18 (d, J=1.60 Hz, 2H), 3.82 (s, 3H), 2.91 (t, J=6.40 Hz, 2H), 1.73-0.88 (m, 11H); MS (ES+APCI) m/z 425.2 (M+1).

Synthesis of 3-(5-(1,3,4-thiadiazol-2-yl)pyridin-3-yl)-4-methoxyphenyl benzylcarbamate (Example-215)

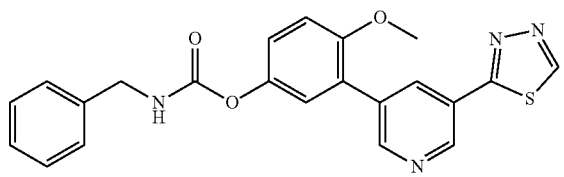

To a stirred solution of 3-(5-(1,3,4-thiadiazol-2-yl)pyridin-3-yl)-4-methoxyphenol (0.08 g, 0.28 mmol) in anhydrous acetonitrile (2 mL) was added TEA (0.06 mL, 0.34 mmol) and benzyl isocyanate (0.05 g, 0.34 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (18 mg) as an off white solid. ¹HNMR (400 MHz, DMSO-d6) δ 9.75 (s, 1H), 9.15 (d, J=2.00 Hz, 1H), 8.87 (d, J=2.00 Hz, 1H), 8.46 (t, J=2.00 Hz, 1H), 8.31 (t, J=6.00 Hz, 1H), 7.38-7.18 (m, 8H), 4.29 (d, J=6.00 Hz, 2H), 3.83 (s, 3H); MS (ES+APCI) m/z 419.0 (M+1).

Synthesis of 3-(5-(1,3,4-thiadiazol-2-yl)pyridin-3-yl)-4-methoxyphenyl cyclopentylcarbamate (Example-216)

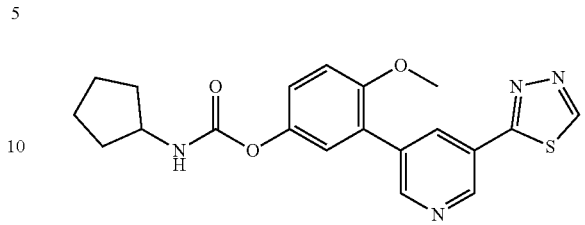

To a stirred solution of 3-(5-(1,3,4-thiadiazol-2-yl)pyridin-3-yl)-4-methoxyphenol (0.08 g, 0.28 mmol) in anhydrous acetonitrile (2 mL) was added TEA (0.06 mL, 0.34 mmol) and cyclopentyl isocyanate (0.04 g, 0.34 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (86 mg) as an off white solid. ¹HNMR (400 MHz, DMSO-d6) δ 9.75 (s, 1H), 9.15 (d, J=2.00 Hz, 1H), 8.87 (d, J=2.40 Hz, 1H), 8.46 (t, J=2.40 Hz, 1H), 7.77 (d, J=7.20 Hz, 1H), 7.28 (s, 1H), 7.18 (d, J=1.20 Hz, 2H), 3.87-3.84 (m, 1H), 3.82 (s, 3H), 1.85-1.45 (m, 8H); MS (ES+APCI) m/z 397.2 (M+1).

Synthesis of 3-(5-(1,3,4-thiadiazol-2-yl)pyridin-3-yl)-4-methoxyphenyl cyclohexylcarbamate (Example-217)

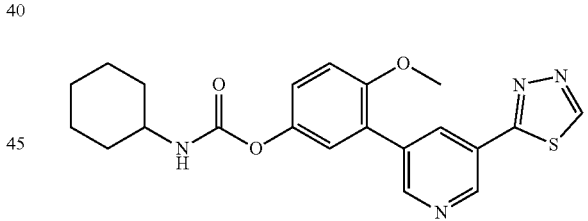

To a stirred solution of 3-(5-(1,3,4-thiadiazol-2-yl)pyridin-3-yl)-4-methoxyphenol (0.08 g, 0.28 mmol) in anhydrous acetonitrile (2 mL) was added TEA (0.06 mL, 0.42 mmol) and cyclohexyl isocyanate (0.04 g, 0.34 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (43 mg) as an off white solid. ¹HNMR (400 MHz, DMSO-d6) δ 9.75 (s, 1H), 9.15 (d, J=2.00 Hz, 1H), 8.87 (d, J=2.00 Hz, 1H), 8.46 (t, J=2.40 Hz, 1H), 7.70 (d, J=8.00 Hz, 1H), 7.27 (s, 1H), 7.18 (d, J=1.20 Hz, 2H), 3.82 (s, 3H), 1.84-1.13 (m, 10H); MS (ES+APCI) m/z 286.2 (M+1).

187

Synthesis of 3-(5-(1,3,4-thiadiazol-2-yl)pyridin-3-yl)-4-methoxyphenyl cycloheptylcarbamate (Example-218)

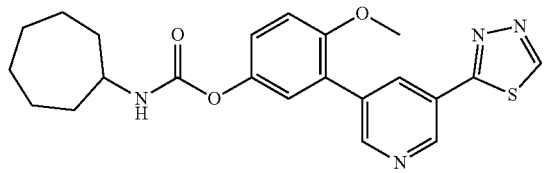 [SMILES: COc1ccc(OC(=O)NC2CCCCCC2)cc1-c1cncc(-c2nncs2)c1]

To a stirred solution of 3-(5-(1,3,4-thiadiazol-2-yl)pyridin-3-yl)-4-methoxyphenol (0.08 g, 0.28 mmol) in anhydrous acetonitrile (2 mL) was added TEA (0.06 mL, 0.34 mmol) and cycloheptyl isocyanate (0.05 g, 0.34 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (81 mg) as an off white solid. $^{1}$HNMR (400 MHz, DMSO-d6) δ 9.75 (s, 1H), 9.15 (d, J=2.40 Hz, 1H), 8.87 (d, J=2.00 Hz, 1H), 8.45 (t, J=2.40 Hz, 1H), 7.73 (d, J=8.00 Hz, 1H), 7.27 (d, J=1.60 Hz, 1H), 7.18 (d, J=1.60 Hz, 2H), 3.82 (s, 3H), 3.56-3.52 (m, 1H), 1.89-1.40 (m, 12H); MS (ES+APCI) m/z 425.2 (M+1).

Scheme IX

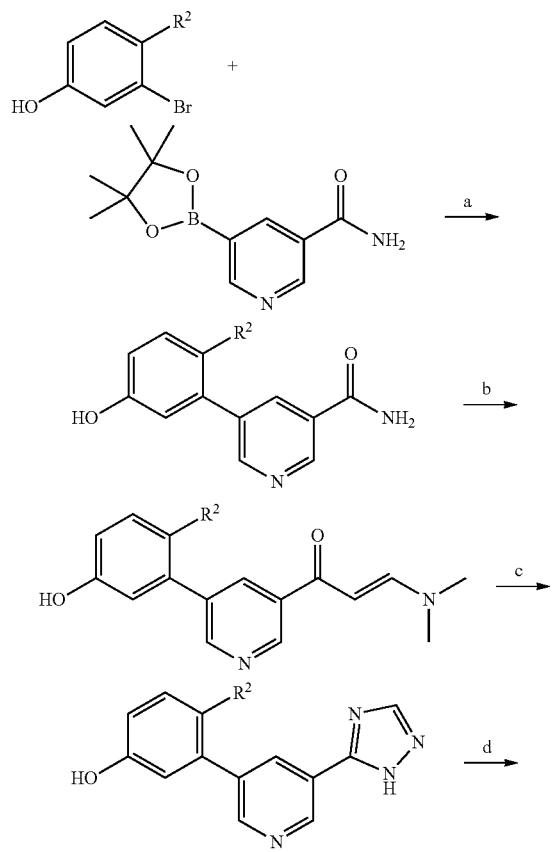

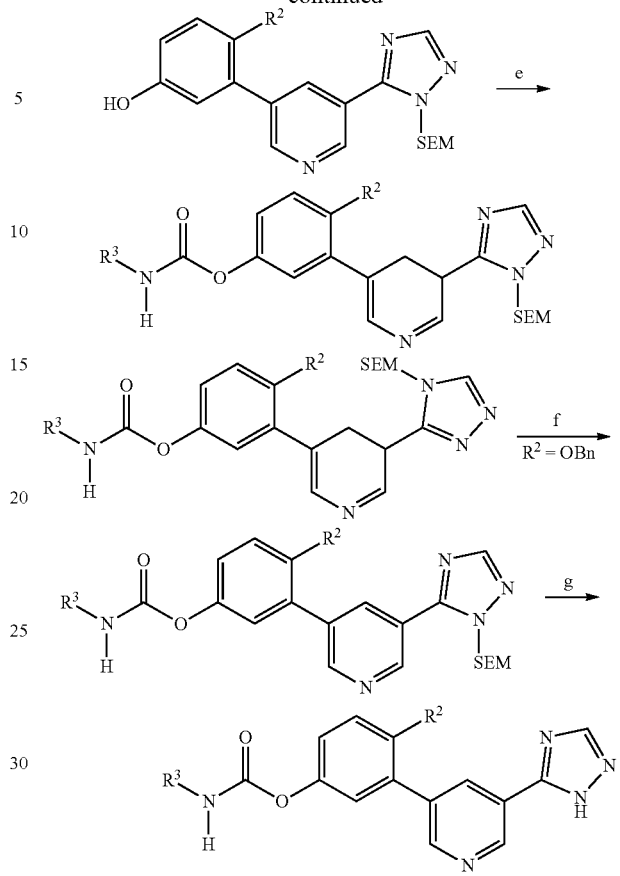

$R^2$ = H, OH, OCH$_3$
Reagents and conditions: a) Pd(PPh$_3$)$_4$, aq K$_2$CO$_3$, 1-4-dioxane, 90° C., 12 h; b) DMF—DMA, Toluene, 100° C., 2 h; c) NH$_2$—NH$_2$·H$_2$O, AcOH, 90° C., 3 h; d) 2-(trimethylsilyl)ethoxymethyl chloride (SEM—Cl), K$_2$CO$_3$, DMF, RT, 12 h; e) R$^2$—NCO, TEA, ACN, 75° C., 12-16 h; f) Pd/C, Pd(OH)$_2$, H$_2$ gas (balloon), THF, IPA, RT, 16 h; g) SnCl$_2$ DCM, RT, 2 h.

Synthesis of 5-(3-hydroxyphenyl)nicotinamide

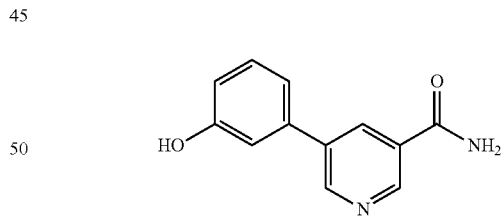

To a stirred solution of 5-bromonicotinamide (2.8 g, 13.93 mmol) in 1,4-dioxane (56 mL) and water (5.6 mL) was added (3-hydroxyphenyl)boronic acid (1.92 g, 13.93 mmol) and K$_2$CO$_3$ (5.78 g, 41.8 mmol) at RT. The reaction mixture was degassed for 15 minutes then Pd(PPh$_3$)$_4$ (0.81 g, 0.70 mmol) was added. The reaction mixture was stirred at 90° C. for 12 h under nitrogen atmosphere. After completion of the reaction (monitored by TLC), The reaction mixture was filtered through celite, washed with DCM/MeOH and the filtrate was concentrated to a residue. The residue was purified by preparative HPLC (0.1% FA) to give 5-(3-hydroxyphenyl)nicotinamide (1.8 g) as an off white solid. MS (ES+APCI) m/z 215.3 (M+1).

Synthesis of ( )—N-((dimethylamino)methylene)-5-(3-hydroxyphenyl)nicotinamide

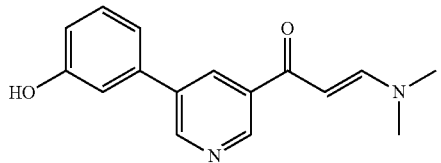 [SMILES: CN(C)/C=C/C(=O)c1cncc(-c2cccc(O)c2)c1]

To a stirred solution of 5-(3-hydroxyphenyl)nicotinamide (1 g, 4.67 mmol) in toluene (3 mL) was added DMF-DMA (1.67 g, 14 mmol) at RT. The reaction mixture was stirred at 100° C. for 2 h. After completion of the reaction (monitored by TLC), the reaction mixture was cooled to RT and concentrated to a residue. The residue was purified by automated normal-phase chromatography and eluted with DCM/MeOH to give (E)-N-((dimethylamino)methylene)-5-(3-hydroxyphenyl)nicotinamide (780 mg) as brown solid. MS (ES+APCI) m/z 270.2 (M+1).

Synthesis of 3-(5-(1H-1,2,4-triazol-5-yl)pyridin-3-yl)phenol

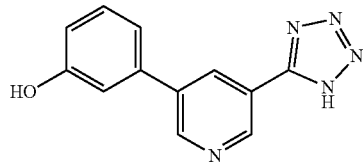 [SMILES: Oc1cccc(-c2cncc(-c3nnn[nH]3)c2)c1]

To a stirred solution of (E)-N-((dimethylamino)methylene)-5-(3-hydroxyphenyl)nicotinamide (0.75 g, 2.78 mmol) in AcOH (9 mL) was added hydrazine monohydrate (1.27 g, 16.54 mmol) at 0° C. The reaction mixture was stirred at 90° C. for 3 h. After completion of the reaction (monitored by TLC), the resulting mixture was concentrated to a residue. The crude residue was stirred with 10% aqueous solution of NaHCO₃ and the precipitated solid was filtered, washed with water and dried to give 3-(5-(1H-1,2,4-triazol-5-yl)pyridin-3-yl)phenol (550 mg), which was used for next step without purification. MS (ES+APCI) m/z 239.3 (M+1).

Synthesis of 3-(5-(1-((2-(trimethylsilyl)ethoxy)methyl)-1H-1,2,4-triazol-5-yl)pyridin-3-yl)phenol and 3-(5-(4-((2-(trimethylsilyl)ethoxy)methyl)-4H-1,2,4-triazol-3-yl)pyridin-3-yl)phenol

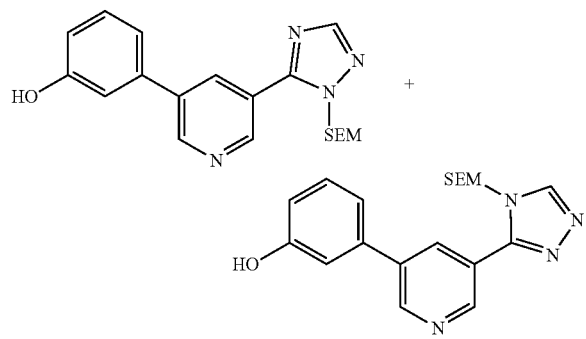

To a stirred solution of 3-(5-(1H-1,2,4-triazol-5-yl)pyridin-3-yl)phenol (0.5 g, 2.09 mmol) in DMF (5 mL) was added potassium carbonate (0.43 g, 3.15 mmol) at 0° C. SEM-Cl (0.39 g, 2.31 mmol) was added and the resultant suspension was stirred at RT for 12 h. After completion of the reaction (monitored by LCMS), the reaction mixture was quenched with cold water. The aqueous layer was extracted with ethyl acetate, and the combined organic layers were washed with water, brine and concentrated to give a residue. The residue was purified by automated normal-phase chromatography and eluted with DCM/MeOH to give a mixture of 3-(5-(1-((2-(trimethylsilyl)ethoxy)methyl)-1H-1,2,4-triazol-5-yl)pyridin-3-yl)phenol and 3-(5-(4-((2-(trimethylsilyl)ethoxy)methyl)-4H-1,2,4-triazol-3-yl)pyridin-3-yl)phenol (370 mg) as brownish liquid. MS (ES+APCI) m/z 369.3 (M+1).

Synthesis of 3-(5-(1-((2-(trimethylsilyl)ethoxy)methyl)-1H-1,2,4-triazol-5-yl)pyridin-3-yl)phenyl octylcarbamate and 3-(5-(4-((2-(trimethylsilyl)ethoxy)methyl)-4H-1,2,4-triazol-5-yl)pyridin-3-yl)phenyl octyl carbamate

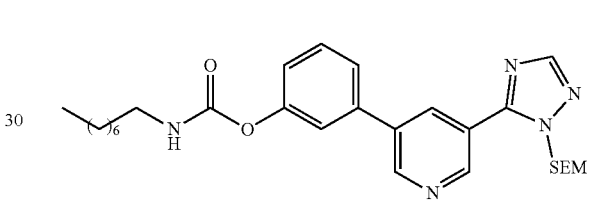

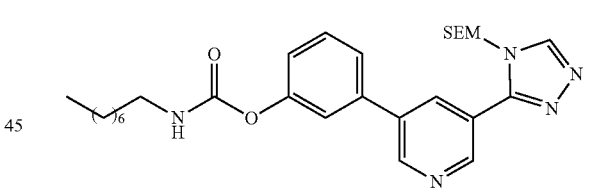

To a stirred solution of 3-(5-(1-((2-(trimethylsilyl)ethoxy)methyl)-1H-1,2,4-triazol-5-yl)pyridin-3-yl)phenol and 3-(5-(4-((2-(trimethylsilyl)ethoxy)methyl)-4H-1,2,4-triazol-3-yl)pyridin-3-yl)phenol (0.08 g, 0.217 mmol) in anhydrous acetonitrile (2 mL) was added TEA (0.1 mL, 0.67 mmol) and n-octylisocyanate (0.03 g, 0.217 mmol) at RT under nitrogen atmosphere. The reaction mixture was stirred at RT for 10 minutes and then stirred at 75° C. for 3 h. An additional amount of n-octylisocyanate (0.012 g, 0.07 mmol) was added to the reaction mixture and the resulting mixture was stirred for an additional 12 h. After completion of the reaction (monitored by LCMS), the reaction mixture was concentrated to give a mixture of 3-(5-(1-((2-(trimethylsilyl)ethoxy)methyl)-1H-1,2,4-triazol-5-yl)pyridin-3-yl)phenyl octyl carbamate and 3-(5-(4-((2-(trimethylsilyl)ethoxy)methyl)-4H-1,2,4-triazol-5-yl)pyridin-3-yl)phenyl octyl carbamate (80 mg), which was used for next step without purification. MS (ES+APCI) m/z 524.3 (M+1).

Synthesis of 3-(5-(1H-1,2,4-triazol-5-yl)pyridin-3-yl)phenyl octyl carbamate (Example-219)

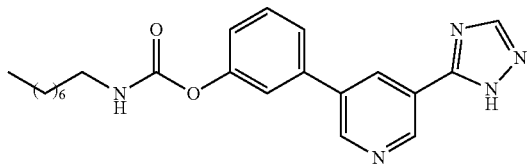

To a stirred solution of 3-(5-(1-((2-(trimethylsilyl)ethoxy)methyl)-1H-1,2,4-triazol-5-yl)pyridin-3-yl)phenyl octyl carbamate and 3-(5-(4-((2-(trimethylsilyl)ethoxy)methyl)-4H-1,2,4-triazol-5-yl)pyridin-3-yl)phenyl octyl carbamate (0.08 g, 0.153 mmol) in DCM (2 mL) was added SnCl₄ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO₃ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (24 mg) as an off white solid. ¹H NMR (400 MHz, DMSO-d6) δ 14.41 (bs, 1H), 9.20 (d, J=2.00 Hz, 1H), 8.96 (d, J=2.40 Hz, 1H), 8.81 (bs, 1H), 8.55 (t, J=2.00 Hz, 1H), 7.83 (t, J=5.60 Hz, 1H), 7.65 (d, J=7.60 Hz, 1H), 7.56-7.53 (m, 2H), 7.20 (dd, J=1.60, 8.00 Hz, 1H), 3.11-3.06 (m, 2H), 1.49 (t, J=7.20 Hz, 2H), 1.29-1.27 (m, 10H), 0.86 (t, J=7.20 Hz, 3H); MS (ES+APCI) m/z 394.3 (M+1).

Synthesis of 3-(5-(1-((2-(trimethylsilyl)ethoxy)methyl)-1H-1,2,4-triazol-5-yl)pyridin-3-yl)phenyl (cyclohexylmethyl)carbamate and 3-(5-(4-((2-(trimethylsilyl)ethoxy)methyl)-4H-1,2,4-triazol-5-yl)pyridin-3-yl)phenyl (cyclohexylmethyl)carbamate

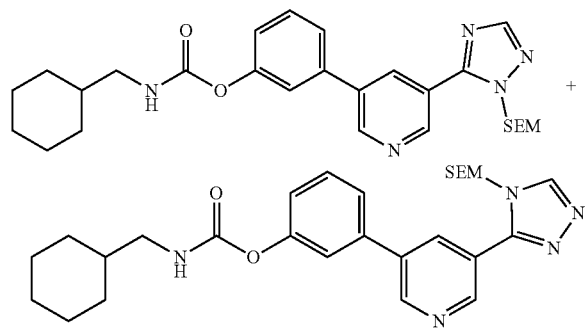

To a stirred solution of 3-(5-(1-((2-(trimethylsilyl)ethoxy)methyl)-1H-1,2,4-triazol-5-yl)pyridin-3-yl)phenol and 3-(5-(4-((2-(trimethylsilyl)ethoxy)methyl)-4H-1,2,4-triazol-3-yl)pyridin-3-yl)phenol (0.08 g, 0.217 mmol) in anhydrous acetonitrile (3 mL) was added TEA (0.09 mL, 0.65 mmol) and cyclohexanemethyl isocyanate (0.03 g, 0.217 mmol) at RT under nitrogen atmosphere. The reaction mixture was stirred at RT for 10 minutes and then stirred at 75° C. for 3 h. An additional amount of cyclohexanemethyl isocyanate (0.01 g, 0.08 mmol) was added to the reaction mixture and the resulting mixture was stirred for an additional 12 h. After completion of the reaction (monitored by LCMS), the reaction mixture was concentrated to give a mixture of 3-(5-(1-((2-(trimethylsilyl)ethoxy)methyl)-1H-1,2,4-triazol-5-yl)pyridin-3 yl)phenyl(cyclohexylmethyl)carbamate and 3-(5-(4-((2-(trimethylsilyl)ethoxy)methyl)-4H-1,2,4-triazol-5-yl)pyridin-3-yl)phenyl(cyclohexylmethyl) carbamate (80 mg), which was used for next step without purification. MS (ES+APCI) m/z 508.3 (M+1).

Synthesis of 3-(5-(1H-1,2,4-triazol-5-yl)pyridin-3-yl)phenyl (cyclohexylmethyl)carbamate (Example-220)

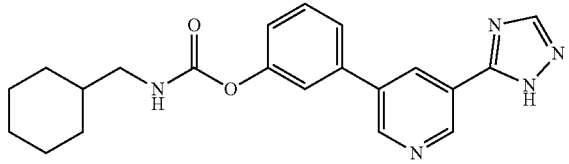 [SMILES: O=C(NCC1CCCCC1)Oc1cccc(-c2cncc(-c3ncn[nH]3)c2)c1]

To a stirred solution of 3-(5-(1-((2-(trimethylsilyl)ethoxy)methyl)-1H-1,2,4-triazol-5-yl)pyridin-3-yl)phenyl (cyclohexylmethyl)carbamate and 3-(5-(4-((2-(trimethylsilyl)ethoxy)methyl)-4H-1,2,4-triazol-5-yl)pyridin-3-yl)phenyl (cyclohexylmethyl)carbamat (0.08 g, 0.158 mmol) in DCM (2 mL) was added SnCl₄ (0.25 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO₃ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (18 mg) as an off white solid. ¹H NMR (400 MHz, DMSO-d6) δ 14.44 (bs, 1H), 9.20 (d, J=2.00 Hz, 1H), 8.96 (d, J=2.40 Hz, 1H), 8.61 (bs, 1H), 8.55 (t, J=2.00 Hz, 1H), 7.85 (t, J=6.00 Hz, 1H), 7.65 (t, J=1.20 Hz, 1H), 7.56-7.52 (m, 2H), 7.20 (dd, J=1.60, 8.00 Hz, 1H), 2.94 (t, J=6.40 Hz, 2H), 1.75-1.62 (m, 5H), 1.49-1.43 (m, 1H), 1.26-1.13 (m, 3H), 1.00-0.87 (m, 2H); MS (ES+APCI) m/z 378.4 (M+1).

Synthesis of 3-(5-(1-((2-(trimethylsilyl)ethoxy)methyl)-1H-1,2,4-triazol-5-yl)pyridin-3-yl)phenyl benzyl carbamate and 3-(5-(4-((2-(trimethylsilyl)ethoxy)methyl)-4H-1,2,4-triazol-5-yl)pyridin-3-yl)phenyl benzyl carbamate

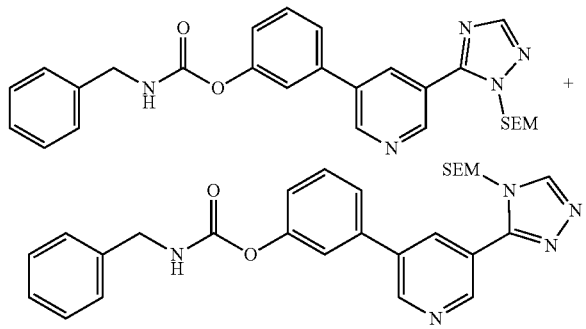

To a stirred solution of 3-(5-(1-((2-(trimethylsilyl)ethoxy)methyl)-1H-1,2,4-triazol-5-yl)pyridin-3-yl)phenol and 3-(5-(4-((2-(trimethylsilyl)ethoxy)methyl)-4H-1,2,4-triazol-3-yl)pyridin-3-yl)phenol (0.08 g, 0.217 mmol) in anhydrous acetonitrile (2 mL) was added TEA (0.1 mL, 0.67 mmol) and benzyl isocyanate (0.029 g, 0.217 mmol) at RT under nitrogen atmosphere. The reaction mixture was stirred at RT for 10 minutes and then stirred at 75° C. for 3 h. An additional amount of benzyl isocyanate (0.012 g, 0.07 mmol) was added to the reaction mixture and the resulting mixture was stirred for an additional 12 h. After completion of the reaction (monitored by LCMS), the reaction mixture was concentrated to give a mixture of 3-(5-(1-((2-(trimethylsilyl)ethoxy)methyl)-1H-1,2,4-triazol-5-yl)pyridin-3-yl)phenyl benzyl carbamate and 3-(5-(4-((2-(trimethylsilyl)ethoxy)methyl)-4H-1,2,4-triazol-5-yl)pyridin-3-yl)phenyl benzyl carbamate (100 mg), which was used for next step without purification. MS (ES+APCI) m/z 502.3 (M+1).

Synthesis of 3-(5-(1H-1,2,4-triazol-5-yl)pyridin-3-yl)phenyl benzyl carbamate (Example-221)

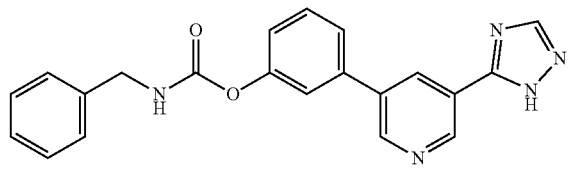 [SMILES: O=C(NCc1ccccc1)Oc1cccc(-c2cncc(-c3ncn[nH]3)c2)c1]

To a stirred solution of 3-(5-(1-((2-(trimethylsilyl)ethoxy)methyl)-1H-1,2,4-triazol-5-yl)pyridin-3-yl)phenyl benzyl carbamate and 3-(5-(4-((2-(trimethylsilyl)ethoxy)methyl)-4H-1,2,4-triazol-5-yl)pyridin-3-yl)phenyl benzyl carbamate (0.08 g, 0.16 mmol) in DCM (2 mL) was added SnCl$_4$ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (28 mg) as an off white solid. $^1$H NMR (400 MHz, DMSO-d6) δ 14.44 (bs, 1H), 9.20 (t, J=3.60 Hz, 1H), 8.97 (d, J=2.40 Hz, 1H), 8.61 (bs, 1H), 8.56 (t, J=2.00 Hz, 1H), 8.41 (t, J=6.40 Hz, 1H), 7.67 (d, J=8.00 Hz, 1H), 7.59-7.54 (m, 2H), 7.37-7.36 (m, 4H), 7.28-7.23 (m, 2H), 4.32 (d, J=6.00 Hz, 2H); MS (ES+APCI) m/z 372.2 (M+1).

Synthesis of 3-(5-(1-((2-(trimethylsilyl)ethoxy)methyl)-1H-1,2,4-triazol-5-yl)pyridin-3-yl)phenyl (naphthalen-2-ylmethyl)carbamate and 3-(5-(4-((2-(trimethylsilyl)ethoxy)methyl)-4H-1,2,4-triazol-5-yl)pyridin-3-yl)phenyl (naphthalen-2-ylmethyl)carbamate

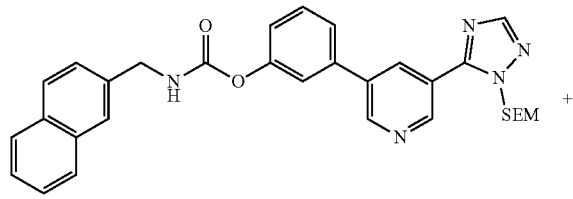

+

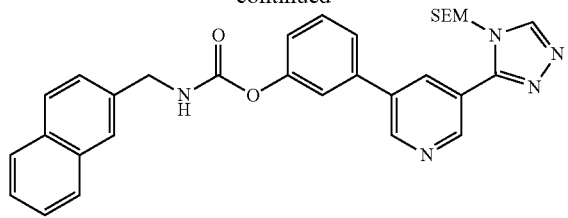

To a stirred solution of 3-(5-(1-((2-(trimethylsilyl)ethoxy)methyl)-1H-1,2,4-triazol-5-yl)pyridin-3-yl)phenol and 3-(5-(4-((2-(trimethylsilyl)ethoxy)methyl)-4H-1,2,4-triazol-3-yl)pyridin-3-yl)phenol (0.05 g, 0.136 mmol) in anhydrous acetonitrile (2 mL) was added TEA (0.06 mL, 0.407 mmol) and 2-(isocyanatomethyl)naphthalene (0.025 g, 0.136 mmol) at RT under nitrogen atmosphere. The reaction mixture was stirred at RT for 10 minutes and then stirred at 75° C. for 16 h. After completion of the reaction (monitored by LCMS), the reaction mixture was concentrated to give a mixture of 3-(5-(1-((2-(trimethylsilyl)ethoxy)methyl)-1H-1,2,4-triazol-5-yl)pyridin-3-yl)phenyl (naphthalen-2-ylmethyl)carbamate and 3-(5-(4-((2-(trimethylsilyl)ethoxy)methyl)-4H-1,2,4-triazol-5-yl)pyridin-3-yl)phenyl (naphthalen-2-ylmethyl)carbamate (70 mg), which was used for next step without purification. MS (ES+APCI) m/z 552.3 (M+1).

Synthesis of 3-(5-(1H-1,2,4-triazol-5-yl)pyridin-3-yl)phenyl (naphthalen-2-ylmethyl)carbamate (Example-222)

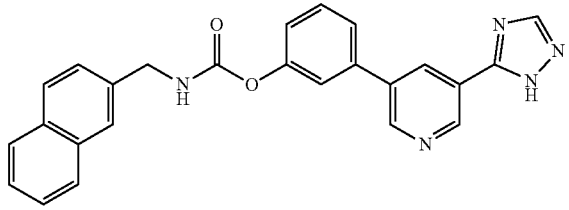 [SMILES: O=C(NCc1ccc2ccccc2c1)Oc1cccc(-c2cncc(-c3ncn[nH]3)c2)c1]

To a stirred solution of 3-(5-(1-((2-(trimethylsilyl)ethoxy)methyl)-1H-1,2,4-triazol-5-yl)pyridin-3-yl)phenyl (naphthalen-2-ylmethyl)carbamate and 3-(5-(4-((2-(trimethylsilyl)ethoxy)methyl)-4H-1,2,4-triazol-5-yl)pyridin-3-yl)phenyl (naphthalen-2-ylmethyl)carbamate (0.07 g, 0.13 mmol) in DCM (2 mL) was added SnCl$_4$ (0.2 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (4 mg) as an off white solid. $^1$H NMR (400 MHz, DMSO-d6) δ 14.44 (bs, 1H), 9.20 (d, J=1.60 Hz, 1H), 8.97 (d, J=1.20 Hz, 1H), 8.61 (bs, 1H), 8.57 (t, J=2.00 Hz, 1H), 8.52 (t, J=6.00 Hz, 1H), 7.94-7.90 (m, 3H), 7.67 (d, J=7.60 Hz, 1H), 7.62-7.49 (m, 5H), 7.26 (dd, J=1.60, 8.20 Hz, 1H), 4.49 (d, J=6.00 Hz, 2H); MS (ES+APCI) m/z 422.3 (M+1).

Synthesis of 3-(5-(1-((2-(trimethylsilyl)ethoxy)
methyl)-1H-1,2,4-triazol-5-yl)pyridin-3-yl)phenyl
cyclopentylcarbamate and 3-(5-(4-((2-(trimethylsi-
lyl)ethoxy)methyl)-4H-1,2,4-triazol-5-yl)pyridin-3-
yl)phenyl cyclopentylcarbamate

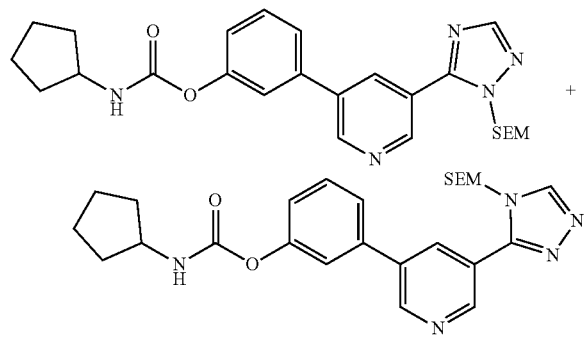

To a stirred solution of 3-(5-(1-((2-(trimethylsilyl)ethoxy)
methyl)-1H-1,2,4-triazol-5-yl)pyridin-3-yl)phenol and 3-(5-
(4-((2-(trimethylsilyl)ethoxy)methyl)-4H-1,2,4-triazol-3-yl)
pyridin-3-yl)phenol (0.08 g, 0.217 mmol) in anhydrous
acetonitrile (3 mL) was added TEA (0.09 mL, 0.65 mmol)
and cyclopentyl isocyanate (0.024 g, 0.217 mmol) at RT
under nitrogen atmosphere. The reaction mixture was stirred
at RT for 10 minutes and then stirred at 75° C. for 3 h. An
additional amount of cyclopentyl isocyanate (0.003 g, 0.02
mmol) was added to the reaction mixture and the resulting
mixture was stirred for an additional 12 h. After completion
of the reaction (monitored by LCMS), the reaction mixture
was concentrated to give a mixture of 3-(5-(1-((2-(trimeth-
ylsilyl)ethoxy)methyl)-1H-1,2,4-triazol-5-yl)pyridin-3-yl)
phenyl cyclopentylcarbamate and 3-(5-(4-((2-(trimethylsi-
lyl)ethoxy)methyl)-4H-1,2,4-triazol-5-yl)pyridin-3-yl)
phenyl cyclopentylcarbamate (80 mg), which was used for
next step without purification. MS (ES+APCI) m/z 480.4
(M+1).

Synthesis of 3-(5-(1H-1,2,4-triazol-5-yl)pyridin-3-
yl)phenyl cyclopentylcarbamate (Example-223)

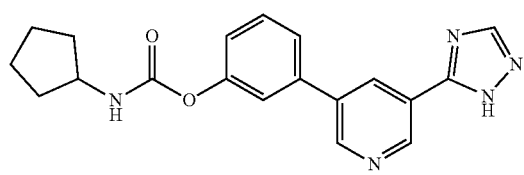 [SMILES: O=C(NC1CCCC1)Oc1cccc(-c2cncc(-c3ncn[nH]3)c2)c1]

To a stirred solution of 3-(5-(1-((2-(trimethylsilyl)ethoxy)
methyl)-1H-1,2,4-triazol-5-yl)pyridin-3-yl)phenyl cyclo-
pentylcarbamate and 3-(5-(4-((2-(trimethylsilyl)ethoxy)
methyl)-4H-1,2,4-triazol-5-yl)pyridin-3-yl)phenyl
cyclopentylcarbamate (0.08 g, 0.167 mmol) in DCM (2 mL)
was added SnCl$_4$ (0.25 mL, 10% solution in DCM) at 0-5°
C. under nitrogen atmosphere. The reaction mixture was
stirred at RT for 2 h. After completion of the reaction
(monitored by LCMS), the reaction mixture was quenched
with aq. 10% NaHCO$_3$ solution and concentrated to give a
residue. The crude residue was triturated with DCM/MeOH
for 20 minutes. The solid was filtered and the filtrate was
concentrated to a crude residue. The residue was purified by
preparative HPLC (0.1% FA) to yield the target compound
(8 mg) as an off white solid. $^1$H NMR (400 MHz, DMSO-
d6) δ 14.48 (bs, 1H), 9.20 (d, J=2.00 Hz, 1H), 8.96 (d,
J=2.00 Hz, 1H), 8.61 (bs, 1H), 8.55 (t, J=2.00 Hz, 1H), 7.87
(d, J=7.20 Hz, 1H), 7.65 (d, J=8.00 Hz, 1H), 7.54 (t, J=8.00
Hz, 2H), 7.20 (t, J=1.60 Hz, 1H), 3.90-3.85 (m, 1H),
1.86-1.85 (m, 2H), 1.68 (m, 2H), 1.52 (m, 4H); MS (ES+
APCI) m/z 350.3 (M+1).

Synthesis of 3-(5-(1-((2-(trimethylsilyl)ethoxy)
methyl)-1H-1,2,4-triazol-5-yl)pyridin-3-yl)phenyl
cyclohexylcarbamate and 3-(5-(4-((2-(trimethylsilyl)
ethoxy)methyl)-4H-1,2,4-triazol-3-yl)pyridin-3-yl)
phenyl cyclohexylcarbamate

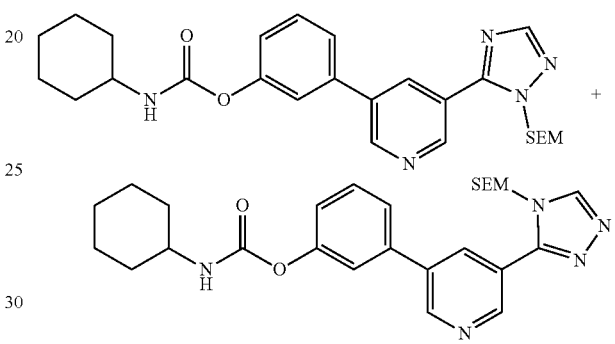

To a stirred solution of 3-(5-(1-((2-(trimethylsilyl)ethoxy)
methyl)-1H-1,2,4-triazol-5-yl)pyridin-3-yl)phenol and 3-(5-
(4-((2-(trimethylsilyl)ethoxy)methyl)-4H-1,2,4-triazol-3-yl)
pyridin-3-yl)phenol (0.1 g, 0.27 mmol) in anhydrous
acetonitrile (3 mL) was added TEA (0.11 mL, 0.81 mmol)
and cyclohexyl isocyanate (0.034 g, 0.27 mmol) at RT under
nitrogen atmosphere. The reaction mixture was stirred at RT
for 10 minutes and then stirred at 75° C. for 3 h. An
additional amount of cyclohexyl isocyanate (0.01 g, 0.08
mmol) was added to the reaction mixture and the resulting
mixture was stirred for an additional 12 h. After completion
of the reaction (monitored by LCMS), the reaction mixture
was concentrated to give a mixture of 3-(5-(1-((2-(trimeth-
ylsilyl)ethoxy)methyl)-1H-1,2,4-triazol-5-yl)pyridin-3-yl)
phenyl cyclohexylcarbamate and 3-(5-(4-((2-(trimethylsilyl)
ethoxy)methyl)-4H-1,2,4-triazol-3-yl)pyridin-3-yl)phenyl
cyclohexylcarbamate (120 mg), which was used for next
step without purification. MS (ES+APCI) m/z 494.3 (M+1).

Synthesis of 3-(5-(1H-1,2,4-triazol-5-yl)pyridin-3-
yl)phenyl cyclohexylcarbamate (Example-224)

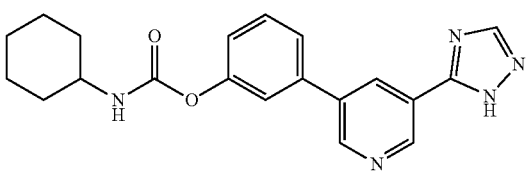 [SMILES: O=C(NC1CCCCC1)Oc1cccc(-c2cncc(-c3ncn[nH]3)c2)c1]

To a stirred solution of 3-(5-(1-((2-(trimethylsilyl)ethoxy)
methyl)-1H-1,2,4-triazol-5-yl)pyridin-3-yl)phenyl cyclo-
hexylcarbamate and 3-(5-(4-((2-(trimethylsilyl)ethoxy)

methyl)-4H-1,2,4-triazol-3-yl)pyridin-3-yl)phenyl cyclohexylcarbamate (0.1 g, 0.21 mmol) in DCM (3 mL) was added SnCl₄ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO₃ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (40 mg) as an off white solid. ¹H NMR (400 MHz, DMSO-d6) δ 14.43 (bs, 1H), 9.20 (d, J=2.00 Hz, 1H), 8.96 (d, J=1.60 Hz, 1H), 8.61-8.51 (m, 2H), 7.80 (d, J=8.00 Hz, 1H), 7.65 (d, J=8.00 Hz, 1H), 7.54 (t, J=7.60 Hz, 2H), 7.20 (dd, J=1.20, 7.80 Hz, 1H), 1.87-1.11 (m, 10H); MS (ES+APCI) m/z 364.4 (M+1).

Synthesis of 3-(5-(1-((2-(trimethylsilyl)ethoxy)methyl)-1H-1,2,4-triazol-5-yl)pyridin-3-yl)phenyl cycloheptylcarbamate and 3-(5-(4-((2-(trimethylsilyl)ethoxy)methyl)-4H-1,2,4-triazol-5-yl)pyridin-3-yl)phenyl cycloheptylcarbamate

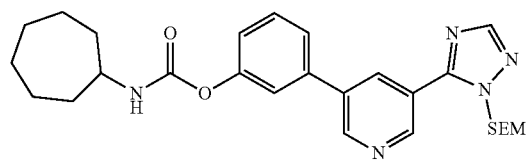

+

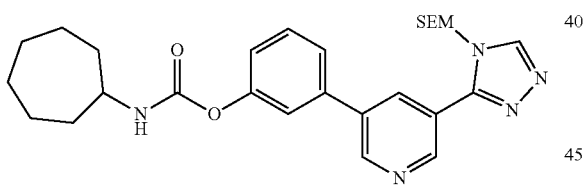

To a stirred solution of 3-(5-(1-((2-(trimethylsilyl)ethoxy)methyl)-1H-1,2,4-triazol-5-yl)pyridin-3-yl)phenol and 3-(5-(4-((2-(trimethylsilyl)ethoxy)methyl)-4H-1,2,4-triazol-3-yl)pyridin-3-yl)phenol (0.1 g, 0.27 mmol) in anhydrous acetonitrile (3 mL) was added TEA (0.09 mL, 0.65 mmol) and cycloheptyl isocyanate (0.038 g, 0.27 mmol) at RT under nitrogen atmosphere. The reaction mixture was stirred at RT for 10 minutes and then stirred at 75° C. for 3 h. An additional amount of cycloheptyl isocyanate (0.013 g, 0.08 mmol) was added to the reaction mixture and the resulting mixture was stirred for an additional 12 h. After completion of the reaction (monitored by LCMS), the reaction mixture was concentrated to give a mixture of 3-(5-(1-((2-(trimethylsilyl)ethoxy)methyl)-1H-1,2,4-triazol-5-yl)pyridin-3-yl)phenylcycloheptylcarbamate and 3-(5-(4-((2-(trimethylsilyl)ethoxy)methyl)-4H-1,2,4-triazol-5-yl)pyridin-3-yl)phenylcycloheptylcarbamate (100 mg), which was used for next step without purification. MS (ES+APCI) m/z 508.4 (M+1).

Synthesis of 3-(5-(1H-1,2,4-triazol-5-yl)pyridin-3-yl)phenyl cycloheptyl carbamate (Example-225)

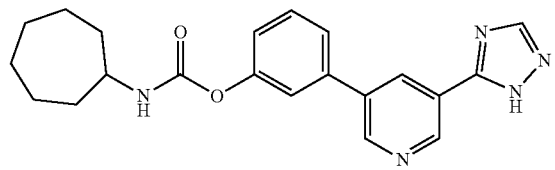 [SMILES: O=C(NC1CCCCCC1)Oc1cccc(-c2cncc(-c3ncn[nH]3)c2)c1]

To a stirred solution of 3-(5-(1-((2-(trimethylsilyl)ethoxy)methyl)-1H-1,2,4-triazol-5-yl)pyridin-3-yl)phenyl cycloheptylcarbamate and 3-(5-(4-((2-(trimethylsilyl)ethoxy)methyl)-4H-1,2,4-triazol-5-yl)pyridin-3-yl)phenyl cycloheptylcarbamate (0.1 g, 0.197 mmol) in DCM (2 mL) was added SnCl₄ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO₃ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (45 mg) as an off white solid. ¹H NMR (400 MHz, DMSO-d6) δ 14.44 (bs, 1H), 9.19 (t, J=3.60 Hz, 1H), 8.96 (d, J=2.40 Hz, 1H), 8.62 (bs, 1H), 8.53 (t, J=2.40 Hz, 1H), 7.84 (d, J=8.00 Hz, 1H), 7.65 (d, J=8.00 Hz, 1H), 7.54 (t, J=8.00 Hz, 2H), 7.20 (dd, J=1.20, 7.60 Hz, 1H), 3.59-3.55 (m, 1H), 1.91-1.87 (m, 2H), 1.67-1.40 (m, 10H); MS (ES+APCI) m/z 378.4 (M+1).

Synthesis of 5-(2-(benzyloxy)-5-hydroxyphenyl)nicotinamide

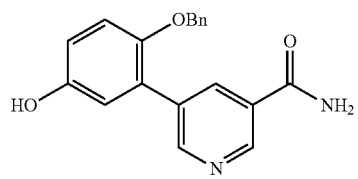 [SMILES: NC(=O)c1cncc(-c2cc(O)ccc2OCc2ccccc2)c1]

To a stirred solution of 4-(benzyloxy)-3-bromophenol (1.13 g, 4.03 mmol) in 1,4-dioxane (24 mL) and water (4 mL) was added 5-(4,4,5,5-tetramethyl-1,3,2-dioxaborolan-2-yl)nicotinamide (1 g, 4.03 mmol) and K₂CO₃ (1.67 g, 12.09 mmol) at RT. The reaction mixture was degassed for 15 minutes then Pd(PPh₃)₄ (0.23 g, 0.20 mmol) was added. The reaction mixture was stirred at 90° C. for 12 h under nitrogen atmosphere. After completion of the reaction (monitored by TLC), The reaction mixture was filtered through celite, washed with DCM/MeOH and the filtrate was concentrated to a residue. The residue was purified by preparative HPLC (0.10% FA) to give 5-(2-(benzyloxy)-5-hydroxyphenyl)nicotinamide (500 mg) as an off white solid. MS (ES+APCI) m/z 321.1 (M+1).

Synthesis of (E)-5-(2-(benzyloxy)-5-hydroxyphenyl)-N-((dimethylamino)methylene)nicotinamide

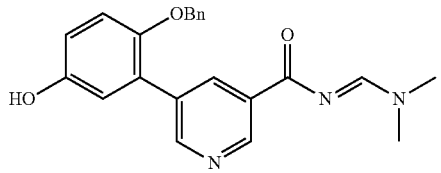 [SMILES: CN(C)/C=N/C(=O)c1cncc(-c2cc(O)ccc2OCc2ccccc2)c1]

To a stirred solution of 5-(2-(benzyloxy)-5-hydroxyphenyl)nicotinamide (1.2 g, 3.75 mmol) in toluene (15 mL) was added DMF-DMA (1.34 g, 11.24 mmol) at RT. The reaction mixture was stirred at 100° C. for 4 h. After completion of the reaction (monitored by TLC), the reaction mixture was cooled to RT and concentrated to a residue. The residue was purified by automated normal-phase chromatography and eluted with DCM/MeOH to give (E)-5-(2-(benzyloxy)-5-hydroxyphenyl)-N-((dimethylamino)methylene)nicotinamide (750 mg) as brown gummy solid. MS (ES+APCI) m/z 376.2 (M+1).

Synthesis of 3-(5-(1H-1,2,4-triazol-5-yl)pyridin-3-yl)-4-(benzyloxy)phenol

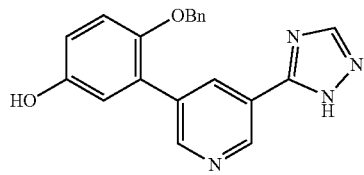 [SMILES: Oc1ccc(OCc2ccccc2)c(-c2cncc(-c3ncn[nH]3)c2)c1]

To a stirred solution of (E)-5-(2-(benzyloxy)-5-hydroxyphenyl)-N-((dimethylamino)methylene)nicotinamide (0.78 g, 2.08 mmol) in AcOH (7.8 mL) was added hydrazine monohydrate (0.95 g, 12.34 mmol) at 0° C. The reaction mixture was stirred at 90° C. for 3 h. After completion of the reaction (monitored by TLC), the resulting mixture was concentrated to a residue. The residue was taken into EtOAc and 10% aqueous solution of NaHCO₃, and the precipitated solid was filtered and dried to give 3-(5-(1H-1,2,4-triazol-5-yl)pyridin-3-yl)-4-(benzyloxy)phenol (420 mg), which was used for next step without purification. MS (ES+APCI) m/z 345.4 (M+1).

4-(benzyloxy)-3-(5-(1-((2-(trimethylsilyl)ethoxy)methyl)-1H-1,2,4-triazol-5-yl)pyridin-3-yl)phenol and 4-(benzyloxy)-3-(5-(4-((2-(trimethylsilyl)ethoxy)methyl)-4H-1,2,4-triazol-3-yl)pyridin-3-yl)phenol

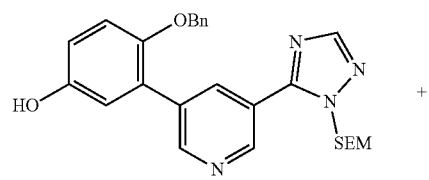

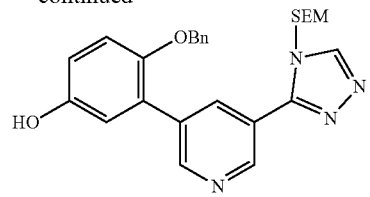

To a stirred solution of 3-(5-(1H-1,2,4-triazol-5-yl)pyridin-3-yl)-4-(benzyloxy)phenol (0.2 g, 0.58 mmol) in DMF (5 mL) was added potassium carbonate (0.12 g, 0.87 mmol) at 0° C. SEM-Cl (0.1 g, 0.58 mmol) was added and the resultant suspension was stirred at RT for 12 h. After completion of the reaction (monitored by LCMS), the reaction mixture was quenched with cold water. The aqueous layer was extracted with ethyl acetate, and the combined organic layers were washed with water, brine and concentrated to give a residue. The residue was purified by automated normal-phase chromatography and eluted with DCM/MeOH to give a mixture of 4-(benzyloxy)-3-(5-(1-((2-(trimethylsilyl)ethoxy)methyl)-1H-1,2,4-triazol-5-yl)pyridin-3-yl)phenol and 4-(benzyloxy)-3-(5-(4-((2-(trimethylsilyl)ethoxy)methyl)-4H-1,2,4-triazol-3-yl)pyridin-3-yl)phenol (150 mg) as viscous liquid. MS (ES+APCI) m/z 475.1 (M+1).

Synthesis of 4-(benzyloxy)-3-(5-(1-((2-(trimethylsilyl)ethoxy)methyl)-1H-1,2,4-triazol-5-yl)pyridin-3-yl)phenyl octylcarbamate and 4-(benzyloxy)-3-(5-(4-((2-(trimethylsilyl)ethoxy)methyl)-4H-1,2,4-triazol-3-yl)pyridin-3-yl)phenyl octylcarbamate

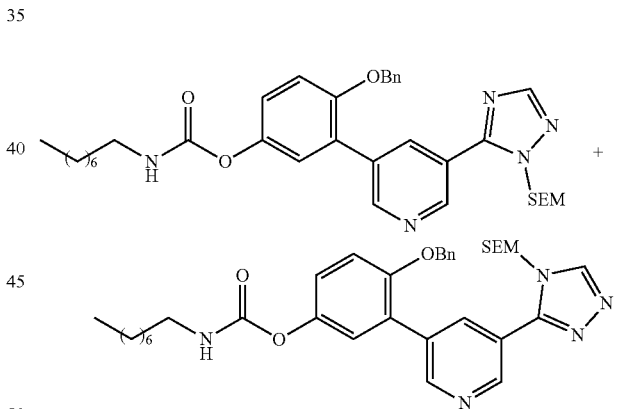

To a stirred solution of 4-(benzyloxy)-3-(5-(1-((2-(trimethylsilyl)ethoxy)methyl)-1H-1,2,4-triazol-5-yl)pyridin-3-yl)phenol and 4-(benzyloxy)-3-(5-(4-((2-(trimethylsilyl)ethoxy)methyl)-4H-1,2,4-triazol-3-yl)pyridin-3-yl)phenol (0.08 g, 0.17 mmol) in anhydrous acetonitrile (2 mL) was added TEA (0.07 mL, 0.51 mmol) and octyl isocyanate (0.026 g, 0.17 mmol) at RT under nitrogen atmosphere. The reaction mixture was stirred at RT for 10 minutes and then stirred at 75° C. for 3 h. An additional amount of octyl isocyanate (0.008 g, 0.05 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with dichloromethane/methanol to give a mixture of 4-(benzyloxy)-3-(5-(1-((2-

(trimethylsilyl)ethoxy)methyl)-1H-1,2,4-triazol-5-yl)pyridin-3-yl)phenyl octylcarbamate and 4-(benzyloxy)-3-(5-(4-((2-(trimethylsilyl)ethoxy)methyl)-4H-1,2,4-triazol-3-yl)pyridin-3-yl)phenyl octylcarbamate (80 mg), which was used for next step without purification. MS (ES+APCI) m/z 630.3 (M+1).

Synthesis of 4-hydroxy-3-(5-(1-((2-(trimethylsilyl)ethoxy)methyl)-1H-1,2,4-triazol-5-yl)pyridin-3-yl)phenyl octylcarbamate and 4-hydroxy-3-(5-(4-((2-(trimethylsilyl)ethoxy)methyl)-4H-1,2,4-triazol-3-yl)pyridin-3-yl)phenyl octylcarbamate

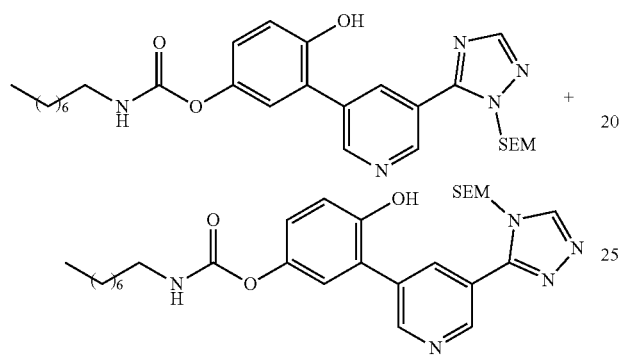

To a stirred solution of 4-(benzyloxy)-3-(5-(1-((2-(trimethylsilyl)ethoxy)methyl)-1H-1,2,4-triazol-5-yl)pyridin-3-yl)phenyl octylcarbamate and 4-(benzyloxy)-3-(5-(4-((2-(trimethylsilyl)ethoxy)methyl)-4H-1,2,4-triazol-3-yl)pyridin-3-yl)phenyl octylcarbamate (0.083 g, 0.13 mmol) in THF (2 mL) and 2-propanol (0.5 mL) was added 10% Pd/C (40 mg) and Pd(OH)$_2$ (40 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to give a mixture of 4-hydroxy-3-(5-(1-((2-(trimethylsilyl)ethoxy)methyl)-1H-1,2,4-triazol-5-yl)pyridin-3-yl)phenyl octyl carbamate and 4-hydroxy-3-(5-(4-((2-(trimethylsilyl)ethoxy)methyl)-4H-1,2,4-triazol-3-yl)pyridin-3-yl)phenyl octyl carbamate (60 mg), which was used for next step without purification. MS (ES+APCI) m/z 540.3 (M+1).

Synthesis of 3-(5-(1H-1,2,4-triazol-5-yl)pyridin-3-yl)-4-hydroxyphenyl octyl carbamate (Example-226)

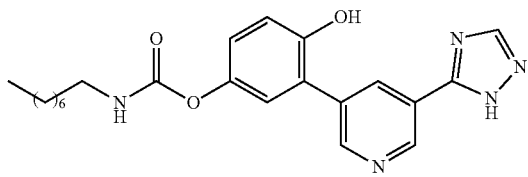

To a stirred solution of 4-hydroxy-3-(5-(1-((2-(trimethylsilyl)ethoxy)methyl)-1H-1,2,4-triazol-5-yl)pyridin-3-yl)phenyl octylcarbamate and 4-hydroxy-3-(5-(4-((2-(trimethylsilyl)ethoxy)methyl)-4H-1,2,4-triazol-3-yl)pyridin-3-yl)phenyl octylcarbamate (0.06 g, 0.11 mmol) in DCM (3 mL) was added SnCl$_4$ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (20 mg) as an off white solid. $^1$H NMR (400 MHz, DMSO-d6) δ 14.36 (bs, 1H), 9.83 (s, 1H), 9.12 (d, J=2.00 Hz, 1H), 8.78 (s, 1H), 8.51 (t, J=2.00 Hz, 1H), 7.66 (t, J=5.60 Hz, 1H), 7.12 (s, 1H), 6.98 (d, J=1.20 Hz, 2H), 3.03 (t, J=6.80 Hz, 2H), 1.48-1.44 (m, 2H), 1.27-1.26 (m, 10H), 0.87-0.84 (m, 3H); MS (ES+APCI) m/z 410.3 (M+1).

Synthesis of 4-(benzyloxy)-3-(5-(1-((2-(trimethylsilyl)ethoxy)methyl)-1H-1,2,4-triazol-5-yl)pyridin-3-yl)phenyl (cyclohexyl methyl)carbamate and 4-(benzyloxy)-3-(5-(4-((2-(trimethylsilyl)ethoxy)methyl)-4H-1,2,4-triazol-3-yl)pyridin-3-yl)phenyl (cyclohexyl methyl)carbamate

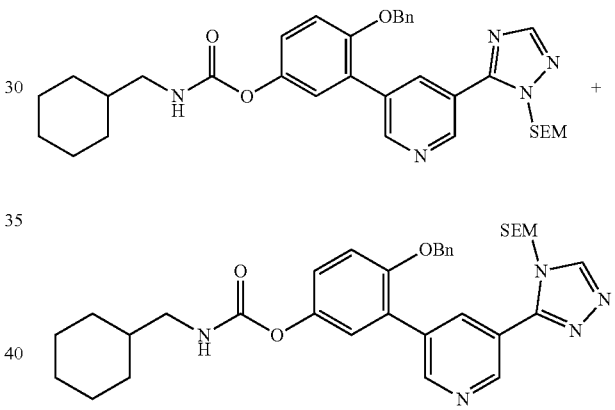

To a stirred solution of 4-(benzyloxy)-3-(5-(1-((2-(trimethylsilyl)ethoxy)methyl)-1H-1,2,4-triazol-5-yl)pyridin-3-yl)phenol and 4-(benzyloxy)-3-(5-(4-((2-(trimethylsilyl)ethoxy)methyl)-4H-1,2,4-triazol-3-yl)pyridin-3-yl)phenol (0.08 g, 0.17 mmol) in anhydrous acetonitrile (2 mL) was added TEA (0.07 mL, 0.51 mmol) and cyclohexanemethyl isocyanate (0.026 g, 0.17 mmol) at RT under nitrogen atmosphere. The reaction mixture was stirred at RT for 10 minutes and then stirred at 75° C. for 3 h. An additional amount of cyclohexanemethyl isocyanate (0.004 g, 0.05 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with dichloromethane/methanol to give a mixture of 4-(benzyloxy)-3-(5-(1-((2-(trimethylsilyl)ethoxy)methyl)-1H-1,2,4-triazol-5-yl)pyridin-3-yl)phenyl (cyclohexyl methyl)carbamate and 4-(benzyloxy)-3-(5-(4-((2-(trimethylsilyl)ethoxy)methyl)-4H-1,2,4-triazol-3-yl)pyridin-3-yl)phenyl (cyclohexyl methyl)carbamate (80 mg), which was used for next step without purification. MS (ES+APCI) m/z 614.2 (M+1).

Synthesis of 4-hydroxy-3-(5-(1-((2-(trimethylsilyl)ethoxy)methyl)-1H-1,2,4-triazol-5-yl)pyridin-3-yl)phenyl (cyclohexyl methyl)carbamate and 4-hydroxy-3-(5-(4-((2-(trimethylsilyl)ethoxy)methyl)-4H-1,2,4-triazol-3-yl)pyridin-3-yl)phenyl (cyclohexyl methyl)carbamate

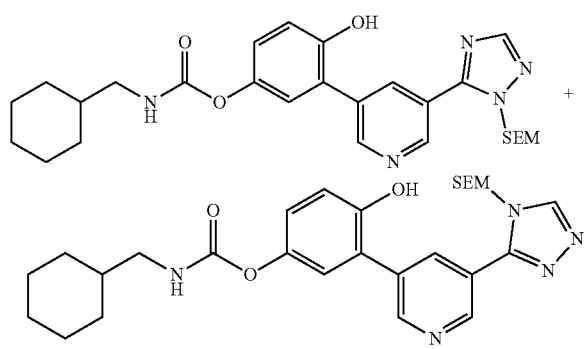

To a stirred solution of 4-(benzyloxy)-3-(5-(1-((2-(trimethylsilyl)ethoxy)methyl)-1H-1,2,4-triazol-5-yl)pyridin-3-yl)phenyl (cyclohexyl methyl)carbamate and 4-(benzyloxy)-3-(5-(4-((2-(trimethylsilyl)ethoxy)methyl)-4H-1,2,4-triazol-3-yl)pyridin-3-yl)phenyl (cyclohexyl methyl)carbamate (0.083 g, 0.13 mmol) in THF (2 mL) and 2-propanol (0.5 mL) was added 10% Pd/C (40 mg) and Pd(OH)$_2$ (40 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to give a mixture of 4-hydroxy-3-(5-(1-((2-(trimethylsilyl)ethoxy)methyl)-1H-1,2,4-triazol-5-yl)pyridin-3-yl)phenyl (cyclohexyl methyl) carbamate and 4-hydroxy-3-(5-(4-((2-(trimethylsilyl)ethoxy)methyl)-4H-1,2,4-triazol-3-yl)pyridin-3-yl)phenyl (cyclohexyl methyl)carbamate (60 mg), which was used for next step without purification. MS (ES+APCI) m/z 524.3 (M+1).

Synthesis of 3-(5-(1H-1,2,4-triazol-5-yl)pyridin-3-yl)-4-hydroxyphenyl (cyclohexyl methyl) carbamate (Example-227)

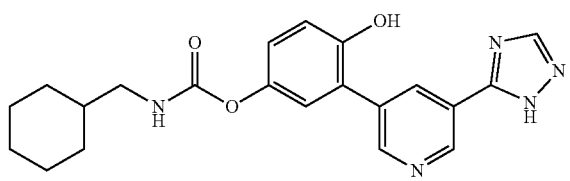 [SMILES: O=C(NCC1CCCCC1)Oc1ccc(O)c(-c2cncc(-c3ncn[nH]3)c2)c1]

To a stirred solution of 4-hydroxy-3-(5-(1-((2-(trimethylsilyl)ethoxy)methyl)-1H-1,2,4-triazol-5-yl)pyridin-3-yl)phenyl (cyclohexyl methyl)carbamate and 4-hydroxy-3-(5-(4-((2-(trimethylsilyl)ethoxy)methyl)-4H-1,2,4-triazol-3-yl)pyridin-3-yl)phenyl (cyclohexyl methyl)carbamate (0.06 g, 0.12 mmol) in DCM (3 mL) was added SnCl$_4$ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (15 mg) as an off white solid. $^1$H NMR (400 MHz, DMSO-d6) δ 14.35 (bs, 1H), 9.85 (bs, 1H), 9.12 (d, J=2.00 Hz, 1H), 8.78 (d, J=2.00 Hz, 1H), 8.59 (bs, 1H), 8.51 (t, J=2.00 Hz, 1H), 7.69 (t, J=5.60 Hz, 1H), 7.13 (t, J=1.20 Hz, 1H), 6.98 (d, J=2.00 Hz, 2H), 2.90 (t, J=6.40 Hz, 2H), 1.72-1.61 (m, 5H), 1.46-1.39 (m, 1H), 1.24-1.11 (m, 3H), 0.97-0.88 (m, 2H); MS (ES+APCI) m/z 394.3 (M+1).

Synthesis of 4-(benzyloxy)-3-(5-(1-((2-(trimethylsilyl)ethoxy)methyl)-1H-1,2,4-triazol-5-yl)pyridin-3-yl)phenyl benzylcarbamate and 4-(benzyloxy)-3-(5-(4-((2-(trimethylsilyl)ethoxy)methyl)-4H-1,2,4-triazol-3-yl)pyridin-3-yl)phenyl benzylcarbamate

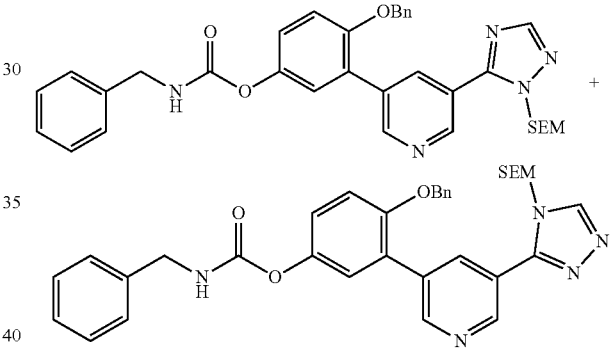

To a stirred solution of 4-(benzyloxy)-3-(5-(1-((2-(trimethylsilyl)ethoxy)methyl)-1H-1,2,4-triazol-5-yl)pyridin-3-yl)phenol and 4-(benzyloxy)-3-(5-(4-((2-(trimethylsilyl)ethoxy)methyl)-4H-1,2,4-triazol-3-yl)pyridin-3-yl)phenol (0.08 g, 0.17 mmol) in anhydrous acetonitrile (2 mL) was added TEA (0.07 mL, 0.51 mmol) and benzyl isocyanate (0.022 g, 0.17 mmol) at RT under nitrogen atmosphere. The reaction mixture was stirred at RT for 10 minutes and then stirred at 75° C. for 3 h. An additional amount of benzyl isocyanate (0.01 g, 0.05 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with dichloromethane/methanol to give a mixture of 4-(benzyloxy)-3-(5-(1-((2-(trimethylsilyl)ethoxy)methyl)-1H-1,2,4-triazol-5-yl)pyridin-3-yl)phenyl benzylcarbamate and 4-(benzyloxy)-3-(5-(4-((2-(trimethylsilyl)ethoxy)methyl)-4H-1,2,4-triazol-3-yl)pyridin-3-yl)phenyl benzylcarbamate (50 mg), which was used for next step without purification. MS (ES+APCI) m/z 608.5 (M+1).

Synthesis of 4-hydroxy-3-(5-(1-((2-(trimethylsilyl)ethoxy)methyl)-1H-1,2,4-triazol-5-yl)pyridin-3-yl)phenyl benzylcarbamate and 4-hydroxy-3-(5-(4-((2-(trimethylsilyl)ethoxy)methyl)-4H-1,2,4-triazol-3-yl)pyridin-3-yl)phenyl benzylcarbamate

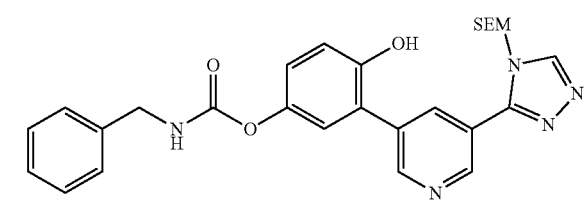

To a stirred solution of 4-(benzyloxy)-3-(5-(1-((2-(trimethylsilyl)ethoxy)methyl)-1H-1,2,4-triazol-5-yl)pyridin-3-yl)phenyl benzylcarbamate and 4-(benzyloxy)-3-(5-(4-((2-(trimethylsilyl)ethoxy)methyl)-4H-1,2,4-triazol-3-yl)pyridin-3-yl)phenyl benzylcarbamate (0.05 g, 0.08 mmol) in THF (2 mL) and 2-propanol (0.5 mL) was added 10% Pd/C (25 mg) and Pd(OH)$_2$ (25 mg). The reaction mixture was stirred RT for 12 h under hydrogen balloon. After completion of the reaction (monitored by LCMS), the resultant mixture was filtered through a pad of celite, washed with DCM/MeOH and the filtrate was concentrated to give a mixture of 4-hydroxy-3-(5-(1-((2-(trimethylsilyl)ethoxy)methyl)-1H-1,2,4-triazol-5-yl)pyridin-3-yl)phenyl benzylcarbamate and 4-hydroxy-3-(5-(4-((2-(trimethylsilyl)ethoxy)methyl)-4H-1,2,4-triazol-3-yl)pyridin-3-yl)phenyl benzylcarbamate (30 mg), which was used for next step without purification. MS (ES+APCI) m/z 518.3 (M+1).

Synthesis of 3-(5-(1H-1,2,4-triazol-5-yl)pyridin-3-yl)-4-hydroxyphenyl benzylcarbamate (Example-228)

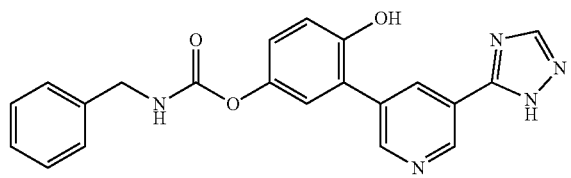 [SMILES: O=C(NCc1ccccc1)Oc1ccc(O)c(-c2cncc(-c3ncn[nH]3)c2)c1]

To a stirred solution of 4-hydroxy-3-(5-(1-((2-(trimethylsilyl)ethoxy)methyl)-1H-1,2,4-triazol-5-yl)pyridin-3-yl) phenyl octylcarbamate and 4-hydroxy-3-(5-(4-((2-(trimethylsilyl)ethoxy)methyl)-4H-1,2,4-triazol-3-yl)pyridin-3-yl) phenyl octylcarbamate (0.03 g, 0.06 mmol) in DCM (2 mL) was added SnCl$_4$ (0.2 mL, 10% solution in DCM) at 0-5° C. under nitrogen atmosphere. The reaction mixture was stirred at for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (9 mg) as an off white solid. $^1$H NMR (400 MHz, DMSO-d6) δ 14.40 (s, 1H), 9.93 (s, 1H), 9.12 (d, J=2.40 Hz, 1H), 8.79 (d, J=2.00 Hz, 1H), 8.59 (s, 1H), 8.52 (t, J=2.00 Hz, 1H), 8.25 (t, J=6.00 Hz, 1H), 7.38-7.25 (m, 5H), 7.17 (d, J=2.40 Hz, 1H), 7.04-6.98 (m, 2H), 4.28 (d, J=6.00 Hz, 2H); MS (ES+APCI) m/z 388.3 (M+1).

Synthesis of 4-(benzyloxy)-3-(5-(1-((2-(trimethylsilyl)ethoxy)methyl)-1H-1,2,4-triazol-5-yl)pyridin-3-yl)phenyl cyclopentylcarbamate and 4-(benzyloxy)-3-(5-(4-((2-(trimethylsilyl)ethoxy)methyl)-4H-1,2,4-triazol-3-yl)pyridin-3-yl)phenyl cyclopentylcarbamate

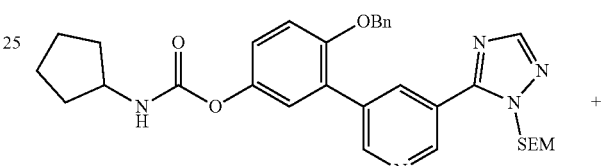

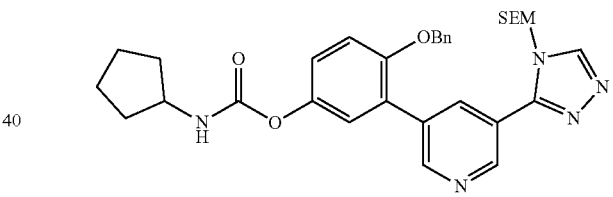

To a stirred solution of 4-(benzyloxy)-3-(5-(1-((2-(trimethylsilyl)ethoxy)methyl)-1H-1,2,4-triazol-5-yl)pyridin-3-yl)phenol and 4-(benzyloxy)-3-(5-(4-((2-(trimethylsilyl)ethoxy)methyl)-4H-1,2,4-triazol-3-yl)pyridin-3-yl)phenol (0.08 g, 0.17 mmol) in anhydrous acetonitrile (2.5 mL) was added TEA (0.07 mL, 0.51 mmol) and cyclopentyl isocyanate (0.02 g, 0.17 mmol) at RT under nitrogen atmosphere. The reaction mixture was stirred at RT for 10 minutes and then stirred at 75° C. for 3 h. An additional amount of cyclopentyl isocyanate (0.01 g, 0.05 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with dichloromethane/methanol to give a mixture of 4-(benzyloxy)-3-(5-(1-((2-(trimethylsilyl)ethoxy)methyl)-1H-1,2,4-triazol-5-yl)pyridin-3-yl)phenyl cyclopentylcarbamate and 4-(benzyloxy)-3-(5-(4-((2-(trimethylsilyl)ethoxy)methyl)-4H-1,2,4-triazol-3-yl)pyridin-3-yl)phenyl cyclopentylcarbamate (50 mg), which was used for next step without purification. MS (ES+APCI) m/z 586.4 (M+1).

Synthesis of 4-hydroxy-3-(5-(1-((2-(trimethylsilyl)ethoxy)methyl)-1H-1,2,4-triazol-5-yl)pyridin-3-yl)phenyl cyclopentylcarbamate and 4-hydroxy-3-(5-(4-((2-(trimethylsilyl)ethoxy)methyl)-4H-1,2,4-triazol-3-yl)pyridin-3-yl)phenyl cyclopentylcarbamate

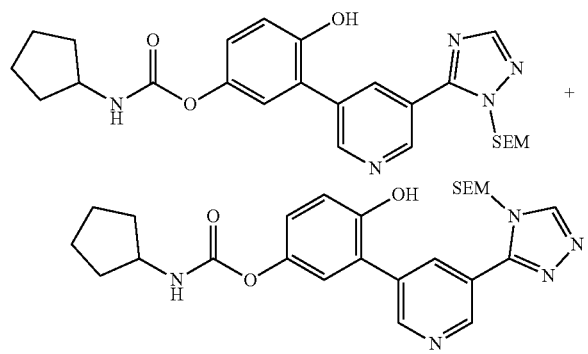

To a stirred solution of 4-(benzyloxy)-3-(5-(1-((2-(trimethylsilyl)ethoxy)methyl)-1H-1,2,4-triazol-5-yl)pyridin-3-yl)phenyl cyclopentylcarbamate and 4-(benzyloxy)-3-(5-(4-((2-(trimethylsilyl)ethoxy)methyl)-4H-1,2,4-triazol-3-yl)pyridin-3-yl)phenyl cyclopentylcarbamate (0.05 g, 0.09 mmol) in THF (2 mL) and 2-propanol (0.5 mL) was added 10% Pd/C (25 mg) and Pd(OH)$_2$ (25 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to give a mixture of 4-hydroxy-3-(5-(1-((2-(trimethylsilyl)ethoxy)methyl)-1H-1,2,4-triazol-5-yl)pyridin-3-yl)phenyl cyclopentylcarbamate and 4-hydroxy-3-(5-(4-((2-(trimethylsilyl)ethoxy)methyl)-4H-1,2,4-triazol-3-yl)pyridin-3-yl)phenyl cyclopentylcarbamate (30 mg), which was used for next step without purification. MS (ES+APCI) m/z 496.3 (M+1).

Synthesis of 3-(5-(1H-1,2,4-triazol-5-yl)pyridin-3-yl)-4-hydroxyphenyl cyclopentylcarbamate (Example-229)

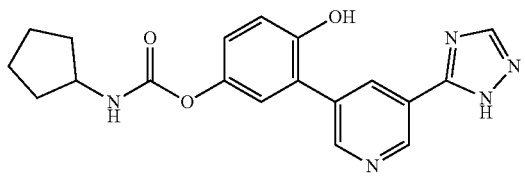 [SMILES: O=C(NC1CCCC1)Oc1ccc(O)c(-c2cncc(-c3ncn[nH]3)c2)c1]

To a stirred solution of 4-hydroxy-3-(5-(1-((2-(trimethylsilyl)ethoxy)methyl)-1H-1,2,4-triazol-5-yl)pyridin-3-yl)phenyl cyclopentylcarbamate and 4-hydroxy-3-(5-(4-((2-(trimethylsilyl)ethoxy)methyl)-4H-1,2,4-triazol-3-yl)pyridin-3-yl)phenyl cyclopentylcarbamate (0.03 g, 0.06 mmol) in DCM (2 mL) was added SnCl$_4$ (0.2 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (6 mg) as an off white solid. $^1$H NMR (400 MHz, DMSO-d6) δ 14.45 (s, 1H), 9.95 (s, 1H), 9.12 (d, J=2.00 Hz, 1H), 8.79 (d, J=2.40 Hz, 1H), 8.58-8.51 (m, 1H), 8.45 (s, 1H), 7.70 (d, J=7.20 Hz, 1H), 7.13 (s, 1H), 7.00 (d, J=10.40 Hz, 2H), 3.88-3.82 (m, 1H), 1.84-1.47 (m, 8H); MS (ES+APCI) m/z 366.3 (M+1).

Synthesis of 4-(benzyloxy)-3-(5-(1-((2-(trimethylsilyl)ethoxy)methyl)-1H-1,2,4-triazol-5-yl)pyridin-3-yl)phenyl cyclohexyl carbamate and 4-(benzyloxy)-3-(5-(4-((2-(trimethylsilyl)ethoxy)methyl)-4H-1,2,4-triazol-3-yl)pyridin-3-yl)phenyl cyclohexyl carbamate

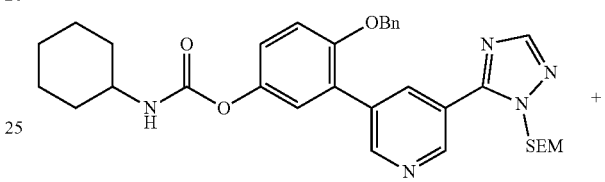

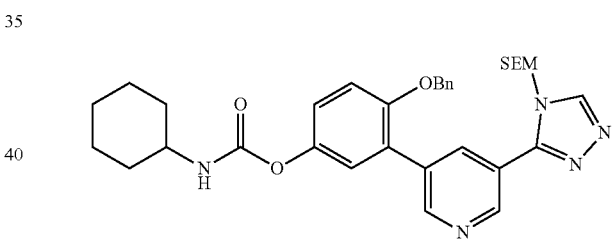

To a stirred solution of 4-(benzyloxy)-3-(5-(1-((2-(trimethylsilyl)ethoxy)methyl)-1H-1,2,4-triazol-5-yl)pyridin-3-yl)phenol and 4-(benzyloxy)-3-(5-(4-((2-(trimethylsilyl)ethoxy)methyl)-4H-1,2,4-triazol-3-yl)pyridin-3-yl)phenol (0.08 g, 0.17 mmol) in anhydrous acetonitrile (2.5 mL) was added TEA (0.07 mL, 0.51 mmol) and cyclohexyl isocyanate (0.02 g, 0.17 mmol) at RT under nitrogen atmosphere. The reaction mixture was stirred at RT for 10 minutes and then stirred at 75° C. for 3 h. An additional amount of cyclohexyl isocyanate (0.01 g, 0.05 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with dichloromethane/methanol to give a mixture of 4-(benzyloxy)-3-(5-(1-((2-(trimethylsilyl)ethoxy)methyl)-1H-1,2,4-triazol-5-yl)pyridin-3-yl)phenyl cyclohexyl carbamate and 4-(benzyloxy)-3-(5-(4-((2-(trimethylsilyl)ethoxy)methyl)-4H-1,2,4-triazol-3-yl)pyridin-3-yl)phenyl cyclohexyl carbamate (83 mg), which was used for next step without purification. MS (ES+APCI) m/z 600.3 (M+1).

Synthesis of 4-hydroxy-3-(5-(1-((2-(trimethylsilyl)ethoxy)methyl)-1H-1,2,4-triazol-5-yl)pyridin-3-yl)phenyl cyclohexyl carbamate and 4-hydroxy-3-(5-(4-((2-(trimethylsilyl)ethoxy)methyl)-4H-1,2,4-triazol-3-yl)pyridin-3-yl)phenyl cyclohexyl carbamate

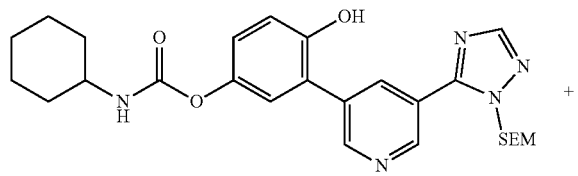

To a stirred solution of 4-(benzyloxy)-3-(5-(1-((2-(trimethylsilyl)ethoxy)methyl)-1H-1,2,4-triazol-5-yl)pyridin-3-yl)phenyl cyclohexyl carbamate and 4-(benzyloxy)-3-(5-(4-((2-(trimethylsilyl)ethoxy)methyl)-4H-1,2,4-triazol-3-yl)pyridin-3-yl)phenyl cyclohexyl carbamate (0.08 g, 0.13 mmol) in THF (2 mL) and 2-propanol (0.5 mL) was added 10% Pd/C (40 mg) and Pd(OH)$_2$ (40 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to give a mixture of 4-hydroxy-3-(5-(1-((2-(trimethylsilyl)ethoxy)methyl)-1H-1,2,4-triazol-5-yl)pyridin-3-yl)phenyl cyclohexyl carbamate and 4-hydroxy-3-(5-(4-((2-(trimethylsilyl)ethoxy)methyl)-4H-1,2,4-triazol-3-yl)pyridin-3-yl)phenyl cyclohexyl carbamate (60 mg), which was used for next step without purification. MS (ES+APCI) m/z 510.4 (M+1).

Synthesis of 3-(5-(1H-1,2,4-triazol-5-yl)pyridin-3-yl)-4-hydroxyphenyl cyclohexyl carbamate (Example-230)

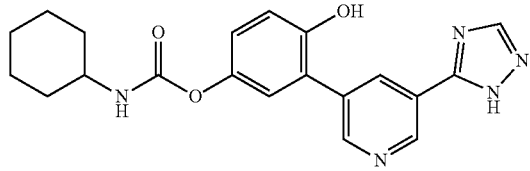 [SMILES: O=C(NC1CCCCC1)Oc1ccc(O)c(-c2cncc(-c3ncn[nH]3)c2)c1]

To a stirred solution of 4-hydroxy-3-(5-(1-((2-(trimethylsilyl)ethoxy)methyl)-1H-1,2,4-triazol-5-yl)pyridin-3-yl)phenyl cyclohexyl carbamate and 4-hydroxy-3-(5-(4-((2-(trimethylsilyl)ethoxy)methyl)-4H-1,2,4-triazol-3-yl)pyridin-3-yl)phenyl cyclohexyl carbamate (0.06 g, 0.12 mmol) in DCM (3 mL) was added SnCl$_4$ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (12 mg) as an off white solid. $^1$H NMR (400 MHz, DMSO-d6) δ 9.85 (s, 1H), 9.12 (d, J=2.00 Hz, 1H), 8.79 (d, J=2.00 Hz, 1H), 8.59 (s, 1H), 8.51 (t, J=2.00 Hz, 1H), 7.63 (d, J=7.60 Hz, 1H), 7.13 (s, 1H), 7.01-6.96 (m, 2H), 1.84-1.12 (m, 10H); MS (ES+APCI) m/z 380.3 (M+1).

Synthesis of 4-(benzyloxy)-3-(5-(1-((2-(trimethylsilyl)ethoxy)methyl)-1H-1,2,4-triazol-5-yl)pyridin-3-yl)phenyl cycloheptylcarbamate and 4-(benzyloxy)-3-(5-(4-((2-(trimethylsilyl)ethoxy)methyl)-4H-1,2,4-triazol-3-yl)pyridin-3-yl)phenyl cycloheptylcarbamate

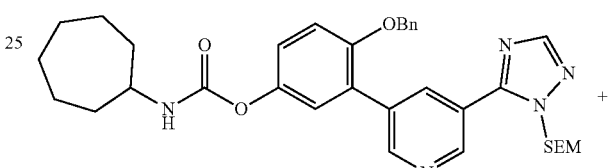

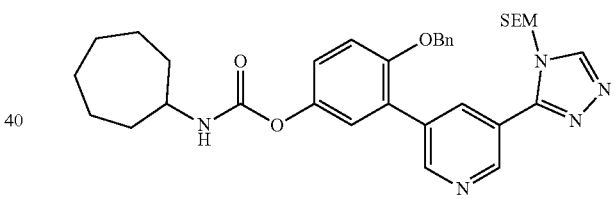

To a stirred solution of 4-(benzyloxy)-3-(5-(1-((2-(trimethylsilyl)ethoxy)methyl)-1H-1,2,4-triazol-5-yl)pyridin-3-yl)phenol and 4-(benzyloxy)-3-(5-(4-((2-(trimethylsilyl)ethoxy)methyl)-4H-1,2,4-triazol-3-yl)pyridin-3-yl)phenol (0.08 g, 0.17 mmol) in anhydrous acetonitrile (2.5 mL) was added TEA (0.07 mL, 0.51 mmol) and cycloheptyl isocyanate (0.02 g, 0.17 mmol) at RT under nitrogen atmosphere. The reaction mixture was stirred at RT for 10 minutes and then stirred at 75° C. for 3 h. An additional amount of cycloheptyl isocyanate (0.01 g, 0.05 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with dichloromethane/methanol to give a mixture of 4-(benzyloxy)-3-(5-(1-((2-(trimethylsilyl)ethoxy)methyl)-1H-1,2,4-triazol-5-yl)pyridin-3-yl)phenyl cycloheptylcarbamate and 4-(benzyloxy)-3-(5-(4-((2-(trimethylsilyl)ethoxy)methyl)-4H-1,2,4-triazol-3-yl)pyridin-3-yl)phenyl cycloheptyl carbamate (80 mg), which was used for next step without purification. MS (ES+APCI) m/z 614.3 (M+1).

Synthesis of 4-hydroxy-3-(5-(1-((2-(trimethylsilyl)ethoxy)methyl)-1H-1,2,4-triazol-5-yl)pyridin-3-yl)phenyl cycloheptylcarbamate and 4-hydroxy-3-(5-(4-((2-(trimethylsilyl)ethoxy)methyl)-4H-1,2,4-triazol-3-yl)pyridin-3-yl)phenyl cycloheptylcarbamate

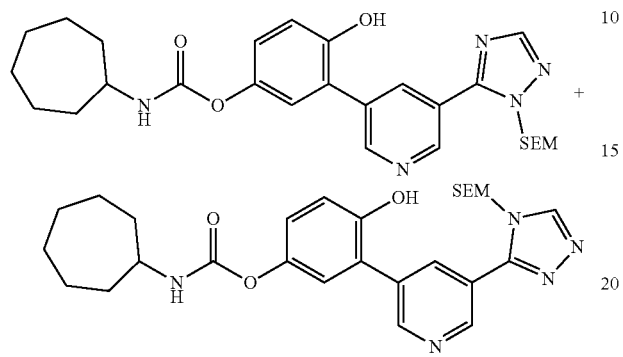

To a stirred solution of 4-(benzyloxy)-3-(5-(1-((2-(trimethylsilyl)ethoxy)methyl)-1H-1,2,4-triazol-5-yl)pyridin-3-yl)phenyl cycloheptylcarbamate and 4-(benzyloxy)-3-(5-(4-((2-(trimethylsilyl)ethoxy)methyl)-4H-1,2,4-triazol-3-yl)pyridin-3-yl)phenyl cycloheptyl carbamate (0.08 g, 0.13 mmol) in THF (2 mL) and 2-propanol (0.5 mL) was added 10% Pd/C (40 mg) and Pd(OH)₂ (40 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to give a mixture of 4-hydroxy-3-(5-(1-((2-(trimethylsilyl)ethoxy)methyl)-1H-1,2,4-triazol-5-yl)pyridin-3-yl)phenyl cycloheptylcarbamate and 4-hydroxy-3-(5-(4-((2-(trimethylsilyl)ethoxy)methyl)-4H-1,2,4-triazol-3-yl)pyridin-3-yl)phenyl cycloheptylcarbamate (60 mg), which was used for next step without purification. MS (ES+APCI) m/z 524.3 (M+1).

Synthesis of 3-(5-(1H-1,2,4-triazol-5-yl)pyridin-3-yl)-4-hydroxyphenyl cycloheptylcarbamate (Example-231)

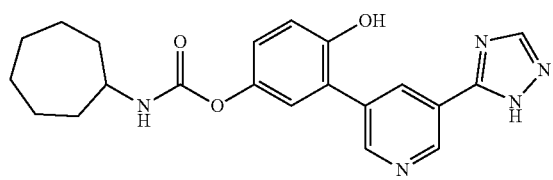 [SMILES: O=C(NC1CCCCCC1)Oc1ccc(O)c(-c2cncc(-c3ncn[nH]3)c2)c1]

To a stirred solution of 4-hydroxy-3-(5-(1-((2-(trimethylsilyl)ethoxy)methyl)-1H-1,2,4-triazol-5-yl)pyridin-3-yl)phenyl cycloheptylcarbamate and 4-hydroxy-3-(5-(4-((2-(trimethylsilyl)ethoxy)methyl)-4H-1,2,4-triazol-3-yl)pyridin-3-yl)phenyl cycloheptyl carbamate (0.06 g, 0.12 mmol) in DCM (3 mL) was added SnCl₄ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO₃ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (5 mg) as an off white solid. ¹H NMR (400 MHz, DMSO-d6) δ 14.43 (bs, 1H), 9.87 (bs, 1H), 9.12 (d, J=2.00 Hz, 1H), 8.78 (bs, 1H), 8.61 (bs, 1H), 8.51 (t, J=2.00 Hz, 1H), 7.67 (d, J=8.00 Hz, 1H), 7.12 (d, J=1.20 Hz, 1H), 6.97 (d, J=10.40 Hz, 2H), 3.57-3.50 (m, 1H), 1.88-1.83 (m, 2H), 1.65-1.37 (m, 10H); MS (ES+APCI) m/z 394.3 (M+1).

Synthesis of 5-(5-hydroxy-2-methoxyphenyl)nicotinamide

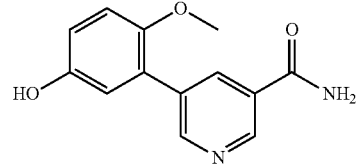 [SMILES: COc1ccc(O)cc1-c1cncc(C(N)=O)c1]

To a stirred solution of 5-(4,4,5,5-tetramethyl-1,3,2-dioxaborolan-2-yl)nicotinamide (2 g, 8.06 mmol) in 1,4-dioxane (30 mL) and water (3 mL) was added 3-bromo-4-methoxyphenol (1.64 g, 8.06 mmol) and K₂CO₃ (3.34 g, 24.18 mmol) at RT. The reaction mixture was degassed for 15 minutes then Pd(PPh₃)₄ (0.47 g, 0.40 mmol) was added. The reaction mixture was stirred at 90° C. for 12 h under nitrogen atmosphere. After completion of the reaction (monitored by TLC), The reaction mixture was filtered through celite, washed with DCM/MeOH and the filtrate was concentrated to a residue. The residue was purified by preparative HPLC (0.1% FA) to give 5-(5-hydroxy-2-methoxyphenyl)nicotinamide (850 mg) as an off white solid. MS (ES+APCI) m/z 245.4 (M+1).

Synthesis of (E)-N-((dimethylamino)methylene)-5-(5-hydroxy-2-methoxyphenyl)nicotinamide

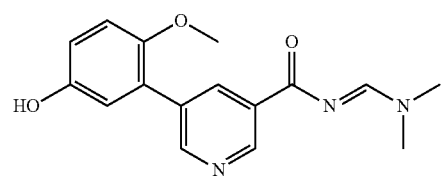 [SMILES: COc1ccc(O)cc1-c1cncc(C(=O)/N=C/N(C)C)c1]

To a stirred solution of 5-(5-hydroxy-2-methoxyphenyl)nicotinamide (0.58 g, 2.38 mmol) in toluene (5 mL) was added DMF-DMA (0.85 g, 7.12 mmol) at RT. The reaction mixture was stirred at 100° C. for 2 h. After completion of the reaction (monitored by TLC), the reaction mixture was cooled to RT and concentrated to a residue. The residue was purified by automated normal-phase chromatography and eluted with DCM/MeOH to give (E)-N-((dimethylamino)methylene)-5-(5-hydroxy-2-methoxyphenyl)nicotinamide (300 mg) as brown solid. MS (ES+APCI) m/z 300.2 (M+1).

Synthesis of 3-(5-(1H-1,2,4-triazol-5-yl)pyridin-3-yl)-4-methoxyphenol

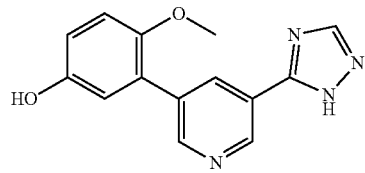 [SMILES: COc1ccc(O)cc1-c1cncc(-c2ncn[nH]2)c1]

To a stirred solution of (E)-N-((dimethylamino)methylene)-5-(5-hydroxy-2-methoxyphenyl) nicotinamide (0.3 g, 1 mmol) in AcOH (1 mL) was added hydrazine monohydrate (0.46 g, 5.95 mmol) at 0° C. The reaction mixture was stirred at 90° C. for 3 h. After completion of the reaction (monitored by TLC), the resulting mixture was concentrated to a residue. The residue was taken into EtOAc and washed with 10% aqueous solution of NaHCO$_3$, and the combined organic layers were washed with water, brine and concentrated to give 3-(5-(1H-1,2,4-triazol-5-yl)pyridin-3-yl)-4-methoxyphenol (180 mg), which was used for next step without purification. MS (ES+APCI) m/z 267.1 (M-1).

Synthesis of 4-methoxy-3-(5-(1-((2-(trimethylsilyl)ethoxy)methyl)-1H-1,2,4-triazol-5-yl)pyridin-3-yl)phenol and 4-methoxy-3-(5-(4-((2-(trimethylsilyl)ethoxy)methyl)-4H-1,2,4-triazol-3-yl)pyridin-3-yl)phenol

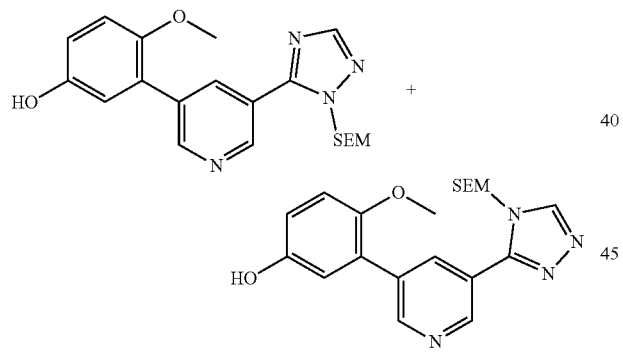

To a stirred solution of 3-(5-(1H-1,2,4-triazol-5-yl)pyridin-3-yl)-4-methoxyphenol 0.19 g, 0.70 mmol) in DMF (2 mL) was added potassium carbonate (0.14 g, 1.03 mmol) at 0° C. SEM-Cl (0.12 g, 0.70 mmol) was added and the resultant suspension was stirred at RT for 12 h. After completion of the reaction (monitored by LCMS), the reaction mixture was quenched with cold water. The aqueous layer was extracted with ethyl acetate, and the combined organic layers were washed with water, brine and concentrated to give a residue. The residue was purified by automated normal-phase chromatography and eluted with DCM/MeOH to give a mixture of 4-methoxy-3-(5-(1-((2-(trimethylsilyl)ethoxy)methyl)-1H-1,2,4-triazol-5-yl)pyridin-3-yl)phenol and 4-methoxy-3-(5-(4-((2-(trimethylsilyl)ethoxy)methyl)-4H-1,2,4-triazol-3-yl)pyridin-3-yl)phenol (120 mg) as brownish liquid. MS (ES+APCI) m/z 399.2 (M+1).

Synthesis of 4-methoxy-3-(5-(1-((2-(trimethylsilyl)ethoxy)methyl)-1H-1,2,4-triazol-5-yl)pyridin-3-yl)phenyl octylcarbamate and 4-methoxy-3-(5-(4-((2-(trimethylsilyl)ethoxy)methyl)-4H-1,2,4-triazol-3-yl)pyridin-3-yl)phenyl octylcarbamate

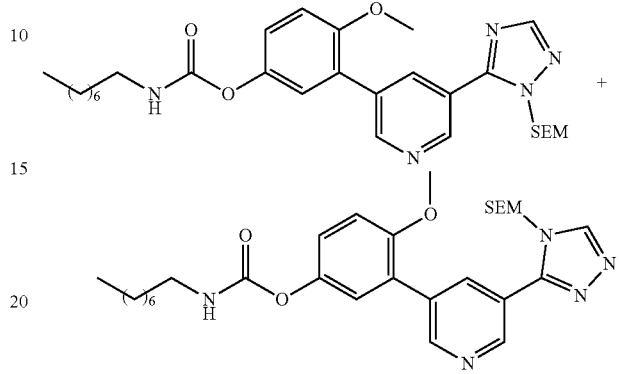

To a stirred solution of 4-methoxy-3-(5-(1-((2-(trimethylsilyl)ethoxy)methyl)-1H-1,2,4-triazol-5-yl)pyridin-3-yl)phenol and 4-methoxy-3-(5-(4-((2-(trimethylsilyl)ethoxy)methyl)-4H-1,2,4-triazol-3-yl)pyridin-3-yl)phenol (0.05 g, 0.125 mmol) in anhydrous acetonitrile (2 mL) was added TEA (0.05 mL, 0.38 mmol) and n-octyl isocyanate (0.02 g, 0.13 mmol) at RT under nitrogen atmosphere. The reaction mixture was stirred at RT for 10 minutes and then stirred at 75° C. for 3 h. An additional amount of n-octyl isocyanate (0.006 g, 0.04 mmol) was added to the reaction mixture and the resulting mixture was stirred for an additional 12 h. After completion of the reaction (monitored by LCMS), the reaction mixture was concentrated to give a mixture of 4-methoxy-3-(5-(1-((2-(trimethylsilyl)ethoxy)methyl)-1H-1,2,4-triazol-5-yl)pyridin-3-yl)phenyl octylcarbamate and 4-methoxy-3-(5-(4-((2-(trimethylsilyl)ethoxy)methyl)-4H-1,2,4-triazol-3-yl)pyridin-3-yl)phenyl octylcarbamate (60 mg), which was used for next step without purification. MS (ES+APCI) m/z 554.3 (M+1).

Synthesis of 3-(5-(1H-1,2,4-triazol-5-yl)pyridin-3-yl)-4-methoxyphenyl octylcarbamate (Example-232)

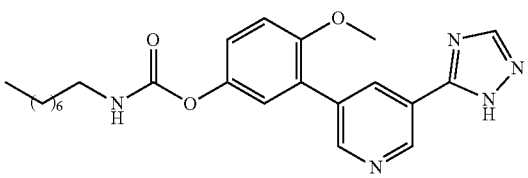

To a stirred solution of 4-methoxy-3-(5-(1-((2-(trimethylsilyl)ethoxy)methyl)-1H-1,2,4-triazol-5-yl)pyridin-3-yl)phenyl octylcarbamate and 4-methoxy-3-(5-(4-((2-(trimethylsilyl)ethoxy)methyl)-4H-1,2,4-triazol-3-yl)pyridin-3-yl)phenyl octylcarbamate (0.05 g, 0.09 mmol) in DCM (2 mL) was added SnCl$_4$ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (15 mg) as an off white solid. $^1$H NMR (400 MHz, DMSO-d6) δ 14.34 (bs, 1H), 9.14 (d, J=2.00 Hz, 1H), 8.73 (d, J=2.00 Hz, 1H), 8.59 (bs, 1H), 8.42 (t, J=2.00 Hz, 1H), 7.72 (t, J=5.60 Hz, 1H), 7.19-7.17 (m, 3H), 3.81 (s, 3H), 3.08-3.03 (m, 2H), 1.46 (t, J=6.80 Hz, 2H), 1.27 (m, 10H), 0.87-0.84 (m, 3H); MS (ES+APCI) m/z 424.4 (M+1).

Synthesis of 4-methoxy-3-(5-(1-((2-(trimethylsilyl) ethoxy)methyl)-1H-1,2,4-triazol-5-yl)pyridin-3-yl) phenyl(cyclohexylmethyl) carbamate and 4-methoxy-3-(5-(4-((2-(trimethylsilyl)ethoxy) methyl)-4H-1,2,4-triazol-3-yl)pyridin-3-yl)phenyl (cyclohexylmethyl) carbamate

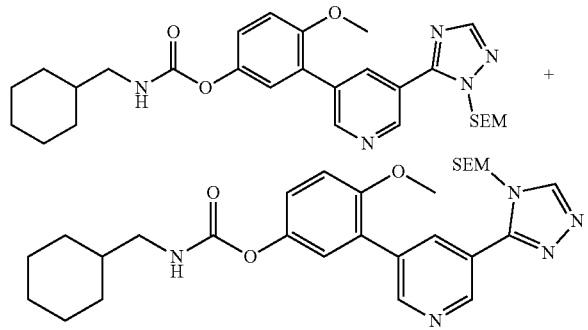

To a stirred solution of 4-methoxy-3-(5-(1-((2-(trimethylsilyl)ethoxy)methyl)-1H-1,2,4-triazol-5-yl)pyridin-3-yl) phenol and 4-methoxy-3-(5-(4-((2-(trimethylsilyl)ethoxy) methyl)-4H-1,2,4-triazol-3-yl)pyridin-3-yl)phenol (0.05 g, 0.13 mmol) in anhydrous acetonitrile (2 mL) was added TEA (0.05 mL, 0.38 mmol) and cyclohexanemethyl isocyanate (0.018 g, 0.13 mmol) at RT under nitrogen atmosphere. The reaction mixture was stirred at RT for 10 minutes and then stirred at 75° C. for 3 h. An additional amount of cyclohexanemethyl isocyanate (0.006 g, 0.04 mmol) was added to the reaction mixture and the resulting mixture was stirred for an additional 12 h. After completion of the reaction (monitored by LCMS), the reaction mixture was concentrated to give a mixture of 4-methoxy-3-(5-(1-((2-(trimethylsilyl)ethoxy)methyl)-1H-1,2,4-triazol-5-yl)pyridin-3-yl)phenyl(cyclohexylmethyl) carbamate and 4-methoxy-3-(5-(4-((2-(trimethylsilyl)ethoxy)methyl)-4H-1,2,4-triazol-3-yl)pyridin-3-yl)phenyl(cyclohexylmethyl) carbamate (60 mg), which was used for next step without purification. MS (ES+APCI) m/z 538.3 (M+1).

Synthesis of 3-(5-(1H-1,2,4-triazol-5-yl)pyridin-3-yl)-4-methoxyphenyl (cyclohexylmethyl) carbamate (Example-233)

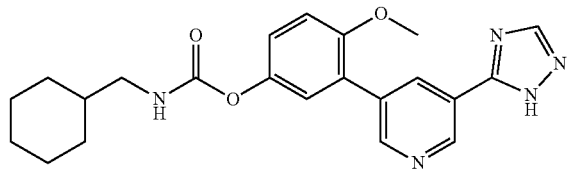 [SMILES: COc1ccc(OC(=O)NCC2CCCCC2)cc1-c1cncc(-c2ncn[nH]2)c1]

To a stirred solution of 4-methoxy-3-(5-(1-((2-(trimethylsilyl)ethoxy)methyl)-1H-1,2,4-triazol-5-yl)pyridin-3-yl) phenyl(cyclohexylmethyl) carbamate and 4-methoxy-3-(5-(4-((2-(trimethylsilyl)ethoxy)methyl)-4H-1,2,4-triazol-3-yl) pyridin-3-yl)phenyl(cyclohexylmethyl) carbamate (0.05 g, 0.093 mmol) in DCM (2 mL) was added SnCl$_4$ (0.25 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (14 mg) as an off white solid. $^1$H NMR (400 MHz, DMSO-d6) δ 14.35 (bs, 1H), 9.14 (d, J=2.00 Hz, 1H), 8.73 (d, J=2.00 Hz, 1H), 8.59 (bs, 1H), 8.42 (t, J=2.00 Hz, 1H), 7.74 (t, J=6.00 Hz, 1H), 7.19-7.16 (m, 3H), 3.81 (s, 3H), 2.91 (t, J=6.40 Hz, 2H), 1.73-1.61 (m, 5H), 1.46-1.41 (m, 1H), 1.21-1.11 (m, 3H), 0.94-0.88 (m, 2H); MS (ES+APCI) m/z 408.4 (M+1).

Synthesis of 4-methoxy-3-(5-(1-((2-(trimethylsilyl) ethoxy)methyl)-1H-1,2,4-triazol-5-yl)pyridin-3-yl) phenyl benzylcarbamate and 4-methoxy-3-(5-(4-((2-(trimethylsilyl)ethoxy)methyl)-4H-1,2,4-triazol-3-yl) pyridin-3-yl)phenyl benzylcarbamate

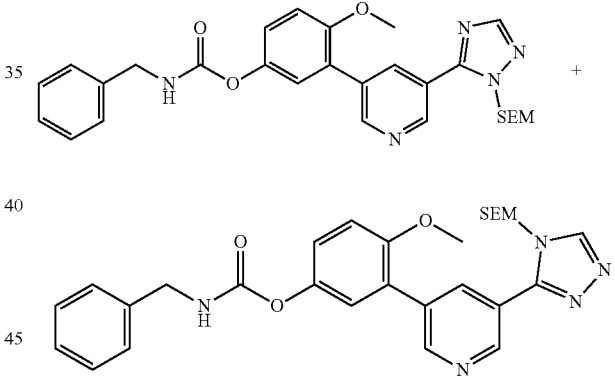

To a stirred solution of 4-methoxy-3-(5-(1-((2-(trimethylsilyl)ethoxy)methyl)-1H-1,2,4-triazol-5-yl)pyridin-3-yl) phenol and 4-methoxy-3-(5-(4-((2-(trimethylsilyl)ethoxy) methyl)-4H-1,2,4-triazol-3-yl)pyridin-3-yl)phenol (0.04 g, 0.1 mmol) in anhydrous acetonitrile (2 mL) was added TEA (0.05 mL, 0.38 mmol) and benzyl isocyanate (0.014 g, 0.1 mmol) at RT under nitrogen atmosphere. The reaction mixture was stirred at RT for 10 minutes and then stirred at 75° C. for 3 h. An additional amount of benzyl isocyanate (0.004 g, 0.04 mmol) was added to the reaction mixture and the resulting mixture was stirred for an additional 12 h. After completion of the reaction (monitored by LCMS), the reaction mixture was concentrated to give a mixture of 4-methoxy-3-(5-(1-((2-(trimethylsilyl)ethoxy)methyl)-1H-1,2,4-triazol-5-yl)pyridin-3-yl)phenyl benzylcarbamate and 4-methoxy-3-(5-(4-((2-(trimethylsilyl)ethoxy)methyl)-4H-1,2,4-triazol-3-yl)pyridin-3-yl)phenyl benzylcarbamate (50 mg), which was used for next step without purification. MS (ES+APCI) m/z 532.3 (M+1).

Synthesis of 3-(5-(1H-1,2,4-triazol-5-yl)pyridin-3-yl)-4-methoxyphenyl benzyl carbamate (Example-234)

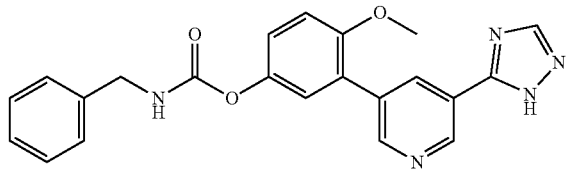 [SMILES: COc1ccc(OC(=O)NCc2ccccc2)cc1-c1cncc(-c2ncn[nH]2)c1]

To a stirred solution of 4-methoxy-3-(5-(1-((2-(trimethylsilyl)ethoxy)methyl)-1H-1,2,4-triazol-5-yl)pyridin-3-yl)phenyl benzyl carbamate and 4-methoxy-3-(5-(4-((2-(trimethylsilyl)ethoxy)methyl)-4H-1,2,4-triazol-3-yl)pyridin-3-yl)phenyl benzyl carbamate (0.05 g, 0.094 mmol) in DCM (2.0 mL) was added SnCl$_4$ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (7 mg) as an off white solid. $^1$H NMR (400 MHz, DMSO-d6) δ 14.44 (bs, 1H), 9.15 (d, J=2.00 Hz, 1H), 8.73 (d, J=2.00 Hz, 1H), 8.58 (bs, 1H), 8.43 (t, J=2.40 Hz, 1H), 8.31 (t, J=6.40 Hz, 1H) 7.38-7.32 (m, 4H), 7.29-7.22 (m, 2H), 7.19-7.16 (m, 2H), 4.29 (d, J=6.0 Hz, 2H), 3.82 (s, 3H); MS (ES+APCI) m/z 402.4 (M+1).

Synthesis of 4-methoxy-3-(5-(1-((2-(trimethylsilyl)ethoxy)methyl)-1H-1,2,4-triazol-5-yl)pyridin-3-yl)phenyl cyclopentylcarbamate and 4-methoxy-3-(5-(4-((2-(trimethylsilyl)ethoxy)methyl)-4H-1,2,4-triazol-3-yl)pyridin-3-yl)phenyl cyclopentylcarbamate

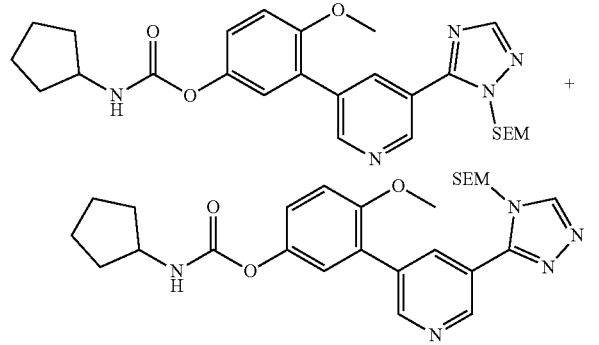

To a stirred solution of 4-methoxy-3-(5-(1-((2-(trimethylsilyl)ethoxy)methyl)-1H-1,2,4-triazol-5-yl)pyridin-3-yl)phenol and 4-methoxy-3-(5-(4-((2-(trimethylsilyl)ethoxy)methyl)-4H-1,2,4-triazol-3-yl)pyridin-3-yl)phenol (0.04 g, 0.11 mmol) in anhydrous acetonitrile (2 mL) was added TEA (0.06 mL, 0.45 mmol) and cyclopentyl isocyanate (0.012 g, 0.1 mmol) at RT under nitrogen atmosphere. The reaction mixture was stirred at RT for 10 minutes and then stirred at 75° C. for 3 h. An additional amount of cyclopentyl isocyanate (0.002 g, 0.01 mmol) was added to the reaction mixture and the resulting mixture was stirred for an additional 12 h. After completion of the reaction (monitored by LCMS), the reaction mixture was concentrated to give a mixture of 4-methoxy-3-(5-(1-((2-(trimethylsilyl)ethoxy)methyl)-1H-1,2,4-triazol-5-yl)pyridin-3-yl)phenyl cyclopentylcarbamate and 4-methoxy-3-(5-(4-((2-(trimethylsilyl)ethoxy)methyl)-4H-1,2,4-triazol-3-yl)pyridin-3-yl)phenyl cyclopentylcarbamate (50 mg), which was used for next step without purification. MS (ES+APCI) m/z 510.3 (M+1).

Synthesis of: 3-(5-(1H-1,2,4-triazol-5-yl)pyridin-3-yl)-4-methoxyphenyl cyclopentylcarbamate (Example-235)

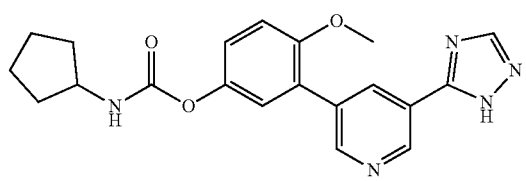 [SMILES: COc1ccc(OC(=O)NC2CCCC2)cc1-c1cncc(-c2ncn[nH]2)c1]

To a stirred solution of 4-methoxy-3-(5-(1-((2-(trimethylsilyl)ethoxy)methyl)-1H-1,2,4-triazol-5-yl)pyridin-3-yl)phenyl cyclopentylcarbamate and 4-methoxy-3-(5-(4-((2-(trimethylsilyl)ethoxy)methyl)-4H-1,2,4-triazol-3-yl)pyridin-3-yl)phenyl cyclopentylcarbamate (0.05 g, 0.098 mmol) in DCM (2.0 mL) was added SnCl$_4$ (0.2 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (18 mg) as an off white solid. $^1$H NMR (400 MHz, DMSO-d6) δ 14.41 (bs, 1H), 9.14 (d, J=2.00 Hz, 1H), 8.73 (d, J=2.00 Hz, 1H), 8.59 (bs, 1H), 8.44-8.42 (m, 1H), 7.77 (d, J=7.20 Hz, 1H), 7.19-7.17 (m, 3H), 3.86 (t, J=6.80 Hz, 1H), 3.81 (s, 3H), 1.84-1.80 (m, 2H), 1.68-1.65 (m, 2H), 1.53-1.46 (m, 4H); MS (ES+APCI) m/z 380.3 (M+1).

Synthesis of 4-methoxy-3-(5-(1-((2-(trimethylsilyl)ethoxy)methyl)-1H-1,2,4-triazol-5-yl)pyridin-3-yl)phenyl cyclohexyl carbamate and 4-methoxy-3-(5-(4-((2-(trimethylsilyl)ethoxy)methyl)-4H-1,2,4-triazol-3-yl)pyridin-3-yl)phenyl cyclohexyl carbamate

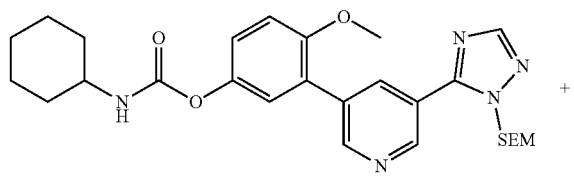

-continued

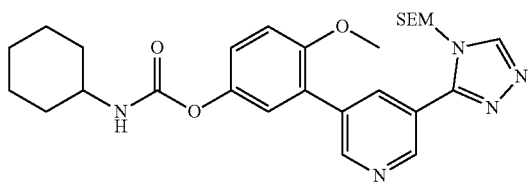

To a stirred solution of 4-methoxy-3-(5-(1-((2-(trimethylsilyl)ethoxy)methyl)-1H-1,2,4-triazol-5-yl)pyridin-3-yl)phenol and 4-methoxy-3-(5-(4-((2-(trimethylsilyl)ethoxy)methyl)-4H-1,2,4-triazol-3-yl)pyridin-3-yl)phenol (0.06 g, 0.15 mmol) in anhydrous acetonitrile (2 mL) was added TEA (0.06 mL, 0.45 mmol) and cyclohexyl isocyanate (0.02 g, 0.15 mmol) at RT under nitrogen atmosphere. The reaction mixture was stirred at RT for 10 minutes and then stirred at 75° C. for 3 h. An additional amount of cyclohexyl isocyanate (0.01 g, 0.05 mmol) was added to the reaction mixture and the resulting mixture was stirred for an additional 12 h. After completion of the reaction (monitored by LCMS), the reaction mixture was concentrated to give a mixture of 4-methoxy-3-(5-(1-((2-(trimethylsilyl)ethoxy)methyl)-1H-1,2,4-triazol-5-yl)pyridin-3-yl)phenyl cyclohexyl carbamate and 4-methoxy-3-(5-(4-((2-(trimethylsilyl)ethoxy)methyl)-4H-1,2,4-triazol-3-yl)pyridin-3-yl)phenyl cyclohexyl carbamate (70 mg), which was used for next step without purification. MS (ES+APCI) m/z 524.3 (M+1).

Synthesis of 3-(5-(1H-1,2,4-triazol-5-yl)pyridin-3-yl)-4-methoxyphenyl cyclohexyl carbamate (Example-236)

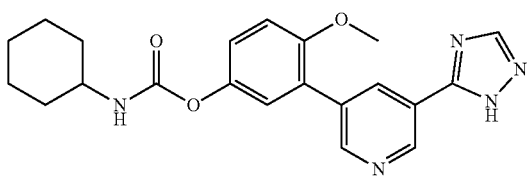 [SMILES: COc1ccc(OC(=O)NC2CCCCC2)cc1-c1cncc(-c2ncn[nH]2)c1]

To a stirred solution of 4-methoxy-3-(5-(1-((2-(trimethylsilyl)ethoxy)methyl)-1H-1,2,4-triazol-5-yl)pyridin-3-yl)phenyl cyclohexyl carbamate and 4-methoxy-3-(5-(4-((2-(trimethylsilyl)ethoxy)methyl)-4H-1,2,4-triazol-3-yl)pyridin-3-yl)phenyl cyclohexyl carbamate (0.07 g, 0.13 mmol) in DCM (2.5 mL) was added SnCl$_4$ (0.25 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (40 mg) as an off white solid. $^1$H NMR (400 MHz, DMSO-d6) δ 14.38 (bs, 1H), 9.14 (d, J=2.00 Hz, 1H), 8.73 (d, J=2.00 Hz, 1H), 8.59 (bs, 1H), 8.42 (t, J=2.00 Hz, 1H), 7.69 (d, J=8.00 Hz, 1H), 7.18 (d, J=6.80 Hz, 3H), 3.81 (s, 3H), 1.84-1.13 (m, 10H); MS (ES+APCI) m/z 394.3 (M+1).

Synthesis of 4-methoxy-3-(5-(1-((2-(trimethylsilyl)ethoxy)methyl)-1H-1,2,4-triazol-5-yl)pyridin-3-yl)phenyl cycloheptylcarbamate and 4-methoxy-3-(5-(4-((2-(trimethylsilyl)ethoxy)methyl)-4H-1,2,4-triazol-3-yl)pyridin-3-yl)phenyl cycloheptylcarbamate

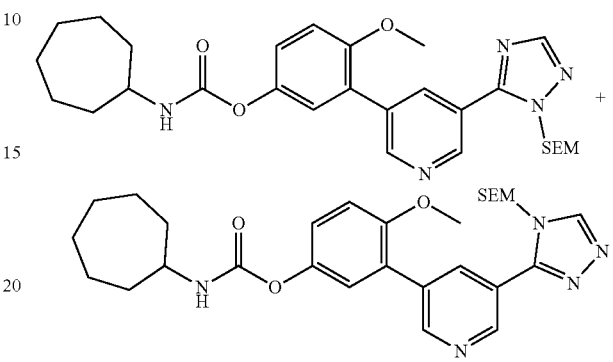

To a stirred solution of 4-methoxy-3-(5-(1-((2-(trimethylsilyl)ethoxy)methyl)-1H-1,2,4-triazol-5-yl)pyridin-3-yl)phenol and 4-methoxy-3-(5-(4-((2-(trimethylsilyl)ethoxy)methyl)-4H-1,2,4-triazol-3-yl)pyridin-3-yl)phenol (0.04 g, 0.11 mmol) in anhydrous acetonitrile (2 mL) was added TEA (0.06 mL, 0.45 mmol) and cycloheptyl isocyanate (0.014 g, 0.1 mmol) at RT under nitrogen atmosphere. The reaction mixture was stirred at RT for 10 minutes and then stirred at 75° C. for 3 h. An additional amount of cycloheptyl isocyanate (0.005 g, 0.03 mmol) was added to the reaction mixture and the resulting mixture was stirred for an additional 12 h. After completion of the reaction (monitored by LCMS), the reaction mixture was concentrated to give a mixture of 4-methoxy-3-(5-(1-((2-(trimethylsilyl)ethoxy)methyl)-1H-1,2,4-triazol-5-yl)pyridin-3-yl)phenyl cycloheptylcarbamate and 4-methoxy-3-(5-(4-((2-(trimethylsilyl)ethoxy)methyl)-4H-1,2,4-triazol-3-yl)pyridin-3-yl)phenyl cycloheptylcarbamate (52 mg), which was used for next step without purification. MS (ES+APCI) m/z 538.3 (M+1).

Synthesis of 3-(5-(1H-1,2,4-triazol-5-yl)pyridin-3-yl)-4-methoxyphenyl cycloheptylcarbamate (Example-237)

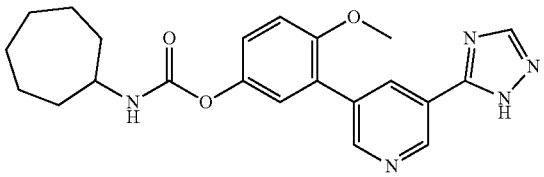 [SMILES: COc1ccc(OC(=O)NC2CCCCCC2)cc1-c1cncc(-c2ncn[nH]2)c1]

To a stirred solution of 4-methoxy-3-(5-(1-((2-(trimethylsilyl)ethoxy)methyl)-1H-1,2,4-triazol-5-yl)pyridin-3-yl)phenyl cycloheptylcarbamate and 4-methoxy-3-(5-(4-((2-(trimethylsilyl)ethoxy)methyl)-4H-1,2,4-triazol-3-yl)pyridin-3-yl)phenyl cycloheptylcarbamate (0.05 g, 0.093 mmol) in DCM (2 mL) was added SnCl$_4$ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO₃ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (25 mg) as an off white solid. $^1$H NMR (400 MHz, DMSO-d6) δ 14.38 (bs, 1H), 9.14 (d, J=2.00 Hz, 1H), 8.73 (d, J=2.00 Hz, 1H), 8.59 (bs, 1H), 8.42 (t, J=2.00 Hz, 1H), 7.73 (d, J=7.60 Hz, 1H), 7.19-7.17 (m, 3H), 3.81 (s, 3H), 3.56-3.51 (m, 1H), 1.89-1.35 (m, 12H); MS (ES+APCI) m/z 408.4 (M+1).

Scheme X

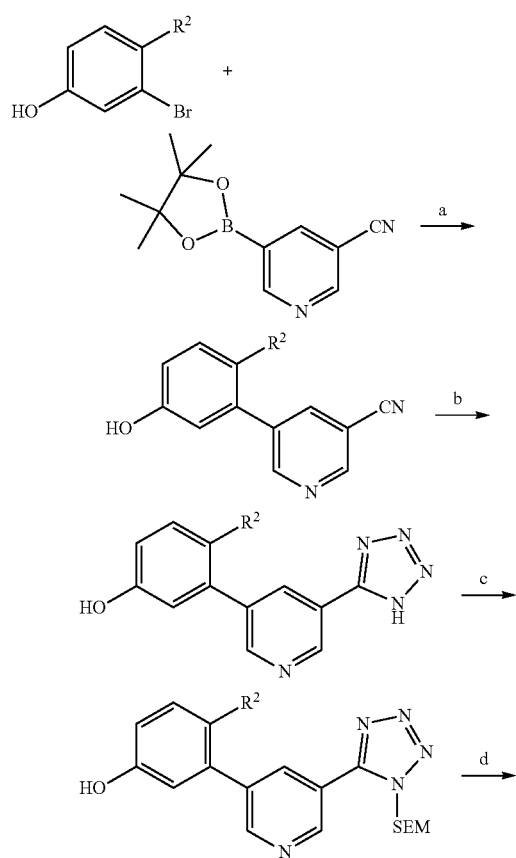

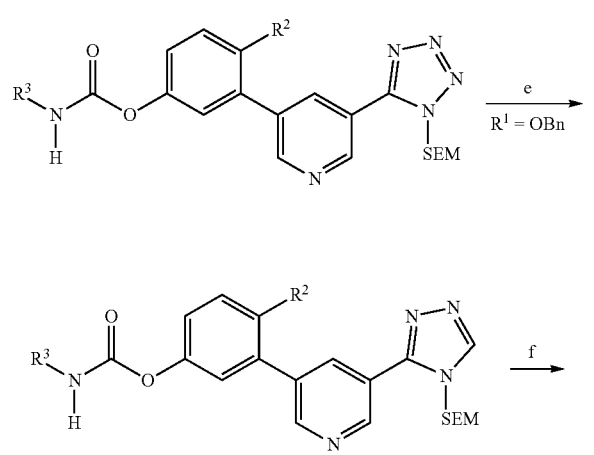

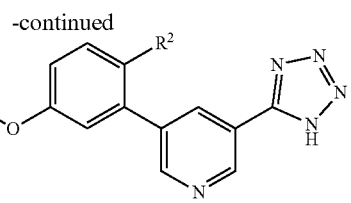

$R^2$ = H, OH, OCH₃

Reagents and conditions: a) Pd(PPh₃)₄, K₂CO₃, 1,4-dioxane, H₂O, 90° C., 12 h; b) TMS-N₃, tetra-n-butylammonium (TBAF), THF, 0 to 65° C., 16 h; c) SEM—Cl, K₂CO₃, DMF, RT, 0 to RT, 2 h; e) R²—NCO, TEA, ACN, 75° C., 2-16 h; f) Pd/C, Pd(OH)₂, H₂ gas (balloon), THF, IPA, 16 h, RT; g) SnCl₂, DCM, RT, 0-5° C., 2 h.

Synthesis of 5-(3-hydroxyphenyl)nicotinonitrile

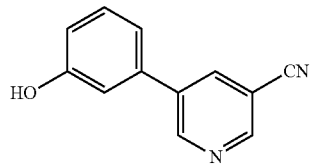 [SMILES: N#Cc1cncc(-c2cccc(O)c2)c1]

To a stirred solution of 5-bromonicotinonitrile (1 g, 5.46 mmol) in 1,4-dioxane (15 mL) and water (2 mL) was added (3-hydroxyphenyl)boronic acid (1.51 g, 10.93 mmol) and K₂CO₃ (2.27 g, 16.4 mmol) at RT. The reaction mixture was degassed for 15 minutes then Pd(PPh₃)₄ (0.32 g, 0.27 mmol) was added. The reaction mixture was stirred at 90° C. for 12 h under nitrogen atmosphere. After completion of the reaction (monitored by TLC), the reaction mixture was filtered through celite, washed with ethyl acetate and the filtrate was concentrated to a residue. The residue was diluted with water and extracted with ethyl acetate, and the combined organic layers were washed with water, brine and concentrated to give a residue. The residue was purified by automated normal-phase chromatography and eluted with ethyl acetate/petroleum ether to give 5-(3-hydroxyphenyl)nicotinonitrile (900 mg) as an off white solid. MS (ES+APCI) m/z 197.3 (M+1).

Synthesis of 3-(5-(1H-tetrazol-5-yl)pyridin-3-yl)phenol

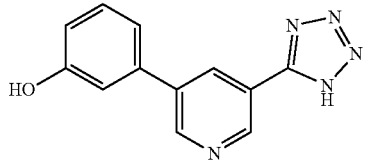 [SMILES: Oc1cccc(-c2cncc(-c3nnn[nH]3)c2)c1]

To a stirred solution of 5-(3-hydroxyphenyl)nicotinonitrile (0.9 g, 4.59 mmol) in THF (18 mL) was added trimethylsilyl azide (0.78 mL, 5.96 mmol) at 0° C. TBAF (1M in THF) (2.29 mL, 2.29 mmol) was added at 0° C. and the resultant suspension was stirred at 65° C. for 16 h. After completion of the reaction (monitored by LCMS), the reaction mixture was quenched with ice cold water. The aqueous layer was extracted with ethyl acetate, and the combined organic layers were washed with water, brine and concentrated to give a residue. The residue was purified by automated normal-phase chromatography and eluted with DCM/MeOH to give 3-(5-(1H-tetrazol-5-yl)pyridin-3-yl)phenol (550 mg) as an off white solid. MS (ES+APCI) m/z 240.3 (M+1).

Synthesis of 3-(5-(1-((2-(trimethylsilyl)ethoxy)methyl)-1H-tetrazol-5-yl)pyridin-3-yl)phenol and 3-(5-(2-((2-(trimethylsilyl)ethoxy)methyl)-2H-tetrazol-5-yl)pyridin-3-yl)phenol

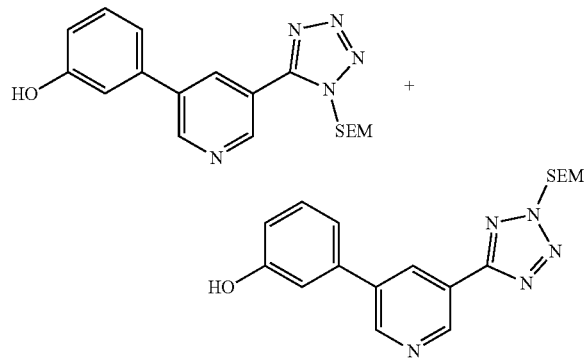

To a stirred solution of 3-(5-(1H-tetrazol-5-yl)pyridin-3-yl)phenol (0.3 g, 1.25 mmol) in DMF (10 mL) was added potassium carbonate (0.26 g, 1.88 mmol) at 0° C. SEM-Cl (0.15 g, 0.88 mmol) was added and the resultant suspension was stirred at 0° C. for 1 h and RT for 1 h. After completion of the reaction (monitored by LCMS), the reaction mixture was quenched with cold water. The aqueous layer was extracted with ethyl acetate, and the combined organic layers were washed with water, brine and concentrated to give a residue. The residue was purified by automated normal-phase chromatography and eluted with ethyl acetate/petroleum ether to give a mixture of 3-(5-(1-((2-(trimethylsilyl)ethoxy)methyl)-1H-tetrazol-5-yl)pyridin-3-yl)phenol and 3-(5-(2-((2-(trimethylsilyl)ethoxy)methyl)-2H-tetrazol-5-yl)pyridin-3-yl)phenol (150 mg) as viscous liquid. MS (ES+APCI) m/z 370.2 (M+1).

Synthesis of 3-(5-(1-((2-(trimethylsilyl)ethoxy)methyl)-1H-tetrazol-5-yl)pyridin-3-yl)phenyl octylcarbamate and 3-(5-(2-((2-(trimethylsilyl)ethoxy)methyl)-2H-tetrazol-5-yl)pyridin-3-yl)phenyl octylcarbamate

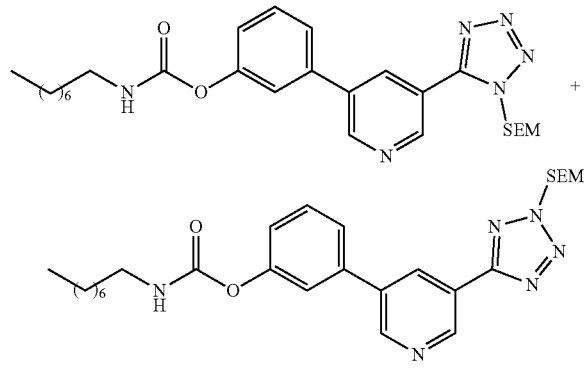

To a stirred solution of 3-(5-(1-((2-(trimethylsilyl)ethoxy)methyl)-1H-tetrazol-5-yl)pyridin-3-yl)phenol and 3-(5-(2-((2-(trimethylsilyl)ethoxy)methyl)-2H-tetrazol-5-yl)pyridin-3-yl)phenol (0.07 g, 0.189 mmol) in anhydrous acetonitrile (2 mL) was added TEA (0.040 mL, 0.284 mmol) and octyl isocyanate (0.032 g, 0.208 mmol) at RT under nitrogen atmosphere. The reaction mixture was stirred at RT for 10 minutes and then stirred at 75° C. for 3 h. An additional amount of octyl isocyanate (0.01 g, 0.08 mmol) was added to the reaction mixture and the resulting mixture was stirred for an additional 12 h. After completion of the reaction (monitored by LCMS), the reaction mixture was concentrated to give a mixture of 3-(5-(1-((2-(trimethylsilyl)ethoxy)methyl)-1H-tetrazol-5-yl)pyridin-3-yl)phenyl octylcarbamate and 3-(5-(2-((2-(trimethylsilyl)ethoxy)methyl)-2H-tetrazol-5-yl)pyridin-3-yl)phenyl octylcarbamate (99 mg), which was used for next step without purification. MS (ES+APCI) m/z 525.3 (M+1).

Synthesis of 3-(5-(1H-tetrazol-5-yl)pyridin-3-yl)phenyl octylcarbamate (Example-238)

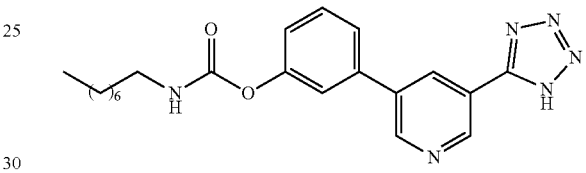

To a stirred solution of 3-(5-(1-((2-(trimethylsilyl)ethoxy)methyl)-1H-tetrazol-5-yl)pyridin-3-yl)phenyl octylcarbamate and 3-(5-(2-((2-(trimethylsilyl)ethoxy)methyl)-2H-tetrazol-5-yl)pyridin-3-yl)phenyl octylcarbamate (0.099 g, 0.190 mmol) in DCM (3 mL) was added $SnCl_4$ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% $NaHCO_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (14 mg) as an off white solid. $^1$H NMR (400 MHz, DMSO-d6) δ 9.23 (d, J=2.00 Hz, 1H), 9.12 (d, J=2.00 Hz, 1H), 8.66 (t, J=2.00 Hz, 1H), 7.85 (t, J=5.60 Hz, 1H), 7.70 (t, J=6.80 Hz, 1H), 7.59-7.55 (m, 2H), 7.24-7.21 (m, 1H), 3.11-3.06 (m, 2H), 1.49 (t, J=7.20 Hz, 2H), 1.29-1.27 (m, 10H), 0.86 (t, J=7.20 Hz, 3H); MS (ES+APCI) m/z 393.2 (M-1).

Synthesis of 3-(5-(1-((2-(trimethylsilyl)ethoxy)methyl)-1H-tetrazol-5-yl)pyridin-3-yl)phenyl (cyclohexylmethyl)carbamate and 3-(5-(2-((2-(trimethylsilyl)ethoxy)methyl)-2H-tetrazol-5-yl)pyridin-3-yl)phenyl (cyclohexylmethyl)carbamate

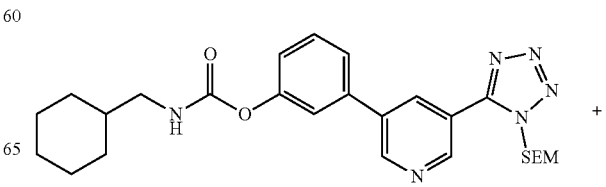

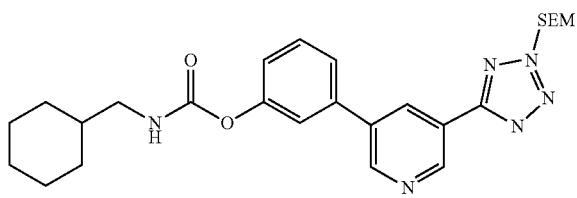

To a stirred solution of 3-(5-(1-((2-(trimethylsilyl)ethoxy)methyl)-1H-tetrazol-5-yl)pyridin-3-yl)phenol and 3-(5-(2-((2-(trimethylsilyl)ethoxy)methyl)-2H-tetrazol-5-yl)pyridin-3-yl)phenol (0.07 g, 0.189 mmol) in anhydrous acetonitrile (2 mL) was added TEA (0.040 mL, 0.284 mmol) and cyclohxanemethyl isocyanate (0.029 g, 0.208 mmol) at RT under nitrogen atmosphere. The reaction mixture was stirred at RT for 10 minutes and then stirred at 75° C. for 3 h. An additional amount of cyclohexanemethyl isocyanate (0.01 g, 0.08 mmol) was added to the reaction mixture and the resulting mixture was stirred for an additional 12 h. After completion of the reaction (monitored by LCMS), the reaction mixture was concentrated to give a mixture of 3-(5-(1-((2-(trimethylsilyl)ethoxy)methyl)-1H-tetrazol-5-yl)pyridin-3-yl)phenyl (cyclohexylmethyl)carbamate and 3-(5-(2-((2-(trimethylsilyl)ethoxy)methyl)-2H-tetrazol-5-yl)pyridin-3-yl)phenyl (cyclohexylmethyl)carbamate (95 mg), which was used for next step without purification. MS (ES+APCI) m/z 509.3 (M+1).

Synthesis of 3-(5-(1H-tetrazol-5-yl)pyridin-3-yl)phenyl (cyclohexylmethyl)carbamate (Example-239)

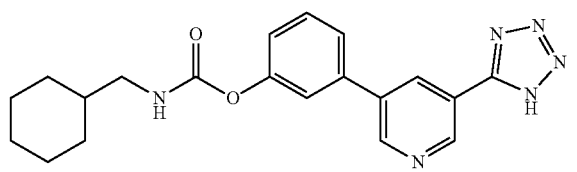 [SMILES: O=C(NCC1CCCCC1)Oc1cccc(-c2cncc(-c3nnn[nH]3)c2)c1]

To a stirred solution of 3-(5-(1-((2-(trimethylsilyl)ethoxy)methyl)-1H-tetrazol-5-yl)pyridin-3-yl)phenyl (cyclohexylmethyl)carbamate and 3-(5-(2-((2-(trimethylsilyl)ethoxy)methyl)-2H-tetrazol-5-yl)pyridin-3-yl)phenyl (cyclohexylmethyl)carbamate (0.095 g, 0.187 mmol) in DCM (3 mL) was added SnCl$_4$ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (10 mg) as an off white solid. $^1$H NMR (400 MHz, DMSO-d6) δ 9.23 (d, J=2.00 Hz, 1H), 9.12 (d, J=2.00 Hz, 1H), 8.66 (t, J=2.00 Hz, 1H), 7.87 (t, J=5.60 Hz, 1H), 7.70 (d, J=8.00 Hz, 1H), 7.60-7.55 (m, 2H), 7.23 (dd, J=1.20, 8.00 Hz, 1H), 3.06-2.93 (m, 2H), 0.88 (m, 11H); MS (ES+APCI) m/z 379.3 (M+1).

Synthesis of 33-(5-(1-((2-(trimethylsilyl)ethoxy)methyl)-1H-tetrazol-5-yl)pyridin-3-yl)phenyl benzylcarbamate and 3-(5-(2-((2-(trimethylsilyl)ethoxy)methyl)-2H-tetrazol-5-yl)pyridin-3-yl)phenyl benzylcarbamate

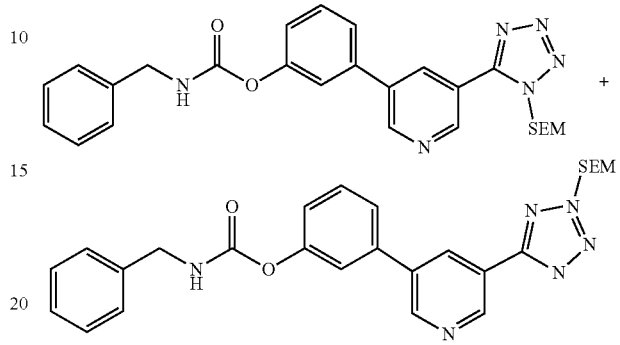

To a stirred solution of 3-(5-(1-((2-(trimethylsilyl)ethoxy)methyl)-1H-tetrazol-5-yl)pyridin-3-yl)phenol and 3-(5-(2-((2-(trimethylsilyl)ethoxy)methyl)-2H-tetrazol-5-yl)pyridin-3-yl)phenol (0.07 g, 0.189 mmol) in anhydrous acetonitrile (2 mL) was added TEA (0.040 mL, 0.284 mmol) and benzyl isocyanate (0.028 g, 0.208 mmol) at RT under nitrogen atmosphere. The reaction mixture was stirred at RT for 10 minutes and then stirred at 75° C. for 3 h. An additional amount of benzyl isocyanate (0.01 g, 0.08 mmol) was added to the reaction mixture and the resulting mixture was stirred for an additional 12 h. After completion of the reaction (monitored by LCMS), the reaction mixture was concentrated to give a mixture of 3-(5-(1-((2-(trimethylsilyl)ethoxy)methyl)-1H-tetrazol-5-yl)pyridin-3-yl)phenyl benzylcarbamate and 3-(5-(2-((2-(trimethylsilyl)ethoxy)methyl)-2H-tetrazol-5-yl)pyridin-3-yl)phenyl benzylcarbamate (95 mg), which was used for next step without purification. MS (ES+APCI) m/z 503.3 (M+1).

Synthesis of 3-(5-(1H-tetrazol-5-yl)pyridin-3-yl)phenyl benzylcarbamate (Example-240)

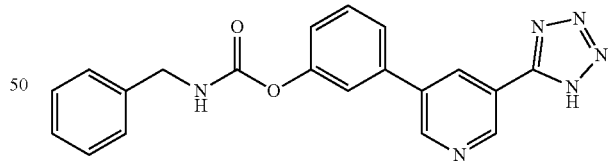

To a stirred solution of 3-(5-(1-((2-(trimethylsilyl)ethoxy)methyl)-1H-tetrazol-5-yl)pyridin-3-yl)phenyl benzylcarbamate and 3-(5-(2-((2-(trimethylsilyl)ethoxy)methyl)-2H-tetrazol-5-yl)pyridin-3-yl)phenyl benzylcarbamate (0.095 g, 0.189 mmol) in DCM (3 mL) was added SnCl$_4$ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (9.0 mg) as an off white solid. $^1$H NMR (400 MHz, DMSO-d6) δ 9.22 (d, J=1.60 Hz, 1H), 9.10 (d, J=2.00 Hz, 1H), 8.65 (t, J=2.00 Hz, 1H), 8.43 (t, J=6.40 Hz, 1H), 7.72-7.62 (m, 1H), 7.62-7.56 (m, 2H), 7.39-7.34 (m, 4H), 7.29-7.25 (m, 2H), 4.32 (d, J=6.40 Hz, 2H); MS (ES+APCI) m/z 373.1 (M+1).

Synthesis of 3-(5-(1-((2-(trimethylsilyl)ethoxy)methyl)-1H-tetrazol-5-yl)pyridin-3-yl)phenyl cyclopentylcarbamate and 3-(5-(2-((2-(trimethylsilyl)ethoxy)methyl)-2H-tetrazol-5-yl)pyridin-3-yl)phenyl cyclopentylcarbamate

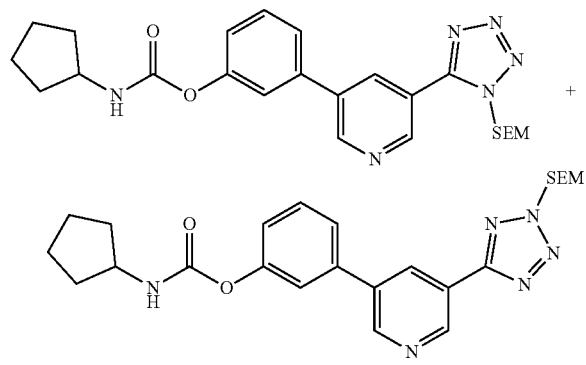

To a stirred solution of 3-(5-(1-((2-(trimethylsilyl)ethoxy)methyl)-1H-tetrazol-5-yl)pyridin-3-yl)phenol and 3-(5-(2-((2-(trimethylsilyl)ethoxy)methyl)-2H-tetrazol-5-yl)pyridin-3-yl)phenol (0.07 g, 0.189 mmol) in anhydrous acetonitrile (2 mL) was added TEA (0.040 mL, 0.284 mmol) and cyclopentyl isocyanate (0.026 g, 0.227 mmol) at RT under nitrogen atmosphere. The reaction mixture was stirred at RT for 10 minutes and then stirred at 75° C. for 3 h. An additional amount of cyclopentyl isocyanate (0.01 g, 0.08 mmol) was added to the reaction mixture and the resulting mixture was stirred for an additional 12 h. After completion of the reaction (monitored by LCMS), the reaction mixture was concentrated to give a mixture of 3-(5-(1-((2-(trimethylsilyl)ethoxy)methyl)-1H-tetrazol-5-yl)pyridin-3-yl)phenyl cyclopentylcarbamate and 3-(5-(2-((2-(trimethylsilyl)ethoxy)methyl)-2H-tetrazol-5-yl)pyridin-3-yl)phenyl cyclopentylcarbamate (90 mg), which was used for next step without purification. MS (ES+APCI) m/z 481.4 (M+1).

Synthesis of 3-(5-(1H-tetrazol-5-yl)pyridin-3-yl)phenyl cyclopentylcarbamate (Example-241)

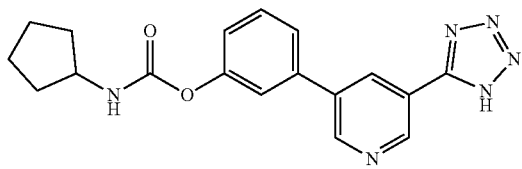 [SMILES: O=C(NC1CCCC1)Oc1cccc(-c2cncc(-c3nnn[nH]3)c2)c1]

To a stirred solution of 3-(5-(1-((2-(trimethylsilyl)ethoxy)methyl)-1H-tetrazol-5-yl)pyridin-3-yl)phenyl cyclopentylcarbamate and 3-(5-(2-((2-(trimethylsilyl)ethoxy)methyl)-2H-tetrazol-5-yl)pyridin-3-yl)phenyl cyclopentylcarbamate (0.09 g, 0.187 mmol) in DCM (3 mL) was added SnCl$_4$ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (19 mg) as an off white solid. $^1$H NMR (400 MHz, DMSO-d6) δ 9.22 (d, J=2.00 Hz, 1H), 9.11 (d, J=2.40 Hz, 1H), 8.65 (t, J=2.40 Hz, 1H), 7.89 (d, J=7.20 Hz, 1H), 7.70 (d, J=7.60 Hz, 1H), 7.60-7.55 (m, 2H), 7.23 (dd, J=1.20, 8.00 Hz, 1H), 3.90-3.85 (m, 1H), 1.89-1.83 (m, 2H), 1.69-1.68 (m, 2H), 1.55-1.47 (m, 4H); MS (ES+APCI) m/z 351.2 (M+1).

Synthesis of 3-(5-(1-((2-(trimethylsilyl)ethoxy)methyl)-1H-tetrazol-5-yl)pyridin-3-yl)phenyl cyclohexylcarbamate and 3-(5-(2-((2-(trimethylsilyl)ethoxy)methyl)-2H-tetrazol-5-yl)pyridin-3-yl)phenyl cyclohexylcarbamate

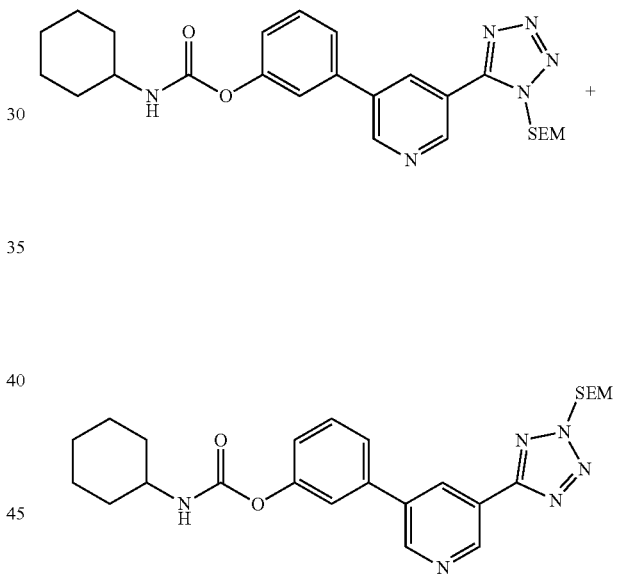

To a stirred solution of 3-(5-(1-((2-(trimethylsilyl)ethoxy)methyl)-1H-tetrazol-5-yl)pyridin-3-yl)phenol and 3-(5-(2-((2-(trimethylsilyl)ethoxy)methyl)-2H-tetrazol-5-yl)pyridin-3-yl)phenol (0.07 g, 0.189 mmol) in anhydrous acetonitrile (2 mL) was added TEA (0.040 mL, 0.284 mmol) and cyclohexyl isocyanate (0.026 g, 0.208 mmol) at RT under nitrogen atmosphere. The reaction mixture was stirred at RT for 10 minutes and then stirred at 75° C. for 3 h. An additional amount of cyclohexyl isocyanate (0.01 g, 0.08 mmol) was added to the reaction mixture and the resulting mixture was stirred for an additional 12 h. After completion of the reaction (monitored by LCMS), the reaction mixture was concentrated to give a mixture of 3-(5-(1-((2-(trimethylsilyl)ethoxy)methyl)-1H-tetrazol-5-yl)pyridin-3-yl)phenyl cyclohexylcarbamate and 3-(5-(2-((2-(trimethylsilyl)ethoxy)methyl)-2H-tetrazol-5-yl)pyridin-3-yl)phenyl cyclohexylcarbamate (95 mg), which was used for next step without purification. MS (ES+APCI) m/z 495.4 (M+1).

Synthesis of 3-(5-(1H-tetrazol-5-yl)pyridin-3-yl) phenyl cyclohexylcarbamate (Example-242)

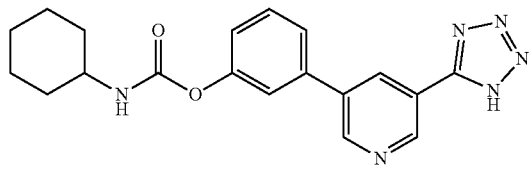 [SMILES: O=C(NC1CCCCC1)Oc1cccc(-c2cncc(-c3nnn[nH]3)c2)c1]

To a stirred solution of 3-(5-(1,3,4-oxadiazol-2-yl)pyridin-3-yl)-5-(benzyloxy)phenyl cyclohexylcarbamate and 3-(5-(4-((2-(trimethylsilyl)ethoxy)methyl)-4H-1,2,4-triazol-3-yl)pyridin-3-yl)phenyl cyclohexylcarbamate (0.09 g, 0.182 mmol) in DCM (3 mL) was added $SnCl_4$ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% $NaHCO_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (15 mg) as an off white solid. $^1$H NMR (400 MHz, DMSO-d6) δ 9.22 (d, J=2.00 Hz, 1H), 9.11 (d, J=2.40 Hz, 1H), 8.65 (t, J=2.40 Hz, 1H), 7.82 (d, J=8.00 Hz, 1H), 7.69 (d, J=8.00 Hz, 1H), 7.59-7.55 (m, 2H), 7.23 (dd, J=1.60, 8.00 Hz, 1H), 3.33 (s, 1H), 1.87-1.11 (m, 10H); MS (ES+APCI) m/z 365.3 (M+1).

Synthesis of 3-(5-(1-((2-(trimethylsilyl)ethoxy) methyl)-1H-tetrazol-5-yl)pyridin-3-yl)phenyl cycloheptylcarbamate and 3-(5-(2-((2-(trimethylsilyl) ethoxy)methyl)-2H-tetrazol-5-yl)pyridin-3-yl)phenyl cycloheptylcarbamate

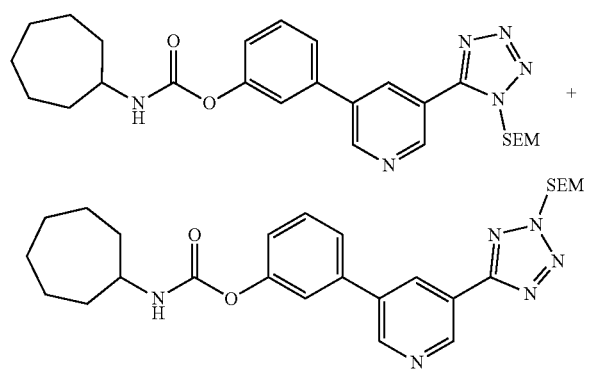

To a stirred solution of 3-(5-(1-((2-(trimethylsilyl)ethoxy)methyl)-1H-tetrazol-5-yl)pyridin-3-yl)phenol and 3-(5-(2-((2-(trimethylsilyl)ethoxy)methyl)-2H-tetrazol-5-yl)pyridin-3-yl)phenol (0.07 g, 0.189 mmol) in anhydrous acetonitrile (2 mL) was added TEA (0.040 mL, 0.284 mmol) and cycloheptyl isocyanate (0.029 g, 0.208 mmol) at RT under nitrogen atmosphere. The reaction mixture was stirred at RT for 10 minutes and then stirred at 75° C. for 3 h. An additional amount of cycloheptyl isocyanate (0.01 g, 0.08 mmol) was added to the reaction mixture and the resulting mixture was stirred for an additional 12 h. After completion of the reaction (monitored by LCMS), the reaction mixture was concentrated to give a mixture of 3-(5-(1-((2-(trimethylsilyl)ethoxy)methyl)-1H-tetrazol-5-yl)pyridin-3-yl)phenyl cycloheptylcarbamate and 3-(5-(2-((2-(trimethylsilyl)ethoxy)methyl)-2H-tetrazol-5-yl)pyridin-3-yl)phenyl cycloheptylcarbamate (95 mg), which was used for next step without purification. MS (ES+APCI) m/z 509.3 (M+1).

Synthesis of 3-(5-(1H-tetrazol-5-yl)pyridin-3-yl) phenyl cycloheptylcarbamate (Example-243)

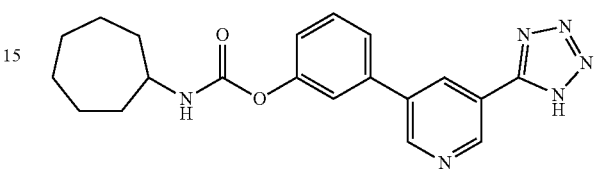

To a stirred solution of 3-(5-(1-((2-(trimethylsilyl)ethoxy)methyl)-1H-tetrazol-5-yl)pyridin-3-yl)phenyl cycloheptylcarbamate and 3-(5-(2-((2-(trimethylsilyl)ethoxy)methyl)-2H-tetrazol-5-yl)pyridin-3-yl)phenyl cycloheptylcarbamate (0.095 g, 0.187 mmol) in DCM (3 mL) was added $SnCl_4$ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% $NaHCO_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (26 mg) as an off white solid. $^1$H NMR (400 MHz, DMSO-d6) δ 9.22 (d, J=2.00 Hz, 1H), 9.11 (d, J=2.40 Hz, 1H), 8.65 (t, J=2.40 Hz, 1H), 7.85 (d, J=7.60 Hz, 1H), 7.69 (d, J=8.40 Hz, 1H), 7.59-7.55 (m, 2H), 7.23 (dd, J=1.60, 8.00 Hz, 1H), 3.58-3.55 (m, 1H), 1.91-1.50 (m, 12H); MS (ES+APCI) m/z 379.3 (M+1).

Synthesis of 5-(2-(benzyloxy)-5-hydroxyphenyl)nicotinonitrile

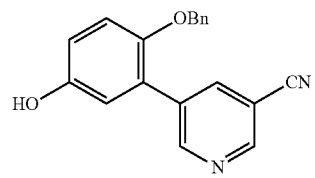 [SMILES: N#Cc1cncc(-c2cc(O)ccc2OCc2ccccc2)c1]

To a stirred solution of 4-(benzyloxy)-3-bromophenol (0.5 g, 1.80 mmol) in 1,4-dioxane (15 mL) and water (2 mL) was added 5-(4,4,5,5-tetramethyl-1,3,2-dioxaborolan-2-yl) nicotinonitrile (0.45 g, 1.97 mmol) and $K_2CO_3$ (0.74 g, 5.37 mmol) at RT. The reaction mixture was degassed for 15 minutes then $Pd(PPh_3)_4$ (0.10 g, 0.09 mmol) was added. The reaction mixture was stirred at 80° C. for 12 h under nitrogen atmosphere. After completion of the reaction (monitored by TLC), the reaction mixture was filtered through celite, washed with ethyl acetate and the filtrate was concentrated to a residue. The residue was diluted with water and extracted with ethyl acetate, and the combined organic layers were washed with water, brine and concentrated to give a residue. The residue was purified by automated normal-phase chromatography and eluted with ethyl acetate/petroleum ether to give 5-(2-(benzyloxy)-5-hydroxyphenyl)nicotinonitrile (450 mg) as an off white solid. MS (ES+APCI) m/z 303.4 (M+1).

Synthesis of 3-(5-(1H-tetrazol-5-yl)pyridin-3-yl)-4-(benzyloxy)phenol

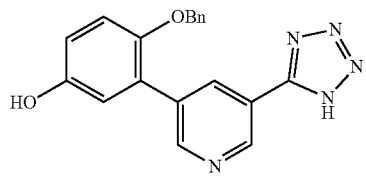 [SMILES: Oc1ccc(OCc2ccccc2)c(-c2cncc(-c3nnn[nH]3)c2)c1]

To a stirred solution of 5-(2-(benzyloxy)-5-hydroxyphenyl)nicotinonitrile (0.45 g, 1.49 mmol) in THF (10 mL) was added trimethylsilyl azide (0.25 mL, 1.94 mmol) at 0° C. TBAF (1M in THF) (0.74 mL, 0.74 mmol) was added at 0° C. and the resultant suspension was stirred at 65° C. for 16 h. After completion of the reaction (monitored by LCMS), the reaction mixture was quenched with ice cold water. The aqueous layer was extracted with ethyl acetate, and the combined organic layers were washed with water, brine and concentrated to give a residue. The residue was purified by automated normal-phase chromatography and eluted with DCM/MeOH to give 3-(5-(1H-tetrazol-5-yl)pyridin-3-yl)-4-(benzyloxy)phenol (0.2 g) as an off white solid. MS (ES+APCI) m/z 346.3 (M+1).

Synthesis of 4-(benzyloxy)-3-(5-(1-((2-(trimethylsilyl)ethoxy)methyl)-1H-tetrazol-5-yl)pyridin-3-yl)phenol and 4-(benzyloxy)-3-(5-(2-((2-(trimethylsilyl)ethoxy)methyl)-2H-tetrazol-5-yl)pyridin-3-yl)phenol

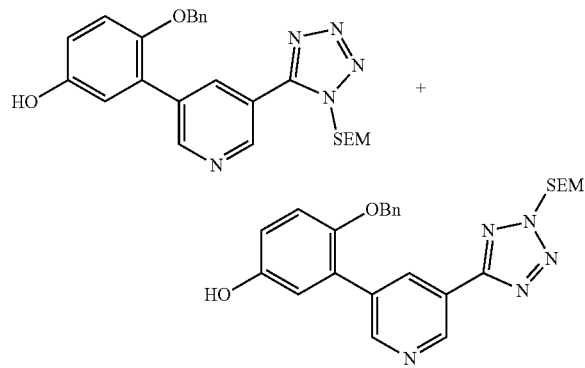

To a stirred solution of 3-(5-(1H-tetrazol-5-yl)pyridin-3-yl)-4-(benzyloxy)phenol (0.38 g, 1.10 mmol) in DMF (10 mL) was added potassium carbonate (0.23 g, 1.65 mmol) at 0° C. SEM-Cl (0.15 g, 0.88 mmol) was added and the resultant suspension was stirred at 0° C. for 1 h and RT for 1 h. After completion of the reaction (monitored by LCMS), the reaction mixture was quenched with cold water. The aqueous layer was extracted with ethyl acetate, and the combined organic layers were washed with water, brine and concentrated to give a residue. The residue was purified by automated normal-phase chromatography and eluted with ethyl acetate/petroleum ether to give a mixture of 4-(benzyloxy)-3-(5-(1-((2-(trimethylsilyl)ethoxy)methyl)-1H-tetrazol-5-yl)pyridin-3-yl)phenol and 4-(benzyloxy)-3-(5-(2-((2-(trimethylsilyl)ethoxy)methyl)-2H-tetrazol-5-yl)pyridin-3-yl)phenol (250 mg) as an off white solid. MS (ES+APCI) m/z 476.2 (M+1)

Synthesis of 4-(benzyloxy)-3-(5-(1-((2-(trimethylsilyl)ethoxy)methyl)-1H-tetrazol-5-yl)pyridin-3-yl)phenyl octylcarbamate and 4-(benzyloxy)-3-(5-(2-((2-(trimethylsilyl)ethoxy)methyl)-2H-tetrazol-5-yl)pyridin-3-yl)phenyl octylcarbamate

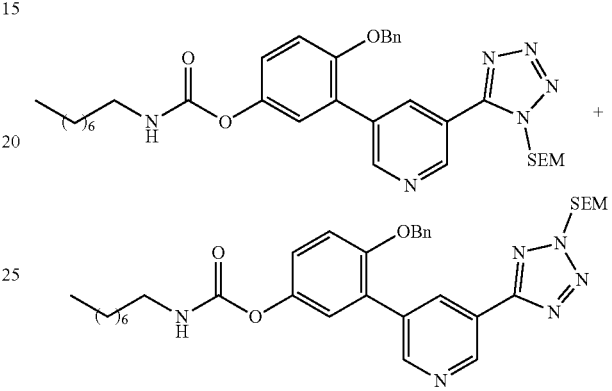

To a stirred solution of 4-(benzyloxy)-3-(5-(1-((2-(trimethylsilyl)ethoxy)methyl)-1H-tetrazol-5-yl)pyridin-3-yl)phenol and 4-(benzyloxy)-3-(5-(2-((2-(trimethylsilyl)ethoxy)methyl)-2H-tetrazol-5-yl)pyridin-3-yl)phenol (0.075 g, 0.158 mmol) in anhydrous acetonitrile (2.5 mL) was added TEA (0.033 mL, 0.237 mmol) and n-octyl isocyanate (0.027 g, 0.173 mmol) at RT under nitrogen atmosphere. The reaction mixture was stirred at RT for 10 minutes and then stirred at 75° C. for 3 h. An additional amount of n-octyl isocyanate (0.009 g, 0.057 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with dichloromethane/methanol to give a mixture of 4-(benzyloxy)-3-(5-(1-((2-(trimethylsilyl)ethoxy)methyl)-1H-tetrazol-5-yl)pyridin-3-yl)phenyl octylcarbamate and 4-(benzyloxy)-3-(5-(2-((2-(trimethylsilyl)ethoxy)methyl)-2H-tetrazol-5-yl)pyridin-3-yl)phenyl octylcarbamate (95 mg), which was used for next step without purification. MS (ES+APCI) m/z 631.4 (M+1).

Synthesis of 4-hydroxy-3-(5-(1-((2-(trimethylsilyl)ethoxy)methyl)-1H-tetrazol-5-yl)pyridin-3-yl)phenyl octylcarbamate and 4-hydroxy-3-(5-(2-((2-(trimethylsilyl)ethoxy)methyl)-2H-tetrazol-5-yl)pyridin-3-yl)phenyl octylcarbamate

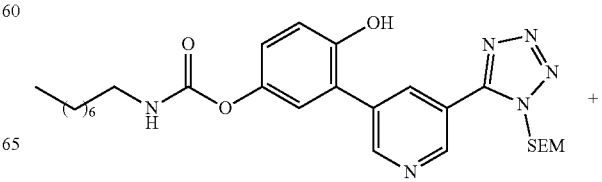

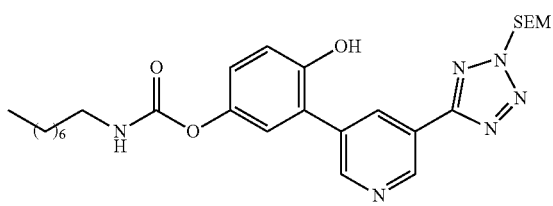

To a stirred solution of 4-(benzyloxy)-3-(5-(1-((2-(trimethylsilyl)ethoxy)methyl)-1H-tetrazol-5-yl)pyridin-3-yl)phenyl octylcarbamate and 4-(benzyloxy)-3-(5-(2-((2-(trimethylsilyl)ethoxy)methyl)-2H-tetrazol-5-yl)pyridin-3-yl)phenyl octylcarbamate (0.095 g, 0.151 mmol) in THF (2 mL) and 2-propanol (0.5 mL) was added 10% Pd/C (50 mg) and Pd(OH)$_2$ (50 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to give a mixture of 4-hydroxy-3-(5-(1-((2-(trimethylsilyl)ethoxy)methyl)-1H-tetrazol-5-yl)pyridin-3-yl)phenyl octylcarbamate and 4-hydroxy-3-(5-(2-((2-(trimethylsilyl)ethoxy)methyl)-2H-tetrazol-5-yl)pyridin-3-yl)phenyl octylcarbamate (70 mg), which was used for next step without purification. MS (ES+APCI) m/z 541.4 (M+1).

Synthesis of 3-(5-(1H-tetrazol-5-yl)pyridin-3-yl)-4-hydroxyphenyl octylcarbamate

To a stirred solution of 4-hydroxy-3-(5-(1-((2-(trimethylsilyl)ethoxy)methyl)-1H-tetrazol-5-yl)pyridin-3-yl)phenyl octylcarbamate and 4-hydroxy-3-(5-(2-((2-(trimethylsilyl)ethoxy)methyl)-2H-tetrazol-5-yl)pyridin-3-yl)phenyl octylcarbamate (0.07 g, 0.129 mmol) in DCM (3 mL) was added SnCl$_4$ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (4 mg) as an off white solid. $^1$H NMR (400 MHz, DMSO-d6) δ; 9.93 (s, 1H), 9.12 (d, J=2.00 Hz, 1H), 8.86 (d, J=2.00 Hz, 1H), 8.53 (t, J=2.00 Hz, 1H), 7.67 (t, J=5.60 Hz, 1H), 7.15-6.97 (m, 3H), 3.07-3.02 (m, 2H), 1.46 (t, J=6.40 Hz, 2H), 1.35-1.24 (m, 10H), 0.87-0.84 (m, 3H); MS (ES+APCI) m/z 411.3 (M+1).

Synthesis of 4-(benzyloxy)-3-(5-(1-((2-(trimethylsilyl)ethoxy)methyl)-1H-tetrazol-5-yl)pyridin-3-yl)phenyl (cyclohexylmethyl)carbamate and 4-(benzyloxy)-3-(5-(2-((2-(trimethylsilyl)ethoxy)methyl)-2H-tetrazol-5-yl)pyridin-3-yl)phenyl (cyclohexylmethyl)carbamate

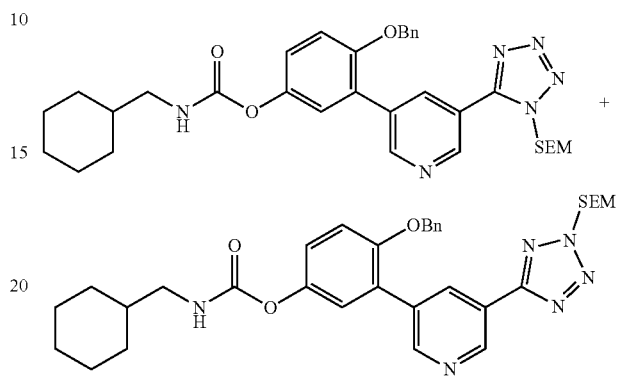

To a stirred solution of 4-(benzyloxy)-3-(5-(1-((2-(trimethylsilyl)ethoxy)methyl)-1H-tetrazol-5-yl)pyridin-3-yl)phenol and 4-(benzyloxy)-3-(5-(2-((2-(trimethylsilyl)ethoxy)methyl)-2H-tetrazol-5-yl)pyridin-3-yl)phenol (0.10 g, 0.21 mmol) in anhydrous acetonitrile (2.5 mL) was added TEA (0.044 mL, 0.316 mmol) and cyclohexanemethyl isocyanate (0.032 g, 0.231 mmol) at RT under nitrogen atmosphere. The reaction mixture was stirred at RT for 10 minutes and then stirred at 75° C. for 3 h. An additional amount of cyclohexanemethyl isocyanate (0.010 g, 0.077 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with dichloromethane/methanol to give a mixture of 4-(benzyloxy)-3-(5-(1-((2-(trimethylsilyl)ethoxy)methyl)-1H-tetrazol-5-yl)pyridin-3-yl)phenyl (cyclohexylmethyl)carbamate and 4-(benzyloxy)-3-(5-(2-((2-(trimethylsilyl)ethoxy)methyl)-2H-tetrazol-5-yl)pyridin-3-yl)phenyl (cyclohexylmethyl)carbam (120 mg), which was used for next step without purification. MS (ES+APCI) m/z 615.3 (M+1).

Synthesis of 4-hydroxy-3-(5-(1-((2-(trimethylsilyl)ethoxy)methyl)-1H-tetrazol-5-yl)pyridin-3-yl)phenyl (cyclohexylmethyl)carbamate and 4-hydroxy-3-(5-(2-((2-(trimethylsilyl)ethoxy)methyl)-2H-tetrazol-5-yl)pyridin-3-yl)phenyl (cyclohexylmethyl)carbamate

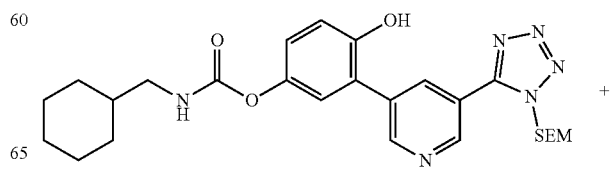

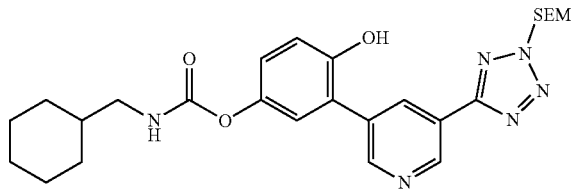

To a stirred solution of 4-(benzyloxy)-3-(5-(1-((2-(trimethylsilyl)ethoxy)methyl)-1H-tetrazol-5-yl)pyridin-3-yl) phenyl (cyclohexylmethyl)carbamate and 4-(benzyloxy)-3-(5-(2-((2-(trimethylsilyl)ethoxy)methyl)-2H-tetrazol-5-yl) pyridin-3-yl)phenyl (cyclohexylmethyl)carbam (0.120 g, 0.195 mmol) in THF (2 mL) and 2-propanol (0.5 mL) was added 10% Pd/C (60 mg) and Pd(OH)$_2$ (60 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to give a mixture of 4-hydroxy-3-(5-(1-((2-(trimethylsilyl)ethoxy)methyl)-1H-tetrazol-5-yl)pyridin-3-yl) phenyl (cyclohexylmethyl)carbamate and 4-hydroxy-3-(5-(2-((2-(trimethylsilyl)ethoxy)methyl)-2H-tetrazol-5-yl) pyridin-3-yl)phenyl (cyclohexylmethyl)carbamate (100 mg), which was used for next step without purification. MS (ES+APCI) m/z 525.3 (M+1).

Synthesis of 3-(5-(1H-tetrazol-5-yl)pyridin-3-yl)-4-hydroxyphenyl (cyclohexylmethyl)carbamate (Example-245)

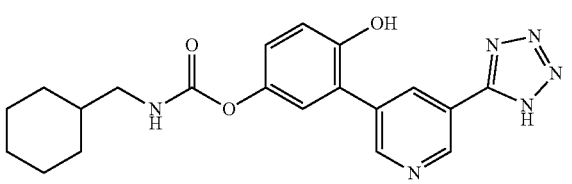 [SMILES: O=C(NCC1CCCCC1)Oc1ccc(O)c(-c2cncc(-c3nnn[nH]3)c2)c1]

To a stirred solution of 4-hydroxy-3-(5-(1-((2-(trimethylsilyl)ethoxy)methyl)-1H-tetrazol-5-yl)pyridin-3-yl)phenyl (cyclohexylmethyl)carbamate and 4-hydroxy-3-(5-(2-((2-(trimethylsilyl)ethoxy)methyl)-2H-tetrazol-5-yl)pyridin-3-yl)phenyl (cyclohexylmethyl)carbamate (0.10 g, 0.191 mmol) in DCM (3 mL) was added SnCl$_4$ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (12 mg) as an off white solid. $^1$H NMR (400 MHz, DMSO-d6) δ; 9.96 (s, 1H), 9.14 (d, J=2.00 Hz, 1H), 8.93 (d, J=2.00 Hz, 1H), 8.55 (t, J=2.40 Hz, 1H), 7.70 (t, J=6.00 Hz, 1H), 7.17 (d, J=2.40 Hz, 1H), 7.03-6.98 (m, 2H), 2.90 (t, J=6.40 Hz, 2H), 1.72-0.93 (m, 11H); MS (ES+APCI) m/z 395.1 (M+1).

Synthesis of 4-(benzyloxy)-3-(5-(1-((2-(trimethylsilyl)ethoxy)methyl)-1H-tetrazol-5-yl)pyridin-3-yl) phenyl benzylcarbamate and 4-(benzyloxy)-3-(5-(2-((2-(trimethylsilyl)ethoxy)methyl)-2H-tetrazol-5-yl) pyridin-3-yl)phenyl benzylcarbamate

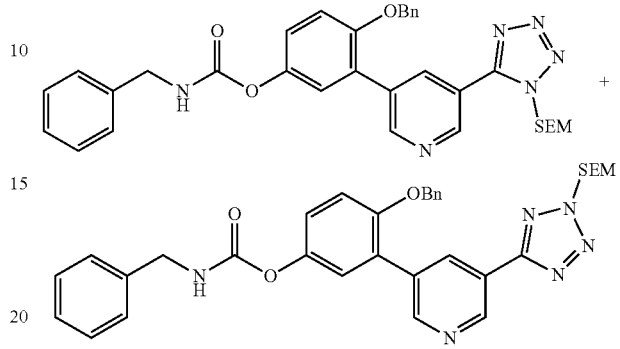

To a stirred solution of 4-(benzyloxy)-3-(5-(1-((2-(trimethylsilyl)ethoxy)methyl)-1H-tetrazol-5-yl)pyridin-3-yl) phenol and 4-(benzyloxy)-3-(5-(2-((2-(trimethylsilyl)ethoxy)methyl)-2H-tetrazol-5-yl)pyridin-3-yl)phenol (0.150 g, 0.315 mmol) in anhydrous acetonitrile (2.5 mL) was added TEA (0.066 mL, 0.473 mmol) and benzyl isocyanate (0.046 g, 0.347 mmol) at RT under nitrogen atmosphere. The reaction mixture was stirred at RT for 10 minutes and then stirred at 75° C. for 3 h. An additional amount of benzyl isocyanate (0.015 g, 0.115 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with dichloromethane/methanol to give a mixture of 4-(benzyloxy)-3-(5-(1-((2-(trimethylsilyl)ethoxy)methyl)-1H-tetrazol-5-yl)pyridin-3-yl)phenyl benzylcarbamate and 4-(benzyloxy)-3-(5-(2-((2-(trimethylsilyl)ethoxy)methyl)-2H-tetrazol-5-yl)pyridin-3-yl)phenyl benzylcarbamate (160 mg), which was used for next step without purification. MS (ES+APCI) m/z 609.3 (M+1).

Synthesis of 4-hydroxy-3-(5-(1-((2-(trimethylsilyl)ethoxy)methyl)-1H-tetrazol-5-yl)pyridin-3-yl)phenyl benzylcarbamate and 4-hydroxy-3-(5-(2-((2-(trimethylsilyl)ethoxy)methyl)-2H-tetrazol-5-yl)pyridin-3-yl)phenyl benzylcarbamate

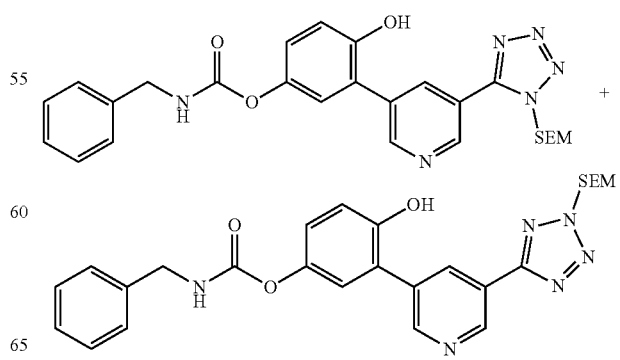

To a stirred solution of 4-(benzyloxy)-3-(5-(1-((2-(trimethylsilyl)ethoxy)methyl)-1H-tetrazol-5-yl)pyridin-3-yl)phenyl benzylcarbamate and 4-(benzyloxy)-3-(5-(2-((2-(trimethylsilyl)ethoxy)methyl)-2H-tetrazol-5-yl)pyridin-3-yl)phenyl benzylcarbamate (0.160 g, 0.263 mmol) in THF (3 mL) and 2-propanol (0.75 mL) was added 10% Pd/C (80 mg) and Pd(OH)₂ (80 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to give a mixture of 4-hydroxy-3-(5-(1-((2-(trimethylsilyl)ethoxy)methyl)-1H-tetrazol-5-yl)pyridin-3-yl)phenyl benzylcarbamate and 4-hydroxy-3-(5-(2-((2-(trimethylsilyl)ethoxy)methyl)-2H-tetrazol-5-yl)pyridin-3-yl)phenyl benzylcarbamate (110 mg), which was used for next step without purification. MS (ES+APCI) m/z 519.3 (M+1).

Synthesis of 3-(5-(1H-tetrazol-5-yl)pyridin-3-yl)-4-hydroxyphenyl benzylcarbamate (Example-246)

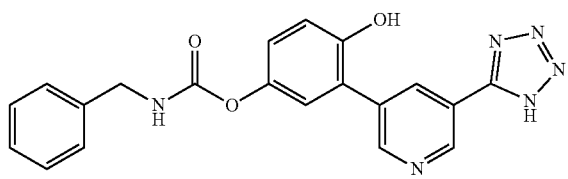 [SMILES: O=C(NCc1ccccc1)Oc1ccc(O)c(-c2cncc(-c3nnn[nH]3)c2)c1]

To a stirred solution of 4-hydroxy-3-(5-(1-((2-(trimethylsilyl)ethoxy)methyl)-1H-tetrazol-5-yl)pyridin-3-yl)phenyl benzylcarbamate and 4-hydroxy-3-(5-(2-((2-(trimethylsilyl)ethoxy)methyl)-2H-tetrazol-5-yl)pyridin-3-yl)phenyl benzylcarbamate (0.100 g, 0.193 mmol) in DCM (3 mL) was added SnCl₄ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO₃ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (18 mg) as an off white solid. ¹H NMR (400 MHz, DMSO-d6) δ; 9.99 (s, 1H), 9.14 (d, J=2.00 Hz, 1H), 8.95 (d, J=2.40 Hz, 1H), 8.56 (t, J=2.00 Hz, 1H), 8.26 (t, J=6.40 Hz, 1H), 7.37-7.21 (m, 6H), 7.06-6.99 (m, 2H), 4.28 (d, J=6.40 Hz, 2H); MS (ES+APCI) m/z 389.3 (M+1).

Synthesis of 4-(benzyloxy)-3-(5-(1-((2-(trimethylsilyl)ethoxy)methyl)-1H-tetrazol-5-yl)pyridin-3-yl)phenyl cyclopentylcarbamate and 4-(benzyloxy)-3-(5-(2-((2-(trimethylsilyl)ethoxy)methyl)-2H-tetrazol-5-yl)pyridin-3-yl)phenyl cyclopentylcarbamate

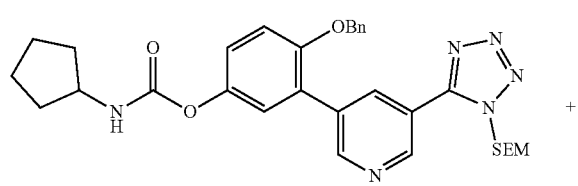

+

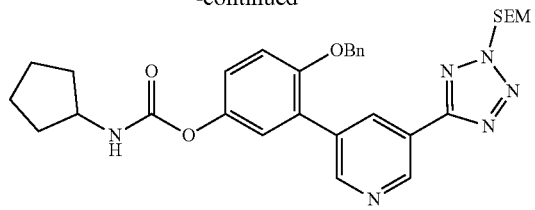

To a stirred solution of 4-(benzyloxy)-3-(5-(1-((2-(trimethylsilyl)ethoxy)methyl)-1H-tetrazol-5-yl)pyridin-3-yl)phenol and 4-(benzyloxy)-3-(5-(2-((2-(trimethylsilyl)ethoxy)methyl)-2H-tetrazol-5-yl)pyridin-3-yl)phenol (0.10 g, 0.21 mmol) in anhydrous acetonitrile (2.5 mL) was added TEA (0.044 mL, 0.315 mmol) and cyclopentyl isocyanate (0.026 g, 0.23 mmol) at RT under nitrogen atmosphere. The reaction mixture was stirred at RT for 10 minutes and then stirred at 75° C. for 3 h. An additional amount of cyclopentyl isocyanate (0.008 g, 0.076 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with dichloromethane/methanol to give a mixture of 4-(benzyloxy)-3-(5-(1-((2-(trimethylsilyl)ethoxy)methyl)-1H-tetrazol-5-yl)pyridin-3-yl)phenyl cyclopentylcarbamate and 4-(benzyloxy)-3-(5-(2-((2-(trimethylsilyl)ethoxy)methyl)-2H-tetrazol-5-yl)pyridin-3-yl)phenyl cyclopentylcarbamate (120 mg), which was used for next step without purification. MS (ES+APCI) m/z 587.2 (M+1).

Synthesis of 4-hydroxy-3-(5-(1-((2-(trimethylsilyl)ethoxy)methyl)-1H-tetrazol-5-yl)pyridin-3-yl)phenyl cyclopentylcarbamate and 4-hydroxy-3-(5-(2-((2-(trimethylsilyl)ethoxy)methyl)-2H-tetrazol-5-yl)pyridin-3-yl)phenyl cyclopentylcarbamate

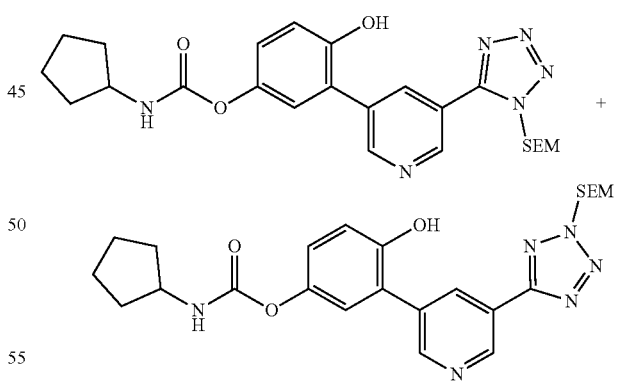

To a stirred solution of 4-(benzyloxy)-3-(5-(1-((2-(trimethylsilyl)ethoxy)methyl)-1H-tetrazol-5-yl)pyridin-3-yl)phenyl cyclopentylcarbamate and 4-(benzyloxy)-3-(5-(2-((2-(trimethylsilyl)ethoxy)methyl)-2H-tetrazol-5-yl)pyridin-3-yl)phenyl cyclopentylcarbamate (0.120 g, 0.204 mmol) in THF (2 mL) and 2-propanol (0.5 mL) was added 10% Pd/C (60 mg) and Pd(OH)₂ (60 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to give a mixture of 4-hydroxy-3-(5-(1-((2-(trimethylsilyl)ethoxy)methyl)-1H-tetrazol-5-yl)pyridin-3-yl)phenyl cyclopentylcarbamate and 4-hydroxy-3-(5-(2-((2-(trimethylsilyl)ethoxy)methyl)-2H-tetrazol-5-yl)pyridin-3-yl)phenyl cyclopentylcarbamate (80 mg), which was used for next step without purification. MS (ES+APCI) m/z 497.3 (M+1).

Synthesis of 3-(5-(1H-tetrazol-5-yl)pyridin-3-yl)-4-hydroxyphenyl cyclopentylcarbamate (Example-247)

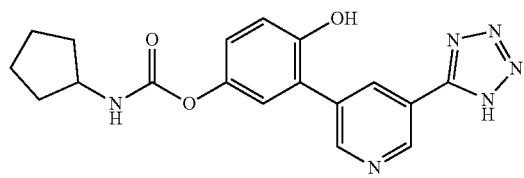 [SMILES: O=C(NC1CCCC1)Oc1ccc(O)c(-c2cncc(-c3nnn[nH]3)c2)c1]

To a stirred solution of 4-hydroxy-3-(5-(1-((2-(trimethylsilyl)ethoxy)methyl)-1H-tetrazol-5-yl)pyridin-3-yl)phenyl cyclopentylcarbamate and 4-hydroxy-3-(5-(2-((2-(trimethylsilyl)ethoxy)methyl)-2H-tetrazol-5-yl)pyridin-3-yl)phenyl cyclopentylcarbamate (0.08 g, 0.161 mmol) in DCM (3 mL) was added SnCl$_4$ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO$_3$ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (17.0 mg) as an off white solid. $^1$H NMR (400 MHz, DMSO-d6) δ; 9.94 (s, 1H), 9.14 (d, J=2.00 Hz, 1H), 8.95 (d, J=2.00 Hz, 1H), 8.56 (t, J=2.00 Hz, 1H), 7.72 (d, J=7.20 Hz, 1H), 7.19 (d, J=2.40 Hz, 1H), 7.03-6.98 (m, 2H), 3.87-3.82 (m, 1H), 1.84-1.24 (m, 8H); MS (ES+APCI) m/z 367.3 (M+1).

Synthesis of 4-(benzyloxy)-3-(5-(1-((2-(trimethylsilyl)ethoxy)methyl)-1H-tetrazol-5-yl)pyridin-3-yl)phenyl cyclohexylcarbamate and 4-(benzyloxy)-3-(5-(4-((2-(trimethylsilyl)ethoxy)methyl)-4H-1,2,4-triazol-3-yl)pyridin-3-yl)phenyl cyclohexylcarbamate

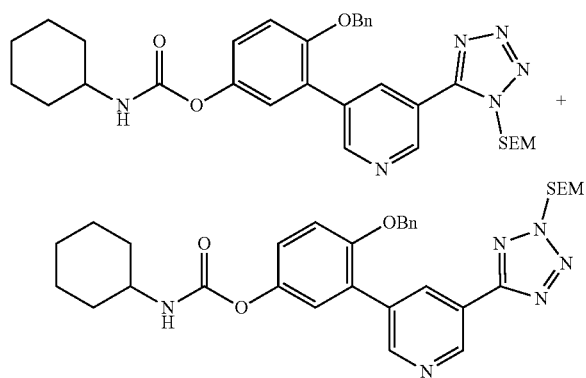

To a stirred solution of 4-(benzyloxy)-3-(5-(1-((2-(trimethylsilyl)ethoxy)methyl)-1H-tetrazol-5-yl)pyridin-3-yl)phenol and 4-(benzyloxy)-3-(5-(2-((2-(trimethylsilyl)ethoxy)methyl)-2H-tetrazol-5-yl)pyridin-3-yl)phenol (0.10 g, 0.21 mmol) in anhydrous acetonitrile (2.5 mL) was added TEA (0.044 mL, 0.316 mmol) and cyclohexyl isocyanate (0.029 g, 0.23 mmol) at RT under nitrogen atmosphere. The reaction mixture was stirred at RT for 10 minutes and then stirred at 75° C. for 3 h. An additional amount of cyclohexyl isocyanate (0.008 g, 0.076 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with dichloromethane/methanol to give a mixture of 4-(benzyloxy)-3-(5-(1-((2-(trimethylsilyl)ethoxy)methyl)-1H-tetrazol-5-yl)pyridin-3-yl)phenyl cyclohexylcarbamate and 4-(benzyloxy)-3-(5-(2-((2-(trimethylsilyl)ethoxy)methyl)-2H-tetrazol-5-yl)pyridin-3-yl)phenyl cyclohexylcarbamate (100 mg), which was used for next step without purification. MS (ES+APCI) m/z 601.3 (M+1).

Synthesis of 4-hydroxy-3-(5-(1-((2-(trimethylsilyl)ethoxy)methyl)-1H-tetrazol-5-yl)pyridin-3-yl)phenyl cyclohexylcarbamate and 4-hydroxy-3-(5-(2-((2-(trimethylsilyl)ethoxy)methyl)-2H-tetrazol-5-yl)pyridin-3-yl)phenyl cyclohexylcarbamate

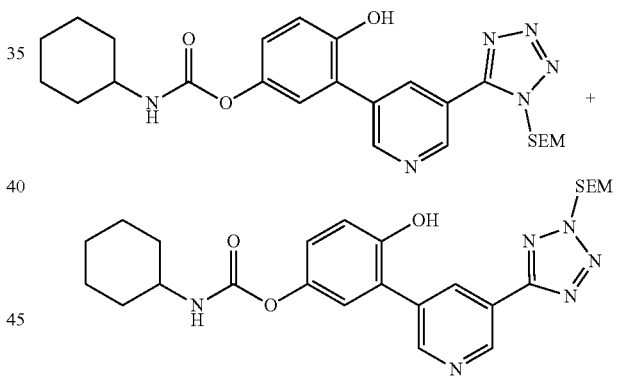

To a stirred solution of 4-(benzyloxy)-3-(5-(1-((2-(trimethylsilyl)ethoxy)methyl)-1H-tetrazol-5-yl)pyridin-3-yl)phenyl cyclohexylcarbamate and 4-(benzyloxy)-3-(5-(2-((2-(trimethylsilyl)ethoxy)methyl)-2H-tetrazol-5-yl)pyridin-3-yl)phenyl cyclohexylcarbamate cyclohexylcarbamate (0.120 g, 0.200 mmol) in THF (2 mL) and 2-propanol (0.5 mL) was added 10% Pd/C (60 mg) and Pd(OH)$_2$ (60 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to give a mixture of 4-hydroxy-3-(5-(1-((2-(trimethylsilyl)ethoxy)methyl)-1H-tetrazol-5-yl)pyridin-3-yl)phenyl cyclohexylcarbamate and 4-hydroxy-3-(5-(2-((2-(trimethylsilyl)ethoxy)methyl)-2H-tetrazol-5-yl)pyridin-3-yl)phenyl cyclohexylcarbamate (100 mg), which was used for next step without purification. MS (ES+APCI) m/z 511.3 (M+1).

Synthesis of 3-(5-(1H-tetrazol-5-yl)pyridin-3-yl)-4-hydroxyphenyl cyclohexylcarbamate (Example-248)

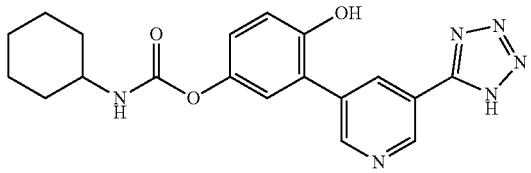 [SMILES: O=C(NC1CCCCC1)Oc1ccc(O)c(-c2cncc(-c3nnn[nH]3)c2)c1]

To a stirred solution of 4-hydroxy-3-(5-(1-((2-(trimethylsilyl)ethoxy)methyl)-1H-tetrazol-5-yl)pyridin-3-yl)phenyl cyclohexylcarbamate and 4-hydroxy-3-(5-(2-((2-(trimethylsilyl)ethoxy)methyl)-2H-tetrazol-5-yl)pyridin-3-yl)phenyl cyclohexylcarbamate (0.10 g, 0.156 mmol) in DCM (3 mL) was added SnCl₄ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO₃ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (3 mg) as an off white solid. $^1$H NMR (400 MHz, DMSO-d6) δ; 9.74 (s, 1H), 9.06 (d, J=2.00 Hz, 1H), 8.61 (d, J=2.00 Hz, 1H), 8.43 (t, J=2.00 Hz, 1H), 7.63 (d, J=8.00 Hz, 1H), 7.07 (s, 1H), 6.96 (d, J=1.60 Hz, 2H), 1.85-1.12 (m, 10H); MS (ES+APCI) m/z 381.4 (M+1).

Synthesis of 4-(benzyloxy)-3-(5-(1-((2-(trimethylsilyl)ethoxy)methyl)-1H-tetrazol-5-yl)pyridin-3-yl)phenyl cycloheptylcarbamate and 4-(benzyloxy)-3-(5-(2-((2-(trimethylsilyl)ethoxy)methyl)-2H-tetrazol-5-yl)pyridin-3-yl)phenyl cycloheptylcarbamate

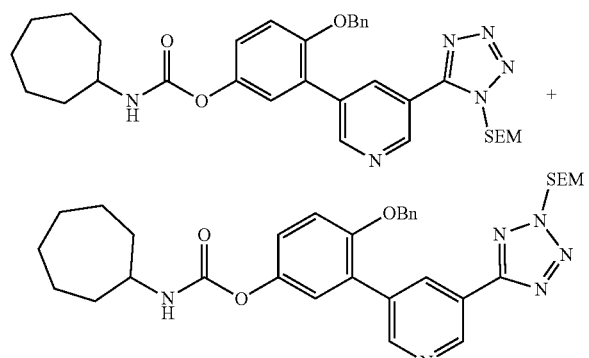

To a stirred solution of 4-(benzyloxy)-3-(5-(1-((2-(trimethylsilyl)ethoxy)methyl)-1H-tetrazol-5-yl)pyridin-3-yl)phenol and 4-(benzyloxy)-3-(5-(2-((2-(trimethylsilyl)ethoxy)methyl)-2H-tetrazol-5-yl)pyridin-3-yl)phenol (0.075 g, 0.158 mmol) in anhydrous acetonitrile (2.5 mL) was added TEA (0.033 mL, 0.237 mmol) and cycloheptyl isocyanate (0.024 g, 0.173 mmol) at RT under nitrogen atmosphere. The reaction mixture was stirred at RT for 10 minutes and then stirred at 75° C. for 3 h. An additional amount of cycloheptyl isocyanate (0.008 g, 0.057 mmol) was added to the reaction mixture and the resulting mixture was stirred for an additional 12 h. After completion of the reaction (monitored by LCMS), the reaction mixture was concentrated to give a residue. The residue was purified by automated normal-phase chromatography and eluted with dichloromethane/methanol to give a mixture of 4-(benzyloxy)-3-(5-(1-((2-(trimethylsilyl)ethoxy)methyl)-1H-tetrazol-5-yl)pyridin-3-yl)phenyl cycloheptylcarbamate and 4-(benzyloxy)-3-(5-(2-((2-(trimethylsilyl)ethoxy)methyl)-2H-tetrazol-5-yl)pyridin-3-yl)phenyl cycloheptylcarbamate (90 mg), which was used for next step without purification. MS (ES+APCI) m/z 615.3 (M+1).

Synthesis of 4-hydroxy-3-(5-(1-((2-(trimethylsilyl)ethoxy)methyl)-1H-tetrazol-5-yl)pyridin-3-yl)phenyl cycloheptylcarbamate and 4-hydroxy-3-(5-(2-((2-(trimethylsilyl)ethoxy)methyl)-2H-tetrazol-5-yl)pyridin-3-yl)phenyl cycloheptylcarbamate

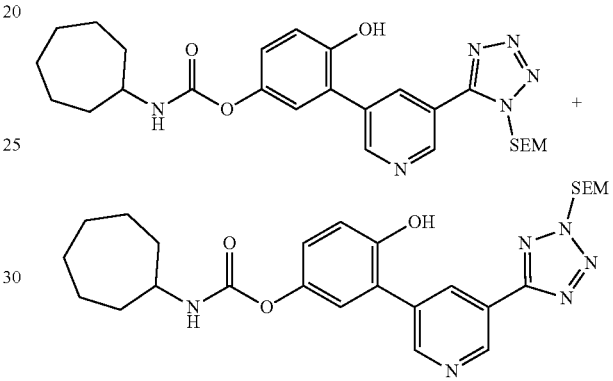

To a stirred solution of 4-(benzyloxy)-3-(5-(1-((2-(trimethylsilyl)ethoxy)methyl)-1H-tetrazol-5-yl)pyridin-3-yl)phenyl cycloheptylcarbamate and 4-(benzyloxy)-3-(5-(2-((2-(trimethylsilyl)ethoxy)methyl)-2H-tetrazol-5-yl)pyridin-3-yl)phenyl cycloheptylcarbamate (0.09 g, 0.146 mmol) in THF (2 mL) and 2-propanol (0.5 mL) was added 10% Pd/C (50 mg) and Pd(OH)₂ (50 mg). The reaction mixture was stirred at RT for 12 h under hydrogen balloon. After completion of the reaction (monitored by LCMS), the resultant mixture was filtered through a pad of celite, washed with DCM/MeOH and the filtrate was concentrated to give a mixture of 4-hydroxy-3-(5-(1-((2-(trimethylsilyl)ethoxy)methyl)-1H-tetrazol-5-yl)pyridin-3-yl)phenyl cycloheptylcarbamate and 4-hydroxy-3-(5-(2-((2-(trimethylsilyl)ethoxy)methyl)-2H-tetrazol-5-yl)pyridin-3-yl)phenyl cycloheptylcarbamate (67 mg), which was used for next step without purification. MS (ES+APCI) m/z 525.3 (M+1).

Synthesis of 3-(5-(1H-tetrazol-5-yl)pyridin-3-yl)-4-hydroxyphenyl cycloheptylcarbamate (Example-249)

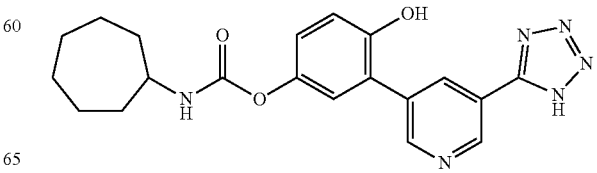

To a stirred solution of 4-hydroxy-3-(5-(1-((2-(trimethylsilyl)ethoxy)methyl)-1H-tetrazol-5-yl)pyridin-3-yl)phenyl cycloheptylcarbamate and 4-hydroxy-3-(5-(2-((2-(trimethylsilyl)ethoxy)methyl)-2H-tetrazol-5-yl)pyridin-3-yl)phenyl cycloheptylcarbamate (0.065 g, 0.123 mmol) in DCM (3 mL) was added SnCl₄ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO₃ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (7 mg) as an off white solid. ¹H NMR (400 MHz, DMSO-d6) δ; 9.74 (s, 1H), 9.06 (d, J=2.00 Hz, 1H), 8.60 (d, J=2.40 Hz, 1H), 8.43 (t, J=2.00 Hz, 1H), 7.66 (d, J=8.00 Hz, 1H), 7.07 (s, 1H), 6.96 (d, J=1.20 Hz, 2H), 3.57-3.51 (m, 1H), 1.87-1.24 (m, 12H); MS (ES+APCI) m/z 395.1 (M+1).

Synthesis of 5-(5-hydroxy-2-methoxyphenyl)nicotinonitrile

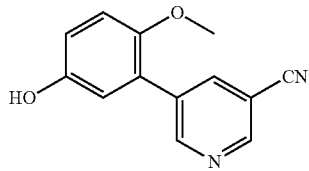 [SMILES: COc1ccc(O)cc1-c1cncc(C#N)c1]

To a stirred solution of 3-bromo-4-methoxyphenol (0.5 g, 2.46 mmol) in 1,4-dioxane (9 mL) and water (1 mL) was added 5-(4,4,5,5-tetramethyl-1,3,2-dioxaborolan-2-yl)nicotinonitrile (0.62 g, 2.71 mmol) and K₂CO₃ (1.02 g, 7.4 mmol) at RT. The reaction mixture was degassed for 15 minutes then Pd(dppf)Cl₂ (0.09 g, 0.12 mmol) was added. The reaction mixture was stirred at 80° C. for 6 h under nitrogen atmosphere. After completion of the reaction (monitored by TLC), the reaction mixture was filtered through celite, washed with ethyl acetate and the filtrate was concentrated to a residue. The residue was diluted with water and extracted with ethyl acetate, and the combined organic layers were washed with water, brine and concentrated to give a residue. The residue was purified by automated normal-phase chromatography and eluted with ethyl acetate/petroleum ether to give 5-(5-hydroxy-2-methoxyphenyl)nicotinonitrile (470 mg) as an off white solid. MS (ES+APCI) m/z 227.2 (M+1).

Synthesis of 3-(5-(1H-tetrazol-5-yl)pyridin-3-yl)-4-methoxyphenol

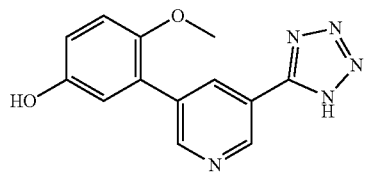 [SMILES: COc1ccc(O)cc1-c1cncc(-c2nnn[nH]2)c1]

To a stirred solution of 5-(5-hydroxy-2-methoxyphenyl)nicotinonitrile (0.4 g, 1.77 mmol) in THF (10 mL) was added trimethylsilyl azide (0.3 mL, 2.30 mmol) at 0° C. TBAF (1M in THF) (0.88 mL, 0.88 mmol) was added at 0° C. and the resultant suspension was stirred at 65° C. for 16 h. After completion of the reaction (monitored by LCMS), the reaction mixture was quenched with ice cold water. The aqueous layer was extracted with ethyl acetate, and the combined organic layers were washed with water, brine and concentrated to give a residue. The residue was purified by automated normal-phase chromatography and eluted with DCM/MeOH to give 3-(5-(1H-tetrazol-5-yl)pyridin-3-yl)-4-methoxyphenol (230 mg) as pale yellow solid. MS (ES+APCI) m/z 270.3 (M+1).

Synthesis of 4-methoxy-3-(5-(1-((2-(trimethylsilyl)ethoxy)methyl)-1H-tetrazol-5-yl)pyridin-3-yl)phenol and 4-methoxy-3-(5-(2-((2-(trimethylsilyl)ethoxy)methyl)-2H-tetrazol-5-yl)pyridin-3-yl)phenol

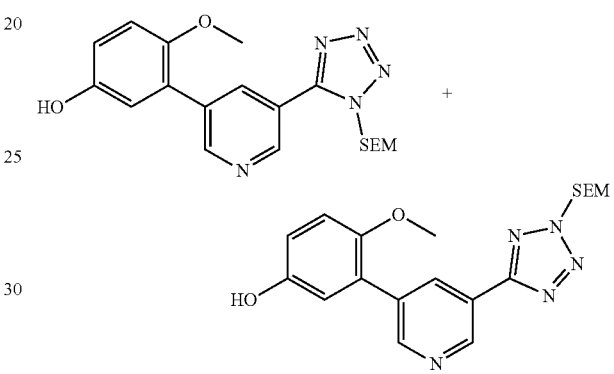

To a stirred solution of 3-(5-(1H-tetrazol-5-yl)pyridin-3-yl)-4-methoxyphenol (0.35 g, 1.30 mmol) in DMF (10 mL) was added potassium carbonate (0.27 g, 1.95 mmol) at 0° C. SEM-Cl (0.15 g, 0.91 mmol) was added and the resultant suspension was stirred at 0° C. for 1 h and RT for 1 h. After completion of the reaction (monitored by LCMS), the reaction mixture was quenched with cold water. The aqueous layer was extracted with ethyl acetate, and the combined organic layers were washed with water, brine and concentrated to give a residue. The residue was purified by automated normal-phase chromatography and eluted with ethyl acetate/petroleum ether to give a mixture of 4-methoxy-3-(5-(1-((2-(trimethylsilyl)ethoxy)methyl)-1H-tetrazol-5-yl)pyridin-3-yl)phenol and 4-methoxy-3-(5-(2-((2-(trimethylsilyl)ethoxy)methyl)-2H-tetrazol-5-yl)pyridin-3-yl)phenol (190 mg) as an off white solid. MS (ES+APCI) m/z 400.3 (M+1).

Synthesis of 4-methoxy-3-(5-(1-((2-(trimethylsilyl)ethoxy)methyl)-1H-tetrazol-5-yl)pyridin-3-yl)phenyl octylcarbamate and 4-methoxy-3-(5-(2-((2-(trimethylsilyl)ethoxy)methyl)-2H-tetrazol-5-yl)pyridin-3-yl)phenyl octylcarbamate

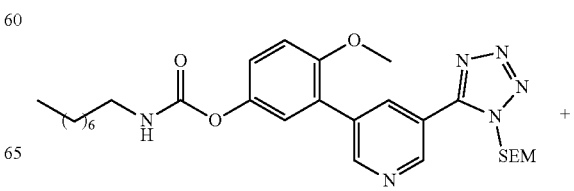

245

-continued

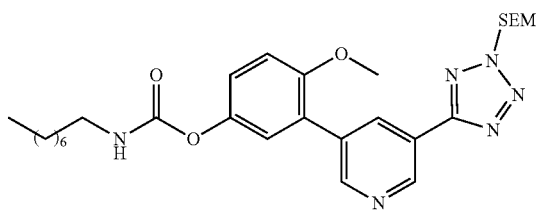

To a stirred solution of 4-methoxy-3-(5-(1-((2-(trimethylsilyl)ethoxy)methyl)-1H-tetrazol-5-yl)pyridin-3-yl)phenol and 4-methoxy-3-(5-(2-((2-(trimethylsilyl)ethoxy)methyl)-2H-tetrazol-5-yl)pyridin-3-yl)phenol (0.06 g, 0.15 mmol) in anhydrous acetonitrile (2 mL) was added TEA (0.03 mL, 0.225 mmol) and n-octyl isocyanate (0.026 g, 0.165 mmol) at RT under nitrogen atmosphere. The reaction mixture was stirred at RT for 10 minutes and then stirred at 75° C. for 4 h. An additional amount of n-octyl isocyanate (0.01 g, 0.03 mmol) was added to the reaction mixture and the resulting mixture was stirred for an additional 12 h. After completion of the reaction (monitored by LCMS), the reaction mixture was concentrated to give a mixture of 4-methoxy-3-(5-(1-((2-(trimethylsilyl)ethoxy)methyl)-1H-tetrazol-5-yl)pyridin-3-yl)phenyl octylcarbamate and 4-methoxy-3-(5-(2-((2-(trimethylsilyl)ethoxy)methyl)-2H-tetrazol-5-yl)pyridin-3-yl)phenyl octylcarbamate (82 mg), which was used for next step without purification. MS (ES+APCI) m/z 555.3 (M+1).

Synthesis of 3-(5-(1H-tetrazol-5-yl)pyridin-3-yl)-4-methoxyphenyl octylcarbamate (Example-250)

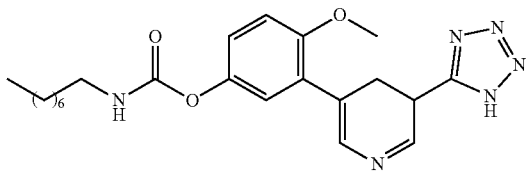

To a stirred solution of 4-methoxy-3-(5-(1-((2-(trimethylsilyl)ethoxy)methyl)-1H-tetrazol-5-yl)pyridin-3-yl)phenyl octylcarbamate and 4-methoxy-3-(5-(2-((2-(trimethylsilyl)ethoxy)methyl)-2H-tetrazol-5-yl)pyridin-3-yl)phenyl octylcarbamate (0.060 g, 0.108 mmol) in DCM (3.0 mL) was added SnCl₄ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO₃ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (24 mg) as an off white solid. $^1$H NMR (400 MHz, DMSO-d6) δ 9.17 (d, J=2.00 Hz, 1H), 8.86 (d, J=2.40 Hz, 1H), 8.47 (t, J=2.40 Hz, 1H), 7.73 (t, J=5.60 Hz, 1H), 7.23-7.19 (m, 3H), 3.83 (s, 3H), 3.08-3.03 (m, 2H), 1.46 (t, J=6.80 Hz, 2H), 1.27-1.26 (m, 10H), 0.86 (t, J=7.20 Hz, 3H); MS (ES+APCI) m/z 425.3 (M+1).

246

Synthesis of 4-methoxy-3-(5-(1-((2-(trimethylsilyl)ethoxy)methyl)-1H-tetrazol-5-yl)pyridin-3-yl)phenyl (cyclohexylmethyl)carbamate and 4-methoxy-3-(5-(2-((2-(trimethylsilyl)ethoxy)methyl)-2H-tetrazol-5-yl)pyridin-3-yl)phenyl (cyclohexylmethyl)carbamate

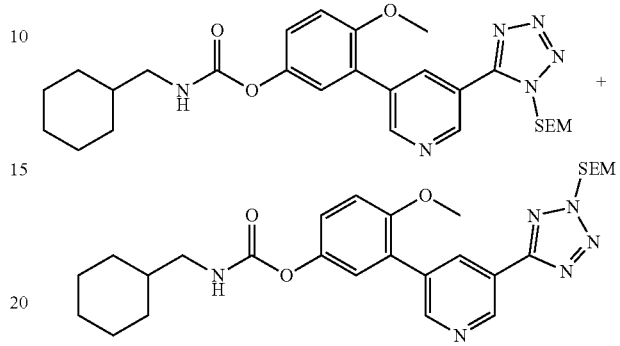

To a stirred solution of 4-methoxy-3-(5-(1-((2-(trimethylsilyl)ethoxy)methyl)-1H-tetrazol-5-yl)pyridin-3-yl)phenol and 4-methoxy-3-(5-(2-((2-(trimethylsilyl)ethoxy)methyl)-2H-tetrazol-5-yl)pyridin-3-yl)phenol (0.06 g, 0.15 mmol) in anhydrous acetonitrile (2 mL) was added TEA (0.03 mL, 0.225 mmol) and cyclohexanemethyl isocyanate (0.023 g, 0.165 mmol) at RT under nitrogen atmosphere. The reaction mixture was stirred at RT for 10 minutes and then stirred at 75° C. for 4 h. An additional amount of cyclohexanemethyl isocyanate (0.01 g, 0.082 mmol) was added to the reaction mixture and the resulting mixture was stirred for an additional 12 h. After completion of the reaction (monitored by LCMS), the reaction mixture was concentrated to give a mixture of 4-methoxy-3-(5-(1-((2-(trimethylsilyl)ethoxy)methyl)-1H-tetrazol-5-yl)pyridin-3-yl)phenyl (cyclohexylmethyl)carbamate and 4-methoxy-3-(5-(2-((2-(trimethylsilyl)ethoxy)methyl)-2H-tetrazol-5-yl)pyridin-3-yl)phenyl (cyclohexylmethyl)carbamate (80 mg), which was used for next step without purification. MS (ES+APCI) m/z 539.3 (M+1).

Synthesis of 3-(5-(1H-tetrazol-5-yl)pyridin-3-yl)-4-methoxyphenyl (cyclohexylmethyl)carbamate (Example-251)

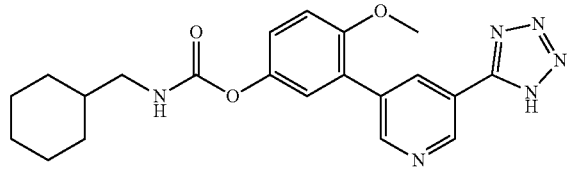 [SMILES: COc1ccc(OC(=O)NCC2CCCCC2)cc1-c1cncc(-c2nnn[nH]2)c1]

To a stirred solution of 4-methoxy-3-(5-(1-((2-(trimethylsilyl)ethoxy)methyl)-1H-tetrazol-5-yl)pyridin-3-yl)phenyl (cyclohexylmethyl)carbamate and 4-methoxy-3-(5-(2-((2-(trimethylsilyl)ethoxy)methyl)-2H-tetrazol-5-yl)pyridin-3-yl)phenyl (cyclohexylmethyl)carbamate (0.08 g, 0.148 mmol) in DCM (3.0 mL) was added SnCl₄ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO₃ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (31 mg) as an off white solid. ¹H NMR (400 MHz, DMSO-d6) δ 9.17 (d, J=2.00 Hz, 1H), 8.90 (d, J=2.40 Hz, 1H), 8.49 (t, J=2.00 Hz, 1H), 7.76 (t, J=5.60 Hz, 1H), 7.24-7.19 (m, 3H), 3.83 (s, 3H), 2.91 (t, J=6.40 Hz, 2H), 1.73-0.94 (m, 11H); MS (ES+APCI) m/z 409.4 (M+1).

Synthesis of 4-methoxy-3-(5-(1-((2-(trimethylsilyl)ethoxy)methyl)-1H-tetrazol-5-yl)pyridin-3-yl)phenyl benzylcarbamate and 4-methoxy-3-(5-(2-((2-(trimethylsilyl)ethoxy)methyl)-2H-tetrazol-5-yl)pyridin-3-yl)phenyl benzylcarbamate

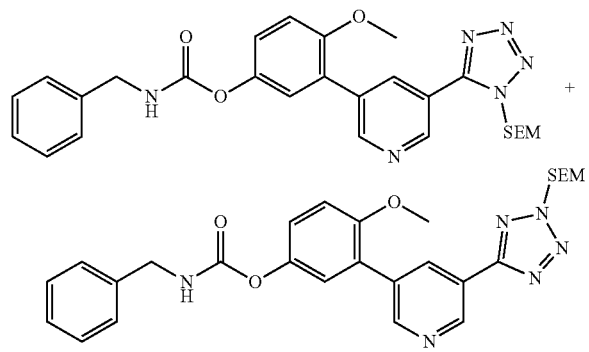

To a stirred solution of 4-methoxy-3-(5-(1-((2-(trimethylsilyl)ethoxy)methyl)-1H-tetrazol-5-yl)pyridin-3-yl)phenol and 4-methoxy-3-(5-(2-((2-(trimethylsilyl)ethoxy)methyl)-2H-tetrazol-5-yl)pyridin-3-yl)phenol (0.08 g, 0.200 mmol) in anhydrous acetonitrile (2 mL) was added TEA (0.042 mL, 0.30 mmol) and benzyl isocyanate (0.029 g, 0.220 mmol) at RT under nitrogen atmosphere. The reaction mixture was stirred at RT for 10 minutes and then stirred at 75° C. for 4 h. An additional amount of benzyl isocyanate (0.01 g, 0.05 mmol) was added to the reaction mixture and the resulting mixture was stirred for an additional 12 h. After completion of the reaction (monitored by LCMS), the reaction mixture was concentrated to give a mixture of 4-methoxy-3-(5-(1-((2-(trimethylsilyl)ethoxy)methyl)-1H-tetrazol-5-yl)pyridin-3-yl)phenyl benzylcarbamate and 4-methoxy-3-(5-(2-((2-(trimethylsilyl)ethoxy)methyl)-2H-tetrazol-5-yl)pyridin-3-yl)phenyl benzylcarbamate (105 mg), which was used for next step without purification. MS (ES+APCI) m/z 533.3 (M+1).

Synthesis of 3-(5-(1H-tetrazol-5-yl)pyridin-3-yl)-4-methoxyphenyl benzylcarbamate (Example-252)

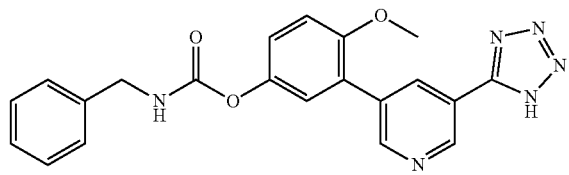 [SMILES: COc1ccc(OC(=O)NCc2ccccc2)cc1-c1cncc(-c2nnn[nH]2)c1]

To a stirred solution of 4-methoxy-3-(5-(1-((2-(trimethylsilyl)ethoxy)methyl)-1H-tetrazol-5-yl)pyridin-3-yl)phenyl benzylcarbamate and 4-methoxy-3-(5-(2-((2-(trimethylsilyl)ethoxy)methyl)-2H-tetrazol-5-yl)pyridin-3-yl)phenyl benzylcarbamate (0.105 g, 0.197 mmol) in DCM (3.0 mL) was added SnCl₄ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO₃ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (40 mg) as an off white solid. ¹H NMR (400 MHz, DMSO-d6) δ 9.18 (d, J=2.00 Hz, 1H), 8.91 (d, J=2.00 Hz, 1H), 8.50 (t, J=2.00 Hz, 1H), 8.32 (t, J=6.00 Hz, 1H), 7.38-7.19 (m, 8H), 4.39-4.28 (m, 2H), 3.83 (s, 3H); MS (ES+APCI) m/z 403.3 (M+1).

Synthesis of 4-methoxy-3-(5-(1-((2-(trimethylsilyl)ethoxy)methyl)-1H-tetrazol-5-yl)pyridin-3-yl)phenyl cyclopentylcarbamate and 4-methoxy-3-(5-(2-((2-(trimethylsilyl)ethoxy)methyl)-2H-tetrazol-5-yl)pyridin-3-yl)phenyl cyclopentylcarbamate

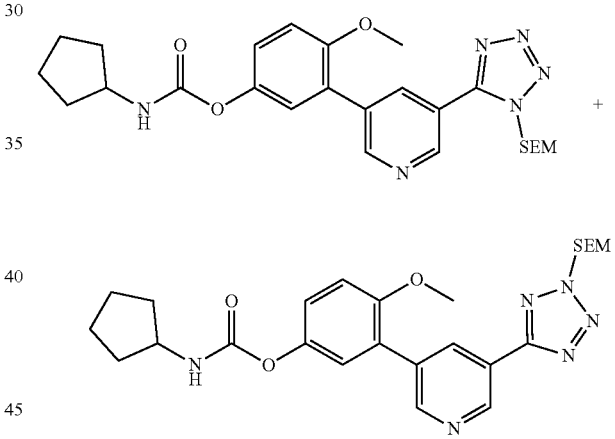

To a stirred solution of 4-methoxy-3-(5-(1-((2-(trimethylsilyl)ethoxy)methyl)-1H-tetrazol-5-yl)pyridin-3-yl)phenol and 4-methoxy-3-(5-(2-((2-(trimethylsilyl)ethoxy)methyl)-2H-tetrazol-5-yl)pyridin-3-yl)phenol (0.07 g, 0.175 mmol) in anhydrous acetonitrile (2 mL) was added TEA (0.037 mL, 0.263 mmol) and cyclopentyl isocyanate (0.021 g, 0.193 mmol) at RT under nitrogen atmosphere. The reaction mixture was stirred at RT for 10 minutes and then stirred at 75° C. for 4 h. An additional amount of cyclopentyl isocyanate (0.01 g, 0.096 mmol) was added to the reaction mixture and the resulting mixture was stirred for an additional 12 h. After completion of the reaction (monitored by LCMS), the reaction mixture was concentrated to give a mixture of 4-methoxy-3-(5-(1-((2-(trimethylsilyl)ethoxy)methyl)-1H-tetrazol-5-yl)pyridin-3-yl)phenyl cyclopentylcarbamate and 4-methoxy-3-(5-(2-((2-(trimethylsilyl)ethoxy)methyl)-2H-tetrazol-5-yl)pyridin-3-yl)phenyl cyclopentylcarbamate (89 mg), which was used for next step without purification. MS (ES+APCI) m/z 511.3 (M+1).

Synthesis of 3-(5-(1H-tetrazol-5-yl)pyridin-3-yl)-4-methoxyphenyl cyclopentylcarbamate

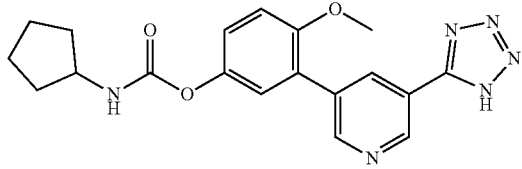 [SMILES: COc1ccc(OC(=O)NC2CCCC2)cc1-c1cncc(-c2nnn[nH]2)c1]

To a stirred solution of 4-methoxy-3-(5-(1-((2-(trimethylsilyl)ethoxy)methyl)-1H-tetrazol-5-yl)pyridin-3-yl)phenyl cyclopentylcarbamate and 4-methoxy-3-(5-(2-((2-(trimethylsilyl)ethoxy)methyl)-2H-tetrazol-5-yl)pyridin-3-yl)phenyl cyclopentylcarbamate (0.078 g, 0.153 mmol) in DCM (3.0 mL) was added SnCl₄ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO₃ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (25 mg) as an off white solid. ¹H NMR (400 MHz, DMSO-d6) δ 9.17 (d, J=2.40 Hz, 1H), 8.90 (d, J=2.00 Hz, 1H), 8.49 (t, J=2.00 Hz, 1H), 7.78 (d, J=7.20 Hz, 1H), 7.24 (d, J=1.20 Hz, 1H), 7.19 (d, J=1.20 Hz, 2H), 3.83 (s, 4H), 1.86-1.46 (m, 8H); MS (ES+APCI) m/z 381.4 (M+1).

Synthesis of 4-methoxy-3-(5-(1-((2-(trimethylsilyl)ethoxy)methyl)-1H-tetrazol-5-yl)pyridin-3-yl)phenyl cyclohexylcarbamate and 4-methoxy-3-(5-(2-((2-(trimethylsilyl)ethoxy)methyl)-2H-tetrazol-5-yl)pyridin-3-yl)phenyl cyclohexylcarbamate

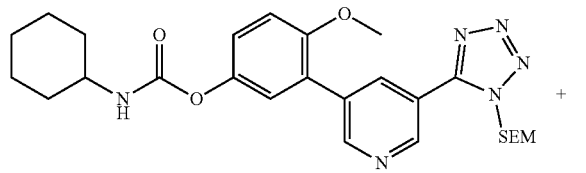

To a stirred solution of 4-methoxy-3-(5-(1-((2-(trimethylsilyl)ethoxy)methyl)-1H-tetrazol-5-yl)pyridin-3-yl)phenol and 4-methoxy-3-(5-(2-((2-(trimethylsilyl)ethoxy)methyl)-2H-tetrazol-5-yl)pyridin-3-yl)phenol (0.06 g, 0.15 mmol) in anhydrous acetonitrile (2 mL) was added TEA (0.03 mL, 0.225 mmol) and cyclohexyl isocyanate (0.021 g, 0.165 mmol) at RT under nitrogen atmosphere. The reaction mixture was stirred at RT for 10 minutes and then stirred at 75° C. for 4 h. An additional amount of cyclohexyl isocyanate (0.01 g, 0.082 mmol) was added to the reaction mixture and the resulting mixture was stirred for an additional 12 h. After completion of the reaction (monitored by LCMS), the reaction mixture was concentrated to give a mixture of 4-methoxy-3-(5-(1-((2-(trimethylsilyl)ethoxy)methyl)-1H-tetrazol-5-yl)pyridin-3-yl)phenyl cyclohexylcarbamate and 4-methoxy-3-(5-(2-((2-(trimethylsilyl)ethoxy)methyl)-2H-tetrazol-5-yl)pyridin-3-yl)phenyl cyclohexylcarbamate (78 mg), which was used for next step without purification. MS (ES+APCI) m/z 525.3 (M+1).

Synthesis of 3-(5-(1H-tetrazol-5-yl)pyridin-3-yl)-4-methoxyphenyl cyclohexylcarbamate (Example-254)

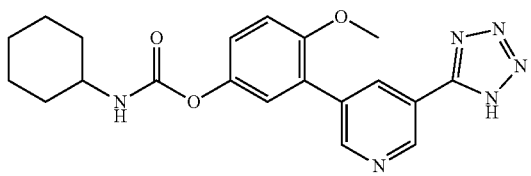 [SMILES: COc1ccc(OC(=O)NC2CCCCC2)cc1-c1cncc(-c2nnn[nH]2)c1]

To a stirred solution of 4-methoxy-3-(5-(1-((2-(trimethylsilyl)ethoxy)methyl)-1H-1,2,4-triazol-5-yl)pyridin-3-yl)phenyl cyclohexylcarbamate and 4-methoxy-3-(5-(4-((2-(trimethylsilyl)ethoxy)methyl)-4H-1,2,4-triazol-3-yl)pyridin-3-yl)phenyl cyclohexylcarbamate (0.078 g, 0.149 mmol) in DCM (3.0 mL) was added SnCl₄ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO₃ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (17 mg) as an off white solid. ¹H NMR (400 MHz, DMSO-d6) δ 9.17 (d, J=2.00 Hz, 1H), 8.90 (d, J=2.00 Hz, 1H), 8.49 (t, J=2.00 Hz, 1H), 7.71 (d, J=8.00 Hz, 1H), 7.24-7.19 (m, 3H), 3.83 (s, 3H), 1.84-1.10 (m, 10H); MS (ES+APCI) m/z 395.3 (M+1).

Synthesis of 4-methoxy-3-(5-(1-((2-(trimethylsilyl)ethoxy)methyl)-1H-tetrazol-5-yl)pyridin-3-yl)phenyl cycloheptylcarbamate and 4-methoxy-3-(5-(2-((2-(trimethylsilyl)ethoxy)methyl)-2H-tetrazol-5-yl)pyridin-3-yl)phenyl cycloheptylcarbamate

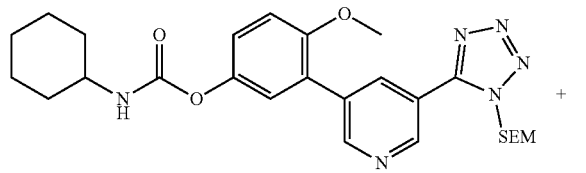

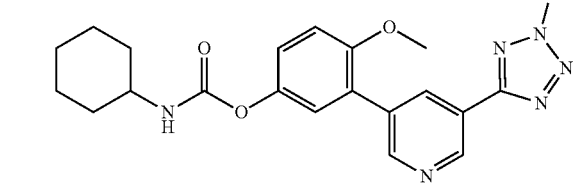

To a stirred solution of 4-methoxy-3-(5-(1-((2-(trimethylsilyl)ethoxy)methyl)-1H-tetrazol-5-yl)pyridin-3-yl)phenol and 4-methoxy-3-(5-(2-((2-(trimethylsilyl)ethoxy)methyl)-2H-tetrazol-5-yl)pyridin-3-yl)phenol (0.08 g, 0.20 mmol) in anhydrous acetonitrile (2 mL) was added TEA (0.042 mL, 0.300 mmol) and cycloheptyl isocyanate (0.031 g, 0.220 mmol) at RT under nitrogen atmosphere. The reaction mixture was stirred at RT for 10 minutes and then stirred at 75° C. for 4 h. An additional amount of cycloheptyl isocyanate (0.01 g, 0.03 mmol) was added to the reaction mixture and the resulting mixture was stirred for an additional 12 h. After completion of the reaction (monitored by LCMS), the reaction mixture was concentrated to give a mixture of 4-methoxy-3-(5-(1-((2-(trimethylsilyl)ethoxy)methyl)-1H-tetrazol-5-yl)pyridin-3-yl)phenyl cycloheptylcarbamate and 4-methoxy-3-(5-(2-((2-(trimethylsilyl)ethoxy)methyl)-2H-tetrazol-5-yl)pyridin-3-yl)phenyl cycloheptylcarbamate (108 mg), which was used for next step without purification. MS (ES+APCI) m/z 539.3 (M+1).

Synthesis of 3-(5-(1H-tetrazol-5-yl)pyridin-3-yl)-4-methoxyphenyl cycloheptylcarbamate (Example-255)

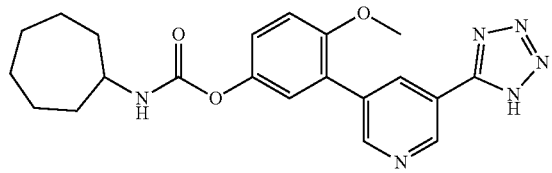 [SMILES: COc1ccc(OC(=O)NC2CCCCCC2)cc1-c1cncc(-c2nnn[nH]2)c1]

To a stirred solution of 4-methoxy-3-(5-(1-((2-(trimethylsilyl)ethoxy)methyl)-1H-tetrazol-5-yl)pyridin-3-yl)phenyl cycloheptylcarbamate and 4-methoxy-3-(5-(2-((2-(trimethylsilyl)ethoxy)methyl)-2H-tetrazol-5-yl)pyridin-3-yl)phenyl cycloheptylcarbamate (0.108 g, 0.200 mmol) in DCM (3.0 mL) was added SnCl₄ (0.3 mL, 10% solution in DCM) at 0-5° C. under nitrogen atmosphere. The reaction mixture was stirred at RT for 2 h. After completion of the reaction (monitored by LCMS), the reaction mixture was quenched with aq. 10% NaHCO₃ solution and concentrated to give a residue. The crude residue was triturated with DCM/MeOH for 20 minutes. The solid was filtered and the filtrate was concentrated to a crude residue. The residue was purified by preparative HPLC (0.1% FA) to yield the target compound (9.0 mg) as an off white solid. $^1$H NMR (400 MHz, DMSO-d6) δ 9.17 (d, J=2.00 Hz, 1H), 8.87 (d, J=2.00 Hz, 1H), 8.48 (t, J=2.00 Hz, 1H), 7.74 (d, J=8.00 Hz, 1H), 7.23-7.18 (m, 3H), 3.83 (s, 3H), 3.56-3.52 (m, 1H), 1.89-1.40 (m, 12H); MS (ES+APCI) m/z 409.4 (M+1).

Scheme XI

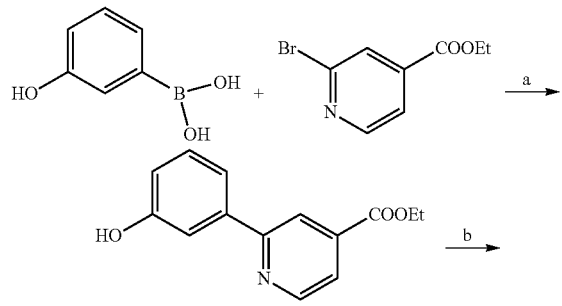

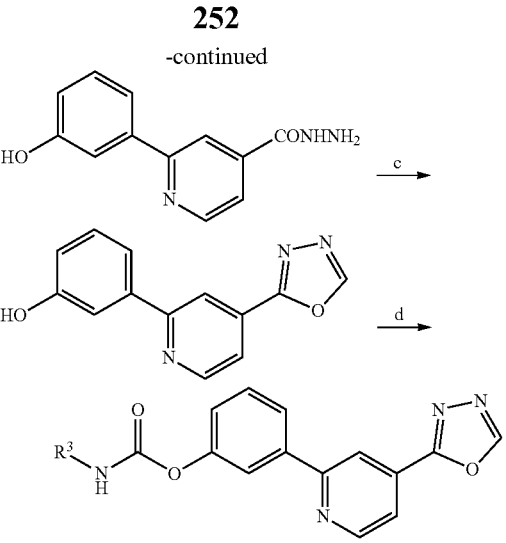

Reagents and conditions: (Pd(PPh₃)₄, Na₂CO₃, 1,4-dioxane, H₂O, 90° C., 4 h; b) NH₂NH₂·H₂O, EtOH, 90° C., 15 h; c) CH(OC₂H₅)₃, 130° C., 5 h d) R³-NCO, TEA, ACN, 75° C., 6 h.

Synthesis of ethyl 2-(3-hydroxyphenyl)isonicotinate

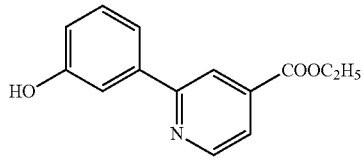

To a stirred solution of ethyl 2-bromoisonicotinate (0.78 g, 3.62 mmol) in 1,4-dioxane (15 mL) was added (3-hydroxyphenyl)boronic acid (0.50 g, 3.62 mmol) and 0.4M Na₂CO₃ (15 mL) at RT. The reaction mixture was degassed for 15 minutes then Pd(PPh₃)₄ (0.02 g, 0.018 mmol) was added. The reaction mixture was heated at 90° C. for 4 h under nitrogen atmosphere. The reaction was monitored by TLC. after completion, the reaction mixture was cooled to RT then evaporated under reduced pressure. The residue was dissolved in water (15 mL) and pH was adjusted to 2-3 by using 2N HCl. The precipitated solid was filtered, washed with water, and then dried under high vacuum to afford the crude acid (450 mg). To a suspension of acid compound in ethanol (15 mL) was added concentrated H₂SO₄ (4-5 drops) at RT then the reaction mixture was heated at 90° C. for 5 h under Nitrogen atmosphere. The reaction progress was monitored by TLC. After reaction completion, the reaction mixture was cooled to RT and then the solvent was evaporated under reduced pressure. The residue was dissolved in ethyl acetate, washed with NaHCO₃ followed by brine. The organic solvent was dried over sodium sulfate then evaporated under reduced pressure. The residue was purified by column chromatography on silica gel eluting with hexane/EtOAc (gradient 10-70% EtOAc) to yield ethyl 2-(3-hydroxyphenyl)isonicotinate (400 mg) as an off white solid. $^1$H NMR (400 MHz, DMSO-d6) δ 9.64 (s, 1H), 8.86 (dd, J=0.9, 5.0 Hz, 1H), 8.22 (dd, J=0.9, 1.6 Hz, 1H), 7.78 (dd, J=1.5, 5.0 Hz, 1H), 7.62-7.46 (m, 2H), 7.32 (t, J=7.8 Hz, 1H), 6.88 (ddd, J=1.0, 2.5, 8.0 Hz, 1H), 3.94 (s, 3H).

Synthesis of
2-(3-hydroxyphenyl)isonicotinohydrazide

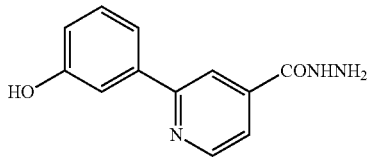

To a solution of ethyl 2-(3-hydroxyphenyl)isonicotinate (0.25 g, 1.028 mmol) in ethanol (6 mL) was added hydrazine hydrate (0.61 g, 6.16 mmol) at RT. The reaction mixture was heated at 90° C. for 15 h. The reaction progress was monitored by TLC, after completion the reaction was cooled to RT. The precipitated product was collected by filtrations and washed by ethanol. The filtrate was evaporated under reduced pressure and the residue was purified by flash chromatography on silica gel eluting with DCM/MeOH (gradient 2-20% MeOH) to yield the 2-(3-hydroxyphenyl)isonicotinohydrazide (180 mg) as a pale yellow solid. $^1$H NMR (400 MHz, DMSO-d6) δ 4.60 (s, 2H), 6.86 (dd, J=7.8, 1.7 Hz, 1H), 7.14 (s, 1H), 7.20 (d, J=7.7 Hz, 1H), 7.32 (m, 1H), 8.35 (m, 1H), 8.94 (m, 2H), 9.67 (s, 1H), 10.06 (s, 1H).

Synthesis of 3-(4-(1,3,4-oxadiazol-2-yl)pyridin-2-yl)phenol

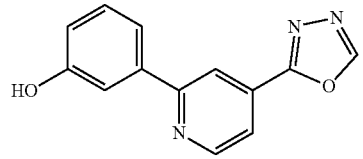 [SMILES: Oc1cccc(-c2cc(-c3nnco3)ccn2)c1]

A suspension of 2-(3-hydroxyphenyl)isonicotinohydrazide (0.22 g, 0.92 mmol) in triethyl orthoformate (6 mL) was heated to 130° C. for 5 h under nitrogen atmosphere. The reaction progress was monitored by TLC, after completion the reaction mixture was cooled to RT and then the solvent was evaporated under reduced pressure. The compound was purified by column chromatography on silica gel eluting with DCM/MeOH (gradient 2-20% MeOH) to yield the 3-(4-(1,3,4-oxadiazol-2-yl)pyridin-2-yl)phenol (120 mg) as a yellowish solid. $^1$H NMR (400 MHz, DMSO-d6) δ $^1$H NMR (400 MHz, DMSO-d6) δ 9.53 (s, 1H), 8.91 (dd, J=0.8, 5.0 Hz, 1H), 8.34 (t, J=1.2 Hz, 1H), 7.92 (dd, J=1.5, 5.0 Hz, 1H), 7.78-7.52 (m, 2H), 7.52-7.18 (m, 1H), 6.90 (ddd, J=1.2, 2.4, 8.0 Hz, 1H).

Synthesis of 3-(4-(1,3,4-oxadiazol-2-yl)pyridin-2-yl)phenyl heptylcarbamate (Example-256)

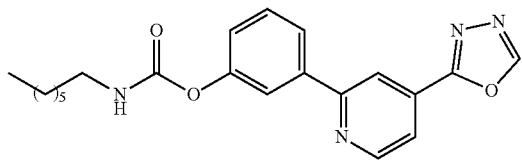

To a suspension of 3-(4-(1,3,4-oxadiazol-2-yl)pyridin-2-yl)phenol (0.06 g, 0.25 mmol) in anhydrous acetonitrile (4 mL) was added TEA (0.04 g, 0.38 mmol) and n-heptyl isocyanate (0.035 g, 0.25 mmol) at RT under nitrogen atmosphere. The reaction mixture was stirred at RT for 10 minutes and then heated at 75° C. for 3 h under nitrogen atmosphere. An additional amount of n-heptyl isocyanate (0.017 g, 0.12 mmol) was added to the reaction mixture and the reaction was heated for additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-40% EtOAc) to yield the target compound (48 mg) as an off white solid. $^1$H NMR (400 MHz, DMSO-d6) 9.55 (s, 1H), 8.83-9.01 (m, 1H), 8.46 (dd, J=1.6, 0.9 Hz, 1H), 7.76-8.11 (m, 4H), 7.49-7.64 (m, 1H), 7.23 (ddd, J=8.1, 2.4, 1.0 Hz, 1H), 2.84-3.17 (m, 2H), 1.49 (td, J=7.3, 3.8 Hz, 2H), 1.16-1.42 (m, 8H), 0.86 (td, J=6.8, 2.6 Hz, 3H).

Synthesis of 3-(4-(1,3,4-oxadiazol-2-yl)pyridin-2-yl)phenyl (cyclohexylmethyl)carbamate (Example-257)

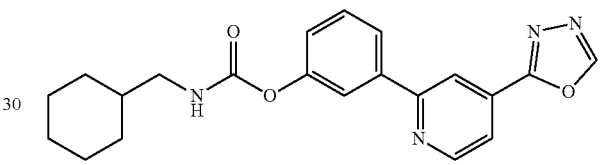

To a suspension of 3-(4-(1,3,4-oxadiazol-2-yl)pyridin-2-yl)phenol (0.06 g, 0.25 mmol) in anhydrous acetonitrile (4 mL) was added TEA (0.04 g, 0.38 mmol) and cyclohexanemethyl isocyanate (0.035 g, 0.25 mmol) at RT under nitrogen atmosphere. The reaction mixture was stirred at RT for 10 minutes and then heated at 75° C. for 3 h under nitrogen atmosphere. An additional amount of cyclohexanemethyl isocyanate (0.017 g, 0.12 mmol) was added to the reaction mixture and the reaction was heated for additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-30% EtOAc) to yield the target compound (42 mg) as an off white solid. $^1$H NMR (400 MHz, DMSO-d6) δ 9.55 (s, 1H), 8.93 (dd, J=5.0, 0.9 Hz, 1H), 8.46 (dd, J=1.6, 0.9 Hz, 1H), 7.76-8.13 (m, 4H), 7.53-7.65 (m, 1H), 7.15-7.39 (m, 1H), 2.87-3.02 (m, 2H), 2.75-2.87 (m, 1H), 1.39-1.78 (m, 5H), 1.07-1.33 (m, 3H), 0.91 (dt, J=22.9, 12.6 Hz, 2H).

Synthesis of 3-(4-(1,3,4-oxadiazol-2-yl)pyridin-2-yl)phenyl benzylcarbamate (Example-258)

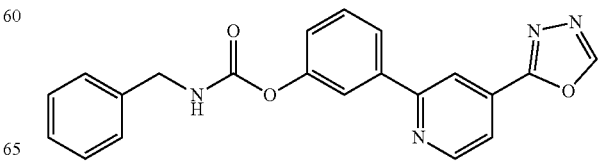

To a suspension of 3-(4-(1,3,4-oxadiazol-2-yl)pyridin-2-yl)phenol (0.06 g, 0.25 mmol) in anhydrous acetonitrile (4 mL) was added TEA (0.04 g, 0.38 mmol) and benzyl isocyanate (0.033 g, 0.25 mmol) at RT under nitrogen atmosphere. The reaction mixture was stirred at RT for 10 minutes and then heated at 75° C. for 3 h under nitrogen atmosphere. An additional amount of benzyl isocyanate (0.016 g, 0.12 mmol) was added to the reaction mixture and the reaction was heated for additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-30% EtOAc) to yield the target compound (38 mg) as an off white solid. $^1$H NMR (400 MHz, DMSO-d6) δ 9.41-9.62 (m, 1H), 8.92 (ddd, J=9.9, 5.0, 0.9 Hz, 1H), 8.23-8.60 (m, 2H), 7.83-8.18 (m, 3H), 7.45-7.62 (m, 2H), 7.20-7.45 (m, 5H), 4.33 (d, J=6.1 Hz, 2H).

Synthesis of 3-(4-(1,3,4-oxadiazol-2-yl)pyridin-2-yl) phenyl cyclopentylcarbamate (Example-259)

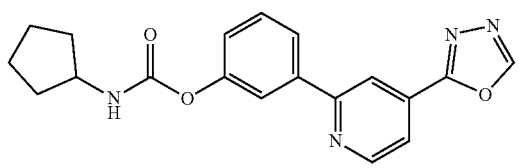 [SMILES: O=C(NC1CCCC1)Oc1cccc(-c2cc(-c3nnco3)ccn2)c1]

To a suspension of 3-(4-(1,3,4-oxadiazol-2-yl)pyridin-2-yl)phenol (0.06 g, 0.25 mmol) in anhydrous acetonitrile (4 mL) was added TEA (0.04 g, 0.38 mmol) and cyclopentyl isocyanate (0.028 g, 0.25 mmol) at RT under nitrogen atmosphere. The reaction mixture was stirred at RT for 10 minutes and then heated at 75° C. for 3 h under nitrogen atmosphere. An additional amount of cyclopentyl isocyanate (0.013 g, 0.12 mmol) was added to the reaction mixture and the reaction was heated for additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-30% EtOAc) to yield the target compound (44 mg) as an off white solid. $^1$H NMR (400 MHz, DMSO-d6) δ 9.44-9.69 (m, 1H), 8.92 (ddd, J=9.8, 5.0, 0.9 Hz, 1H), 8.43-8.55 (m, 1H), 7.81-8.12 (m, 3H), 7.49-7.71 (m, 2H), 7.13-7.43 (m, 1H), 3.81-4.05 (m, 1H), 1.41-1.98 (m, 8H).

Synthesis of 3-(4-(1,3,4-oxadiazol-2-yl)pyridin-2-yl) phenyl cyclohexylcarbamate (Example-260)

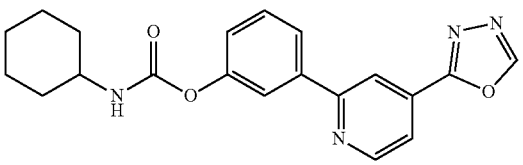 [SMILES: O=C(NC1CCCCC1)Oc1cccc(-c2cc(-c3nnco3)ccn2)c1]

To a suspension of 3-(4-(1,3,4-oxadiazol-2-yl)pyridin-2-yl)phenol (0.06 g, 0.25 mmol) in anhydrous acetonitrile (4 mL) was added TEA (0.04 g, 0.38 mmol) and cyclohexyl isocyanate (0.031 g, 0.25 mmol) at RT under nitrogen atmosphere. The reaction mixture was stirred at RT for 10 minutes and then heated at 75° C. for 3 h under nitrogen atmosphere. An additional amount of cyclohexyl isocyanate (0.015 g, 0.12 mmol) was added to the reaction mixture and the reaction was heated for additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-30% EtOAc) to yield the target compound (46 mg) as an off white solid. 1H NMR (400 MHz, DMSO-d6) δ 9.60 (s, 1H), 8.99 (dd, J=5.0, 0.8 Hz, 1H), 8.52 (t, J=1.2 Hz, 1H), 7.80-8.22 (m, 4H), 7.60 (t, J=7.9 Hz, 1H), 7.22-7.38 (m, 1H), 1.47-1.97 (m, 5H), 0.93-1.47 (m, 6H).

Synthesis of 3-(4-(1,3,4-oxadiazol-2-yl)pyridin-2-yl) phenyl (4-methylcyclohexyl)carbamate (Example-261)

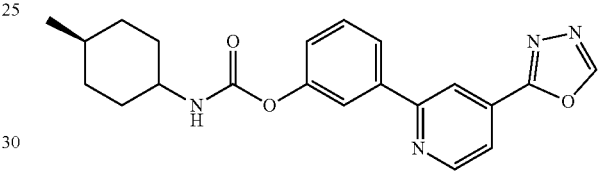

To a suspension of 3-(4-(1,3,4-oxadiazol-2-yl)pyridin-2-yl)phenol (0.06 g, 0.25 mmol) in anhydrous acetonitrile (4 mL) was added TEA (0.04 g, 0.38 mmol) and trans-4-methylcyclohexyl isocyanate (0.035 g, 0.25 mmol) at RT under nitrogen atmosphere. The reaction mixture was stirred at RT for 10 minutes and then heated at 75° C. for 3 h under nitrogen atmosphere. An additional amount of trans-4-methylcyclohexyl isocyanate (0.017 g, 0.12 mmol) was added to the reaction mixture and the reaction was heated for additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-30% EtOAc) to yield the target compound (41 mg) as an off white solid. 1H NMR (400 MHz, DMSO-d6) δ 9.55 (s, 1H), 8.93 (dd, J=5.1, 0.9 Hz, 1H), 8.27-8.71 (m, 1H), 7.66-8.17 (m, 4H), 7.44-7.66 (m, 1H), 6.94-7.44 (m, 1H), 3.27 (ddd, J=11.8, 7.8, 3.9 Hz, 1H), 1.79 (ddd, J=77.8, 14.0, 3.7 Hz, 3H), 1.18-1.50 (m, 4H), 0.98 (qd, J=13.4, 3.4 Hz, 2H), 0.88 (d, J=6.5 Hz, 3H).

Synthesis of 3-(4-(1,3,4-oxadiazol-2-yl)pyridin-2-yl) phenyl cycloheptylcarbamate (Example-262)

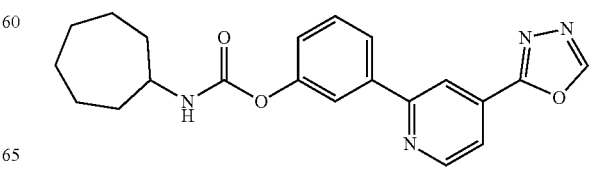

To a suspension of 3-(4-(1,3,4-oxadiazol-2-yl)pyridin-2-yl)phenol (0.06 g, 0.25 mmol) in anhydrous acetonitrile (4 mL) was added TEA (0.04 g, 0.38 mmol) and cycloheptyl isocyanate (0.035 g, 0.25 mmol) at RT under nitrogen atmosphere. The reaction mixture was stirred at RT for 10 minutes and then heated at 75° C. for 3 h under nitrogen atmosphere. An additional amount of cycloheptyl isocyanate (0.017 g, 0.12 mmol) was added to the reaction mixture and the reaction was heated for additional 3 h. The reaction progress was monitored by TLC, after completion the reaction mixture was cooled to RT and then the solvent was evaporated under reduced pressure. The crude product was purified by flash column chromatography on silica gel eluting with hexane/EtOAc (gradient 10-30% EtOAc) to yield the target compound (45 mg) as an off white solid.

Scheme XII

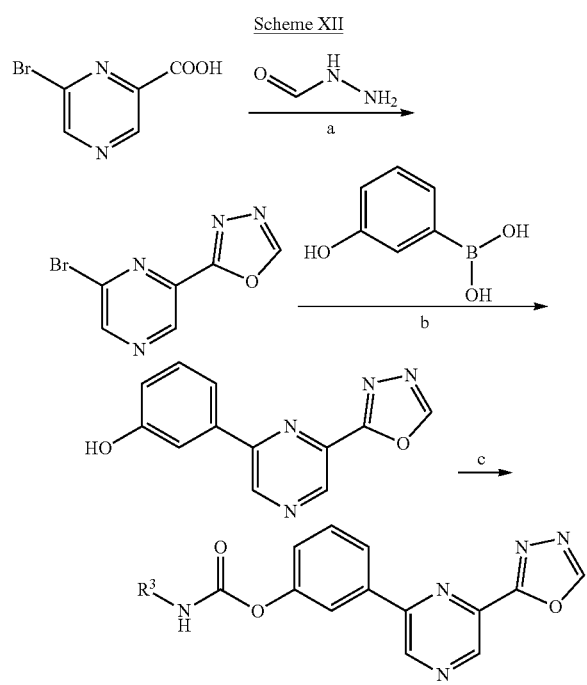

Reagents and conditions: a) Propylphosphonic anhydride (T3P), TEA, ethyl acetate (EtOAc), 80° C., 5 h; b) Pd(PPh3)4, K2CO3, 1,4-Dioxane, H2O, 90° C., 4 h; c) R³-NCO, TEA, ACN, 75° C., 12 h.

Synthesis of
2-(6-bromopyrazin-2-yl)-1,3,4-oxadiazole

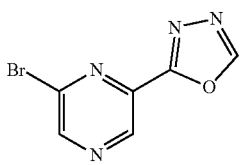 [SMILES: Brc1cncc(-c2nnco2)n1]

To a stirred solution of 6-bromopyrazine-2-carboxylic acid (1 g, 4.93 mmol) in ethyl acetate (20 mL) was added formohydrazide (0.3 g, 4.93 mmol), TEA (1.50 g, 14.78 mmol) and T3P (50% in EA) (7.84 g, 12.32 mmol) at 0° C. The resulting mixture was stirred at 80° C. for 5 h under nitrogen atmosphere. After completion of the reaction (monitored by TLC), the reaction mixture was cooled to RT, and poured onto ice-water. The product was extracted with ethyl acetate. The combined organic phase was washed with saturated sodium hydrogen carbonate solution, brine and dried over sodium sulfate. The solvent was removed under reduced pressure and the crude product was purified by automated normal-phase chromatography and eluted with ethyl acetate/petroleum ether to give 2-(6-bromopyrazin-2-yl)-1,3,4-oxadiazole (700 mg) as an off white solid. MS (ES+APCI) m/z 227.1

Synthesis of 3-(6-(1,3,4-oxadiazol-2-yl)pyrazin-2-yl)phenol

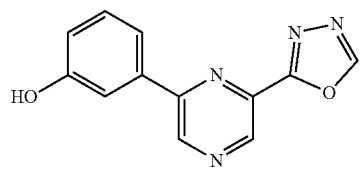 [SMILES: Oc1cccc(-c2cncc(-c3nnco3)n2)c1]

To a stirred solution of 2-(6-bromopyrazin-2-yl)-1,3,4-oxadiazole (0.5 g, 2.20 mmol) in 1,4-dioxane (4.5 mL) and water (0.5 mL) was added (3-hydroxyphenyl)boronic acid (0.61 g, 4.40 mmol) and $K_2CO_3$ (0.91 g, 6.61 mmol) at RT. The reaction mixture was degassed for 15 minutes then Pd(PPh$_3$)$_4$ (0.13 g, 0.11 mmol) was added. The reaction mixture was stirred at 90° C. for 4 h under nitrogen atmosphere. After completion of the reaction (monitored by TLC), the reaction mixture was cooled to RT and then the solvent was evaporated under reduced pressure. The residue was dissolved in ethyl acetate, washed with water followed by brine. The organic layer was dried over sodium sulfate then evaporated under reduced pressure. The residue was purified by automated normal-phase chromatography and eluted with ethyl acetate/petroleum ether to give 3-(6-(1,3,4-oxadiazol-2-yl)pyrazin-2-yl)phenol (240 mg) as an off white solid. MS (ES+APCI) m/z 241.1 (M+1).

Synthesis of 3-(6-(1,3,4-oxadiazol-2-yl)pyrazin-2-yl)phenyl octylcarbamate (Example-263)

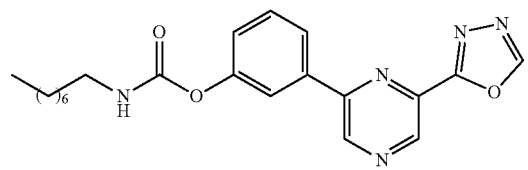

To a stirred solution of 3-(6-(1,3,4-oxadiazol-2-yl) pyrazin-2-yl)phenol (0.05 g, 0.21 mmol) in anhydrous acetonitrile (2 mL) was added TEA (0.04 mL, 0.27 mmol) and octyl isocyanate (0.04 g, 0.25 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (16 mg) as an off white solid. $^1$H NMR (400 MHz, DMSO-d6) δ 9.55 (d, J=8.00 Hz, 2H), 9.36 (s, 1H), 8.11 (d, J=7.60 Hz, 1H), 7.97 (d, J=1.60 Hz, 1H), 7.86 (t, J=5.60 Hz, 1H), 7.61 (t, J=8.00 Hz, 1H), 7.32 (dd, J=1.60, 8.00 Hz, 1H), 3.09 (q, J=6.80 Hz, 2H), 1.49 (t, J=6.80 Hz, 2H), 1.29-1.27 (m, 10H), 0.86 (t, J=6.80 Hz, 3H); MS (ES+APCI) m/z 396.5 (M+1).

Synthesis of 3-(6-(1,3,4-oxadiazol-2-yl)pyrazin-2-yl)phenyl (cyclohexylmethyl)carbamate

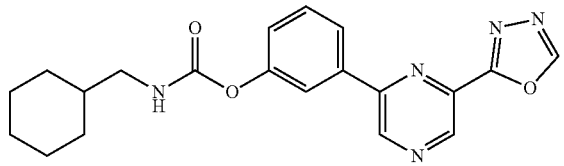 [SMILES: O=C(NCC1CCCCC1)Oc1cccc(-c2cncc(-c3nnco3)n2)c1]

To a stirred solution of 3-(6-(1,3,4-oxadiazol-2-yl)pyrazin-2-yl)phenol (0.1 g, 0.42 mmol) in anhydrous acetonitrile (2.5 mL) was added TEA (0.08 mL, 0.27 mmol) and cyclohexanemethyl isocyanate (0.09 g, 0.62 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (4.2 mg) as an off white solid. $^{1}$H NMR (400 MHz, DMSO-d6) δ 9.55 (d, J=8.00 Hz, 2H), 9.36 (s, 1H), 8.11 (d, J=8.00 Hz, 1H), 7.97 (t, J=1.60 Hz, 1H), 7.89 (t, J=6.00 Hz, 1H), 7.61 (t, J=8.00 Hz, 1H), 7.33-7.31 (m, 1H), 2.95 (t, J=6.40 Hz, 2H), 1.75-1.63 (m, 5H), 1.48-1.46 (m, 1H), 1.24-1.16 (m, 3H), 0.97-0.91 (m, 2H); MS (ES+APCI) m/z 380.3 (M+1).

Synthesis of 3-(6-(1,3,4-oxadiazol-2-yl)pyrazin-2-yl)phenyl benzylcarbamate (Example-265)

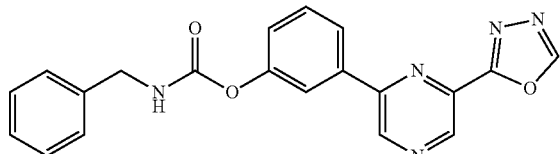

To a stirred solution of 3-(6-(1,3,4-oxadiazol-2-yl)pyrazin-2-yl)phenol (0.1 g, 0.42 mmol) in anhydrous acetonitrile (2.5 mL) was added TEA (0.08 mL, 0.54 mmol) and benzyl isocyanate (0.07 g, 0.50 mmol) at RT under nitrogen atmosphere. The reaction mixture was stirred at RTe for 10 minutes and then stirred at 75° C. for 12 h. After completion of the reaction (monitored by LCMS), the reaction mixture was concentrated to a residue. The residue was purified by preparative HPLC (0.1% FA) to yield the target compound (16 mg) as an off white solid. $^{1}$H NMR (400 MHz, DMSO-d6) δ 9.55 (d, J=8.00 Hz, 2H), 9.36 (s, 1H), 8.45 (t, J=6.00 Hz, 1H), 8.13 (d, J=8.00 Hz, 1H), 8.01 (t, J=2.00 Hz, 1H), 7.62 (t, J=8.00 Hz, 1H), 7.40-7.31 (m, 5H), 7.30-7.27 (m, 1H), 4.33 (d, J=6.40 Hz, 2H); MS (ES+APCI) m/z 374.3 (M+1).

Synthesis of 3-(6-(1,3,4-oxadiazol-2-yl)pyrazin-2-yl)phenyl cyclopentylcarbamate

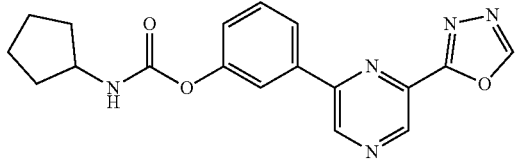 [SMILES: O=C(NC1CCCC1)Oc1cccc(-c2cncc(-c3nnco3)n2)c1]

To a stirred solution of 3-(6-(1,3,4-oxadiazol-2-yl)pyrazin-2-yl)phenol (0.05 g, 0.21 mmol) in anhydrous acetonitrile (2 mL) was added TEA (0.04 mL, 0.27 mmol) and cyclopentyl isocyanate (0.028 g, 0.25 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (10 mg) as an off white solid. $^{1}$H NMR (400 MHz, DMSO-d6) δ 9.55 (d, J=8.40 Hz, 2H), 9.36 (s, 1H), 8.11 (d, J=8.00 Hz, 1H), 7.98 (t, J=1.60 Hz, 1H), 7.91 (d, J=7.20 Hz, 1H), 7.61 (t, J=8.00 Hz, 1H), 7.34-7.32 (m, 1H), 3.88 (d, J=6.40 Hz, 1H), 1.90-1.86 (m, 2H), 1.69 (m, 2H), 1.55-1.53 (m, 4H); MS (ES+APCI) m/z 352.3 (M+1).

Synthesis of 3-(6-(1,3,4-oxadiazol-2-yl)pyrazin-2-yl)phenyl cyclohexylcarbamate (Example-267)

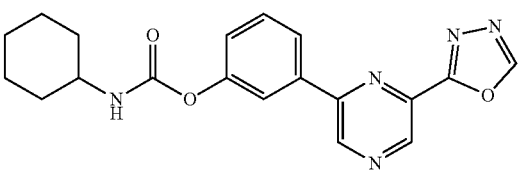 [SMILES: O=C(NC1CCCCC1)Oc1cccc(-c2cncc(-c3nnco3)n2)c1]

To a stirred solution of 3-(6-(1,3,4-oxadiazol-2-yl)pyrazin-2-yl)phenol (0.05 g, 0.21 mmol) in anhydrous acetonitrile (2 mL) was added TEA (0.04 mL, 0.27 mmol) and cyclohexyl isocyanate (0.03 g, 0.25 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (14 mg) as an off white solid. $^{1}$H NMR (400 MHz, DMSO-d6) δ 9.55 (d, J=8.80 Hz, 2H), 9.36 (s, 1H), 8.11 (d, J=8.00 Hz, 1H), 7.97 (t, J=2.00 Hz, 1H), 7.84 (d, J=8.00 Hz, 1H), 7.61 (t, J=8.00 Hz, 1H), 7.34-7.31 (m, 1H), 1.87-1.25 (m, 10H); MS (ES+APCI) m/z 366.3 (M+1).

Synthesis of 3-(6-(1,3,4-oxadiazol-2-yl)pyrazin-2-yl)phenyl cycloheptylcarbamate (Example-268)

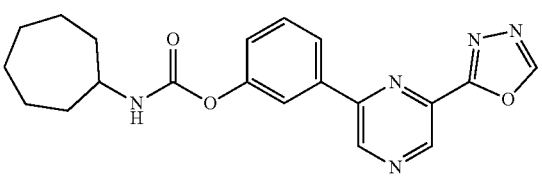 [SMILES: O=C(NC1CCCCCC1)Oc1cccc(-c2cncc(-c3nnco3)n2)c1]

To a stirred solution of 3-(6-(1,3,4-oxadiazol-2-yl)pyrazin-2-yl)phenol (0.1 g, 0.42 mmol) in anhydrous acetonitrile (2.5 mL) was added TEA (0.08 mL, 0.27 mmol) and cycloheptyl isocyanate (0.09 g, 0.62 mmol) at RT under nitrogen atmosphere. The reaction mixture was stirred at RT for 10 minutes and then stirred at 75° C. for 12 h. After completion of the reaction (monitored by LCMS), the reaction mixture was concentrated to a residue. The residue was purified by preparative HPLC (0.1% FA) to yield the target compound (3.4 mg) as an off white solid. $^1$H NMR (400 MHz, DMSO-d6) δ 9.55 (d, J=8.40 Hz, 2H), 9.36 (s, 1H), 8.11 (d, J=8.00 Hz, 1H), 7.97 (t, J=2.00 Hz, 1H), 7.87 (d, J=8.00 Hz, 1H), 7.61 (t, J=8.00 Hz, 1H), 7.33-7.31 (m, 1H), 3.88 (d, J=6.40 Hz, 1H), 1.89-1.87 (m, 2H), 1.66-1.61 (m, 2H), 1.58-1.50 (m, 6H), 1.49-1.40 (m, 2H); MS (ES+APCI) m/z 380.3 (M+1)

Example 269: In Vitro Inhibition on FAAH and MAGL Activity

The inhibitory effect of compounds of Formula (I-IV) on the activity of human recombinant FAAH was studied using a commercial inhibitor screening kit (Cayman Chemicals, Godlewski et al., 2010 [19]). In brief, FAAH hydrolyzes AMC arachidonoyl amide resulting in the release of the fluorescent product, while the inhibitor will inhibit the FAAH activity and thus reduce the fluorescent signal. The resulting fluorophore can be analyzed using an excitation wavelength of 340-360 nm and an emission wavelength of 450-465 nm by a plate reader (Synergy H1, Biotek). Inhibition is calculated as a percentage of the treated sample over the non-treated control based on the signal values, and where possible, a range of concentrations of compounds was tested to find the IC50 values (i.e. the concentration of compound that inhibited 50% FAAH activity).

The inhibitory effect of the compounds on activity of human recombinant MAGL was also studied using a commercial inhibitor screening kit (Cayman Chemicals). In brief, MAGL hydrolyzes 4-nitrophenylacetate resulting in a yellow product, 4-nitrophenol with an absorbance at 405-412 nm, while the inhibitor will inhibit the MAGL activity and thus reduce the yellow signal. The absorbance of the yellow product can be analyzed using the plate reader. Inhibition is calculated as a percentage of the treated sample over the non-treated MAGL control based on the signal values.

TABLE 1

In vitro inhibitory efficacy of compounds of Formula (I-IV) on human recombinant FAAH or MAGL

| Compound | Inhibition on FAAH activity (IC50, nM) | Inhibition on MAGL activity (IC50, nM) |
| --- | --- | --- |
| Example 1 | 10-100 | >10,000 |
| Example 2 | 10-100 | 1,000-10,000 |
| Example 3 | 10-100 | >10,000 |
| Example 4 | 1-10 | 1,000-10,000 |
| Example 5 | 10-100 | >10,000 |
| Example 6 | >100 | >100 |
| Example 7 | >1,000 | >10,000 |
| Example 8 | 10-100 | >10,000 |
| Example 9 | 1-10 | >10,000 |
| Example 10 | 1-10 | >1,000 |
| Example 11 | 10-100 | >10,000 |
| Example 12 | 10-100 | >10,000 |
| Example 13 | >1,000 | >10,000 |
| Example 14 | 10-100 | 10,000-50,000 |
| Example 15 | 10-100 | 10,000-50,000 |
| Example 16 | 10-100 | 1,000-10,000 |
| Example 17 | 10-100 | >10,000 |
| Example 18 | 10-100 | >10,000 |
| Example 19 | ~1,000 | >10,000 |
| Example 20 | 100-1,000 | >10,000 |
| Example 21 | >1,000 | >10,000 |
| Example 22 | 10-1,000 | >1,000 |
| Example 23 | >1,000 | >10,000 |
| Example 24 | <10 | >10,000 |
| Example 25 | >1,000 | >10,000 |
| Example 26 | 10-100 | >10,000 |
| Example 27 | 10-100 | >10,000 |
| Example 28 | 100-1,000 | >10,000 |
| Example 29 | ~100 | >10,000 |
| Example 30 | 10-100 | >10,000 |
| Example 31 | 10-100 | >1,000 |
| Example 32 | 10-100 | >10,000 |
| Example 33 | 100-1,000 | >10,000 |
| Example 34 | 100-1,000 | >10,000 |
| Example 35 | 10-100 | >10,000 |
| Example 36 | 100-1,000 | ~10,000 |
| Example 37 | ~1,000 | >10,000 |
| Example 38 | 100-1,000 | >10,000 |
| Example 39 | 100-1,000 | >10,000 |
| Example 40 | 10-100 | ~10,000 |
| Example 41 | 10-100 | >10,000 |
| Example 42 | 100-1,000 | ~10,000 |
| Example 43 | >1,000 | >10,000 |
| Example 44 | >1,000 | >10,000 |
| Example 45 | >1,000 | >10,000 |
| Example 46 | 100-1,000 | >10,000 |
| Example 47 | 1-10 | ~10,000 |
| Example 48 | 10-100 | ~10,000 |
| Example 49 | 100-1,000 | >10,000 |
| Example 50 | 10-100 | ~10,000 |
| Example 51 | 76.1 | >10,000 |
| Example 52 | 10-100 | ~10,000 |
| Example 53 | 10-100 | ~10,000 |
| Example 54 | 100-1,000 | ~10,000 |
| Example 55 | ~1,000 | ~10,000 |
| Example 56 | 100-1,000 | >10,000 |
| Example 57 | 100-1,000 | >10,000 |
| Example 58 | 100-1,000 | >10,000 |
| Example 59 | 10-100 | >10,000 |
| Example 60 | 10-100 | >10,000 |
| Example 61 | ~100 | >10,000 |
| Example 62 | 10-100 | ~10,000 |
| Example 63 | 10-100 | >10,000 |
| Example 64 | 39.1 | >10,000 |
| Example 65 | 10-100 | ~10,000 |
| Example 66 | 100-1,000 | ~10,000 |
| Example 67 | >1,000 | >10,000 |
| Example 68 | 100-1,000 | ~10,000 |
| Example 69 | 100-1,000 | >10,000 |
| Example 70 | 100-1,000 | >10,000 |
| Example 71 | 10-1,000 | >10,000 |
| Example 72 | 1-10 | >1,000 |
| Example 73 | 1-10 | >10,000 |
| Example 74 | 10-100 | >1,000 |
| Example 75 | 10-1,000 | >10,000 |
| Example 76 | 10-1,000 | 1,000-10,000 |
| Example 77 | >1,000 | >10,000 |
| Example 78 | 10-100 | 1,000-10,000 |
| Example 80 | 10-100 | >10,000 |
| Example 81 | 10-100 | >10,000 |
| Example 82 | 100-1,000 | >10,000 |
| Example 83 | 10-100 | >10,000 |
| Example 84 | 100-1,000 | ~10,000 |
| Example 85 | 10-100 | >10,000 |
| Example 86 | 10-100 | >10,000 |

TABLE 1-continued

In vitro inhibitory efficacy of compounds of Formula (I-IV) on human recombinant FAAH or MAGL

| | Inhibition on FAAH activity (IC50, nM) | Inhibition on MAGL activity (IC50, nM) |
|---|---|---|
| Example 87 | 23.9 | >10,000 |
| Example 88 | 10-100 | ~10,000 |
| Example 89 | 100-1,000 | >10,000 |
| Example 90 | 100-1,000 | >1,000 |
| Example 91 | 100-1,000 | >10,000 |
| Example 92 | 100-1,000 | >10,000 |
| Example 93 | >1,000 | 1,000-10,000 |
| Example 94 | >1,000 | >1,000 |
| Example 95 | >1,000 | >1,000 |
| Example 96 | >1,000 | >10,000 |
| Example 97 | >1,000 | >1,000 |
| Example 98 | >1,000 | ~1,000 |
| Example 99 | 100-1,000 | ~10,000 |
| Example 100 | >1,000 | >10,000 |
| Example 101 | >1,000 | >10,000 |
| Example 102 | >1,000 | >10,000 |
| Example 103 | 100-1,000 | ~10,000 |
| Example 104 | 100-1,000 | ~10,000 |
| Example 105 | 1-10 | >10,000 |
| Example 106 | 10-100 | >10,000 |
| Example 107 | 10-100 | >10,000 |
| Example 108 | 10-100 | >1,000 |
| Example 109 | 1-10 | ~10,000 |
| Example 110 | 10-100 | ~10,000 |
| Example 111 | 100-1,000 | >10,000 |
| Example 112 | ~100 | >10,000 |
| Example 113 | ~100 | >10,000 |
| Example 115 | 1-10 | ~10,000 |
| Example 116 | 10-100 | ~10,000 |
| Example 117 | 100-1,000 | >10,000 |
| Example 118 | ~100 | >10,000 |
| Example 119 | 10-100 | >10,000 |
| Example 120 | 10-100 | ~10,000 |
| Example 121 | 10-100 | ~10,000 |
| Example 122 | 100-1,000 | ~10,000 |
| Example 123 | ~1,000 | >10,000 |
| Example 124 | 100-1,000 | >10,000 |
| Example 125 | 100-1,000 | >10,000 |
| Example 126 | 100-1,000 | >10,000 |
| Example 127 | 10-100 | >50,000 |
| Example 128 | 10-20 | >50,000 |
| Example 129 | 1-10 | >10,000 |
| Example 130 | 1-10 | >10,000 |
| Example 131 | 10-20 | <10,000 |
| Example 132 | <20 | <10,000 |
| Example 134 | 10-20 | >10,000 |
| Example 135 | >100 | >50,000 |
| Example 136 | 10-100 | 10,000-50,000 |
| Example 137 | 10-20 | >10,000 |
| Example 138 | 10-100 | >50,000 |
| Example 139 | 10-100 | >50,000 |
| Example 140 | >100 | >50,000 |
| Example 141 | ~1,000 | >10,000 |
| Example 142 | 1,000-10,000 | >10,000 |
| Example 143 | ~10,000 | >10,000 |
| Example 144 | >1,000 | >10,000 |
| Example 145 | >1,000 | >10,000 |
| Example 146 | 400.7 | >10,000 |
| Example 147 | 10-100 | >10,000 |
| Example 148 | >1,000 | >10,000 |
| Example 149 | 10-100 | 1,000-10,000 |
| Example 150 | >1,000 | >10,000 |
| Example 151 | 1,000-10,000 | >10,000 |
| Example 152 | >1,000 | >10,000 |
| Example 153 | 1,000-10,000 | >10,000 |
| Example 154 | 100-1,000 | ~10,000 |
| Example 155 | >1,000 | ~10,000 |
| Example 156 | 1-10 | >20,000 |
| Example 157 | 1-10 | >10,000 |
| Example 158 | 123.6 | >50,000 |
| Example 159 | 10-100 | >10,000 |
| Example 160 | 1-10 | 1,000-10,000 |
| Example 161 | 10-100 | 10,000-50,000 |
| Example 162 | ~100 | >10,000 |
| Example 163 | 10-100 | >50,000 |
| Example 164 | 10-100 | >50,000 |
| Example 165 | 25.8 | >10,000 |
| Example 166 | 10-100 | >10,000 |
| Example 167 | 1-10 | >10,000 |
| Example 168 | 100-1,000 | >10,000 |
| Example 169 | 10-100 | >10,000 |
| Example 170 | 100-1,000 | ~10,000 |
| Example 171 | 100-1,000 | >10,000 |
| Example 172 | 112.4 | >10,000 |
| Example 173 | 110.5 | >10,000 |
| Example 174 | 1-10 | ~10,000 |
| Example 175 | ~100 | >10,000 |
| Example 176 | >1,000 | >10,000 |
| Example 177 | 100-1,000 | >10,000 |
| Example 178 | ~100 | >10,000 |
| Example 179 | 91.06 | 10,000-50,000 |
| Example 180 | 10-100 | >10,000 |
| Example 181 | ~1,000 | >10,000 |
| Example 182 | >1,000 | >10,000 |
| Example 183 | >1,000 | >10,000 |
| Example 184 | >1,000 | >10,000 |
| Example 185 | 100-1,000 | >10,000 |
| Example 186 | 10-100 | ~10,000 |
| Example 187 | 100-1,000 | >10,000 |
| Example 188 | >1,000 | >10,000 |
| Example 189 | 100-1,000 | >10,000 |
| Example 190 | 100-1,000 | >10,000 |
| Example 191 | 153.3 | >10,000 |
| Example 192 | 10-100 | >10,000 |
| Example 193 | 10-100 | >10,000 |
| Example 194 | 49.1 | >10,000 |
| Example 195 | 1-10 | ~1,000 |
| Example 196 | >1,000 | ~10,000 |
| Example 197 | 100-1,000 | >10,000 |
| Example 198 | 132.0 | >10,000 |
| Example 199 | 10-100 | 1,000-10,000 |
| Example 200 | 100-1,000 | >10,000 |
| Example 201 | 100-1,000 | >1,000 |
| Example 202 | 100-1,000 | >10,000 |
| Example 203 | >1,000 | >10,000 |
| Example 204 | 10-100 | >10,000 |
| Example 205 | 10-100 | >10,000 |
| Example 206 | 10-100 | >10,000 |
| Example 207 | 1-10 | ~10,000 |
| Example 208 | 10-100 | >10,000 |
| Example 209 | ~100 | >10,000 |
| Example 210 | ~100 | >10,000 |
| Example 211 | >1,000 | >10,000 |
| Example 212 | 10-100 | >10,000 |
| Example 213 | 1-10 | ~10,000 |
| Example 214 | 10-100 | >10,000 |
| Example 215 | 100-1,000 | >10,000 |
| Example 216 | 100-1,000 | >10,000 |
| Example 217 | 100-1,000 | >10,000 |
| Example 218 | 10-100 | >10,000 |
| Example 219 | 1-10 | ~10,000 |
| Example 220 | 10-100 | ~10,000 |
| Example 221 | 100-1,000 | >10,000 |
| Example 222 | 10-100 | ~10,000 |
| Example 223 | 100-1,000 | >10,000 |
| Example 224 | 100-1,000 | >10,000 |
| Example 225 | 176.5 | ~10,000 |
| Example 226 | 1-10 | >10,000 |
| Example 227 | 100-1,000 | >10,000 |
| Example 228 | 100-1,000 | >10,000 |
| Example 229 | 10-100 | >10,000 |
| Example 230 | 100-1,000 | >10,000 |
| Example 231 | 137.1 | >10,000 |
| Example 232 | 10-100 | ~10,000 |
| Example 233 | 100-1,000 | ~10,000 |
| Example 234 | >1,000 | >10,000 |

TABLE 1-continued

In vitro inhibitory efficacy of compounds of Formula
(I-IV) on human recombinant FAAH or MAGL

|  | Inhibition on FAAH activity (IC50, nM) | Inhibition on MAGL activity (IC50, nM) |
|---|---|---|
| Example 235 | 100-1,000 | >10,000 |
| Example 236 | 100-1,000 | >10,000 |
| Example 237 | 100-1,000 | >10,000 |
| Example 238 | 10-100 | ~10,000 |
| Example 239 | >1,000 | >10,000 |
| Example 240 | >1,000 | >10,000 |
| Example 241 | >1,000 | >10,000 |
| Example 242 | >1,000 | >10,000 |
| Example 243 | >1,000 | >10,000 |
| Example 244 | 100-1,000 | >10,000 |
| Example 245 | >1,000 | >10,000 |
| Example 246 | >1,000 | >10,000 |
| Example 247 | >1,000 | >10,000 |
| Example 248 | >1,000 | >10,000 |
| Example 249 | >1,000 | >10,000 |
| Example 250 | 100-1,000 | ~10,000 |
| Example 251 | >1,000 | >10,000 |
| Example 252 | >1,000 | >10,000 |
| Example 253 | >1,000 | >10,000 |
| Example 254 | >1,000 | >10,000 |
| Example 255 | >1,000 | >10,000 |
| Example 256 | 1-10 | >1,000 |
| Example 257 | 10-100 | >10,000 |
| Example 258 | 100-1,000 | >10,000 |
| Example 259 | 100-1,000 | >10,000 |
| Example 260 | 100-1,000 | >10,000 |
| Example 261 | 100-1,000 | >1,000 |
| Example 262 | 10-100 | >1,000 |
| Example 263 | 1-10 | 1,000-10,000 |
| Example 264 | 10-100 | ~10,000 |
| Example 265 | 100-1,000 | >10,000 |
| Example 266 | 10-100 | 1,000-10,000 |
| Example 267 | 140.3 | >10,000 |
| Example 268 | 10-100 | 1,000-10,000 |
| Reference compounds | | |
| URB597 | 87.7 | >50,000 |
| JNJ-42165279 | 105.6 | >50,000 |

*Compound of Example 79 was not tested, because of low yield.

The FAAH inhibitory activity (nM) of compounds of Formula (I-IV) is listed in Table 1. Known FAAH inhibitors (URB597 and JNJ-42165279) were used as reference compounds. Among the compounds tested, several inhibitors have IC50 values below 10 nM under test conditions and more active than the known reference FAAH inhibitors.

Specificity is also important to avoid cross-reactivity which may be associated with unwanted side effects. Most commonly, MAGL enzyme is considered to be a main cross-reactive inhibitory target with its close association or overlapping functional features with FAAH enzyme. Most active inhibitors described above require >10 μM to significantly inhibit MAGL enzyme, with a selectivity index of >1,000 times over MAGL, indicating high selectivity of test compounds for FAAH. The fold-selectivity over MAGL for the reference compounds, URB597 and JNJ-42165279, is 570 and 473 times, respectively.

Example 270. Solubility

Compounds as described herewith were analyzed for their aqueous solubility.

The aqueous solubility of compounds were determined using standard protocols. To illustrate the experimental protocol, the analysis of a representative compound is described. Exemplary compound of Example 158 (MW: 380.4 g/mol) was analyzed in a buffer system at specified pH (phosphate buffer, pH 7.4). This was accomplished by spiking a DMSO stock solution of the test compound at a final concentration of 100 μM in buffer.

TABLE 2

| | |
|---|---|
| Assay Matrix | PBS buffer (pH = 7.4) |
| Main Stock Conc. | |
| Testing Conc. | |
| Final % DMSO | |
| Replicates | 2 |
| Incubation Parameters | Room Temperature |
| Time Points | 0, 15, 30, 60, 120 min |
| Assay Control (IS) | |
| Assay Reference (QC) | |
| Analysis Method | MRM by LC-MS/MS with standard curve |
| Results | |

Calibration Standards

The calibration curve was obtained as follows:
1. Main Stock Solution 760 μg/mL
   Accurately weigh 0.760 mg of KV-202-24 into an amber 2 mL vial. Using 1000 μL pipette, add 1.0 mL DMSO and mix well to dissolve.
2. Working Standard Solution 7.6 μg/LL (WSTD)
   To a 4 mL amber vial, add 1980 μL of acetonitrile and 20 μL of main stock solution and mix well. This is 100× dilution.
3. Calibration Standard Prep

TABLE 3

Calibration curve preparations:

| | Final Conc. (μg/mL) | Final Conc. (μM) | Volume of stock 7.6 μg/mL (μL) | Volume of diluent (μL) | Total (μL) |
|---|---|---|---|---|---|
| Cal 1 | 0.038 | 0.1 | 20 | 3980 | 4000 |
| Cal 2 | 0.076 | 0.2 | 40 | 3960 | 4000 |
| Cal 3 | 0.19 | 0.5 | 100 | 3900 | 4000 |
| Cal 4 | 0.38 | 1 | 100 | 1900 | 2000 |
| Cal 5 | 1.9 | 5 | 500 | 1500 | 2000 |
| Cal 6 | 3.8 | 10 | 1000 | 1000 | 2000 |

Sample Preparation

The sample was prepared according to the protocol depicted in FIG. 1.

Solubility calculation: This is a quantitative assay. The mixture at the end of the assay is filtered by 0.22 micron syringe filter and after 5× dilution in diluent, it was analyzed versus a calibration curve using LC-MS.

The results of the solubility analysis are summarized in Table 5 provided below.

As can be seen from Table 5, compounds, possessing a basic amine charge site, such as a pyridine ring, exhibit greater aqueous solubility than URB-597, a molecule lacking a basic nitrogen center.

Example 271. Plasma Stability

Exemplary compounds described herewith were assayed for plasma stability (various species).

TABLE 4

Summary of assay conditions

| | |
|---|---|
| Assay Matrix | Plasma whole (rat, human, etc.) |
| Main Stock Conc. | 5 mM in DMSO |
| Testing Conc. | 1 μM |

TABLE 4-continued

Summary of assay conditions

| | | |
|---|---|---|
| Final DMSO % | 0.1% (plus 0.5% acetonitrile) | |
| Replicates | n = 2 | |
| Assay Control (IS) | Telmisartan or Tolbutamide | 250 ng/ml in cold ACN |
| Assay Reference (QC) | Propantheline bromide | 1 μM |
| Incubation parameter | 0-240 mins @ 37° C. | |
| Incubation Time | 0, 15, 30, 60, 120 and 240 mins | |
| Shaking speed (rpm) | 300-500 | |
| Test compound/Incubation concentration | 1 μM (test article, e.g., KV-202-119 & Diclofenac at test trial) | |
| Analysis | Semi-Quantitative by LC-MS/MS | |
| Results | % Parent compound remaining (% PCR), Half-life (min) | |

Operational Components

Materials

Timer: for alarming at each sampling time point.
Plasma & sample tubes: thaw at RT or 37° C.; 1.5 ml tubes: ×2/drug+2 for blank.
Extracting tubes: 1.5 ml tubes, ×2×(1+No. of drugs)/time point, labelled.
Tube of ACN (acetonitrile) only: >2 ml (for 100 μM working stocks).
DMSO/dH2O: ~100/500 μL (for 100 μM working stocks).
Ice box: at the beginning
Incubator oven: 37° C., turned on.
Thermomixer: warm up to 37° C.
Centrifuge 1: Program set up & T° C. ready: 14,000 rpm, 5 min, 4° C., for extracting tubes.
Centrifuge 2: 4,000 rpm, 10 min, RT for plasma clearance.
Drug stocks: 10 mM in DMSO, >5 μL, each, thaw at RT.
Internal standard in ACN: >10 ml (300 μL/extracting tubes). Refer to Appendix 1.
Solvent mixture for 100 μM stock: refer to Appendix 2.

Methods

1. Plasma Preparation:
Determine the volume of plasma needed: 300 L/tube)+T0 plasma tube (refer to below)+>0.2 ml extra, before thawing and centrifugation.
Plasma was removed from deep freezer and allowed to thaw at room temperature (or at 37° C. if needed). Plasma was then centrifuged at 4,000 rpm at RT for 10 min and supernatant was collected and used for the assay:
  Drug test tubes: 297 μL plasma/drug test tube, duplicate/drug.
  Blank test tubes: 297 μL plasma/Blank test tube, duplicate, too. (Optional, if assay system is stable and consistent)
  T0 plasma tube: 50 μM×No. of total sample tubes+50 μL extra for T0 extraction.
    (Note: equivalent proportion of solvent mixture as added in drug test tubes will be added before T0 extraction!)
Pre-warm the above tubes at 37° C. incubator for 10-15 min before spiked with test drugs.
2. Preparation of Working Stock (100 μM)
3. Preparation of Extracting Tubes:
T0 blank extracting tubes: 300 L/tube of regular Internal standard in ACN.
T0 drug extracting tubes:
For drug 1: first, add 0.9 ml Internal standard in ACN to a 1.5 ml tube, remove 1.5 μL, then add 1.5 μL of 100 μM stock solution of the drug 1. Mix and aliquot to 300 μL/tube X2 for drug 1.
For drug 2: Repeat the same procedures for drug 2 or more.
T15-240 extracting tubes: 300 L/tube of regular Internal standard in CAN.
Place extracting tubes on ice.
4. Assay Procedures:
Preparation of Test Sample Tubes:
Take out the pre-warmed plasma tubes from the 37° C. incubator. Add 3 μL of 100 μM stock solution (or, equivalent proportion of the solvent mixture to T0 plasma tube for T0 extraction) to each corresponding sample tubes in order, vortex gently (3×) to mix. Finish the sample tubes orderly and quickly, then transfer them to the Thermomixer (program & 37° C. ready), and start the Thermomixer. Record starting time on paper & start the timer for 15 min for the $1^{st}$ sampling time point.
Preparation of Drug Extracting Samples
Now add the equivalent amount of solvent mixture to the T0 plasma tube, mix, and transfer 50 μL plasma to each of the T0 extracting tubes, vortex 20 s and placed on ice. Vortex 10 s again before centrifuging the samples at 14,000 rpm for 5 min at 4° C.
After centrifugation, the samples (kept on ice) are ready for LC-MS analysis, or the supernatant (portion) be transferred to a new set of tubes and stored at −20° C. before sample analysis.
Repeat the above procedures at each time point (15, 30, 60, 120, 240 min) by transferring 50 μL plasma samples from the testing tubes to the corresponding extracting tubes, in the same order and time scheme as in the addition of the drug to the plasma samples at the beginning of the study.
5 LC/MS analysis
6. Calculations:

Kel=Slope of LN % PCR vs time $$\text{Half life } (t\frac{1}{2}) = 0.693/\text{Kel} \quad (1)$$

$$\text{\% Parent compound remaining (\% PCR)} \quad (2)$$

Notes

Abbreviation

ACN: acetonitrile
DMSO: dimethyl sulfoxide
IS: Internal standard
LC-MS: Liquid chromatography-mass spectrometry
LN: natural log
MRM: Multiple reaction monitoring
% PCR: % Parent compound remaining

APPENDIX 1: PREPARATION OF INTERNAL STANDARD IN ACN

Prepare 40 mg/mL stock solution of Tolbutamide and 10 mg/mL Telmisartan in DMSO. Add 6.25 μL of 40 mg/mL of Tolbutamide and 25 μL of 10 mg/mL stock solution of Telmisartan to 1 L of Acetonitrile for preparing 250 ng/mL/250 ng/mL Tolbutamide/Telmisartan as an internal standard.

APPENDIX 2: PREPARATION OF INTERMEDIATE STOCK SOLUTION (100 µM)

Diluting 2 µL of 10 mM master stock with 198 µL of solvent mixture as below for 100 µM stock:

Each 1.5 ml tube:ACN:dH2O:DMSO=100:80:18 (L)

Solvent final concentration in the 100 µM stock solution: ACN: 50%; dH2 O: 40%; DMSO: 10%

Certain compounds of this invention were found to have greater plasma stability than URB-597, a molecule lacking a basic nitrogen center (see Table 5).

TABLE 5

Results of Solubility Analysis (see Example 270 "Solubility") and Plasma Stability Analysis (see Example 271 "Plasma stability")

| Compound | $IC_{50}$ (nM) | Human Plasma Stability ($t_{1/2}$, min) | Solubility (µM) |
|---|---|---|---|
| Example 87 | 23.9 | 7 | 8.6 |
| Example 83 | 111 | 194 | 16.3 |
| Example 91 | 492 | 14 | 2.4 |
| Example 158 | 127 | 350 | 92.5 |
| Example 172 | 112 | 361 | 16.2 |
| Example 179 | 91.1 | 18 | 9.2 |
| Example 194 | 49.1 | 41 | — |
| Example 198 | 132 | — | 5.7 |
| Example 191 | 153 | 31 | 11.9 |
| Example 225 | 176 | 47 | 8.6 |
| Example 231 | 137 | 634 | 78.8 |
| Example 165 | 25.8 | 28 | 22.6 |
| Example 146 | 401 | 186 | 82.7 |
| Example 267 | 140 | 12 | 73.6 |
| Example 51 | 76.1 | 8 | 1.4 |
| Example 64 | 39.1 | 24 | — |
| Example 173 | 110 | N/A | N/A |
| URB-597 (Reference) | 87.7 | 47 | 2.8 |

Note:
Plasma stability of Example 198 is 4.7 min

Example 272: Oral Bioavailability

In pharmacokinetic (PK) studies, animals were administered compounds of the present disclosure and PK parameters were measured. Rats (male, Sprague Dawley) were administered compound of Example 158 at a dose of 1.0 mg/kg intravenously (IV) or 10 mg/kg via oral gavage (PO). Blood samples were taken at t=0.083, 0.25. 0.5, 1, 2, 4, 6, 8 and 24 h post-dose and the plasma was analyzed for concentration of test article (compound of Example 158). Using standard analytical methodology (HPLC analysis), the following parameters were obtained:

| Cmpd | Species | IV Dose (mg/kg) | $C_o$ (ng/mL) [uM] | $AUC_{0-Y}$ (ng h/mL) | CLp (mL/min/kg) | Vdss (L/kg) |
|---|---|---|---|---|---|---|
| Example 158 | Rat (SD, male) | 1.0 | 4829 [12.7 uM] | 1342 | 12 (~20% HBF) | 0.62 |

| Cmpd | $t_{1/2}$ (h) | Brain/ Plasma (0.5, 1 h) | PO Dose (mg/kg) | Cmax (ng/mL) [uM] | Tmax (h) | $AUC_{0-Y}$ (ng h/mL) | $t_{1/2}$ (h) | F (%) |
|---|---|---|---|---|---|---|---|---|
| Example 158 | 0.31 | 0.01 0.02 | 10.0 | 1919 [5.05 uM] | 0.50 | 7054 | 2.85 | 53 |

Compound of Example 158 exhibits the following PK properties:
Good oral bioavailability (53% F);
High plasma exposures upon oral dosing ($C_{max}$=1919 ng/mL=5.05 µM; $AUC_{0 \to inf}$=7054 ng·h/mL))
Low hepatic clearance (CLp=12 mL/min/kg~ 20% hepatic blood flow (HBF) in rat;
Low volume of distribution (0.62 L/kg);
Long oral half-life ($T_{1/2}$=2.85 h).
Brain/Plasma ratio=0.01 (0.5 h), 0.02 (1 h) (low brain penetration).

Example 273. Oral Bioavailability and Brain Penetration

Rats were administered compound of Example 172 at a dose of 1.0 mg/kg intravenously (IV) or 10 mg/kg via oral gavage (PO). Using standard analytical methodology (HPLC analysis), the following parameters were obtained:

| Cmpd | Species | IV Dose (mg/kg) | $C_o$ (ng/mL) [uM] | $AUC_{0-Y}$ (ng h/mL) | CLp (mL/min/kg) | Vdss (L/kg) |
|---|---|---|---|---|---|---|
| Example 172 | Rat (SD, make) | 1.0 | 1528 [4.02 uM] | 424 | 40 (~70% HBF) | 1.58 |

| Cmpd | $t_{1/2}$ (h) | Brain/ Plasma (0.5, 1 h) | PO Dose (mg/kg) | Cmax (ng/mL) [uM] | Tmax (h) | $AUC_{0-Y}$ (ng h/mL) | $t_{1/2}$ (h) | F (%) |
|---|---|---|---|---|---|---|---|---|
| Example 172 | 0.80 | 0.15 0.19 | 10.0 | 2246 [5.91 uM] | 0.50 | 5257 | 1.25 | >100 |

Compound of Example 172 exhibits the following PK properties:
Very high oral bioavailability (>100% F);
High plasma exposures upon oral dosing ($C_{max}$=2246 ng/mL=5.91 μM; $AUC_{0 \to inf}$=5257 ng·h/mL)
Moderate hepatic clearance (CLp=40 mL/min/kg~ 70% hepatic blood flow (HBF) in rat;
Moderate volume of distribution (1.58 L/kg);
Good brain penetration (Brain/Plasma ratio=0.15 (0.5 h), 0.19 (1 h).
By comparison, URB597, lacking a basic pyridine center, exhibits low exposures upon oral dosing with a reported approximate $C_{max}$~200 ng/mL obtained at a dose of 250 mg/kg. Other doses confirm low in vivo exposure—see FIG. 8 in *Pharmacological profile of FAAH Inhibitor URB597 (KDS-4103)*—CNS Drug Reviews 2006 12 (1) 21 (D Piomelli)
This dose is 25× (twenty-five times greater) than the dose of compounds of Examples 158 and 172, which achieved an approximate 10× (ten-fold greater) $C_{max}$ exposure thus translating to a~250× (two hundred and fifty-fold) improvement in oral exposure maximums compared to URB597.

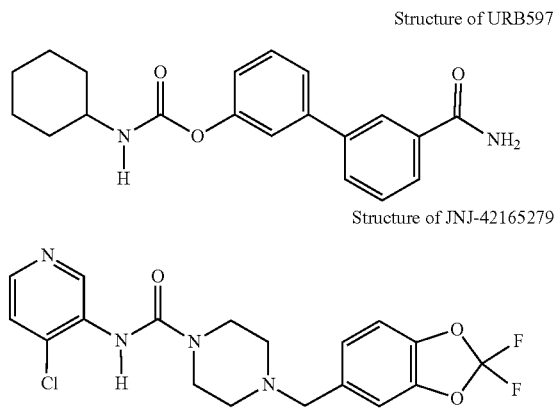

Structure of URB597

Structure of JNJ-42165279

As shown in Table 1, compounds having formula I, II, III or IV inhibited FAAH activity, while also showing limited cross reactivity with MAGL. Without wishing to be bound by theory, compound wherein $R_1$ is cyclyic (for example wherein $R_1$ is heteroaryl) exhibited higher selectivity towards FAAH than MAGL. Conversely, compound wherein $R_1$ is noncyclic (for example wherein $R_1$ is —C(O)OR$_4$, —C(O)NHOH, —C(O)NHNH$_2$, CF$_3$, CHO, CN) showed lower selectivity towards FAAH than MAGL. It was further found that compounds wherein $R_2$ is an electron donating group (for example OH, OCH$_3$, SCH$_3$, or N(CH$_3$)$_2$) exhibited improved plasma stability compared to compounds wherein $R_2$ is a electron withdrawing group (for example F or OCF$_3$). In some examples, it was shown that when $R_3$ is $C_5$-$C_{20}$ alkyl chain the compound had high potency, but less metabolic stability, compared to some of the other groups that where tested.

All citations are hereby incorporated by references.

The present invention has been described with regard to one or more embodiments. However, it will be apparent to persons skilled in the art that a number of variations and modifications can be made without departing from the scope of the invention as defined in the claims. The scope of the claims should not be limited by the embodiments set forth in the examples but should be given the broadest interpretation consistent with the description as a whole.

REFERENCES

1. Fowler, C. J., K.-O. Jonsson, and G. Tiger. Fatty acid amide hydrolase: biochemistry, pharmacology, and therapeutic possibilities for an enzyme hydrolyzing anandamide, 2-arachidonoylglycerol, palmitoylethanolamide, and oleamide. Biochemical Pharmacology, 2001, 62(5): 517-526.
2. Labar, G. and C. Michaux. Fatty Acid Amide Hydrolase: From Characterization to Therapeutics. Chemistry & Biodiversity, 2007, 4(8): 1882-1902.
3. Bisogno, T., L. Petrocellis, and V. Marzo, Fatty Acid Amide Hydrolase, an Enzyme with Many Bioactive Substrates. Possible Therapeutic Implications. Current Pharmaceutical Design, 2002, 8(7): 533-547.
4. Ahn, K., Johnson, D. S., Mileni, M., Beidler, D., Long, J. Z., McKinney, M. K., Weerapana, E., Sadagopan, N., Liimatta, M., Smith, S. E., Lazerwith, S., Stiff, C., Kamtekar, S., Bhattacharya, K., Zhang, Y., Swaney, S., Van Becelaere, K., Stevens, R. C., & Cravatt, B. F. Discovery and Characterization of a Highly Selective FAAH Inhibitor that Reduces Inflammatory Pain. Chemistry & Biology. 2009, 16(4): 411-420.
5. Fernández-Ruiz, J., M. A. Moro, and J. Martinez-Orgado. Cannabinoids in Neurodegenerative Disorders and Stroke/Brain Trauma: From Preclinical Models to Clinical Applications. Neurotherapeutics, 2015, 12(4): 793-806.
6. Schmidt W., Schafer F., Striggow V., Frohlich K., Striggow F. Cannabinoid receptor subtypes 1 and 2 mediate long-lasting neuroprotection and improve motor behavior deficits after transient focal cerebral ischemia. Neuroscience, 2012, 227: 313-26.
7. Fazio D, Criscuolo E, Piccoli A, Barboni B, Fezza F, Maccarrone M. Advances in the discovery of fatty acid amide hydrolase inhibitors: what does the future hold? Expert Opin Drug Discov. 2020, 15(7):765-778.

8. Jayamanne A, Greenwood R, Mitchell V A, Aslan S, Piomelli D, Vaughan C W. Actions of the FAAH inhibitor URB597 in neuropathic and inflammatory chronic pain models. Br J Pharmacol. 2006, 147(3):281-8.

9. Ahn K, Johnson D S, Cravatt B F. Fatty acid amide hydrolase as a potential therapeutic target for the treatment of pain and CNS disorders. Expert Opin Drug Discov. 2009, 4(7):763-784.

10. Paulus M P, Stein M B, Simmons A N, Risbrough V B, Halter R, Chaplan S R. The effects of FAAH inhibition on the neural basis of anxiety-related processing in healthy male subjects: A randomized clinical trial. Neuropsychopharmacology. 2021, 46:1011-1019.

11. Lodola A, Castelli R, Mor M, Rivara S. Fatty acid amide hydrolase inhibitors: a patent review (2009-2014). Expert Opin Ther Pat. 2015, 25(11):1247-1266.

12. McDougall J J, Muley M M, Philpott H T, Reid A, Krustev E. Early blockade of joint inflammation with a fatty acid amide hydrolase inhibitor decreases end-stage osteoarthritis pain and peripheral neuropathy in mice. Arthritis Res Ther. 2017, 19(1):106.

13. Schmidt M E, Liebowitz M R, Stein M B, Grunfeld J, Van Hove I, Simmons W K, Van Der Ark P, Palmer J A, Saad Z S, Pemberton D J, Van Nueten L, Drevets W C. The effects of inhibition of fatty acid amide hydrolase (FAAH) by JNJ-42165279 in social anxiety disorder: a double-blind, randomized, placebo-controlled proof-of-concept study. Neuropsychopharmacology. 2021, 46(5): 1004-1010.

14. Saghatelian A, McKinney M K, Bandell M, Patapoutian A, Cravatt B F. A FAAH-Regulated Class of N-Acyl Taurines That Activates TRP Ion Channels. Biochemistry, 2006, 45(30): 9007-9015.

15. Dale L B, Robert A F, Jean E P, Hiroshi M., Matthew P P, and Benjamin F C. Fatty Acid Amide Hydrolase Substrate Specificity. Bioorganic & Medicinal Chemistry Letters, 2000, 10: 2613-2616.

16. Michele K M and Benjamin F C. Structure and function of fatty acid amide hydrolase. Annu. Rev. Biochem. 2005, 74: 411-432.

17. Handbook of Pharmaceutical Salts: Properties Selection and Use Edited by P. H. Stahl and C. G. Wermuth. Verlag Helvetica Chimica Acta/Wiley-VCH: Zurich. ISBN 3-906-390-26-8. Organic Process Research & Development. 2003, 7 (2), 222-223.

18. Remington, J. P. and A. R. Gennaro, Remington's pharmaceutical sciences. 1990, Easton, Pa.: Mack Pub. Co.

19. Godlewski G, Alapafuja S O, Bitkai S, Nikas S P, Cinar R, Offertiler L, Osei-Hyiaman D, Liu J, Mukhopadhyay B, Harvey-White J, Tam J, Pacak K, Blankman J L, Cravatt B F, Makriyannis A, Kunos G. Inhibitor of fatty acid amide hydrolase normalizes cardiovascular function in hypertension without adverse metabolic effects. Chem Biol. 2010, 17(11): 1256-1266.

20. O'Brien J, Wilson I, Orton T, Pognan F. Investigation of the Alamar Blue (resazurin) fluorescent dye for the assessment of mammalian cell cytotoxicity. Eur J Biochem. 2000, 267(17): 5421-5426.

The invention claimed is:

1. A compound of Formula I:

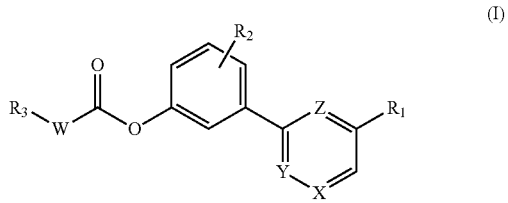

a prodrug thereof, a pharmaceutically acceptable salt thereof, or a pharmaceutically active metabolite thereof; wherein W is NH, N(CH$_3$), or none, wherein when W is none R$_3$ is directly attached to C(O) by a single bond;

X is CH or N;

Y is CH or N;

Z is CH or N;

wherein one of X, Y or Z is N;

R$_1$ is independently —C(O)OR$_4$, —C(O)NHOH, —C(O)NHNH$_2$, CF$_3$, CHO, CN or heteroaryl; wherein R$_4$ may be independently C$_1$-C$_5$ alkyl;

R$_2$ is independently hydrogen, halogen, hydroxy, alkyl, alkoxy, thioalkyl, haloalkoxy, cyano, N(CH$_3$)$_2$, wherein R$_2$ may be linked via any position on the phenyl ring;

R$_3$ is independently C$_5$-C$_{20}$ alkyl, C$_3$-C$_8$ cycloalkyl, C$_4$-C$_8$ heterocycloalkyl, C$_{5-12}$ fused heterocycloalkyl, C$_{6-12}$ spirocycloalkyl, or aryl, wherein R$_3$ may be unsubstituted or substituted at a carbon ring member with halogen or alkyl group.

2. The compound of claim 1, wherein R$_1$ is monocycles: 2-pyrrolyl, 2-furanyl, 2-thienyl, 2-oxazolyl, 5-isoxazolyl, 2-thiazolyl, 1,3,4-oxadiazolyl, 1,2,4-oxadiazolyl, 1,3,4-thiadiazolyl, 1,2,4-triazolyl, or 1,2,3,4-tetrazolyl.

3. The compound of claim 1, wherein R$_2$ is H, OH, OCH$_3$, SCH$_3$, F, OCF$_3$, CN, or N(CH$_3$)$_2$.

4. The compound of claim 1, wherein
W is NH;
X is N;
Y is CH;
Z is CH;
R$_1$ is oxadiazole, oxazole, thiazole, pyrazole or imidazole;
R$_2$ is halogen, hydroxy, C$_1$-C$_4$ alkoxy, cyano, or fluoroalkyl; and
R$_3$ is C$_1$-C$_8$ alkyl or C$_3$-C$_8$ cycloalkyl.

5. The compound of claim 1, wherein the compound has the formula of any one of ethyl 5-(3-((pentylcarbamoyl)oxy)phenyl) nicotinate, ethyl 5-(3-((heptylcarbamoyl)oxy)phenyl) nicotinate, ethyl 5-(3-((octylcarbamoyl)oxy)phenyl) nicotinate, ethyl 5-(3-((tetradecylcarbamoyl)oxy)phenyl) nicotinate, ethyl 5-(3-((cyclopentylcarbamoyl)oxy)phenyl) nicotinate, ethyl 5-(3-((cyclohexylcarbamoyl)oxy)phenyl) nicotinate, ethyl 5-(3-(((4-fluorophenyl) carbamoyl)oxy) phenyl) nicotinate, methyl 5-(3-((pentylcarbamoyl)oxy)phenyl) nicotinate, methyl 5-(3-((heptylcarbamoyl)oxy)phenyl) nicotinate, methyl 5-(3-((octylcarbamoyl)oxy)phenyl) nicotinate, methyl 5-(3-((cyclopentylcarbamoyl)oxy)phenyl) nicotinate, methyl 5-(3-((cyclohexylcarbamoyl)oxy)phenyl) nicotinate, methyl 5-(3-((((1s,3s)-adamantan-1-yl) carbamoyl)oxy)phenyl) nicotinate, 3-(5-formylpyridin-3-yl)phenyl pentylcarbamate, 3-(5-formylpyridin-3-yl)phenyl heptylcarbamate, 3-(5-formylpyridin-3-yl)phenyl octylcarbamate, 3-(5-formylpyridin-3-yl)phenyl (cyclohexylmethyl) carbamate, 3-(5-formylpyridin-3-yl)phenyl cyclopentylcarbamate, 3-(5-formylpyridin-3-yl)phenyl cyclohexylcarbamate, 3-(5-formylpyridin-3-yl)phenyl cycloheptylcarbamate, 3-(5-formylpyridin-3-yl)phenyl ((1s,3s)-adamantan-1-yl) carbamate, 3-(5-(hydroxycarbamoyl)pyridin-3-yl)phenyl heptylcarbamate, 3-(5-(hydroxycarbamoyl)pyridin-3-yl)phenyl octylcarbamate, 3-(5-(hydroxycarbamoyl)pyridin-3-yl)phenyl tetradecylcarbamate, 3-(5-(hydrazinecarbonyl)pyridin-3-yl)pyridin-3-yl)phenyl octylcarbamate, 3-(5-cyanopyridin-3-yl)phenyl heptylcarbamate, 3-(5-cyanopyridin-3-yl)phenyl octylcarbamate, 3-(5-cyanopyridin-3-yl)phenyl cyclohexylcarbamate, 3-(5-cyanopyridin-3-yl)phenyl cycloheptylcarbamate, 3-(5-(trifluoromethyl)pyridin-3-yl)phenyl octylcarbamate, 3-(5-(trifluoromethyl)pyridin-3-yl)phenyl (cyclohexylmethyl) carbamate, 3-(5-(trifluoromethyl)pyridin-3-yl)phenyl cyclopentylcarbamate, 3-(5-(trifluoromethyl)pyridin-3-yl)phenyl cyclohexylcarbamate, 3-(5-(trifluoromethyl)pyridin-3-yl)phenyl cycloheptylcarbamate, 3-(5-(1H-pyrrol-2-yl)pyridin-3-yl)phenyl octylcarbamate, 3-(5-(1H-pyrrol-2-yl)pyridin-3-yl)phenyl (cyclohexylmethyl) carbamate, 3-(5-(1H-pyrrol-2-yl)pyridin-3-yl)phenyl benzylcarbamate, 3-(5-(1H-pyrrol-2-yl)pyridin-3-yl)phenyl cyclopentylcarbamate, 3-(5-(1H-pyrrol-2-yl)pyridin-3-yl)phenyl cyclohexylcarbamate, 3-(5-(1H-pyrrol-2-yl)pyridin-3-yl)phenyl cycloheptylcarbamate, 3-(5-(1H-pyrrol-2-yl)pyridin-3-yl)-4-methoxyphenyl octylcarbamate, 3-(5-(1H-pyrrol-2-yl)pyridin-3-yl)-4-methoxyphenyl (cyclohexylmethyl) carbamate, 3-(5-(1H-pyrrol-2-yl)pyridin-3-yl)-4-methoxyphenyl benzylcarbamate, 3-(5-(1H-pyrrol-2-yl)pyridin-3-yl)-4-methoxyphenyl cyclopentylcarbamate, 3-(5-(1H-pyrrol-2-yl)pyridin-3-yl)-4-methoxyphenyl cyclohexylcarbamate, 3-(5-(1H-pyrrol-2-yl)pyridin-3-yl)-4-methoxyphenyl cycloheptylcarbamate, 3-(5-(furan-2-yl)pyridin-3-yl)phenyl octylcarbamate, 3-(5-(furan-2-yl)pyridin-3-yl)phenyl (cyclohexylmethyl) carbamate, 3-(5-(furan-2-yl)pyridin-3-yl)phenyl benzylcarbamate, 3-(5-(furan-2-yl)pyridin-3-yl)phenyl cyclopentylcarbamate, 3-(5-(furan-2-yl)pyridin-3-yl)phenyl cyclohexylcarbamate, 3-(5-(furan-2-yl)pyridin-3-yl)phenyl cycloheptylcarbamate, 3-(5-(furan-2-yl)pyridin-3-yl)-4-methoxyphenyl octylcarbamate, 3-(5-(furan-2-yl)pyridin-3-yl)-4-methoxyphenyl (cyclohexylmethyl) carbamate, 3-(5-(furan-2-yl)pyridin-3-yl)-4-methoxyphenyl benzylcarbamate, 3-(5-(furan-2-yl)pyridin-3-yl)-4-methoxyphenyl cyclopentylcarbamate, 3-(5-(furan-2-yl)pyridin-3-yl)-4-methoxyphenyl cyclohexylcarbamate, 3-(5-(furan-2-yl)pyridin-3-yl)-4-methoxyphenyl cycloheptylcarbamate, 3-(5-(thiophen-2-yl)pyridin-3-yl)phenyl octylcarbamate, 3-(5-(thiophen-2-yl)pyridin-3-yl)phenyl (cyclohexylmethyl) carbamate, 3-(5-(thiophen-2-yl)pyridin-3-yl)phenyl benzylcarbamate, 3-(5-(thiophen-2-yl)pyridin-3-yl)phenyl cyclopentylcarbamate, 3-(5-(thiophen-2-yl)pyridin-3-yl)phenyl cyclohexylcarbamate, 3-(5-(thiophen-2-yl)pyridin-3-yl)phenyl cycloheptylcarbamate, 4-methoxy-3-(5-(thiophen-2-yl)pyridin-3-yl)phenyl octylcarbamate, 4-methoxy-3-(5-(thiophen-2-yl)pyridin-3-yl)phenyl (cyclohexylmethyl) carbamate, 4-methoxy-3-(5-(thiophen-2-yl)pyridin-3-yl)phenyl benzylcarbamate, 4-methoxy-3-(5-(thiophen-2-yl)pyridin-3-yl)phenyl cyclopentylcarbamate, 4-methoxy-3-(5-(thiophen-2-yl)pyridin-3-yl)phenyl cyclohexylcarbamate, 4-methoxy-3-(5-(thiophen-2-yl)pyridin-3-yl)phenyl cycloheptylcarbamate, 3-(5-(oxazol-2-yl)pyridin-3-yl)phenyl pentylcarbamate, 3-(5-(oxazol-2-yl)pyridin-3-yl)phenyl heptylcarbamate, 3-(5-(oxazol-2-yl)pyridin-3-yl)phenyl octylcarbamate, 3-(5-(oxazol-2-yl)pyridin-3-yl)phenyl (cyclohexylmethyl) carbamate, 3-(5-(oxazol-2-yl)pyridin-3-yl)phenyl cyclopentylcarbamate, 3-(5-(oxazol-2-yl)pyridin-3-yl)phenyl cyclohexylcarbamate, 3-(5-(oxazol-2-yl)pyridin-3-yl)phenyl ((1s,3s)-adamantan-1-yl) carbamate, 4-methoxy-3-(5-(oxazol-2-yl)pyridin-3-yl)phenyl octylcarbamate, 4-methoxy-3-(5-(oxazol-2-yl)pyridin-3-yl)phenyl (cyclohexylmethyl) carbamate, 4-methoxy-3-(5-(oxazol-2-yl)pyridin-3-yl)phenyl cyclopentylcarbamate, 4-methoxy-3-(5-(oxazol-2-yl)pyridin-3-yl)phenyl cyclohexylcarbamate, 4-methoxy-3-(5-(oxazol-2-yl)pyridin-3-yl)phenyl (4-methylcyclohexyl) carbamate, 4-methoxy-3-(5-(oxazol-2-yl)pyridin-3-yl)phenyl cycloheptylcarbamate, 2-methoxy-5-(5-(oxazol-2-yl)pyridin-3-yl)phenyl octylcarbamate, 4-fluoro-3-(5-(oxazol-2-yl)pyridin-3-yl)phenyl cyclopentylcarbamate, 4-fluoro-3-(5-(oxazol-2-yl)pyridin-3-yl)phenyl (4-methylcyclohexyl) carbamate, 4-fluoro-3-(5-(oxazol-2-yl)pyridin-3-yl)phenyl cycloheptylcarbamate, 3-(5-(oxazol-2-yl)pyridin-3-yl)-4-(trifluoromethoxy)phenyl octylcarbamate, 3-(5-(oxazol-2-yl)pyridin-3-yl)-4-(trifluoromethoxy)phenyl cyclohexylcarbamate, 3-(5-(oxazol-2-yl)pyridin-3-yl)-4-(trifluoromethoxy)phenyl (4-methylcyclohexyl) carbamate, 3-(5-(oxazol-2-yl)pyridin-3-yl)-4-(trifluoromethoxy)phenyl cycloheptylcarbamate, 2-methyl-5-(5-(oxazol-2-yl)pyridin-3-yl)phenyl octylcarbamate, 2-methyl-5-(5-(oxazol-2-yl)pyridin-3-yl)phenyl (cyclohexylmethyl) carbamate, 2-methyl-5-(5-(oxazol-2-yl)pyridin-3-yl)phenyl benzylcarbamate, 2-methyl-5-(5-(oxazol-2-yl)pyridin-3-yl)phenyl cyclohexylcarbamate, 3-methyl-5-(5-(oxazol-2-yl)pyridin-3-yl)phenyl (4-methylcyclohexyl) carbamate, 2-methyl-5-(5-(oxazol-2-yl)pyridin-3-yl)phenyl cycloheptylcarbamate, 2-methyl-5-(5-(oxazol-2-yl)pyridin-3-yl)phenyl cyclooctylcarbamate, 3-methyl-5-(5-(oxazol-2-yl)pyridin-3-yl)phenyl (cyclohexylmethyl) carbamate, 3-methyl-5-(5-(oxazol-2-yl)pyridin-3-yl)phenyl benzylcarbamate, 3-methyl-5-(5-(oxazol-2-yl)pyridin-3-yl)phenyl cyclohexylcarbamate, 3-methyl-5-(5-(oxazol-2-yl)pyridin-3-yl)phenyl (4-methylcyclohexyl) carbamate, 3-methyl-5-(5-(oxazol-2-yl)pyridin-3-yl)phenyl cycloheptylcarbamate, 3-methyl-5-(5-(oxazol-2-yl)pyridin-3-yl)phenyl cyclooctylcarbamate, 3-(5-(isoxazol-5-yl)pyridin-3-yl)phenyl octylcarbamate, 3-(5-(isoxazol-5-yl)pyridin-3-yl)phenyl cyclopentylcarbamate, 3-(5-(isoxazol-5-yl)pyridin-3-yl)phenyl cyclohexylcarbamate, 3-(5-(isoxazol-5-yl)pyridin-3-yl)phenyl cycloheptylcarbamate, 3-(5-(isoxazol-5-yl)pyridin-3-yl)-4-methoxyphenyl octylcarbamate, 3-(5-(isoxazol-5-yl)pyridin-3-yl)-4-methoxyphenyl (cyclohexylmethyl) carbamate, 3-(5-(isoxazol-5-yl)pyridin-3-yl)-4-methoxyphenyl benzylcarbamate, 3-(5-(isoxazol-5-yl)pyridin-3-yl)-4-methoxyphenyl cyclopentylcarbamate, 3-(5-(isoxazol-5-yl)pyridin-3-yl)-4-methoxyphenyl cyclohexylcarbamate, 3-(5-(isoxazol-5-yl)pyridin-3-yl)-4-methoxyphenyl cycloheptylcarbamate, 3-(5-(thiazol-2-yl)pyridin-3-yl)phenyl octylcarbamate, 3-(5-(thiazol-2-yl)pyridin-3-yl)phenyl (cyclohexylmethyl) carbamate, 3-(5-(thiazol-2-yl)pyridin-3-yl)phenyl benzylcarbamate, 3-(5-(thiazol-2-yl)pyridin-3-yl)phenyl cyclopentylcarbamate, 3-(5-(thiazol-2-yl)pyridin-3-yl)phenyl cyclohexylcarbamate, 3-(5-(thiazol-2-yl)pyridin-3-yl)phenyl cycloheptylcarbamate, 4-methoxy-3-(5-(thiazol-2-yl)pyridin-3-yl)phenyl octylcarbamate, 4-methoxy-3-(5-(thiazol-2-yl)pyridin-3-yl)phenyl (cyclohexylmethyl) carbamate, 4-methoxy-3-(5-(thiazol-2-yl)pyridin-3-yl)phenyl benzylcarbamate, 4-methoxy-3-(5-(thiazol-2-yl)pyridin-3-yl)phenyl cyclopentylcarbamate, 4-methoxy-3-(5-(thiazol-2-yl)pyridin-3-yl)phenyl cyclohexylcarbamate, 4-methoxy-3-(5-(thiazol-2-yl)pyridin-3-yl)phenyl cycloheptylcarbamate, 3-(5-(1,3,4-oxadiazol-2-yl)pyridin-3-yl)phenyl pentylcarbamate, 3-(5-(1,3,4-oxadiazol-2-yl)pyridin-3-yl)phenyl hexylcarbamate, 3-(5-(1,3,4-oxadiazol-2-yl)pyridin-3-yl)phenyl heptylcarbamate, 3-(5-(1,3,4-oxadiazol-2-yl)pyridin-3-yl)phenyl octylcarbamate, 3-(5-(1,3,4-oxadiazol-2-yl)pyridin-3-yl)phenyl dodecylcarbamate, 3-(5-(1,3,4-oxadiazol-2-yl)pyridin-3-yl)phenyl tetradecylcarbamate, 3-(5-(1,3,4-oxadiazol-2-yl)pyridin-3-yl)phenyl octadecylcarbamate, 3-(5-(1,3,4-oxadiazol-2-yl)pyridin-3-yl)phenyl (cyclohexylmethyl) carbamate, 3-(5-(1,3,4-oxadiazol-2-yl)pyridin-3-yl)phenyl benzylcarbamate, 3-(5-(1,3,4-oxadiazol-2-yl)pyridin-3-yl)phenyl (3-phenylpropyl) carbamate, 3-(5-(1,3,4-oxadiazol-2-yl)pyridin-3-yl)phenyl (cyclohexylmethyl) carbamate, 3-(5-(1,3,4-oxadiazol-2-yl)pyridin-3-yl)phenyl cyclopentylcarbamate, 3-(5-(1,3,4-oxadiazol-2-yl)pyridin-3-yl)phenyl cyclohexylcarbamate, 3-(5-(1,3,4-oxadiazol-2-yl)pyridin-3-yl)phenyl naphthalen-1-ylcarbamate, 3-(5-(1,3,4-oxadiazol-2-yl)pyridin-3-yl)phenyl piperidine-1-carboxylate, 3-(5-(1,3,4-oxadiazol-2-yl)pyridin-3-yl)phenyl cyclohexyl(methyl) carbamate, 3-(5-(1,3,4-oxadiazol-2-yl)pyridin-3-yl)phenyl 2-methylpiperidine-1-carboxylate, 3-(5-(1,3,4-oxadiazol-2-yl)pyridin-3-yl)phenyl cycloheptyl(methyl) carbamate, 3-(5-(1,3,4-oxadiazol-2-yl)pyridin-3-yl)phenyl azocane-1-carboxylate, 3-(5-(1,3,4-oxadiazol-2-yl)pyridin-3-yl)phenyl 2-azaspiro[3.3]heptane-2-carboxylate, 3-(5-(1,3,4-oxadiazol-2-yl)pyridin-3-yl)phenyl spiro[3.3]heptan-2-ylcarbamate, 3-(5-(1,3,4-oxadiazol-2-yl)pyridin-3-yl)phenyl 3-azabicyclo[3.1.0]hexane-3-carboxylate, 3-(5-(1,3,4-oxadiazol-2-yl)pyridin-3-yl)phenyl hexahydrocyclopenta[c]pyrrole-2(1H)-carboxylate, 3-(5-(1,3,4-oxadiazol-2-yl)pyridin-3-yl)phenyl 8-azabicyclo[3.2.1]octane-8-carboxylate, 3-(5-(1,3,4-oxadiazol-2-yl)pyridin-3-yl)phenyl morpholine-4-carboxylate, 3-(5-(1,3,4-oxadiazol-2-yl)pyridin-3-yl)phenyl 2-oxa-6-azaspiro[3.3]heptane-6-carboxylate, 3-(5-(1,3,4-oxadiazol-2-yl)pyridin-3-yl)phenyl 2-oxa-7-azaspiro[3.5]nonane-7-carboxylate, 3-(5-(1,3,4-oxadiazol-2-yl)pyridin-3-yl)phenyl heptyl(methyl) carbamate, 3-(5-(1,3,4-oxadiazol-2-yl)pyridin-3-yl)phenyl dibutylcarbamate, 3-(5-(1,3,4-oxadiazol-2-yl)pyridin-3-yl)-4-hydroxyphenyl heptylcarbamate, 3-(5-(1,3,4-oxadiazol-2-yl)pyridin-3-yl)-4-hydroxyphenyl octylcarbamate, 3-(5-(1,3,4-oxadiazol-2-yl)pyridin-3-yl)-4-hydroxyphenyl cyclohexylcarbamate, 3-(5-(1,3,4-oxadiazol-2-yl)pyridin-3-yl)-4-hydroxyphenyl (4-methylcyclohexyl) carbamate, 3-(5-(1,3,4-oxadiazol-2-yl)pyridin-3-yl)-5-hydroxyphenyl heptylcarbamate, 3-(5-(1,3,4-oxadiazol-2-yl)pyridin-3-yl)-5-hydroxyphenyl (cyclohexylmethyl) carbamate, 3-(5-(1,3,4-oxadiazol-2-yl)pyridin-3-yl)-5-hydroxyphenyl benzylcarbamate, 3-(5-(1,3,4-oxadiazol-2-yl)pyridin-3-yl)-5-hydroxyphenyl cyclopentylcarbamate, 3-(5-(1,3,4-oxadiazol-2-yl)pyridin-3-yl)-5-hydroxyphenyl cyclohexylcarbamate, 3-(5-(1,3,4-oxadiazol-2-yl)pyridin-3-yl)-5-hydroxyphenyl cycloheptylcarbamate, 3-(5-(1,3,4-oxadiazol-2-yl)pyridin-3-yl)-4-methoxyphenyl heptylcarbamate, 3-(5-(1,3,4-oxadiazol-2-yl)pyridin-3-yl)-4-methoxyphenyl octylcarbamate, 3-(5-(1,3,4-oxadiazol-2-yl)pyridin-3-yl)-4-methoxyphenyl (cyclohexylmethyl) carbamate, 3-(5-(1,3,4-oxadiazol-2-yl)pyridin-3-yl)-4-methoxyphenyl cyclopentylcarbamate, 3-(5-(1,3,4-oxadiazol-2-yl)pyridin-3-yl)-4-methoxyphenyl cyclohexylcarbamate, 3-(5-(1,3,4-oxadiazol-2-yl)pyridin-3-yl)-4-methoxyphenyl (4-methylcyclohexyl) carbamate, 3-(5-(1,3,4-oxadiazol-2-yl)pyridin-3-yl)-4-methoxyphenyl cycloheptylcarbamate, 3-(5-(1,3,4-oxadiazol-2-yl)pyridin-3-yl)-4-methoxyphenyl cyclooctylcarbamate, 3-(5-(1,3,4-oxadiazol-2-yl)pyridin-3-yl)-5-methoxyphenyl octylcarbamate, 3-(5-(1,3,4-oxadiazol-2-yl)pyridin-3-yl)-5-methoxyphenyl (cyclohexylmethyl) carbamate, 3-(5-(1,3,4-oxadiazol-2-yl)pyridin-3-yl)-5-methoxyphenyl benzylcarbamate, 3-(5-(1,3,4-oxadiazol-2-yl)pyridin-3-yl)-5-methoxyphenyl cyclopentylcarbamate, 3-(5-(1,3,4-oxadiazol-2-yl)pyridin-3-yl)-5-methoxyphenyl cyclohexylcarbamate, 3-(5-(1,3,4-oxadiazol-2-yl)pyridin-3-yl)-5-methoxyphenyl cycloheptylcarbamate, 3-(5-(1,3,4-oxadiazol-2-yl)pyridin-3-yl)-4-(dimethylamino)phenyl octylcarbamate, 3-(5-(1,3,4-oxadiazol-2-yl)pyridin-3-yl)-4-(dimethylamino)phenyl (cyclohexylmethyl) carbamate, 3-(5-(1,3,4-oxadiazol-2-yl)pyridin-3-yl)-4-(dimethylamino)phenyl benzylcarbamate, 3-(5-(1,3,4-oxadiazol-2-yl)pyridin-3-yl)-4-(dimethylamino)phenyl cyclopentylcarbamate, 3-(5-(1,3,4-oxadiazol-2-yl)pyridin-3-yl)-4-(dimethylamino)phenyl cyclohexylcarbamate, 3-(5-(1,3,4-oxadiazol-2-yl)pyridin-3-yl)-4-(dimethylamino)phenyl cycloheptylcarbamate, 3-(5-(1,3,4-oxadiazol-2-yl)pyridin-3-yl)-4-(methylthio)phenyl octylcarbamate, 3-(5-(1,3,4-oxadiazol-2-yl)pyridin-3-yl)-4-(methylthio)phenyl (cyclohexylmethyl) carbamate, 3-(5-(1,3,4-oxadiazol-2-yl)pyridin-3-yl)-4-(methylthio)phenyl benzylcarbamate, 3-(5-(1,3,4-oxadiazol-2-yl)pyridin-3-yl)-4-(methylthio)phenyl cyclopentylcarbamate, 3-(5-(1,3,4-oxadiazol-2-yl)pyridin-3-yl)-4-(methylthio)phenyl cyclohexylcarbamate, 3-(5-(1,3,4-oxadiazol-2-yl)pyridin-3-yl)-4-(methylthio)phenyl cycloheptylcarbamate, 3-(5-(1,3,4-oxadiazol-2-yl)pyridin-3-yl)-4-fluorophenyl cyclohexylcarbamate, 3-(5-(1,3,4-oxadiazol-2-yl)pyridin-3-yl)-4-fluorophenyl (4-methylcyclohexyl) carbamate, 3-(5-(1,3,4-oxadiazol-2-yl)pyridin-3-yl)-4-fluorophenyl cycloheptylcarbamate, 3-(5-(1,3,4-oxadiazol-2-yl)pyridin-3-yl)-5-fluorophenyl heptyl carbamate, 3-(5-(1,3,4-oxadiazol-2-yl)pyridin-3-yl)-5-fluorophenyl benzylcarbamate, 3-(5-(1,3,4-oxadiazol-2-yl)pyridin-3-yl)-5-fluorophenyl cyclohexylcarbamate, 3-(5-(1,3,4-oxadiazol-2-yl)pyridin-3-yl)-5-fluorophenyl cycloheptylcarbamate, 3-(5-(1,3,4-oxadiazol-2-yl)pyridin-3-yl)-4-(trifluoromethoxy)phenyl octylcarbamate, 3-(5-(1,3,4-oxadiazol-2-yl)pyridin-3-yl)-4-(trifluoromethoxy)phenyl cyclohexylcarbamate, 3-(5-(1,3,4-oxadiazol-2-yl)pyridin-3-yl)-4-(trifluoromethoxy)phenyl (4-methylcyclohexyl) carbamate, 3-(5-(1,3,4-oxadiazol-2-yl)pyridin-3-yl)-4-(trifluoromethoxy)phenyl cycloheptylcarbamate, 3-(5-(1,3,4-oxadiazol-2-yl)pyridin-3-yl)-4-(trifluoromethoxy)phenyl phenylcarbamate, 3-(5-(1,2,4-oxadiazol-5-yl)pyridin-3-yl)phenyl (cyclohexylmethyl) carbamate, 3-(5-(1,2,4-oxadiazol-5-yl)pyridin-3-yl)phenyl cyclohexylcarbamate, 3-(5-(1,2,4-oxadiazol-5-yl)pyridin-3-yl)phenyl cycloheptylcarbamate, 3-(5-(1,3,4-thiadiazol-2-yl)pyridin-3-yl)phenyl octylcarbamate, 3-(5-(1,3,4-thiadiazol-2-yl)pyridin-3-yl)phenyl (cyclohexylmethyl) carbamate, 3-(5-(1,3,4-thiadiazol-2-yl)pyridin-3-yl)phenyl benzylcarbamate, 3-(5-(1,3,4-thiadiazol-2-yl)pyridin-3-yl)phenyl cyclopentylcarbamate, 3-(5-(1,3,4-thiadiazol-2-yl)pyridin-3-yl)phenyl cyclohexylcarbamate, 3-(5-(1,3,4-thiadiazol-2-yl)pyridin-3-yl)phenyl cycloheptylcarbamate, 3-(5-(1,3,4-thiadiazol-2-yl)pyridin-3-yl)-4-methoxyphenyl octylcarbamate, 3-(5-(1,3,4-thiadiazol-2-yl)pyridin-3-yl)-4-methoxyphenyl (cyclohexylmethyl) carbamate, 3-(5-(1,3,4-thiadiazol-2-yl)pyridin-3-yl)-4-methoxyphenyl benzylcarbamate, 3-(5-(1,3,4-thiadiazol-2-yl)pyridin-3-yl)-4-methoxyphenyl cyclopentylcarbamate, 3-(5-(1,3,4-thiadiazol-2-yl)pyridin-3-yl)-4-methoxyphenyl cyclohexylcarbamate, 3-(5-(1,3,4-thiadiazol-2-yl)pyridin-3-yl)-4-methoxyphenyl cycloheptylcarbamate, 3-(5-(1H-1,2,4-triazol-5-yl)pyridin-3-yl)phenyl octyl carbamate, 3-(5-(1H-1,2,4-triazol-5-yl)pyridin-3-yl)phenyl (cyclohexylmethyl) carbamate, 3-(5-(1H-1,2,4-triazol-5-yl)pyridin-3-yl)phenyl benzylcarbamate, 3-(5-(1H-1,2,4-triazol-5-yl)pyridin-3-yl)phenyl (naphthalen-2-ylmethyl) carbamate, 3-(5-(1H-1,2,4-triazol-5-yl)pyridin-3-yl)phenyl cyclopentylcarbamate, 3-(5-(1H-1,2,4-triazol-5-yl)pyridin-3-yl)phenyl cyclohexylcarbamate, 3-(5-(1H-1,2,4-triazol-5- yl)pyridin-3-yl)phenyl cyclohepytl carbamate, 3-(5-(1H-1,2,4-triazol-5-yl)pyridin-3-yl)-4-hydroxyphenyl octylcarbamate, 3-(5-(1H-1,2,4-triazol-5-yl)pyridin-3-yl)-4-hydroxyphenyl (cyclohexylmethyl) carbamate, 3-(5-(1H-1,2,4-triazol-5-yl)pyridin-3-yl)-4-hydroxyphenyl benzylcarbamate, 3-(5-(1H-1,2,4-triazol-5-yl)pyridin-3-yl)-4-hydroxyphenyl cyclopentylcarbamate, 3-(5-(1H-1,2,4-triazol-5-yl)pyridin-3-yl)-4-hydroxyphenyl cyclohexylcarbamate, 3-(5-(1H-1,2,4-triazol-5-yl)pyridin-3-yl)-4-hydroxyphenyl cycloheptylcarbamate, 3-(5-(1H-1,2,4-triazol-5-yl)pyridin-3-yl)-4-methoxyphenyl octylcarbamate, 3-(5-(1H-1,2,4-triazol-5-yl)pyridin-3-yl)-4-methoxyphenyl (cyclohexylmethyl) carbamate, 3-(5-(1H-1,2,4-triazol-5-yl)pyridin-3-yl)-4-methoxyphenyl benzylcarbamate, 3-(5-(1H-1,2,4-triazol-5-yl)pyridin-3-yl)-4-methoxyphenyl cyclopentylcarbamate, 3-(5-(1H-1,2,4-triazol-5-yl)pyridin-3-yl)-4-methoxyphenyl cyclohexylcarbamate, 3-(5-(1H-1,2,4-triazol-5-yl)pyridin-3-yl)-4-methoxyphenyl cycloheptylcarbamate, 3-(5-(1H-tetrazol-5-yl)pyridin-3-yl)phenyl octylcarbamate, 3-(5-(1H-tetrazol-5-yl)pyridin-3-yl)phenyl (cyclohexylmethyl) carbamate, 3-(5-(1H-tetrazol-5-yl)pyridin-3-yl)phenyl benzylcarbamate, 3-(5-(1H-tetrazol-5-yl)pyridin-3-yl)phenyl cyclopentylcarbamate, 3-(5-(1H-tetrazol-5-yl)pyridin-3-yl)phenyl cyclohexylcarbamate, 3-(5-(1H-tetrazol-5-yl)pyridin-3-yl)phenyl cycloheptylcarbamate, 3-(5-(1H-tetrazol-5-yl)pyridin-3-yl)-4-hydroxyphenyl octylcarbamate, 3-(5-(1H-tetrazol-5-yl)pyridin-3-yl)-4-hydroxyphenyl (cyclohexylmethyl) carbamate, 3-(5-(1H-tetrazol-5-yl)pyridin-3-yl)-4-hydroxyphenyl benzylcarbamate, 3-(5-(1H-tetrazol-5-yl)pyridin-3-yl)-4-hydroxyphenyl cyclopentylcarbamate, 3-(5-(1H-tetrazol-5-yl)pyridin-3-yl)-4-hydroxyphenyl cyclohexylcarbamate, 3-(5-(1H-tetrazol-5-yl)pyridin-3-yl)-4-hydroxyphenyl cycloheptylcarbamate, 3-(5-(1H-tetrazol-5-yl)pyridin-3-yl)-4-methoxyphenyl octylcarbamate, 3-(5-(1H-tetrazol-5-yl)pyridin-3-yl)-4-methoxyphenyl (cyclohexylmethyl) carbamate, 3-(5-(1H-tetrazol-5-yl)pyridin-3-yl)-4-methoxyphenyl benzylcarbamate, 3-(5-(1H-tetrazol-5-yl)pyridin-3-yl)-4-methoxyphenyl cyclopentylcarbamate, 3-(5-(1H-tetrazol-5-yl)pyridin-3-yl)-4-methoxyphenyl cyclohexylcarbamate, 3-(5-(1H-tetrazol-5-yl)pyridin-3-yl)-4-methoxyphenyl cycloheptylcarbamate, 3-(4-(1,3,4-oxadiazol-2-yl)pyridin-2-yl)phenyl (2-methylhexyl) carbamate, 3-(4-(1,3,4-oxadiazol-2-yl)pyridin-2-yl)phenyl (cyclohexylmethyl) carbamate, 3-(4-(1,3,4-oxadiazol-2-yl)pyridin-2-yl) phenyl benzylcarbamate, 3-(4-(1,3,4-oxadiazol-2-yl)pyridin-2-yl)phenyl cyclopentylcarbamate, 3-(4-(1,3,4-oxadiazol-2-yl)pyridin-2-yl)phenyl cyclohexylcarbamate, 3-(4-(1,3,4-oxadiazol-2-yl)pyridin-2-yl)phenyl (4-methylcyclohexyl) carbamate, or 3-(4-(1,3,4-oxadiazol-2-yl)pyridin-2-yl)phenyl cycloheptylcarbamate.

6. The compound of claim 1, wherein the compound has the formula of any one of ethyl 5-(3-((tetradecylcarbamoyl)oxy)phenyl) nicotinate, methyl 5-(3-((heptylcarbamoyl)oxy)phenyl) nicotinate, methyl 5-(3-((octylcarbamoyl)oxy) phenyl) nicotinate, 3-(5-(furan-2-yl)pyridin-3-yl)phenyl octylcarbamate, 3-(5-(furan-2-yl)pyridin-3-yl)phenyl cyclohexylcarbamate, 3-(5-(thiophen-2-yl)pyridin-3-yl)phenyl cycloheptylcarbamate, 3-(5-(oxazol-2-yl)pyridin-3-yl)phenyl heptylcarbamate, 3-(5-(oxazol-2-yl)pyridin-3-yl)phenyl octylcarbamate, 4-fluoro-3-(5-(oxazol-2-yl)pyridin-3-yl) phenyl cycloheptylcarbamate, 3-(5-(isoxazol-5-yl)pyridin-3-yl)phenyl octylcarbamate, 3-(5-(isoxazol-5-yl)pyridin-3-yl)-4-methoxyphenyl octylcarbamate, 3-(5-(thiazol-2-yl) pyridin-3-yl)phenyl octylcarbamate, 3-(5-(1,3,4-oxadiazol-2-yl)pyridin-3-yl)phenyl hexylcarbamate, 3-(5-(1,3,4-oxadiazol-2-yl)pyridin-3-yl)phenyl octylcarbamate, 3-(5-(1,3,4-oxadiazol-2-yl)pyridin-3-yl)phenyl dodecylcarbamate, 3-(5-(1,3,4-oxadiazol-2-yl)pyridin-3-yl)phenyl tetradecylcarbamate, 3-(5-(1,3,4-oxadiazol-2-yl)pyridin-3-yl)phenyl (cyclohexylmethyl) carbamate, 3-(5-(1,3,4-oxadiazol-2-yl)pyridin-3-yl)phenyl (cyclohexylmethyl) carbamate, 3-(5-(1,3,4-oxadiazol-2-yl)pyridin-3-yl)-4-hydroxyphenyl heptylcarbamate, 3-(5-(1,3,4-oxadiazol-2-yl)pyridin-3-yl)-4-hydroxyphenyl octylcarbamate, 3-(5-(1,3,4-oxadiazol-2-yl)pyridin-3-yl)-5-hydroxyphenyl heptylcarbamate, 3-(5-(1,3,4-oxadiazol-2-yl)pyridin-3-yl)-5-hydroxyphenyl cycloheptylcarbamate, 3-(5-(1,3,4-oxadiazol-2-yl)pyridin-3-yl)-4-methoxyphenyl octylcarbamate, 3-(5-(1,3,4-oxadiazol-2-yl)pyridin-3-yl)-5-methoxyphenyl octylcarbamate, 3-(5-(1,3,4-oxadiazol-2-yl)pyridin-3-yl)-4-fluorophenyl cycloheptylcarbamate, 3-(5-(1,3,4-oxadiazol-2-yl)pyridin-3-yl)-5-fluorophenyl heptyl carbamate, 3-(5-(1,3,4-thiadiazol-2-yl)pyridin-3-yl)phenyl octylcarbamate, 3-(5-(1,3,4-thiadiazol-2-yl)pyridin-3-yl)-4-methoxyphenyl octylcarbamate, 3-(5-(1H-1,2,4-triazol-5-yl)pyridin-3-yl) phenyl octyl carbamate, 3-(5-(1H-1,2,4-triazol-5-yl)pyridin-3-yl)-4-hydroxyphenyl octylcarbamate, or 3-(4-(1,3,4-oxadiazol-2-yl)pyridin-2-yl)phenyl (2-methylhexyl) carbamate.

7. The compound of claim 1, having Formula II

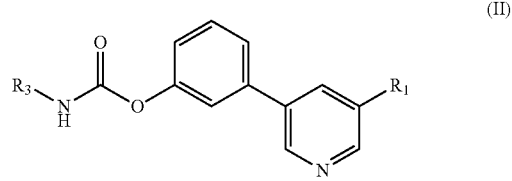

(II)

a prodrug thereof, a pharmaceutically acceptable salt thereof, or a pharmaceutically active metabolite thereof; wherein $R_1$ is independently —C(O)O$R_4$, —C(O)NHOH, —C(O)NHNH$_2$, CF$_3$, CHO, CN; wherein $R_4$ is independently $C_1$-$C_5$ alkyl;

$R_3$ is independently $C_5$-$C_{18}$ alkyl, $C_3$-$C_8$ cycloalkyl, $C_{6-12}$ fused heterocycloakyl, or aryl.

8. The compound of claim 7, wherein
$R_1$ is oxadiazole, oxazole, thiazole, pyrazole or imidazole; and
$R_3$ is $C_1$-$C_8$ alkyl or $C_3$-$C_8$ cycloalkyl.

9. The compound of claim 1, having Formula III

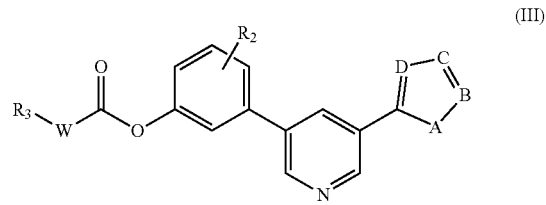

(III)

a prodrug thereof, a pharmaceutically acceptable salt thereof, or a pharmaceutically active metabolite thereof; wherein W is NH, N(CH$_3$), or none, wherein when W is none $R_3$ is directly attached to C(O) by a single bond;

A is O, S, or NH;

B is CH or N;

C is CH or N;

D is CH or N;

$R_2$ is independently hydrogen, halogen, alkyl, alkoxy, thioalkyl, or haloalkoxy; wherein $R_2$ may be linked via any position on the phenyl ring;

$R_3$ is independently $C_5$-$C_{20}$ alkyl, $C_3$-$C_8$ cycloalkyl, $C_4$-$C_8$ heterocycloalkyl, $C_{6-12}$ fused heterocycloakyl, $C_{6-12}$ spirocycloalkyl, aryl, wherein $R_3$ may be unsubstituted or substituted at a carbon ring member with halogen or alkyl group.

10. The compound of claim 9, wherein $R_2$ is H, OH, $OCH_3$, $SCH_3$, F, $OCF_3$, CN or $N(CH_3)_2$.

11. The compound of claim 9, wherein
A is O;
B is CH;
C is N;
D is N;
$R_2$ is halogen, hydroxy, $C_1$-$C_4$ alkoxy, cyano, or fluoroalkyl; and
$R_3$ is $C_1$-$C_8$ alkyl or $C_3$-$C_8$ cycloalkyl.

12. The compound of claim 9, wherein
A is S;
B is CH;
C is N;
D is N;
$R_2$ is halogen, hydroxy, $C_1$-$C_4$ alkoxy, cyano, or fluoroalkyl; and
$R_3$ is $C_1$-$C_8$ alkyl or $C_3$-$C_8$ cycloalkyl.

13. The compound of claim 9, wherein
A is O;
B is CH;
C is CH;
D is N;
$R_2$ is halogen, hydroxy, $C_1$-$C_4$ alkoxy, cyano, or fluoroalkyl; and
$R_3$ is $C_1$-$C_8$ alkyl or $C_3$-$C_8$ cycloalkyl.

14. The compound of claim 9, wherein
A is O;
B is CH;
C is N;
D is CH;
$R_2$ is halogen, hydroxy, $C_1$-$C_4$ alkoxy, or fluoroalkyl; and
$R_3$ is $C_1$-$C_8$ alkyl or $C_3$-$C_8$ cycloalkyl.

15. The compound of claim 1, having Formula IV:

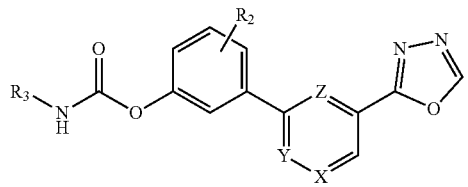

(IV)

16. The compound of claim 1, wherein
X is N;
Y is CH;
Z is CH;
$R_2$ is halogen, hydroxy, $C_1$-$C_4$ alkoxy, cyano, or fluoroalkyl; and
$R_3$ is $C_1$-$C_8$ alkyl or $C_3$-$C_8$ cycloalkyl.

17. The compound of claim 1, wherein
X is N;
Y is CH;
Z is CH;
$R_2$ is hydroxy or $C_1$-$C_4$ alkoxy; and
$R_3$ is $C_1$-$C_8$ alkyl or $C_3$-$C_8$ cycloalkyl.

18. A pharmaceutical composition comprising the compound of claim 1 and optionally one or more pharmaceutically acceptable excipients or adjuvants.

19. A method of treating a disease, disorder or condition by administering to a subject in need thereof the pharmaceutical composition of claim 18, wherein the disease, disorder or condition is selected from the group consisting of pain, acute pain, chronic pain, nociceptive pain, and non-nociceptive pain, inflammatory diseases, inflammatory bowel disease, neuroinflammation, neuropathy, anxiety and mood disorder, sleep disorder, eating disorders, obesity, cardiovascular diseases, hypertension, coronary heart disease, ischemia, congestive heart failure, atherosclerosis, myocardial infarction, peripheral vascular disease, dyslipidemia, hyperlipidemia, hypoalphalipoproteinemia, hypertriglyceridemia, hypercholesterolemia, and low high-density lipoprotein (HDL), diabetes (type 1 and type 2), allergic airway disease, cough, asthma, chronic obstructive diseases, cerebrovascular disorders, stroke, cerebral vasospasm, learning and memory disorders, drug or alcohol withdrawal, addiction, liver diseases, non-alcoholic fatty liver disease (NAFLD), non-alcoholic steatohepatitis (NASH), hepatitis, cancer, chemotherapy-induced nausea and vomiting (CINV), neurodegenerative disease, Alzheimer and Parkinson diseases, central nervous system (CNS) disorders, depression, post-traumatic stress disorder, schizophrenia, seizures, cognitive disorders, autoimmune diseases, psoriasis, rheumatoid arthritis, Crohn's disease, systemic lupus erythematosis, Sjogren's syndrome, Huntington's chorea, multiple sclerosis, skin disorders, itching, eczema, pruritis, dermatitis, impaired wound healing, gastrointestinal disorders, nausea, gastrointestinal motility disorder, paralytic ileus, eye diseases, cataract, and glaucoma.

20. The compound of claim 1, wherein X is CH or N; Y is CH or N; Z is CH; and wherein one of X or Y is N.

* * * * *